US011879128B2

(12) United States Patent
Losada et al.

(10) Patent No.: US 11,879,128 B2
(45) Date of Patent: Jan. 23, 2024

(54) TARGETING OF GLUTEN BY GENOME EDITING

(71) Applicant: Consejo Superior De Investigaciones Cientificas (CSIC)—Delegación Andalucía, Seville (ES)

(72) Inventors: Francisco Barro Losada, Cordova (ES); Javier Gil Humanes, Circle Pines, MN (US); Susana Sánchez León, Cordova (ES)

(73) Assignee: CONSEJO SUPERIOR DE INVESTIGACIONES CIENTÍFICAS (CSIC)—DELEGACIÓN ANDALUCÍA, Seville (ES)

( * ) Notice: Subject to any disclaimer, the term of this patent is extended or adjusted under 35 U.S.C. 154(b) by 350 days.

(21) Appl. No.: 16/619,180

(22) PCT Filed: Jun. 5, 2018

(86) PCT No.: PCT/EP2018/064791

§ 371 (c)(1), (2) Date: Dec. 4, 2019

(87) PCT Pub. No.: WO2018/224508

PCT Pub. Date: Dec. 13, 2018

(65) Prior Publication Data

US 2020/0231978 A1 Jul. 23, 2020

(30) Foreign Application Priority Data

Jun. 5, 2017 (EP) .................................... 17382335

(51) Int. Cl.
*C12N 15/82* (2006.01)
*A23L 25/00* (2016.01)
*C12N 15/11* (2006.01)

(52) U.S. Cl.
CPC .......... *C12N 15/8213* (2013.01); *A23L 25/00* (2016.08); *C12N 15/11* (2013.01); *A23V 2002/00* (2013.01); *C12N 2310/20* (2017.05); *C12N 2800/80* (2013.01)

(58) Field of Classification Search
CPC ............ C12N 15/8213; C12N 15/8218; C12N 2310/20
See application file for complete search history.

(56) References Cited

U.S. PATENT DOCUMENTS

| | | | |
|---|---|---|---|
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,697,359 | B1 | 4/2014 | Zhang |
| 2012/0167253 | A1 | 6/2012 | Barro Losada et al. |

OTHER PUBLICATIONS

Jouanin, Aurélie, et al. "Outlook for coeliac disease patients: towards bread wheat with hypoimmunogenic gluten by gene editing of α-and γ-gliadin gene families." BMC plant biology 19.1 (2019): 1-16.*

Van Belle, J., and Jan G. Schaart. "Towards TALEN-mediated Targeting and Exclusion of Immunogenic Epitopes of Gluten Proteins in Wheat Species Causing Celiac Disease." Feb. 14, 2014 (Feb. 14, 2014), pp. 1-66, ISBN: 9781321252422 (supplemented in the IDS filed by Applicant on Apr. 16, 2020.) (Year: 2014).*

Shewry, Peter R., and Arthur S. Tatham. "Improving wheat to remove coeliac epitopes but retain functionality." Journal of Cereal Science 67 (2016): 12-21. (supplemented in the IDS filed by Applicant on Apr. 16, 2020.) (Year: 2016).*

Zhang, Yi, et al. "Efficient and transgene-free genome editing in wheat through transient expression of CRISPR/Cas9 DNA or RNA." Nature communications 7.1 (2016): 1-8. (supplemented in the IDS filed by Applicant on Apr. 16, 2020.) (Year: 2016).*

Jouanin, Aurélie, et al. "Outlook for coeliac disease patients: towards bread wheat with hypoimmunogenic gluten by gene editing of α-and γ-gliadin gene families." BMC plant biology 19.1 (2019): 1-16. (Year: 2019).*

Van Belle, "Towards Talen-mediated Targeting and Exclusion of Immunogenic Epitopes of Gluten Proteins in Wheat Species Causing Celiac Disease", Feb. 14, 2014 (Feb. 14, 2014), pp. 1-66, ISBN: 9781321252422.

Shewry et al., "Improving wheat to remove coeliac epitopes but retain functionality", Journal of Cereal Science, Academic Press Ltd, GB, Jun. 26, 2015 (Jun. 26, 2015), p. 12-21, vol. 67, XP029408880.

Ozuna et al., "Diversification of the celiac disease [alpha]-gliadin complex in wheat: a 33-mer peptide with six overlapping epitopes, evolved following polyploidization", The Plant Journal, May 2015 (May 11, 2015), p. 794-805, vol. 82, No. 5, 11, XP055497171.

Zhang et al., "Efficient and transgene-free genome editing in wheat through transient expression of CRISPR/Cas9 DNA or RNA", Nature Communications, Aug. 25, 2016 (Aug. 25, 2016), p. 12617, vol. 7, XP055409394.

Barro et al., "Targeting of prolamins by RNAi in bread wheat: effectiveness of seven silencing-fragment combinations for obtaining lines devoid of coeliac disease epitopes from highly immunogenic gliadins", Plant Biotechnology Journal, No. 3, Mar. 24, 2016 (Mar. 24, 2016), p. 986-996, vol. 14, XP055305355.

Jouanin et al., "Food processing and breeding strategies for coeliac-safe and healthy wheat products", Food Research International, Apr. 26, 2017 (Apr. 26, 2017), p. 11-21, vol. 110, XP055497315.

Van De Wiel et al., "New traits in crops produced by genome editing techniques based on deletions", Plant Biotechnology Reports, Springer Japan, JP, Feb. 13, 2017 (Feb. 13, 2017), p. 1-8, vol. 11, No. 1, XP036195063.

Wang et al., "Genome-wide analysis of complex wheat gliadins, the dominant carriers of celiac disease epitopes", Scientific Reports, Mar. 16, 2017 (Mar. 16, 2017), pp. 1-14, vol. 7, XP055448141.

* cited by examiner

*Primary Examiner* — Weihua Fan
(74) *Attorney, Agent, or Firm* — Greer, Burns & Crain, Ltd.

(57) ABSTRACT

The present invention relates to methods for producing wheat lines that are low gliadin, low-gluten and transgene-free using genome editing. Also described are nucleic acid constructs and sgRNA molecules for use in genome editing, as well as genetically altered plants obtained by these methods.

23 Claims, 38 Drawing Sheets

Specification includes a Sequence Listing.

a

Figure 4 continued (a)
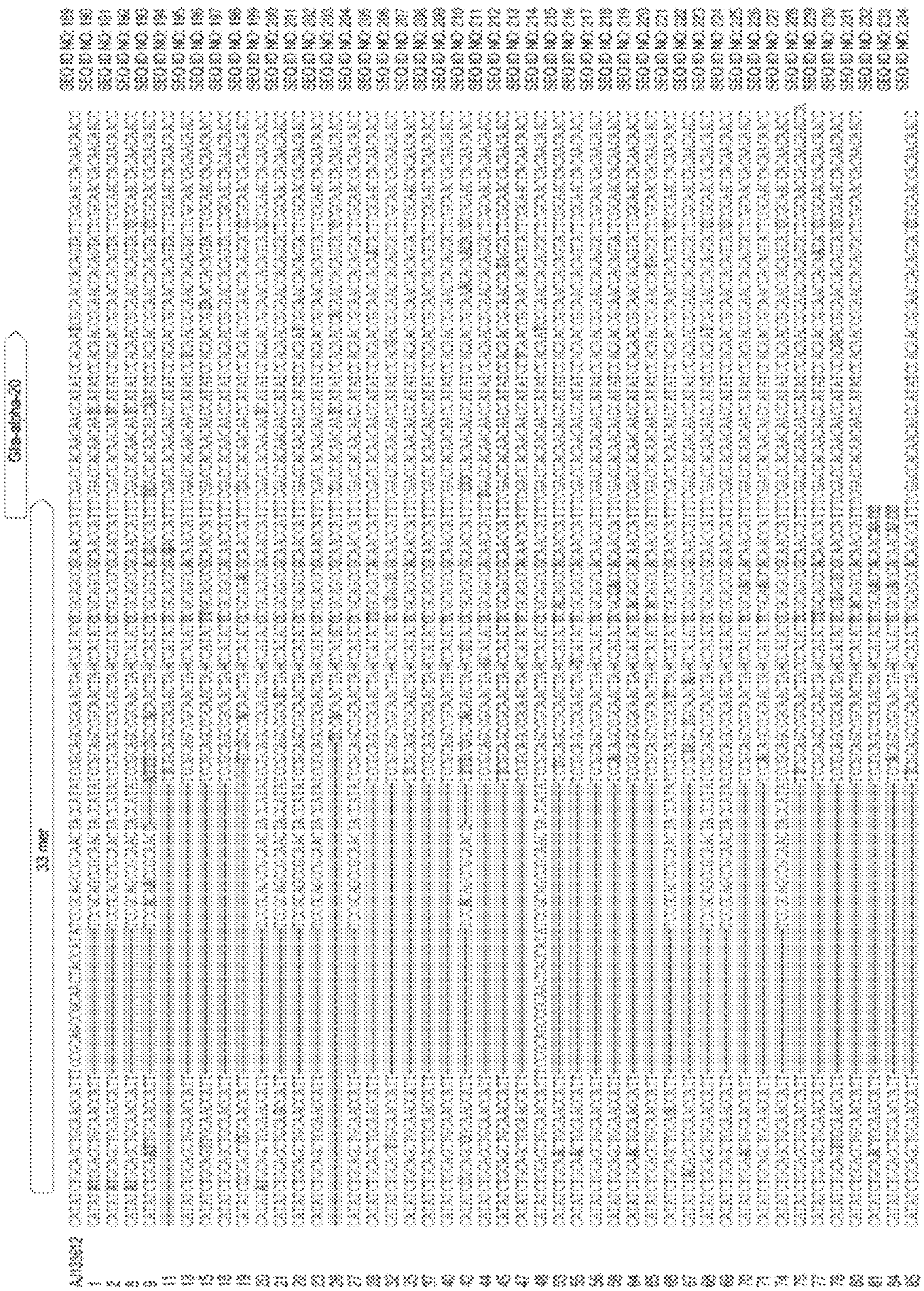

(b)

(b)

(c)

Figure 4 continued (c)
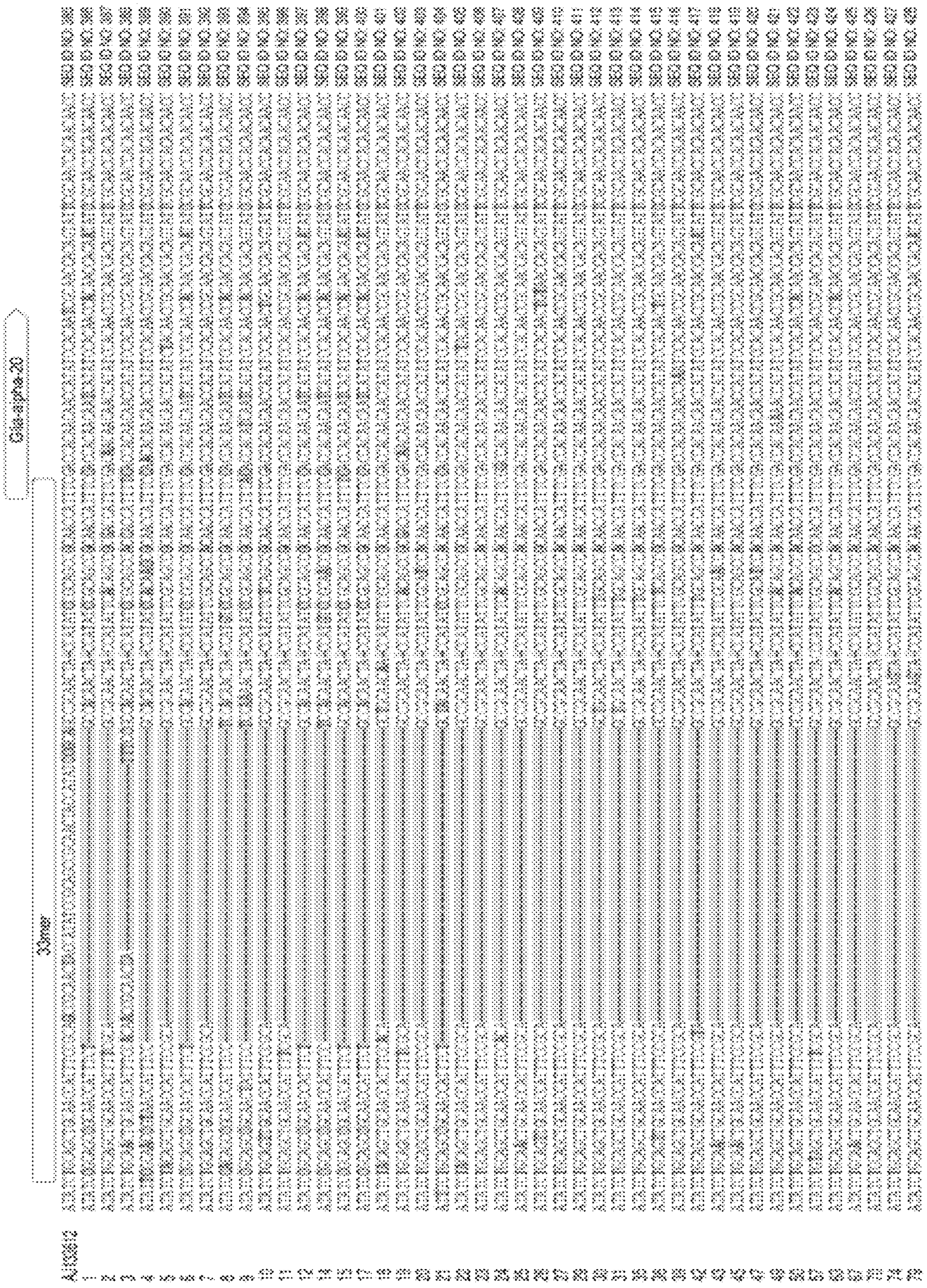

a
b
c
p31-43
PAM+sgAlpha-2
33mer
DQ2.5-glia-α3

Figure 12 a

SEQ ID NO: 573

BW208 wt, group 1

ATGAAGACCTTACTCATCCAAACAATCCTCGTGATGGCAATAACCATCGCCACCGCCAATATGCAGGTCGACCCTAGCGGCCAAGTACCATGG
CCACAACAACAACCATTCCCGCAGCCTCACCAACCATTCTCCCAGCAACCGCAACAAACATTTCCCCAACCCCAACAAACATTCCCCCATCAACC
ACAACAACAATTTTCCCAGCCTCAGCAACCACAACAACAATTTATCCAGCCCCAACAACCATTCCCCCAACAACCACAACAAACATATCCCCAGC
GACCACAACAACCATTCCCCCAGACTCAACAACCCCAACAACCATTTCCCAGTCCCAGCAACCACAACAACCTTTTCCCCAGCCCCAACAACAA
TTCCCGCAGCCCCAACAACCACAACAATCATTCCCCCAACAACAACCATCGTTGATTCAACAATCTCTACAACAACAGTTGAACCCATGCAAGAA
TTTCCTCTTGCAACAATGCAAACCTGTGTCCTTGGTGTCATCCCTCTGGTCAATGATCTTGCCACGAAGCGATTGCCAGGTGATGCGGCAACAA
TGTTGCCAACAACTAGCACAAATTCCTCAGCAACTCCAGTGTGCAGCCATCCATAGCATCGTGCATTCCATCATCATGCAGCAAGAACAACAAG
AACAACGACAGGGTGTGCAAATCCTGGTGCCACTGTCTCAACAGCAACAGGTAGGTCAAGGTACTCTCGTCCAAGGTCAGGGCATCATCCAAC
CTCAACAACCAGCTCAATTGGAGGTGATTAGGTCATTGGTGTTGCAAACTCTTGCAACCATGTGCAACGTGTATGT

SEQ ID NO: 574

BW208 wt, group 2

ATGAAGACCTTACTCATCCTAACAATCCTTGCGATGGCAACAACAATCGCCACTGCCAATATGCAGGTCGACCCTAGCAGCCGAGTACAATGG
CCACAAGAACAACCACCCCCCCAGTCCCAACAACCATTCTCCCAGCAACCACAACAAATATTTCCCCAACCCCAACAAACATTCCCCCATCAACC
ACAACAAGCATTTCTCCAACCTCAACAAACATTCCCCCGTCGACCACAACAACAATTTCCCCAGCCCCAGCAACCACAACAACCATTTCCCAGC
CCCAACAACCCCAACTACCATTTCCCCAACAACCACAACAACCATTCCCCCAGCCTCAACAACCCCAACAACCATTTCCCAGTCACAGCAACCA
CAACAACCTTTTCCCCAGCCCCAACAACAATTTCCGCAGCCCCAACAACCACAACAATCATTCCCCCAACAACAACAATGGATGATTCAGTCATT
TCTACAACAACAGATGAACCCCTGCAAGAATTTCCTCTTGCAGCAATGCAACCCTGTGTCATTGGTGTCATCTCTCGTGTCAATAATCTTGCCAC
GAAGTGATTGCCAGCTGATGCAGCAACAATGTTGCCAACAACTAGCACAAATTCCTCAACAACTCCAGTGCGCAGCCATCCACAACGTCGCGC
ATTCCATCATCATGCAGCAAGAACAACAACGAGGCGTGCAGATCCTGCGGCCACTATTTCAGCTCGCCCAGGGTCTGGGTATCATCCAACCTC
AACAACCAGCTCAATTGGAGGGGATCAGGTCATTGGTATTGAAAACTCTTCCAACCATGTGCAACGTGTATGT

SEQ ID NO: 575

BW208 wt, group 3

ATGAAGACCTTACTCATCCTGACAATCATTGCGGTGGCACTAACTACCACCACCGCCAATATACAGGTCGACCCTAGTGGCCAAGTACAATGGC
CACAACAACAACAACCATTCCCCCAGCCCCAACAACCACAACAAATTTTTCCCCAACCCCAACAAACATTCCCCCATCAACCACAACAAGCATTT
CCCCAACCCCAACAAACATTCCCCCATCAACCACAACAACAATTTCCCCAGCCCCAGCAACCACAACAACCATTTCCCAGCAACCACAACAACA
ATTTCCCCAGCCCCAACAACCACAACAACCATTTCCCAGCAACCACAACAACAATTTCCCCAGCCCCAACAACCACAACAACCATTTCCCAGC
CCCAACAACCCCAACAACCATTTCCCAACAACCACAACAACCATTCCCCCAGCCTCAACAACCCCAACAACCATTTCCCAGTTACAGCAACCA
CAACAACCTTTACCCCAGCCCCAACAACCGCAACAACCATTCCCCCAGCAACAACAACCATTGATTCAGCCATACCTACAACAACAGATGAACC
CCTGCAAGAATTACCTCTTGCAACAATGCAACCCTGTGTCATTGGTGTCATCCCTCGTGTCAATGATCTTGCCACGAAGTGATTGCAAGGTGAT
GCGGCAACAATGTTGCCAACAACTAGCACAGATTCCTCAGCAGCTCCAGTGCGCAGCCATCCATGGCGTCGTGCATTCCATCATCATGCAGCA
AGAACGACAACAACAACAACAACAACAACAAGGCATACAGATCATGCGGCCACTATTTCAGCTCGTCCAGGGTCAGGGCATCATCCAACCTCA
ACAACCAGCTCAATTGGAGGTGATCAGGTCATTGGTATTGGGAACTCTTCCAACCATGTGCAACGTGTATGT

SEQ ID NO: 576

BW208 wt, group 4

ATGAAGACCTTACTCATCCWAACAATCCTYGYGATGGCAATAACCATCGGCACCGCCAATATSCAGGTCGACCCTAGCRGCCAAGTACAATGG
CYACAACAACAACYAGTCCCMCAGCYYCAMCARCCATTMTCCCAGCAACCACAACAAACATTTCCCCRACCYCAACAAACATTCCCCCATCAAC
CACAACAACAAKTTYCCCAGCCTCAGCAACCACAACAACMATTTCTCCAGCCCCGACAACCATTCCCCCAACAACCACAACAACCATATCCCCA
GCAACCACAGCAACCGTTCCCCCAGACTCAACAACCCCAACAACCATTTCCCAGTCCAAGCAACCACAACAACCTTTTCCCCAGCCCCAACAAC
CGCAACAATCATTCCCCCAACAACAACCATCGTTGATTCAACAATCTCTACAACAACAGTTGAACCCATGCAAGAATTTCCTCTTGCAGCAATGC
AAACCTGTGTCCTTGGTGTCATCSCTCTGGTCAATCATCTTGCCACCAAGCGATTGCCAGGTGATGCGGCAACAATGTTGTCAACAACTAGCAC
AAATTCCTCAGCAACTCCAGTGTGCAGCCATCCATAGCGTCGTGCATTCCATCATCATGCAGCAAGAACAACAAGAACAACTACAGGGTGTGC
AAATCCTGGTGCCACTGTCTCAACAGCAACAAGTGGGTCAAGGTATTCTCGTCCAGGGTCAAGGCATCATCCAACCTCAACAACCAGCTCAATT
GGAGGTGATCAGGTCATTGGTGTTGCAAACTCTTCCAACCATGTGCAACGTGTATGT

SEQ ID NO: 577

BW208 wt, group 5

ATGAAGACCTTACTCATCCTGACAATCCTTGCGATGGCAATAACCATCGGCACCGCCAATATCCAGGTCGACCCTAGCGGCCAAGTACAATGG
CTACAACAACAACTAGTCCCCCAGCTCCAACAGCCATTATCCCAGCAACCACAACAAACATTTCCCCAACCTCAACAAACATTCCCCCATCAACC
ACAACAACAAGTTCCCCAGCCTCAGCAACCACAACAACCATTTCTCCAGCCCCAACAACCATTCCCCCAACAACCACAACAACCATTCCCCCAGA
CTCAACAACCACAACAACCATTTCCCAGCAACCACAACAACCATTTCCCAGACTCAACAACCCCAACAACCATTTCCCAACAACCACAACAA
CCATTCCCCCAGACTCAACAACCCCAACAACCATTTCCCAGCTCCAGCAACCACAACAACCTTTTCCCCAGCCCCAACAACAATTGCCGCAGCC
CCAACAACCGCAACAATCATTCCCCCAACAACAACGGCCATTCATTCAACCATCTCTACAACAACAGTTGAACCCATGCAAGAATATCCTCTTGC
AACAATGCAAACCTGCGTCATTGGTGTCATCCCTCTGGTCAATAATCTGGCCACAAAGCGATTGCCAAGTGATGCGGCAACAATGCTGCCAAC
AACTAGCACAGATTCCTCAACAGCTCCAGTGCGCAGCCATCCATAGCGTCGTGCATTCCATCATCATGCAGCAGCAGCAGCAACAACAACAAC
AACAAGGCATGCATATCTTTCTGCCACTATCTCAGCAGCAACAGGTGGGTCAAGGTTCTCTAGTCCAAGGCCAGGGCATCATCCAACCACAAC
AACCAGCTCAATTGGAGGCGATCAGATCATTGGTGTTGCAAACTCTTCCATCCATGTGCAACGTGTATGT (b)    T544, Group 1

[Sequence alignment showing SEQ ID NOs: 578-597 for T544 Group 1]

T544, Group 2

[Sequence alignment showing SEQ ID NOs: 598-601 for T544 Group 2, followed by additional sequences]

T544, Group 3

[Sequence alignment showing SEQ ID NOs: 602-604 for T544 Group 3, followed by additional sequences]

T544, Group 4

[Sequence alignment showing SEQ ID NOs: 605-609 for T544 Group 4]

Figure 13
a
Group 1
SEQ ID NO: 643
SEQ ID NO: 644
SEQ ID NO: 645
b
Group 2
SEQ ID NO: 646
SEQ ID NO: 647
SEQ ID NO: 648
SEQ ID NO: 649
SEQ ID NO: 650
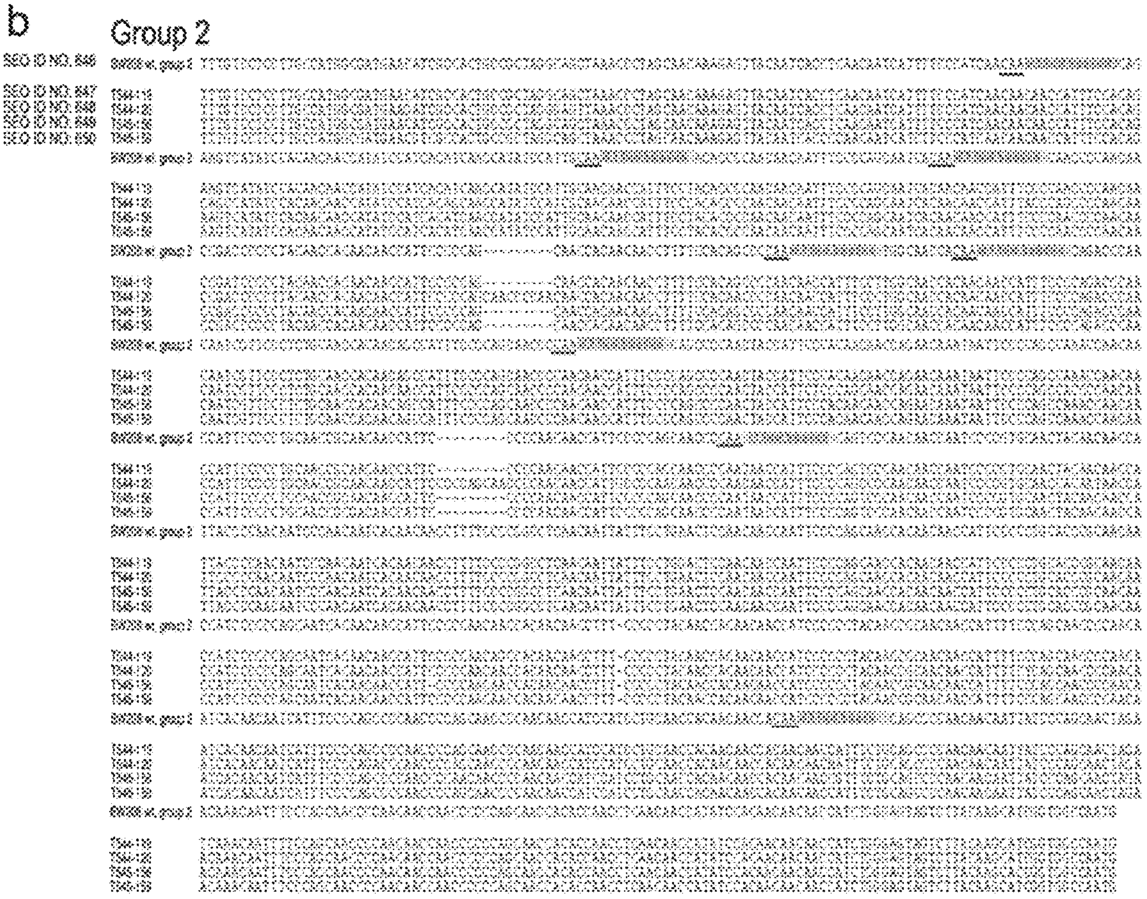

(c) Group 3

(c)(continued) Group 3

(d)

Group 4

Figure 14

| | | |
|---|---|---|
| BW208 wt (1) | AACCACCACAACAATT-CCCCCAACAACAATTTCCAATACCATACCCACCCCAGCAATCA | SEQ ID NO: 676 |
| BW208 wt (2) | AACCACCACAACAATT-CCCCCAACAACAATTTCCAATACCATACCCACCCCAACAATCA | SEQ ID NO: 677 |
| T544-16 | AACCACCACAACAATT-CCCCCAACAACAATTTCCAATACCATACCCACCCCAGCAATCA | SEQ ID NO: 678 |
| T544-25 | AACCACCACAACAATT-CCCCCAACAACAATTTCCAATACCATACCCACCCCAGCAATCA | SEQ ID NO: 679 |
| T544-26 | AACCACCACAACAATT-CCCCCAACAACAATTTCCAATACCATACCCACCCCAGCAATCA | SEQ ID NO: 680 |
| T544-30 | AACCACCACAACAATT-CCCCCAACAACAATTTCCAATACCATACCCACCCCAGCAATCA | SEQ ID NO: 681 |
| T545-40 | AACCACCACAACAATTCCCCCCAACAACAATTTCCAATACCATACCCACCCCAGCAATCA | SEQ ID NO: 682 |
| T545-41 | AACCACCACAACAATTCCCCCCAACAACAATTTCCAATACCATACCCACCCCAGCAATCA | SEQ ID NO: 683 |
| T545-42 | AACCACCACAACAATTCCCCCCAACAACAATTTCCAATACCATACCCACCCCAGCAATCA | SEQ ID NO: 684 |
| T545-45 | AACCACCACAACAATT-CCCCCAACAACAATTTCCAATACCATACCCACCCCAACAATCA | SEQ ID NO: 685 |
| T545-46 | AACCACCACAACAATT-CCCCCAACAACAATTTCCAATACCATACCCACCCCAGCAATCA | SEQ ID NO: 686 |
| T544-68 | AACCACCACAACAATT-CCCCCAACAACAATTTCCAATACCATACCCACCCCAGCAATCA | SEQ ID NO: 687 |
| T545-97 | AACCACCACAACAATT-CCCCCAACAACAATTTCCAATACCATACCCACCCCAACAATCA | SEQ ID NO: 688 |
| T544-115 | AACCACCACAACAATT-CCCCCAACAACAATTTCCAATACCATACCCACCCCAGCAATCA | SEQ ID NO: 689 |
| T544-116 | AACCACCACAACAATTCCCCCCAACAACAATTTCCAATACCATACCCACCCCTGCAATCA | SEQ ID NO: 690 |
| T544-125 | AGCAACCACAACAATT-TCTCCAACAACAATTTCCAATACCATACCCACCCCAGCAATCA | SEQ ID NO: 691 |
| T544-122 | A---ACCACAACAATT-CCCCCAACAACAATTTCCAATACCATACCCACCCCAGCAATCA | SEQ ID NO: 692 |
| T545-154 | AACCACCACAACAATT-CCCCCAACAACAATTTCCAATACCATACCCACCCCAGCAATCA | SEQ ID NO: 693 |
| T545-157 | AACCACCACAACAATT-CCCCCAACAACAATTTCCAATACCATACCCACCCCAGCAATCA | SEQ ID NO: 694 |
| T545-158 | AACCACCACAACAATT-CCCCCAACAACAATTTCCAATACCATACCCACCCCAGCAATCA | SEQ ID NO: 695 |
| T545-161 | AACCACCACAACAATT-CCCCCAACAACAATTTCCAATACCATACCCACCCCAGCAATCA | SEQ ID NO: 696 |

Figure 15 a

Prolamin off-target

| | No. of analyzed sequences | No. of off-target hits minimal sequence sgRNA+PAM* | |
|---|---|---|---|
| | | sgAlpha-1 | sgAlpha-2 |
| α-gliadins | 156 | 152 | 153 |
| γ-gliadins | 179 | 0 | 0 |
| ω-gliadins | 15 | 0 | 0 |
| HMW-glutenins | 40 | 0 | 0 |
| LMW-glutenins | 239 | 0 | 71 |

*up to one mismatch in the seed sequence + perfect PAM b

PAM sgAlpha-2 seed

SEQ ID NO: 697 LMW_BW208 wt CCCATCCAACAACAACCACAACCATTTCCACAACAGCCACCATGTTCACA

SEQ ID NO: 698 LMW_T544-1 CCCATCCAACAACAACCACAACCATTTCCACAACAGCCACCATGTTCACA
SEQ ID NO: 699 LMW_T544-2 CCGATCCAACAACAACCACAACCATTTCCACAACAGCCACCATGTTCACA
SEQ ID NO: 700 LMW_T544-3 CCCATCCAACAACAACCACACCAATTTCCACAACAGCAACCATGTTCACA
SEQ ID NO: 701 LMW_T544-5 CCCATCCAACAACAACCACAACCATTTCCACAACAGCCACCATGTTCACA
SEQ ID NO: 702 LMW_T544-6 CCCATCCAACAACAACCACACCAATTTCCACAACAGCAACCATGTTCACA
SEQ ID NO: 703 LMW_T544-7 CCCATCCAACAACAACCACAACCATTTCCACAACAGCCACCATGTTCACA
SEQ ID NO: 704 LMW_T544-9 CCCATCCAACAACAACCACAACCATTTCCACAACAGCCACCATGTTCACA
SEQ ID NO: 705 LMW_T544-11 CCCATCCAACAACAACCACACCAATTTCCACAACAGCAACCATGTTCACA
SEQ ID NO: 706 LMW_T544-12 CCCATCCAACAACAACCACAACCATTTCCACAACAGCCACCATGTTCACA
SEQ ID NO: 707 LMW_T544-70 CCCATCCAACAACAACCACAACCATTTCCACAACAGCCACCATGTTCACA
SEQ ID NO: 708 LMW_T544-72 CCTGTCCAACAACAACCACAACCATTTCCACAACAGCAACCATGTTCACA
SEQ ID NO: 709 LMW_T544-73 CCCATCCAACAACAACCACACCAATTTCCACAACAGCAACCATGTTCACA
SEQ ID NO: 710 LMW_T544-74 CCCATCCAACAACAACCACAACCATTTCCACAACAGCCACCATGTTCACA
SEQ ID NO: 711 LMW_T544-78 CCTGTCCAACAACAACCACAACCATTTCCACAACAGCAACCATGTTCACA
SEQ ID NO: 712 LMW_T544-79 CCCATCCAACAACAACCACAACCATTTCCACAACAGCCACCATGTTCACA
SEQ ID NO: 713 LMW_T544-80 CCCATCCAACAACAACCACACCAATTTCCACAACAGCAACCATGTTCACA c

Non-prolamin off-target

| sgRNA* | No. of off-target hits | Annotated genes | Description | No. of clones sequenced | No. of clones with mutations |
|---|---|---|---|---|---|
| sgAlpha-1 | 41 | Traes_4AL_4FF5B8837 | Alpha-gliadin pseudo gene | | |
| sgAlpha-2 | 50 | Traes_4AL_4FF5B8837 | Alpha-gliadin pseudo gene | NA | - |
| | | Traes_2AS_8FCC59363 | Uncharacterized | 24 | 0 |
| | | Traes_2AS_D659E88E9 | Uncharacterized | 28 | 0 |
| | | Traes_7BL_F621D9B9E | MADS box transcription factor | 30 | 0 |

* Perfect match seed sequence (12 nt) + PAM d

PAM sgAlpha-2 seed

SEQ ID NO: 714 2ASF8_BW208 wt CGCAGCCGCCGGCCATCCACAACCATTTCCATCCTCAGGACAGAGTCACG

SEQ ID NO: 715 2ASF8_T544-1 CGCAGCCGCCGGCCATCCACAACCATTTCCATCCTCAGGACAGAGTCACG
SEQ ID NO: 716 2ASF8_T544-25 CGCAGCCGCCGGCCATCCACAACCATTTCCATCCTCAGGACAGAGTCACG
SEQ ID NO: 717 2ASF8_T544-26 CGCAGCCGCCGGCCATCCACAACCATTTCCATCCTCAGGACAGAGTCACG
SEQ ID NO: 718 2ASF8_T544-27 CGCAGCCGCCGGCCATCCACAACCATTTCCATCCTCAGGACAGAGTCACG
SEQ ID NO: 719 2ASF8_T544-28 CGCAGCCGCCGGCCATCCACAACCATTTCCATCCTCAGGACAGAGTCACG
SEQ ID NO: 720 2ASF8_T544-112 CGCAGCCGCCGGCCATCCACAACCATTTCCATCCTCAGGACAGAGTCACG
SEQ ID NO: 721 2ASF8_T544-114 CGCAGCCGCCGGCCATCCACAACCATTTCCATCCTCAGGACAGAGTCACG e

PAM sgAlpha-2 seed

SEQ ID NO: 722 2ASD6_BW208 wt CGCAACCGCCGGCCTTCCACAACCATTTCCACCCTCAGGACAAAGCCACG

SEQ ID NO: 723 2ASD6_T544-1 CGCAACCGCCGGCCTTCCACAACCATTTCCACCCTCAGGACAAAGCCACG
SEQ ID NO: 724 2ASD6_T544-2 CGCAACCGCCGGCCTTCCACAACCATTTCCACCCTCAGGACAAAGCCACG
SEQ ID NO: 725 2ASD6_T544-30 CGCAACCGCCGGCCTTCCACAACCATTTCCACCCTCAGGACAAAGCCACG
SEQ ID NO: 726 2ASD6_T544-31 CGCAACCGCCGGCCTTCCACAACCATTTCCACCCTCAGGACAAAGCCACG
SEQ ID NO: 727 2ASD6_T544-35 CGCAACCGCCGGCCTTCCACAACCATTTCCACCCTCAGGACAAAGCCACG
SEQ ID NO: 728 2ASD6_T544-36 CGCAACCGCCGGCCTTCCACAACCATTTCCACCCTCAGGACAAAGCCACG
SEQ ID NO: 729 2ASD6_T544-37 CGCAACCGCCGGCCTTCCACAACCATTTCCACCCTCAGGACAAAGCCACG
SEQ ID NO: 730 2ASD6_T544-44 CGCAACCGCCGGCCTTCCACAACCATTTCCACCCTCAGGACAAAGCCACG
SEQ ID NO: 731 2ASD6_T544-49 CGCAACCGCCGGCCTTCCACAACCATTTCCACCCTCAGGACAAAGCCACG f

PAM sgAlpha-2 seed

SEQ ID NO: 732 7BL_BW208 ACCGGTTGAACAAAGCCCGCAACCATTTCCATATGGTTGCCCCAGTGTTC

SEQ ID NO: 733 7BL-T544-138 ACCGGTTGAACAAAGCCCGCAACCATTTCCATATGGTTGCCCCAGTGTTC
SEQ ID NO: 734 7BL-T544-139 ACCGGTTGAACAAAGCCCGCAACCATTTCCATATGGTTGCCCCAGTGTTC
SEQ ID NO: 735 7BL-T544-140 ACCGGTTGAACAAAGCCCGCAACCATTTCCATATGGTTGCCCCAGTGTTC
SEQ ID NO: 736 7BL-T544-141 ACTGGTTGAACAAAGCCCGCAACCATTTCCATATGGTTGCCCCAGTGTTC
SEQ ID NO: 737 7BL-T544-142 ACCGGTTGAACAAAGCCCGCAACCATTTCCATATGGTTGCCCCAGTGTTC
SEQ ID NO: 738 7BL-T544-143 ACCGGTTGAACAAAGCCCGCAACCATTTCCATATGGTTGCCCCAGTGTTC
SEQ ID NO: 739 7BL-T544-144 ACCGGTTGAACAAAGCCCGCAACCATTTCCATATGGTTGCCCCAGTGTTC
SEQ ID NO: 740 7BL-T544-145 ACCGGTTGAACAAAGCCCGCAACCATTTCCATATGGTTGCCCCAGTGTTC
SEQ ID NO: 741 7BL-T544-146 ACCGGTTGAACAAAGCCCGCAACCATTTCCATATGGTTGCCCCAGTGTTC
SEQ ID NO: 742 7BL-T544-147 ACCGGTTGAACAAGGCCCGCAACCATTTCCATATGGTTGCCCCAGTGTTC b

Figure 19

Supplementary Table 1. List and sequence of primers for PCR and Illumina sequencing

| | name | sequence (5'-3') | Description |
|---|---|---|---|
| SEQ ID NO: 744 | aGli900 F1 | GTTAGAGTTCCAGTGCCACAA | Forward primer for amplicon deep sequencing |
| SEQ ID NO: 745 | 33mer1R2_Ok | GGTTGTTGTGGTTGCGRATA | Reverse primer for amplicon deep sequencing |
| SEQ ID NO: 746 | BAR1F | GTCTGCACCATCGTCAACC | Forward primer for detection of *bar* gene |
| SEQ ID NO: 747 | BAR2R | GAAGTCCAGCTGCCAGAAAC | Reverse primer for detection of *bar* gene |
| SEQ ID NO: 748 | fJG218F | TAAGGTCCTCTCCGCCTACA | Forward primer for detection of Cas9 |
| SEQ ID NO: 749 | fJG218R | GGCGGTAAGGATCTGAGCTA | Reverse primer for detection of Cas9 |
| SEQ ID NO: 750 | M13 Reverse | TCACACAGGAAACAGCTATGAC | Forward primer for sequencing with pGEM®-T Easy Vector system |
| SEQ ID NO: 751 | M13 Forward | CGCCAGGGTTTTCCCAGTCACGAC | Reverse primer for sequencing with pGEM®-T Easy Vector system |
| SEQ ID NO: 752 | KanR_Fw | TTATGCCTCTTCCGACCATC | Forward primer for detection of kanamycin resistance gene |
| SEQ ID NO: 753 | KanR_Rv | ATTCCGACTCGTCCAACATC | Reverse primer for detection of kanamycin resistance gene |
| SEQ ID NO: 754 | PvUbi1_Fw | CGTCTCGCAAAATAGCACAA | Forward primer for detection of *Panicum virgatum L.* ubiquitin promoter |
| SEQ ID NO: 755 | PvUbi1_Rv | CATAATCGATCGAGGGGAGA | Reverse primer for detection of *Panicum virgatum L.* ubiquitin promoter |
| SEQ ID NO: 756 | STA_Fw | GCTGCGTATATGATGCGATG | Forward primer for detection of stability region from PVS1 plasmid |
| SEQ ID NO: 757 | STA_Rv | GACTCAAGAATGGGCAGCTC | Reverse primer for detection of stability region from PVS1 plasmid |
| SEQ ID NO: 758 | OCS_Fw | CCGGTTTCGGTTCATTCTAA | Forward primer for detection of octopine synthase polyA signal |
| SEQ ID NO: 759 | OCS_Rv | GTTGAATGGTGCCCGTAACT | Reverse primer for detection of octopine synthase polyA signal |
| | **Primers for detection of insertions in T1 and T2 plants (all with forward primer aGli900F1)** | | |
| SEQ ID NO: 760 | pJG001 | ATCGATCGTGGTGTCGAAGT | Reverse primer for detection of +158 bp insertion |
| SEQ ID NO: 761 | pJG002 | TGATGGAAATGGCGTTTTATTATTACA | Reverse primer for detection of +36 bp insertion |
| SEQ ID NO: 762 | pJG003 | ACTCAAAGGCGGTAATACGGT | Reverse primer for detection of +47 bp insertion |
| SEQ ID NO: 763 | pJG004 | TCGTAATCCCACACACTGGC | Reverse primer for detection of +51 bp insertion |
| SEQ ID NO: 764 | pJG005 | ACTAACAGAACATCGGCCCC | Reverse primer for detection of +83 bp insertion |
| | **Primers for cloning and sequencing of possible off-target** | | |
| SEQ ID NO: 765 | pJG006 | AGACCTTCCTCATCTTTGC | Forward primer for cloning of LMW for sequencing |
| SEQ ID NO: 766 | pJG007 | TGCTGCGATAATGGTGGTTG | Reverse primer for cloning of LMW for sequencing |
| SEQ ID NO: 767 | pJG008 | TGTTATAGTTCCAATATTTTTGCCAAT | Forward primer for detection of mutatin in Traes_7BL_F621D9B9E (MADS box protein) |
| SEQ ID NO: 768 | pJG009 | TTGAGCGATGCACAAAGC | Reverse primer for detection of mutatin in Traes_7BL_F621D9B9E (MADS box protein) |
| SEQ ID NO: 769 | pJG010 | CGCCTCGTATTTGATGTTCA | Forward primer for detection of mutatin in Traes_2AS_D659E88E9.1 (uncharacterized gene) |
| SEQ ID NO: 770 | pJG011 | GTAACAGCTTGCCGATGGAC | Reverse primer for detection of mutatin in Traes_2AS_D659E88E9.1 (uncharacterized gene) |
| SEQ ID NO: 771 | pJG012 | GCCTCCTTCCTGATGTTC | Forward primer for detection of mutatin in Traes_2AS_8FCC59363.1 (uncharacterized gene) |
| SEQ ID NO: 772 | pJG013 | TGCCGGTGTACACTTCTAGT | Reverse primer for detection of mutatin in Traes_2AS_8FCC59363.1 (uncharacterized gene) |
| SEQ ID NO: 773 | pJG014 | ATGAAGACCTTAYTCATCC | Forward primer for cloning of gamma-gliadins for sequencing |
| SEQ ID NO: 774 | pJG015 | ACATACACGTTGCACATG | Reverse primer for cloning of gamma-gliadins for sequencing |
| SEQ ID NO: 775 | pJG020 | TTTGTCCTCCTTGCCATGGC | Forward primer for cloning of omega-gliadins for sequencing |
| SEQ ID NO: 776 | | ATACTTATAACGTCGCTCCCA | |
| SEQ ID NO: 777 | pJG021 | GAT | Reverse primer for cloning of omega-gliadins for sequencing |
| SEQ ID NO: 778 | pJG022 | TCATTGGCCACCGATGCTT | Reverse primer for cloning of omega-gliadins for sequencing |

Figure 20

Supplementary Table 2. Illumina sequencing of alpha-gliadins in 18 T1 bread and durum wheat transgenic lines

| | | | | No. of reads | | | | Frequency (%) | | | |
|---|---|---|---|---|---|---|---|---|---|---|---|
| **Genotype** | **Construct** | **T0 plant** | **T1 plant** | **Filtered reads** | **Insertions** | **Deletions** | **Total indels** | **Insertions** | **Deletions** | **Total indels** | **Cas9** |
| **BW208 wt** | **NA** | **NA** | **NA** | **211,415** | **0** | **0** | **0** | **0** | **0** | **0** | **NA** |
| | sgAlpha-2 | 10 | T544 | 153,087 | 29,156 | 66,216 | 95,372 | 19.05 | 43.25 | 62.30 | + |
| | sgAlpha-2 | 10 | T545 | 163,004 | 20,564 | 101,903 | 122,467 | 12.62 | 62.52 | 75.13 | + |
| | sgAlpha-2 | 10 | T553 | 178,498 | 27,595 | 97,306 | 124,901 | 15.46 | 54.51 | 69.97 | + |
| | sgAlpha-1 | 14 | T567 | 105,983 | 0 | 1,058 | 1,058 | 0 | 1.00 | 1.00 | + |
| | sgAlpha-1 | 14 | T573 | 123,020 | 0 | 3,981 | 3,981 | 0 | 3.24 | 3.24 | + |
| **THA53 wt** | **NA** | **NA** | **NA** | **196,316** | **0** | **0** | **0** | **0** | **0** | **0** | **NA** |
| | sgAlpha-2 | 20 | V464 | 254,732 | 0 | 15,179 | 15,179 | 0 | 5.96 | 5.96 | - |
| | sgAlpha-2 | 20 | V465 | 126,518 | 112 | 9,835 | 9,947 | 0.09 | 7.77 | 7.86 | + |
| | sgAlpha-2 | 20 | V467 | 141,935 | 0 | 7,346 | 7,346 | 0 | 5.18 | 5.18 | + |
| | sgAlpha-2 | 20 | V468 | 279,894 | 0 | 14,450 | 14,450 | 0 | 5.16 | 5.16 | - |
| **DP wt** | **NA** | **NA** | **NA** | **258,339** | **0** | **0** | **0** | **0** | **0** | **0** | **NA** |
| | sgAlpha-2 | 2 | V525 | 192,189 | 457 | 22,040 | 22,497 | 0.24 | 11.47 | 11.71 | - |
| | sgAlpha-2 | 2 | V528 | 262,623 | 972 | 21,401 | 22,373 | 0.37 | 8.15 | 8.52 | - |
| | sgAlpha-2 | 2 | T666 | 144,275 | 0 | 15,722 | 15,722 | 0 | 10.90 | 10.90 | + |
| | sgAlpha-2 | 2 | T670 | 115,822 | 1,276 | 5,660 | 6,936 | 1.10 | 4.89 | 5.99 | - |
| | sgAlpha-2 | 5 | V520 | 264,423 | 0 | 39,047 | 39,047 | 0 | 14.77 | 14.77 | - |
| | sgAlpha-2 | 5 | T654 | 138,007 | 19,027 | 305 | 19,332 | 13.79 | 0.22 | 14.01 | + |
| | sgAlpha-2 | 32 | V511 | 152,378 | 0 | 2,414 | 2,414 | 0 | 1.58 | 1.58 | + |
| | sgAlpha-2 | 32 | V517 | 154,244 | 0 | 4,461 | 4,461 | 0 | 2.89 | 2.89 | + |

Figure 21

| Genotype | Construct | Line | Plant Id | ω-gliadins | α-gliadins | γ-gliadins | Total gliadin | HMW | LMW | Total glutenin | Prolamin | Gli/Glu |
|---|---|---|---|---|---|---|---|---|---|---|---|---|
| **BW208** | **NA** | **BW208** | **wt** | 14.6 | 37.4 | 36.6 | 88.6 | 10.3 | 23.1 | 33.4 | 122.0 | 2.734 |
| | sgAlpha-1 | B686-6-C1-1 | 44 | 14.7 | **12.2*** | **17.4*** | **44.3*** | **25.7*** | 26.9 | **52.7*** | **96.9*** | **0.850*** |
| | | B686-10-C3-1 | 14 | **21.6*** | **24.1*** | **27.8*** | 73.6 | **21.6*** | 25.5 | **47.2*** | 120.7 | **1.819*** |
| | | B686-10-C1-1 | 28 | **39.3*** | 27.8 | 33.1 | 100.3 | **26.6*** | 25.2 | **51.8*** | **152.1*** | 2.377 |
| | | B686-6-C1-2 | 52B | **36.2*** | 32.4 | 37.7 | 106.4 | **24.5*** | 21.8 | 46.2 | 152.6 | 2.323 |
| | sgAlpha-2 | B683-3-C2-1 | 12 | 23.1 | **12.7*** | **18.6*** | 54.4 | **31.3*** | 23.3 | 54.6 | 109.1 | **0.988*** |
| | | B683-3-C4-1 | 10 | 9.2 | **4.9*** | **2.1*** | **16.1*** | **41.9*** | **13.2*** | **55.1*** | **71.3*** | **0.313*** |
| | | B683-3-C6-1 | 48 | 17.3 | **13.6*** | **21.1*** | **52.0*** | **24.8*** | 31.5 | **56.4*** | 108.3 | **0.925*** |
| | | B683-3-C5-2 | 49 | 16.9 | **14.7*** | **24.1*** | **55.7*** | **24.2*** | **31.8*** | **56.0*** | 111.7 | **1.025*** |
| **THA53** | **NA** | **THA53** | **wt** | 13.2 | 38.4 | 35.3 | 86.9 | 12.4 | 23.5 | 35.9 | 122.8 | 2.598 |
| | sgAlpha-1 | B689-11-C1-1 | 77 | **35.0*** | **24.3*** | 42.2 | 101.5 | **26.7*** | 18.6 | 45.3 | 146.8 | 2.241 |
| | sgAlpha-2 | B677-6-C1-1 | 20 | 14.4 | **16.0*** | **19.2*** | **49.6*** | **24.0*** | 18.4 | 42.4 | **92.0*** | **1.199*** |
| | | B677-6-C3-1 | 6 | 14.9 | **7.8*** | **10.9*** | **33.6*** | **30.7*** | 30.8 | **61.5*** | 95.0 | **0.569*** |
| | | B680-1-C1-1 | 15 | 15.7 | **20.2*** | **21.0*** | **56.9*** | **30.1*** | 31.9 | **62.1*** | 118.9 | **1.058*** |
| | | B680-1-C1-3 | 17 | 11.9 | **9.9*** | **16.3*** | **38.0*** | **25.2*** | 30.6 | 55.7 | 93.8 | **0.681*** |
| | | B680-1-C2-1 | 21 | 15.6 | **14.0*** | **21.2*** | **50.9*** | **34.0*** | 22.0 | **55.9*** | 106.8 | **0.928*** |
| **DP** | **NA** | **DP** | **wt** | 8.3 | 35.2 | 33.0 | 76.5 | 5.6 | 27.0 | 32.6 | 109.1 | 2.423 |
| | sgAlpha-2 | B680-5-C1-1 | 32 | 6.9 | **9.8*** | **7.7*** | **24.4*** | **9.5*** | **17.8*** | 27.3 | **51.7*** | **0.899*** |
| | | B681-2-C1-1 | 5 | 8.4 | **10.4*** | **13.0*** | **31.9*** | **11.1*** | 20.6 | 31.7 | **63.7*** | **1.200*** |
| | | B681-2-C1-2 | 2 | 6.3 | **8.4*** | **9.4*** | **24.2*** | **9.6*** | 24.4 | 34.0 | **58.2*** | **0.729*** |
| | | B681-5-C1-1 | 53 | 7.8 | **15.2*** | **10.7*** | **33.7*** | 9.6 | **39.7*** | **49.3*** | **82.9*** | **0.695*** |

Figure 22

| | | | | | No. of reads | | | | Frequency (%) | | | |
|---|---|---|---|---|---|---|---|---|---|---|---|---|
| Genotype | Construct | T0 plant | T1 plant | T2 plant | Filtered reads | Insertions | Deletions | Total indels | Insertions | Deletions | Total indels | Cas9 |
| **BW208 wt** | **NA** | **NA** | **NA** | **NA** | **244,228** | **0** | **0** | **0** | **0.00** | **0.00** | **0.00** | **NA** |
| | sgAlpha-2 | 10 | T544 | V601 | 247,674 | 18,350 | 145,801 | 164,151 | 7.41 | 58.87 | 66.28 | - |
| | sgAlpha-2 | 10 | T544 | V603 | 213,965 | 19,471 | 123,189 | 142,660 | 9.10 | 57.57 | 66.67 | - |
| | sgAlpha-2 | 10 | T545 | V723 | 173,544 | 8,817 | 106,803 | 115,620 | 5.08 | 61.54 | 66.62 | + |
| | sgAlpha-2 | 10 | T545 | V726 | 218,717 | 11,200 | 131,426 | 142,626 | 5.12 | 60.09 | 65.21 | + |
| | sgAlpha-2 | 10 | T553 | V657 | 232,478 | 5,494 | 140,636 | 146,130 | 2.36 | 60.49 | 62.86 | - |
| | sgAlpha-2 | 10 | T553 | V660 | 281,734 | 5,516 | 177,520 | 183,036 | 1.96 | 63.01 | 64.97 | - |
| | sgAlpha-2 | 10 | T549 | V581 | 252,645 | 5,089 | 137,775 | 142,864 | 2.01 | 54.53 | 56.55 | - |
| | sgAlpha-2 | 12 | T557 | V701 | 292,782 | 0 | 2,545 | 2,545 | 0.00 | 0.87 | 0.87 | + |
| | sgAlpha-2 | 12 | T557 | V704 | 172,220 | 27 | 7,023 | 7,050 | 0.02 | 4.08 | 4.09 | - |
| | sgAlpha-2 | 12 | T557 | V705 | 231,067 | 0 | 1,761 | 1,761 | 0.00 | 0.76 | 0.76 | - |
| | sgAlpha-2 | 12 | T559 | V733 | 223,210 | 0 | 902 | 902 | 0.00 | 0.40 | 0.40 | + |
| | sgAlpha-2 | 12 | T559 | V738 | 219,081 | 0 | 997 | 997 | 0.00 | 0.46 | 0.46 | + |
| | sgAlpha-2 | 12 | T559 | V739 | 197,923 | 0 | 824 | 824 | 0.00 | 0.42 | 0.42 | - |
| | sgAlpha-2 | 12 | T559 | V740 | 218,499 | 0 | 851 | 851 | 0.00 | 0.39 | 0.39 | - |
| | sgAlpha-1 | 14 | T567 | V631 | 122,997 | 0 | 2,892 | 2,896 | 0.00 | 2.35 | 2.35 | + |
| | sgAlpha-1 | 14 | T567 | V634 | 118,898 | 246 | 4,427 | 4,673 | 0.21 | 3.72 | 3.93 | + |
| | sgAlpha-1 | 14 | T573 | V641 | 157,236 | 61 | 1,958 | 2,019 | 0.04 | 1.25 | 1.28 | + |
| | sgAlpha-1 | 14 | T573 | V644 | 181,483 | 128 | 1,808 | 1,936 | 0.07 | 1.00 | 1.07 | + |
| **THA53 wt** | **NA** | **NA** | **NA** | **NA** | **196,316** | **0** | **0** | **0** | **0.00** | **0.00** | **0.00** | **NA** |
| | sgAlpha-2 | 6 | T450 | V791 | 215,380 | 0 | 2,841 | 2,841 | 0.00 | 1.32 | 1.32 | + |
| **DP wt** | **NA** | **NA** | **NA** | **NA** | **380,497** | **0** | **0** | **0** | **0.00** | **0.00** | **0.00** | **NA** |
| | sgAlpha-2 | 2 | T666 | V773 | 124,504 | 0 | 29,778 | 29,778 | 0.00 | 23.92 | 23.92 | + |
| | sgAlpha-2 | 2 | T666 | V775 | 248,952 | 0 | 43,119 | 43,119 | 0.00 | 17.32 | 17.32 | - |
| | sgAlpha-2 | 2 | T666 | V778 | 157,464 | 0 | 37,633 | 37,633 | 0.00 | 23.90 | 23.90 | - |
| | sgAlpha-2 | 2 | T666 | V780 | 270,513 | 0 | 27,929 | 27,929 | 0.00 | 10.32 | 10.32 | - |
| | sgAlpha-2 | 2 | T670 | V752 | 152,753 | 1,591 | 7,000 | 8,591 | 1.04 | 4.58 | 5.62 | - |
| | sgAlpha-2 | 2 | T670 | V756 | 232,321 | 2,247 | 11,119 | 13,366 | 0.97 | 4.79 | 5.75 | - |
| | sgAlpha-2 | 2 | T670 | V759 | 182,702 | 2,243 | 9,106 | 11,349 | 1.23 | 4.98 | 6.21 | - |
| | sgAlpha-2 | 5 | T654 | V768 | 183,188 | 16,688 | 4,462 | 21,150 | 9.11 | 2.44 | 11.55 | + |
| | sgAlpha-2 | 5 | V520 | X458 | 167,940 | 0 | 20,201 | 20,201 | 0.00 | 12.03 | 12.03 | - |
| | sgAlpha-2 | 5 | V520 | X459 | 196,867 | 0 | 22,389 | 22,389 | 0.00 | 11.37 | 11.37 | - |

Figure 23

| Genotype | Construct | T0 plant id | T1 plant | ω-gliadins | α-gliadins | γ-gliadins | Total gliadins | HMW | LMW | Total glutenins | Prolamins | Gli/Glu |
|---|---|---|---|---|---|---|---|---|---|---|---|---|
| **BW208** | NA | **wt** | **wt** | 14.3 | 35.2 | 37.7 | 87.2 | 10.1 | 22.6 | 32.6 | 119.9 | 2.702 |
| | sgAlpha-1 | 14 | T566 | **30.9*** | **14.5*** | **26.4*** | **71.9*** | 22.2 | 22.0 | 44.1 | 116.0 | **1.633*** |
| | | | T567 | **31.4*** | **13.6*** | **26.6*** | **71.6*** | **34.4*** | 27.9 | **62.2*** | 133.8 | **1.276*** |
| | | | T571 | **29.8*** | **17.5*** | **27.0*** | **74.3*** | **38.2*** | 27.9 | **66.1*** | **140.4*** | **1.156*** |
| | | | T572 | **35.1*** | **16.5*** | **32.5*** | 84.1 | **44.4*** | 28.9 | **73.3*** | **157.4*** | **1.154*** |
| | | | T573 | **37.7*** | **13.8*** | **26.1*** | 77.6 | **33.6*** | 25.2 | **58.8*** | 136.4 | **1.327*** |
| | sgAlpha-2 | 10 | T544 | 13.6 | **4.1*** | **6.3*** | **24.1*** | 19.6 | **9.1*** | 28.6 | **52.7*** | **0.859*** |
| | | | T545 | 13.5 | **4.5*** | **4.2*** | **22.2*** | **21.8*** | **6.8*** | 28.6 | **50.8*** | **0.786*** |
| | | | T546 | 14.0 | **3.6*** | **4.4*** | **22.0*** | **24.4*** | **10.7*** | 35.2 | **57.2*** | **0.641*** |
| | | | T547 | 15.4 | **4.7*** | **6.0*** | **26.1*** | **46.3*** | **11.7*** | **57.9*** | **84.0*** | **0.451*** |
| | | | T548 | 11.5 | **3.4*** | **3.6*** | **18.5*** | **32.1*** | **6.5*** | 38.6 | **57.1*** | **0.484*** |
| | | | T549 | 16.5 | **5.8*** | **6.5*** | **28.8*** | **37.2*** | **12.2*** | **49.3*** | **78.2*** | **0.647*** |
| | | | T550 | 13.0 | **2.4*** | **4.3*** | **19.6*** | **23.7*** | **9.5*** | 33.2 | **52.8*** | **0.599*** |
| | | | T551 | 16.3 | **6.6*** | **6.4*** | **29.2*** | **53.9*** | **13.5*** | **67.4*** | **96.6*** | **0.445*** |
| | | | T552 | 13.0 | **4.4*** | **3.9*** | **21.2*** | **38.6*** | **9.3*** | 47.9 | **69.1*** | **0.473*** |
| | | | T553 | 17.9 | **5.9*** | **5.6*** | **29.4*** | **23.3*** | **7.6*** | 30.9 | **60.2*** | **0.956*** |
| | | 12 | T558 | 17.0 | **8.1*** | **13.6*** | **38.6*** | **31.5*** | 20.5 | **52.0*** | **90.7*** | **0.849*** |
| | | | T559 | 17.1 | **12.3*** | **21.9*** | **51.9*** | **31.2*** | 25.3 | **56.5*** | 108.4 | **0.931*** |
| | | | T561 | **20.6*** | **8.6*** | **15.0*** | **44.3*** | **25.3*** | 10.8 | 36.0 | **80.3*** | **1.305*** |
| **THA53** | NA | **wt** | **wt** | 14.5 | 34.1 | 34.9 | 83.5 | 14.0 | 25.8 | 39.8 | 123.3 | 2.124 |
| | sgAlpha-2 | 6 | T450 | **18.3*** | **11.2*** | **24.1*** | **53.5*** | 18.6 | **18.1*** | 36.7 | **90.1*** | **1.470*** |
| | | | T454 | 16.2 | **13.1*** | **25.2*** | **54.5*** | **42.6*** | 27.9 | **70.5*** | 125.0 | **0.795*** |
| | | | T455 | **19.5*** | **10.9*** | **24.9*** | **55.3*** | **22.9*** | **18.8*** | 41.7 | **97.0*** | **1.337*** |
| **DP** | NA | **wt** | **wt** | 11.0 | 31.5 | 33.6 | 76.0 | 6.4 | 29.7 | 36.1 | 112.0 | 2.170 |
| | Alpha-2 | 5 | T654 | **18.9*** | **20.6*** | 36.5 | 76.0 | **21.5*** | 40.2 | **61.7*** | 121.9 | **1.417*** |
| | | 2 | T666 | **17.8*** | **11.2*** | 30.5 | **59.5*** | **30.1*** | 31.8 | **61.8*** | 109.3 | **0.799*** |
| | | | T668 | 13.1 | **5.9*** | **23.8*** | **42.9*** | **30.5*** | 28.7 | **59.2*** | 108.2 | **0.850*** |
| | | | T670 | **25.1*** | **8.6*** | 40.1 | 73.8 | **17.5*** | 34.2 | **51.7*** | 107.8 | **1.110*** |

Figure 24

| Genotype | Construct | T0 plant id | T1 plant | ω-gliadins | α-gliadins | γ-gliadins | Total gliadins | HMW | LMW | Total glutenins | Prolamins | Gli/Glu |
|---|---|---|---|---|---|---|---|---|---|---|---|---|
| BW208 | NA | wt | wt | 12.9 | 38.0 | 30.4 | 81.3 | 15.6 | 29.3 | 44.9 | 126.2 | 1.809 |
| | sgAlpha-1 | 14 | T567 | 18.3* | 15.0* | 24.4* | 57.7* | 28.9* | 29.7 | 58.5 | 116.2 | 0.985* |
| | | | T573 | 19.0* | 14.9* | 23.3* | 57.2* | 35.9* | 34.6 | 70.5* | 127.8 | 0.810* |
| | sgAlpha-2 | 10 | T544 | 8.8* | 6.1* | 4.6* | 19.6* | 20.9 | 13.5* | 34.4 | 54.0 | 0.568* |
| | | | T545 | 9.9 | 5.5* | 3.6* | 19.0* | 26.2* | 11.3* | 37.5 | 56.6 | 0.507* |
| | | | T546 | 7.2* | 3.9* | 2.6* | 13.5* | 20.3 | 7.7* | 28.0 | 41.6 | 0.482* |
| | | | T549 | 11.2 | 6.8* | 6.4* | 24.3* | 34.1* | 13.2* | 47.4 | 71.7 | 0.513* |
| | | | T550 | 10.7 | 6.5* | 4.9* | 22.1* | 35.7* | 12.6* | 48.4 | 70.4 | 0.456* |
| | | | T553 | 12.6 | 6.9* | 5.7* | 25.3* | 38.9* | 13.2* | 52.1 | 77.4 | 0.485* |
| | | 12 | T558 | 15.9 | 10.4* | 11.9* | 38.3* | 41.2* | 24.4 | 65.6* | 103.9 | 0.583* |
| | | | T559 | 17.8 | 27.0* | 23.4* | 68.2* | 32.4* | 34.5 | 66.8* | 135.0 | 1.019* |
| | | | T561 | 15.6 | 10.1* | 11.2* | 36.9* | 33.1* | 17.7 | 50.9 | 87.8 | 0.725* |
| THA53 | NA | wt | wt | 11.8 | 42.9 | 32.3 | 86.9 | 17.7 | 37.0 | 54.7 | 141.6 | 1.649 |
| | sgAlpha-2 | 6 | T450 | 13.9 | 16.7* | 20.8* | 51.5* | 28.7* | 19.0 | 47.7 | 99.2* | 1.082 |
| | | | T455 | 12.6 | 11.9* | 17.8* | 42.3* | 29.8* | 23.6 | 53.3 | 95.6* | 0.793* |
| DP | NA | wt | wt | 7.4 | 35.5 | 26.8 | 69.6 | 8.9 | 42.9 | 51.8 | 121.4 | 1.370 |
| | Alpha-2 | 5 | T654 | 11.5* | 18.2* | 25.8 | 55.5* | 20.3* | 30.7 | 51.0 | 106.5* | 1.089 |
| | | 2 | T666 | 7.9 | 6.4* | 14.1* | 28.4* | 23.4* | 25.7* | 49.1 | 77.5* | 0.579* |
| | | | T670 | 12.0* | 8.1* | 28.4 | 48.5* | 17.7* | 39.9 | 57.6 | 106.0* | 0.842* |

TARGETING OF GLUTEN BY GENOME EDITING

CROSS-REFERENCE TO RELATED APPLICATIONS

This application is the U.S. National phase application corresponding to PCT/EP2018/064791 which was assigned an international filing date of Jun. 5, 2018 and associated with publication WO 2018/224508 A1 and which claims priority to EP 17382335.2 filed on Jun. 5, 2017, the disclosures of which are expressly incorporated herein by reference.

FIELD OF THE INVENTION

The present invention relates to methods for producing wheat lines that are low gliadin, low-gluten and transgene-free using genome editing. Also described are nucleic acid constructs and sgRNA molecules for use in genome editing, as well as genetically altered plants obtained by these methods.

BACKGROUND OF THE INVENTION

Cereal grains contain about 10-15% (dry weight) of protein, from which gluten is the most important fraction as it is the major determinant of the technological properties of baking cereals. However, gluten is not a single protein but a complex mix of proteins, which are deposited in the starchy endosperm during grain development. Gluten proteins are divided into two major fractions: the gliadins and the glutenins, which are different in terms of structure and functionality. In turn, gliadins are formed by three different fractions/types; ω-, γ-, and α gliadins (the wheat a gliadins, are sometimes also referred to as α/β gliadins based on their separation by acid electrophoresis. However, both α and β gliadins have a very similar primary structure and for these reasons are currently considered a single gliadin type (α/β type). Therefore, the terms α-gliadins and α/β-gliadins are interchangeable). The glutenins comprise two fractions; the high molecular weight (HMW) and the low molecular weight (LMW) subunits. The gliadins are generally present as monomers and contribute extensibility to wheat flour dough. The glutenins contribute elasticity to dough and form large polymers linked by disulphide bonds.

These proteins make up a complex mixture that in a typical bread wheat cultivar may be comprised of up to 45 different gliadins, 7 to 16 LMW glutenin subunits, and 3 to 6 HMW glutenin subunits. Gliadins and glutenins are not present at the same amount in the grain of cereals, and their proportions can vary within a broad range depending on both genotype (variety) and growing conditions (soil, climate, fertilisation, etc.). The ratio of gliadins to glutenins was examined in a range of cereals (Wieser and Koehler, 2009), and hexaploid common wheat showed the lowest ratio (1.5-3.1), followed by durum wheat (3.1-3.4), emmer wheat (3.5-7.6) and einkorn wheat (4.0-13.9).

In addition to their unique viscoelastic properties, gluten proteins are responsible for triggering certain pathologies in susceptible individuals: i) coeliac disease (CD), which affects both children and adults throughout the world at various frequencies (from 0.1% to >2.8%) (Mustalahti et al., 2010; Abadie et al., 2011), and ii) non-coeliac gluten sensitivity (NCGS), a newly-recognised pathology of intolerance to gluten (Sapone et al., 2011) with an estimated prevalence of 6% for the USA population. At present the only treatment available for these pathologies is a complete gluten-free diet for life.

However, gliadins and glutenins do not contribute equally to CD, and gliadins are indubitably the main toxic component of gluten since most (DQ2 or DQ8)-specific CD4+ T lymphocytes obtained from small intestinal biopsies from coeliac patients seem to recognize this fraction (Arentz Hansen et al., 2002). In the immune epitope database (IEDB) (http://www.iedb.org/) 190 T-lymphocytes stimulating epitopes related to CD can be found. Of these, 180 (95%) map to gliadins while only 10 (5%) map to glutenins.

However, not all gliadin epitopes are equally important in triggering CD. The α-gliadin family contain the 33-mer peptide, present in the N-terminal repetitive region, with six overlapping copies of three different DQ2-restricted T-cell epitopes with high stimulatory properties and highly resistant to human intestinal proteases (Shan et al., 2002; Tye-Din et al., 2010). The α-gliadins also contain the peptide p31-43, which has been reported to induce mucosal damage via a non-T-cell-dependent pathway (innate response) (Maiuri et al., 2003; Di Sabatino and Corazza, 2009). Moreover, an additional DQ2-restricted epitope (DQ2.5-glia-α3) which partially overlaps with 33-mer peptide (Vader et al., 2002) is present in α-2-gliadins. A DQ8-restricted epitope (DQ8-glia-α1) located on the C-terminal region of α-gliadin is also present in the α-gliadins (Van de Wal Y et al., 1998).

Tye-Din et al. (Tye-Din et al., 2010) comprehensively assessed the potentially toxic peptides contained within wheat, but also barley, and rye, and identified which ones stimulate T-cells from coeliac disease patients. They found that the 33-mer peptide from wheat α-gliadin was highly stimulatory, and another peptide (QPFPQPEQPFPW, SEQ ID NO: 779) from ω-gliadin/C-hordein was immunodominant after eating wheat, barley and rye. These two peptides present in wheat, plus another from barley, can elicit 90% of the immunogenic response induced by wheat, barley and rye (Tye-Din et al., 2010). These findings showed that the immunotoxicity of gluten could be reduced to three highly immunogenic peptides, which make the development of varieties with low-toxic epitopes more feasible.

However, traditional mutagenesis and plant breeding have been tried and have failed to obtain low immunogenic wheat varieties, and while targeted genome editing is potentially a very powerful technique, it is complicated by the complex polyploid genome of wheat. To our knowledge, the only studies that have achieved a strong down-regulation of α-gliadins and other reactive gliadins have been made using RNAi. However, the final products are genetically altered organisms (GMOs) and fall under the current regulation for transgenic crops in most countries. Consequently, commercialisation of these RNAi wheat lines becomes difficult due to the associated costs of regulation plus the publics' rejection of traditional GM crops.

There therefore exists a need to produce low-gluten and preferably transgene-free wheat lines that can be used to produce low gluten foodstuffs for celiac patients and other consumers. The present invention addresses this need.

SUMMARY OF THE INVENTION

The inventors have successfully undertaken genome editing of hexaploid wheat to produce wheat lines that are low-gliadin and therefore low-gluten, as well as transgene-free. These wheat lines described herein produce an unprecedented advantage and the resultant lines could be used to produce low gluten foodstuffs and serve as source material in plant breeding programs to introgress this trait into elite wheat varieties or to serve as source material for a new round of genome editing to obtain gliadin free wheat. In one embodiment, the inventors have designed a number of constructs for genome editing that target a conserved region in the N-terminal region of α-gliadins, and adjacent to the coding sequence for three coeliac disease related epitopes, the p31-43, 33-mer, and DQ2.5-glia-α3 in the α-gliadin genes. Twenty-one (15 bread wheat and 6 durum wheat) mutant lines were generated, all showing a strong reduction in α-gliadin content as well as other groups of gliadins. High-throughput sequencing demonstrated the efficiency of the CRISPR/Cas9 or CRISPR/Cpf1 system to produce mutations in the α-gliadin gene family. Up to 35 different genes were mutated in one of the lines of the 45 different genes identified in the wild type, while immunoreactivity was reduced by ~6-fold as revealed in the R5 and G12 ELISA tests. Importantly, no off-target mutations have been detected in any of the potential targets. In a further embodiment, the inventors have also designed a number of constructs for genome editing that similarly target conserved regions in the gamma and omega-gliadin genes.

In one aspect, the invention relates to a nucleic acid construct comprising a nucleic acid sequence encoding at least one DNA-binding domain, wherein said DNA-binding domain can bind to a target sequence in one of the alpha-, gamma- and/or omega gliadin genes, wherein said target sequence is selected from SEQ ID Nos 1 to 24, 790 and/or SEQ ID Nos 792 to 803.

In one embodiment, the nucleic acid sequence encodes at least one protospacer element, wherein the sequence of the at least one protospacer element is selected from SEQ ID Nos 25 to 48 and/or SEQ ID Nos 807 to 818 or a variant thereof (as defined herein), preferably a sequence that is at least 90% identical to a sequence defined in SEQ ID Nos 25 to 48 and/or SEQ ID Nos 807 to 818.

In a further embodiment, the construct comprises at least one sequence selected from SEQ ID Nos 25 to 30, 805 or SEQ ID Nos 807 to 811 or a variant thereof (as defined herein), preferably a sequence that is at least 90% identical thereto. In another embodiment, the construct comprises at least one, preferably all, of the sequences selected from SEQ ID Nos 37 to 42 or a variant thereof (as defined herein), preferably a sequence that is at least 90% identical thereto, or at least one sequence and preferably all, of the sequences selected from SEQ ID Nos 43 to 48 or a variant thereof (as defined herein), preferably a sequence that is at least 90% identical thereto. Alternatively the construct comprises at least one sequence selected from SEQ ID Nos 815 to 818. In a further alternative embodiment, the construct comprises at least one sequence selected from SEQ ID Nos 31 to 36 or a variant thereof (as defined herein), preferably a sequence that is at least 90% identical thereto. Alternatively the construct comprises at least one sequence selected from SEQ ID Nos 812 to 814.

In one embodiment, the construct comprises or consists of at least one protospacer element, wherein the protospacer element targets an alpha-gliadin target sequence and wherein the sequence of the protospacer element is selected from SEQ ID NO: 807 to 811 and/or the the protospacer element targets an omega-gliadin target sequence and wherein the sequence of the protospacer element is selected from SEQ ID NO: 812 to 814 and/or the protospacer element targets an gamma-gliadin target sequence and wherein the sequence of the protospacer element is selected from SEQ ID NO: 815 to 818 and wherein optionally, the construct further comprises a CRISPR enzyme, as described in further detail below, and wherein the CRISPR enzyme is Cpf1.

In a further embodiment, the construct further comprises a nucleic acid sequence encoding a CRISPR RNA (crRNA) sequence, wherein said crRNA sequence comprises the protospacer element sequence and additional nucleotides. Preferably, said additional nucleotides comprise or consist of a sequence defined in SEQ ID NO: 49 or a variant thereof (as defined herein), preferably a sequence that is at least 90% identical thereto.

In a further embodiment, the construct further comprises a nucleic acid sequence encoding a transactivating RNA (tracrRNA). Preferably said sequence comprises or consists of SEQ ID No. 50 or a variant thereof (as defined herein), preferably a sequence that is at least 90% identical thereto.

In a more preferred embodiment, the construct encodes at least one single-guide RNA (sgRNA), wherein said sgRNA comprises the crRNA sequence and the tracrRNA sequence, wherein the sgRNA has a sequence selected from SEQ ID NO: 51 to 74 or a variant thereof (as defined herein), preferably a sequence that is at least 90% identical thereto.

In one embodiment, the construct is operably linked to a promoter. Preferably, the promoter is a constitutive promoter.

In another embodiment, the nucleic acid construct further comprises a nucleic acid sequence encoding a CRISPR enzyme. Preferably, the CRISPR enzyme is a Cas protein. More preferably, the Cas protein is Cas9 or a functional variant thereof. Alternatively the CRISPR enzyme is Cpf1 or a variant thereof.

In an alternative embodiment, the nucleic acid construct encodes a TAL effector. Preferably, the nucleic acid construct further comprises a sequence encoding an endonuclease or DNA-cleavage domain thereof. More preferably, the endonuclease is FokI.

In another aspect of the invention there is provided a single guide (sg) RNA molecule wherein said sgRNA comprises a crRNA sequence and a tracrRNA sequence, wherein the crRNA sequence can bind to at least one sequence selected from SEQ ID Nos 1 to 24, 790 and 792 to 803 or a variant thereof (as defined herein), preferably a sequence that is at least 90% identical thereto. Preferably, the sequence of the sgRNA molecule is selected from SEQ ID NO: 75 to 99 or a variant thereof (as defined herein), preferably a sequence that is at least 90% identical thereto. More preferably, the sgRNA molecule targets the alpha-gliadin gene and has a sequence selected from SEQ ID NO: 75 to 80 or a variant thereof (as defined herein), preferably a sequence that is at least 90% identical thereto, or wherein the sgRNA molecule targets the omega gliadin gene and has a sequence selected from SEQ ID NO: 81 to 86 or a variant thereof (as defined herein), preferably a sequence that is at least 90% identical thereto, or wherein the sgRNA molecule targets the gamma gliadin gene and has a sequence selected from SEQ ID NO: 87 to 99 or a variant thereof (as defined herein), preferably a sequence that is at least 90% identical thereto.

In another aspect of the invention, there is provided an isolated plant cell transfected with at least one nucleic acid construct as defined herein. In one embodiment, the isolated plant cell is transfected with at least one nucleic acid construct as defined herein and a second nucleic acid construct, wherein said second nucleic acid construct comprises a nucleic acid sequence encoding a CRISPR enzyme such as Cpf1 or a Cas protein, preferably a Cas9 protein or a functional variant thereof. Preferably, the second nucleic acid construct is transfected before, after or concurrently with the nucleic acid construct as defined herein. In an alternative embodiment, the isolated plant cell is transfected with at least one sgRNA molecule as defined herein.

In another aspect of the invention, there is provided a genetically altered plant or mutant plant, wherein said plant comprises the transfected cell as defined herein. In one embodiment, the nucleic acid encoding a sgRNA as defined herein and/or the nucleic acid encoding a CRISPR enzyme is integrated in a stable form.

In a further aspect of the invention, there is provided a genetically altered plant characterised in that said plant has reduced expression and/or content of at least one of alpha-, gamma- and/or omega gliadins, reduced total gliadin content, reduced gluten content, a reduced gliadin to glutenin ratio and/or increased expression and/or content of glutenins, wherein said plant is obtained by transfecting at least one plant cell with at least one nucleic acid construct as defined herein or at least one sgRNA molecule as defined herein.

In one embodiment, the plant is obtained by further transfecting the at least one plant cell with a second nucleic acid construct, wherein said second nucleic acid construct comprises a nucleic acid sequence encoding a CRISPR enzyme, preferably a Cas or Cpf1 protein. Preferably, the Cas protein is preferably a Cas9 protein or a functional variant thereof.

Preferably, the plant is further characterised by a mutation in at least one of alpha-, gamma- and/or omega gliadin, wherein said mutation is preferably an insertion and/or deletion.

In one embodiment, the plant is characterised by a mutation in alpha-gliadin and wherein the plant is obtained by transfecting at least one plant cell with at least one nucleic acid construct as defined herein, or a nucleic acid construct comprising at least on sgRNA sequence selected from SEQ ID NO 51 to 56 or a variant thereof (as defined herein), preferably a sequence that is at least 90% identical thereto or at least one sgRNA molecule, wherein sgRNA molecule has a sequence selected from one any of SEQ ID Nos 75 to 80 or a variant thereof (as defined herein), preferably a sequence that is at least 90% identical thereto.

In an alternative or further embodiment, the plant is characterised by a mutation in gamma-gliadin and wherein the plant is obtained by transfecting at least one plant cell with at least one nucleic acid construct according as defined herein or a nucleic acid construct comprising at least one, preferably all of the sgRNA sequences selected from SEQ ID Nos 63 to 68 or at least one, preferably all of the sgRNA sequences selected from SEQ ID Nos 69 to 74 or at least one, preferably all of the sgRNA molecules defined in any of SEQ ID Nos 87 to 92 or at least one, preferably all of the sgRNA molecules defined in any of SEQ ID Nos 93 to 98, or a variant of any of the above (as defined herein), preferably a sequence that is at least 90% identical thereto.

In another further or alternative embodiment, the plant is characterised by a mutation in omega-gliadin and wherein the plant is obtained by transfecting at least one plant cell with a nucleic acid construct according as defined herein, or a nucleic acid construct comprising at least on sgRNA sequence selected from SEQ ID NO 57 to 62 or a variant thereof (as defined herein), preferably a sequence that is at least 90% identical thereto or a sgRNA molecule, wherein said molecule comprises an RNA sequence as defined in any of SEQ ID Nos 81 to 86 or a variant thereof (as defined herein), preferably a sequence that is at least 90% identical thereto.

The plant may be characterised by a mutation in at least one gene in one, two or all three of alpha-, gamma- and omega-gliadins by transfecting the plant with any combination of nucleic acid construct or sgRNA molecule as defined herein.

In one embodiment, the nucleic acid construct is not incorporated into the plant genome.

In another aspect of the invention, there is provided a genetically altered plant characterised by at least one mutation in at least one target sequence selected from any of SEQ ID Nos 1 to 24 and/or 790 and/or 792 to 803 or a variant thereof. Preferably, the mutation is an insertion and/or deletion, and wherein the mutation is introduced using targeted genome modification.

The plant may belong to the genus *Triticum*. Preferably, the plant is selected from the species *Triticum aestivum* or *Triticum turgidum*. More preferably, the plant is a Bobwhite cultivar or THA53 cultivar or a Don Pedro cultivar.

In another aspect of the invention, there is provided a seed derived from the genetically altered plant as defined herein, wherein said seed comprises at least one mutation in at least one of alpha-, gamma- and/or omega gliadin, wherein said mutation is preferably a deletion.

In a further aspect of the invention there is provided a pollen, propagule, progeny or part of the plant derived from any of the genetically altered plants as defined herein, wherein said pollen, propagule, progeny or part of the plant comprises at least one mutation in at least one of alpha-, gamma- and/or omega gliadin, wherein said mutation is preferably a deletion.

In another aspect of the invention there is provided the use of a nucleic acid construct as defined herein or a sgRNA molecule as defined herein to silence or reduce the expression and/or content of at least one of alpha-, gamma- and/or omega gliadins of the *Triticum* spp.

In a further aspect of the invention, there is provided a method of silencing or reducing the expression and/or content of at least one immunotoxic protein in the *Triticum* spp., the method comprising using targeted genome modification to modify the genome of the plant, wherein the modification is a mutation of at least one of alpha-, gamma- and/or omega gliadins.

In another aspect of the invention, there is provided a method of silencing or reducing the expression and/or content of at least one of alpha-, gamma- and/or omega gliadins of preferably the *Triticum* spp. the method comprising using targeted genome modification to silence or reduce the expression and/or content of at least one of alpha-, gamma- and/or omega gliadins, preferably of the *Triticum* spp.

In another aspect of the invention, there is provided a method of reducing total gliadin content and/or reducing gluten content and/or reducing gluten immunoreactivity in preferably the *Triticum* spp. the method comprising using targeted genome modification to silence or reduce the expression and/or content of at least one of alpha, gamma- and/or omega gliadins preferably of the *Triticum* spp.

In another aspect of the invention, there is provided a method of reducing the gliadin to glutenin ratio and/or increasing the expression and/or content of glutenins, preferably high molecular weight glutenins, in preferably the *Triticum* spp. the method comprising using targeted genome modification to silence or reduce the expression and/or content of at least one of alpha-, gamma- and/or omega gliadins of preferably the *Triticum* spp.

In one embodiment, the targeted genome modification is used to introduce at least one mutation into a target sequence selected from SEQ ID Nos 1 to 24, 790 and 792 to 803. In one embodiment, the gliadin is alpha-gliadin.

Preferably, the targeted genome modification is selected from TALENS, ZFNs and the CRISPR/Cas9 system or CRISPR/Cpf1 system. More preferably, the targeted genome modification is the CRISPR/Cas9 system.

In one embodiment, the method comprises introducing and expressing into a plant a nucleic acid construct as defined herein. In another embodiment, the method comprises introducing and expressing into a plant a nucleic acid construct as defined herein and a second nucleic acid construct comprising a nucleic acid encoding a CRISPR enzyme. Preferably, the CRISPR enzyme is a Cas or Cpf1 protein, preferably Cas9 or a functional variant thereof. More preferably, the second nucleic acid construct is transfected before, after or concurrently with the nucleic acid construct as defined herein.

In another embodiment, the method comprises transfecting at least one plant cell with at least one sgRNA molecule as defined herein.

In one embodiment, the nucleic acid construct is defined herein or wherein the nucleic acid construct comprises at least one sgRNA sequence, wherein said sequence is selected from SEQ ID Nos 51 to 56 or a variant thereof (as defined herein), preferably a sequence that is at least 90% identical thereto, and wherein the sgRNA molecule comprises an RNA sequence as defined in any of SEQ ID Nos 75 to 80 or a variant thereof (as defined herein), preferably a sequence that is at least 90% identical thereto.

In another embodiment, the nucleic acid construct is defined herein, or wherein the nucleic acid construct comprises at least one, sgRNA sequence, wherein said sequence is selected from SEQ ID Nos 63 to 68 or 69 to 74 or a variant thereof (as defined herein), preferably a sequence that is at least 90% identical thereto and wherein the sgRNA molecule comprises an RNA sequence as defined in any of SEQ ID Nos 87 to 99 or a variant thereof (as defined herein), preferably a sequence that is at least 90% identical thereto.

In a further embodiment, the nucleic acid construct is defined herein, or wherein the nucleic acid construct comprises at least one sgRNA sequence, wherein said sequence is selected from SEQ ID Nos 57 to 62 or a variant thereof (as defined herein), preferably a sequence that is at least 90% identical thereto and wherein the sgRNA molecule comprises an RNA sequence as defined in any of SEQ ID Nos 81 to 86 or a variant thereof (as defined herein), preferably a sequence that is at least 90% identical thereto.

The method may comprise introducing at least one mutation in at least one gene of one, two or all three of alpha-, gamma- and omega-gliadins by transfecting the plant with any combination of nucleic acid construct or sgRNA molecule as defined herein.

In a further embodiment, the method further comprises further silencing at least one of alpha-, gamma- and/or omega gliadins of the *Triticum* spp. using RNAi.

In another aspect of the invention there is provided a genetically altered plant obtained or obtainable by any one of the methods defined herein.

In a further aspect of the invention there is provided the use of the seed defined herein for the preparation of a flour, a food composition, a vitamin or nutritional supplement. Also provided is a food composition prepared from a seed as defined herein.

In another aspect of the present invention, there is provided a method for obtaining the genetically altered plant as defined herein, the method comprising:

a. selecting a part of the plant;

b. transfecting at least one cell of the part of the plant of paragraph (a) with the nucleic acid construct as defined herein or at least one sgRNA molecule as defined herein;

c. regenerating at least one plant derived from the transfected cell or cells;

d. selecting one or more plants obtained according to paragraph (c) that show silencing or reduced expression and/or content of at least one of alpha-, gamma- and/or omega gliadins, reduced total gliadin content, reduced gluten content, a reduced gliadin to glutenin ratio and/or increased expression and/or content of glutenins.

In another aspect of the invention, there is provided a method for producing a food composition with a reduced gliadin and/or gluten content and/or reduced immunotoxicity, the method comprising producing a genetically altered plant, characterised in that said plant has reduced expression and/or content of at least one of alpha-, gamma- and/or omega gliadins, reduced total gliadin content, reduced gluten content, a reduced gliadin to glutenin ratio and/or increased expression and/or content of glutenins, wherein said plant is obtained by transfecting at least one plant cell with at least one nucleic acid construct as defined herein or at least one sgRNA molecule as defined herein in the seeds of said plant, producing seeds from said plant in which at least one of alpha-, gamma- and/or omega gliadins is silenced or reduced in expression and/or content and preparing a food composition from said seeds.

In a further aspect of the invention, there is provided a method for modulating an immune response to gliadins and/or gluten, the method comprising providing a diet of a food composition as defined herein to a subject in need thereof.

In yet another aspect of the present invention, there is provided a method for affecting or modulating a T-cell response to gluten in a subject, the method comprising providing a diet of a food composition as described herein to a subject in need thereof.

In a final aspect of the invention, there is provided a method of genome modification comprising introducing double-strand breaks at two or more selected sites in at least one gene of at least one of alpha-, gamma- and/or omega gliadin of a plant cell by providing said cell with a clustered, regularly interspaced, short palindromic repeats (CRISPR)-associated Cas endonuclease and a sgRNA as defined herein.

DESCRIPTION OF THE FIGURES

The invention is further described in the following non-limiting figures:

FIG. 14 shows off-target mutations detection in ω5-gliadin genes of BW208 wild type and two T1 mutant lines (T544 and T545). Nineteen ω5-gliadin clones were sequenced by Sanger sequencing and aligned to the wild type reads. The only region containing a sgAlpha-2 potential target sequences (12 nt of the seed sequence with up to 1 mismatch) is shown. sgAlpha-2 site is highlighted in blue, with the PAM sequence underlined, and mismatches highlighted in red. No NGG PAM sequence was identified in any of the sgRNA sites.

FIG. 15 shows off-target mutations detection in BW208 mutant lines. (a) Off-target mutations in the prolamin-encoding genes (α-gliadins, γ-gliadins, ω-gliadins, HMW-glutenins, and LMW-glutenins). The 12 nt of the seed sequence of sgAlpha-1 and sgAlpha-2 plus the NGG PAM sequence was used to search for homology in 40 HMW-glutenins, 239 LMW-glutenins, 179 γ-gliadins, and 15 ω-gliadins found in GeneBank (http://www.ncbi.nlm.nih.gov/). Up to two mismatches were allowed between sgRNA and genomic targets; (b) Sequence alignment of 16 different clones of LMW-glutenins from BW208 T1 mutant line T544; (c) Off-target mutations in the non-prolamin genes. The 12 nt of the seed sequence of sgAlpha-1 and sgAlpha-2 plus the NGG PAM sequence was used to search for homology by BLAST in the wheat genome database (http://plants.ensembl.org/*Triticum_aestivum*/Info/Index). No mismatches were allowed between the sgRNA and genomic targets; (d) Sequence alignment of the 7 different clones of gene Traes_2AS_8FCC59363 sequenced from BW208 T1 mutant line T544; (e) Sequence alignment of the 9 different clones of gene Traes_2AS_D659E88E9 sequenced from BW208 T1 mutant line T544; (f) Sequence alignment of 10 different clones of gene Traes_7BL_F621D9B9E sequenced from BW208 T1 mutant line T544.

Some tracks are not continuous and were spliced together.

[1], Glufosinate resistance bar gene

[2], *Panicum virgatum* L. ubiquitin promoter

[3], Kanamycin resistance gene

[4], PVS1 stability(sta) region

[5], Octopine synthase polyA signal

[6], CDC; cell division control protein, AAA-superfamily of ATPases, Ta54227

[7], Insertions as determined by Illumina deep sequencing

NA, Not applicable

ND, Not determined

Figure 18:
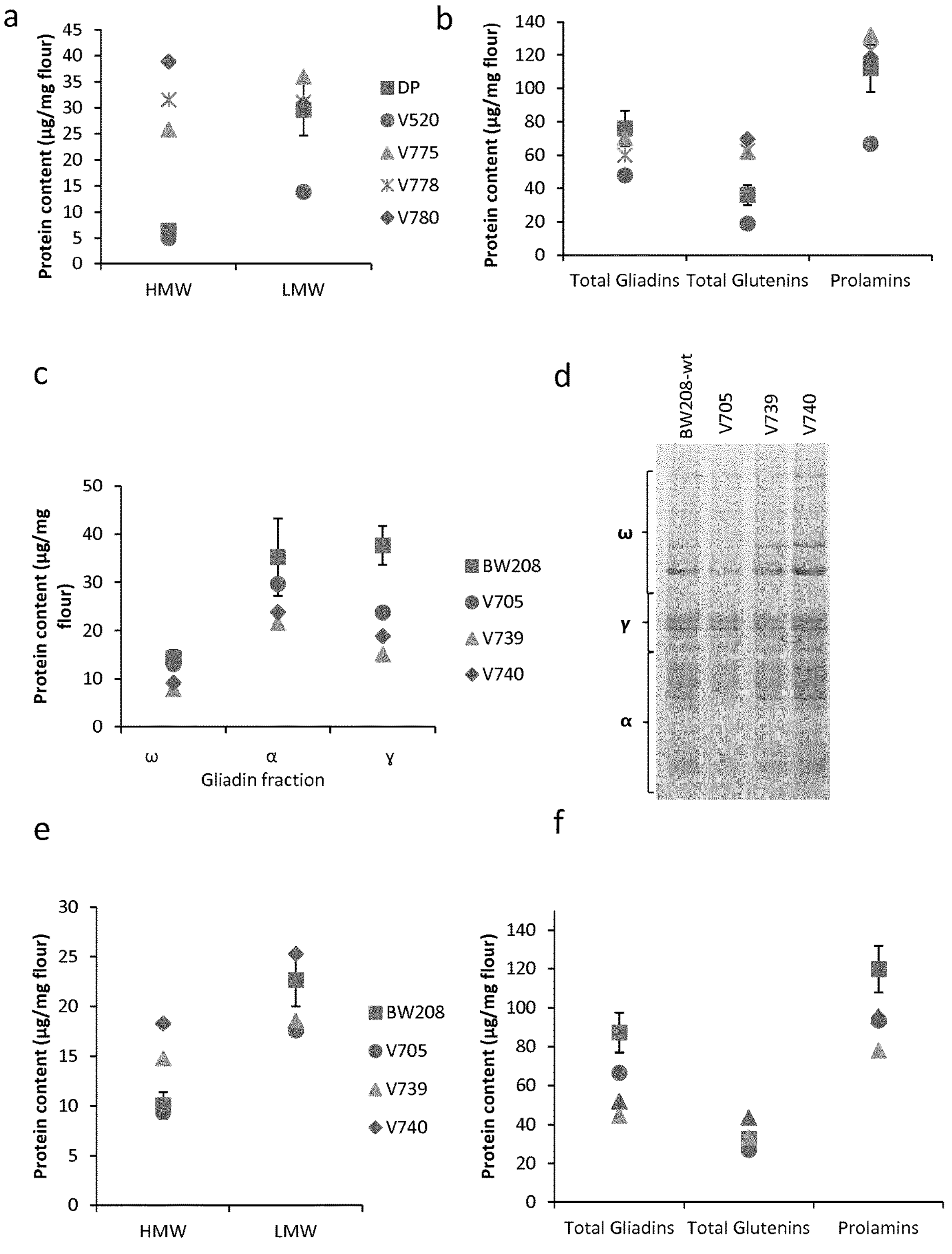

FIG. 18 shows a protein analysis of non-transgenic transgenic (transgene-free and insertion-free) lines determined by RP-HPLC and A-PAGE gels. Glutenin content (a), and total gliadins, glutenins, and prolamins content (b) of cv DP and four non-transgenic lines. (c) Content of omega, alpha, and gamma gliadins of cv BW208 and three non-transgenic lines. (d) A-PAGE of the gliadin profile in T2 seed lines from cv BW208 and three non-transgenic lines. Migration of α-, γ-, ω-gliadin protein bands are outlined by brackets. (e) Glutenin content of cv BW208 and three non-transgenic lines. (f) Total gliadins, glutenins, and prolamins content of cv BW208 and three non-transgenic lines.

HMW, high molecular weight; LMW, low molecular weight. Error bars, 5% Confidence Interval of the mean value of the wild type line.

FIG. 19 shows a list and the sequence of primers for PCR and Illumina sequencing.

FIG. 20 shows Illumina sequencing of alpha-gliadins in 18 T1 bread and durum wheat transgenic lines.

FIG. 21 shows gliadin and glutenin contents, total prolamin content, and gliadin to glutenin ratio of transgenic and wild-type T1 half-seeds from TO lines. Gliadin and glutenin fractions were determined by RP-HPLC and expressed as μg/mg flour.

Values for protein fraction are the mean of 10 grains from each TO line. H MW, high molecular weight; LMW, low molecular weight; NA, Non applicable; wt, wild type. * Means are significantly different to wild types as determined by Dunnett's multiple comparisons at $P<0.05$.

FIG. 22 shows Illumina sequencing of alpha-gliadins in 29 T2 bread and durum wheat transgenic lines.

FIG. 23 shows gliadin and glutenin contents, total prolamin content, gliadin to glutenin ratio, and SDS sedimentation test of transgenic and wild-type T2 seeds from T1 lines. Gliadin and glutenin fractions were determined by RP-HPLC and expressed as μg/mg flour. Values for protein fraction are the mean of 5-10 hal-seeds from each T1 line. HMW, high molecular weight; LMW, low molecular weight; NA, Non applicable; ND, data not determined; wt, wildtype. * Means are significantly different to wild types as determined by Dunnett's multiple comparisons at $P<0.05$.

FIG. 24 shows gliadin and glutenin contents, total prolamin content, gliadin to glutenin ratio, and SDS sedimentation test of transgenic and wild-type T3 seeds from T2 lines. Gliadin and glutenin fractions were determined by RP-HPLC and expressed as μg/mg flour. T2 lines from FIG. 23 were multiplied and equivalent amounts of grains from each line were bulked and milled for protein determination. Values for each protein fraction are the mean of four replications. HMW, high molecular weight; LMW, low molecular weight; NA, Non applicable; ND, data not determined; wt, wild type.

* Means are significantly different to wild types as determined by Dunnett's multiple comparisons at $P<0.05$.

DETAILED DESCRIPTION OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA, siRNA, sRNA, dsRNA, miRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs, CDS or genomic DNA in combination with regulatory sequences.

The invention relates to genome editing of tetraploid and hexaploid wheat to produce wheat lines that are low gliadin, and therefore low-gluten as well as transgene-free. Genome editing is a form of genetic engineering in which DNA is inserted, deleted or replaced in a plant's genome using engineered nucleases or site-specific nucleases (SSN) to create site-specific double-strand breaks (DSB) in the genome, that are then repaired using homologous recombination or non-homologous end-joining to form targeted mutations.

To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Cermak T et al. describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct a CRISPR enzyme, such as a Cas or Cpf1 nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences.

Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted (Wiles et al., 2015).

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3.

Cas9 expression plasmids for use in the methods of the invention can be constructed as described in the art.

Alternatively, Cpf1, which is another Cas protein, can be used as the endonuclease. Cpf1 differs from Cas9 in several ways; Cpf1 requires a T-rich PAM sequence (TTTV) for target DNA recognition, Cpf1 does not require a tracrRNA, and as such only crRNA is required and unlike Cas9, the Cpf1-cleavage site is located distal and downstream relative to the PAM sequence in the protospacer sequence (Li et al. 2017). Furthermore, after identification of the PAM motif, Cpf1 introduces a sticky-end-like DNA double-stranded break with several nucleotides of overhang. As such, the CRISPR/Cpf1 system consists of a Cpf1 enzyme and a guide RNA.

By "crRNA" or CRISPR RNA is meant the sequence of RNA that contains the protospacer element and optionally additional nucleotides that are complementary to the tracrRNA.

By "tracrRNA" (transactivating RNA) is meant the sequence of RNA that hybridises to the crRNA and binds a CRISPR enzyme, such as Cas9 thereby activating the nuclease complex to introduce double-stranded breaks at specific sites within the genomic sequence of at least one of the alpha-, gamma- and/or omega gliadin. Where the CRISPR enzyme used is Cpf1, a tracrRNA sequence is not required.

By "protospacer element" is meant the portion of crRNA (or sgRNA) that is complementary to the genomic DNA target sequence, usually around 20 nucleotides in length. This may also be known as a spacer or targeting sequence.

By "sgRNA" (single-guide RNA) is meant the combination of tracrRNA and crRNA in a single RNA molecule, preferably also including a linker loop (that links the tracrRNA and crRNA into a single molecule). "sgRNA" may also be referred to as "gRNA" and in the present context, the terms are interchangeable. The sgRNA or gRNA provide both targeting specificity and scaffolding/binding ability for a Cas nuclease. A gRNA may refer to a dual RNA molecule comprising a crRNA molecule and a tracrRNA molecule.

By "TAL effector" (transcription activator-like (TAL) effector) or TALE is meant a protein sequence that can bind the genomic DNA target sequence (a sequence within at least one of the alpha-, gamma- and/or omega gliadin genes) and that can be fused to the cleavage domain of an endonuclease such as FokI to create TAL effector nucleases or TALENS or meganucleases to create megaTALs. A TALE protein is composed of a central domain that is responsible for DNA binding, a nuclear-localisation signal and a domain that activates target gene transcription. The DNA-binding domain consists of monomers and each monomer can bind one nucleotide in the target nucleotide sequence. Monomers are tandem repeats of 33-35 amino acids, of which the two amino acids located at positions 12 and 13 are highly variable (repeat variable diresidue, RVD). It is the RVDs that are responsible for the recognition of a single specific nucleotide. HD targets cytosine; NI targets adenine, NG targets thymine and NN targets guanine (although NN can also bind to adenine with lower specificity).

Thus, aspects of the invention involve targeted mutagenesis methods, specifically genome editing, and in a preferred embodiment exclude embodiments that are solely based on generating plants by traditional breeding methods.

In one aspect of the invention there is provided a nucleic acid construct wherein the nucleic acid construct comprises a nucleic acid sequence that encodes at least one DNA-binding domain, wherein the DNA-binding domain can bind to a target sequence in one of the alpha-, gamma- and/or omega gliadin genes and wherein said target sequence is selected from one of SEQ ID Nos 1 to 24, 790 and 792 to 803 or a variant thereof. Preferably the nucleic acid construct comprises at least one DNA-binding domain, but in other embodiments, the nucleic acid construct may comprises two, three, four, five, six, seven, eight, nine, ten, eleven or twelve different DNA-binding domains. In one embodiment, the nucleic acid construct may comprise up to six different DNA-binding domains.

In one embodiment, said construct further comprises a nucleic acid encoding a SSN, such as FokI or a CRISPR enzyme, such as a Cas protein.

In one embodiment, the nucleic acid sequence comprises a nucleic acid sequence that encodes at least one protospacer element wherein the sequence of the protospacer element is selected from SEQ ID Nos 25 to 48 and 807 to 818 or a variant thereof. The protospacer element will respectively target a target sequence selected from SEQ ID NO: 1 to 24 and 792 to 803 respectively.

In one embodiment, the nucleic acid construct targets alpha-gliadins, and comprises a sequence that encodes at least one protospacer element selected from SEQ ID Nos 25 to 30, 805 and 792 to 796 or a variant thereof. In an alternative embodiment, the nucleic acid construct targets gamma gliadins and comprises at least one nucleic acid sequence or multiple nucleic acid sequences that encode at least one, but preferably at least two, at least three, at least four, at least five or most preferably all six of the protospacer elements as defined in SEQ ID Nos 37 to 42 or a variant thereof. Alternatively, the nucleic acid construct targets gamma gliadins and comprises at least one nucleic acid sequence or multiple nucleic acid sequences that encode at least one, but preferably at least two, at least three, at least four, at least five or most preferably all six of the protospacer elements defined in SEQ ID Nos 43 to 48 or a variant thereof. In a further alternative, the nucleic acid construct targeting gamma gliadins comprises at least one sequence selected from SEQ ID Nos 800 to 803 or a variant thereof. In a final alternative embodiment, the nucleic acid construct targets omega gliadins and comprises at least one nucleic acid sequence or multiple nucleic acid sequences that encode at least one, but preferably at least two, at least three, at least four, at least five or all six of the protospacer elements defined in SEQ ID Nos 31 to 36 or a variant thereof. In a further alternative, the nucleic acid construct targeting omega gliadins comprises at least one sequence selected from SEQ ID Nos 797 to 799 or a variant thereof.

In a further embodiment, the nucleic acid construct comprises a crRNA-encoding sequence. As defined above, a crRNA sequence may comprise the protospacer elements as defined above and preferably 5' or 3' positioned additional nucleotides. Where the construct is to be used with Cas9, the additional nucleotides may be complementary to the tracrRNA. An appropriate sequence for the additional nucleotides will be known to the skilled person as these are defined by the choice of Cas protein. However, in one embodiment the additional nucleotides may comprises or consist of SEQ ID NO: 49 or 823. Accordingly, in one embodiment, the crRNA sequence as defined herein comprises at least one protospacer sequence as defined herein and at least one copy of the nucleotide sequence defined in SEQ ID NO: 49 or 823 functional variant thereof. In one embodiment where the additional nucleotides comprise or consist of SEQ ID NO: 49, the sequence of the protospacer element is selected from one of SEQ ID NO: 25 to 48 or a variant thereof. In an alternative embodiment, where the additional nucleotides comprise or consist of SEQ ID NO: 823, the sequence of the protospacer sequence is selected from one of SEQ ID NO: 807 to 818 or a variant thereof.

In another embodiment, the nucleic acid construct further comprises a 5' or 3' positioned tracrRNA sequence (respective to the crRNA). Again, an appropriate tracrRNA sequence would be known to the skilled person as this sequence is defined by the choice of Cas protein. Nonetheless, in one embodiment said sequence comprises or consists of a sequence as defined in SEQ ID NO: 50 or a variant thereof. In an alternative embodiment, the tracrRNA sequence comprises or consists of a sequence as defined in SEQ ID No: 107 or a variant thereof. In a specific embodiment, wherein said tracrRNA sequence is SEQ ID NO: 107, said target sequence is selected from SEQ ID NO: 1 or 2 and/or the protospacer sequence is selected from SEQ ID NO: 25 or 26. That is, where the target sequence is alpha-1 or alpha-2, the tracrRNA sequence preferably consists or comprises SEQ ID NO: 107. Where the CRISPR enzyme is Cpf1 however, the additional nucleotides or the tracrRNA sequence is not needed.

In a further embodiment, the nucleic acid construct comprises at least one nucleic acid sequence that encodes a sgRNA (or gRNA). Again, as already discussed, sgRNA typically comprises a crRNA sequence, optionally a tracrRNA sequence and preferably a sequence for a linker loop. In this embodiment, the CRISPR enzyme to be used with the sgRNA is a Cas protein, preferably Cas9. In a preferred embodiment, the nucleic acid construct comprises at least one nucleic acid sequence that encodes a sgRNA sequence as defined in any of SEQ ID Nos 51 to 74 or variant thereof.

In another aspect of the invention, there is provided a nucleic acid construct comprising a nucleic acid sequence encoding a sgRNA, wherein the sequence of the sgRNA is selected from SEQ ID Nos 51 to 74 or variant thereof. In an alternative embodiment, the sgRNA comprises a protospacer element, where the sequence of the protospacer element is selected from one of SEQ ID NO: 807 to 818 or a variant thereof. In a further embodiment, the sgRNA comprises a crRNA sequence, where the crRNA sequence comprises a protospacer element, where the sequence of the protospacer element is selected from one of SEQ ID NO: 807 to 818 or a variant thereof and additional nucleotides, where the additional nucleotides comprise or consist of SEQ ID NO: 823 or a variant thereof.

In a preferred embodiment, the nucleic acid construct targets alpha-gliadins and comprises at least one sgRNA nucleic acid sequence, as defined in SEQ ID NO: 51 to 56 or variant thereof. In one embodiment, the nucleic acid construct comprises at least one, but preferably at least two, at least three, at least four, at least five or at least six nucleic acid constructs as defined in any of SEQ ID NO: 51 to 56. In an alternative embodiment, the at least one sgRNA comprises a protospacer element, where the sequence of the protospacer element is selected from one of SEQ ID NO: 807 to 811 or a variant thereof.

In an alternative embodiment, the nucleic acid construct targets gamma gliadins and comprises at least one, but preferably at least two, at least three, at least four, at least five or most preferably all six of the sgRNA nucleic acid sequence as defined in SEQ ID NO 63 to 68 (referred to herein as set 5 in Table 1) or variants thereof or the nucleic acid construct comprises at least one, but preferably at least two, at least three, at least four, at least five or most preferably all six of the sgRNA sequences defined in SEQ ID NO 69 to 74 (referred to herein as set 6 in Table 1) or variants thereof. In an alternative embodiment, the at least one sgRNA comprises a protospacer element, where the sequence of the protospacer element is selected from one of SEQ ID NO: 815 to 818 or a variant thereof.

In a final alternative, the nucleic acid construct targets omega gliadins and comprises at least one, at least two, at least three, at least four, at least five or all six of the sgRNA nucleic acid sequences defined in SEQ ID Nos 57 to 62 or variants thereof. In an alternative embodiment, the at least one sgRNA comprises a protospacer element, where the sequence of the protospacer element is selected from one of SEQ ID NO: 812 to 814 or a variant thereof.

In a further embodiment, the nucleic acid construct comprises any combination of the above. That is, at least one alpha-gliadin sgRNA nucleic acid sequence and/or at least one gamma-gliadin sgRNA nucleic acid sequence and/or at least one omega-gliadin sgRNA nucleic acid sequence as defined above.

In a further embodiment, the nucleic acid construct may further comprise at least one nucleic acid sequence encoding an endoribonuclease cleavage site. Preferably the endoribonuclease is Csy4 (also known as Cas6f). Where the nucleic acid construct comprises multiple sgRNA nucleic acid sequences the construct may comprise the same number of endoribonuclease cleavage sites. In one embodiment the Csy4 cleavage site is defined in SEQ ID NO: 103. In another embodiment, the cleavage site is 5' of the sgRNA nucleic acid sequence. Accordingly, each sgRNA nucleic acid sequence is flanked by a endoribonuclease cleavage site.

Therefore, the complete gRNA or sgRNA sequence is composed of the synthetic nucleotide sequence comprising the following sequences in the 5' to 3' direction: the 20 nt of the Csy4 cleavage site, the 20 nt of the protospacer, the 12 nt of additional nucleotides that together with the protospacer form the crRNA sequence and the 64 (SEQ ID NO: 5) or 71 (SEQ ID NO: 107) nt of the tracrRNA sequence. For alpha1 and alpha2 the TaU6 promoter was used, and therefore there are 7 thymines (T) at the end of the tracrRNA, as described in SEQ ID NO: 107. In a preferred embodiment, the nucleic acid contruct comprises a fusion of 2-6 gRNAs, driven by the CmYLCV or PvUbi1 promoters flanked by at least one, but preferably equal numbers of Csy4 cleavage site(s) as the gRNAs, as described above.

The term 'variant' refers to a nucleotide sequence where the nucleotides are substantially identical to one of the above sequences. The variant may be achieved by modifications such as insertion, substitution or deletion of one or more nucleotides. In a preferred embodiment, the variant has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to any one of the above sequences, such as SEQ ID NOs 1 to 99, preferably over the full length of the sequence. In one embodiment, sequence identity is at least 90%. In another embodiment, sequence identity is 100%. Sequence identity can be determined by any one known sequence alignment program in the art.

The invention also relates to a nucleic acid construct comprising a nucleic acid sequence operably linked to a suitable plant promoter. A suitable plant promoter may be a constitutive or strong promoter or may be a tissue-specific promoter. In one embodiment, suitable plant promoters are selected from, but not limited to, cestrum yellow leaf curling virus (CmYLCV) promoter (SEQ ID NO: 104) or switchgrass ubiquitin 1 promoter (PvUbi1) (SEQ ID NO: 105) wheat U6 RNA polymerase III (TaU6) (SEQ ID NO: 108), CaMV35S, wheat U6 or maize ubiquitin (e.g. Ubi1)(SEQ ID NO: 106) promoters. Alternatively, expression can be specifically directed to particular tissues of wheat seeds through gene expression-regulating sequences such as, for example, the promoter of the gene that codes for a D-hordein. Other suitable promoters are those related with meiosis; megasporogenesis and microsporogenesis. For example, homologs to the pollen-late-stage-promoter 1 (PLP1) and pollen-late-stage-promoter 2 (PLP2), which are active in late-stage pollen grains in rice (Yan et al, 2015). Another example of a pollen specific promoter is the PSG076 from wheat, which is expressed in late bicellular pollen grains and increases rapidly in mature pollen (Chen et al., 2012). In one embodiment, where the promoter is the U6 RNA polymerase III promoter (TaU6), the tracrRNA is SEQ ID NO: 107.

The nucleic acid construct of the present invention may also further comprise a nucleic acid sequence that encodes a CRISPR enzyme. By "CRISPR enzyme" is meant an RNA-guided DNA endonuclease that can associate with the CRISPR system. Specifically, such an enzyme binds to the tracrRNA sequence. In one embodiment, the CRISPR enzyme is a Cas protein ("CRISPR associated protein), preferably Cas 9 or Cpf1. In a specific embodiment Cas9 is wheat codon-optimised Cas9, and more preferably, has the sequence described in SEQ ID NO: 100 or a functional variant or homolog thereof. In another embodiment, the CRISPR enzyme is a protein from the family of Class 2 candidate x proteins, such as C2c1, C2C2 and/or C2c3. In one embodiment, the Cas protein is from *Streptococcus pyogenes*. In an alternative embodiment, the Cas protein may be from any one of *Staphylococcus aureus, Neisseria meningitides, Streptococcus thermophilus* or *Treponema denticola.*

In an alternative embodiment, the CRISPR enzyme is Cpf1, preferably from Lachnospiraceae bacterium. In a further embodiment, the Cpf1 enzyme is wheat codon-optimised and preferably comprises or consists of SEQ ID NO: 819 or a variant thereof. The term "functional variant" as used herein with reference to Cas9 or Cpf1 refers to a variant Cas9 or Cpf1 gene sequence or part of the gene sequence which retains the biological function of the full non-variant sequence, for example, acts as a DNA endonuclease, or recognition or/and binding to DNA. A functional variant also comprises a variant of the gene of interest which has sequence alterations that do not affect function, for example non-conserved residues. Also encompassed is a variant that is substantially identical, i.e. has only some sequence variations, for example in non-conserved residues, compared to the wild type sequences as shown herein and is biologically active. In one embodiment, a functional variant of SEQ ID No. 100 or 819 has at least 90%, 91%, 92%, 93%, 94%, 95%, 96%, 97%, 98%, or 99% overall sequence identity to the amino acid represented by SEQ ID NO: 100 or 819.

Suitable homologs or orthologs can be identified by sequence comparisons and identifications of conserved domains. The function of the homolog or ortholog can be identified as described herein and a skilled person would thus be able to confirm the function when expressed in a plant.

In a further embodiment, the Cas9 protein has been modified to improve activity. For example, in one embodiment, the Cas9 protein may comprise the D10A amino acid substitution; this nickase cleaves only the DNA strand that is complementary to and recognized by the gRNA. Accordingly, in one example, the sequence of the Cas9 comprises or consists of SEQ ID NO: 822 or a variant thereof. In an alternative embodiment, the Cas9 protein may alternatively or additionally comprise the H840A amino acid substitution; this nickase cleaves only the DNA strand that does not interact with the sRNA. In this embodiment, Cas9 may be used with a pair (i.e. two) sgRNA molecules (or a construct expressing such a pair) and as a result can cleave the target region on the opposite DNA strand, with the possibility of improving specificity by 100-1500 fold. In a further embodiment, the cas9 protein may comprise a D1135E substitution. The Cas 9 protein may also be the VQR variant. Alternatively, the Cas protein may comprise a mutation in both nuclease domains, HNH and RuvC-like and therefore is catalytically inactive. Rather than cleaving the target strand, this catalytically inactive Cas protein can be used to prevent the transcription elongation process, leading to a loss of function of incompletely translated proteins when co-expressed with a sgRNA molecule. An example of a catalytically inactive protein is dead Cas9 (dCas9) caused by a point mutation in RuvC and/or the HNH nuclease domains (Komor et al., 2016 and Nishida et al., 2016).

In another example, a variant Cpf1 sequence may comprise or consist of SEQ ID NO: 820 or a variant thereof.

In a specific embodiment of any of the above, where the CRISPR enzyme is Cpf1, the alpha gliadin target sequence is selected from at least one of SEQ ID NO: 792, 793, 794, 795 and 796; the omega gliadin target sequence is selected from at least one of SEQ ID NO: 797, 798 and 799 and the gamma gliadin sequence is selected from at least one SEQ ID NO: 800, 801, 802 and 803. Similarly, where Cpf1 is the CRISPR enzyme in any of the above described aspects, or embodiments the sequence of the alpha gliadin protospacer element is selected from SEQ ID NO: 807, 808, 809, 810 and 811; the sequence of the omega gliadin protospacer element is selected from SEQ ID NO: 812, 813 and 814 and the sequence of the gamma gliadin protospacer element is selected from SEQ ID NO: 815, 816, 817 and 818. In a further embodiment, a Cas protein, such as Cas9 or Cpf1 may be further fused with a repression effector, such as a histone-modifying/DNA methylation enzyme or a Cytidine deaminase (Komor et al. 2016) to effect site-directed mutagenesis. In the latter, the cytidine deaminase enzyme does not induce dsDNA breaks, but mediates the conversion of cytidine to uridine, thereby effecting a C to T (or G to A) substitution. These approaches may be particularly valuable to target glutamine and proline residues in gliadins, to break the toxic epitopes while conserving gliadin functionality. In one example, the CRISPR enzyme can be fused with a deaminase such as APOBEC1 (apolipoprotein B mRNA editing enzyme catalytic polypeptide-like). A Cas-APOBEC1 fusion may be used in one example to induce specific indels in a target sequence. In one example the sequence of APOBEC1 comprises or consists of SEQ ID NO: 821.

In one embodiment, where a APOBEC1-Cas fusion protein is used (either on the same or on a different construct to the sgRNA), the alpha gliadin target sequence is selected form at least one of SEQ ID Nos 789, 790 and 791 and the protospacer element sequence is selected from at least one of SEQ ID Nos 804, 805 and 806.

In a further embodiment, APOBEC1 is fused to a modified Cpf1, preferably a catalytically inactive Cpf1. In one example, Cpf1 comprises at least one of the following mutations, D832A, E925A and D148A. In a preferred embodiment, the catalytically inactive Cpf1 comprises or consists of SEQ ID NO: 820 or a variant thereof. In this example, the base editor recognises a T-rich PAM sequence and catalyses a conversion of C to Tin target cells (Li et al., 2017). In a further embodiment, the nucleic acid construct comprises an endoribonuclease. Preferably the endoribonuclease is Csy4 (also known as Cas6f) and more preferably a wheat codon optimised Csy4, for example as defined in SEQ ID NO: 102. In one embodiment, where the nucleic acid construct comprises a Cas protein, the nucleic acid construct may comprise sequences for the expression of an endoribonuclease, such as Csy4 expressed as a 5' terminal P2A fusion (used as a self-cleaving peptide) to a Cas protein, such as Cas9, for example, as defined in SEQ ID NO: 101. In another aspect, there is provided a nucleic acid construct comprising the nucleic acid sequence as defined in SEQ ID NO: 101 or a variant thereof.

In one embodiment, the Cas protein, the endoribonuclease and/or the endoribonuclease-Cas fusion sequence may be operably linked to a suitable plant promoter. Suitable plant promoters are already described above, but in one embodiment, may be the *Zea Mays* Ubiquitin 1 promoter, as defined, for example in SEQ ID NO: 106.

In a specific embodiment, final vectors comprise a nucleotide sequence comprising sequences for the expression of Csy4 endoribonuclease expressed as a 5' terminal P2A fusion to Cas9 gene, both driven by the *Zea* Maize Ubiquitin 1 promoter; a cassette of two to six polycistronic gRNAs, driven by a cestrum yellow leaf curling virus (CmYLCV) promoter or switchgrass ubiquitin 1 promoter (PvUbi1), wherein each gRNA unit is flanked by the 20 bp Csy4 cleavage site.

In an alternative aspect of the invention, the nucleic acid construct comprises at least one nucleic acid sequence that encodes a TAL effector, wherein said effector targets a gliadin sequence selected from SEQ ID Nos 1 to 24, 790 and 792 to 803. Methods for designing a TAL effector would be well known to the skilled person, given the target sequence. However, examples of suitable methods are given in Sanjana et al., and Cermak T et al., both incorporated herein by reference. Preferably, said nucleic acid construct comprises two nucleic acid sequences encoding a TAL effector, to produce a TALEN pair. In a further embodiment, the nucleic acid construct further comprises a sequence-specific nuclease (SSN). Preferably such SSN is a endonuclease such as FokI. In a further embodiment, the TALENs are assembled by the Golden Gate cloning method in a single plasmid or nucleic acid construct.

In another aspect of the invention, there is provided a sgRNA molecule, wherein the sgRNA molecule comprises a crRNA sequence and a tracrRNA sequence and wherein the crRNA sequence can bind to at least one sequence selected from SEQ ID Nos 1 to 24, 790 and 792 to 803 or a variant thereof. In a further embodiment, the tracrRNA sequence comprises or consists of SEQ ID NO: 99 or a variant thereof. In one embodiment, the sequence of the sgRNA molecule is defined in any of SEQ ID NO: 75-99 or variant thereof. A "variant" is as defined herein. In one embodiment, the sgRNA molecule may comprise at least one chemical modification, for example that enhances its stability and/or binding affinity to the target sequence or the crRNA sequence to the tracrRNA sequence. Such modifications would be well known to the skilled person, and include for example, but not limited to, the modifications described in Randar et al., 2015, incorporated herein by reference. In this example the crRNA may comprise a phosphorothioate backbone modification, such as 2'-fluoro (2'-F), 2'-O-methyl (2'-O-Me) and S-constrained ethyl (cET) substitutions.

In another aspect of the invention, there is provided an isolated nucleic acid sequence that encodes for a protospacer element (as defined in any of SEQ ID Nos 25 to 48), or a sgRNA (as described in any of SEQ ID NO: 51 to 74).

In another aspect of the invention there is provided a kit for reducing gliadin and/or gluten content in a plant, the kit comprises at least one nucleic acid construct as described herein. For example, the kit may comprise a first nucleic acid construct targeting at least one alpha-gliadin target sequence, a second nucleic acid construct targeting at least one gamma-gliadin target sequence as described above and a third nucleic acid sequence targeting at least one omega-gliadin target sequence as described above.

Methods of Producing Genetically Altered Plants

In another aspect of the invention, there is provided a plant or part thereof or at least one isolated plant cell transfected with at least one nucleic acid construct as described herein. Cas9 and sgRNA may be combined or in separate expression vectors (or nucleic acid constructs, such terms are used interchangeably). In other words, in one embodiment, an isolated plant cell is transfected with a single nucleic acid construct comprising at least one sgRNA and Cas9 as described in detail above. In an alternative embodiment, an isolated plant cell is transfected with at least two nucleic acid constructs, a first (or multiple) nucleic acid construct(s) comprising at least one sgRNA as defined above and a second nucleic acid construct comprising Cas9 or a functional variant or homolog thereof. The second nucleic acid construct may be transfected below, after or concurrently with the first nucleic acid construct. The advantage of a separate, second construct comprising a Cas protein is that the nucleic acid construct encoding at least one sgRNA can be paired with any type of Cas protein, as described herein, and therefore are not limited to a single Cas function (as would be the case when both Cas and sgRNA are encoded on the same nucleic acid construct). In one embodiment, the nucleic acid construct comprising a Cas protein is transfected first and is stably incorporated into the genome, before the second transfection with a nucleic acid construct comprising at least one sgRNA nucleic acid. In an alternative embodiment, a plant or part thereof or at least one isolated plant cell is transfected with mRNA encoding a Cas protein and co-transfected with at least one nucleic acid construct as defined herein.

Cas9 expression vectors for use in the present invention can be constructed as described in the art. In one example, the expression vector comprises a nucleic acid sequence as defined in SEQ ID NO: 100 or a functional variant or homolog thereof, wherein said nucleic acid sequence is operably linked to a suitable promoter. Examples of suitable promoters include, but are not limited to, Cestrum yellow leaf curling virus (CmYLCV) promoter (SEQ ID NO: 104), switchgrass ubiquitin 1 promoter (PvUbi1) (SEQ ID NO: 105), *Zea Mays* Ubiquitin 1 promoter (SEQ ID NO: 106), the maize Ubi1 promoter, wheat U6 RNA polymerase III, CaMV35S or wheat U6. Alternatively, expression can be specifically directed to particular tissues of wheat seeds through gene expression-regulating sequences such as, for example, the promoter of the gene that codes for a D-hordein.

In an alternative aspect of the present invention, there is provided an isolated plant cell transfected with at least one sgRNA molecule as described herein.

In a further aspect of the invention, there is provided a genetically altered or edited plant comprising the transfected cell described herein. In one embodiment, the nucleic acid construct or constructs may be integrated in a stable form. In an alternative embodiment, the nucleic acid construct or constructs are not integrated (i.e. are transiently expressed). Accordingly, in a preferred embodiment, the genetically altered plant is free of any sgRNA and/or Cas protein nucleic acid. In other words, the plant is transgene free.

In a related aspect there is therefore provided a genetically altered plant, characterised in that the plant has reduced expression and/or content of at least one of alpha-, gamma- and/or omega gliadins, reduced total gliadin content, reduced gluten content, a reduced gliadin to glutenin ratio and/or increased expression and/or content of glutenins, wherein said plant is obtained by transfecting at least one plant cell with at least one nucleic acid construct as described herein or least one sgRNA molecule as described herein.

In a further aspect there is provided a genetically altered plant, characterised in that the plant has at least one mutation in at least one of alpha-, gamma- and/or omega gliadins genes. By "at least one of alpha-, gamma- and/or omega gliadins" is meant at least one mutation in at least one alpha, gamma and/or omega gliadin gene. For example, as described in the examples, wheat alpha-gliadins are encoded by approximately one hundred genes and pseudogenes. Accordingly, using the genome editing techniques described herein at least one alpha-gliadin gene may be mutated, but preferably at least 5%, 10%, 15%, 20%, 25%, 30%, 35%, 40%, 45%, 50%, 55%, 60%, 65%, 70%, 75%, 80%, 85%, 90%, 95% or 100% of the alpha-gliadin genes are mutated. The same is applicable to the omega and gamma-gliadin genes.

Preferably said mutation is an insertion and/or deletion and/or substiution (as described herein), with reference to a wild-type or control sequence. More preferably, the plant is obtained by transfecting at least one plant cell with at least one nucleic acid construct as described herein or least one sgRNA molecule as described herein.

As used herein, an "insertion" may refer to the insertion of at least one nucleotide, preferably between 20 and 200 base pairs, more preferably between 30 and 160 base pairs, and even more preferably, between 36 and 158 base pairs.

As used herein, a "deletion" may refer to the deletion of at least one nucleotide, preferably between 1 and 200 base pairs, more preferably between 1 and 150 base pairs, and even more preferably between 1 and 126 base pairs.

In another aspect, there is provided a genetically altered plant, characterised in that said plant has at least one mutation in at least one of the target sequences selected from SEQ ID Nos 1 to 24, 790 and 792 to 803 or variants thereof. Preferably, said mutation is an insertion and/or deletion. More preferably said mutation is introduced using targeted genome editing, for example, any method that uses a site-specific nuclease (SSN), such as ZFNs, TALENs or CRISPR/Cas9.

In a preferred embodiment, the genetically altered plant is produced by transforming wheat embryos, preferably immature scutella.

The term "introduction", "transfection" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art.

The transfer of foreign genes into the genome of a plant is called transformation. Transformation of plants is now a routine technique in many species. Any of several transformation methods known to the skilled person may be used to introduce the nucleic acid construct or sgRNA molecule of interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant (microinjection), gene guns (or biolistic particle delivery systems (biolistics), lipofection, transformation using viruses or pollen and microprojection. Methods may be selected from the calcium/polyethylene glycol method for protoplasts, ultrasound-mediated gene transfection, optical or laser transfection, transfection using silicon carbide fibers, electroporation of protoplasts, microinjection into plant material, DNA or RNA-coated particle bombardment, infection with (non-integrative) viruses and the like. Transgenic plants can also be produced via *Agrobacterium tumefaciens* mediated transformation, including but not limited to using the floral dip/*Agrobacterium* vacuum infiltration method as described in Clough & Bent (1998) and incorporated herein by reference.

Accordingly, in one embodiment, at least one nucleic acid construct or sgRNA molecule as described herein can be introduced to at least one plant cell using any of the above described methods. In an alternative embodiment, any of the nucleic acid constructs described herein may be first transcribed to form a preassembled Cas9-sgRNA ribonucleoprotein and then delivered to at least one plant cell using any of the above described methods, such as lipofection, electroporation or microinjection. In one embodiment, the method may comprise the delivery of at least one, at least two, at least three, at least four, at least five or at least six sgRNA molecules as defined in one of SEQ ID Nos 75 to 80, 81 to 86 or 87 to 99 or any combination thereof. In one example, the method comprises the delivery of all six of the sgRNA molecules defined in SEQ ID Nos 87 to 92. Alternatively, the method comprises the delivery of all six of the sgRNA molecules defined in SEQ ID Nos 93 to 98.

Optionally, to select transformed plants, the plant material obtained in the transformation is subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. As described in the examples, a suitable marker can be bar-phosphinothricin or PPT. Alternatively, the transformed plants are screened for the presence of a selectable marker, such as, but not limited to, GFP, GUS (β-glucuronidase). Other examples would be readily known to the skilled person. Alternatively, no selection is performed, and the seeds obtained in the above-described manner are planted and grown and gliadin and/or gluten content measured at an appropriate time using standard techniques in the art. This alternative, which avoids the introduction of transgenes, is preferable to produce transgene-free plants.

Following DNA transfer and regeneration, putatively transformed plants may also be evaluated, for instance using PCR to detect the presence of the gene of interest, copy number and/or genomic organisation. Alternatively or additionally, integration and expression levels of the newly introduced DNA may be monitored using Southern, Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

In a further related aspect of the invention, there is also provided, a method of obtaining a genetically altered plant as described herein, the method comprising a. selecting a part of the plant;
b. transfecting at least one cell of the part of the plant of paragraph (a) with at least one nucleic acid construct as described herein or at least one sgRNA molecule as described herein, using the transfection or transformation techniques described above;
c. regenerating at least one plant derived from the transfected cell or cells;
d. selecting one or more plants obtained according to paragraph (c) that show silencing or reduced expression and/or content of at least one of alpha-, gamma- and/or omega gliadins, reduced total gliadin content, reduced gluten content, a reduced gliadin to glutenin ratio and/or increased expression and/or content of glutenins.

In a further embodiment, the method also comprises the step of screening the genetically altered plant for SSN (preferably CRISPR)-induced mutations in at least one of alpha-, gamma- and/or omega gliadins. In one embodiment, the method comprises obtaining a DNA sample from a transformed plant and carrying out DNA amplification to detect a mutation, preferably an insertion or deletion, in at least one of alpha-, gamma- and/or omega gliadins.

In another embodiment, the method may further comprise the step of screening the genetically altered plant for the presence of exogenous nucleic acid, such as that encoding for Cas9 genes and/or sgRNA, the method also comprising obtaining a DNA sample from a transformed plant and carrying out DNA amplification to detect the presence of any exogenous DNA. As an example, the primers that can be used for such DNA amplification are described in FIG. 11.

In a further embodiment, the methods comprise generating stable T2 plants preferably homozygous for the mutation (that is a deletion and/or insertion in at least one of alpha-, gamma- and/or omega gliadins).

Plants that have a mutation in at least one of alpha-, gamma- and/or omega gliadins can also be crossed with another plant also containing at least one mutation in at least one of alpha-, gamma- and/or omega gliadins to obtain plants with additional mutations in at least one of alpha-, gamma- and/or omega gliadins. The combinations will be apparent to the skilled person. Accordingly, this method can be used to generate T2 plants with mutations on all or an increased number of homeologs, when compared to the number of homeolog mutations in a single T1 plant transformed as described above.

A plant obtained or obtainable by the methods described above is also within the scope of the invention.

A genetically altered plant of the present invention may also be obtained by transference of any of the sequences of the invention by crossing, e.g., using pollen of the genetically altered plant described herein to pollinate a wild-type or control plant, or pollinating the gynoecia of plants described herein with other pollen that does not contain a mutation in at least one of alpha-, gamma- and/or omega gliadins. The methods for obtaining the plant of the invention are not exclusively limited to those described in this paragraph; for example, genetic transformation of germ cells from the ear of wheat could be carried out as mentioned, but without having to regenerate a plant afterward.

In another embodiment, the present invention provides regenerable mutant plant cells for use in tissue culture. The tissue culture will preferably be capable of regenerating plants having essentially all of the physiological and morphological characteristics of the foregoing mutant wheat plant, and of regenerating plants having substantially the same genotype. Preferably, the regenerable cells in such tissue cultures will be callus, protoplasts, meristematic cells, cotyledons, hypocotyl, leaves, pollen, embryos, roots, root tips, anthers, pistils, shoots, stems, petiole, flowers, and seeds. Still further, the present invention provides wheat plants regenerated from the tissue cultures of the invention.

Methods of Reducing Gliadin and/or Gluten Content

In another aspect of the invention, there is provided a method of silencing or reducing the expression and/or content of at least one immunotoxic protein in the *Triticum* spp., the method comprising using targeted genome modification to modify the genome of the plant, wherein the modification is a mutation of at least one of alpha-, gamma- and/or omega gliadins. Preferably, said mutation is an insertion and/or deletion. More preferably said mutation is in at least one target sequence selected from SEQ ID Nos 1 to 24, 790 and 792 to 803.

In an alternative aspect of the invention there is provided a method of silencing or reducing the expression and/or content of at least one of alpha-, gamma- and/or omega gliadins of the *Triticum* spp. the method comprising using targeted genome modification to silence or reduce the expression and/or content of at least one of alpha-, gamma- and/or omega gliadins of the *Triticum* spp.

In another aspect of the invention, there is provided a method of reducing total gliadin content and/or reducing gluten content and/or reducing gluten immunoreactivity in the *Triticum* spp. the method comprising using targeted genome modification to silence or reduce the expression and/or content of at least one of alpha-, gamma- and/or omega gliadins of the *Triticum* spp.

In a further aspect of the invention, there is provided a method of reducing the gliadin to glutenin ratio and/or increasing the expression and/or content of glutenins, preferably high molecular weight glutenins, in the *Triticum* spp. the method comprising using targeted genome modification to silence or reduce the expression and/or content of at least one of alpha-, gamma- and/or omega gliadins of the *Triticum* spp.

In one embodiment, the method comprises using targeted genome modification to introduce at least one mutation into at least one of the alpha-, gamma- and/or omega gliadins genes, wherein preferably said mutation is an insertion and/or deletion, and wherein said target sequence is selected from SEQ ID Nos: 1 to 24, 790 and 792 to 803 or a variant thereof. Again, by "at least one of alpha-, gamma- and/or omega gliadins" is meant at least one mutation in at least one alpha, gamma and/or omega gliadin gene.

In one embodiment, the methods comprise introducing and expressing at least one nucleic acid construct as described herein or at least one sgRNA molecule as described herein into a plant.

In a further aspect of the present invention there is provided the use of a nucleic acid construct as defined herein or a sgRNA molecule as defined herein, to silence or reduce the expression and/or content of at least one of alpha-, gamma- and/or omega gliadins of the *Triticum* spp.

A reduction as used herein in reference to any of alpha-, gamma- and/or omega gliadin expression and/or content levels, total gliadin, gluten content and/or gluten immunoreactivity is meant a reduction of at least 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% compared to the levels in a control or wild-type plant. A 100% reduction can also be considered as silencing. Alternatively, said reduction is at least a two, three, four, five, six, seven, eight, nine or ten-fold or up to a twenty-fold reduction compared to the levels in a control or wild-type plant.

These reductions can be measured by any standard technique known to the skilled person. For example, a reduction in the expression and/or content levels of at least one of alpha-, gamma- and/or omega gliadin and total gliadin levels may be a measure of protein and/or nucleic acid levels and can be measured by any technique known to the skilled person, such as, but not limited to, any form of gel electrophoresis or chromatography (e.g. HPLC) as described in the examples. Techniques for measuring total gluten and gluten immunoreactivity are also known to the skilled person, but again as a non-limiting example, can include measurement using the monoclonal antibodies R5 and G12, as described in the examples.

Interestingly, in one embodiment, the method or use comprises the silencing or a reduction in the expression and/or content levels of alpha-gliadin only. In other words, the invention comprises reducing the expression and/or content levels of at least alpha-gliadin, and additionally gamma- and/or omega gliadin and/or total gliadin and/or gluten levels by targeting only alpha-gliadin. In this embodiment, the method comprises using targeted genome modification to introduce at least one mutation into at least one alpha-gliadin gene. Preferably said mutation is an insertion and/or deletion, and preferably said mutation is introduced using CRISPR/Cas9. In a further preferred embodiment, the mutation is introduced into a target sequence selected from SEQ ID Nos 1 to 6 or a variant thereof. More preferably said method comprises introducing and expressing a nucleic acid construct comprising at least one nucleic acid sequence defined in SEQ ID NO 25 to 30, 850 or 51 to 56 or at least one sgRNA molecule as defined in SEQ ID NO: 75 to 80 into a plant cell, as described herein.

Also covered are plants obtained or obtainable by the above-described method. That is, a genetically altered plant, wherein said plant is characterised by at least one mutation in an alpha-gliadin gene, and wherein said plant is also characterised by a reduction in the expression and/or content levels of at least one, preferably two, more preferably three of alpha-, gamma- and omega-gliadins, a reduction in the level of total gliadin levels, a reduction in total gluten levels and/or a reduction in gluten immunoreactivity. In this embodiment, the mutation is an insertion and/or deletion in at least one target sequence selected from SEQ ID Nos 1 to 6. Preferably said mutation is introduced by genome editing as described herein.

The methods described herein may also further comprise the steps of measuring (as described above) and/or selecting plants with reduced alpha-, gamma- and/or omega gliadin expression and/or content levels, total gliadin, gluten content and/or gluten immunoreactivity. The method may further comprise the step of regenerating a selected plant as described herein.

In another embodiment, the method may further comprise the step of screening the genetically altered plant for the presence of exogenous nucleic acid, such as that encoding for Cas9 genes and/or sgRNA, and optionally also obtaining a DNA sample from a transformed plant and carrying out DNA amplification to detect the presence of any exogenous DNA. As an example, the primers that can be used for such DNA amplification are described in FIG. 11. In other words, the method may comprise the step of checking that the plant is transgene free.

Preferably targeted genome editing is selected from TALENS, ZFNs and the CRISPR/Cas9 system, and more preferably the CRISPR/Cas9 system.

In a further embodiment, the methods described herein may further comprise silencing at least one of alpha-, gamma- and/or omega gliadins genes using RNAi. Such methods may be used to further enhance the reduction in the level of alpha-, gamma- and/or omega gliadin expression and/or content levels, total gliadin levels, gluten content and/or gluten immunoreactivity compared to the levels in a control or wild-type plant or compared to the levels in a plant separately transformed with only one of a nucleic acid construct or RNA molecule of the invention or an RNAi molecule as also described herein.

As used herein "a RNAi molecule" of the invention refers to a double stranded oligonucleotide capable of mediating target mRNA cleavage via RNA interference.

RNA interference (RNAi) is a post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

Thus, according to the various aspects of the invention a plant may be transformed to introduce a RNAi, shRNA, snRNA, dsRNA, siRNA, miRNA, ta-siRNA, amiRNA or cosuppression molecule that has been designed to target at least one alpha-, gamma- and/or omega gliadin gene, and preferably at least one target sequence selected from SEQ ID Nos 1 to 24, 792 to 803, and selectively decrease or inhibit the expression of the gene or stability of its transcript. Preferably, the RNAi, snRNA, dsRNA, shRNA siRNA, miRNA, amiRNA, ta-siRNA or cosuppression molecule used according to the various aspects of the invention comprises a fragment of at least 17 nt, preferably 22 to 26 nt and can be designed on the basis of the information shown in SEQ ID Nos. 1 to 24, 790 and 792 to 803. Guidelines for designing effective siRNAs are known to the skilled person. Briefly, a short fragment of the target gene sequence (e.g., 19-40 nucleotides in length) is chosen as the target sequence of the siRNA of the invention. The short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, 5) a sequence from the target gene mRNA that is unique to the target gene, 6) avoids regions within 75 bases of a start codon. The sequence fragment from the target gene mRNA may meet one or more of the criteria identified above. The selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides that are typically made by chemical synthesis. In addition to siRNA which is complementary to the mRNA target region, degenerate siRNA sequences may be used to target homologous regions. siRNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligonucleotide synthesis suppliers.

The silencing RNA molecule is introduced into the plant using conventional methods, for example using a vector and *Agrobacterium*-mediated transformation.

An example of a suitable RNAi molecule that may be used according to the present invention is described in US 2012/0167253, which is incorporated herein by reference.

In one embodiment, the method may comprise introducing and expressing at least one nucleic acid construct as described herein or at least one sgRNA molecule as described herein before, after or concurrently with an RNAi construct or molecule as described herein. Alternatively, the method may comprise crossing a plant obtained by transfection with a nucleic acid construct or sgRNA molecule of the present invention with a plant obtained by transfection with a RNAi molecule to produce a second-generation (or T2) transformants with an increased reduction in alpha-, gamma- and/or omega gliadin expression and/or content levels, total gliadin levels, gluten content and/or gluten immunoreactivity as described above. The T2 plants may then further be propagated through classical breeding techniques.

In another aspect of the invention, there is provided the use of a seed derived from a genetically altered plant as described herein in the preparation of a food composition.

The food composition is prepared from, but not limited to, the flour and/or semolina of the seeds of the invention, combined or not with other flours and/or semolinas, or other compounds.

The term “flour” as it is understood in the present invention refers to the product obtained by milling of any seed or plants of the genus *Triticum*, with the bran or husk of the seed removed to a greater or lesser degree.

The term “semolina” refers to coarse flour (slightly milled wheat seeds), i.e., fragments of the endosperm with a variable amount of seed husks.

The prepared food is selected from, but not limited to, the list comprising bread, bakery products, pastries, confectionery products, food pasta, food dough, grains, drinks, or dairy products.

Another aspect of the invention is use of the composition of the invention to prepare a food product, vitamin supplement, or nutritional supplement. As understood in the present invention, a food product fulfils a specific function, such as improving the diet of those who consume it. For this purpose, a vitamin and/or nutritional supplement may be added to the food product.

The food product that comprises the food composition of the present invention may be consumed even by persons who are allergic to gluten, i.e., suffer from celiac disease.

In a further aspect of the invention, there is provided a method for producing a food composition, wherein said food composition preferably has a reduced gliadin and/or gluten content and/or reduced immunotoxicity, the method comprising producing a genetically altered plant, characterised in that said plant has reduced expression and/or content of at least one of alpha-, gamma- and/or omega gliadins, reduced total gliadin content, reduced gluten content, a reduced gliadin to glutenin ratio and/or increased expression and/or content of glutenins. Alternatively, said plant is characterised by having at least one mutation in at least one gliadin target sequence selected from SEQ ID Nos 1 to 24, 790 and 792 to 803, wherein preferably said mutation is an insertion and/or deletion and wherein preferably said mutation is introduced using targeted genome modification. Preferably, said plant is obtained by transfecting at least one plant cell with at least one nucleic acid construct as described herein or at least one sgRNA molecule as described herein in the seeds of said plant, producing seeds from said plant and preparing a food composition from said seeds.

In another aspect of the invention, there is provided a method for modulating an immune response to gliadins and/or gluten or affecting or modulating a T-cell response to gluten in a subject, the method comprising providing a diet of a food composition as described herein to a subject in need thereof.

In a final aspect of the invention, there is provided a method of genome modification comprising introducing double-strand breaks at two or more selected sites in at least one gene of at least one of alpha-, gamma- and/or omega gliadin of a plant cell by providing said cell with a clustered, regularly interspaced, short palindromic repeats (CRISPR)-associated Cas endonuclease and a sgRNA as described herein. Preferably said sites are within the target sequences defined in SEQ ID Nos 1 to 24, 790 and 792 to 803.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid construct/RNA molecule of interest. The term "plant" also encompasses plant cells, suspension cultures, protoplasts, callus tissue, embryos, meristematic regions, gametophytes, sporophytes, pollen and microspores, again wherein each of the aforementioned comprises the gene/nucleic acid construct/RNA molecule of interest.

The invention also extends to harvestable parts of a mutant plant of the invention as described above such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, flour, starch or proteins. The invention also relates to food products and food supplements comprising the plant of the invention or parts thereof.

The wheat plant is selected from the list that includes, but is not limited to, *Triticum aestivum, T. aethiopicum, T. araraticum, T. boeoticum, T. carthlicum, T. compactum, T. dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii* and *T. zhukovskyi.*

According to another embodiment the various aspects of the invention described herein, the plant is of the species *Triticum aestivum* or *Triticum turgidum*. According to another preferred embodiment, the plant belongs to the cultivar Bobwhite or the cultivar THA53 or the cultivar Don Pedro. More preferably, the cultivars BW208 (Bobwhite) and THA53, which belong to the wheat species *Triticum aestivum* L. ssp *aestivum*, and the variety Don Pedro, which belongs to the wheat species *Triticum turgidum* L. ssp durum, are selected.

Bobwhite is the name of the cultivar obtained from the International Maize and Wheat Improvement Center (CIMMYT). BW208 is a Bobwhite lines. Don Pedro (DP) is a hard wheat variety, also from CIMMYT. TAH53 is an advanced breeding line from the International Maize and Wheat Improvement Center (CIMMYT).

A control plant as used herein is a plant, which has not been modified according to the methods of the invention. Accordingly, the control plant does not have a mutation in at least one nucleic acid sequence of alpha-, gamma- and/or omega gliadins as described herein. In one embodiment, the control plant is a wild type wheat plant. In another embodiment, the control plant is a plant that does not have a mutant alpha-, gamma- and/or omega gliadin nucleic acid sequence as described here, but is otherwise modified. The control plant is typically of the same plant species, preferably the same ecotype or the same or similar genetic background as the plant to be assessed.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification, including reference to sequence database identifiers, are incorporated herein by reference in their entirety. Unless otherwise specified, when reference to sequence database identifiers is made, the version number is 1.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLE

Wheat is one of the most widely grown crops in the world and a major component of the human diet. Wheat grain contains gluten proteins, which are responsible for the unique viscoelastic properties of wheat-derived foods; however, they also trigger certain pathologies in susceptible individuals. Amongst these, the α-gliadin family is the main protein group associated with the development of celiac disease and non-celiac gluten sensitivity, which affect more than 7% of the Western population[1,2]. In bread wheat, α-gliadins are encoded by approximately 100 genes and pseudogenes[3] organized in tandem at the Gli-2 loci of chromosomes 6A, 6B, and 6D. Traditional mutagenesis and plant breeding have failed to obtain low immunogenic wheat varieties for celiac patients. Here, we show that CRISPR/Cas9 technology can be used to precisely and efficiently reduce the amount of α-gliadins in the seed kernel, providing bread and durum wheat lines with reduced immunoreactivity for gluten-intolerant consumers.

Figure 4:
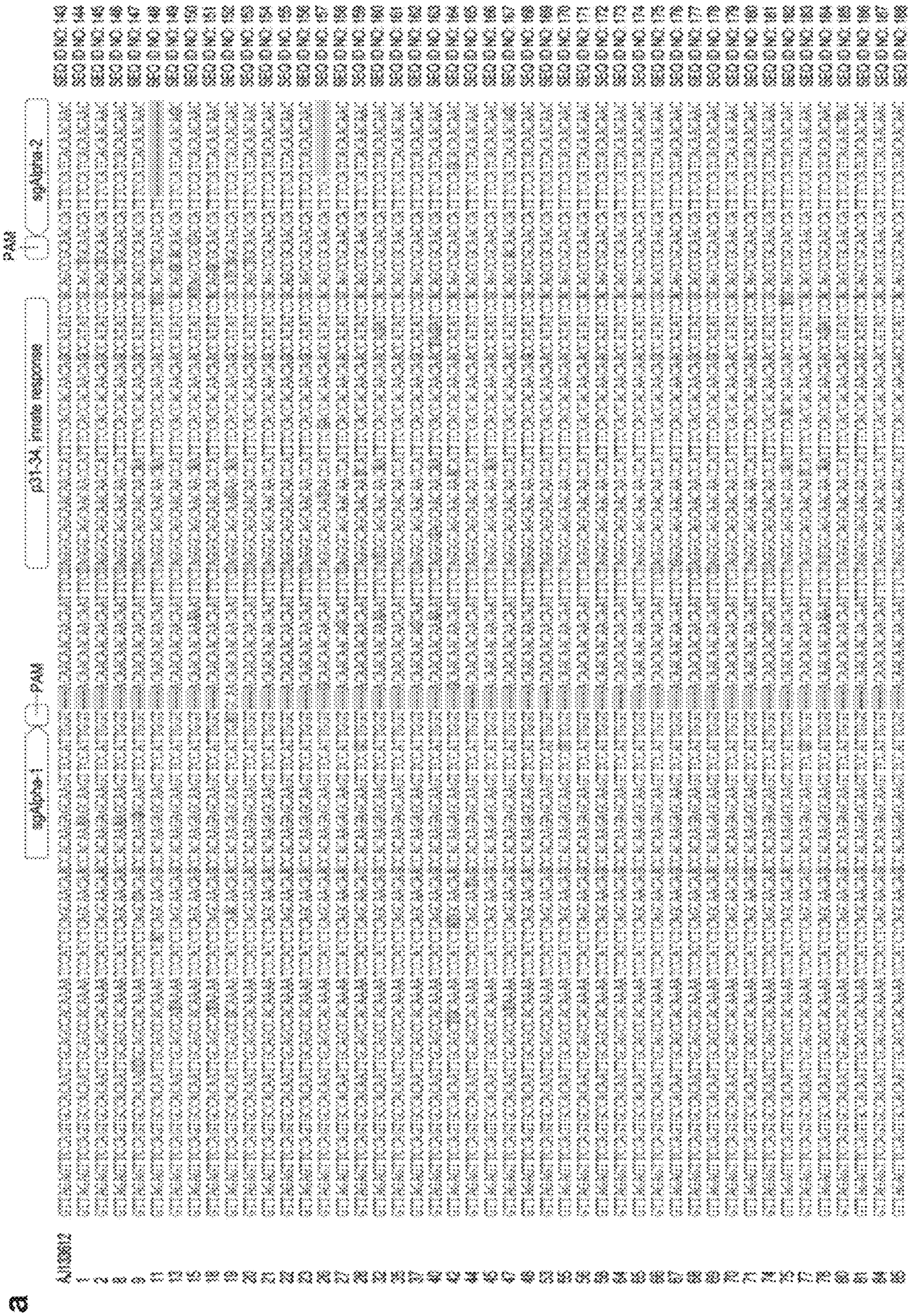
FIG. 4 shows alignments of the highly-represented α-gliadin genes detected by Illumina sequencing (accounting for nearly 85% of the total reads) in the wild type lines of bread wheat (a) cv BW208, (b) cv TAH53, and (c) durum wheat cv DP.
Figure 4:
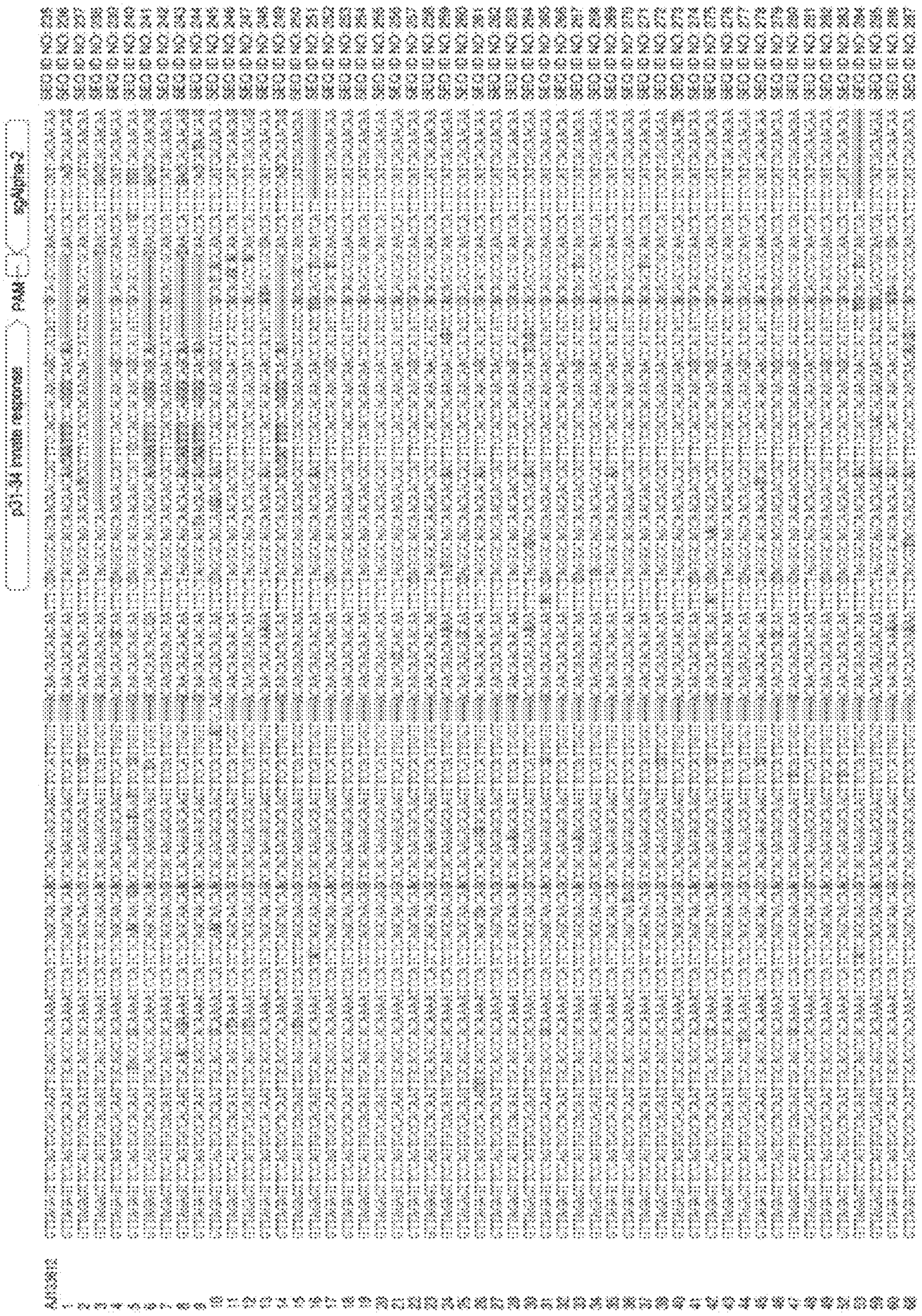
Figure 4:
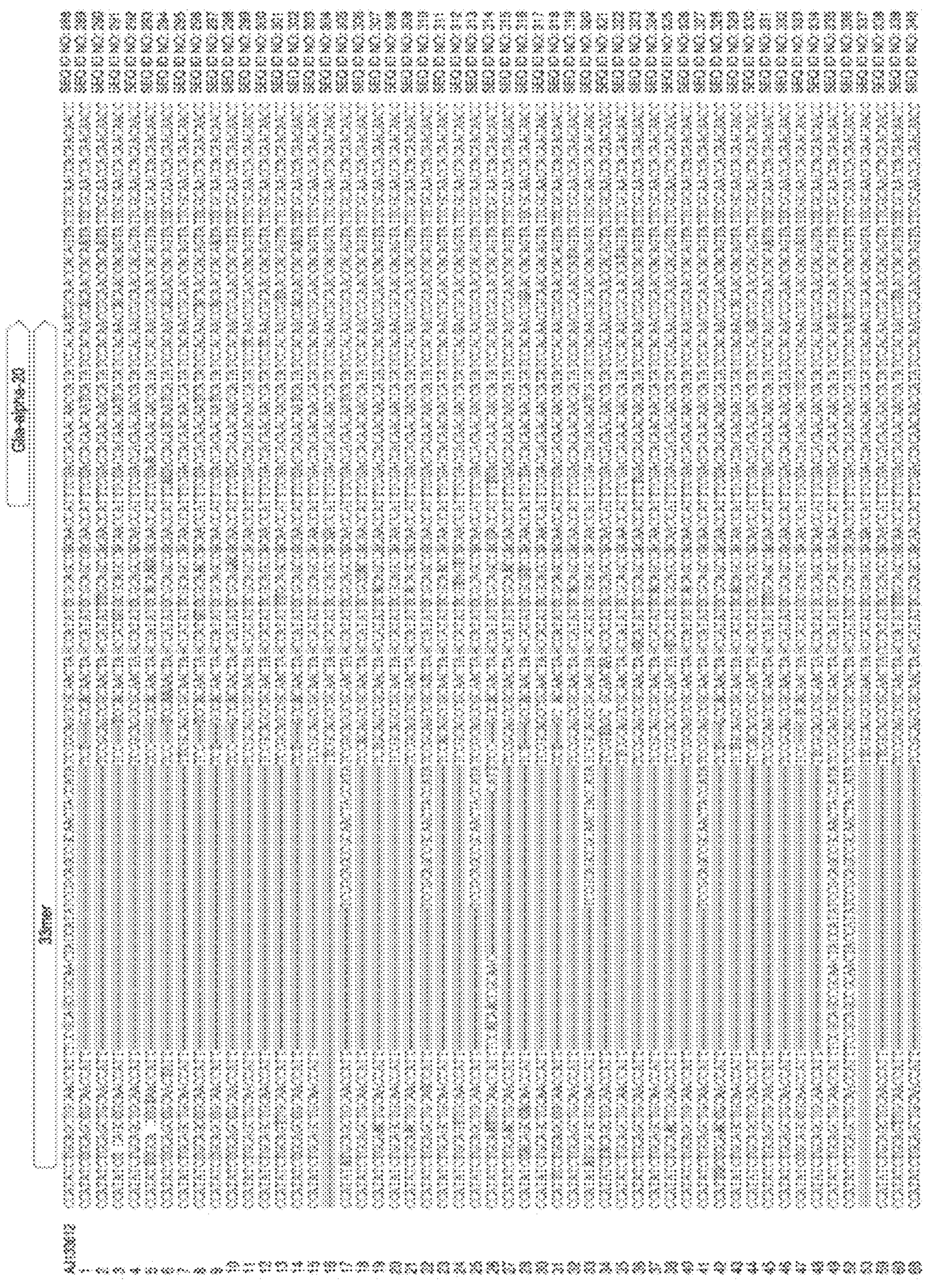
Figure 4:
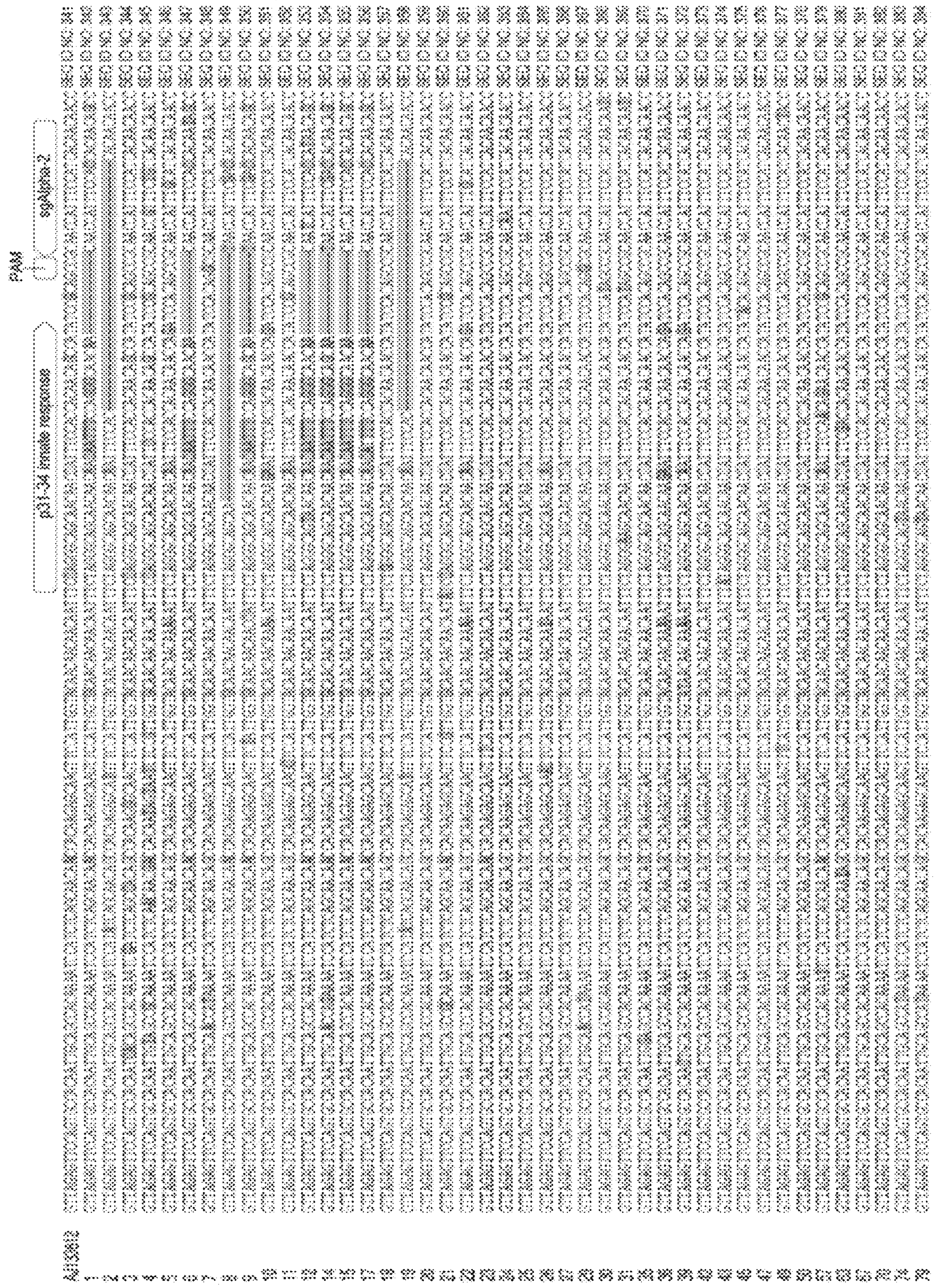
Figure 5:
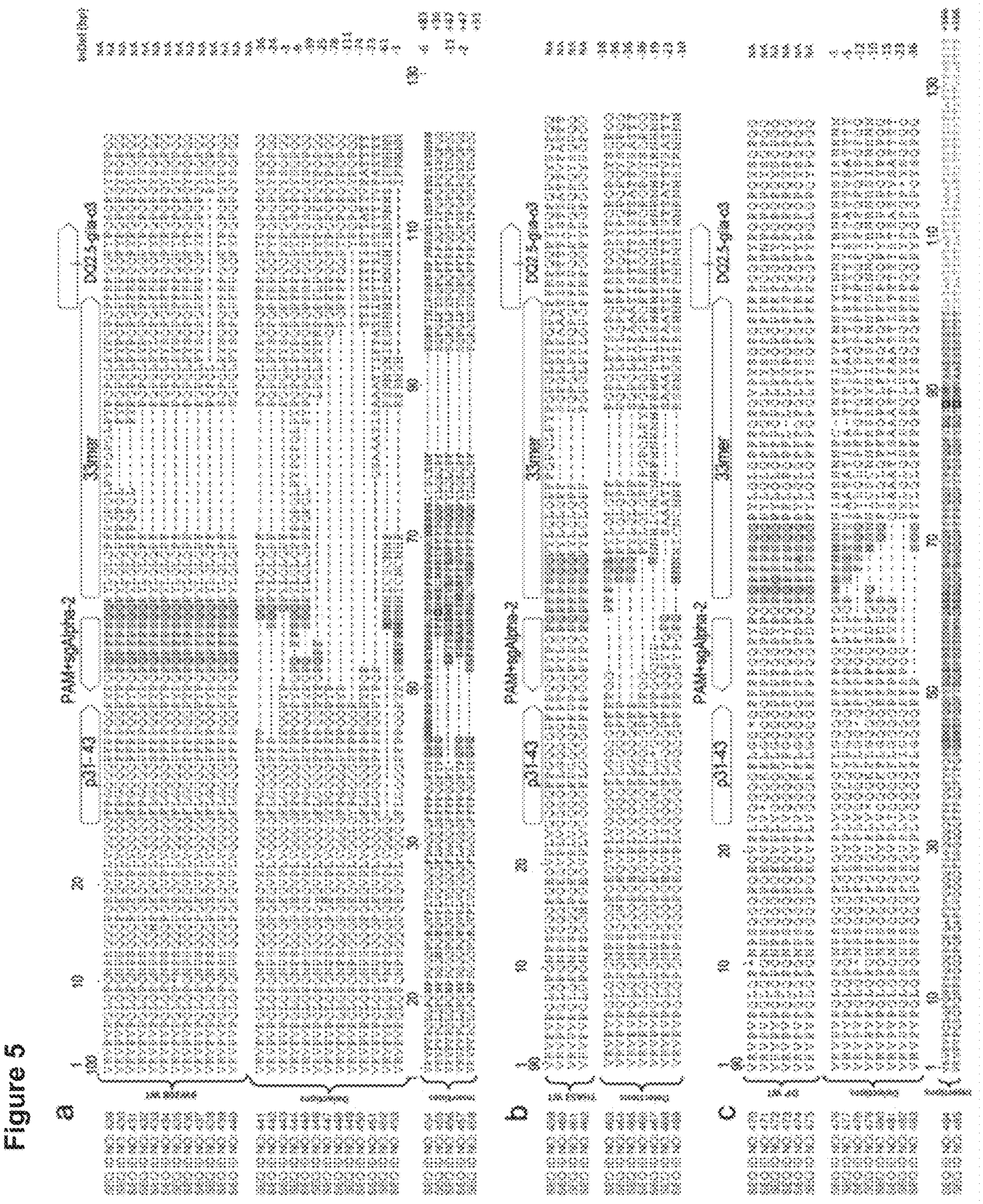
FIG. 5 shows protein alignments of the highly-represented α-gliadin genes in the wild type lines of bread wheat cv BW208 (a) and cv TAH53 (b), and durum wheat cv DP (c). Comparisons are made with the most frequent deletions in mutant lines of bread wheat cv BW208, cv THA53, and durum wheat cv DP, and insertions in mutant bread wheat cv BW208 and durum wheat cv DP.
Figure 6:
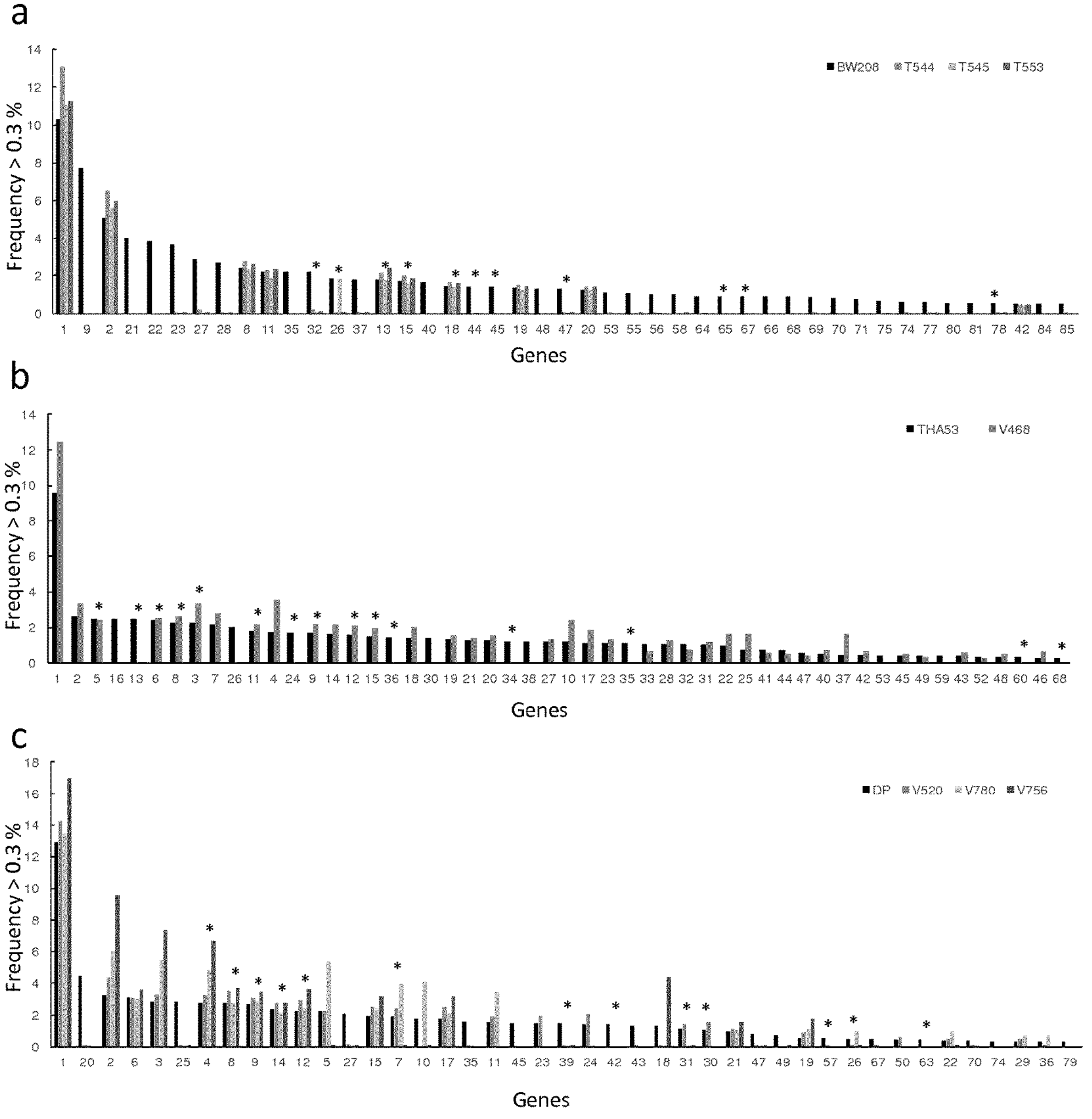
FIG. 6 shows the estimated α-gliadin genes present in the wild type lines and mutated in the mutant lines by sgAlpha-2. A minimum frequency threshold of 0.3% for each genotype was considered. The set of genes are different for each genotype. Gene numbers are assigned by the clustering software and are different within each genotype. (a) For BW208, 45 α-gliadin genes were found in the wild type and 35 (77.8%) were mutated in the T544 and T553 genotypes. (b) For THA53, the estimated number of α-gliadin genes was 52, of which 13 (25%) were mutated in the V468 genotype. (c) For DP, 43 α-gliadin genes were present in the wild type, of which 29 (67%) were mutated in the V756 genotype. Black asterisks indicate sequences containing stop codons within the sequenced amplicon.

To precisely modify the immunoreactive α-gliadin genes, we designed two sgRNAs (sgAlpha-1 and sgAlpha-2) (FIG. 1*a*) to target conserved regions adjacent to the coding sequence for the immunodominant epitope in wheat gluten, a protease-resistant, 33-amino acid peptide that contains six overlapping copies of three distinct, tandemly-organized epitopes (DQ2.5-glia-α1a, PFPQPELPY (SEQ ID NO: 780); DQ2.5-glia-α2, PQPELPYPQ (SEQ ID NO: 781); and DQ2.5-glia-α1b, PYPQPELPY (SEQ ID NO: 782))[4]. The CRISPR/Cas9 constructs were transformed into two bread wheat (BW028 and TAH53) and one durum wheat (DP) cultivars, resulting in twenty-one (15 bread wheat and 6 durum wheat) TO transgenic lines. DNA was isolated from leaves of 17 T1 transgenic plants (5 BW208, 4 TAH53, and 8 DP) and the corresponding wild type varieties, and PCR amplicons encompassing the sgAlpha-1 and sgAlpha-2 target sites were subjected to Illumina high-throughput DNA sequencing (FIG. 1*a*, FIG. 19). We observed considerable variability in the bread wheat and durum wheat wild type sequences, due to randomly distributed SNPs and differences in the number of encoded epitopes in the 33-mer region (FIG. 4). As expected, a number of sequences were pseudogenes with premature stop codons, and frameshift mutations in the C-terminus (FIG. 5). We found 45, 52 and 43 different α-gliadin sequences that were highly represented (frequencies higher than 0.3%) in BW208, THA53 and DP, respectively. Of these, 35, 13, and 29 were respectively mutated by CRISPR/Cas9 (FIG. 6). The mutation spectrum in the α-gliadins was characterized in the various T1 transgenic plants (FIGS. 1*b-d*, FIGS. 7-9 and FIG. 20). Due to the presence of the Cas9 expression vector in some of the mutant lines, the frequency of mutations observed might be overestimated, as a consequence of somatic mutations. However, in most cases we observed similar mutation frequencies in T1 plants generated from the same TO plant, with or without Cas9—i.e. V467 (+Cas9, 5.18% NHEJ) and V468 (−Cas9, 5.17% NHEJ), both derived from TO plant #20 (FIG. 20).

Figure 1:
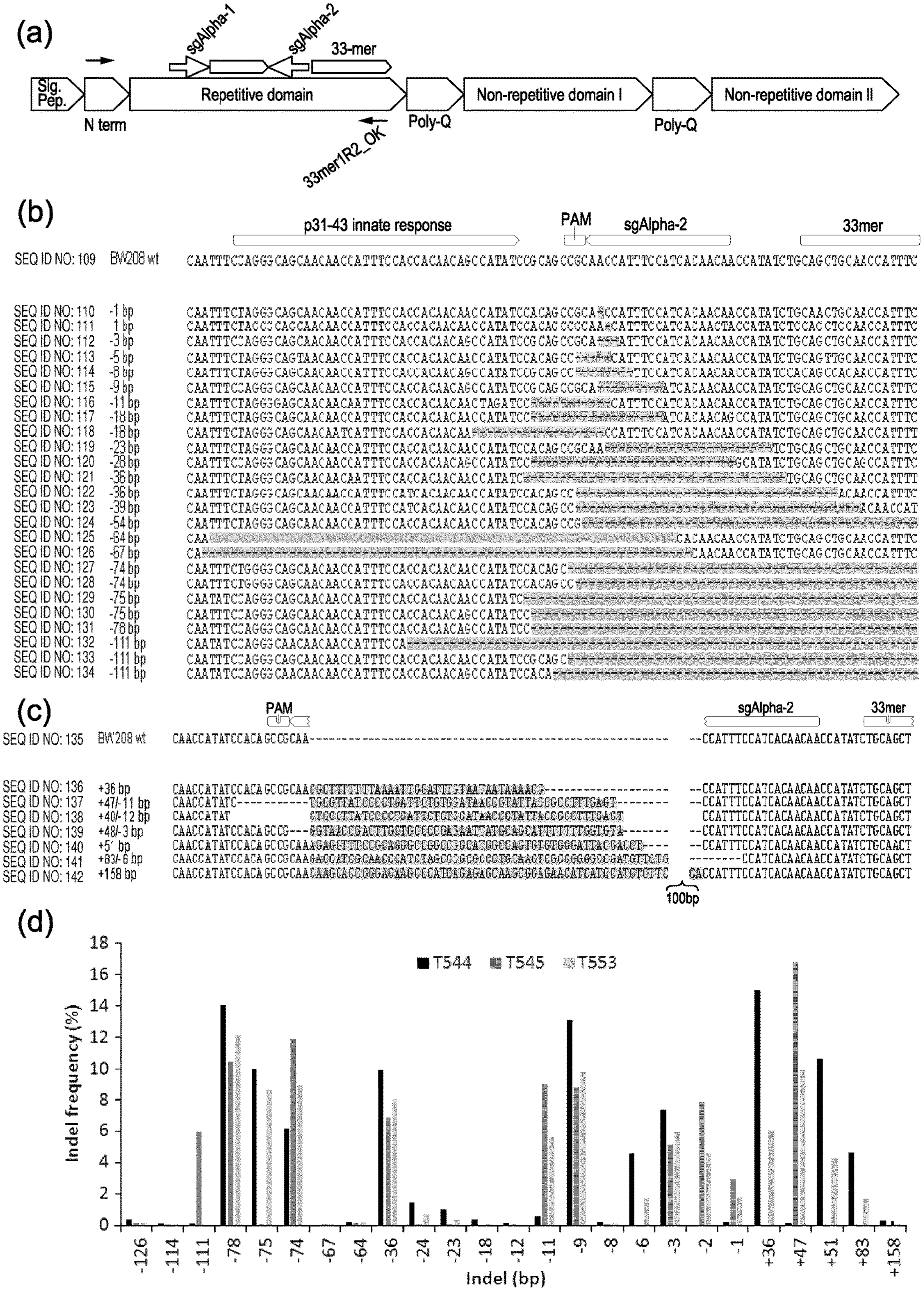
FIG. 1 shows gene editing of α-gliadins in bread wheat. (a) Schematic of a typical α-gliadin gene indicating the different protein domains. Two of the peptide sequences involved in gluten intolerance (p31-43 and the 33-mer) are represented by red arrows, whereas the target sequences for the sgRNAs (sgAlpha-1 and sgAlpha-2) are represented by blue arrows. Black arrows indicate primers used for Illumina sequencing. (b to d) Illumina sequencing of the α-gliadin genes of 3 T1 BW208 mutant lines (T544, T545, and T553) transformed with sgAlpha-2. (b) Alignment of the different deletion types found at the target locus of sgAlpha-2; (c) Alignment of the different insertions at the target locus of sgAlpha-2; and (d) frequency of the different type of insertions and deletions.
Figure 7:
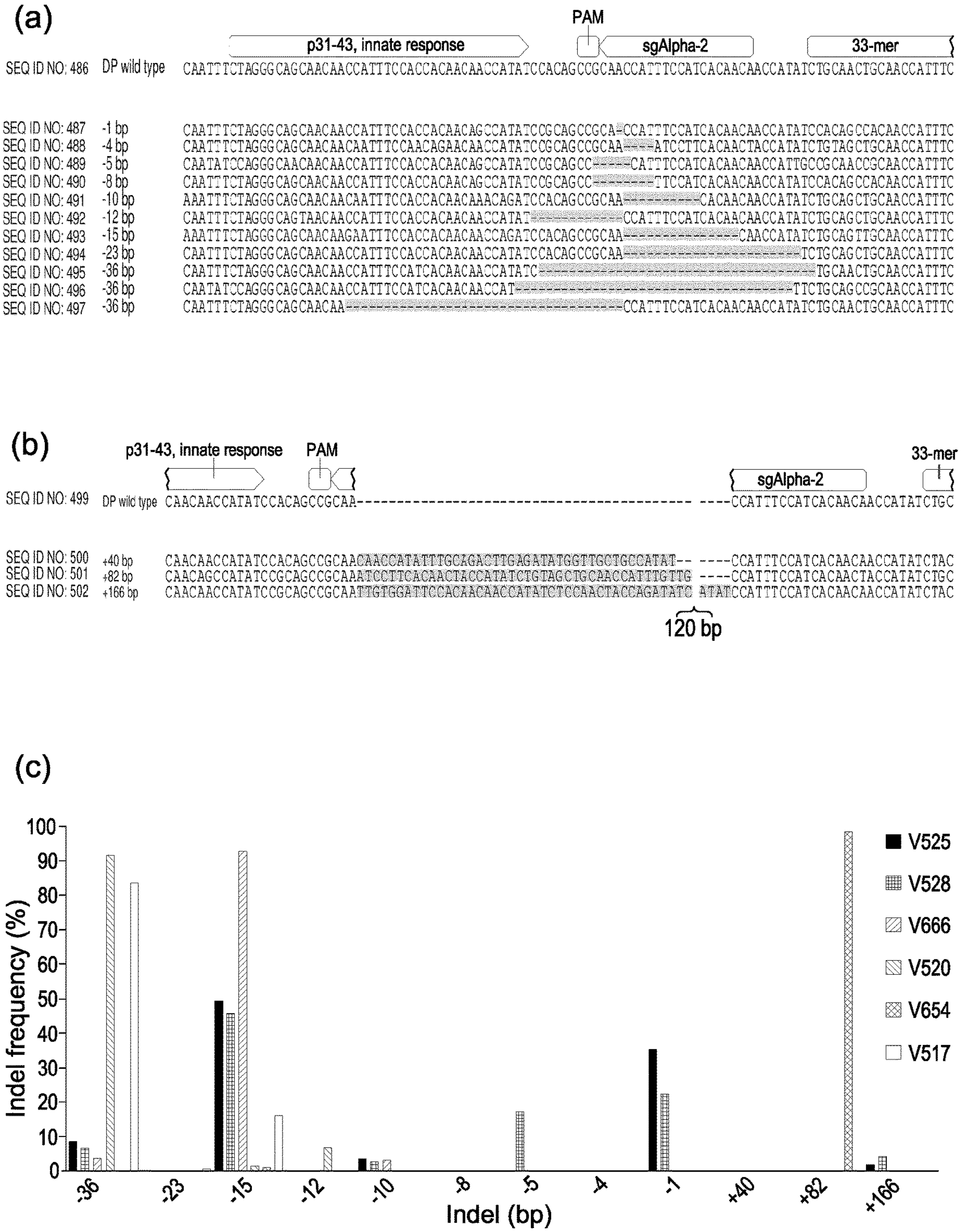
FIG. 7 shows gene editing of α-gliadins in durum wheat cv DP. Illumina sequencing of the α-gliadin genes of 6 T1 DP mutant lines transformed with sgAlpha-2. (a) Alignment of the different deletion types found at the target locus of sgAlpha-2; (b) Alignment of the different insertions at the target locus of sgAlpha-2; and (c) frequency of the different type of insertions and deletions.
Figure 8:
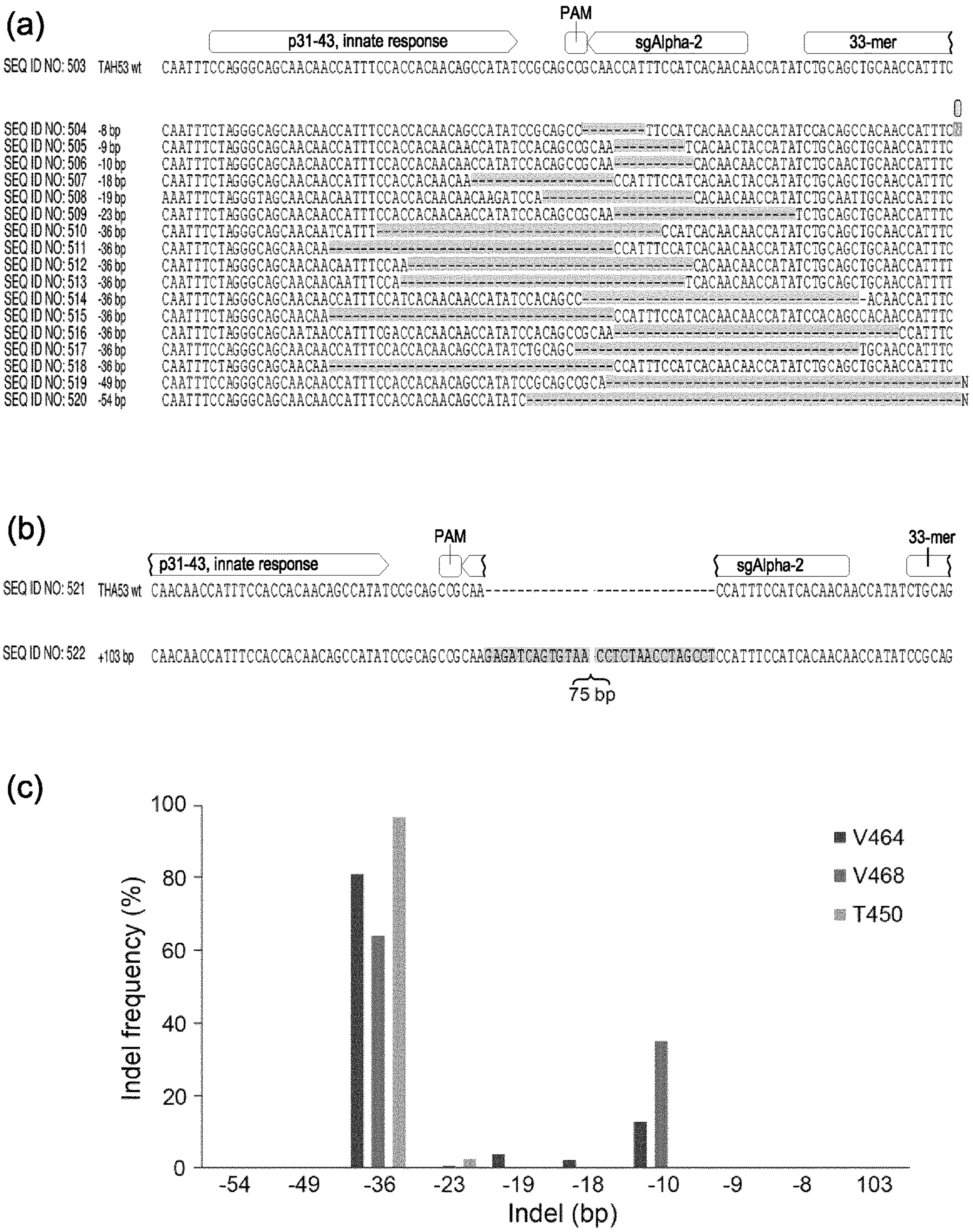
FIG. 8 shows gene editing of α-gliadins in bread wheat cv TAH53. Illumina sequencing of the α-gliadin genes of T1 TAH53 mutant lines transformed with sgAlpha-2. (a) Alignment of the different deletion types found at the target locus of sgAlpha-2; (b) Alignment of the different insertions at the target locus of sgAlpha-2; and (c) frequency of the different type of insertions and deletions.
Figure 9:
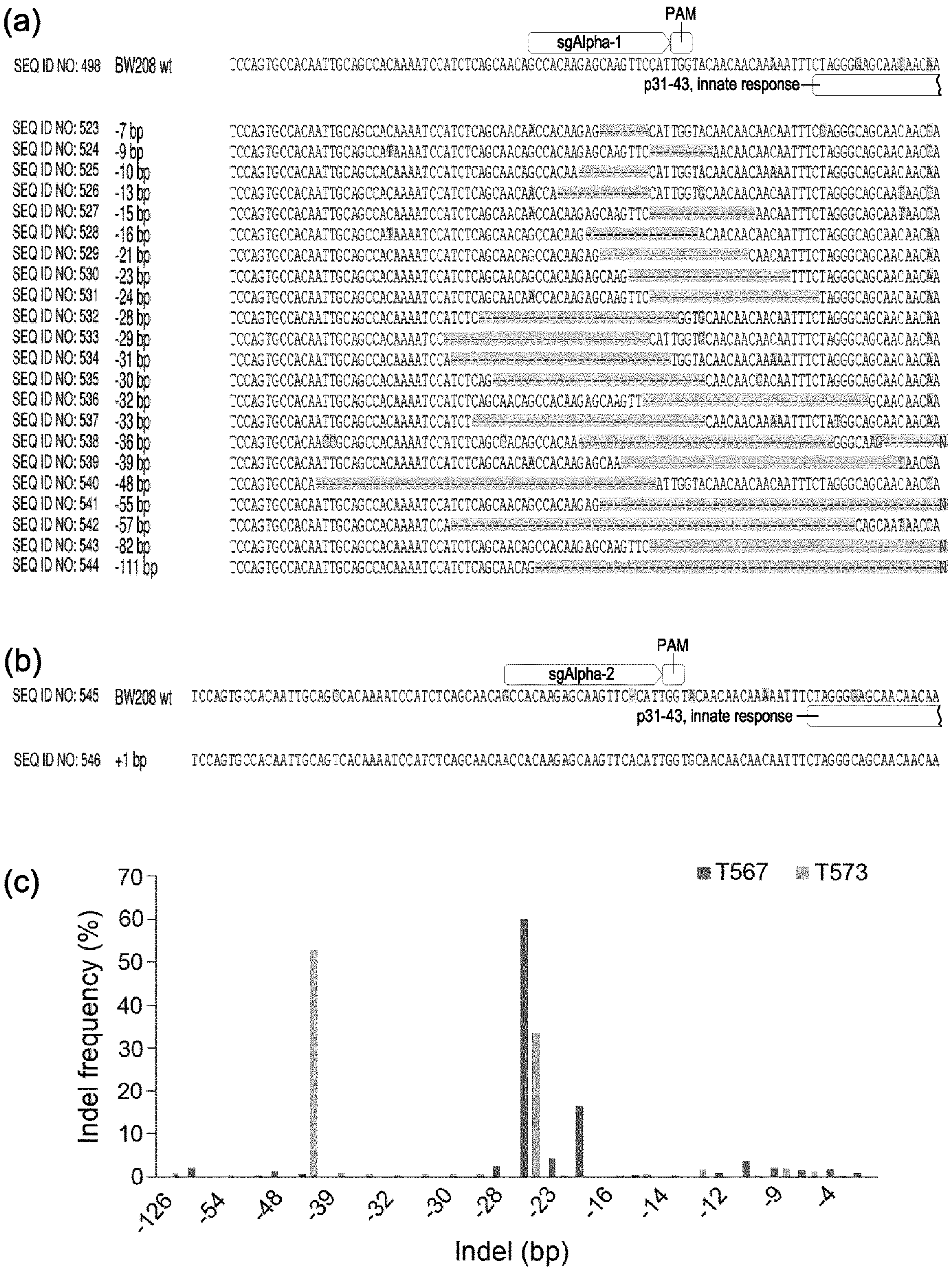
FIG. 9 shows gene editing of α-gliadins in bread wheat cv BW208. Illumina sequencing of the α-gliadin genes of 2 T1 BW208 mutant lines transformed with sgAlpha-1. (a) Alignment of the different deletion types found at the target locus of sgAlpha-1; (b) Alignment of the different insertions at the target locus of sgAlpha-1; and (c) frequency of the different type of insertions and deletions.
Figure 10:
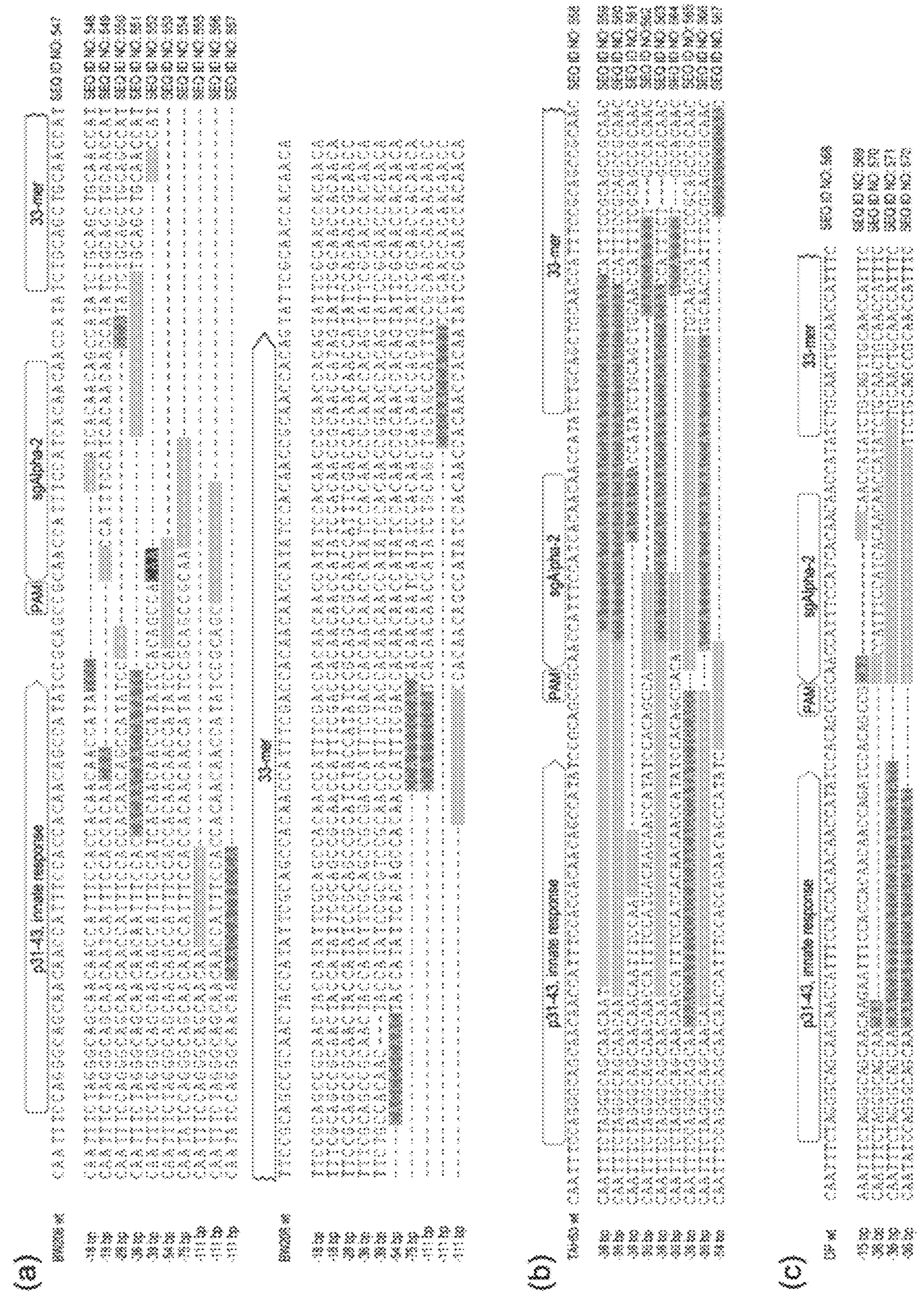
FIG. 10 shows microhomology-mediated repair of α-gliadins targeted with sgAlpha-2. Nucleotide alignment of Illumina sequencing reads of α-gliadins in (a) bread wheat cv BW208, (b) bread wheat cv TAH53, and (c) durum wheat cv DP. Regions of microhomology are highlighted in red and gray. sgAlpha-2 and PAM sequence are also indicated.

In general, sgAlpha-2 was more effective than sgAlpha-1. It should be noted that lower regeneration was observed in transgenic plants containing sgAlpha1 (0.3% transformation frequency) than plants with sgAlpha2 (1% transformation frequency), indicating possible toxic effects of sgAlpha-1. The highest mutation frequencies (62.3% to 75.1%) were observed in the BW208-derived lines transformed with sgAlpha-2 (FIG. 20). Three of these T1 lines (T544, T545, and T553) had insertions and deletions (indels) at the target site of between +36 and +158 bp and −1 and −126 bp, respectively (FIG. 1*b-d*). Line T545 had the highest mutation frequency of all analyzed lines: ~75% of the sequence reads had indels (FIG. 20). Transgenic lines of cv DP and cv THA53 showed lower indel frequencies, ranging between 1.50-14.77% and 5.16-7.86%, respectively. Interestingly, the typical −1 bp deletion normally observed with CRISPR/Cas9 was very frequent in two of the DP sgAlpha-2 lines (22.4-35.6%), but only represented 0.18-2.9% of the mutations found in the BW208 sgAlpha-2 lines (FIG. 1, FIG. 7). The −1 bp deletion was not found in the THA53 lines or in the sgAlpha-1 lines. The +1 bp insertion, also reported as a typical mutation of CRISPR/Cas9, was only found at low frequency in one of the sgAlpha-1 lines. A possible explanation for this observation is the preference of certain types of deletions due to microhomology-mediated repair. The target sites of sgAlpha-1 and sgAlpha-2 are highly repetitive, and as shown in FIG. 10, repeats between 3 bp and 36 bp are commonly found flanking the targeted break. The repeats could explain the bias in favor of some of the most frequent mutations observed, such as the −75 bp and −11 bp deletions in BW208 sgAlpha-2 lines, the −15 bp deletion in DP sgAlpha-2 lines, and the −36 bp deletion in all BW208, TAH53, and DP lines. DNA insertions represented up to 19% of the total indels (Line T544, FIG. 20), and they were found to be either fragments of the transformation vectors or other α-gliadin genes, probably inserted by microhomology-mediated repair. These results demonstrate that high mutation frequency and specificity can be achieved using CRISPR/Cas9 to modify complex genomic loci such as the α-gliadin gene family in bread and durum wheat.

Figure 11:
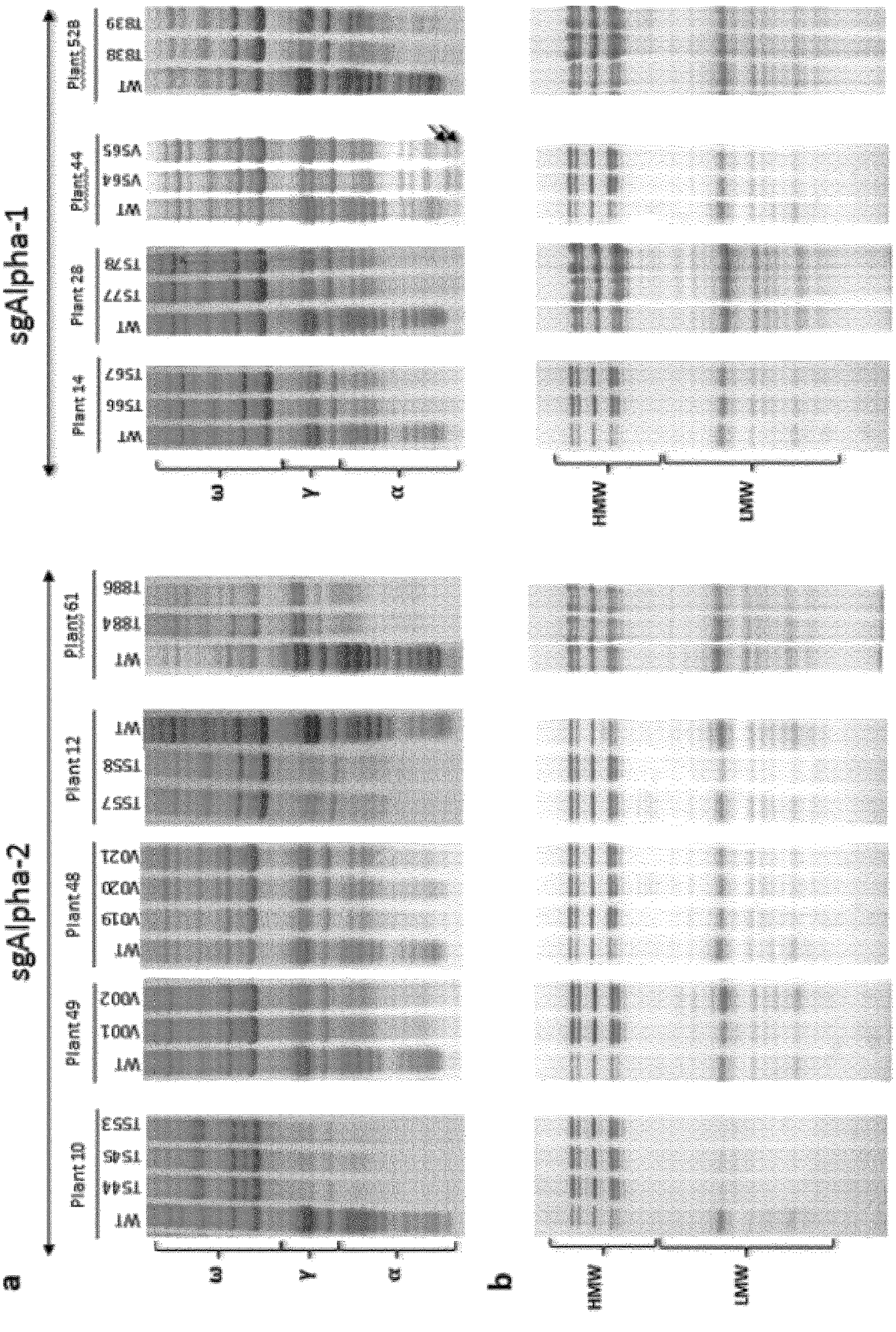
FIG. 11 shows gliadin and glutenin protein fractions analyzed by A-PAGE and SDS-PAGE from T1 half-seeds derived from TO lines transformed with sgAlpha-1 and sgAlpha-2 constructs. (a) A-PAGE of gliadin profile of T1 half-seeds mutant lines derived from BW08 lines. Migration of α-, γ-, ω-gliadin protein bands are outlined by brackets. Arrows indicate new additional bands present in some lines but not in the wild type. (b) SDS-PAGE of glutenins for the same T1 lines in (a). Migration of high molecular weight (HMW) and low molecular weight (LMW) glutenin subunits are outlined by brackets. (c) A-PAGE of the gliadin profile in T1 half-seeds mutant lines derived from THA53 lines. Arrows indicate new additional bands present in some lines but not in the wild type. (d) SDS-PAGE of glutenins for the same T1 lines in (c). (e) A-PAGE of gliadin profile of T1 half-seeds mutant lines derived from DP lines. Arrows indicate new additional bands present in some lines but not in the wild type. (f) SDS-PAGE of glutenins for the same T1 lines in (e). Note that A-PAGE analysis is not a quantitative test, and intensity differences observed in the gels might be explained in part by differences in the amount of protein loaded and/or by differences in the staining/distaining process. Some tracks are not continuous and were spliced together.
Figure 11:
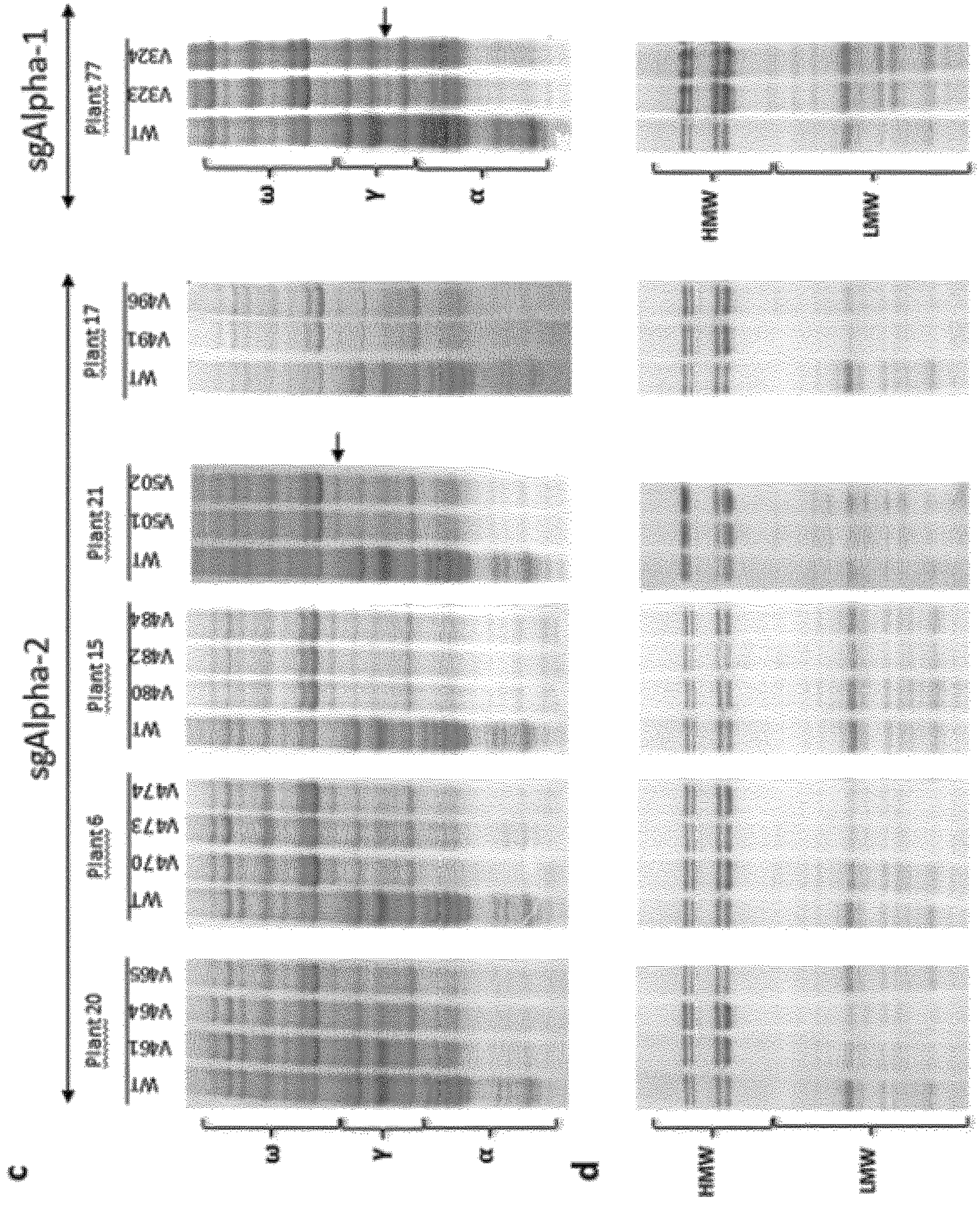
Figure 11:
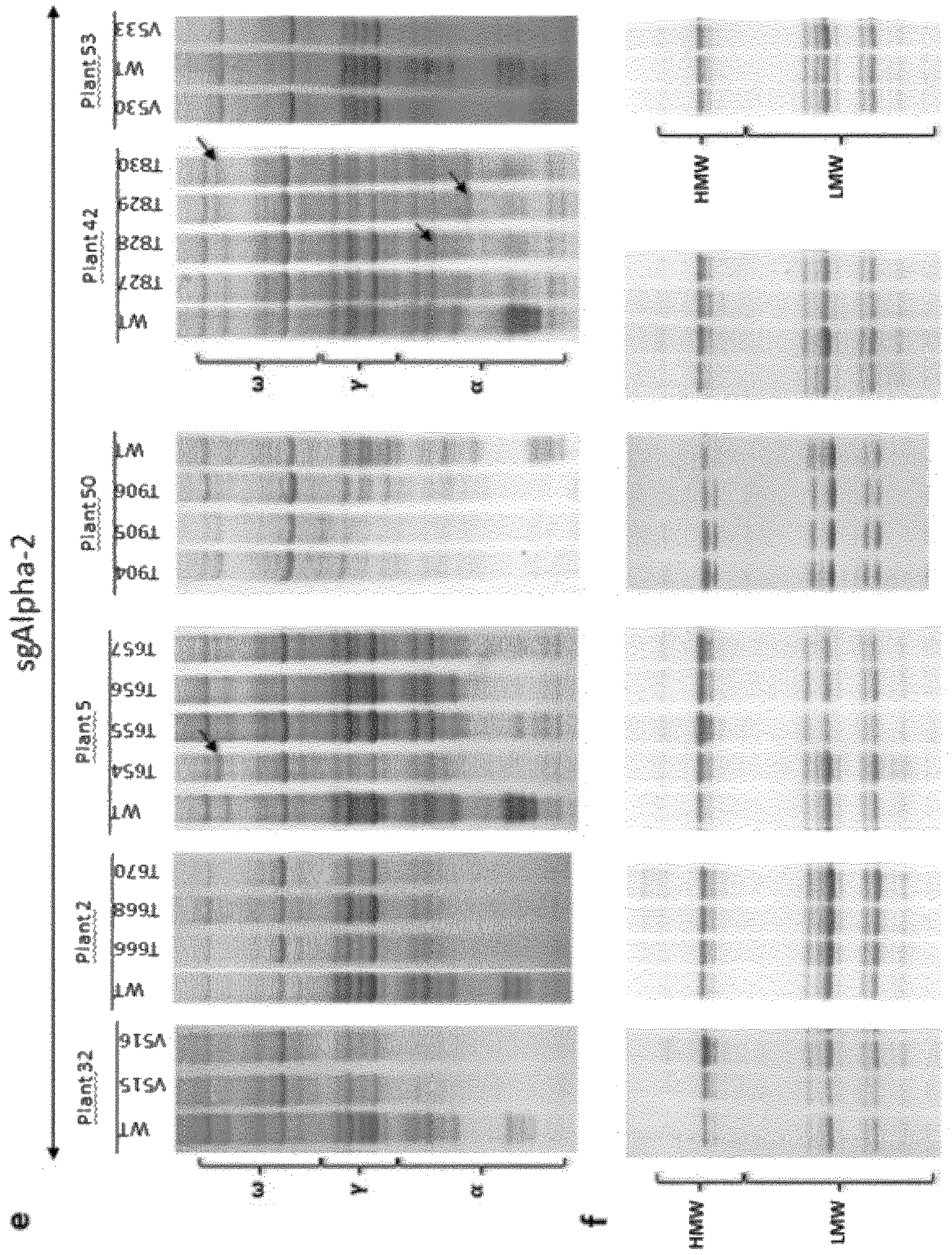

To assess the impact of the observed mutations on seed protein composition, gliadin and glutenin content in T1 half seeds was qualitatively assessed by A-PAGE and SDS-PAGE, respectively (FIGS. 2*a* and 2*c*, and FIG. 11). A-PAGE demonstrated that α-gliadins were strongly reduced in some of the bread and durum wheat T1 lines (e.g. plants #6, 10, 12, 15, 17, 32, and 50), and partially reduced in others (e.g. plants #14, 21, 28, and 48). The γ- and ω-gliadins were also strongly decreased in some lines (e.g. plants #6, 10, 12, 15, and 21). Additional, novel bands, especially in the region of the gel corresponding to the α-gliadins, were clearly visible in the A-PAGE gels, perhaps due to truncation of α-gliadin coding sequences by mutation (FIG. 11). Mass spectrometry (MALDI-TOF) confirmed the sharp reduction of α-gliadins in both sgAlpha-1 and sgAlpha-2 lines, with the sgAlpha-2 lines showing a greater reduction in the number of visible peaks (FIGS. 2*b* and 2*d*). As suggested by the Illumina sequencing results, sgAlpha-2 more effective reduced the α-gliadin content, particularly in the BW208 bread wheat lines. The glutenin profile for all lines was comparable to that of the wild type, however, differences in the intensity of the two glutenin fractions were observed, suggesting a mechanism for compensatory reduction in the abundance of these proteins in response to the reduction of α-gliadins (FIG. 11).

Figure 2:
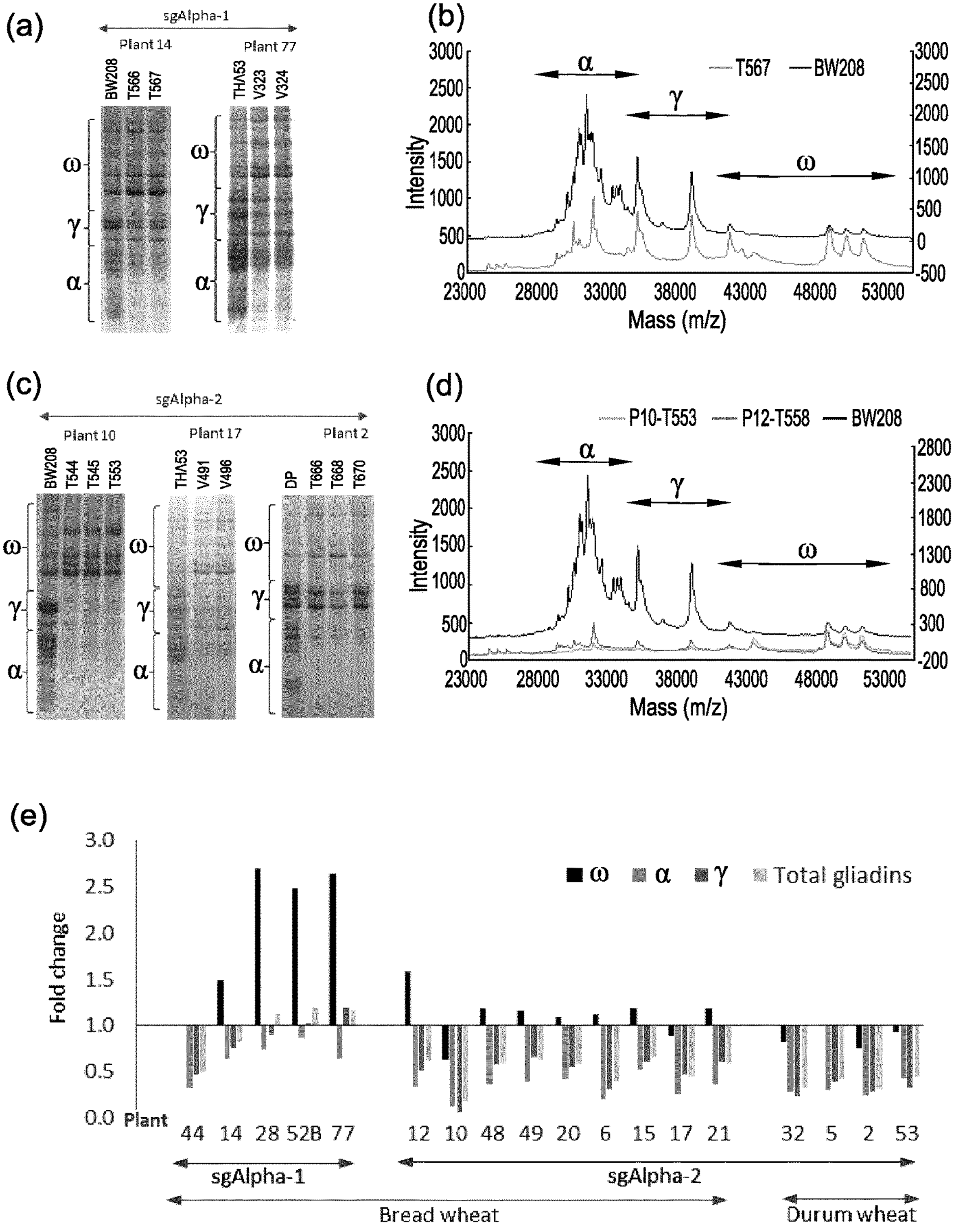
FIG. 2 shows the characterization of sgAlpha-1 and sgAlpha-2 mutant plants. (a) A-PAGE of gliadins from sg Alpha-1 T1 half-seeds (named as T566 and T567 lines) derived from T0 plant 14, and V323 and V343 (from TO plant 77) and the corresponding wild type lines BW208 and THA53. Migration of α-, γ-, ω-gliadin protein bands are outlined by brackets (b) MALDI-TOF analysis of the same gliadin extract in (a) from T567 track and the BW208 wild type. Values are in absolute intensity. Left axis corresponds to T567 and the right axis to the BW208 line. The corresponding range of masses (m/z) for α-, γ-, ω-gliadins are indicated by arrows. (c) A-PAGE of gliadins from sgAlpha-2 T1 half-seeds (named as T544, T545 and T553 lines) from TO plant 10, V491 and V496 (plant 17), T666, T668 and T670 (plant 2) and the wild type lines BW208, THA53 and DP. (d) MALDI-TOF analysis of the same gliadin extracts in (a) from T553 track (plant 10) and T558 (plant 12, FIG. 11), and the BW208 wild type. (e) Bar graph of fold change of α-, γ-, ω-, and total gliadin fractions in bread and durum wheat transformed with sgAlpha-1 and sgAlpha-2. Values for each plant were normalized by values of the corresponding wild type lines. Note that A-PAGE analysis is not a quantitative test, and intensity differences observed in the gels might be explained in part by differences in the amount of protein loaded and/or by differences in the staining/distaining process.

Encouraged by these results, HPLC analysis was performed to accurately quantify and characterize the different groups of gliadins and glutenins (FIG. 2 and FIG. 21). As expected, α-gliadin content was significantly reduced in most of the transgenic lines compared to the wild type (32-82% reduction), especially in the bread and durum wheat lines transformed with sgAlpha-2. The γ-gliadins were also significantly reduced by 25-94% in 15 out of the 18 T1 lines analyzed, whereas the ω-gliadins showed the greatest variability: ω-gliadins were not affected in all four durum wheat lines, significantly up-regulated (2-3 fold) in all four bread wheat sgAlpha-1 T1 lines (FIG. 2*e*), and down-regulated by 33% in bread wheat Plant 10. Interestingly, this line had the highest reduction in α-gliadins (82%) and γ-gliadins (92%), and consequently showed the highest overall gliadin reduction (82%). Amongst the durum wheat lines, Plant 2 had the highest overall gliadin reduction (69%). The reduction in the gliadin content promoted a compensatory effect in glutenins, increasing the HMW fraction, especially in the BW208 and THA53 bread wheat lines (FIG. 21). The LMW fraction was significantly reduced only in Plant 10 and 32. Similar compensatory effects were observed previously[5] in wheat lines in which the α-, γ-, and ω-gliadins were down-regulated by RNAi. In those RNAi lines, compensatory effects provided wheat lines with no difference in the total protein content; however, changes in seed protein expression had important implications on the properties of the flour[6], as higher glutenin contents, particularly HMWs, are usually associated with stronger flours. The lines reported here show reduced total gliadin content (specifically the α-gliadins containing the 33-mer epitope), increased HMW-glutenins, and lower gli/glu ratios than the wild type.

Figure 3:
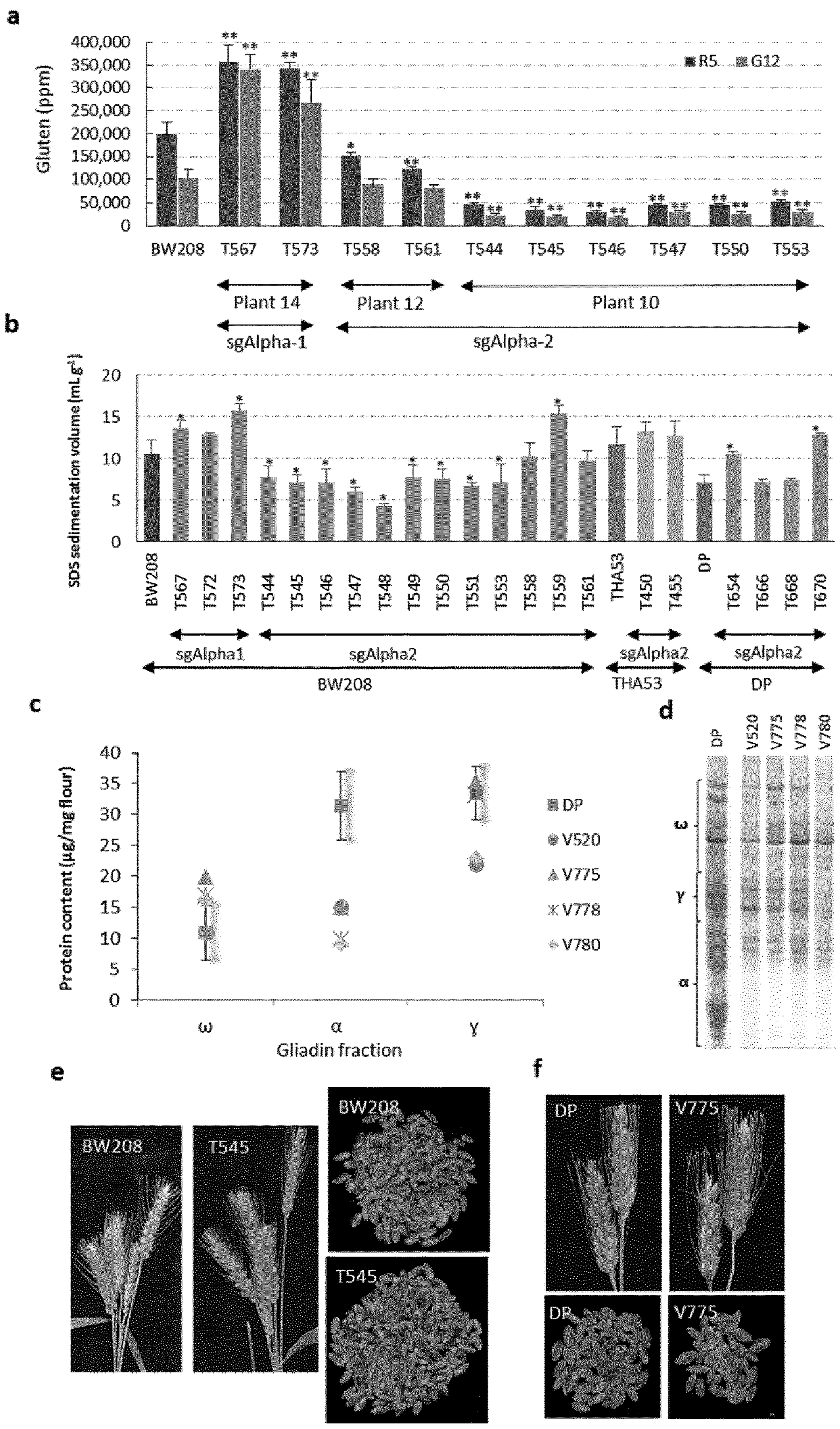
FIG. 3 shows an analysis of Immune-reactivity, SDS sedimentation volumes and gliadin profile of non-transgenic DP derived lines, and phenotype of sgAlpha derived lines. (a) Analysis of T2 seeds of the sgAlpha-1 and sgAlpha-2 mutant lines with the monoclonal antibodies (mAb) R5 and G12. Error bars, mean±s.d. Statistically significant differences between each mutant line and the wild type were denoted * $P<0.05$, ** $P<0.01$ (Tukey HSD All-Pairwise Comparisons Test) (b) Sodium dodecyl sulfate (SDS) sedimentation test expressed as $mLg^{-1}$. T2 and T3 seeds from each line were bulked and three independent biological replications analyzed. Error bars, mean±s.d. * Means are significantly different to wild types as determined by Dunnett's multiple comparisons at $P<0.05$. (c) Content of the omega, alpha, and gamma-gliadin fraction of the non-transgenic DP derived lines. Error bars, 5% Confidence Interval of the mean value of the wild type DP line. (d) A-PAGE of gliadins from half-seeds of the non-transgenic DP derived lines. Migration of α-, γ-, ω-gliadin protein bands are outlined by brackets. (e) Spikes and seeds of sgAlpha-2 BW208 mutant line in comparison with its wild type. (f) Spikes and seeds of sgAlpha-2 DP mutant line in comparison with its wild type.

To confirm that the altered gliadin content effectively reduced the immune reactivity of the flour, we analyzed the T2 seeds of the mutant lines with the monoclonal antibodies (mAb) R5 and G12 (FIG. 3). R5 is the mAb of choice in the food industry to quantify gluten content and detects a conserved domain (QQPFP) found in most gliadins (not only the ones that are immune reactive)'. The G12 mAb is more specific for detecting reactive epitopes, since it was developed against the 33-mer peptide. ELISA tests with both mAbs showed a strong reduction in gluten content in the sgAlpha-2 derived lines compared to that of the BW208 wild type. In those lines, we observed up to 85% reduction in gluten content (Line T546), and an average reduction of 66.7% and 61.7%, respectively with the R5 and G12 mAbs. However, both mAbs revealed an increase in the gluten content for lines with sgAlpha-1. These two lines have a higher ω-gliadin content—a consequence of the knock-down of the α-gliadins (FIGS. 21-22)—which could explain the observed increment in gluten content. Similar increases in gluten content when only the γ-gliadins were downregulated by RNAi were previously reported[9]. In total, these results demonstrate that gluten immunoreactivity can be significantly reduced by editing the α-gliadin genes containing the immunodominant 33-mer epitope.

Figure 12:
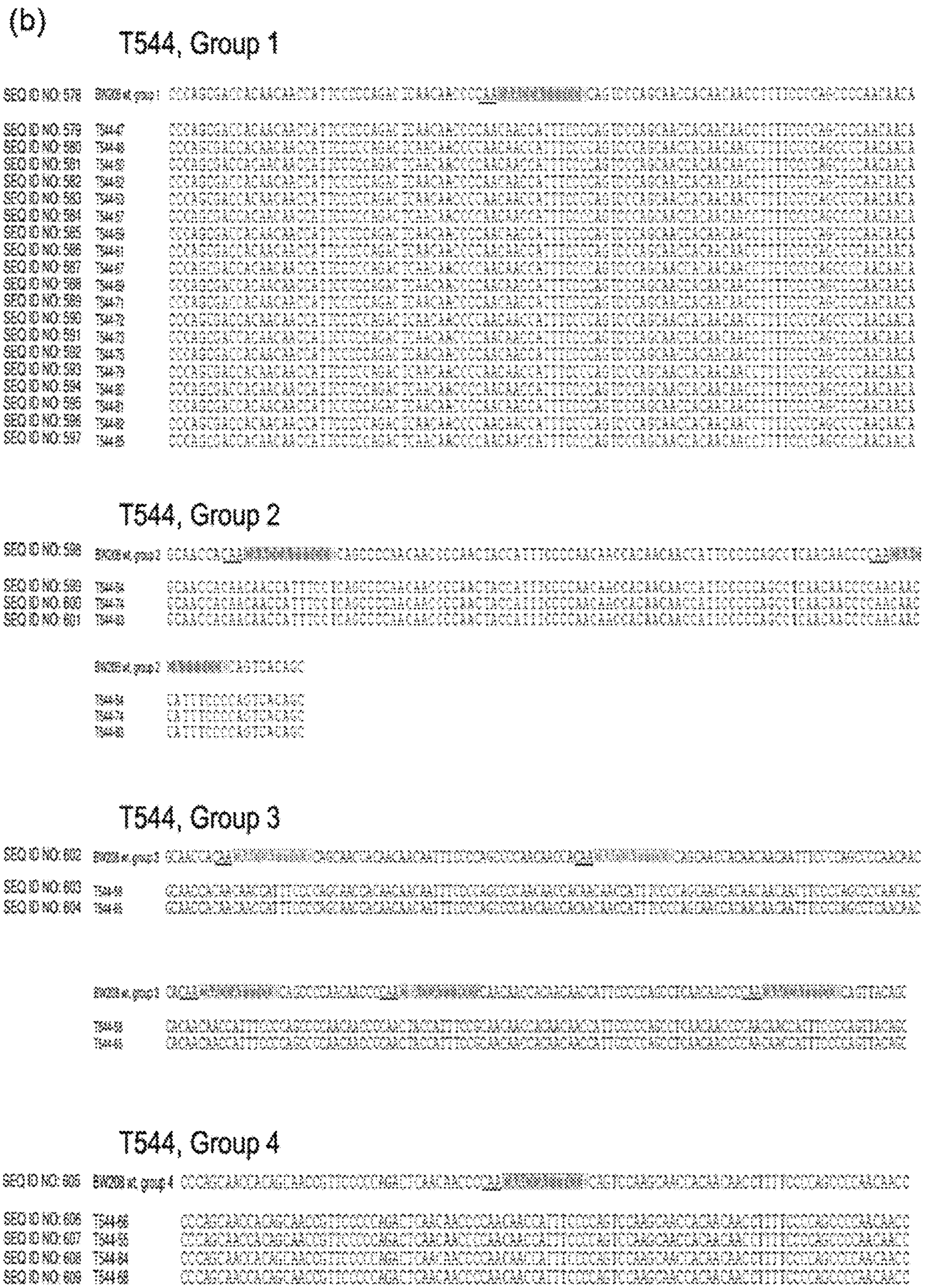
FIG. 12 shows off-target mutations detection in γ-gliadin genes of BW208 wild type and two T1 mutant lines. (a) BW208 wild type consensus sequences of the five main γ-gliadins groups obtained after Sanger sequencing of 35 clones. sgAlpha-1 and sgAlpha-2 potential target sequences (12 nt of the seed sequence with up to 1 mismatch) are highlighted in blue, with the PAM sequences underlined, and mismatches highlighted in red. (b) Sanger sequencing results of 28 γ-gliadins clones from the T1 mutant line T544 aligned to the corresponding γ-gliadin group described in (a). (c) Sanger sequencing results of 29 γ-gliadin clones from the T1 mutant line T545 aligned to the corresponding γ-gliadin group described in (a). No NGG PAM sequence was identified in any of the sgRNA sites.
Figure 12:
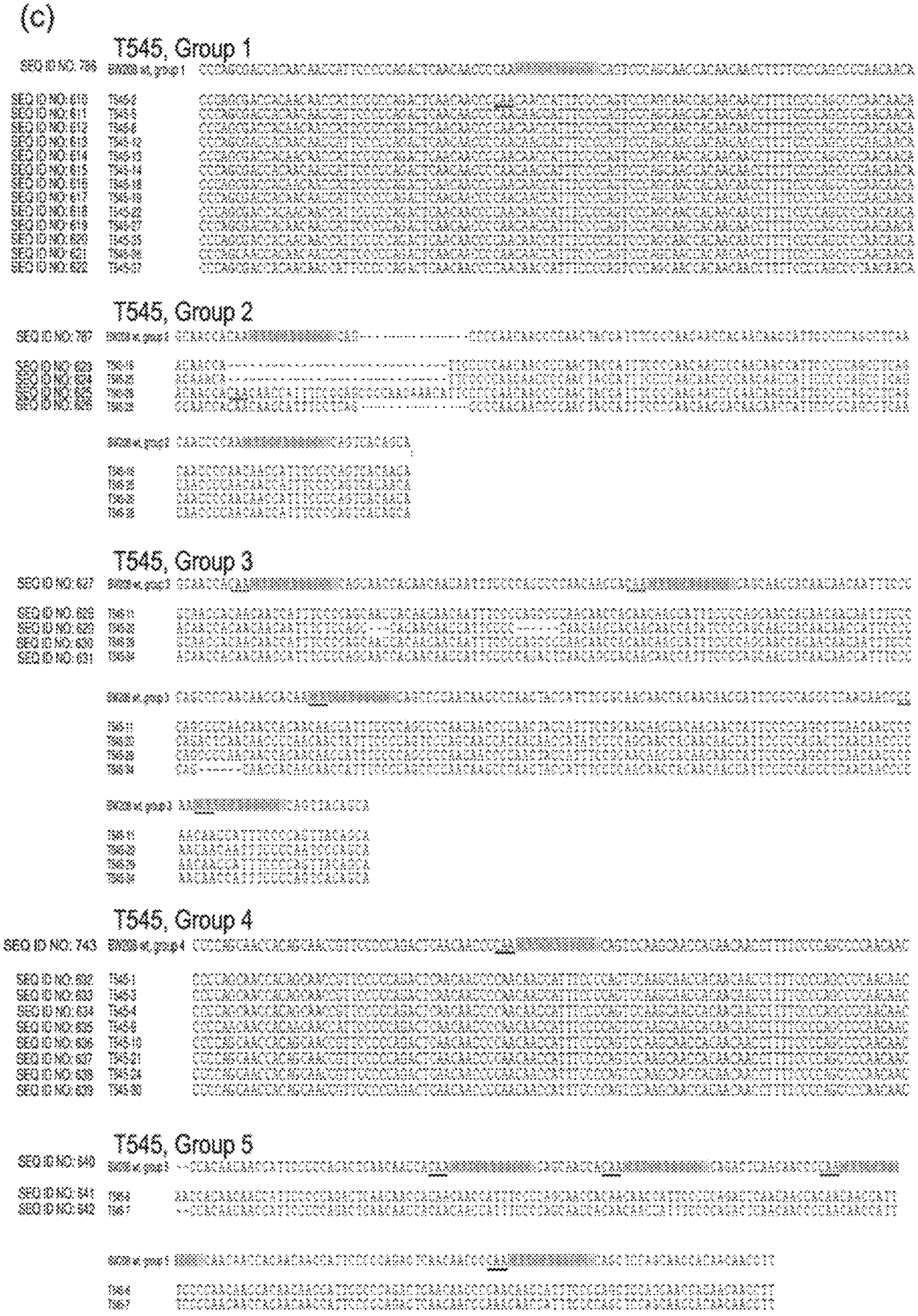
Figure 13:
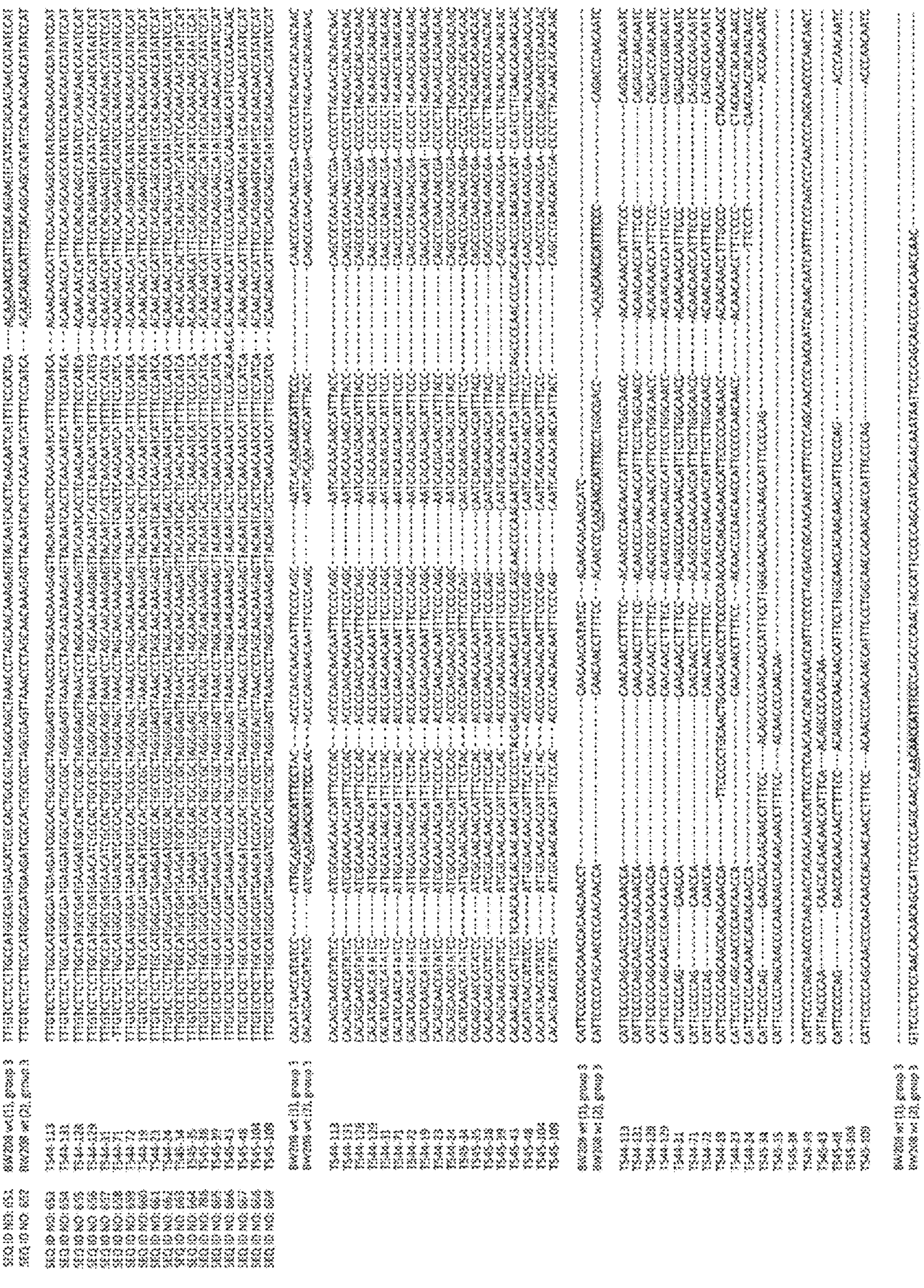
FIG. 13 shows off-target mutations detection in ω1,2-gliadin genes of BW208 wild type and two T1 mutant lines. Twenty-seven ω-gliadins clones were sequenced by Sanger sequence and aligned to one of the main four groups (α-d) observed in BW208 wild type. sgAlpha-1 and sgAlpha-2 potential target sequences (12 nt of the seed sequence with up to 1 mismatch) are highlighted in blue, with the PAM sequences underlined, and mismatches highlighted in red. No NGG PAM sequence was identified in any of the sgRNA sites.
Figure 13:
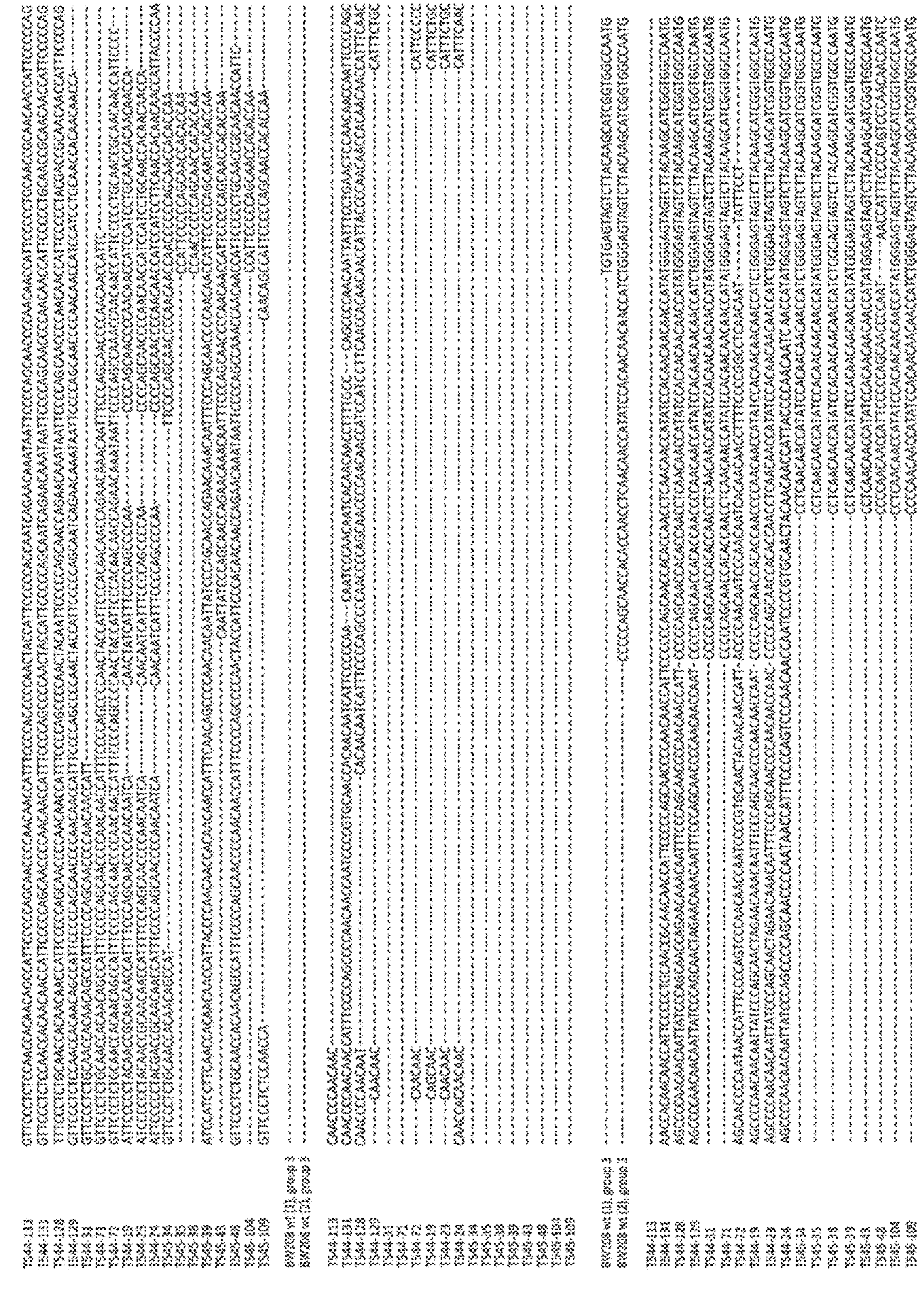
Figure 13:
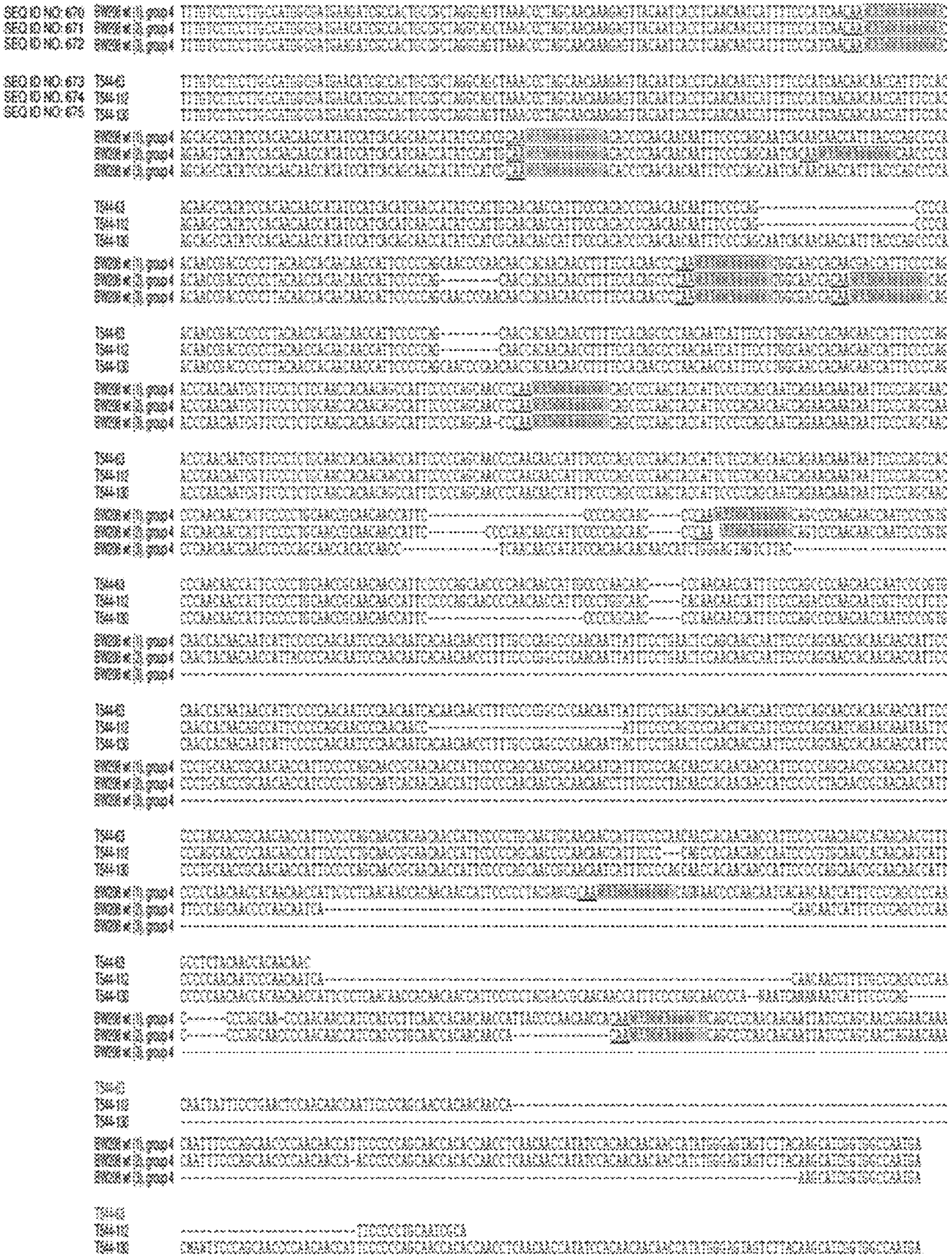

Once we had demonstrated the high efficiency of CRISPR/Cas9 to simultaneously mutate most of the α-gliadin genes, we next asked whether off-target mutations were occurring at other sites due to sgAlpha-1 and sgAlpha-2-mediated cleavage. First, we looked for possible off-target mutations in the γ- and ω-gliadin genes, since these proteins were reduced in the mutant lines. Sanger sequencing of fifty-seven clones containing γ-gliadin genes (FIG. 12) and forty-three clones with ω-gliadins genes—twenty-four ω1,2-gliadins (FIG. 13) and nineteen ω5-gliadins (FIG. 14)—showed no off-target mutations. These results were confirmed by in silico search of the sgAlpha-1 and sgAlpha-2 sequences (NGG PAM plus 12 nt seed sequence, allowing for up to 2 mismatches) in the wheat prolamin genes annotated in the GeneBank (FIG. 15*a*). Additional sequencing of 11-16 clones of amplified LMW from 3 T1 mutant lines (T544, T545, and T553) showed no mutation in the only potential target site identified (FIG. 15*b*). We therefore concluded that the observed decrease in the γ- and ω-gliadins and the glutenins in the mutant lines was not a consequence of off-target mutations. Rather, we speculate that antisense α-gliadin sequences could be expressed, resulting in the observed broad reduction of α-gliadin, as well as the downregulation of the other gliadin proteins. Antisense sequences of α-gliadins could originate in the mutant lines as a consequence of cleavage at two target sites and inversion of the intervening DNA sequence. We tried to detect such hypothetical inversions by predicting the inversion product and performing PCR assays (data not shown); however, none were detected in any of the tested lines.

Next, we expanded our search for off-target sites to the entire bread wheat genome (FIG. 15*c*). Amongst all potential off-target sites (41 for sgAlpha1 and 50 for sgAlpha2), only four were annotated genes: a putative MADS-box transcription factor (Traes_7BL_F621D9B9E), two genes with unknown function (Traes_2AS_D659E88E9.1, Traes_2AS_8FCC59363.1), and one gene with homology with α-gliadins (Traes_4AL_4FF5B8837). No mutations were identified in any of these genes in approximately 10 clones sequenced from each gene in the T1 mutant lines T544 (FIG. 15*d*), T545, and T553. Collectively, these results demonstrate the high specificity of the sgRNAs designed to target the α-gliadins. Further characterization of potential off-target sites in other non-annotated genes in the genome would be necessary to confirm the lack of undesired mutations.

We next examined whether the mutations were transmitted to the next (T2) generation. Illumina sequencing of 29 T2 plants, with and without Cas9, showed heritability of the mutations (FIG. 22). Confirming our observations in the T1 generation, the presence/absence of the Cas9 expression vector in T2 plants did not affect the mutation frequencies (FIG. 22), and we believe that the variability observed between different lines can be explained by 1) stable and somatic mutagenesis due to activity of Cas9 and 2) segregation of heterozygous stable mutations produced in the previous generations. T2 lines derived from TO plant #10 were selected for sequencing because they had the least amount of integrated DNA at the cut sites.

The phenotype observed in the prolamin (gliadins and glutenins) content was also inherited, as assessed by evaluating 25 different T2 lines (FIG. 23), and 16 T3 lines (FIG. 24) by RP-HPLC. This demonstrated that the low gluten trait is stable and heritable, and will enable its introgression into elite wheat varieties. As observed in T1 seeds, the HMW-glutenins were also increased in T2 and T3 seeds of mutant lines (FIGS. 23 and 24). The HMW fraction is a major determinant of the functionality of wheat flour. We assessed the bread-making quality of the mutant lines using the SDS sedimentation test by bulking T2 and T3 seeds from each line (FIG. 3*b*). Although some mutant lines showed higher SDS values (higher quality) than the wild type control, we observed significant reductions in the SDS values (lower quality) in the mutant lines with the greatest reduction of gliadins. However, in most cases SDS values in the sgAlpha2 lines were comparable to those of some RNAi lines previously reported showing 97% reduction in the gluten content[10]. Flour from those low gluten RNAi lines showed increased stability and better tolerance to over-mixing[6] and allowed the production of bread with baking and sensory properties comparable to those of normal wheat flour[11]. Consequently, one might expect that mutant lines reported here will produce flour of a good quality and bread-making performance.

Figure 17:
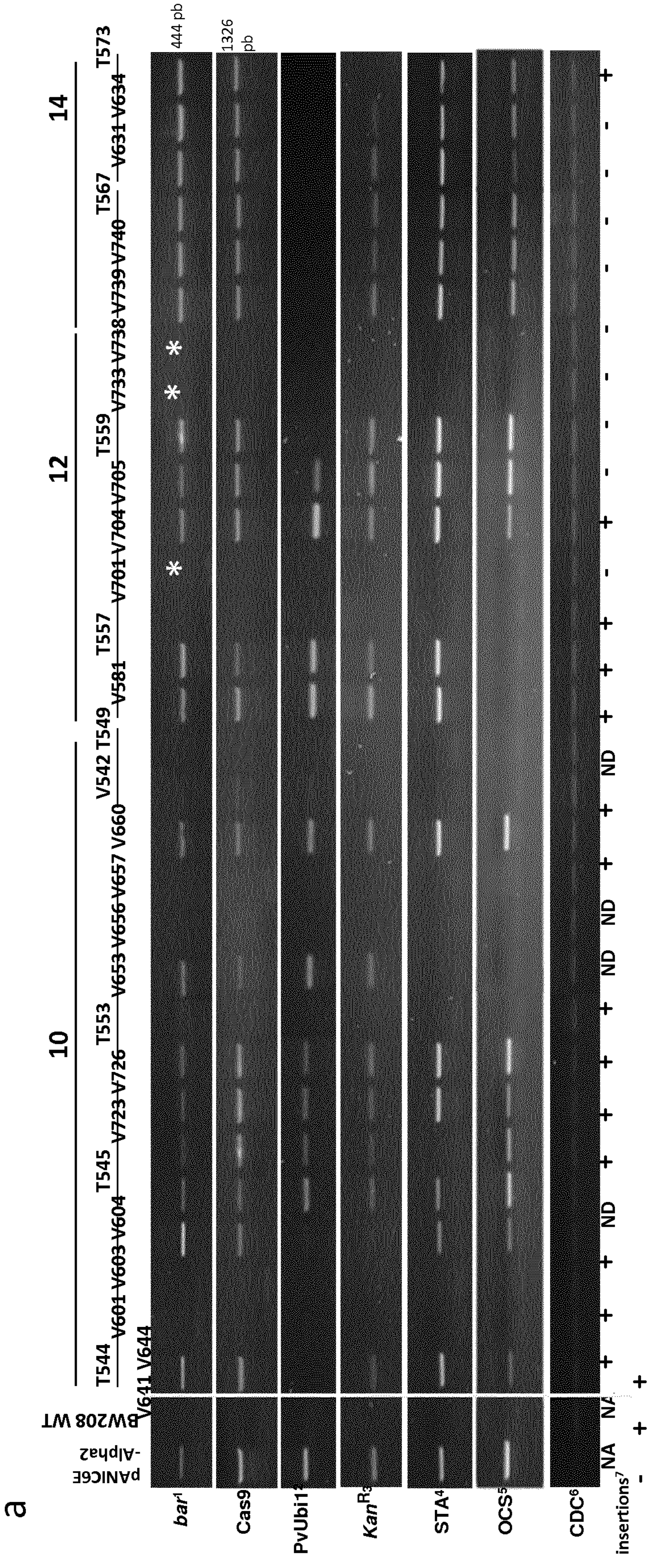
FIG. 17 shows an analysis by PCR and Illumina high-throughput sequencing for the presence of the plasmid DNA; bar and Cas9 genes, PVS1 stability (sta) region, Octopine synthase polyA signal, and *Panicum virgatum* ubiquitin 1 promoter; and insertions in sgAlpha-2 derived lines. Asterisks non-transgenic (transgene-free and insertion-free) mutant lines. (a) cv BW208, (b) durum wheat cv DP, and (c) cv TAH53.
Figure 17:
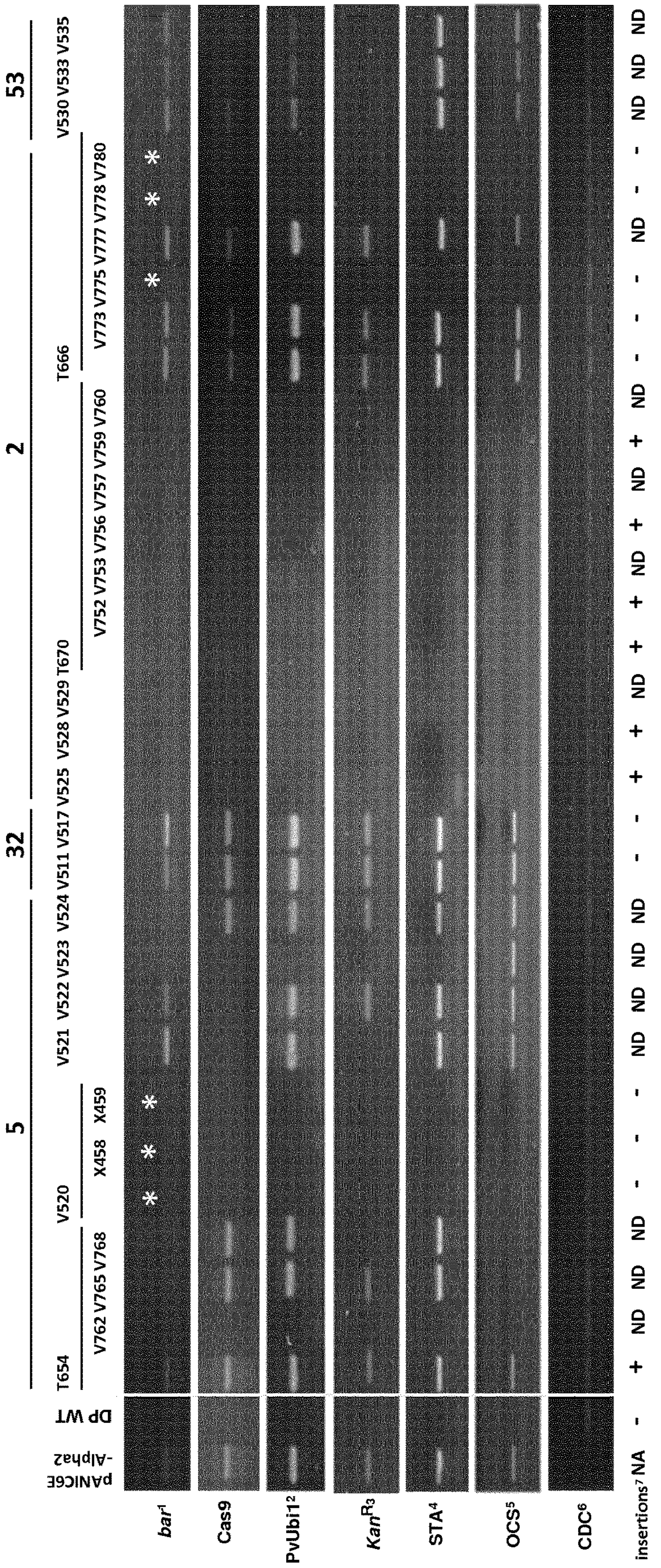
Figure 17:
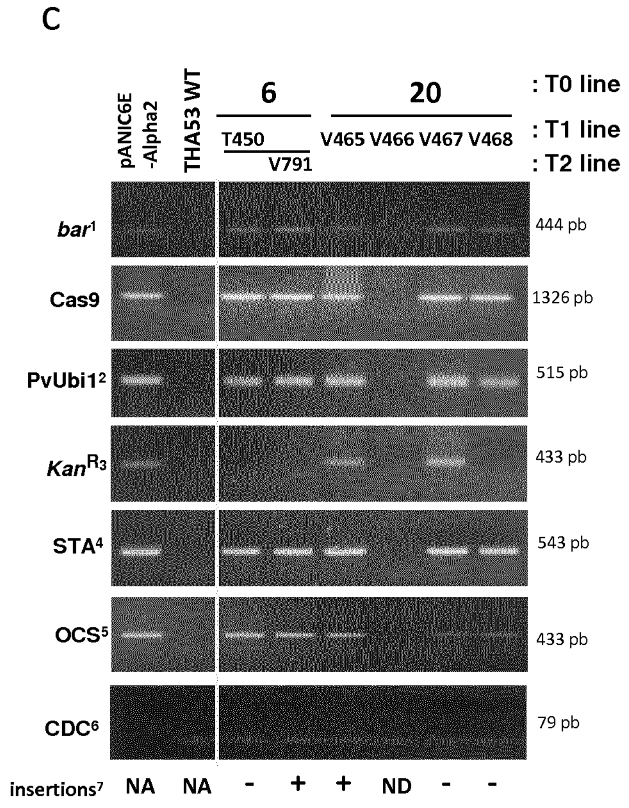

Finally, we tested whether any of the low gluten wheat lines we generated were transgene- and insertion-free (i.e. lacked insertions at the cleavage site). We screened the T1 and T2 wheat lines by PCR and Illumina high-throughput sequencing for the presence of plasmid DNA (FIG. 17). Three bread wheat (BW208) and six durum wheat (DP) T2 plants were identified as transgene-free and insertion-free (FIG. 17). These non-transgenic lines showed reduction of α-gliadins (FIGS. 3*c* and *d*, FIG. 18) showing. In all cases, all TO, T1, and T2 generations of sgAlpha-1 and sgAlpha-2 mutant bread and durum wheat were fully fertile and set seeds, and had normal chromosome numbers (FIG. 3*c*).

We modified the celiac disease-causing α-gliadin gene array using CRISPR/Cas9 technology to obtain non-transgenic, low-gluten wheat lines. Because of the complexity of the Gli-2 locus and the high copy number of the α-gliadin genes, traditional plant breeding and mutagenesis have failed to achieve low gluten wheat. However, CRISPR/Cas9 efficiently and precisely targeted conserved regions of the α-gliadin genes in both bread and durum wheat, leading to high frequency mutagenesis in most gene copies. Immunoreactivity of the CRISPR-edited wheat lines was reduced by 85%, as revealed the R5 and G12 ELISA tests. The low-gluten, transgene-free wheat lines described here constitute an unprecedented advance, and the resultant lines provide excellent source material for plant breeding programs to introgress the low-gluten trait into elite wheat varieties.

Expression of Cas9 and gRNA Casette

Final vectors are composed of nucleotide sequence comprising sequences for the expression of Csy4 endoribonuclease expressed as a 5' terminal P2A fusion to Cas9 gene, both driven by the *Zea* Maize Ubiquitin 1 promoter; a cassette of two to six polycistronic gRNAs, driven by a cestrum yellow leaf curling virus (CmYLCV) promoter or switchgrass ubiquitin 1 promoter (PvUbi1). Each gRNA unit is flanked by the 20 bp Csy4 cleavage site.

The Csy4-P2A-TaCas9 sequence is shown in SEQ ID NO: 101 and is composed of a synthetic nucleotide sequence comprising the following sequences in the 5' to 3' direction: the 561 nt of the Csy4 codon-optimized for monocots (highlighted in grey), the 9 nt of the CSG linker (dashed line), the 57 nt of P2A (indicated with bold letters), and the 4155 nt of the Cas9 protein sequence codon-optimized for monocots (TaCas9) (indicated with italics letters).

```
gRNA cassette
                                          (SEQ ID NO: 783)
5'GTTCACTGCCGTATAGGCAGNNNNNNNNNNNNNNNNNNNNGTTTTAGAGCTAG

AAATAGCAAGTTAAAATAAGGCTAGTCCGTTATCAACTTGAAAAAGTGGCACCGAG

TCGGTGCGTTCACTGCCGTATAGGCAGNNNNNNNNNNNNNNNNNNNNGTTTTAG

AGCTAGAAATAGCAAGTTAAAATAAGGCTAGTCCGTTATCAACTTGAAAAAGTGGC

ACCGAGTCGGTGCGTTCACTGCCGTATAGGCAG 3'
```

The complete gRNA cassette is composed by synthetic nucleotide sequence comprising the following sequences in the 5' to 3' direction: the 20 nt of the Csy4 cleavage site (dashed line (SEQ ID NO: 103)), the 20 nt of the protospacer sequence (highlighted in grey), the 12 nt of the crRNA sequence (indicated with italic and bold letters), and the 64 nt of the tracrRNA sequence (underlined).

*GAAA linking sequence between crRNA and tracrRNA

The sgRNA sequences are engineered to lead the CRISPR/Cas9 complex to the target gene. We designed 22 sequence to target different gliadins in hexaploid wheat; 12 sgRNA to target the gamma-gliadins, 6 for the omega-gliadins, and 4 for the alpha-gliadins. Therefore, in one embodiment, the nucleic acid construct comprises a sequence encoding at least one sgRNA nucleic acid operably linked to a regulatory sequence as described in the below table. The number of sgRNA nucleic acids in each construct is defined in the below table. Preferably, said nucleic acid construct further comprises at least one nucleic acid sequence encoding an endoribonuclease cleavage site. Preferably the endoribonuclease is Csy4 (also known as Cas6f).

TABLE 1 gliadin nucleic acid constructs

| Plasmid ID | Target | Number of sgRNA | gRNAs cassette promoter | sgRNA SEQ. ID Nos |
|---|---|---|---|---|
| pSSLGamma1 | Gamma gliadins | 6 | CmYLCV | 63, 70, 65, 72, 67, 68 |
| pSSLGamma3 | Gamma gliadins | 5 | CmYLCV | 69, 64, 71, 73, 74 |
| pSSLGamma5 | Gamma gliadins | 3 | CmYLCV | 69, 65, 74 |
| pSSLGamma6 | Gamma gliadins | 3 | CmYLCV | 63, 66, 68 |
| pSSLGamma8 | Gamma gliadins | 6 | CmYLCV | 63, 64, 65, 66, 67, 68 |
| pSSLGamma9 | Gamma gliadins | 6 | CmYLCV | 69, 70, 71, 72, 73, 74 |
| pSSLGamma10 | Gamma gliadins | 6 | PvUbi1 | 63, 64, 65, 66, 67, 68 |
| pSSLGamma11 | Gamma gliadins | 6 | PvUbi1 | 69, 70, 71, 72, 73, 74 |
| pSSLGamma12 | Gamma gliadins | 3 | PvUbi1 | 69, 65, 74 |
| pSSLGamma13 | Gamma gliadins | 3 | PvUbi1 | 63, 66, 68 |
| pSSLGamma14 | Gamma gliadins | 4 | PvUbi1 | 63, 68, 64, 66 |
| pSSLGamma15 | Gamma gliadins | 4 | PvUbi1 | 69, 70, 72, 74 |
| pSSLAlpha1 | Alpha gliadins | 2 | PvUbi1 | 54, 55 |

TABLE 1-continued gliadin nucleic acid constructs

| Plasmid ID | Target | Number of sgRNA | gRNAs cassette promoter | sgRNA SEQ. ID Nos |
|---|---|---|---|---|
| pSSLAlpha2 | Alpha gliadins | 2 | CmYLCV | 54, 55 |
| pSSLAlpha3 | Alpha gliadins | 3 | PvUbi1 | 54, 53, 55 |
| pSSLAlpha4 | Alpha gliadins | 3 | CmYLCV | 54, 53, 55 |
| pSSL33mer-1 | 33mer | 2 | PvUbi1 | 55, 56 |
| pSSL33mer-2 | 33mer | 2 | CmYLCV | 55, 56 |
| pSSLAlpha5 | Alpha gliadins | 2 | PvUbi1 | 54, 53 |
| pSSLAlpha6 | Alpha gliadins | 2 | CmYLCV | 54, 53 |
| pSSLOmega1 | Omega Gliadins | 6 | PvUbi1 | 61, 59, 57, 60, 58, 62 |
| pSSLOmega2 | Omega Gliadins | 6 | CmYLCV | 61, 59, 57, 60, 58, 62 |
| pSSLOmega3 | Omega Gliadins | 3 | PvUbi1 | 61, 59, 57 |
| pSSLOmega4 | Omega Gliadins | 3 | CmYLCV | 61, 59, 57 |
| pSSLOmega5 | Omega Gliadins | 3 | PvUbi1 | 60, 58, 62 |
| pSSLOmega6 | Omega Gliadins | 3 | CmYLCV | 60, 58, 62 |
| pANIC6E-CR-Alpha1 | Alpha gliadins | 1 | TaU6 | 51 |
| pANIC6E-CR-Alpha2 | Alpha gliadins | 1 | TaU6 | 52 |

The nucleic acid construct comprises the gliadin sgRNA nucleic acids in the same sequence presented in Table 1 or any combination thereof. For example, the nucleic acid construct pSSLGamma1 comprises six sgRNA nucleic acid sequences in the order 63, 70, 65, 72, 67, 68 or any combination thereof.

Methods sgRNAs Design and Plasmid Construction

Figure 16:
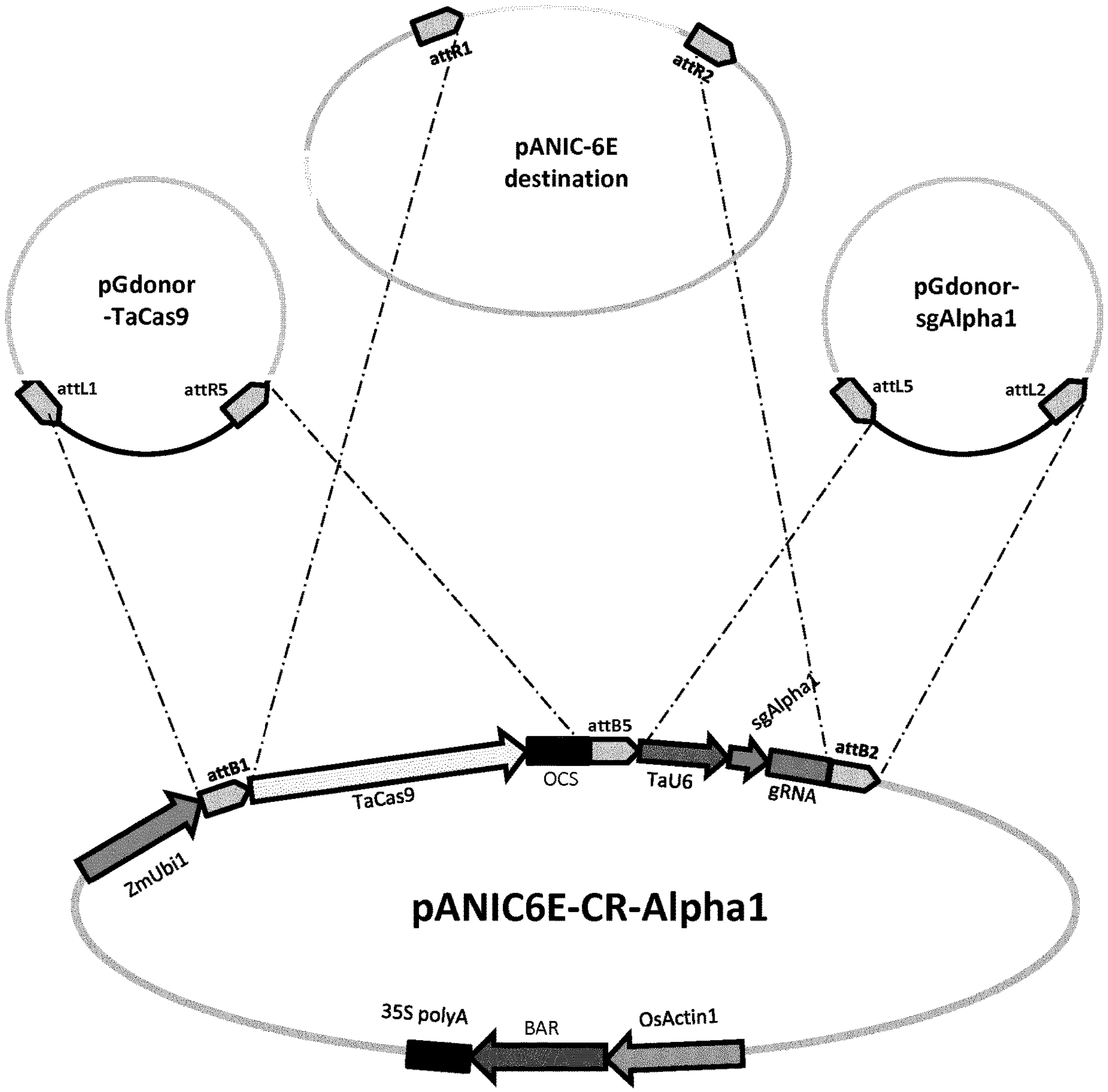
FIG. 16 shows multisite Gateway cloning of pANIC6E-CR-Alpha1 vector. Note that for cloning of pANIC6E-CR-Alpha2, vector pGdonor-Alpha2 is used instead pGdonor-Alpha1. ZmUbi1: maize Ubiquitin) promoter; TaCas9: wheat-codon optimized Cas9; OCS: OCS terminator; TaU6; wheat U6 polymerase III promoter; sgAlpha: 20 nt sgRNA; gRNA: crRNA:tracrRNA fusion sequence; OsActin1: rice Actin) promoter; BAR: bar gene; 35S polyA: 35S polyA terminator.

CRISPR/Cas9 reagents were cloned into the pANIC-6E destination vector[13] downstream the Ubiquitin) promoter from maize. Two sgRNAs (sgAlpha-1: GCCACAAGAGCAAGTTCCAT (SEQ ID NO: 784) and sgAlpha-2: GGTTGTGATGGAAATGGTTG (SEQ ID NO: 785)) were designed to recognize conserved regions in the coding sequence of α-gliadins in hexaploid wheat. To synthesize the expression vectors pANIC-CR-Alpha) and pANIC-CR-Alpha2 two Gateway-compatible donor vectors, one containing TaCas9 (pGdonor-TaCas9) and another containing the sgRNA (pGdonor-sgAlpha1 or pGdonor-sgAlpha2), were combined with pANIC-6E in a multisite Gateway recombination reaction (FIG. 16). pGdonor-TaCas9 contained a wheat-codon optimized Cas9 sequence (TaCas9), with an N- and C-terminal nuclear localization signals (NLS) from the simian vacuolating virus 40 (SV40) and nucleoplasmin, respectively, and the OCS terminator sequence. pGdonor-sgAlpha contained the *Triticum aestivum* U6 RNA polymerase III promoter (TaU6) for expression of the sgRNA, followed by the gRNA sequence (FIG. 16).

Plant Material and Genetic Transformation

Transgenic lines were produced using immature scutella as explants for genetic transformation as described previously[13]. Two bread wheat lines, denoted BW208 and THA53, and one durum wheat line, cv Don Pedro (DP) were used as sources for scutellum isolation and in vitro culture. Plasmids carrying the sgRNAs were precipitated onto 0.6-μm gold particles at 0.75 pmol/mg gold. Regeneration medium was supplemented with 2 mg $L^{-1}$ of PPT for selecting transgenic plants. Putative transgenic plants were then transferred to soil and grown to maturity in the greenhouse, and the presence of transformation vectors was confirmed by PCR (FIG. 19).

Polyacrylamide Gel Electrophoresis Analysis

Between 6-12 mature wheat grains per line were crushed into a fine powder and used to extract sequentially the endosperm storage proteins. Gliadins and glutenins were then separated in A-PAGE and SDS-PAGE gels as described[15].

Reversed-Phase High-Performance Liquid Chromatography (RP-HPLC)

Gliadins and glutenins were extracted and quantified by RP-HPLC following the protocol reported[16]. Ten half-seed biological replications were carried out for each transgenic line and wild type. Protein content was expressed as μg protein/mg flour. For each line 10 half-grains were analyzed.

Gluten Content Determination by Competitive ELISA

Gluten content were determined by competitive ELISA assays using two monoclonal antibodies; R5 and G12. Samples for R5 were analyzed at Centro Nacional de Biotecnologia (CSIC, Campus of Cantoblanco, 28049-Madrid) as described elsewhere[17]. Samples for G12 were analyzed as described previously[18]. Between three and five biological replications for each line was carried out.

Sodium Dodecyl Sulfate (SDS) Sedimentation Test.

The SDS sedimentation volume was determined as described[19]. Between two and four biological replications for each line was carried out.

DNA Extraction and PCR Conditions for Illumina Amplicon Sequencing

The Illumina MiSeq system was used for amplicon sequencing producing 2×280 paired-end reads. PCR amplification was carried out using the forward primer aGli900F1 and the reverse primer 33 mer1R2_ok (FIG. 19) with following conditions: 94° C. for 1 min followed by 30 cycles at 94° C. for 15 s, 62° C. for 45 s and 72° C. for 1 min with final extension at 72° C. for 2 min. For PCR amplification, 5 ng of DNA in a 25 uL volume reaction with the following final concentrations: 1× FastStart buffer, 200 nM forward and reverse primers, 200 uM dNTP mix, 1.25 units of FastStart High Fidelity polymerase (Roche Diagnostics, Mannheim, Germany) was used. Preparation of the Illumina amplicon library and sequencing was carried out at the Unidad de Genómica Cantoblanco of Fundación Parque Cientifico de Madrid (FPCM, Spain). The range of amplicon lengths were check using the Agilent 2100 Bioanalyzer system (Agilent Technologies, Santa Clara, CA 95051 United States).

Amplicon Sequence Clustering

Fifty-three samples were subjected to amplicon sequencing: six samples corresponded to wild type DNA (2 BW208, 2 DP and 2 THA53), and 47 to DNA from transgenic lines (FIGS. 20 and 22). In total 33.817 millions of reads were obtained. For clustering, the USEARCH software v8.0.1517[20] was used. Merging of paired-end reads was using the –fastq_mergepairs command, and for quality filtering by expected errors –fastq_filter (–fastq_maxee 1) commands were used[21]. Then, all 11.676 millions of cleaned and filtered reads were clustered with -cluster_otus mode, 100% homology and -search_exact command for mapping and to extract the consensus sequence for each cluster. To extract the high-confidence amplicon variants for each sample, samples with less than five reads in a given cluster were removed from that cluster. As clustering was at 100%, consensus clusters were considered as unique genes. As samples have different numbers of reads, frequencies were calculated for each sample by dividing the number of reads for a given amplicon gene (n) by the total count for a sample (N). Then, all gene sequences were processed using Geneious version 9.1.4 (Biomatters Ltd., Auckland, New Zealand; available at http://www.gene-ious.com/). First, a reference unique gene library was constructed for each of the wild type lines. Genes with different lengths were used as reference sequences for aligning and mapping of amplicon genes from mutant lines. Second, genes present in mutant lines were aligned and mapped to reference gene library constructed previously using the BBmap aligner (https://sourceforge.net/proiects/bbmap/). MAFFT software v7.222[22] and FastTree software[23] were used for multiple sequence alignment and maximum-likelihood phylogenetic trees, respectively, to determine the corresponding non mutated sequences.

PCR Amplification of γ- and θ-Gliadin Genes and Sequencing by Sanger

The gene-specific primers for Sanger sequencing of γ- and ω-gliadin genes are in FIG. 19 1. These primers amplified from signal peptide in the 5' to end of the coding region in the 3'. The complete γ- and ω-gliadin genes were amplified by PCR as follow: 94° C. for 4 min followed by 35 cycles at 94° C. for 15 s, 60° C. or 66° C. (γ-gliadins and ω-gliadins, respectively) for 1 min and 72° C. for 1 min 30 s, with final extension at 72° C. for 7 min. For PCR amplification, 200 ng of DNA in a 25 uL volume reaction consisting of 400 nM forward and reverse primers, 320 uM dNTP mix, a mixture of 0.013 units Pfu DNA polymerase (Biotools, B&M Labs, Madrid, Spain) and 0.650 units Taq DNA polymerase (Biotools) was used. PCR products were checked by 1% agarose gel electrophoresis.

Full-length DNA sequences were ligated into pGEM-T Easy vector (Promega, Madison, WI, USA) and cloned into *Escherichia coli* DH5a cells. Sequencing was carried out by Stab Vida (Caparica, Portugal). We sequenced 102 clones (35 wild types and 67 mutant lines) and 78 clones (26 wild types and 52 mutant lines) for the γ- and ω-gliadin genes, respectively.

Detection of Bar and Cas9 Genes, and Other DNA Plasmid Regions

PCR was performed to detect insertions of plasmid DNA using primers listed in FIG. 19. For detection of bar and Cas9 genes, and PVS1 stability (sta) region, Octopine synthase polyA signal, kanamycin resistance gene, and *Panicum virgatum* ubiquitin 1 promoter, 300 ng of DNA were used in a 25 uL volume reaction, consisting of 400 nM forward and reverse primers, 320 uM dNTP mix, and 0.650 units Taq DNA polymerase (Biotools, Madrid, Spain). PCR conditions were: 94° C. for 4 min followed by 35 cycles at 94° C. for 15 s, 58° C. for 45 s or 30 s for Cas9 and the other genes, respectively, and 72° C. for 1 min 30 s with final extension at 72° C. for 7 min.

Specifics primers (FIG. 19) were designed to be used with aGli900 Forward primer for the amplification of each insertion detected by deep sequencing. PCR conditions for the amplification of insertions were as followed: 94° C. for 5 min followed by 35 cycles at 94° C. for 30 s, 60° C. for 30 s, and 72° C. for 30 s with a final extension at 72° C. for 5 min. For PCR amplification, 300 ng of DNA in a 25 uL volume reaction consisting of 400 nM forward and reverse primers, 320 uM dNTP mix, and 0.650 units Taq DNA polymerase (Biotools) was used. All PCR products were checked by 1% agarose gel electrophoresis.

Analysis of Off-Target Mutations

Potential off-targets in the wheat genome were detected by two different methods. First, we performed an in silico search of the minimal active sequence of the sgRNAs in the prolamin genes (except α-gliadins) deposited in the GeneBank database (http://www.ncbi.nlm.nih.gov/). We used the seed sequence (12 nt upstream the PAM sequence) of the sgAlpha-1 and sgAlpha-2 plus the NGG PAM sequence and searched for homology in 179 γ-gliadins, 15 ω-gliadins, 40 HMW-glutenins, and 239 LMW-glutenins, allowing up to 2 mismatches in the seed sequence. Then, we expanded our in silico search for off-target sites to the whole genome of wheat by searching for perfect matches of the seed sequence (12 nt) plus PAM in the reference genome of bread wheat (http://plants.ensembl.org/index.html).

Potential off-targeted genes were characterized in 3 T1 mutant plants (T544, T545, and T553). Specific primers were designed to PCR amplify a 267-323 bp fragment encompassing the potential off-target site of sgAlpha-1 or sgAlpha-2 in the identified genes (Traes_7BL_F621D9B9E (MADS box transcription factor), Traes_2AS_D659E88E9.1, Traes_2AS_8FCC59363.1, and the gene family of LMW-glutenins) (FIG. 19). Amplicons were cloned, and between 24-39 clones were sequenced for each of the genes.

Matrix Assisted Laser Desorption Ionization-Time of Flight (MALDI-TOF) Analysis

Gliadin fractions were extracted from wheat flours using 60% ethanol for 1 h at room temperature in a rotary shaker and centrifuged at 12000 g for 5 min at room temperature. Previously, samples were washed twice with 0.5 M NaCl for 30 min at 4° C. in a rotary shaker and centrifuged at 12000 g for 5 min at 4° C., in order to remove albumins/globulins fraction.

The ethanolic supernatants obtained for each sample were diluted at 1:1 ratio (v/v) with matrix solution (10 mg/ml 2,5 Dihydroxyacetophenone in 50% aqueous acetonitrile and 100 mM ammonium citrate). A 1.0 µl aliquot of this mixture was manually deposited onto a 386-well OptiTOF™ Plate (Sciex) and allowed to dry at room temperature. For MALDI-TOF/TOF analysis, samples were automatically acquired in an ABi 4800 MALDI TOF/TOF mass spectrometer (Sciex) in positive ion linear mode (the ion acceleration voltage was 25 kV for MS acquisition). The detection mass range was set between 1500 and 80000 m/z.

Statistical Analysis

Data were analyzed with the statistical software Statistix v10 (Analytical software, PO Box 12185, Tallahassee, FL 32317). The differences in the data were assessed using analysis of the variance (ANOVA), followed by the two-tailed Dunnett's post hoc test for median multiple comparisons. P values lower than 0.05 were considered significant. Shapiro-Wilk Normality test was used to verify that data was normally distributed, and logarithmic or Box Cox transformations were applied whenever a variable did not pass the test. Figures were drawn using the Microsoft Excel and PowerPoint software (Microsoft Corporation).

SEQUENCES

Alpha-gliadin-target sequence
SEQ ID NO: 1; sgAlpha-1
GCCACAAGAGCAAGTTCCATNGG

SEQ ID NO: 2; sgAlpha-2
GTTGTGATGGAAATGGTTGNGG

SEQ ID NO: 3; sgAlpha-3
TGTGGCTGCAATTGTGGCACNGG

SEQ ID NO: 4; sgAlpha-4
TCTTGTGGTTGTTGCTGAGANGG

SEQ ID NO: 5; sg33mer1
GGTAGTTGCGGCTGCGGAAANGG

SEQ ID NO: 6; sgGlia20-1
TATGGTTGTTGTGGTCGAAANGG

Omega-gliadin-target sequence
SEQ ID NO: 7; sgOmega6
AAAGGTTGTTGTGGTTGTTGNGG

SEQ ID NO: 8; sgOmega4
AATGGTTGTTGGGGTTGCTGNGG

SEQ ID NO: 9; sgOmega3
TGATGGGGGGAATATTGTTGNGG

SEQ ID NO: 10; sgOmega2
TGCTGGGGGAATGGTTGTTGNGG

-continued

| SEQUENCES |
|---|
| SEQ ID NO: 11; sgOmega1<br>TGTTCATCGCCATGGCAAGGNGG |
| SEQ ID NO: 12; sgOmega5<br>CTTATAACGTCGCTCCCAGANGG |
| Gamma-gliadin-target sequence<br>SEQ ID NO: 13; sgGamma13<br>GAGAATGGTTGGTGAGGCTGNGG |
| SEQ ID NO: 14; sgGamma4<br>AATTGTTGTTGTGGTTGCTGNGG |
| SEQ ID NO: 15; sgGamma5<br>GTTGGGGTTGTTGAGTCTGGNGG |
| SEQ ID NO: 16; sgGamma9<br>TGTTGGGGGAATGATTGTTGNGG |
| SEQ ID NO: 17; sgGamma10<br>GCAAGAGGAAATTCTTGCATNGG |
| SEQ ID NO: 18; sgGamma11<br>ATTGAGCTGGTTGTTGAGGTNGG |
| SEQ ID NO: 19; sgGamma2<br>TGATGGGGGAATGTTTGTTGNGG |
| SEQ ID NO: 20; sgGamma3<br>ATTGTTGTTGTGGTTGATGGNGG |
| SEQ ID NO: 21; sgGamma8<br>GGCTGGGGAAAAGGTTGTTGNGG |
| SEQ ID NO: 22; sgGamma6<br>AATGATTGTTGTGGTTGTTGNGG |
| SEQ ID NO: 23; sgGamma7<br>CAGGTTTGCATTGTTGCAAGNGG |
| SEQ ID NO: 24; sgGamma12<br>TCAACAACCAGCTCAATTGGNGG |
| Alpha-gliadin-protospacer sequence<br>SEQ ID NO: 25; sgAlpha-1<br>GCCACAAGAGCAAGTTCCAT |
| SEQ ID NO: 26; sgAlpha-2<br>GGTTGTGATGGAAATGGTTG |
| SEQ ID NO: 27; sgAlpha-3<br>TGTGGCTGCAATTGTGGCAC |
| SEQ ID NO: 28; sgAlpha-4<br>TCTTGTGGTTGTTGCTGAGA |
| SEQ ID NO: 29; sg33mer1<br>GGTAGTTGCGGCTGCGGAAA |
| SEQ ID NO: 30; glia20-1<br>TATGGTTGTTGTGGTCGAAA |
| Omega-gliadin-protospacer sequence<br>SEQ ID NO: 31; sgOmega6<br>AAAGGTTGTTGTGGTTGTTG |
| SEQ ID NO: 32; sgOmega4<br>AATGGTTGTTGGGGTTGCTG |
| SEQ ID NO: 33; sgOmega3<br>TGATGGGGGGAATATTGTTG |
| SEQ ID NO: 34; sgOmega2<br>TGCTGGGGGAATGGTTGTTG |

-continued

| SEQUENCES |
|---|

SEQ ID NO: 35; sgOmega1
TGTTCATCGCCATGGCAAGG

SEQ ID NO: 36; sgOmega5
CTTATAACGTCGCTCCCAGA

Gamma-gliadin-protospacer sequence
SEQ ID NO: 37; sgGamma13
GAGAATGGTTGGTGAGGCTG SEQ ID NO: 38; sgGamma4
AATTGTTGTTGTGGTTGCTG SEQ ID NO: 39; sgGamma5
GTTGGGGTTGTTGAGTCTGG SEQ ID NO: 40; sgGamma9
TGTTGGGGGAATGATTGTTG SEQ ID NO: 41; sgGamma10
GCAAGAGGAAATTCTTGCAT SEQ ID NO: 42; sgGamma11
ATTGAGCTGGTTGTTGAGGT SEQ ID NO: 43; sgGamma2
TGATGGGGGAATGTTTGTTG SEQ ID NO: 44; sgGamma3
ATTGTTGTTGTGGTTGATGG SEQ ID NO: 45; sgGamma8
GGCTGGGGAAAAGGTTGTTG SEQ ID NO: 46; sgGamma6
AATGATTGTTGTGGTTGTTG SEQ ID NO: 47; sgGamma7
CAGGTTTGCATTGTTGCAAG SEQ ID NO: 48; sgGamma12
TCAACAACCAGCTCAATTGG SEQ ID NO: 49; crRNA additional nucleotides
GTTTTAGAGCTA SEQ ID NO: 50; tracrRNA; nucleotide sequence
GAAATAGCAAGTTAAAATAAGGCTAGTCCGTTATCAACTTGAAAAAGTGGCACCGA
GTCGGTGC SEQ ID NO: 51-74; complete sgRNA nucleic acid sequences
Alpha-gliadin complete sgRNA nucleic acid sequences
SEQ ID NO: 51; sgAlpha-1
GCCACAAGAGCAAGTTCCATGTTTTAGAGCTA*GAAATAGCAAGTTAAAATAAGG*

*CTAGTCCGTTATCAACTTGAAAAAGTGGCACCGAGTCGGTGC*TTTTTTT

SEQ ID NO: 52; sgAlpha-2
GGTTGTGATGGAAATGGTTGGTTTTAGAGCTA*GAAATAGCAAGTTAAAATAAGG*

*CTAGTCCGTTATCAACTTGAAAAAGTGGCACCGAGTCGGTGC*TTTTTTT

SEQ ID NO: 53; sgAlpha-3
TGTGGCTGCAATTGTGGCACGTTTTAGAGCTA*GAAATAGCAAGTTAAAATAAGG*

*CTAGTCCGTTATCAACTTGAAAAAGTGGCACCGAGTCGGTGC*

-continued

| SEQUENCES |
|---|

SEQ ID NO: 54; sgAlpha-4
TCTTGTGGTTGTTGCTGAGAGTTTTAGAGCTA*GAAATAGCAAGTTAAAATAAGGC*

*TAGTCCGTTATCAACTTGAAAAAGTGGCACCGAGTCGGTGC*

SEQ ID NO: 55; sg33mer1
GGTAGTTGCGGCTGCGGAAAGTTTTAGAGCTA*GAAATAGCAAGTTAAAATAAGG*

*CTAGTCCGTTATCAACTTGAAAAAGTGGCACCGAGTCGGTGC*

SEQ ID NO: 56; glia20-1
TATGGTTGTTGTGGTCGAAAGTTTTAGAGCTA*GAAATAGCAAGTTAAAATAAGGC*

*TAGTCCGTTATCAACTTGAAAAAGTGGCACCGAGTCGGTGC*

Omega-gliadin complete sgRNA nucleic acid sequences
SEQ ID NO: 57; sgOmega6
AAAGGTTGTTGTGGTTGTTGGTTTTAGAGCTA*GAAATAGCAAGTTAAAATAAGGC*

*TAGTCCGTTATCAACTTGAAAAAGTGGCACCGAGTCGGTGC*

SEQ ID NO: 58; sgOmega4
AATGGTTGTTGGGGTTGCTGGTTTTAGAGCTA*GAAATAGCAAGTTAAAATAAGG*

*CTAGTCCGTTATCAACTTGAAAAAGTGGCACCGAGTCGGTGC*

SEQ ID NO: 59; sgOmega3
TGATGGGGGGAATATTGTTGGTTTTAGAGCTA*GAAATAGCAAGTTAAAATAAGG*

*CTAGTCCGTTATCAACTTGAAAAAGTGGCACCGAGTCGGTGC*

SEQ ID NO: 60; sgOmega2
TGCTGGGGGAATGGTTGTTGGTTTTAGAGCTA*GAAATAGCAAGTTAAAATAAGG*

*CTAGTCCGTTATCAACTTGAAAAAGTGGCACCGAGTCGGTGC*

SEQ ID NO: 61; sgOmega1
TGTTCATCGCCATGGCAAGGGTTTTAGAGCTA*GAAATAGCAAGTTAAAATAAGG*

CTAGTCCGTTATCAACTTGAAAAAGTGGCACCGAGTCGGTGC

SEQ ID NO: 62; sgOmega5
CTTATAACGTCGCTCCCAGAGTTTTAGAGCTAGAAATAGCAAGTTAAAATAAGGC

TAGTCCGTTATCAACTTGAAAAAGTGGCACCGAGTCGGTGC

Gamma-gliadin-complete sgRNA nucleic acid sequences
SEQ ID NO: 63; sgGamma13
GAGAATGGTTGGTGAGGCTGGTTTTAGAGCTAGAAATAGCAAGTTAAAATAAGG

CTAGTCCGTTATCAACTTGAAAAAGTGGCACCGAGTCGGTGC

SEQ ID NO: 64; sgGamma4
AATTGTTGTTGTGGTTGCTGGTTTTAGAGCTAGAAATAGCAAGTTAAAATAAGGC

*TAGTCCGTTATCAACTTGAAAAAGTGGCACCGAGTCGGTGC*

-continued

| SEQUENCES |
| --- |

SEQ ID NO: 65; sgGamma5
GTTGGGGTTGTTGAGTCTGGGTTTTAGAGCTA*GAAATAGCAAGTTAAAATAAGG*

*CTAGTCCGTTATCAACTTGAAAAAGTGGCACCGAGTCGGTGC*

SEQ ID NO: 66; sgGamma9
TGTTGGGGGAATGATTGTTGGTTTTAGAGCTA*GAAATAGCAAGTTAAAATAAGG*

*CTAGTCCGTTATCAACTTGAAAAAGTGGCACCGAGTCGGTGC*

SEQ ID NO: 67; sgGamma10
GCAAGAGGAAATTCTTGCATGTTTTAGAGCTA*GAAATAGCAAGTTAAAATAAGGC*

*TAGTCCGTTATCAACTTGAAAAAGTGGCACCGAGTCGGTGC*

SEQ ID NO: 68; sgGamma11
ATTGAGCTGGTTGTTGAGGTGTTTTAGAGCTA*GAAATAGCAAGTTAAAATAAGG*

*CTAGTCCGTTATCAACTTGAAAAAGTGGCACCGAGTCGGTGC*

SEQ ID NO: 69; sgGamma2
TGATGGGGGAATGTTTGTTGGTTTTAGAGCTA*GAAATAGCAAGTTAAAATAAGG*

*CTAGTCCGTTATCAACTTGAAAAAGTGGCACCGAGTCGGTGC*

SEQ ID NO: 70; sgGamma3
ATTGTTGTTGTGGTTGATGGGTTTTAGAGCTA*GAAATAGCAAGTTAAAATAAGGC*

*TAGTCCGTTATCAACTTGAAAAAGTGGCACCGAGTCGGTGC*

SEQ ID NO: 71; sgGamma8
GGCTGGGGAAAAGGTTGTTGGTTTTAGAGCTA*GAAATAGCAAGTTAAAATAAGG*

*CTAGTCCGTTATCAACTTGAAAAAGTGGCACCGAGTCGGTGC*

SEQ ID NO: 72; sgGamma6
AATGATTGTTGTGGTTGTTGGTTTTAGAGCTA*GAAATAGCAAGTTAAAATAAGGC*

*TAGTCCGTTATCAACTTGAAAAAGTGGCACCGAGTCGGTGC*

SEQ ID NO: 73; sgGamma7
CAGGTTTGCATTGTTGCAAGGTTTTAGAGCTA*GAAATAGCAAGTTAAAATAAGGC*

*TAGTCCGTTATCAACTTGAAAAAGTGGCACCGAGTCGGTGC*

SEQ ID NO: 74; sgGamma12
TCAACAACCAGCTCAATTGGGTTTTAGAGCTA*GAAATAGCAAGTTAAAATAAGGC*

*TAGTCCGTTATCAACTTGAAAAAGTGGCACCGAGTCGGTGC*

SEQ ID NO: 75-99; RNA sequence for above targets
Alpha-gliadin-complete sgRNA nucleic acid sequences
SEQ ID NO: 75; sgAlpha-1
GCCACAAGAGCAAGUUCCAUGUUUUAGAGCUA*GAAAUAGCAAGUUAAAAUAAG*

*GCUAGUCCGUUAUCAACUUGAAAAAGUGGCACCGAGUCGGUGCUUUUUUU*

-continued

SEQUENCES

SEQ ID NO: 76; sgAlpha-2
GGUUGUGAUGGAAAUGGUUGGUUUUAGAGCUA*GAAAUAGCAAGUUAAAAUAA*

*GGCUAGUCCGUUAUCAACUUGAAAAAGUGGCACCGAGUCGGUGCUUUUUUU*

SEQ ID NO: 77; sgAlpha-3
UGUGGCUGCAAUUGUGGCACGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 78; sgAlpha-4
UCUUGUGGUUGUUGCUGAGAGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 79; sg33mer1
GGUAGUUGCGGCUGCGGAAAGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 80; g1ia20-1
UAUGGUUGUUGUGGUCGAAAGUUUUAGAGCUA*GAAAUAGCAAGUUAAAAUAA*

*GGCUAGUCCGUUAUCAACUUGAAAAAGUGGCACCGAGUCGGUGC*

Omega-gliadin-complete sgRNA nucleic acid sequences
SEQ ID NO: 81; sgOmega6
AAAGGUUGUUGUGGUUGUUGGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 82; sgOmega4
AAUGGUUGUUGGGGUUGCUGGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 83; sgOmega3
UGAUGGGGGGAAUAUUGUUGGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 84; sgOmega2
UGCUGGGGGAAUGGUUGUUGGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 85; sgOmega1
UGUUCAUCGCCAUGGCAAGGGUUUUAGAGCUA*GAAAUAGCAAGUUAAAAUAA*

*GGCUAGUCCGUUAUCAACUUGAAAAAGUGGCACCGAGUCGGUGC*

SEQ ID NO: 86; sgOmega5
CUUAUAACGUCGCUCCCAGAGUUUUAGAGCUA*GAAAUAGCAAGUUAAAAUAA*

*GGCUAGUCCGUUAUCAACUUGAAAAAGUGGCACCGAGUCGGUGC*

-continued

| SEQUENCES |
|---|

Gamma-gliadin-compleUe sgRNA nucleic acid sequences
SEQ ID NO: 87; sgGamma13
GAGAAUGGUUGGUGAGGCUG**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 88; sgGamma4
AAUUGUUGUUGUGGUUGCUG**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 89; sgGamma5
GUUGGGGUUGUUGAGUCUGG**GUUUUAGAGCUA*GAAAUAGCAAGUUAAAUAA***

*GGCUAGUCCGUUAUCAACUUGAAAAAGUGGCACCGAGUCGGUGC*

SEQ ID NO: 90; sgGamma9
UGUUGGGGGAAUGAUUGUUG**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 91; sgGamma10
GCAAGAGGAAAUUCUUGCAU**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 92; sgGamma11
AUUGAGCUGGUUGUUGAGGU**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 93; sgGamma2
UGAUGGGGGAAUGUUUGUUG**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 94; sgGamma3
AUUGUUGUUGUGGUUGAUGG**GUUUUAGAGCUA*GAAAGAGCAAGUUAAAAUAA***

*GGCUAGUCCGUUAUCAACUUGAAAAAGUGGCACCGAGUCGGUGC*

SEQ ID NO: 95; sgGamma8
GGCUGGGGAAAAGGUUGUUG**GUUUUAGAGCUA*GAAAUAGCAAGUUAAAAUAA***

*GGCUGGGGAAAAGGUUGUUGGUUUUAGAGCUAGAAAUAGCAAGUUAAAAUA*

SEQ ID NO: 96; sgGamma6
AAUGAUUGUUGUGGUUGUUG**GUUUUAGAGCUA*GAAAUAGCAAGUUAAAAUAA***

*GGCUAGUCCGUUAUCAACUUGAAAAAGUGGCACCGAGUCGGUGC*

SEQ ID NO: 97; sgGamma7
CAGGUUUGCAUUGUUGCAAG**GUUUUAGAGCUA*GAAAUAGCAAGUUAAAAUAA***

*GGCUAGUCCGUUAUCAACUUGAAAAAGUGGCACCGAGUCGGUGC*

-continued

| SEQUENCES |
|---|

SEQ ID NO: 98; sgGamma12
UCAACAACCAGCUCAAUUGG<u>GUUUUAGAGCUA</u>*GAAUGCAAGUUAAAAUAAG*

*GCUAGUCCGUUAUCAACUUGAAAAAGUGGCACCGAGUCGGUGC*

SEQ ID NO: 99 RNA sequence for tracrRNA
GAAAUAGCAAGUUAAAAUAAGGCUAGUCCGUUAUCAACUUGAAAAAGUGGCACC
GAGUCGGUGC
SEQ ID NO: 100 nucleic acid sequence of Cas9
5'ATGGACAAGAAGTACTCGATCGGCCTCGACATCGGGACGAACTCAGTTGGCTG
GGCCGTGATCACCGACGAGTACAAGGTGCCCTCTAAGAAGTTCAAGGTCCTGGG
GAACACCGACCGCCATTCCATCAAGAAGAACCTCATCGGCGCTCTCCTGTTCGAC
AGCGGGGAGACCGCTGAGGCTACGAGGCTCAAGAGAACCGCTAGGCGCCGGTA
CACGAGAAGGAAGAACAGGATCTGCTACCTCCAAGAGATTTTCTCCAACGAGATG
GCCAAGGTTGACGATTCATTCTTCCACCGCCTGGAGGAGTCTTTCCTCGTGGAGG
AGGATAAGAAGCACGAGCGGCATCCCATCTTCGGCAACATCGTGGACGAGGTTG
CCTACCACGAGAAGTACCCTACGATCTACCATCTGCGGAAGAAGCTCGTGGACTC
CACCGATAAGGCGGACCTCAGACTGATCTACCTCGCTCTGGCCCACATGATCAAG
TTCCGCGGCCATTTCCTGATCGAGGGGGATCTCAACCCAGACAACAGCGATGTT
GACAAGCTGTTCATCCAACTCGTGCAGACCTACAACCAACTCTTCGAGGAGAACC
CGATCAACGCCTCTGGCGTGGACGCGAAGGCTATCCTGTCCGCGAGGCTCTCGA
AGTCCAGGAGGCTGGAGAACCTGATCGCTCAGCTCCCAGGCGAGAAGAAGAACG
GCCTGTTCGGGAACCTCATCGCTCTCAGCCTGGGGCTCACCCCGAACTTCAAGT
CGAACTTCGATCTCGCTGAGGACGCCAAGCTGCAACTCTCCAAGGACACCTACG
ACGATGACCTCGATAACCTCCTGGCCCAGATCGGCGATCAATACGCGGACCTGTT
CCTCGCTGCCAAGAACCTGTCGGACGCCATCCTCCTGTCAGATATCCTCCGCGT
GAACACCGAGATCACGAAGGCTCCACTCTCTGCCTCCATGATCAAGCGCTACGAC
GAGCACCATCAGGATCTGACCCTCCTGAAGGCGCTGGTCCGCCAACAGCTCCCG
GAGAAGTACAAGGAGATTTTCTTCGATCAGTCGAAGAACGGCTACGCTGGGTACA
TCGACGGCGGGGCCTCACAAGAGGAGTTCTACAAGTTCATCAAGCCAATCCTGG
AGAAGATGGACGGCACGGAGGAGCTCCTGGTGAAGCTCAACAGGGAGGACCTC
CTGCGGAAGCAGAGAACCTTCGATAACGGCAGCATCCCCCACCAAATCCATCTC
GGGGAGCTGCACGCCATCCTGAGAAGGCAAGAGGACTTCTACCCTTTCCTCAAG
GATAACCGGGAGAAGATCGAGAAGATCCTGACCTTCAGAATCCCATACTACGTCG
GCCCTCTCGCGCGGGGGAACTCAAGATTCGCTTGGATGACCCGCAAGTCTGAGG
AGACCATCACGCCGTGGAACTTCGAGGAGGTGGTGGACAAGGGCGCTAGCGCT
CAGTCGTTCATCGAGAGGATGACCAACTTCGACAAGAACCTGCCCAACGAGAAG
GTGCTCCCTAAGCACTCGCTCCTGTACGAGTACTTCACCGTCTACAACGAGCTCA
CGAAGGTGAAGTACGTCACCGAGGGCATGCGCAAGCCAGCGTTCCTGTCCGGG
GAGCAGAAGAAGGCTATCGTGGACCTCCTGTTCAAGACCAACCGGAAGGTCACG
GTTAAGCAACTCAAGGAGGACTACTTCAAGAAGATCGAGTGCTTCGATTCGGTCG
AGATCAGCGGCGTTGAGGACCGCTTCAACGCCAGCCTCGGGACCTACCACGATC
TCCTGAAGATCATCAAGGATAAGGACTTCCTGGACAACGAGGAGAACGAGGATAT
CCTGGAGGACATCGTGCTGACCCTCACGCTGTTCGAGGACAGGGAGATGATCGA
GGAGCGCCTGAAGACGTACGCCCATCTCTTCGATGACAAGGTCATGAAGCAACT
CAAGCGCCGGAGATACACCGGCTGGGGGAGGCTGTCCCGCAAGCTCATCAACG
GCATCCGGGACAAGCAGTCCGGGAAGACCATCCTCGACTTCCTCAAGAGCGATG
GCTTCGCCAACAGGAACTTCATGCAACTGATCCACGATGACAGCCTCACCTTCAA
GGAGGATATCCAAAAGGCTCAAGTGAGCGGCCAGGGGGACTCGCTGCACGAGC
ATATCGCGAACCTCGCTGGCTCCCCCGCGATCAAGAAGGGCATCCTCCAGACCG
TGAAGGTTGTGGACGAGCTCGTGAAGGTCATGGGCCGGCACAAGCCTGAGAACA
TCGTCATCGAGATGGCCAGAGAGAACCAAACCACGCAGAAGGGGCAAAAGAACT
CTAGGGAGCGCATGAAGCGCATCGAGGAGGGCATCAAGGAGCTGGGGTCCCAA
ATCCTCAAGGAGCACCCAGTGGAGAACACCCAACTGCAGAACGAGAAGCTCTAC
CTGTACTACCTCCAGAACGGCAGGGATATGTACGTGGACCAAGAGCTGGATATCA
ACCGCCTCAGCGATTACGACGTCGATCATATCGTTCCCCAGTCTTTCCTGAAGGA
TGACTCCATCGACAACAAGGTCCTCACCAGGTCGGACAAGAACCGCGGCAAGTC
AGATAACGTTCCATCTGAGGAGGTCGTTAAGAAGATGAAGAACTACTGGAGGCAG
CTCCTGAACGCCAAGCTGATCACGCAAAGGAAGTTCGACAACCTCACCAAGGCT
GAGAGAGGCGGGCTCTCAGAGCTGGACAAGGCCGGCTTCATCAAGCGGCAGCT
GGTCGAGACCAGACAAATCACGAAGCACGTTGCGCAAATCCTCGACTCTCGGAT
GAACACGAAGTACGATGAGAACGACAAGCTGATCAGGGAGGTTAAGGTGATCAC
CCTGAAGTCTAAGCTCGTCTCCGACTTCAGGAAGGATTTCCAGTTCTACAAGGTT
CGCGAGATCAACAACTACCACCATGCCCATGACGCTTACCTCAACGCTGTGGTCG
GCACCGCTCTGATCAAGAAGTACCCAAAGCTGGAGTCCGAGTTCGTGTACGGGG
ACTACAAGGTTTACGATGTGCGCAAGATGATCGCCAAGTCGGAGCAAGAGATCG
GCAAGGCTACCGCCAAGTACTTCTTCTACTCAAACATCATGAACTTCTTCAAGACC
GAGATCACGCTGGCCAACGGCGAGATCCGGAAGAGACCGCTCATCGAGACCAAC
GGCGAGACGGGGGAGATCGTGTGGGACAAGGGCAGGGATTTCGCGACCGTCCG
CAAGGTTCTCTCCATGCCCCAGGTGAACATCGTCAAGAAGACCGAGGTCCAAAC
GGGCGGGTTCTCAAAGGAGTCTATCCTGCCTAAGCGGAACAGCGACAAGCTCAT
CGCCAGAAAGAAGGACTGGGACCCAAAGAAGTACGGCGGGTTCGACAGCCCTAC
CGTGGCCTACTCGGTCCTGGTTGTGGCGAAGGTTGAGAAGGGCAAGTCCAAGAA
GCTCAAGAGCGTGAAGGAGCTCCTGGGGATCACCATCATGGAGAGGTCCAGCTT
CGAGAAGAACCCAATCGACTTCCTGGAGGCCAAGGGCTACAAGGAGGTGAAGAA -continued

| SEQUENCES |
| --- |

GGACCTGATCATCAAGCTCCCGAAGTACTCTCTCTTCGAGCTGGAGAACGGCAG
GAAGAGAATGCTGGCTTCCGCTGGCGAGCTCCAGAAGGGGAACGAGCTCGCGC
TGCCAAGCAAGTACGTGAACTTCCTCTACCTGGCTTCCCACTACGAGAAGCTCAA
GGGCAGCCCGGAGGACAACGAGCAAAAGCAGCTGTTCGTCGAGCAGCACAAGC
ATTACCTCGACGAGATCATCGAGCAAATCTCCGAGTTCAGCAAGCGCGTGATCCT
CGCCGACGCGAACCTGGATAAGGTCCTCTCCGCCTACAACAAGCACCGGGACAA
GCCCATCAGAGAGCAAGCGGAGAACATCATCCATCTCTTCACCCTGACGAACCTC
GGCGCTCCTGCTGCTTTCAAGTACTTCGACACCACGATCGATCGGAAGAGATACA
CCTCCACGAAGGAGGTCCTGGACGCGACCCTCATCCACCAGTCGATCACCGGCC
TGTACGAGACGAGGATCGACCTCTCACAACTCGGCGGGGATAAGAGACCCGCAG
CAACCAAGAAGGCAGGGCAAGCAAAGAAGAAGAAGTGA 3'

SEQ ID NO: 101; Cys4-P2A-TaCas9 nucleic acid sequence

5'ATGGACCACTACCTCGACACAGGCTCAGGCCAGACCCAGAGTTCCCACCAGC

CCAGCTCATGTCCGTCCTCTTCGGCAAGCTCCACCAGGCCCTCGTGGCCCAGGG

CGGCGACAGGATCGGCGTGTCCTTCCCAGACCTCGACGAGTCCAGGTCCAGGCT

CGGCGAGAGGCTCCGCATCCACGCCTCCGCCGACGACCTCAGGGCCCTCCTCG

CCAGGCCGTGGCTGGAGGGCCTCAGGGACCACCTCCAGTTCGGCGAGCCAGCC

GTGGTGCCACACCCAACCCCATACAGGCAAGTGTCCAGGGTGCAAGCCAAGTCC

AACCCAGAGAGGCTCAGGAGGAGGCTCATGAGGAGGCACGACCTCTCCGAGGA

AGAGGCCAGGAAGCGCATCCCAGACACCGTGGCCAGGGCCCTCGACCTCCCATT

CGTGACCCTCAGGTCCCAGTCCACCGGCCAGCACTTCCGCCTCTTCATCAGGCA

CGGCCCACTCCAGGTGACCGCCGAGGAGGGCGGCTTTACCTGCTACGGCCTCT

CCAAGGGCGGCTTCGTGCCGTGGTTCGGCTCCGGCGCCACCAACTTCTCCCTCC

TCAAGCAAGCCGGCGACGTGGAGGAGAACCCAGGCCCA*ATGGACAAGAAGTAC*
*TCGATCGGCCTCGACATCGGGACGAACTCAGTTGGCTGGGCCGTGATCACCGAC*
*GAGTACAAGGTGCCCTCTAAGAAGTTCAAGGTCCTGGGGAACACCGACCGCCAT*
*TCCATCAAGAAGAACCTCATCGGCGCTCTCCTGTTCGACAGCGGGGAGACCGCT*
*GAGGCTACGAGGCTCAAGAGAACCGCTAGGCGCCGGTACACGAGAAGGAAGAA*
*CAGGATCTGCTACCTCCAAGAGATTTTCTCCAACGAGATGGCCAAGGTTGACGAT*
*TCATTCTTCCACCGCCTGGAGGAGTCTTTCCTCGTGGAGGAGGATAAGAAGCACG*
*AGCGGCATCCCATCTTCGGCAACATCGTGGACGAGGTTGCCTACCACGAGAAGT*
*ACCCTACGATCTACCATCTGCGGAAGAAGCTCGTGGACTCCACCGATAAGGCGG*
*ACCTCAGACTGATCTACCTCGCTCTGGCCCACATGATCAAGTTCCGCGGCCATTT*
*CCTGATCGAGGGGGATCTCAACCCAGACAACAGCGATGTTGACAAGCTGTTCATC*
*CAACTCGTGCAGACCTACAACCAACTCTTCGAGGAGAACCCGATCAACGCCTCTG*
*GCGTGGACGCGAAGGCTATCCTGTCCGCGAGGCTCTCGAAGTCCAGGAGGCTG*
*GAGAACCTGATCGCTCAGCTCCCAGGCGAGAAGAAGAACGGCCTGTTCGGGAAC*
*CTCATCGCTCTCAGCCTGGGGCTCACCCCGAACTTCAAGTCGAACTTCGATCTCG*
*CTGAGGACGCCAAGCTGCAACTCTCCAAGGACACCTACGACGATGACCTCGATA*
*ACCTCCTGGCCCAGATCGGCGATCAATACGCGGACCTGTTCCTCGCTGCCAAGA*
*ACCTGTCGGACGCCATCCTCCTGTCAGATATCCTCCGCGTGAACACCGAGATCAC*
*GAAGGCTCCACTCTCTGCCTCCATGATCAAGCGCTACGACGAGCACCATCAGGAT*
*CTGACCCTCCTGAAGGCGCTGGTCCGCCAACAGCTCCCGGAGAAGTACAAGGAG*
*ATTTTCTTCGATCAGTCGAAGAACGGCTACGCTGGGTACATCGACGGCGGGGCC*
*TCACAAGAGGAGTTCTACAAGTTCATCAAGCCAATCCTGGAGAAGATGGACGGCA*
*CGGAGGAGCTCCTGGTGAAGCTCAACAGGGAGGACCTCCTGCGGAAGCAGAGA*
*ACCTTCGATAACGGCAGCATCCCCCACCAAATCCATCTCGGGGAGCTGCACGCC*
*ATCCTGAGAAGGCAAGAGGACTTCTACCCTTTCCTCAAGGATAACCGGGAGAAGA*
*TCGAGAAGATCCTGACCTTCAGAATCCCATACTACGTCGGCCCTCTCGCGCGGG*
*GGAACTCAAGATTCGCTTGGATGACCCGCAAGTCTGAGGAGACCATCACGCCGT*
*GGAACTTCGAGGAGGTGGTGGACAAGGGCGCTAGCGCTCAGTCGTTCATCGAGA*
*GGATGACCAACTTCGACAAGAACCTGCCCAACGAGAAGGTGCTCCCTAAGCACT*
*CGCTCCTGTACGAGTACTTCACCGTCTACAACGAGCTCACGAAGGTGAAGTACGT*
*CACCGAGGGCATGCGCAAGCCAGCGTTCCTGTCCGGGGAGCAGAAGAAGGCTA*
*TCGTGGACCTCCTGTTCAAGACCAACCGGAAGGTCACGGTTAAGCAACTCAAGGA*
*GGACTACTTCAAGAAGATCGAGTGCTTCGATTCGGTCGAGATCAGCGGCGTTGA*
*GGACCGCTTCAACGCCAGCCTCGGGACCTACCACGATCTCCTGAAGATCATCAA*
*GGATAAGGACTTCCTGGACAACGAGGAGAACGAGGATATCCTGGAGGACATCGT*
*GCTGACCCTCACGCTGTTCGAGGACAGGGAGATGATCGAGGAGCGCCTGAAGAC*
*GTACGCCCATCTCTTCGATGACAAGGTCATGAAGCAACTCAAGCGCCGGAGATAC*
*ACCGGCTGGGGGAGGCTGTCCCGCAAGCTCATCAACGGCATCCGGGACAAGCA*

-continued

SEQUENCES

*GTCCGGGAAGACCATCCTCGACTTCCTCAAGAGCGATGGCTTCGCCAACAGGAA*
*CTTCATGCAACTGATCCACGATGACAGCCTCACCTTCAAGGAGGATATCCAAAAG*
*GCTCAAGTGAGCGGCCAGGGGGACTCGCTGCACGAGCATATCGCGAACCTCGCT*
*GGCTCCCCCGCGATCAAGAAGGGCATCCTCCAGACCGTGAAGGTTGTGGACGAG*
*CTCGTGAAGGTCATGGGCCGGCACAAGCCTGAGAACATCGTCATCGAGATGGCC*
*AGAGAGAACCAAACCACGCAGAAGGGGCAAAAGAACTCTAGGGAGCGCATGAAG*
*CGCATCGAGGAGGGCATCAAGGAGCTGGGGTCCCAAATCCTCAAGGAGCACCCA*
*GTGGAGAACACCCAACTGCAGAACGAGAAGCTCTACCTGTACTACCTCCAGAACG*
*GCAGGGATATGTACGTGGACCAAGAGCTGGATATCAACCGCCTCAGCGATTACG*
*ACGTCGATCATATCGTTCCCCAGTCTTTCCTGAAGGATGACTCCATCGACAACAA*
*GGTCCTCACCAGGTCGGACAAGAACCGCGGCAAGTCAGATAACGTTCCATCTGA*
*GGAGGTCGTTAAGAAGATGAAGAACTACTGGAGGCAGCTCCTGAACGCCAAGCT*
*GATCACGCAAAGGAAGTTCGACAACCTCACCAAGGCTGAGAGAGGCGGGCTCTC*
*AGAGCTGGACAAGGCCGGCTTCATCAAGCGGCAGCTGGTCGAGACCAGACAAAT*
*CACGAAGCACGTTGCGCAAATCCTCGACTCTCGGATGAACACGAAGTACGATGA*
*GAACGACAAGCTGATCAGGGAGGTTAAGGTGATCACCCTGAAGTCTAAGCTCGTC*
*TCCGACTTCAGGAAGGATTTCCAGTTCTACAAGGTTCGCGAGATCAACAACTACC*
*ACCATGCCCATGACGCTTACCTCAACGCTGTGGTCGGCACCGCTCTGATCAAGAA*
*GTACCCAAAGCTGGAGTCCGAGTTCGTGTACGGGGACTACAAGGTTTACGATGT*
*GCGCAAGATGATCGCCAAGTCGGAGCAAGAGATCGGCAAGGCTACCGCCAAGTA*
*CTTCTTCTACTCAAACATCATGAACTTCTTCAAGACCGAGATCACGCTGGCCAACG*
*GCGAGATCCGGAAGAGACCGCTCATCGAGACCAACGGCGAGACGGGGGAGATC*
*GTGTGGGACAAGGGCAGGGATTTCGCGACCGTCCGCAAGGTTCTCTCCATGCCC*
*CAGGTGAACATCGTCAAGAAGACCGAGGTCCAAACGGGCGGGTTCTCAAAGGAG*
*TCTATCCTGCCTAAGCGGAACAGCGACAAGCTCATCGCCAGAAAGAAGGACTGG*
*GACCCAAAGAAGTACGGCGGGTTCGACAGCCCTACCGTGGCCTACTCGGTCCTG*
*GTTGTGGCGAAGGTTGAGAAGGGCAAGTCCAAGAAGCTCAAGAGCGTGAAGGAG*
*CTCCTGGGGATCACCATCATGGAGAGGTCCAGCTTCGAGAAGAACCCAATCGAC*
*TTCCTGGAGGCCAAGGGCTACAAGGAGGTGAAGAAGGACCTGATCATCAAGCTC*
*CCGAAGTACTCTCTCTTCGAGCTGGAGAACGGCAGGAAGAGAATGCTGGCTTCC*
*GCTGGCGAGCTCCAGAAGGGGAACGAGCTCGCGCTGCCAAGCAAGTACGTGAA*
*CTTCCTCTACCTGGCTTCCCACTACGAGAAGCTCAAGGGCAGCCCGGAGGACAA*
*CGAGCAAAAGCAGCTGTTCGTCGAGCAGCACAAGCATTACCTCGACGAGATCATC*
*GAGCAAATCTCCGAGTTCAGCAAGCGCGTGATCCTCGCCGACGCGAACCTGGAT*
*AAGGTCCTCTCCGCCTACAACAAGCACCGGGACAAGCCCATCAGAGAGCAAGCG*
*GAGAACATCATCCATCTCTTCACCCTGACGAACCTCGGCGCTCCTGCTGCTTTCA*
*AGTACTTCGACACCACGATCGATCGGAAGAGATACACCTCCACGAAGGAGGTCCT*
*GGACGCGACCCTCATCCACCAGTCGATCACCGGCCTGTACGAGACGAGGATCGA*
*CCTCTCACAACTCGGCGGGGATAAGAGACCCGCAGCAACCAAGAAGGCAGGGCA*
*AGCAAAGAAGAAGAAGTGA 3'*

SEQ ID NO: 102: Cys 4 endoriboneclease nucleic acid sequence
5'ATGGACCACTACCTCGACATCAGGCTCAGGCCAGACCCAGAGTTCCCACCAGC
CCAGCTCATGTCCGTCCTCTTCGGCAAGCTCCACCAGGCCCTCGTGGCCCAGGG
CGGCGACAGGATCGGCGTGTCCTTCCCAGACCTCGACGAGTCCAGGTCCAGGCT
CGGCGAGAGGCTCCGCATCCACGCCTCCGCCGACGACCTCAGGGCCCTCCTCG
CCAGGCCGTGGCTGGAGGGCCTCAGGGACCACCTCCAGTTCGGCGAGCCAGCC
GTGGTGCCACACCCAACCCCATACAGGCAAGTGTCCAGGGTGCAAGCCAAGTCC
AACCCAGAGAGGCTCAGGAGGAGGCTCATGAGGAGGCACGACCTCTCCGAGGA
AGAGGCCAGGAAGCGCATCCCAGACACCGTGGCCAGGGCCCTCGACCTCCCATT
CGTGACCCTCAGGTCCCAGTCCACCGGCCAGCACTTCCGCCTCTTCATCAGGCA
CGGCCCACTCCAGGTGACCGCCGAGGAGGGCGGCTTTACCTGCTACGGCCTCT
CCAAGGGCGGCTTCGTGCCGTGGTTC 3'

SEQ ID NO: 103; Cys4 cleavage site
GTTCACTGCCGTATAGGCAG

SEQ ID NO: 104; cestrum yellow leaf curling virus (CmYLCV) promoter
5'TGGCAGACATACTGTCCCACAAATGAAGATGGAATCTGTAAAAGAAAACGCGTG
AAATAATGCGTCTGACAAAGGTTAGGTCGGCTGCCTTTAATCAATACCAAAGTGGT
CCCTACCACGATGGAAAAACTGTGCAGTCGGTTTGGCTTTTTCTGACGAACAAAT
AAGATTCGTGGCCGACAGGTGGGGGTCCACCATGTGAAGGCATCTTCAGACTCC
AATAATGGAGCAATGACGTAAGGGCTTACGAAATAAGTAAGGGTAGTTTGGGAAA
TGTCCACTCACCCGTCAGTCTATAAATACTTAGCCCCTCCCTCATTGTTAAGGGAG
CAAAATCTCAGAGAGATAGTCCTAGAGAGAGAAAGAGAGCAAGTAGCCTAGAAGT
AGTCAAGGCGGCGAAGTATTCAGGCACGTGGCCAGGAAGAAGAAAAGCCAAGAC
GACGAAAACAGGTAAGAGCTAAGCTT 3'

SEQ ID NO: 105; switchgrass ubiquitin 1 promoter (PvUbi1)
5'CACGTCAGTGTTTGGTTTCCACTAGCACGAGTAGCGCAATCAGAAAATTTTCAAT
GCATGAAGTACTAAACGAAGTTTATTTAGAAATTTTTTTAAGAAATGAGTGTAATTT
TTTGCGACGAATTTAATGACAATAATTAATCGATGATTGCCTACAGTAATGCTACA
GTAACCAACCTCTAATCATGCGTCGAATGCGTCATTAGATTCGTCTCGCAAAATAG
CACAAGAATTATGAAATTAATTTTACAAACTATTTTTATTTAATACTAATAATTAACT
GTCAAAGTTTGTGCTACTCGCAAGAGTAGCGCGAACCAAACACGGCCTGGAGGA
GCACGGTAACGGCGTCGACAAACTAACGGCCACCACCCGCCAACGCAAAGGAGA
CGGATGAGAGTTGACTTCTTGACGGTTCTCCACCCCTCTGTCTCTCTGTCACTGG -continued

| SEQUENCES |
|---|

GCCCTGGGTCCCCCTCTCGAAAGTTCCTCTGGCCGAAATTGCGCGGCGGAGACG
AGGCGGGCGGAACCGTCACGGCAGAGGATTCCTTCCCCACCCTGCCTGGCCCG
GCCATATATAAACAGCCACCGCCCCTCCCCGTTCCCCATCGCGTCTCGTCTCGTG
TTGTTCCCAGAACACAACCAAAATCCAAATCCTCCTCCTCCTCCCGAGCCTCGT
CGATCCCTCACCCGCTTCAAG*GTACGGCGATCCTCCTCTCCCTTCTCCCCTCGAT*
*CGATTATGCGTGTTCCGTTTCCGTTTCCGATCGAGCGAATCGATGGTTAGGACCC*
*ATGGGGGACCCATGGGGTGTCGTGTGGTGGTCTGGTTTGATCCGCGATATTTCT*
*CCGTTCGTAGTGTAGATCTGATCGAATCCCTGGTGAAATCGTTGATCGTGCTATTC*
*GTGTGAGGGTTCTTAGGTTTGGAGTTGTGGAGGTAGTTCTGATCGGTTTGTAGGT*
*GAGATTTTCCCCATGATTTTGCTTGGCTCGTTTGTCTTGGTTAGATTAGATCTGCC*
*CGCATTTTGTTCGATATTTCTGATGCAGATATGATGAATAATTTCGTCCTTGTATCC*
*CGCGTCCGTATGTGTATTAAGTTTGCAGGTCCTAGTTAGGTTTTTCCTACTGATTT*
*GTCTTATCCATTCTGTTTAGCTTGCAAGGTTTGGTAATGGTCCGGCATGTTTGTCT*
*CTATAGATTAGAGTAGAATAAGATTATCTCAACAAGCTGTTGGCTTATCAATTTTGG*
*ATCTGCATGTGTTTCGCATCTATATCTTTGCAATTAAGATGGTAGATGGACATATG*
*CTCCTGTTGAGTTGATGTTGTACCTTTTACCTGAGGTCTGAGGAACATGCATCCTC*
*CTGCTACTTTGTGCTTATACAGATCATCAAGATTATGCAGCTAATATTCGATCAGTT*
*TCTAGTATCTACATGGTAAACTTGCATGCACTTGCTACTTATTTTTGATATACTTGG*
*ATGATAACATATGCTGCTGGTTGATTCCTACCTACATGATGAACATTTTACAGGCC*
*ATTAGTGTCTGTCTGTATGTGTTGTTCCTGTTTGCTTCAGTCTATTTCTGTTTCATT*
*CCTAGTTTATTGGTTCTCTGCTAGATACTTACCCTGCTGGGCTTAGTTATCATCTTA*
*TCTCGAATGCATTTTCATGTTTATAGATGAATATACACTCAGATAGGTGTAGATGTA*
*TGCTACTGTTTCTCTACGTTGCTGTAGGTTTTACCTGTGGCAACTGCATACTCCTG*
*TTGCTTCGCTAGATATGTATGTGCTTATATAGATTAAGATATGTGTGATGGTTCTTT*
*AGTATATCTGATGATCATGTATGCTCTTTTAACTTCTTGCTACACTTGGTAACATGC*
*TGTGATGCTGTTTGTTGATTCTGTAGCACTACCAATGATGACCTTATCTCTCTTTGT*
*ATATGATGTTTCTGTTTGTTTGAGGCTTGTGTTACTGCTAGTTACTTACCCTGTTGC*
*CTGGCTAATCTTCTGCAG* 3'

In this promoter, in bold the PvUbi1 5' UTR a 93 bp non-coding exon, and in italic the
PvUbi1 intron1.
SEQ ID NO: 106; Zea Mays Ubiquitin 1 promoter
5'TGCAGTGCAGCGTGACCCGGTCGTGCCCCTCTCTAGAGATAATGAGCATTGCA
TGTCTAAGTTATAAAAAATTACCACATATTTTTTTTGTCACACTTGTTTGAAGTGCA
GTTTATCTATCTTTATACATATATTTAAACTTTACTCTACGAATAATATAATCTATAG
TACTACAATAATATCAGTGTTTTAGAGAATCATATAAATGAACAGTTAGACATGGTC
TAAAGGACAATTGAGTATTTTGACAACAGGACTCTACAGTTTTATCTTTTTAGTGTG
CATGTGTTCTCCTTTTTTTTTGCAAATAGCTTCACCTATATAATACTTCATCCATTTT
ATTAGTACATCCATTTAGGGTTTAGGGTTAATGGTTTTTATAGACTAATTTTTTTAG
TACATCTATTTTATTCTATTTTAGCCTCTAAATTAAGAAAACTAAAACTCTATTTTAG
TTTTTTTATTTAATAATTTAGATATAAAATAGAATAAAATAAAGTGACTAAAAATTAA
ACAAATACCCTTTAAGAAATTAAAAAAACTAAGGAAACATTTTTCTTGTTTCGAGTA
GATAATGCCAGCCTGTTAAACGCCGTCGACGAGTCTAACGGACACCAACCAGCG
AACCAGCAGCGTCGCGTCGGGCCAAGCGAAGCAGACGGCACGGCATCTCTGTC
GCTGCCTCTGGACCCCTCTCGAGAGTTCCGCTCCACCGTTGGACTTGCTCCGCT
GTCGGCATCCAGAAATTGCGTGGCGGAGCGGCAGACGTGAGCCGGCACGGCAG
GCGGCCTCCTCCTCCTCTCACGGCACCGGCAGCTACGGGGGATTCCTTTCCCAC
CGCTCCTTCGCTTTCCCTTCCTCGCCCGCCGTAATAAATAGACACCCCCTCCACA
CCCTCTTTCCCCAACCTCGTGTTGTTCGGAGCGCACACACACACAACCAGATCT
CCCCCAAATCCACCCGTCGGCACCTCCGCTTCAAG*GTACGCCGCTCGTCCTCCC*
*CCCCCCCCCTCTCTACCTTCTCTAGATCGGCGTTCCGGTCCATGGTTAGGGCCC*
*GGTAGTTCTACTTCTGTTCATGTTTGTGTTAGATCCGTGTTTGTGTTAGATCCGTG*
*CTGCTAGCGTTCGTACACGGATGCGACCTGTACGTCAGACACGTTCTGATTGCTA*
*ACTTGCCAGTGTTTCTCTTTGGGGAATCCTGGGATGGCTCTAGCCGTTCCGCAGA*
*CGGGATCGATTTCATGATTTTTTTTGTTTCGTTGCATAGGGTTTGGTTTGCCCTTTT*
*CCTTTATTTCAATATATGCCGTGCACTTGTTTGTCGGGTCATCTTTTCATGCTTTTT*
*TTTGTCTTGGTTGTGATGATGTGGTCTGGTTGGGCGGTCGTTCTAGATCGGAGTA*
*GAATTAATTCTGTTTCAAACTACCTGGTGGATTTATTAATTTTGGATCTGTATGTGT*
*GTGCCATACATATTCATAGTTACGAATTGAAGATGATGGATGGAAATATCGATCTA*
*GGATAGGTATACATGTTGATGCGGGTTTTACTGATGCATATACAGAGATGCTTTTT*
*GTTCGCTTGGTTGTGATGATGTGGTGTGGTTGGGCGGTCGTTCATTCGTTCTAGA*
*TCGGAGTAGAATACTGTTTCAAACTACCTGGTGTATTTATTAATTTTGGAACTGTAT*
*GTGTGTGTCATACATCTTCATAGTTACGAGTTTAAGATGGATGGAAATATCGATCT*
*AGGATAGGTATACATGTTGATGTGGGTTTTACTGATGCATATACATGATGGCATAT*
*GCAGCATCTATTCATATGCTCTAACCTTGAGTACCTATCTATTATAATAAACAAGTA*
*TGTTTTATAATTATTTTGATCTTGATATACTTGGATGATGGCATATGCAGCAGCTAT*
*ATGTGGATTTTTTTAGCCCTGCCTTCATACGCTATTTATTTGCTTGGTACTGTTTCT*
*TTTGTCGATGCTCACCCTGTTGTTTGGTGTTACTTCTGCA* 3'

In this promoter, in bold the ZmUbi1 5'UTR a 83 bp non-coding exon, and in italic the ZmUbi1 intron1
SEQ ID NO: 107; tracrRNA; nucleotide sequence for alpha-1 and alpha-2
GAAATAGCAAGTTAAAATAAGGCTAGTCCGTTATCAACTTGAAAAAGTGGCACCGA
GTCGGTGCTTTTTTT

-continued

| SEQUENCES |
| --- |

SEQ ID NO: 108; *T. aestivum* UG RNA polymerase III promoter (TaU6)
GACCAAGCCCGTTATTCTGACAGTTCTGGTGCTCAACACATTTATATTTATCAAGG
AGCACATTGTTACTCACTGCTAGGAGGGAATCGAACTAGGAATATTGATCAGAGG
AACTACGAGAGAGCTGAAGATAACTGCCCTCTAGCTCTCACTGATCTGGGTCGCA
TAGTGAGATGCAGCCCACGTGAGTTCAGCAACGGTCTAGCGCTGGGCTTTTAGG
CCCGCATGATCGGGCTTTTGTCGGGTGGTCGACGTGTTCACGATTGGGGAGAGC
AACGCAGCAGTTCCTCTTAGTTTAGTCCCACCTCGCCTGTCCAGCAGAGTTCTGA
CCGGTTTATAAACTCGCTTGCTGCATCAGACTT Alpha-gliadin-target sequence for APOBEC-nTaCas9 (Nickase Cas9)
SEQ ID NO: 789; DsgGlia20-1
TATGGTTGTTGTGGTCGAAANGG SEQ ID NO: 790; DsgDQ2.5-1
GGATATGGTAGTTGCGGCTGNGG SEQ ID NO: 791; DsgDQ2.5Glila
GGTAGTTGCGGCTGCGGAAANGG Alpha-gliadin-target sequence for Cpf1
SEQ ID NO: 792; sgCpf1Alpha-1
TTTNTGGCTGCAATTGTGGCACTG SEQ ID NO: 793; sgCpf1Alpha-2
TTTNCATCACAACAACCATATCTG SEQ ID NO: 794; sgCpf1Alpha-3
TTTNTAGGGCAGCAACAACCATTT SEQ ID NO: 795; sgCpf133mer1
TTTNCGCAGCCGCAACTACCATAT SEQ ID NO: 796; sgCpf1Glia20
TTTNGACCACAACAACCATATCCA Omega-gliadin-target sequence for Cpf1
SEQ ID NO: 797; sgCpf1Omega-1
TTTNTCCTCCTTGCCATGGCGATG SEQ ID NO: 798; sgCpf1Omega-2
TTTNCCATCAACAACAACCATTTC SEQ ID NO: 799; sgCpf1Omega-3
TTTNCCAGCAACCCCAACAACCAT Gamma-gliadin-target sequence for Cpf1
SEQ ID NO: 800; sgCpf1Gamma-1
TTTNCCCAACCCCAACAAACATTC SEQ ID NO: 801; sgCpf1Gamma-2
TTTNTGCTAGTTGTTGGCAACATT SEQ ID NO: 802; sgCpf1Gamma-3
TTTNTCCAGCCCCAACAACCATTC SEQ ID NO: 803; sgCpf1Gamma-4
TTTNTTGGGGTTGGGGAAATGTTT Alpha-gliadin-protospacer sequence for APOBEC-nTaCas9
SEQ ID NO: 804; DsgGlia20-1
TATGGTTGTTGTGGTCGAAA SEQ ID NO: 805; DsgDQ2.5-1
GGATATGGTAGTTGCGGCTG SEQ ID NO: 806; DsgDQ2.5Glila
GGTAGTTGCGGCTGCGGAAA Alpha-gliadin-protospacer sequence for Cpf1
SEQ ID NO: 807; sgCpf1Alpha-1
TGGCTGCAATTGTGGCACTG SEQ ID NO: 808; sgCpf1Alpha-2
CATCACAACAACCATATCTG -continued

| SEQUENCES |
|---|

SEQ ID NO: 809; sgCpf1Alpha-3
TAGGGCAGCAACAACCATTT

SEQ ID NO: 810; sgCpf133mer1
CGCAGCCGCAACTACCATAT

SEQ ID NO: 811; sgCpf1Glia20
GACCACAACAACCATATCCA

Omega-gliadin-protospacer sequence for Cpf1
SEQ ID NO: 812; sgCpf1Omega-1
TCCTCCTTGCCATGGCGATG SEQ ID NO: 813; sgCpf1Omega-2
CCATCAACAACAACCATTTC SEQ ID NO: 814; sgCpf1Omega-3
CCAGCAACCCCAACAACCAT Gamma-gliadin-protospacer sequence for Cpf1
SEQ ID NO: 815; sgCpf1Gamma-1
CCCAACCCCAACAAACATTC SEQ ID NO: 816; sgCpf1Gamma-2
TGCTAGTTGTTGGCAACATT SEQ ID NO: 817; sgCpf1Gamma-3
TCCAGCCCCAACAACCATTC SEQ ID NO: 818; sgCpf1Gamma-4
TTGGGGTTGGGGAAATGTTT SEQ ID NO: 819 nucleic acid sequence of Ta-LbCpf1
5'ATGAGCAAGCTGGAGAAGTTTACGAATTGCTACAGTCTGTCCAAGACGTTGCGC
TTCAAGGCCATACCAGTCGGGAAGACTCAAGAGAACATAGACAACAAGCGACTCC
TTGTGGAAGACGAGAAACGCGCGGAGGACTATAAGGGGGTCAAAAAGCTTCTTG
ACAGATACTATTTGTCTTTTATAAACGATGTCCTACATTCTATCAAATTAAAGAATC
TCAACAATTACATCTCGCTATTTCGAAAGAAGACGCGGACGGAAAAGGAAAACAA
AGAATTAGAAAATCTTGAGATAAATCTTCGTAAGGAAATAGCCAAGGCTTTTAAAG
GCAACGAAGGCTATAAGTCACTATTCAAAAAAGATATCATTGAAACAATCCTTCCC
GAATTCCTAGACGACAAGGATGAAATCGCACTGGTTAATTCATTCAACGGGTTCA
CGACTGCATTCACTGGATTCTTCGATAATCGGGAAAATATGTTTTCAGAGGAGGC
CAAGTCCACGTCAATCGCTTTTAGGTGCATAAATGAAAATTTAACCCGGTATATAT
CCAATATGGATATCTTTGAGAAGGTAGACGCCATATTTGACAAGCATGAAGTGCAA
GAAATTAAGGAAAAGATTCTCAACAGTGACTATGACGTGGAGGACTTTTTCGAGG
GGGAATTCTTCAATTTCGTACTAACTCAGGAGGGCATAGATGTCTATAACGCGATC
ATCGGTGGGTTCGTGACTGAGAGTGGCGAAAAGATCAAGGGTTTGAACGAGTATA
TAAATTTATATAACCAGAAGACCAAGCAAAAGCTTCCTAAGTTTAAGCCACTCTATA
AACAGGTACTGAGCGACCGGGAAAGCCTTTCCTTTTACGGCGAAGGATATACATC
GGACGAAGAAGTACTGGAGGTATTCCGCAACACATTGAACAAAAATTCTGAGATT
TTCAGCTCCATAAAAAAGTTGGAAAAACTTTTCAAAAATTTTGATGAATACTCTTCG
GCGGGAATCTTCGTTAAGAACGGGCCTGCTATTTCAACCATTAGCAAAGACATCT
TCGGCGAATGGAATGTTATTCGCGATAAATGGAATGCTGAGTACGACGATATACA
CCTTAAGAAGAAGGCTGTTGTCACAGAAAAATATGAAGACGACCGGAGGAAGTCA
TTCAAGAAGATTGGTTCTTTCAGCCTCGAACAGCTGCAGGAGTATGCTGATGCTG
ACCTCTCAGTGGTGGAGAAACTTAAGGAGATTATTATCCAAAAGGTTGACGAGAT
ATACAAAGTGTATGGCAGCTCTGAGAAACTTTTCGATGCAGATTTTGTGCTAGAGA
AATCACTAAAGAAAAACGACGCGGTGGTGGCAATTATGAAGGACTTGCTCGACTC
TGTTAAGAGCTTTGAGAACTACATAAAGGCGTTCTTCGGCGAGGGCAAGGAGACC
AACAGAGATGAGTCCTTCTACGGTGACTTTGTCTTGGCGTACGACATTCTTTTGAA
GGTGGATCACATTTATGACGCTATTAGAAATTACGTCACGCAGAAGCCGTATTCTA
AAGATAAATTCAAACTGTATTTTCAGAATCCACAGTTCATGGGTGGCTGGGATAAG
GATAAAGAGACTGATTACAGGGCAACAATCCTCCGCTACGGCAGTAAGTATTATC
TGGCGATCATGGATAAAAAATACGCCAAGTGCTTGCAAAAGATTGATAAAGACGA
CGTGAACGGAAATTATGAGAAGATTAATTATAAACTTCTACCGGGGCCAAACAAGA
TGTTGCCAAAGGTCTTCTTCTCTAAAAAGTGGATGGCTTATTACAATCCGAGCGAG
GATATACAAAAGATTTACAAAAACGGTACGTTTAAGAAGGGTGACATGTTTAATTT
GAACGACTGTCACAAGCTCATTGACTTTTTTAAGGATTCTATCTCAAGATACCCTA
AATGGAGTAACGCATACGATTTTAACTTCAGTGAGACAGAGAAGTACAAAGACATC
GCAGGTTTTTACAGAGAGGTTGAGGAGCAGGGATACAAAGTTAGCTTTGAGTCAG
CGAGTAAGAAGGAGGTCGATAAACTGGTGGAGGAGGGTAAGCTGTACATGTTCC
AGATCTACAATAAGGATTTCTCAGACAAGTCGCACGGTACGCCAAACCTCCATAC
AATGTACTTTAAGTTGTTGTTCGACGAGAACAATCACGGGCAAATCCGGCTGTCT
GGGGGAGCAGAGTTGTTTATGCGGCGAGCATCGCTGAAGAAGGAGGAGCTCGTT
GTTCATCCTGCAAATTCTCCGATCGCCAATAAGAACCCAGACAATCCGAAGAAGA
CCACTACTCTCTCCTACGATGTCTACAAGGATAAGCGTTTCTCCGAGGACCAATA -continued

| SEQUENCES |
| --- |

CGAGCTCCATATCCCAATCGCCATTAACAAGTGTCCCAAGAACATTTTCAAGATCA
ATACAGAGGTGCGCGTCCTGCTGAAGCACGATGACAACCCCTACGTTATTGGAAT
TGATCGTGGGGAGCGCAACCTGCTCTACATCGTTGTTGTGGATGGAAAGGGAAA
CATTGTGGAGCAATACTCCCTGAACGAGATTATCAACAACTTTAACGGGATCAGG
ATTAAGACTGACTACCACTCACTCCTCGACAAGAAGGAGAAGGAGAGGTTTGAGG
CGCGTCAGAACTGGACCAGCATCGAGAACATCAAGGAGCTCAAGGCTGGATACA
TCTCCCAAGTGGTCCACAAGATCTGCGAGCTGGTCGAGAAGTACGACGCGGTCA
TCGCCCTGGAGGACCTCAACTCGGGGTTCAAGAACTCCCGTGTGAAGGTCGAGA
AGCAGGTCTACCAAAAGTTCGAGAAGATGCTCATCGATAAGCTGAACTACATGGT
GGATAAGAAGTCGAACCCATGCGCTACCGGCGGCGCGCTCAAGGGCTACCAAAT
CACCAACAAGTTCGAGAGCTTCAAGAGCATGTCCACCCAAAACGGGTTCATCTTC
TACATCCCCGCGTGGCTGACCTCGAAGATCGATCCGAGCACCGGCTTCGTGAAC
CTCCTGAAGACCAAGTACACCAGCATCGCCGACTCGAAGAAGTTCATCTCGTCCT
TCGACAGGATCATGTACGTCCCGGAGGAGGACCTCTTCGAGTTCGCGCTGGACT
ACAAGAACTTCAGCCGCACCGACGCCGACTACATCAAGAAGTGGAAGCTCTACTC
GTACGGCAACAGGATCCGCATCTTCAGGAACCCTAAGAAGAACAACGTCTTCGAC
TGGGAGGAGGTGTGCCTGACCTCCGCGTACAAGGAGCTCTTCAACAAGTACGGC
ATCAACTACCAACAAGGCGACATCCGCGCCCTGCTCTGCGAGCAAAGCGACAAG
GCGTTCTACTCCTCGTTCATGGCCCTGATGAGCCTCATGCTCCAGATGCGCAACT
CCATCACCGGCAGGACCGACGTGGACTTCCTGATCTCCCCCGTGAAGAACTCCG
ACGGCATCTTCTACGACTCCAGGAACTACGAGGCCCAGGAGAACGCCATCCTCC
CCAAGAACGCCGACGCCAACGGCGCCTACAACATCGCCAGGAAGGTGCTCTGG
GCCATCGGCCAATTCAAGAAGGCCGAGGACGAGAAGCTCGACAAGGTCAAGATC
GCCATCAGCAACAAGGAGTGGCTCGAGTACGCCCAGACCAGCGTCAAGCAC 3'

SEQ ID NO: 820 nucleic acid sequence of Ta-dLbCpf1 D832A E925A D1148A
5'ATGAGCAAGCTGGAGAAGTTTACGAATTGCTACAGTCTGTCCAAGACGTTGCGC
TTCAAGGCCATACCAGTCGGGAAGACTCAAGAGAACATAGACAACAAGCGACTCC
TTGTGGAAGACGAGAAACGCGCGGAGGACTATAAGGGGGTCAAAAAGCTTCTTG
ACAGATACTATTTGTCTTTTATAAACGATGTCCTACATTCTATCAAATTAAAGAATC
TCAACAATTACATCTCGCTATTTCGAAAGAAGACGCGGACGGAAAAGGAAAACAA
AGAATTAGAAAATCTTGAGATAAATCTTCGTAAGGAAATAGCCAAGGCTTTTAAAG
GCAACGAAGGCTATAAGTCACTATTCAAAAAAGATATCATTGAAACAATCCTTCCC
GAATTCCTAGACGACAAGGATGAAATCGCACTGGTTAATTCATTCAACGGGTTCA
CGACTGCATTCACTGGATTCTTCGATAATCGGGAAAATATGTTTTCAGAGGAGGC
CAAGTCCACGTCAATCGCTTTTAGGTGCATAAATGAAAATTTAACCCGGTATATAT
CCAATATGGATATCTTTGAGAAGGTAGACGCCATATTTGACAAGCATGAAGTGCAA
GAAATTAAGGAAAAGATTCTCAACAGTGACTATGACGTGGAGGACTTTTTCGAGG
GGGAATTCTTCAATTTCGTACTAACTCAGGAGGGCATAGATGTCTATAACGCGATC
ATCGGTGGGTTCGTGACTGAGAGTGGCGAAAAGATCAAGGGTTTGAACGAGTATA
TAAATTTATATAACCAGAAGACCAAGCAAAAGCTTCCTAAGTTTAAGCCACTCTATA
AACAGGTACTGAGCGACCGGGAAAGCCTTTCCTTTTACGGCGAAGGATATACATC
GGACGAAGAAGTACTGGAGGTATTCCGCAACACATTGAACAAAAATTCTGAGATT
TTCAGCTCCATAAAAAAGTTGGAAAAACTTTTCAAAAATTTTGATGAATACTCTTCG
GCGGGAATCTTCGTTAAGAACGGGCCTGCTATTTCAACCATTAGCAAAGACATCT
TCGGCGAATGGAATGTTATTCGCGATAAATGGAATGCTGAGTACGACGATATACA
CCTTAAGAAGAAGGCTGTTGTCACAGAAAAATATGAAGACGACCGGAGGAAGTCA
TTCAAGAAGATTGGTTCTTTCAGCCTCGAACAGCTGCAGGAGTATGCTGATGCTG
ACCTCTCAGTGGTGGAGAAACTTAAGGAGATTATTATCCAAAAGGTTGACGAGAT
ATACAAAGTGTATGGCAGCTCTGAGAAACTTTTCGATGCAGATTTTGTGCTAGAGA
AATCACTAAAGAAAAACGACGCGGTGGTGGCAATTATGAAGGACTTGCTCGACTC
TGTTAAGAGCTTTGAGAACTACATAAAGGCGTTCTTCGGCGAGGGCAAGGAGACC
AACAGAGATGAGTCCTTCTACGGTGACTTTGTCTTGGCGTACGACATTCTTTTGAA
GGTGGATCACATTTATGACGCTATTAGAAATTACGTCACGCAGAAGCCGTATTCTA
AAGATAAATTCAAACTGTATTTTCAGAATCCACAGTTCATGGGTGGCTGGGATAAG
GATAAAGAGACTGATTACAGGGCAACAATCCTCCGCTACGGCAGTAAGTATTATC
TGGCGATCATGGATAAAAAATACGCCAAGTGCTTGCAAAAGATTGATAAAGACGA
CGTGAACGGAAATTATGAGAAGATTAATTATAAACTTCTACCGGGGCCAAACAAGA
TGTTGCCAAAGGTCTTCTTCTCTAAAAAGTGGATGGCTTATTACAATCCGAGCGAG
GATATACAAAAGATTTACAAAAACGGTACGTTTAAGAAGGGTGACATGTTTAATTT
GAACGACTGTCACAAGCTCATTGACTTTTTTAAGGATTCTATCTCAAGATACCCTA
AATGGAGTAACGCATACGATTTTAACTTCAGTGAGACAGAGAAGTACAAAGACATC
GCAGGTTTTTACAGAGAGGTTGAGGAGCAGGGATACAAAGTTAGCTTTGAGTCAG
CGAGTAAGAAGGAGGTCGATAAACTGGTGGAGGAGGGTAAGCTGTACATGTTCC
AGATCTACAATAAGGATTTCTCAGACAAGTCGCACGGTACGCCAAACCTCCATAC
AATGTACTTTAAGTTGTTGTTCGACGAGAACAATCACGGGCAAATCCGGCTGTCT
GGGGGAGCAGAGTTGTTTATGCGGCGAGCATCGCTGAAGAAGGAGGAGCTCGTT
GTTCATCCTGCAAATTCTCCGATCGCCAATAAGAACCCAGACAATCCGAAGAAGA
CCACTACTCTCTCCTACGATGTCTACAAGGATAAGCGTTTCTCCGAGGACCAATA
CGAGCTCCATATCCCAATCGCCATTAACAAGTGTCCCAAGAACATTTTCAAGATCA
ATACAGAGGTGCGCGTCCTGCTGAAGCACGATGACAACCCCTACGTTATTGGAAT
TGCTCGTGGGGAGCGCAACCTGCTCTACATCGTTGTTGTGGATGGAAAGGGAAA
CATTGTGGAGCAATACTCCCTGAACGAGATTATCAACAACTTTAACGGGATCAGG
ATTAAGACTGACTACCACTCACTCCTCGACAAGAAGGAGAAGGAGAGGTTTGAGG
CGCGTCAGAACTGGACCAGCATCGAGAACATCAAGGAGCTCAAGGCTGGATACA
TCTCCCAAGTGGTCCACAAGATCTGCGAGCTGGTCGAGAAGTACGACGCGGTCA
TCGCCCTGGCCGACCTCAACTCGGGGTTCAAGAACTCCCGTGTGAAGGTCGAGA -continued

| SEQUENCES |
|---|

AGCAGGTCTACCAAAAGTTCGAGAAGATGCTCATCGATAAGCTGAACTACATGGT
GGATAAGAAGTCGAACCCATGCGCTACCGGCGGCGCGCTCAAGGGCTACCAAAT
CACCAACAAGTTCGAGAGCTTCAAGAGCATGTCCACCCAAAACGGGTTCATCTTC
TACATCCCCGCGTGGCTGACCTCGAAGATCGATCCGAGCACCGGCTTCGTGAAC
CTCCTGAAGACCAAGTACACCAGCATCGCCGACTCGAAGAAGTTCATCTCGTCCT
TCGACAGGATCATGTACGTCCCGGAGGAGGACCTCTTCGAGTTCGCGCTGGACT
ACAAGAACTTCAGCCGCACCGACGCCGACTACATCAAGAAGTGGAAGCTCTACTC
GTACGGCAACAGGATCCGCATCTTCAGGAACCCTAAGAAGAACAACGTCTTCGAC
TGGGAGGAGGTGTGCCTGACCTCCGCGTACAAGGAGCTCTTCAACAAGTACGGC
ATCAACTACCAACAAGGCGACATCCGCGCCCTGCTCTGCGAGCAAAGCGACAAG
GCGTTCTACTCCTCGTTCATGGCCCTGATGAGCCTCATGCTCCAGATGCGCAACT
CCATCACCGGCAGGACCGACGTGGCCTTCCTGATCTCCCCCGTGAAGAACTCCG
ACGGCATCTTCTACGACTCCAGGAACTACGAGGCCCAGGAGAACGCCATCCTCC
CCAAGAACGCCGACGCCAACGGCGCCTACAACATCGCCAGGAAGGTGCTCTGG
GCCATCGGCCAATTCAAGAAGGCCGAGGACGAGAAGCTCGACAAGGTCAAGATC
GCCATCAGCAACAAGGAGTGGCTCGAGTACGCCCAGACCAGCGTCAAGCAC 3'

SEQ ID NO: 821 nucleic acid sequence of APOBEC1
5'ATGTCATCGGAGACCGGCCCTGTTGCTGTTGACCCCACCCTGCGGCGGAGAAT
CGAGCCACACGAGTTCGAGGTGTTCTTCGACCCAAGGGAGCTCCGCAAGGAGAC
GTGCCTCCTGTACGAGATCAACTGGGGCGGCAGGCACTCCATCTGGAGGCACAC
CAGCCAAAACACCAACAAGCACGTGGAGGTCAACTTCATCGAGAAGTTCACCACC
GAGAGGTACTTCTGCCCAAACACCCGCTGCTCCATCACCTGGTTCCTGTCCTGGA
GCCCATGCGGCGAGTGCTCCAGGGCCATCACCGAGTTCCTCAGCCGCTACCCAC
ACGTCACCCTGTTCATCTACATCGCCAGGCTCTACCACCACGCCGACCCAAGGAA
CAGGCAGGGCCTCCGCGACCTGATCTCCAGCGGCGTGACCATCCAAATCATGAC
CGAGCAGGAGTCCGGCTACTGCTGGAGGAACTTCGTCAACTACTCCCCAAGCAA
CGAGGCCCACTGGCCAAGGTACCCACACCTCTGGGTGCGCCTCTACGTGCTGGA
GCTGTACTGCATCATCCTCGGCCTGCCACCATGCCTCAACATCCTGAGGCGCAA
GCAACCACAGCTGACCTTCTTCACCATCGCCCTCCAAAGCTGCCACTACCAGAGG
CTCCCACCACACATCCTGTGGGCTACCGGCCTC 3'

SEQ ID NO: 822 nucleic acid sequence of nTaCas9 D10A
5'ATGAAGGACAAGAAGTACTCGATCGGCCTCGCCATCGGGACGAACTCAGTTGG
CTGGGCCGTGATCACCGACGAGTACAAGGTGCCCTCTAAGAAGTTCAAGGTCCT
GGGGAACACCGACCGCCATTCCATCAAGAAGAACCTCATCGGCGCTCTCCTGTT
CGACAGCGGGGAGACCGCTGAGGCTACGAGGCTCAAGAGAACCGCTAGGCGCC
GGTACACGAGAAGGAAGAACAGGATCTGCTACCTCCAAGAGATTTTCTCCAACGA
GATGGCCAAGGTTGACGATTCATTCTTCCACCGCCTGGAGGAGTCTTTCCTCGTG
GAGGAGGATAAGAAGCACGAGCGGCATCCCATCTTCGGCAACATCGTGGACGAG
GTTGCCTACCACGAGAAGTACCCTACGATCTACCATCTGCGGAAGAAGCTCGTGG
ACTCCACCGATAAGGCGGACCTCAGACTGATCTACCTCGCTCTGGCCCACATGAT
CAAGTTCCGCGGCCATTTCCTGATCGAGGGGGATCTCAACCCAGACAACAGCGA
TGTTGACAAGCTGTTCATCCAACTCGTGCAGACCTACAACCAACTCTTCGAGGAG
AACCCGATCAACGCCTCTGGCGTGGACGCGAAGGCTATCCTGTCCGCGAGGCTC
TCGAAGTCCAGGAGGCTGGAGAACCTGATCGCTCAGCTCCCAGGCGAGAAGAAG
AACGGCCTGTTCGGGAACCTCATCGCTCTCAGCCTGGGGCTCACCCCCGAACTTC
AAGTCGAACTTCGATCTCGCTGAGGACGCCAAGCTGCAACTCTCCAAGGACACCT
ACGACGATGACCTCGATAACCTCCTGGCCCAGATCGGCGATCAATACGCGGACC
TGTTCCTCGCTGCCAAGAACCTGTCGGACGCCATCCTCCTGTCAGATATCCTCCG
CGTGAACACCGAGATCACGAAGGCTCCACTCTCTGCCTCCATGATCAAGCGCTAC
GACGAGCACCATCAGGATCTGACCCTCCTGAAGGCGCTGGTCCGCCAACAGCTC
CCGGAGAAGTACAAGGAGATTTTCTTCGATCAGTCGAAGAACGGCTACGCTGGGT
ACATCGACGGCGGGGCCTCACAAGAGGAGTTCTACAAGTTCATCAAGCCAATCCT
GGAGAAGATGGACGGCACGGAGGAGCTCCTGGTGAAGCTCAACAGGGAGGACC
TCCTGCGGAAGCAGAGAACCTTCGATAACGGCAGCATCCCCCACCAAATCCATCT
CGGGGAGCTGCACGCCATCCTGAGAAGGCAAGAGGACTTCTACCCTTTCCTCAA
GGATAACCGGGAGAAGATCGAGAAGATCCTGACCTTCAGAATCCCATACTACGTC
GGCCCTCTCGCGCGGGGAACTCAAGATTCGCTTGGATGACCCGCAAGTCTGAG
GAGACCATCACGCCGTGGAACTTCGAGGAGGTGGTGGACAAGGGCGCTAGCGC
TCAGTCGTTCATCGAGAGGATGACCAACTTCGACAAGAACCTGCCCAACGAGAAG
GTGCTCCCTAAGCACTCGCTCCTGTACGAGTACTTCACCGTCTACAACGAGCTCA
CGAAGGTGAAGTACGTCACCGAGGGCATGCGCAAGCCAGCGTTCCTGTCCGGG
GAGCAGAAGAAGGCTATCGTGGACCTCCTGTTCAAGACCAACCGGAAGGTCACG
GTTAAGCAACTCAAGGAGGACTACTTCAAGAAGATCGAGTGCTTCGATTCGGTCG
AGATCAGCGGCGTTGAGGACCGCTTCAACGCCAGCCTCGGGACCTACCACGATC
TCCTGAAGATCATCAAGGATAAGGACTTCCTGGACAACGAGGAGAACGAGGATAT
CCTGGAGGACATCGTGCTGACCCTCACGCTGTTCGAGGACAGGGAGATGATCGA
GGAGCGCCTGAAGACGTACGCCCATCTCTTCGATGACAAGGTCATGAAGCAACT
CAAGCGCCGGAGATACACCGGCTGGGGGAGGCTGTCCCGCAAGCTCATCAACG
GCATCCGGGACAAGCAGTCCGGGAAGACCATCCTCGACTTCCTCAAGAGCGATG
GCTTCGCCAACAGGAACTTCATGCAACTGATCCACGATGACAGCCTCACCTTCAA
GGAGGATATCCAAAAGGCTCAAGTGAGCGGCCAGGGGGACTCGCTGCACGAGC
ATATCGCGAACCTCGCTGGCTCCCCCGCGATCAAGAAGGGCATCCTCCAGACCG
TGAAGGTTGTGGACGAGCTCGTGAAGGTCATGGGCCGGCACAAGCCTGAGAACA
TCGTCATCGAGATGGCCAGAGAGAACCAAACCACGCAGAAGGGGCAAAAGAACT
CTAGGGAGCGCATGAAGCGCATCGAGGAGGGCATCAAGGAGCTGGGGTCCCAA -continued

SEQUENCES

```
ATCCTCAAGGAGCACCCAGTGGAGAACACCCAACTGCAGAACGAGAAGCTCTAC
CTGTACTACCTCCAGAACGGCAGGGATATGTACGTGGACCAAGAGCTGGATATCA
ACCGCCTCAGCGATTACGACGTCGATCATATCGTTCCCCAGTCTTTCCTGAAGGA
TGACTCCATCGACAACAAGGTCCTCACCAGGTCGGACAAGAACCGCGGCAAGTC
AGATAACGTTCCATCTGAGGAGGTCGTTAAGAAGATGAAGAACTACTGGAGGCAG
CTCCTGAACGCCAAGCTGATCACGCAAAGGAAGTTCGACAACCTCACCAAGGCT
GAGAGAGGCGGGCTCTCAGAGCTGGACAAGGCCGGCTTCATCAAGCGGCAGCT
GGTCGAGACCAGACAAATCACGAAGCACGTTGCGCAAATCCTCGACTCTCGGAT
GAACACGAAGTACGATGAGAACGACAAGCTGATCAGGGAGGTTAAGGTGATCAC
CCTGAAGTCTAAGCTCGTCTCCGACTTCAGGAAGGATTTCCAGTTCTACAAGGTT
CGCGAGATCAACAACTACCACCATGCCCATGACGCTTACCTCAACGCTGTGGTCG
GCACCGCTCTGATCAAGAAGTACCCAAAGCTGGAGTCCGAGTTCGTGTACGGGG
ACTACAAGGTTTACGATGTGCGCAAGATGATCGCCAAGTCGGAGCAAGAGATCG
GCAAGGCTACCGCCAAGTACTTCTTCTACTCAAACATCATGAACTTCTTCAAGACC
GAGATCACGCTGGCCAACGGCGAGATCCGGAAGAGACCGCTCATCGAGACCAAC
GGCGAGACGGGGGAGATCGTGTGGGACAAGGGCAGGGATTTCGCGACCGTCCG
CAAGGTTCTCTCCATGCCCCAGGTGAACATCGTCAAGAAGACCGAGGTCCAAAC
GGGCGGGTTCTCAAAGGAGTCTATCCTGCCTAAGCGGAACAGCGACAAGCTCAT
CGCCAGAAAGAAGGACTGGGACCCAAAGAAGTACGGCGGGTTCGACAGCCCTAC
CGTGGCCTACTCGGTCCTGGTTGTGGCGAAGGTTGAGAAGGGCAAGTCCAAGAA
GCTCAAGAGCGTGAAGGAGCTCCTGGGGATCACCATCATGGAGAGGTCCAGCTT
CGAGAAGAACCCAATCGACTTCCTGGAGGCCAAGGGCTACAAGGAGGTGAAGAA
GGACCTGATCATCAAGCTCCCGAAGTACTCTCTCTTCGAGCTGGAGAACGGCAG
GAAGAGAATGCTGGCTTCCGCTGGCGAGCTCCAGAAGGGGAACGAGCTCGCGC
TGCCAAGCAAGTACGTGAACTTCCTCTACCTGGCTTCCCACTACGAGAAGCTCAA
GGGCAGCCCGGAGGACAACGAGCAAAAGCAGCTGTTCGTCGAGCAGCACAAGC
ATTACCTCGACGAGATCATCGAGCAAATCTCCGAGTTCAGCAAGCGCGTGATCCT
CGCCGACGCGAACCTGGATAAGGTCCTCTCCGCCTACAACAAGCACCGGGACAA
GCCCATCAGAGAGCAAGCGGAGAACATCATCCATCTCTTCACCCTGACGAACCTC
GGCGCTCCTGCTGCTTTCAAGTACTTCGACACCACGATCGATCGGAAGAGATACA
CCTCCACGAAGGAGGTCCTGGACGCGACCCTCATCCACCAGTCGATCACCGGCC
TGTACGAGACGAGGATCGACCTCTCACAACTCGGCGGGGATAAGAGACCCGCAG
CAACCAAGAAGGCAGGGCAAGCAAAGAAGAAGAAG 3'

SEQ ID NO: 823; crRNA for Lachnospiraceae bacterium (Lb)
5'-UAAUUUCUACUAAGUGUAGAU-3'
```

REFERENCES

1. Mustalahti, K. et al. The prevalence of celiac disease in Europe: results of a centralized, international mass screening project. Ann Med 42, 587-595 (2010).
2. Sapone, A. et al. Divergence of gut permeability and mucosal immune gene expression in two gluten-associated conditions: celiac disease and gluten sensitivity. BMC Med 9, 23 (2011).
3. Ozuna, C. V. et al. Diversification of the celiac disease α-gliadin complex in wheat: a 33-mer peptide with six overlapping epitopes, evolved following polyploidization. Plant J 82, 794-805 (2015).
4. Tye-Din, J. A. et al. Comprehensive, Quantitative Mapping of T Cell Epitopes in Gluten in Celiac Disease. Sci Transl Med 2, 41ra51 (2010).
5. Gil-Humanes, J., Pistón, F., Shewry, P. R., Tosi, P. & Barro, F. Suppression of gliadins results in altered protein body morphology in wheat. J Exp Bot 62, 4203-4213 (2011).
6. Gil-Humanes, J., Pistón, F., Barro, F. & Rosell, C. M. The Shutdown of Celiac Disease-Related Gliadin Epitopes in Bread Wheat by RNAi Provides Flours with Increased Stability and Better Tolerance to Over-Mixing. PLoS ONE 9, e91931 (2014).
7. Valdés, I., García, E., Llorente, M. & Méndez, E. Innovative approach to low-level gluten determination in foods using a novel sandwich enzyme-linked immunosorbent assay protocol. Eur J Gastroenterol Hepatol 15, 465-747 (2003).
8. Morón, B. et al. Sensitive detection of cereal fractions that are toxic to celiac disease patients by using monoclonal antibodies to a main immunogenic wheat peptide. Am J Clin Nutr 87, 405-414 (2008).
9. Gil-Humanes, J. et al. Silencing of γ-gliadins by RNA interference (RNAi) in bread wheat. J Cereal Sci 48, 565-568 (2008).
10. Gil-Humanes, J. et al. Effective shutdown in the expression of celiac disease-related wheat gliadin T-cell epitopes by RNA interference. *Proc. Natl. Acad. Sci. USA* 107, 17023-17028 (2010).
11. Gil-Humanes, J. et al. Reduced-Gliadin Wheat Bread: An Alternative to the Gluten-Free Diet for Consumers Suffering Gluten-Related Pathologies. *PLoS ONE* 9, e90898 (2014).
12. Payne, P. I. Genetics of Wheat Storage Proteins and the Effect of Allelic Variation on Bread-Making Quality. Annu. Rev. Plant. Physiol. 38, 141-153 (1987).
13. Mann, D. G. J. et al. Gateway-compatible vectors for high-throughput gene functional analysis in switchgrass (*Panicum virgatum* L.) and other monocot species. *Plant Biotechnol J* 10, 226-236 (2012).
14. Piston, F., Marin, S., Hernando, A. & Barro, F. Analysis of the activity of a γ-gliadin promoter in transgenic wheat and characterization of gliadin synthesis in wheat by MALDI-TOF during grain development. *Mol Breeding* 23, 655-667 (2009).
15. Gil-Humanes, J., Piston, F., Rosell, C. M. & Barro, F. Significant down-regulation of gamma-gliadins has minor effect on gluten and starch properties of bread wheat. *J Cereal Sci* 56, 161-170 (2012).
16. Piston, F., Gil-Humanes, J., Rodriguez-Quijano, M. & Barro, F. Down-regulating γ-gliadins in bread wheat leads to non-specific increases in other gluten proteins and has no major effect on dough gluten strength. *PLoS ONE* 6, e24754 (2011).

17. Valdés, I., García, E., Llorente, M. & Méndez, E. Innovative approach to low-level gluten determination in foods using a novel sandwich enzyme-linked immunosorbent assay protocol. *Eur J Gastroenterol Hepatol* 15, 465-747 (2003).
18. Barro, F. et al. Targeting of prolamins by RNAi in bread wheat: effectiveness of seven silencing-fragment combinations for obtaining lines devoid of coeliac disease epitopes from highly immunogenic gliadins. *Plant Biotechnol J* 14, 986-996 (2016).
19. Williams, P. et al. Crop quality evaluation methods and guidelines. Technical Manual (ICARDA), (International Center for Agricultural Research in the Dry Areas, Aleppo, Syria), p 145 (1986).
20. Edgar, R. C. *Search and clustering orders of magnitude faster than BLAST. Bioinformatics* (*Oxford, England*) 26, 2460-2461 (Oxford University Press, 2010).
21. Edgar, R. C. & Flyvbjerg, H. Error filtering, pair assembly and error correction for next-generation sequencing reads. *Bioinformatics* (2015).
22. Katoh, K., Misawa, K., Kuma, K.-I. & Miyata, T. MAFFT: a novel method for rapid multiple sequence alignment based on fast Fourier transform. *Nucleic Acids Res* 30, 3059-3066 (2002).
23. Price, M. N., Dehal, P. S. & Arkin, A. P. FastTree 2—approximately maximum-likelihood trees for large alignments. *PLoS ONE* 5, e9490 (2010).
24. Komor, A. C.; Kim, Y. B.; Packer, M. S.; Zuris, J. A.; Liu, D. R. Programmable editing of a target base in genomic DNA without double-stranded DNA cleavage. *Nature* 2016, 533, 420-424
25. Nishida, K.; Arazoe, T.; Yachie, N.; Banno, S.; Kakimoto, M.; Tabata, M.; Mochizuki, M.; *Miyabe*, A.; Araki, M.; Hara, K. Y.; Shimatani, Z.; Kondo, A. Targeted nucleotide editing using hybrid prokaryotic and vertebrate adaptive immune systems. *Science* 2016, 353.
26. Clough, S. J. and Bent, A. F. (1998), Floral dip: a simplified method for *Agrobacterium*-mediated transformation of *Arabidopsis thaliana*. The Plant Journal, 16: 735-743. doi:10.1046/j.1365-313x.1998.00343.x
27. Meghdad Randar, Moira A. McMahon, Thazha P. Prakash, Eric E. Swayze, C. Frank Bennett and Don W. Cleveland, Synthetic CRISPR RNA-Cas9—guided genome editing in human cells PNAS 2015 112 (51) E7110-E7117; published ahead of print Nov. 16, 2015, doi:10.1073/pnas.1520883112
28. Wiles, M. V., Qin, W., Cheng, A. W. et al., CRISPR—Cas9-mediated genome editing and guide RNA design, 2015) 26: 501.
29. Neville E Sanjana—Le Cong, Yang Zhou, Margaret M Cunniff, Guoping Feng & Feng Zhang A transcription activator-like effector toolbox for genome engineering, Nature Protocols 7, 171-192 (2012).
30. Mustalahti K, Catassi C, Reunanen A, Fabiani E, Heier M, McMillan S, Murray L, Metzger M H, Gasparin M, Bravi E, Maki M. 2010. The prevalence of celiac disease in Europe: Results of a centralized, international mass screening project. Annals of Medicine 42, 587-595.
31. Abadie V, Sollid L M, Barreiro L B. 2011. Integration of genetic and immunological insights intoa model of celiac disease pathogenesis. Annual Review of Immunology 29, 493-525.
322. Sapone A, Lammers K M, Casolaro V, Cammarota M, Giuliano M T, De Rosa M, Stefanile R, Mazzarella G, Tolone C, Russo M I. 2011. Divergence of gut permeability and mucosal immune gene expression in two gluten-associated conditions: celiac disease and gluten sensitivity. BMC Medicine 9, 23.
33. Arentz Hansen H, Mcadam S N, Molberg Ø, Fleckenstein B, Lundin K E A, Jørgensen T J D, Jung G, Roepstorff P, Sollid L M. 2002. Celiac lesion T cells recognize epitopes that cluster in regions of gliadins rich in proline residues. Gastroenterology 123, 803-809.
34. Shan L, Molberg Ø, Parrot I, Hausch F, Filiz F, Gray G M, Sollid L M, Khosla C. 2002. Structural Basis for Gluten Intolerance in Celiac Sprue. Science 297, 2275-2279.
35. Tye-Din J A, Stewart J A, Dromey J A, et al. 2010. Comprehensive, Quantitative Mapping of T Cell Epitopes in Gluten in Celiac Disease. Science Translational Medicine 2, 41ra51.
36. Maiuri L, Ciacci C, Ricciardelli I, Vacca L, Raia V, Auricchio S, Picard J, Osman M, Quaratino S, Londei M. 2003. Association between innate response to gliadin and activation of pathogenic T cells in coeliac disease. Lancet 362, 30-37.
37. Di Sabatino A, Corazza G R. 2009. Coeliac disease. The Lancet 373, 1480-1493.
38. Vader W, Kooy Y, van Veelen P, de Ru A, Harris D, Benckhuijsen W, Pena S, Mearin L, Drijfhout J W, Koning F. 2002. The gluten response in children with celiac disease is directed toward multiple gliadin and glutenin peptides. Gastroenterology 122, 1729-1737.
39. Cermak, T. et al. Efficient design and assembly of custom TALEN and other TAL effector-based constructs for DNA targeting. Nucleic Acids Res. 39 (2011).
40. van de Wal Y, Kooy Y, van Veelen P, Pena S, Mearin L, Papadopoulos G, Koning F (1998) Selective deamidation by tissue transglutaminase strongly enhances gliadin-specific T cell reactivity. J Immunol 161:1585-1588
41. Yan, S., Wang, Z., Liu, Y. et al. Plant Mol Biol (2015) 88: 415.
42. Chen, L., Miao, Y., Wang, C. et al. Plant Mol Biol Rep (2012) 30: 1426.
43. Tsai S Q, Wyvekens N, Khayter C, Foden J A, Thapar V, Reyon D, et al. Dimeric CRISPR RNA-guided FokI nucleases for highly specific genome editing. Nat Biotechnol 2014; 32:569-76
44. Stavolone, L., Kononova, M., Pauli, S. et al. Plant Mol Biol (2003) 53: 703.
45. Li et al. Base editing with a Cpf1-cytidine deaminase fusion. Nature Biotechnology. 2018. 4 (36).

The invention claimed is:

1. A nucleic acid construct comprising a nucleic acid sequence encoding at least one DNA-binding domain, wherein said DNA-binding domain can bind to a sequence in one of the alpha-, gamma- and/or omega gliadin genes, wherein the sequence in the alpha-, gamma- and/or omega gliadin genes to which the DNA-binding domain can bind is selected from SEQ ID Nos 1 to 4, 6 to 24, 790, 792 to 794 and 796 to 803 or a variant thereof wherein the variant has at least 90% sequence identity over the full length non-variant sequence.

2. The nucleic acid construct of claim 1, wherein said construct encodes at least one single-guide RNA (sgRNA), wherein the sgRNA has a sequence selected from SEQ ID NO: 51 to 54 and 56 to 74 or a variant thereof wherein the variant has at least 90% sequence identity over the full length non-variant sequence.

3. The nucleic acid construct of claim 1, wherein said construct is operably linked to a promoter.

4. The nucleic acid construct of claim 1, wherein the nucleic acid construct further comprises a nucleic acid sequence encoding a CRISPR enzyme.

5. The nucleic acid construct of claim 1, wherein the nucleic acid construct encodes a TAL effector, and wherein the nucleic acid construct further comprises a sequence encoding an endonuclease or DNA-cleavage domain thereof, wherein the endonuclease is FokI.

6. A single guide (sg) RNA molecule wherein said sgRNA comprises at least a crRNA sequence wherein the crRNA sequence can bind to at least one sequence selected from SEQ ID Nos 1 to 4, 6 to 24, 790, 792 to 794 and 796 to 803 or a variant thereof wherein the variant has at least 90% sequence identity over the full length non-variant sequence.

7. An isolated plant cell transfected with at least one nucleic acid construct as defined in claim 1.

8. An isolated plant cell transfected with at least one sgRNA molecule as defined in claim 6.

9. A genetically altered plant characterised in that said plant has reduced expression and/or content of at least one of alpha-, gamma- and/or omega gliadins, reduced total gliadin content, reduced gluten content, a reduced gliadin to glutenin ratio and/or increased expression and/or content of glutenins, wherein said plant is obtained by transfecting at least one plant cell with at least one nucleic acid construct of claim 1 or at least one sgRNA molecule of any of SEQ ID NOs 75 to 78 and 80 to 99 or a variant thereof wherein the variant has at least 90% sequence identity over the full length non-variant sequence.

10. The genetically altered plant of claim 9, wherein the plant belongs to the genus *Triticum.*

11. A seed derived from the genetically altered plant as defined in claim 9, wherein said seed comprises at least one mutation in at least one of alpha-, gamma- and/or omega gliadin.

12. The pollen, propagule, progeny or part of the plant derived from any of the genetically altered plants as defined in claim 9, wherein said pollen, propagule, progeny or part of the plant comprises at least one mutation in at least one of alpha-, gamma- and/or omega gliadin.

13. A method of reducing total gliadin content and/or reducing gluten content and/or reducing gluten immunoreactivity in the *Triticum* spp. the method comprising using targeted genome modification to silence or reduce the expression and/or content of at least one of alpha-, gamma- and/or omega gliadins of the *Triticum* spp wherein said targeted genome modification is used to introduce at least one mutation into a target sequence selected from SEQ ID Nos 1 to 4, 6 to 24, 790, 792 to 794 and 796 to 803 or a variant thereof wherein the variant has at least 90% sequence identity over the full length non-variant sequence.

14. The method of claim 13, wherein the method comprises introducing and expressing into a plant a nucleic acid construct comprising an sgRNA sequence selected from SEQ ID NO: 51 to 54 and 56 to 74 or a variant thereof wherein the variant has at least 90% sequence identity over the full length non-variant sequence.

15. The method of claim 13, wherein the method comprises transfecting at least one plant cell with at least one sgRNA molecule as defined in claim 6.

16. The method of claim 13, wherein the method further comprises further silencing at least one of alpha-, gamma- and/or omega gliadins of the *Triticum* spp. using RNAi.

17. A food composition wherein said food composition is flour comprising milled seeds as defined in claim 11.

18. A method for obtaining the genetically altered plant as defined in claim 9, the method comprising:

a. selecting a part of the plant;

b. transfecting at least one cell of the part of the plant of paragraph (a) with the nucleic acid construct as defined in from SEQ ID Nos 25 to 28 and 30 to 48 and 807 to 809 and 811 to 818 or a variant thereof or at least one sgRNA molecule as defined in any of SEQ ID NOs 75 to 78 and 80 to 99 or a variant thereof wherein the variant has at least 90% sequence identity over the full length non-variant sequence;

c. regenerating at least one plant derived from the transfected cell or cells;

d. selecting one or more plants obtained according to paragraph (c) that show silencing or reduced expression and/or content of at least one of alpha-, gamma- and/or omega gliadins, reduced total gliadin content, reduced gluten content, a reduced gliadin to glutenin ratio and/or increased expression and/or content of glutenins.

19. A method for producing a food composition with a reduced gliadin and/or gluten content and/or reduced immunotoxicity, the method comprising producing a genetically altered plant, characterised in that said plant has reduced expression and/or content of at least one of alpha-, gamma- and/or omega gliadins, reduced total gliadin content, reduced gluten content, a reduced gliadin to glutenin ratio and/or increased expression and/or content of glutenins, wherein said plant is obtained by transfecting at least one plant cell with at least one nucleic acid construct of claim 1 or at least one sgRNA molecule of claim 6 in the seeds of said plant, producing seeds from said plant in which at least one of alpha-, gamma- and/or omega gliadins is silenced or reduced in expression and/or content and preparing a food composition from said seeds.

20. A method of genome modification comprising introducing double-strand breaks at two or more selected sites in at least one gene of at least one of alpha-, gamma- and/or omega gliadin of a plant cell by providing said cell with a clustered, regularly interspaced, short palindromic repeats (CRISPR)-associated Cas endonuclease and at least one sgRNA of claim 6.

21. The nucleic acid construct of claim 1, wherein the sequence that the DNA-binding domain can bind is selected from the group consisting of SEQ ID Nos 1-4, 9, 11, 12, 13, 17, 19, 20, 23, 792, 793, 794, 797, 798, 800, 801, 803 and the variant thereof wherein the variant has at least 90% sequence identity over the full length non-variant sequence.

22. The single guide (sg) RNA molecule of claim 6, wherein said at least one sequence is selected from the group consisting of SEQ ID Nos 1-4, 9, 11, 12, 13, 17, 19, 20, 23, 792, 793, 794, 797, 798, 800, 801, 803 and the variant thereof wherein the variant has at least 90% sequence identity over the full length non-variant sequence.

23. The method of claim 13, wherein the target sequence is selected from the group consisting of SEQ ID Nos 1-4, 9, 11, 12, 13, 17, 19, 20, 23, 792, 793, 794, 797, 798, 800, 801, 803 and the variant thereof wherein the variant has at least 90% sequence identity over the full length non-variant sequence.

* * * * *

SEQUENCE LISTING

```
<160> NUMBER OF SEQ ID NOS: 823

<210> SEQ ID NO 1
<211> LENGTH: 23
<212> TYPE: DNA
```

<213> ORGANISM: Artificial Sequence
<220> FEATURE:
<223> OTHER INFORMATION: sgAlpha-1
<220> FEATURE:
<221> NAME/KEY: misc_feature
<222> LOCATION: 21..21
<223> OTHER INFORMATION: /note="n is a, c, g, or t"

<400> SEQUENCE: 1
gccacaagag caagttccat ngg 23

<210> SEQ ID NO 2
<211> LENGTH: 22
<212> TYPE: DNA
<213> ORGANISM: Artificial Sequence
<220> FEATURE:
<223> OTHER INFORMATION: sgAlpha-2
<220> FEATURE:
<221> NAME/KEY: misc_feature
<222> LOCATION: 20..20
<223> OTHER INFORMATION: /note="n is a, c, g, or t"

<400> SEQUENCE: 2
gttgtgatgg aaatggttgn gg 22

<210> SEQ ID NO 3
<211> LENGTH: 23
<212> TYPE: DNA
<213> ORGANISM: Artificial Sequence
<220> FEATURE:
<223> OTHER INFORMATION: sgAlpha-3
<220> FEATURE:
<221> NAME/KEY: misc_feature
<222> LOCATION: 21..21
<223> OTHER INFORMATION: /note="n is a, c, g, or t"

<400> SEQUENCE: 3
tgtggctgca attgtggcac ngg 23

<210> SEQ ID NO 4
<211> LENGTH: 23
<212> TYPE: DNA
<213> ORGANISM: Artificial Sequence
<220> FEATURE:
<223> OTHER INFORMATION: sgAlpha-4
<220> FEATURE:
<221> NAME/KEY: misc_feature
<222> LOCATION: 21..21
<223> OTHER INFORMATION: /note="n is a, c, g, or t"

<400> SEQUENCE: 4
tcttgtggtt gttgctgaga ngg 23

<210> SEQ ID NO 5
<211> LENGTH: 23
<212> TYPE: DNA
<213> ORGANISM: Artificial Sequence
<220> FEATURE:
<223> OTHER INFORMATION: sg33mer1
<220> FEATURE:
<221> NAME/KEY: misc_feature
<222> LOCATION: 21..21
<223> OTHER INFORMATION: /note="n is a, c, g, or t"

<400> SEQUENCE: 5
ggtagttgcg gctgcggaaa ngg 23

<210> SEQ ID NO 6
<211> LENGTH: 23

<212> TYPE: DNA
<213> ORGANISM: Artificial Sequence
<220> FEATURE:
<223> OTHER INFORMATION: sgGlia20-1
<220> FEATURE:
<221> NAME/KEY: misc_feature
<222> LOCATION: 21..21
<223> OTHER INFORMATION: /note="n is a, c, g, or t"

<400> SEQUENCE: 6
tatggttgtt gtggtcgaaa ngg 23

<210> SEQ ID NO 7
<211> LENGTH: 23
<212> TYPE: DNA
<213> ORGANISM: Artificial Sequence
<220> FEATURE:
<223> OTHER INFORMATION: sgOmega6
<220> FEATURE:
<221> NAME/KEY: misc_feature
<222> LOCATION: 21..21
<223> OTHER INFORMATION: /note="n is a, c, g, or t"

<400> SEQUENCE: 7
aaaggttgtt gtggttgttg ngg 23

<210> SEQ ID NO 8
<211> LENGTH: 23
<212> TYPE: DNA
<213> ORGANISM: Artificial Sequence
<220> FEATURE:
<223> OTHER INFORMATION: sgOmega4
<220> FEATURE:
<221> NAME/KEY: misc_feature
<222> LOCATION: 21..21
<223> OTHER INFORMATION: /note="n is a, c, g, or t"

<400> SEQUENCE: 8
aatggttgtt ggggttgctg ngg 23

<210> SEQ ID NO 9
<211> LENGTH: 23
<212> TYPE: DNA
<213> ORGANISM: Artificial Sequence
<220> FEATURE:
<223> OTHER INFORMATION: sgOmega3
<220> FEATURE:
<221> NAME/KEY: misc_feature
<222> LOCATION: 21..21
<223> OTHER INFORMATION: /note="n is a, c, g, or t"

<400> SEQUENCE: 9
tgatgggggg aatattgttg ngg 23

<210> SEQ ID NO 10
<211> LENGTH: 23
<212> TYPE: DNA
<213> ORGANISM: Artificial Sequence
<220> FEATURE:
<223> OTHER INFORMATION: sgOmega2
<220> FEATURE:
<221> NAME/KEY: misc_feature
<222> LOCATION: 21..21
<223> OTHER INFORMATION: /note="n is a, c, g, or t"

<400> SEQUENCE: 10
tgctggggga atggttgttg ngg 23

<210> SEQ ID NO 11

```
<211> LENGTH: 23
<212> TYPE: DNA
<213> ORGANISM: Artificial Sequence
<220> FEATURE:
<223> OTHER INFORMATION: sgOmega1
<220> FEATURE:
<221> NAME/KEY: misc_feature
<222> LOCATION: 21..21
<223> OTHER INFORMATION: /note="n is a, c, g, or t"

<400> SEQUENCE: 11

tgttcatcgc catggcaagg ngg                                              23


<210> SEQ ID NO 12
<211> LENGTH: 23
<212> TYPE: DNA
<213> ORGANISM: Artificial Sequence
<220> FEATURE:
<223> OTHER INFORMATION: sgOmega5
<220> FEATURE:
<221> NAME/KEY: misc_feature
<222> LOCATION: 21..21
<223> OTHER INFORMATION: /note="n is a, c, g, or t"

<400> SEQUENCE: 12

cttataacgt cgctcccaga ngg                                              23


<210> SEQ ID NO 13
<211> LENGTH: 23
<212> TYPE: DNA
<213> ORGANISM: Artificial Sequence
<220> FEATURE:
<223> OTHER INFORMATION: sgGamma13
<220> FEATURE:
<221> NAME/KEY: misc_feature
<222> LOCATION: 21..21
<223> OTHER INFORMATION: /note="n is a, c, g, or t"

<400> SEQUENCE: 13

gagaatggtt ggtgaggctg ngg                                              23


<210> SEQ ID NO 14
<211> LENGTH: 23
<212> TYPE: DNA
<213> ORGANISM: Artificial Sequence
<220> FEATURE:
<223> OTHER INFORMATION: sgGamma4
<220> FEATURE:
<221> NAME/KEY: misc_feature
<222> LOCATION: 21..21
<223> OTHER INFORMATION: /note="n is a, c, g, or t"

<400> SEQUENCE: 14

aattgttgtt gtggttgctg ngg                                              23


<210> SEQ ID NO 15
<211> LENGTH: 23
<212> TYPE: DNA
<213> ORGANISM: Artificial Sequence
<220> FEATURE:
<223> OTHER INFORMATION: sgGamma5
<220> FEATURE:
<221> NAME/KEY: misc_feature
<222> LOCATION: 21..21
<223> OTHER INFORMATION: /note="n is a, c, g, or t"

<400> SEQUENCE: 15

gttggggttg ttgagtctgg ngg                                              23
```

<210> SEQ ID NO 16
<211> LENGTH: 23
<212> TYPE: DNA
<213> ORGANISM: Artificial Sequence
<220> FEATURE:
<223> OTHER INFORMATION: sgGamma9
<220> FEATURE:
<221> NAME/KEY: misc_feature
<222> LOCATION: 21..21
<223> OTHER INFORMATION: /note="n is a, c, g, or t"

<400> SEQUENCE: 16
tgttggggga atgattgttg ngg 23

<210> SEQ ID NO 17
<211> LENGTH: 23
<212> TYPE: DNA
<213> ORGANISM: Artificial Sequence
<220> FEATURE:
<223> OTHER INFORMATION: sgGamma10
<220> FEATURE:
<221> NAME/KEY: misc_feature
<222> LOCATION: 21..21
<223> OTHER INFORMATION: /note="n is a, c, g, or t"

<400> SEQUENCE: 17
gcaagaggaa attcttgcat ngg 23

<210> SEQ ID NO 18
<211> LENGTH: 23
<212> TYPE: DNA
<213> ORGANISM: Artificial Sequence
<220> FEATURE:
<223> OTHER INFORMATION: sgGamma11
<220> FEATURE:
<221> NAME/KEY: misc_feature
<222> LOCATION: 21..21
<223> OTHER INFORMATION: /note="n is a, c, g, or t"

<400> SEQUENCE: 18
attgagctgg ttgttgaggt ngg 23

<210> SEQ ID NO 19
<211> LENGTH: 23
<212> TYPE: DNA
<213> ORGANISM: Artificial Sequence
<220> FEATURE:
<223> OTHER INFORMATION: sgGamma2
<220> FEATURE:
<221> NAME/KEY: misc_feature
<222> LOCATION: 21..21
<223> OTHER INFORMATION: /note="n is a, c, g, or t"

<400> SEQUENCE: 19
tgatggggga atgtttgttg ngg 23

<210> SEQ ID NO 20
<211> LENGTH: 23
<212> TYPE: DNA
<213> ORGANISM: Artificial Sequence
<220> FEATURE:
<223> OTHER INFORMATION: sgGamma3
<220> FEATURE:
<221> NAME/KEY: misc_feature
<222> LOCATION: 21..21
<223> OTHER INFORMATION: /note="n is a, c, g, or t"

<400> SEQUENCE: 20
attgttgttg tggttgatgg ngg 23

<210> SEQ ID NO 21
<211> LENGTH: 23
<212> TYPE: DNA
<213> ORGANISM: Artificial Sequence
<220> FEATURE:
<223> OTHER INFORMATION: sgGamma8
<220> FEATURE:
<221> NAME/KEY: misc_feature
<222> LOCATION: 21..21
<223> OTHER INFORMATION: /note="n is a, c, g, or t"

<400> SEQUENCE: 21
ggctggggaa aaggttgttg ngg 23

<210> SEQ ID NO 22
<211> LENGTH: 23
<212> TYPE: DNA
<213> ORGANISM: Artificial Sequence
<220> FEATURE:
<223> OTHER INFORMATION: sgGamma6
<220> FEATURE:
<221> NAME/KEY: misc_feature
<222> LOCATION: 21..21
<223> OTHER INFORMATION: /note="n is a, c, g, or t"

<400> SEQUENCE: 22
aatgattgtt gtggttgttg ngg 23

<210> SEQ ID NO 23
<211> LENGTH: 23
<212> TYPE: DNA
<213> ORGANISM: Artificial Sequence
<220> FEATURE:
<223> OTHER INFORMATION: sgGamma7
<220> FEATURE:
<221> NAME/KEY: misc_feature
<222> LOCATION: 21..21
<223> OTHER INFORMATION: /note="n is a, c, g, or t"

<400> SEQUENCE: 23
caggtttgca ttgttgcaag ngg 23

<210> SEQ ID NO 24
<211> LENGTH: 23
<212> TYPE: DNA
<213> ORGANISM: Artificial Sequence
<220> FEATURE:
<223> OTHER INFORMATION: sgGamma12
<220> FEATURE:
<221> NAME/KEY: misc_feature
<222> LOCATION: 21..21
<223> OTHER INFORMATION: /note="n is a, c, g, or t"

<400> SEQUENCE: 24
tcaacaacca gctcaattgg ngg 23

<210> SEQ ID NO 25
<211> LENGTH: 20
<212> TYPE: DNA
<213> ORGANISM: Artificial Sequence
<220> FEATURE:
<223> OTHER INFORMATION: protospacer sgAlpha-1

<400> SEQUENCE: 25
gccacaagag caagttccat 20

<210> SEQ ID NO 26
<211> LENGTH: 20

<212> TYPE: DNA
<213> ORGANISM: Artificial Sequence
<220> FEATURE:
<223> OTHER INFORMATION: protospacer sgAlpha-2

<400> SEQUENCE: 26
ggttgtgatg gaaatggttg 20

<210> SEQ ID NO 27
<211> LENGTH: 20
<212> TYPE: DNA
<213> ORGANISM: Artificial Sequence
<220> FEATURE:
<223> OTHER INFORMATION: protospacer sgAlpha-3

<400> SEQUENCE: 27
tgtggctgca attgtggcac 20

<210> SEQ ID NO 28
<211> LENGTH: 20
<212> TYPE: DNA
<213> ORGANISM: Artificial Sequence
<220> FEATURE:
<223> OTHER INFORMATION: protospacer sgAlpha-4

<400> SEQUENCE: 28
tcttgtggtt gttgctgaga 20

<210> SEQ ID NO 29
<211> LENGTH: 20
<212> TYPE: DNA
<213> ORGANISM: Artificial Sequence
<220> FEATURE:
<223> OTHER INFORMATION: protospacer sg33mer1

<400> SEQUENCE: 29
ggtagttgcg gctgcggaaa 20

<210> SEQ ID NO 30
<211> LENGTH: 20
<212> TYPE: DNA
<213> ORGANISM: Artificial Sequence
<220> FEATURE:
<223> OTHER INFORMATION: protospacer glia20-1

<400> SEQUENCE: 30
tatggttgtt gtggtcgaaa 20

<210> SEQ ID NO 31
<211> LENGTH: 20
<212> TYPE: DNA
<213> ORGANISM: Artificial Sequence
<220> FEATURE:
<223> OTHER INFORMATION: protospacer sgOmega6

<400> SEQUENCE: 31
aaaggttgtt gtggttgttg 20

<210> SEQ ID NO 32
<211> LENGTH: 20
<212> TYPE: DNA
<213> ORGANISM: Artificial Sequence
<220> FEATURE:
<223> OTHER INFORMATION: protospacer sgOmega4

<400> SEQUENCE: 32
aatggttgtt ggggttgctg 20

<210> SEQ ID NO 33
<211> LENGTH: 20
<212> TYPE: DNA
<213> ORGANISM: Artificial Sequence
<220> FEATURE:
<223> OTHER INFORMATION: protospacer sgOmega3

<400> SEQUENCE: 33
tgatgggggg aatattgttg 20

<210> SEQ ID NO 34
<211> LENGTH: 20
<212> TYPE: DNA
<213> ORGANISM: Artificial Sequence
<220> FEATURE:
<223> OTHER INFORMATION: protospacer sgOmega2

<400> SEQUENCE: 34
tgctggggga atggttgttg 20

<210> SEQ ID NO 35
<211> LENGTH: 20
<212> TYPE: DNA
<213> ORGANISM: Artificial Sequence
<220> FEATURE:
<223> OTHER INFORMATION: protospacer sgOmega1

<400> SEQUENCE: 35
tgttcatcgc catggcaagg 20

<210> SEQ ID NO 36
<211> LENGTH: 20
<212> TYPE: DNA
<213> ORGANISM: Artificial Sequence
<220> FEATURE:
<223> OTHER INFORMATION: protospacer sgOmega5

<400> SEQUENCE: 36
cttataacgt cgctcccaga 20

<210> SEQ ID NO 37
<211> LENGTH: 20
<212> TYPE: DNA
<213> ORGANISM: Artificial Sequence
<220> FEATURE:
<223> OTHER INFORMATION: protospacer sgGamma13

<400> SEQUENCE: 37
gagaatggtt ggtgaggctg 20

<210> SEQ ID NO 38
<211> LENGTH: 20
<212> TYPE: DNA
<213> ORGANISM: Artificial Sequence
<220> FEATURE:
<223> OTHER INFORMATION: protospacer sgGamma4

<400> SEQUENCE: 38
aattgttgtt gtggttgctg 20

<210> SEQ ID NO 39

<211> LENGTH: 20
<212> TYPE: DNA
<213> ORGANISM: Artificial Sequence
<220> FEATURE:
<223> OTHER INFORMATION: protospacer sgGamma5

<400> SEQUENCE: 39
gttggggttg ttgagtctgg 20

<210> SEQ ID NO 40
<211> LENGTH: 20
<212> TYPE: DNA
<213> ORGANISM: Artificial Sequence
<220> FEATURE:
<223> OTHER INFORMATION: protospacer sgGamma9

<400> SEQUENCE: 40
tgttggggga atgattgttg 20

<210> SEQ ID NO 41
<211> LENGTH: 20
<212> TYPE: DNA
<213> ORGANISM: Artificial Sequence
<220> FEATURE:
<223> OTHER INFORMATION: protospacer sgGamma10

<400> SEQUENCE: 41
gcaagaggaa attcttgcat 20

<210> SEQ ID NO 42
<211> LENGTH: 20
<212> TYPE: DNA
<213> ORGANISM: Artificial Sequence
<220> FEATURE:
<223> OTHER INFORMATION: protospacer sgGamma11

<400> SEQUENCE: 42
attgagctgg ttgttgaggt 20

<210> SEQ ID NO 43
<211> LENGTH: 20
<212> TYPE: DNA
<213> ORGANISM: Artificial Sequence
<220> FEATURE:
<223> OTHER INFORMATION: protospacer sgGamma2

<400> SEQUENCE: 43
tgatggggga atgtttgttg 20

<210> SEQ ID NO 44
<211> LENGTH: 20
<212> TYPE: DNA
<213> ORGANISM: Artificial Sequence
<220> FEATURE:
<223> OTHER INFORMATION: protospacer sgGamma3

<400> SEQUENCE: 44
attgttgttg tggttgatgg 20

<210> SEQ ID NO 45
<211> LENGTH: 20
<212> TYPE: DNA
<213> ORGANISM: Artificial Sequence
<220> FEATURE:
<223> OTHER INFORMATION: protospacer sgGamma8

<400> SEQUENCE: 45
ggctggggaa aaggttgttg 20

<210> SEQ ID NO 46
<211> LENGTH: 20
<212> TYPE: DNA
<213> ORGANISM: Artificial Sequence
<220> FEATURE:
<223> OTHER INFORMATION: protospacer sgGamma6

<400> SEQUENCE: 46
aatgattgtt gtggttgttg 20

<210> SEQ ID NO 47
<211> LENGTH: 20
<212> TYPE: DNA
<213> ORGANISM: Artificial Sequence
<220> FEATURE:
<223> OTHER INFORMATION: protospacer sgGamma7

<400> SEQUENCE: 47
caggtttgca ttgttgcaag 20

<210> SEQ ID NO 48
<211> LENGTH: 20
<212> TYPE: DNA
<213> ORGANISM: Artificial Sequence
<220> FEATURE:
<223> OTHER INFORMATION: protospacer sgGamma12

<400> SEQUENCE: 48
tcaacaacca gctcaattgg 20

<210> SEQ ID NO 49
<211> LENGTH: 12
<212> TYPE: DNA
<213> ORGANISM: Artificial Sequence
<220> FEATURE:
<223> OTHER INFORMATION: crRNA additional nucleotides

<400> SEQUENCE: 49
gttttagagc ta 12

<210> SEQ ID NO 50
<211> LENGTH: 64
<212> TYPE: DNA
<213> ORGANISM: Artificial Sequence
<220> FEATURE:
<223> OTHER INFORMATION: tracrRNA nucleotide sequence

<400> SEQUENCE: 50
gaaatagcaa gttaaaataa ggctagtccg ttatcaactt gaaaaagtgg caccgagtcg 60
gtgc 64

<210> SEQ ID NO 51
<211> LENGTH: 103
<212> TYPE: DNA
<213> ORGANISM: Artificial Sequence
<220> FEATURE:
<223> OTHER INFORMATION: complete sgAlpha-1

<400> SEQUENCE: 51
gccacaagag caagttccat gttttagagc tagaaatagc aagttaaaat aaggctagtc 60
cgttatcaac ttgaaaaagt ggcaccgagt cggtgctttt ttt 103

<210> SEQ ID NO 52
<211> LENGTH: 103
<212> TYPE: DNA
<213> ORGANISM: Artificial Sequence
<220> FEATURE:
<223> OTHER INFORMATION: complete sgAlpha-2

<400> SEQUENCE: 52
ggttgtgatg gaaatggttg gttttagagc tagaaatagc aagttaaaat aaggctagtc 60
cgttatcaac ttgaaaaagt ggcaccgagt cggtgctttt ttt 103

<210> SEQ ID NO 53
<211> LENGTH: 96
<212> TYPE: DNA
<213> ORGANISM: Artificial Sequence
<220> FEATURE:
<223> OTHER INFORMATION: complete sgAlpha-3

<400> SEQUENCE: 53
tgtggctgca attgtggcac gttttagagc tagaaatagc aagttaaaat aaggctagtc 60
cgttatcaac ttgaaaaagt ggcaccgagt cggtgc 96

<210> SEQ ID NO 54
<211> LENGTH: 96
<212> TYPE: DNA
<213> ORGANISM: Artificial Sequence
<220> FEATURE:
<223> OTHER INFORMATION: complete sgAlpha-4

<400> SEQUENCE: 54
tcttgtggtt gttgctgaga gttttagagc tagaaatagc aagttaaaat aaggctagtc 60
cgttatcaac ttgaaaaagt ggcaccgagt cggtgc 96

<210> SEQ ID NO 55
<211> LENGTH: 96
<212> TYPE: DNA
<213> ORGANISM: Artificial Sequence
<220> FEATURE:
<223> OTHER INFORMATION: complete sg33mer1

<400> SEQUENCE: 55
ggtagttgcg gctgcggaaa gttttagagc tagaaatagc aagttaaaat aaggctagtc 60
cgttatcaac ttgaaaaagt ggcaccgagt cggtgc 96

<210> SEQ ID NO 56
<211> LENGTH: 96
<212> TYPE: DNA
<213> ORGANISM: Artificial Sequence
<220> FEATURE:
<223> OTHER INFORMATION: complete glia20-1

<400> SEQUENCE: 56
tatggttgtt gtggtcgaaa gttttagagc tagaaatagc aagttaaaat aaggctagtc 60
cgttatcaac ttgaaaaagt ggcaccgagt cggtgc 96

<210> SEQ ID NO 57

<211> LENGTH: 96
<212> TYPE: DNA
<213> ORGANISM: Artificial Sequence
<220> FEATURE:
<223> OTHER INFORMATION: complete sgOmega6

<400> SEQUENCE: 57
aaaggttgtt gtggttgttg gttttagagc tagaaatagc aagttaaaat aaggctagtc 60
cgttatcaac ttgaaaaagt ggcaccgagt cggtgc 96

<210> SEQ ID NO 58
<211> LENGTH: 96
<212> TYPE: DNA
<213> ORGANISM: Artificial Sequence
<220> FEATURE:
<223> OTHER INFORMATION: complete sgOmega4

<400> SEQUENCE: 58
aatggttgtt ggggttgctg gttttagagc tagaaatagc aagttaaaat aaggctagtc 60
cgttatcaac ttgaaaaagt ggcaccgagt cggtgc 96

<210> SEQ ID NO 59
<211> LENGTH: 96
<212> TYPE: DNA
<213> ORGANISM: Artificial Sequence
<220> FEATURE:
<223> OTHER INFORMATION: complete sgOmega3

<400> SEQUENCE: 59
tgatgggggg aatattgttg gttttagagc tagaaatagc aagttaaaat aaggctagtc 60
cgttatcaac ttgaaaaagt ggcaccgagt cggtgc 96

<210> SEQ ID NO 60
<211> LENGTH: 96
<212> TYPE: DNA
<213> ORGANISM: Artificial Sequence
<220> FEATURE:
<223> OTHER INFORMATION: complete sgOmega2

<400> SEQUENCE: 60
tgctggggga atggttgttg gttttagagc tagaaatagc aagttaaaat aaggctagtc 60
cgttatcaac ttgaaaaagt ggcaccgagt cggtgc 96

<210> SEQ ID NO 61
<211> LENGTH: 96
<212> TYPE: DNA
<213> ORGANISM: Artificial Sequence
<220> FEATURE:
<223> OTHER INFORMATION: complete sgOmega1

<400> SEQUENCE: 61
tgttcatcgc catggcaagg gttttagagc tagaaatagc aagttaaaat aaggctagtc 60
cgttatcaac ttgaaaaagt ggcaccgagt cggtgc 96

<210> SEQ ID NO 62
<211> LENGTH: 96
<212> TYPE: DNA
<213> ORGANISM: Artificial Sequence
<220> FEATURE:
<223> OTHER INFORMATION: complete sgOmega5

<400> SEQUENCE: 62
cttataacgt cgctcccaga gttttagagc tagaaatagc aagttaaaat aaggctagtc 60
cgttatcaac ttgaaaaagt ggcaccgagt cggtgc 96

<210> SEQ ID NO 63
<211> LENGTH: 96
<212> TYPE: DNA
<213> ORGANISM: Artificial Sequence
<220> FEATURE:
<223> OTHER INFORMATION: complete sgGamma13

<400> SEQUENCE: 63
gagaatggtt ggtgaggctg gttttagagc tagaaatagc aagttaaaat aaggctagtc 60
cgttatcaac ttgaaaaagt ggcaccgagt cggtgc 96

<210> SEQ ID NO 64
<211> LENGTH: 96
<212> TYPE: DNA
<213> ORGANISM: Artificial Sequence
<220> FEATURE:
<223> OTHER INFORMATION: complete sgGamma4

<400> SEQUENCE: 64
aattgttgtt gtggttgctg gttttagagc tagaaatagc aagttaaaat aaggctagtc 60
cgttatcaac ttgaaaaagt ggcaccgagt cggtgc 96

<210> SEQ ID NO 65
<211> LENGTH: 96
<212> TYPE: DNA
<213> ORGANISM: Artificial Sequence
<220> FEATURE:
<223> OTHER INFORMATION: complete sgGamma5

<400> SEQUENCE: 65
gttggggttg ttgagtctgg gttttagagc tagaaatagc aagttaaaat aaggctagtc 60
cgttatcaac ttgaaaaagt ggcaccgagt cggtgc 96

<210> SEQ ID NO 66
<211> LENGTH: 96
<212> TYPE: DNA
<213> ORGANISM: Artificial Sequence
<220> FEATURE:
<223> OTHER INFORMATION: complete sgGamma9

<400> SEQUENCE: 66
tgttggggga atgattgttg gttttagagc tagaaatagc aagttaaaat aaggctagtc 60
cgttatcaac ttgaaaaagt ggcaccgagt cggtgc 96

<210> SEQ ID NO 67
<211> LENGTH: 96
<212> TYPE: DNA
<213> ORGANISM: Artificial Sequence
<220> FEATURE:
<223> OTHER INFORMATION: complete sgGamma10

<400> SEQUENCE: 67
gcaagaggaa attcttgcat gttttagagc tagaaatagc aagttaaaat aaggctagtc 60
cgttatcaac ttgaaaaagt ggcaccgagt cggtgc 96

<210> SEQ ID NO 68
<211> LENGTH: 96
<212> TYPE: DNA
<213> ORGANISM: Artificial Sequence
<220> FEATURE:
<223> OTHER INFORMATION: complete sgGamma11

<400> SEQUENCE: 68
attgagctgg ttgttgaggt gttttagagc tagaaatagc aagttaaaat aaggctagtc 60
cgttatcaac ttgaaaaagt ggcaccgagt cggtgc 96

<210> SEQ ID NO 69
<211> LENGTH: 96
<212> TYPE: DNA
<213> ORGANISM: Artificial Sequence
<220> FEATURE:
<223> OTHER INFORMATION: complete sgGamma2

<400> SEQUENCE: 69
tgatggggga atgtttgttg gttttagagc tagaaatagc aagttaaaat aaggctagtc 60
cgttatcaac ttgaaaaagt ggcaccgagt cggtgc 96

<210> SEQ ID NO 70
<211> LENGTH: 96
<212> TYPE: DNA
<213> ORGANISM: Artificial Sequence
<220> FEATURE:
<223> OTHER INFORMATION: complete sgGamma3

<400> SEQUENCE: 70
attgttgttg tggttgatgg gttttagagc tagaaatagc aagttaaaat aaggctagtc 60
cgttatcaac ttgaaaaagt ggcaccgagt cggtgc 96

<210> SEQ ID NO 71
<211> LENGTH: 96
<212> TYPE: DNA
<213> ORGANISM: Artificial Sequence
<220> FEATURE:
<223> OTHER INFORMATION: complete sgGamma8

<400> SEQUENCE: 71
ggctggggaa aaggttgttg gttttagagc tagaaatagc aagttaaaat aaggctagtc 60
cgttatcaac ttgaaaaagt ggcaccgagt cggtgc 96

<210> SEQ ID NO 72
<211> LENGTH: 96
<212> TYPE: DNA
<213> ORGANISM: Artificial Sequence
<220> FEATURE:
<223> OTHER INFORMATION: complete sgGamma6

<400> SEQUENCE: 72
aatgattgtt gtggttgttg gttttagagc tagaaatagc aagttaaaat aaggctagtc 60
cgttatcaac ttgaaaaagt ggcaccgagt cggtgc 96

<210> SEQ ID NO 73
<211> LENGTH: 96
<212> TYPE: DNA
<213> ORGANISM: Artificial Sequence
<220> FEATURE:
<223> OTHER INFORMATION: complete sgGamma7

<400> SEQUENCE: 73
caggtttgca ttgttgcaag gttttagagc tagaaatagc aagttaaaat aaggctagtc 60
cgttatcaac ttgaaaaagt ggcaccgagt cggtgc 96

<210> SEQ ID NO 74
<211> LENGTH: 96
<212> TYPE: DNA
<213> ORGANISM: Artificial Sequence
<220> FEATURE:
<223> OTHER INFORMATION: complete sgGamma12

<400> SEQUENCE: 74
tcaacaacca gctcaattgg gttttagagc tagaaatagc aagttaaaat aaggctagtc 60
cgttatcaac ttgaaaaagt ggcaccgagt cggtgc 96

<210> SEQ ID NO 75
<211> LENGTH: 103
<212> TYPE: RNA
<213> ORGANISM: Artificial Sequence
<220> FEATURE:
<223> OTHER INFORMATION: complete sgAlpha-1

<400> SEQUENCE: 75
gccacaagag caaguuccau guuuuagagc uagaaauagc aaguuaaaau aaggcuaguc 60
cguuaucaac uugaaaaagu ggcaccgagu cggugcuuuu uuu 103

<210> SEQ ID NO 76
<211> LENGTH: 103
<212> TYPE: RNA
<213> ORGANISM: Artificial Sequence
<220> FEATURE:
<223> OTHER INFORMATION: complete sgAlpha-2

<400> SEQUENCE: 76
gguugugaug gaaaugguug guuuuagagc uagaaauagc aaguuaaaau aaggcuaguc 60
cguuaucaac uugaaaaagu ggcaccgagu cggugcuuuu uuu 103

<210> SEQ ID NO 77
<211> LENGTH: 96
<212> TYPE: RNA
<213> ORGANISM: Artificial Sequence
<220> FEATURE:
<223> OTHER INFORMATION: complete sgAlpha-3

<400> SEQUENCE: 77
uguggcugca auuguggcac guuuuagagc uagaaauagc aaguuaaaau aaggcuaguc 60
cguuaucaac uugaaaaagu ggcaccgagu cggugc 96

<210> SEQ ID NO 78
<211> LENGTH: 96
<212> TYPE: RNA
<213> ORGANISM: Artificial Sequence
<220> FEATURE:
<223> OTHER INFORMATION: complete sgAlpha-4

<400> SEQUENCE: 78
ucuugugguu guugcugaga guuuuagagc uagaaauagc aaguuaaaau aaggcuaguc 60
cguuaucaac uugaaaaagu ggcaccgagu cggugc 96

<210> SEQ ID NO 79
<211> LENGTH: 96

<212> TYPE: RNA
<213> ORGANISM: Artificial Sequence
<220> FEATURE:
<223> OTHER INFORMATION: complete sg33mer1

<400> SEQUENCE: 79
gguaguugcg gcugcggaaa guuuuagagc uagaaauagc aaguuaaaau aaggcuaguc 60
cguuaucaac uugaaaaagu ggcaccgagu cggugc 96

<210> SEQ ID NO 80
<211> LENGTH: 96
<212> TYPE: RNA
<213> ORGANISM: Artificial Sequence
<220> FEATURE:
<223> OTHER INFORMATION: complete glia20-1

<400> SEQUENCE: 80
uaugguuguu guggucgaaa guuuuagagc uagaaauagc aaguuaaaau aaggcuaguc 60
cguuaucaac uugaaaaagu ggcaccgagu cggugc 96

<210> SEQ ID NO 81
<211> LENGTH: 96
<212> TYPE: RNA
<213> ORGANISM: Artificial Sequence
<220> FEATURE:
<223> OTHER INFORMATION: complete sgOmega6

<400> SEQUENCE: 81
aaagguuguu gugguuguug guuuuagagc uagaaauagc aaguuaaaau aaggcuaguc 60
cguuaucaac uugaaaaagu ggcaccgagu cggugc 96

<210> SEQ ID NO 82
<211> LENGTH: 96
<212> TYPE: RNA
<213> ORGANISM: Artificial Sequence
<220> FEATURE:
<223> OTHER INFORMATION: complete sgOmega4

<400> SEQUENCE: 82
aaugguuguu gggguugcug guuuuagagc uagaaauagc aaguuaaaau aaggcuaguc 60
cguuaucaac uugaaaaagu ggcaccgagu cggugc 96

<210> SEQ ID NO 83
<211> LENGTH: 96
<212> TYPE: RNA
<213> ORGANISM: Artificial Sequence
<220> FEATURE:
<223> OTHER INFORMATION: complete sgOmega3

<400> SEQUENCE: 83
ugaugggggg aauauuguug guuuuagagc uagaaauagc aaguuaaaau aaggcuaguc 60
cguuaucaac uugaaaaagu ggcaccgagu cggugc 96

<210> SEQ ID NO 84
<211> LENGTH: 96
<212> TYPE: RNA
<213> ORGANISM: Artificial Sequence
<220> FEATURE:
<223> OTHER INFORMATION: complete sgOmega2

<400> SEQUENCE: 84
ugcuggggga augguuguug guuuuagagc uagaaauagc aaguuaaaau aaggcuaguc 60
cguuaucaac uugaaaaagu ggcaccgagu cggugc 96

<210> SEQ ID NO 85
<211> LENGTH: 96
<212> TYPE: RNA
<213> ORGANISM: Artificial Sequence
<220> FEATURE:
<223> OTHER INFORMATION: complete sgOmega1

<400> SEQUENCE: 85
uguucaucgc cauggcaagg guuuuagagc uagaaauagc aaguuaaaau aaggcuaguc 60
cguuaucaac uugaaaaagu ggcaccgagu cggugc 96

<210> SEQ ID NO 86
<211> LENGTH: 96
<212> TYPE: RNA
<213> ORGANISM: Artificial Sequence
<220> FEATURE:
<223> OTHER INFORMATION: complete sgOmega5

<400> SEQUENCE: 86
cuuauaacgu cgcucccaga guuuuagagc uagaaauagc aaguuaaaau aaggcuaguc 60
cguuaucaac uugaaaaagu ggcaccgagu cggugc 96

<210> SEQ ID NO 87
<211> LENGTH: 96
<212> TYPE: RNA
<213> ORGANISM: Artificial Sequence
<220> FEATURE:
<223> OTHER INFORMATION: complete sgGamma13

<400> SEQUENCE: 87
gagaaugguu ggugaggcug guuuuagagc uagaaauagc aaguuaaaau aaggcuaguc 60
cguuaucaac uugaaaaagu ggcaccgagu cggugc 96

<210> SEQ ID NO 88
<211> LENGTH: 96
<212> TYPE: RNA
<213> ORGANISM: Artificial Sequence
<220> FEATURE:
<223> OTHER INFORMATION: complete sgGamma4

<400> SEQUENCE: 88
aauuguuguu gugguugcug guuuuagagc uagaaauagc aaguuaaaau aaggcuaguc 60
cguuaucaac uugaaaaagu ggcaccgagu cggugc 96

<210> SEQ ID NO 89
<211> LENGTH: 96
<212> TYPE: RNA
<213> ORGANISM: Artificial Sequence
<220> FEATURE:
<223> OTHER INFORMATION: complete sgGamma5

<400> SEQUENCE: 89 guuggguug uugagucugg guuuuagagc uagaaauagc aaguuaaaau aaggcuaguc 60
cguuaucaac uugaaaaagu ggcaccgagu cggugc 96

<210> SEQ ID NO 90

<211> LENGTH: 96
<212> TYPE: RNA
<213> ORGANISM: Artificial Sequence
<220> FEATURE:
<223> OTHER INFORMATION: complete sgGamma9

<400> SEQUENCE: 90
uguuggggga augauuguug guuuuagagc uagaaauagc aaguuaaaau aaggcuaguc 60
cguuaucaac uugaaaaagu ggcaccgagu cggugc 96

<210> SEQ ID NO 91
<211> LENGTH: 96
<212> TYPE: RNA
<213> ORGANISM: Artificial Sequence
<220> FEATURE:
<223> OTHER INFORMATION: complete sgGamma10

<400> SEQUENCE: 91
gcaagaggaa auucuugcau guuuuagagc uagaaauagc aaguuaaaau aaggcuaguc 60
cguuaucaac uugaaaaagu ggcaccgagu cggugc 96

<210> SEQ ID NO 92
<211> LENGTH: 96
<212> TYPE: RNA
<213> ORGANISM: Artificial Sequence
<220> FEATURE:
<223> OTHER INFORMATION: complete sgGamma11

<400> SEQUENCE: 92
auugagcugg uuguugaggu guuuuagagc uagaaauagc aaguuaaaau aaggcuaguc 60
cguuaucaac uugaaaaagu ggcaccgagu cggugc 96

<210> SEQ ID NO 93
<211> LENGTH: 96
<212> TYPE: RNA
<213> ORGANISM: Artificial Sequence
<220> FEATURE:
<223> OTHER INFORMATION: complete sgGamma2

<400> SEQUENCE: 93
ugauggggga auguuuguug guuuuagagc uagaaauagc aaguuaaaau aaggcuaguc 60
cguuaucaac uugaaaaagu ggcaccgagu cggugc 96

<210> SEQ ID NO 94
<211> LENGTH: 96
<212> TYPE: RNA
<213> ORGANISM: Artificial Sequence
<220> FEATURE:
<223> OTHER INFORMATION: complete sgGamma3

<400> SEQUENCE: 94
auuguuguug ugguugaugg guuuuagagc uagaaauagc aaguuaaaau aaggcuaguc 60
cguuaucaac uugaaaaagu ggcaccgagu cggugc 96

<210> SEQ ID NO 95
<211> LENGTH: 96
<212> TYPE: RNA
<213> ORGANISM: Artificial Sequence
<220> FEATURE:
<223> OTHER INFORMATION: complete sgGamma8

<400> SEQUENCE: 95
ggcuggggaa aagguuguug guuuuagagc uagaaauagc aaguuaaaau aaggcuaguc 60
cguuaucaac uugaaaaagu ggcaccgagu cggugc 96

<210> SEQ ID NO 96
<211> LENGTH: 96
<212> TYPE: RNA
<213> ORGANISM: Artificial Sequence
<220> FEATURE:
<223> OTHER INFORMATION: complete sgGamma6

<400> SEQUENCE: 96
aaugauuguu gugguuguug guuuuagagc uagaaauagc aaguuaaaau aaggcuaguc 60
cguuaucaac uugaaaaagu ggcaccgagu cggugc 96

<210> SEQ ID NO 97
<211> LENGTH: 96
<212> TYPE: RNA
<213> ORGANISM: Artificial Sequence
<220> FEATURE:
<223> OTHER INFORMATION: complete sgGamma7

<400> SEQUENCE: 97
cagguuugca uuguugcaag guuuuagagc uagaaauagc aaguuaaaau aaggcuaguc 60
cguuaucaac uugaaaaagu ggcaccgagu cggugc 96

<210> SEQ ID NO 98
<211> LENGTH: 96
<212> TYPE: RNA
<213> ORGANISM: Artificial Sequence
<220> FEATURE:
<223> OTHER INFORMATION: complete sgGamma12

<400> SEQUENCE: 98
ucaacaacca gcucaauugg guuuuagagc uagaaauagc aaguuaaaau aaggcuaguc 60
cguuaucaac uugaaaaagu ggcaccgagu cggugc 96

<210> SEQ ID NO 99
<211> LENGTH: 64
<212> TYPE: RNA
<213> ORGANISM: Artificial Sequence
<220> FEATURE:
<223> OTHER INFORMATION: RNA sequence for tracrRNA

<400> SEQUENCE: 99
gaaauagcaa guuaaaauaa ggcuaguccg uuaucaacuu gaaaaagugg caccgagucg 60
gugc 64

<210> SEQ ID NO 100
<211> LENGTH: 4155
<212> TYPE: DNA
<213> ORGANISM: Artificial Sequence
<220> FEATURE:
<223> OTHER INFORMATION: Cas9

<400> SEQUENCE: 100
atggacaaga agtactcgat cggcctcgac atcgggacga actcagttgg ctgggccgtg 60
atcaccgacg agtacaaggt gccctctaag aagttcaagg tcctggggaa caccgaccgc 120
cattccatca agaagaacct catcggcgct ctcctgttcg acagcgggga gaccgctgag 180

-continued

```
gctacgaggc tcaagagaac cgctaggcgc cggtacacga gaaggaagaa caggatctgc    240
tacctccaag agattttctc caacgagatg gccaaggttg acgattcatt cttccaccgc    300
ctggaggagt ctttcctcgt ggaggaggat aagaagcacg agcggcatcc catcttcggc    360
aacatcgtgg acgaggttgc ctaccacgag aagtacccta cgatctacca tctgcggaag    420
aagctcgtgg actccaccga taaggcggac ctcagactga tctacctcgc tctggcccac    480
atgatcaagt tccgcggcca tttcctgatc gagggggatc tcaacccaga caacagcgat    540
gttgacaagc tgttcatcca actcgtgcag acctacaacc aactcttcga ggagaacccg    600
atcaacgcct ctggcgtgga cgcgaaggct atcctgtccg cgaggctctc gaagtccagg    660
aggctggaga acctgatcgc tcagctccca ggcgagaaga agaacggcct gttcgggaac    720
ctcatcgctc tcagcctggg gctcaccccg aacttcaagt cgaacttcga tctcgctgag    780
gacgccaagc tgcaactctc caaggacacc tacgacgatg acctcgataa cctcctggcc    840
cagatcggcg atcaatacgc ggacctgttc ctcgctgcca agaacctgtc ggacgccatc    900
ctcctgtcag atatcctccg cgtgaacacc gagatcacga aggctccact ctctgcctcc    960
atgatcaagc gctacgacga gcaccatcag gatctgaccc tcctgaaggc gctggtccgc   1020
caacagctcc cggagaagta caaggagatt ttcttcgatc agtcgaagaa cggctacgct   1080
gggtacatcg acggcggggc ctcacaagag gagttctaca agttcatcaa gccaatcctg   1140
gagaagatgg acggcacgga ggagctcctg gtgaagctca acagggagga cctcctgcgg   1200
aagcagagaa ccttcgataa cggcagcatc ccccaccaaa tccatctcgg ggagctgcac   1260
gccatcctga gaaggcaaga ggacttctac cctttcctca aggataaccg ggagaagatc   1320
gagaagatcc tgaccttcag aatcccatac tacgtcggcc ctctcgcgcg ggggaactca   1380
agattcgctt ggatgacccg caagtctgag gagaccatca cgccgtggaa cttcgaggag   1440
gtggtggaca agggcgctag cgctcagtcg ttcatcgaga ggatgaccaa cttcgacaag   1500
aacctgccca acgagaaggt gctccctaag cactcgctcc tgtacgagta cttcaccgtc   1560
tacaacgagc tcacgaaggt gaagtacgtc accgagggca tgcgcaagcc agcgttcctg   1620
tccggggagc agaagaaggc tatcgtggac ctcctgttca agaccaaccg gaaggtcacg   1680
gttaagcaac tcaaggagga ctacttcaag aagatcgagt gcttcgattc ggtcgagatc   1740
agcggcgttg aggaccgctt caacgccagc ctcgggacct accacgatct cctgaagatc   1800
atcaaggata aggacttcct ggacaacgag gagaacgagg atatcctgga ggacatcgtg   1860
ctgaccctca cgctgttcga ggacagggag atgatcgagg agcgcctgaa gacgtacgcc   1920
catctcttcg atgacaaggt catgaagcaa ctcaagcgcc ggagatacac cggctggggg   1980
aggctgtccc gcaagctcat caacggcatc cgggacaagc agtccgggaa gaccatcctc   2040
gacttcctca agagcgatgg cttcgccaac aggaacttca tgcaactgat ccacgatgac   2100
agcctcacct tcaaggagga tatccaaaag gctcaagtga gcggccaggg ggactcgctg   2160
cacgagcata tcgcgaacct cgctggctcc cccgcgatca agaagggcat cctccagacc   2220
gtgaaggttg tggacgagct cgtgaaggtc atgggccggc acaagcctga gaacatcgtc   2280
atcgagatgg ccagagagaa ccaaaccacg cagaaggggc aaaagaactc tagggagcgc   2340
atgaagcgca tcgaggaggg catcaaggag ctggggtccc aaatcctcaa ggagcaccca   2400
gtggagaaca cccaactgca gaacgagaag ctctacctgt actacctcca gaacggcagg   2460
gatatgtacg tggaccaaga gctggatatc aaccgcctca gcgattacga cgtcgatcat   2520
atcgttcccc agtctttcct gaaggatgac tccatcgaca acaaggtcct caccaggtcg   2580
```

gacaagaacc gcggcaagtc agataacgtt ccatctgagg aggtcgttaa gaagatgaag 2640
aactactgga ggcagctcct gaacgccaag ctgatcacgc aaaggaagtt cgacaacctc 2700
accaaggctg agagaggcgg gctctcagag ctggacaagg ccggcttcat caagcggcag 2760
ctggtcgaga ccagacaaat cacgaagcac gttgcgcaaa tcctcgactc tcggatgaac 2820
acgaagtacg atgagaacga caagctgatc agggaggtta aggtgatcac cctgaagtct 2880
aagctcgtct ccgacttcag gaaggatttc cagttctaca aggttcgcga gatcaacaac 2940
taccaccatg cccatgacgc ttacctcaac gctgtggtcg gcaccgctct gatcaagaag 3000
tacccaaagc tggagtccga gttcgtgtac ggggactaca aggtttacga tgtgcgcaag 3060
atgatcgcca agtcggagca agagatcggc aaggctaccg ccaagtactt cttctactca 3120
aacatcatga acttcttcaa gaccgagatc acgctggcca acggcgagat ccggaagaga 3180
ccgctcatcg agaccaacgg cgagacgggg gagatcgtgt gggacaaggg cagggatttc 3240
gcgaccgtcc gcaaggttct ctccatgccc caggtgaaca tcgtcaagaa gaccgaggtc 3300
caaacgggcg ggttctcaaa ggagtctatc ctgcctaagc ggaacagcga caagctcatc 3360
gccagaaaga aggactggga cccaaagaag tacggcgggt tcgacagccc taccgtggcc 3420
tactcggtcc tggttgtggc gaaggttgag aagggcaagt ccaagaagct caagagcgtg 3480
aaggagctcc tggggatcac catcatggag aggtccagct tcgagaagaa cccaatcgac 3540
ttcctggagg ccaagggcta caaggaggtg aagaaggacc tgatcatcaa gctcccgaag 3600
tactctctct tcgagctgga gaacggcagg aagagaatgc tggcttccgc tggcgagctc 3660
cagaagggga acgagctcgc gctgccaagc aagtacgtga acttcctcta cctggcttcc 3720
cactacgaga agctcaaggg cagcccggag gacaacgagc aaaagcagct gttcgtcgag 3780
cagcacaagc attacctcga cgagatcatc gagcaaatct ccgagttcag caagcgcgtg 3840
atcctcgccg acgcgaacct ggataaggtc ctctccgcct acaacaagca ccgggacaag 3900
cccatcagag agcaagcgga gaacatcatc catctcttca ccctgacgaa cctcggcgct 3960
cctgctgctt tcaagtactt cgacaccacg atcgatcgga agagatacac ctccacgaag 4020
gaggtcctgg acgcgaccct catccaccag tcgatcaccg gcctgtacga gacgaggatc 4080
gacctctcac aactcggcgg ggataagaga cccgcagcaa ccaagaaggc agggcaagca 4140
aagaagaaga agtga 4155

<210> SEQ ID NO 101
<211> LENGTH: 4782
<212> TYPE: DNA
<213> ORGANISM: Artificial Sequence
<220> FEATURE:
<223> OTHER INFORMATION: Cys4-P2A-TaCas9

<400> SEQUENCE: 101
atggaccact acctcgacat caggctcagg ccagacccag agttcccacc agcccagctc 60
atgtccgtcc tcttcggcaa gctccaccag gccctcgtgg cccagggcgg cgacaggatc 120
ggcgtgtcct tcccagacct cgacgagtcc aggtccaggc tcggcgagag gctccgcatc 180
cacgcctccg ccgacgacct cagggccctc ctcgccaggc cgtggctgga gggcctcagg 240
gaccacctcc agttcggcga gccagccgtg gtgccacacc caaccccata caggcaagtg 300
tccagggtgc aagccaagtc caacccagag aggctcagga ggaggctcat gaggaggcac 360
gacctctccg aggaagaggc caggaagcgc atcccagaca ccgtggccag ggccctcgac 420

-continued

```
ctcccattcg tgaccctcag gtcccagtcc accggccagc acttccgcct cttcatcagg    480
cacggcccac tccaggtgac cgccgaggag ggcggcttta cctgctacgg cctctccaag    540
ggcggcttcg tgccgtggtt cggctccggc gccaccaact tctccctcct caagcaagcc    600
ggcgacgtgg aggagaaccc aggcccaatg gacaagaagt actcgatcgg cctcgacatc    660
gggacgaact cagttggctg ggccgtgatc accgacgagt acaaggtgcc ctctaagaag    720
ttcaaggtcc tggggaacac cgaccgccat tccatcaaga agaacctcat cggcgctctc    780
ctgttcgaca gcggggagac cgctgaggct acgaggctca agagaaccgc taggcgccgg    840
tacacgagaa ggaagaacag gatctgctac ctccaagaga ttttctccaa cgagatggcc    900
aaggttgacg attcattctt ccaccgcctg gaggagtctt tcctcgtgga ggaggataag    960
aagcacgagc ggcatcccat cttcggcaac atcgtggacg aggttgccta ccacgagaag   1020
taccctacga tctaccatct gcggaagaag ctcgtggact ccaccgataa ggcggacctc   1080
agactgatct acctcgctct ggcccacatg atcaagttcc gcggccattt cctgatcgag   1140
ggggatctca acccagacaa cagcgatgtt gacaagctgt tcatccaact cgtgcagacc   1200
tacaaccaac tcttcgagga gaacccgatc aacgcctctg gcgtggacgc gaaggctatc   1260
ctgtccgcga ggctctcgaa gtccaggagg ctggagaacc tgatcgctca gctcccaggc   1320
gagaagaaga acggcctgtt cgggaacctc atcgctctca gcctggggct caccccgaac   1380
ttcaagtcga acttcgatct cgctgaggac gccaagctgc aactctccaa ggacacctac   1440
gacgatgacc tcgataacct cctggcccag atcggcgatc aatacgcgga cctgttcctc   1500
gctgccaaga acctgtcgga cgccatcctc ctgtcagata tcctccgcgt gaacaccgag   1560
atcacgaagg ctccactctc tgcctccatg atcaagcgct acgacgagca ccatcaggat   1620
ctgaccctcc tgaaggcgct ggtccgccaa cagctcccgg agaagtacaa ggagattttc   1680
ttcgatcagt cgaagaacgg ctacgctggg tacatcgacg gcggggcctc acaagaggag   1740
ttctacaagt tcatcaagcc aatcctggag aagatggacg gcacggagga gctcctggtg   1800
aagctcaaca gggaggacct cctgcggaag cagagaacct tcgataacgg cagcatcccc   1860
caccaaatcc atctcgggga gctgcacgcc atcctgagaa ggcaagagga cttctaccct   1920
ttcctcaagg ataaccggga gaagatcgag aagatcctga ccttcagaat cccatactac   1980
gtcggccctc tcgcgcgggg gaactcaaga ttcgcttgga tgacccgcaa gtctgaggag   2040
accatcacgc cgtggaactt cgaggaggtg gtggacaagg gcgctagcgc tcagtcgttc   2100
atcgagagga tgaccaactt cgacaagaac ctgcccaacg agaaggtgct ccctaagcac   2160
tcgctcctgt acgagtactt caccgtctac aacgagctca cgaaggtgaa gtacgtcacc   2220
gagggcatgc gcaagccagc gttcctgtcc ggggagcaga agaaggctat cgtggacctc   2280
ctgttcaaga ccaaccggaa ggtcacggtt aagcaactca aggaggacta cttcaagaag   2340
atcgagtgct tcgattcggt cgagatcagc ggcgttgagg accgcttcaa cgccagcctc   2400
gggacctacc acgatctcct gaagatcatc aaggataagg acttcctgga caacgaggag   2460
aacgaggata tcctggagga catcgtgctg accctcacgc tgttcgagga cagggagatg   2520
atcgaggagc gcctgaagac gtacgcccat ctcttcgatg acaaggtcat gaagcaactc   2580
aagcgccgga gatacaccgg ctgggggagg ctgtcccgca agctcatcaa cggcatccgg   2640
gacaagcagt ccgggaagac catcctcgac ttcctcaaga gcgatggctt cgccaacagg   2700
aacttcatgc aactgatcca cgatgacagc ctcaccttca aggaggatat ccaaaaggct   2760
caagtgagcg gccaggggga ctcgctgcac gagcatatcg cgaacctcgc tggctccccc   2820
```

gcgatcaaga agggcatcct ccagaccgtg aaggttgtgg acgagctcgt gaaggtcatg 2880
ggccggcaca agcctgagaa catcgtcatc gagatggcca gagagaacca aaccacgcag 2940
aaggggcaaa agaactctag ggagcgcatg aagcgcatcg aggagggcat caaggagctg 3000
gggtcccaaa tcctcaagga gcacccagtg gagaacaccc aactgcagaa cgagaagctc 3060
tacctgtact acctccagaa cggcagggat atgtacgtgg accaagagct ggatatcaac 3120
cgcctcagcg attacgacgt cgatcatatc gttccccagt ctttcctgaa ggatgactcc 3180
atcgacaaca aggtcctcac caggtcggac aagaaccgcg gcaagtcaga taacgttcca 3240
tctgaggagg tcgttaagaa gatgaagaac tactggaggc agctcctgaa cgccaagctg 3300
atcacgcaaa ggaagttcga caacctcacc aaggctgaga gaggcgggct ctcagagctg 3360
gacaaggccg gcttcatcaa gcggcagctg gtcgagacca gacaaatcac gaagcacgtt 3420
gcgcaaatcc tcgactctcg gatgaacacg aagtacgatg agaacgacaa gctgatcagg 3480
gaggttaagg tgatcaccct gaagtctaag ctcgtctccg acttcaggaa ggatttccag 3540
ttctacaagg ttcgcgagat caacaactac caccatgccc atgacgctta cctcaacgct 3600
gtggtcggca ccgctctgat caagaagtac ccaaagctgg agtccgagtt cgtgtacggg 3660
gactacaagg tttacgatgt gcgcaagatg atcgccaagt cggagcaaga gatcggcaag 3720
gctaccgcca agtacttctt ctactcaaac atcatgaact tcttcaagac cgagatcacg 3780
ctggccaacg gcgagatccg gaagagaccg ctcatcgaga ccaacggcga gacgggggag 3840
atcgtgtggg acaagggcag ggatttcgcg accgtccgca aggttctctc catgccccag 3900
gtgaacatcg tcaagaagac cgaggtccaa acgggcgggt tctcaaagga gtctatcctg 3960
cctaagcgga acagcgacaa gctcatcgcc agaaagaagg actgggaccc aaagaagtac 4020
ggcgggttcg acagccctac cgtggcctac tcggtcctgg ttgtggcgaa ggttgagaag 4080
ggcaagtcca agaagctcaa gagcgtgaag gagctcctgg ggatcaccat catggagagg 4140
tccagcttcg agaagaaccc aatcgacttc ctggaggcca agggctacaa ggaggtgaag 4200
aaggacctga tcatcaagct cccgaagtac tctctcttcg agctggagaa cggcaggaag 4260
agaatgctgg cttccgctgg cgagctccag aaggggaacg agctcgcgct gccaagcaag 4320
tacgtgaact tcctctacct ggcttcccac tacgagaagc tcaagggcag cccggaggac 4380
aacgagcaaa agcagctgtt cgtcgagcag cacaagcatt acctcgacga gatcatcgag 4440
caaatctccg agttcagcaa gcgcgtgatc ctcgccgacg cgaacctgga taaggtcctc 4500
tccgcctaca acaagcaccg ggacaagccc atcagagagc aagcggagaa catcatccat 4560
ctcttcaccc tgacgaacct cggcgctcct gctgctttca agtacttcga caccacgatc 4620
gatcggaaga gatacacctc cacgaaggag gtcctggacg cgaccctcat ccaccagtcg 4680
atcaccggcc tgtacgagac gaggatcgac ctctcacaac tcggcgggga taagagaccc 4740
gcagcaacca agaaggcagg gcaagcaaag aagaagaagt ga 4782

<210> SEQ ID NO 102
<211> LENGTH: 561
<212> TYPE: DNA
<213> ORGANISM: Artificial Sequence
<220> FEATURE:
<223> OTHER INFORMATION: Cys 4 endoribonuclease

<400> SEQUENCE: 102
atggaccact acctcgacat caggctcagg ccagacccag agttcccacc agcccagctc 60
atgtccgtcc tcttcggcaa gctccaccag gccctcgtgg cccagggcgg cgacaggatc 120
ggcgtgtcct tcccagacct cgacgagtcc aggtccaggc tcggcgagag gctccgcatc 180
cacgcctccg ccgacgacct cagggccctc ctcgccaggc cgtggctgga gggcctcagg 240
gaccacctcc agttcggcga gccagccgtg gtgccacacc caaccccata caggcaagtg 300
tccagggtgc aagccaagtc caacccagag aggctcagga ggaggctcat gaggaggcac 360
gacctctccg aggaagaggc caggaagcgc atcccagaca ccgtggccag ggccctcgac 420
ctcccattcg tgaccctcag gtcccagtcc accggccagc acttccgcct cttcatcagg 480
cacggcccac tccaggtgac cgccgaggag ggcggcttta cctgctacgg cctctccaag 540
ggcggcttcg tgccgtggtt c 561

<210> SEQ ID NO 103
<211> LENGTH: 20
<212> TYPE: DNA
<213> ORGANISM: Artificial Sequence
<220> FEATURE:
<223> OTHER INFORMATION: Cys4 cleavage site

<400> SEQUENCE: 103
gttcactgcc gtataggcag 20

<210> SEQ ID NO 104
<211> LENGTH: 465
<212> TYPE: DNA
<213> ORGANISM: Artificial Sequence
<220> FEATURE:
<223> OTHER INFORMATION: Cestrum yellow leaf curling virus (CmYLCV)
promoter

<400> SEQUENCE: 104
tggcagacat actgtcccac aaatgaagat ggaatctgta aaagaaaacg cgtgaaataa 60
tgcgtctgac aaaggttagg tcggctgcct ttaatcaata ccaaagtggt ccctaccacg 120
atggaaaaac tgtgcagtcg gtttggcttt ttctgacgaa caaataagat tcgtggccga 180
caggtggggg tccaccatgt gaaggcatct tcagactcca ataatggagc aatgacgtaa 240
gggcttacga aataagtaag ggtagtttgg gaaatgtcca ctcacccgtc agtctataaa 300
tacttagccc ctccctcatt gttaagggag caaaatctca gagagatagt cctagagaga 360
gaaagagagc aagtagccta gaagtagtca aggcggcgaa gtattcaggc acgtggccag 420
gaagaagaaa agccaagacg acgaaaacag gtaagagcta agctt 465

<210> SEQ ID NO 105
<211> LENGTH: 1973
<212> TYPE: DNA
<213> ORGANISM: Artificial Sequence
<220> FEATURE:
<223> OTHER INFORMATION: switchgrass ubiquitin 1 promoter (PvUbi1)

<400> SEQUENCE: 105
cacgtcagtg tttggtttcc actagcacga gtagcgcaat cagaaaattt tcaatgcatg 60
aagtactaaa cgaagtttat ttagaaattt ttttaagaaa tgagtgtaat tttttgcgac 120
gaatttaatg acaataatta atcgatgatt gcctacagta atgctacagt aaccaacctc 180
taatcatgcg tcgaatgcgt cattagattc gtctcgcaaa atagcacaag aattatgaaa 240
ttaattttac aaactatttt tatttaatac taataattaa ctgtcaaagt ttgtgctact 300
cgcaagagta gcgcgaacca aacacggcct ggaggagcac ggtaacggcg tcgacaaact 360
aacggccacc acccgccaac gcaaaggaga cggatgagag ttgacttctt gacggttctc 420
cacccctctg tctctctgtc actgggccct gggtccccct ctcgaaagtt cctctggccg 480
aaattgcgcg gcggagacga ggcgggcgga accgtcacgg cagaggattc cttccccacc 540
ctgcctggcc cggccatata taaacagcca ccgcccctcc ccgttcccca tcgcgtctcg 600
tctcgtgttg ttcccagaac acaaccaaaa tccaaatcct cctcctcctc ccgagcctcg 660
tcgatccctc acccgcttca aggtacggcg atcctcctct cccttctccc ctcgatcgat 720
tatgcgtgtt ccgtttccgt ttccgatcga gcgaatcgat ggttaggacc catgggggac 780
ccatggggtg tcgtgtggtg gtctggtttg atccgcgata tttctccgtt cgtagtgtag 840
atctgatcga atccctggtg aaatcgttga tcgtgctatt cgtgtgaggg ttcttaggtt 900
tggagttgtg gaggtagttc tgatcggttt gtaggtgaga ttttccccat gattttgctt 960
ggctcgtttg tcttggttag attagatctg cccgcatttt gttcgatatt tctgatgcag 1020
atatgatgaa taatttcgtc cttgtatccc gcgtccgtat gtgtattaag tttgcaggtc 1080
ctagttaggt ttttcctact gatttgtctt atccattctg tttagcttgc aaggtttggt 1140
aatggtccgg catgtttgtc tctatagatt agagtagaat aagattatct caacaagctg 1200
ttggcttatc aattttggat ctgcatgtgt ttcgcatcta tatctttgca attaagatgg 1260
tagatggaca tatgctcctg ttgagttgat gttgtacctt ttacctgagg tctgaggaac 1320
atgcatcctc ctgctacttt gtgcttatac agatcatcaa gattatgcag ctaatattcg 1380
atcagtttct agtatctaca tggtaaactt gcatgcactt gctacttatt tttgatatac 1440
ttggatgata acatatgctg ctggttgatt cctacctaca tgatgaacat tttacaggcc 1500
attagtgtct gtctgtatgt gttgttcctg tttgcttcag tctatttctg tttcattcct 1560
agtttattgg ttctctgcta gatacttacc ctgctgggct tagttatcat cttatctcga 1620
atgcattttc atgtttatag atgaatatac actcagatag gtgtagatgt atgctactgt 1680
ttctctacgt tgctgtaggt tttacctgtg gcaactgcat actcctgttg cttcgctaga 1740
tatgtatgtg cttatataga ttaagatatg tgtgatggtt ctttagtata tctgatgatc 1800
atgtatgctc ttttaacttc ttgctacact tggtaacatg ctgtgatgct gtttgttgat 1860
tctgtagcac taccaatgat gaccttatct ctctttgtat atgatgtttc tgtttgtttg 1920
aggcttgtgt tactgctagt tacttaccct gttgcctggc taatcttctg cag 1973

<210> SEQ ID NO 106
<211> LENGTH: 1994
<212> TYPE: DNA
<213> ORGANISM: Artificial Sequence
<220> FEATURE:
<223> OTHER INFORMATION: Zea Mays Ubiquitin 1 promoter

<400> SEQUENCE: 106
tgcagtgcag cgtgacccgg tcgtgcccct ctctagagat aatgagcatt gcatgtctaa 60
gttataaaaa attaccacat attttttttg tcacacttgt ttgaagtgca gtttatctat 120
ctttatacat atatttaaac tttactctac gaataatata atctatagta ctacaataat 180
atcagtgttt tagagaatca tataaatgaa cagttagaca tggtctaaag gacaattgag 240
tattttgaca acaggactct acagttttat ctttttagtg tgcatgtgtt ctcctttttt 300
tttgcaaata gcttcaccta tataatactt catccatttt attagtacat ccatttaggg 360
tttagggtta atggttttta tagactaatt tttttagtac atctatttta ttctatttta 420
gcctctaaat taagaaaact aaaactctat tttagttttt ttatttaata atttagatat 480
aaaatagaat aaaataaagt gactaaaaat taaacaaata ccctttaaga aattaaaaaa 540
actaaggaaa catttttctt gtttcgagta gataatgcca gcctgttaaa cgccgtcgac 600
gagtctaacg gacaccaacc agcgaaccag cagcgtcgcg tcgggccaag cgaagcagac 660
ggcacggcat ctctgtcgct gcctctggac ccctctcgag agttccgctc caccgttgga 720
cttgctccgc tgtcggcatc cagaaattgc gtggcggagc ggcagacgtg agccggcacg 780
gcaggcggcc tcctcctcct ctcacggcac cggcagctac gggggattcc tttcccaccg 840
ctccttcgct ttcccttcct cgcccgccgt aataaataga cacccctcc acaccctctt 900 tccccaacct cgtgttgttc ggagcgcaca cacacacaac cagatctccc ccaaatccac 960
ccgtcggcac ctccgcttca aggtacgccg ctcgtcctcc cccccccccc tctctacctt 1020
ctctagatcg gcgttccggt ccatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattaattc tgtttcaaac tacctggtgg atttattaat tttggatctg 1440
tatgtgtgtg ccatacatat tcatagttac gaattgaaga tgatggatgg aaatatcgat 1500
ctaggatagg tatacatgtt gatgcgggtt ttactgatgc atatacagag atgctttttg 1560
ttcgcttggt tgtgatgatg tggtgtggtt gggcggtcgt tcattcgttc tagatcggag 1620
tagaatactg tttcaaacta cctggtgtat ttattaattt tggaactgta tgtgtgtgtc 1680
atacatcttc atagttacga gtttaagatg gatggaaata tcgatctagg ataggtatac 1740
atgttgatgt gggttttact gatgcatata catgatggca tatgcagcat ctattcatat 1800
gctctaacct tgagtaccta tctattataa taaacaagta tgttttataa ttattttgat 1860
cttgatatac ttggatgatg gcatatgcag cagctatatg tggatttttt tagccctgcc 1920
ttcatacgct atttatttgc ttggtactgt ttcttttgtc gatgctcacc ctgttgtttg 1980
gtgttacttc tgca 1994

<210> SEQ ID NO 107
<211> LENGTH: 71
<212> TYPE: DNA
<213> ORGANISM: Artificial Sequence
<220> FEATURE:
<223> OTHER INFORMATION: tracrRNA; nucleotide sequence for alpha-1 and alpha-2

<400> SEQUENCE: 107
gaaatagcaa gttaaaataa ggctagtccg ttatcaactt gaaaaagtgg caccgagtcg 60
gtgctttttt t 71

<210> SEQ ID NO 108
<211> LENGTH: 362
<212> TYPE: DNA
<213> ORGANISM: Artificial Sequence
<220> FEATURE:

<223> OTHER INFORMATION: T. aestivum UG RNA polymerase III promoter
(TaU6)

<400> SEQUENCE: 108
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
tt 362

<210> SEQ ID NO 109
<211> LENGTH: 100
<212> TYPE: DNA
<213> ORGANISM: Artificial Sequence
<220> FEATURE:
<223> OTHER INFORMATION: fig 1b BW208wt

<400> SEQUENCE: 109
caatttccag ggcagcaaca accatttcca ccacaacagc catatccgca gccgcaacca 60
tttccatcac aacaaccata tctgcagctg caaccatttc 100

<210> SEQ ID NO 110
<211> LENGTH: 99
<212> TYPE: DNA
<213> ORGANISM: Artificial Sequence
<220> FEATURE:
<223> OTHER INFORMATION: fig 1b -1bp (1)

<400> SEQUENCE: 110
caatttctag ggcagcaaca accatttcca ccacaacaac catatccaca gccgcaccat 60
ttccatcaca acaaccatat ctgcaactgc aaccatttc 99

<210> SEQ ID NO 111
<211> LENGTH: 99
<212> TYPE: DNA
<213> ORGANISM: Artificial Sequence
<220> FEATURE:
<223> OTHER INFORMATION: fig 1b -1bp (2)

<400> SEQUENCE: 111
caatttctag ggcagcaaca accatttcca ccacaacaac catatccaca gccgcaacat 60
ttccatcaca actaccatat ctgcagctgc aaccatttc 99

<210> SEQ ID NO 112
<211> LENGTH: 97
<212> TYPE: DNA
<213> ORGANISM: Artificial Sequence
<220> FEATURE:
<223> OTHER INFORMATION: fig 1b -3bp

<400> SEQUENCE: 112
caatttccag ggcagcaaca accatttcca ccacaacagc catatccgca gccgcaattt 60
ccatcacaac aaccatatct gcagctgcaa ccatttc 97

<210> SEQ ID NO 113
<211> LENGTH: 95
<212> TYPE: DNA

<213> ORGANISM: Artificial Sequence
<220> FEATURE:
<223> OTHER INFORMATION: fig 1b -5bp

<400> SEQUENCE: 113
caatttctag ggcagtaaca accatttcca ccacaacaac catatccaca gcccatttcc 60
atcacaacaa ccatatctgc agttgcaacc atttc 95

<210> SEQ ID NO 114
<211> LENGTH: 92
<212> TYPE: DNA
<213> ORGANISM: Artificial Sequence
<220> FEATURE:
<223> OTHER INFORMATION: fig 1b -8bp

<400> SEQUENCE: 114
caatttctag ggcagcaaca accatttcca ccacaacagc catatccgca gccttccatc 60
acaacaacca tatccacagc cacaaccatt tc 92

<210> SEQ ID NO 115
<211> LENGTH: 91
<212> TYPE: DNA
<213> ORGANISM: Artificial Sequence
<220> FEATURE:
<223> OTHER INFORMATION: fig 1b -9bp

<400> SEQUENCE: 115
caatttccag ggcagcaaca accatttcca ccacaacagc catatccgca gccgcaatca 60
caacaaccat atctgcagct gcaaccattt c 91

<210> SEQ ID NO 116
<211> LENGTH: 89
<212> TYPE: DNA
<213> ORGANISM: Artificial Sequence
<220> FEATURE:
<223> OTHER INFORMATION: fig 1b -11bp

<400> SEQUENCE: 116
caatttctag gggagcaaca acaatttcca ccacaacaac tagatcccat ttccatcaca 60
acaaccatat ctgcagctgc aaccatttc 89

<210> SEQ ID NO 117
<211> LENGTH: 82
<212> TYPE: DNA
<213> ORGANISM: Artificial Sequence
<220> FEATURE:
<223> OTHER INFORMATION: fig 1b -18bp

<400> SEQUENCE: 117
caatttctag ggcagcaaca accatttcca ccacaacaac catatccatc acaacagcca 60
tatctgcagc tgcaaccatt tc 82

<210> SEQ ID NO 118
<211> LENGTH: 82
<212> TYPE: DNA
<213> ORGANISM: Artificial Sequence
<220> FEATURE:
<223> OTHER INFORMATION: fig 1b -18bp (2)

<400> SEQUENCE: 118
caatttctag ggcagcaaca accatttcca ccacaacaac catttccatc acaacaacca 60
tatctgcagc tgcaaccatt tt 82

<210> SEQ ID NO 119
<211> LENGTH: 77
<212> TYPE: DNA
<213> ORGANISM: Artificial Sequence
<220> FEATURE:
<223> OTHER INFORMATION: fig 1b -23bp

<400> SEQUENCE: 119
caatttctag ggcagcaaca accatttcca ccacaacaac catatccaca gccgcaatct 60
gcagctgcaa ccatttc 77

<210> SEQ ID NO 120
<211> LENGTH: 72
<212> TYPE: DNA
<213> ORGANISM: Artificial Sequence
<220> FEATURE:
<223> OTHER INFORMATION: fig 1b -28bp

<400> SEQUENCE: 120
caatttccag ggcagcaaca accatttcca ccacaacagc catatccgca tatctgcagc 60
tgcagccatt tc 72

<210> SEQ ID NO 121
<211> LENGTH: 64
<212> TYPE: DNA
<213> ORGANISM: Artificial Sequence
<220> FEATURE:
<223> OTHER INFORMATION: fig 1b -36bp

<400> SEQUENCE: 121
caatttctag ggcagcaaca acaatttcca ccacaacaac catatctgca gctgcaacca 60
tttt 64

<210> SEQ ID NO 122
<211> LENGTH: 64
<212> TYPE: DNA
<213> ORGANISM: Artificial Sequence
<220> FEATURE:
<223> OTHER INFORMATION: fig 1b -36bp (2)

<400> SEQUENCE: 122
caatttctag ggcagcaaca accatttcca tcacaacaac catatccaca gccacaacca 60
tttc 64

<210> SEQ ID NO 123
<211> LENGTH: 61
<212> TYPE: DNA
<213> ORGANISM: Artificial Sequence
<220> FEATURE:
<223> OTHER INFORMATION: fig 1b -39bp

<400> SEQUENCE: 123
caatttctag ggcagcaaca accatttcca tcacaacaac catatccaca gccacaacca 60
t 61

<210> SEQ ID NO 124
<211> LENGTH: 54
<212> TYPE: DNA
<213> ORGANISM: Artificial Sequence
<220> FEATURE:
<223> OTHER INFORMATION: fig 1b -54bp

<400> SEQUENCE: 124
caatttctag ggcagcaaca accatttcca ccacaacaac catatccaca gccg 54

<210> SEQ ID NO 125
<211> LENGTH: 36
<212> TYPE: DNA
<213> ORGANISM: Artificial Sequence
<220> FEATURE:
<223> OTHER INFORMATION: fig 1b -64bp

<400> SEQUENCE: 125
caacacaaca accatatctg cagctgcaac catttc 36

<210> SEQ ID NO 126
<211> LENGTH: 33
<212> TYPE: DNA
<213> ORGANISM: Artificial Sequence
<220> FEATURE:
<223> OTHER INFORMATION: fig 1b -67bp

<400> SEQUENCE: 126
cacaacaacc atatctgcag ctgcaaccat ttc 33

<210> SEQ ID NO 127
<211> LENGTH: 52
<212> TYPE: DNA
<213> ORGANISM: Artificial Sequence
<220> FEATURE:
<223> OTHER INFORMATION: fig 1b -74bp

<400> SEQUENCE: 127
caatttctgg ggcagcaaca accatttcca ccacaacaac catatccaca gc 52

<210> SEQ ID NO 128
<211> LENGTH: 53
<212> TYPE: DNA
<213> ORGANISM: Artificial Sequence
<220> FEATURE:
<223> OTHER INFORMATION: fig 1b -74bp (2)

<400> SEQUENCE: 128
caatttctgg ggcagcaaca accatttcca ccacaacaac catatccaca gcc 53

<210> SEQ ID NO 129
<211> LENGTH: 46
<212> TYPE: DNA
<213> ORGANISM: Artificial Sequence
<220> FEATURE:
<223> OTHER INFORMATION: fig 1b -75bp

<400> SEQUENCE: 129
caatatccag ggcagcaaca accatttcca ccacaacaac catatc 46

<210> SEQ ID NO 130
<211> LENGTH: 47
<212> TYPE: DNA
<213> ORGANISM: Artificial Sequence
<220> FEATURE:
<223> OTHER INFORMATION: fig 1b -75bp (2)

<400> SEQUENCE: 130
caatttccag ggcagcaaca accatttcca ccacaacagc catatcc 47

<210> SEQ ID NO 131
<211> LENGTH: 47

-continued

<212> TYPE: DNA
<213> ORGANISM: Artificial Sequence
<220> FEATURE:
<223> OTHER INFORMATION: fig 1b -78bp

<400> SEQUENCE: 131
caatttccag ggcagcaaca accatttcca ccacaacagc catatcc 47

<210> SEQ ID NO 132
<211> LENGTH: 30
<212> TYPE: DNA
<213> ORGANISM: Artificial Sequence
<220> FEATURE:
<223> OTHER INFORMATION: fig 1b -111bp

<400> SEQUENCE: 132
caatatccag ggcaacaaca accatttcca 30

<210> SEQ ID NO 133
<211> LENGTH: 52
<212> TYPE: DNA
<213> ORGANISM: Artificial Sequence
<220> FEATURE:
<223> OTHER INFORMATION: fig 1b -111bp (2)

<400> SEQUENCE: 133
caatttccag ggcagcaaca accatttcca ccacaacaac catatccgca gc 52

<210> SEQ ID NO 134
<211> LENGTH: 50
<212> TYPE: DNA
<213> ORGANISM: Artificial Sequence
<220> FEATURE:
<223> OTHER INFORMATION: fig 1b -111bp (3)

<400> SEQUENCE: 134
caatatccag ggcaacaaca accatttcca ccacaacagc catatccaca 50

<210> SEQ ID NO 135
<211> LENGTH: 53
<212> TYPE: DNA
<213> ORGANISM: Artificial Sequence
<220> FEATURE:
<223> OTHER INFORMATION: fig 1c BW208 wt

<400> SEQUENCE: 135
caaccatatc cacagccgca accatttcca tcacaacaac catatctgca gct 53

<210> SEQ ID NO 136
<211> LENGTH: 89
<212> TYPE: DNA
<213> ORGANISM: Artificial Sequence
<220> FEATURE:
<223> OTHER INFORMATION: fig 1c +36bp

<400> SEQUENCE: 136
caaccatatc cacagccgca acgctttttt taaaattgga tttgtaataa taaaacgcca 60
tttccatcac aacaaccata tctgcagct 89

<210> SEQ ID NO 137
<211> LENGTH: 89
<212> TYPE: DNA
<213> ORGANISM: Artificial Sequence
<220> FEATURE:
<223> OTHER INFORMATION: fig 1c +47/-11bp

<400> SEQUENCE: 137
caaccatatc tgcgttatcc cctgattctg tggataaccg tattaccgcc tttgagtcca 60
tttccatcac aacaaccata tctgcagct 89

<210> SEQ ID NO 138
<211> LENGTH: 89
<212> TYPE: DNA
<213> ORGANISM: Artificial Sequence
<220> FEATURE:
<223> OTHER INFORMATION: fig 1c +48/-12bp

<400> SEQUENCE: 138
caaccatatc tgcgttatcc cctgattctg tggataaccg tattaccgcc tttgagtcca 60
tttccatcac aacaaccata tctgcagct 89

<210> SEQ ID NO 139
<211> LENGTH: 98
<212> TYPE: DNA
<213> ORGANISM: Artificial Sequence
<220> FEATURE:
<223> OTHER INFORMATION: fig 1c +48bp/-3bp

<400> SEQUENCE: 139
caaccatatc cacagccggg taaccgactt gctgccccga gaattatgca gcattttttt 60
ggtgtaccat ttccatcaca acaaccatat ctgcagct 98

<210> SEQ ID NO 140
<211> LENGTH: 104
<212> TYPE: DNA
<213> ORGANISM: Artificial Sequence
<220> FEATURE:
<223> OTHER INFORMATION: fig 1c + 51bp

<400> SEQUENCE: 140
caaccatatc cacagccgca aagaggtttc cgcagggccg gccggcatgg ccagtgtgtg 60
ggattacgac ctccatttcc atcacaacaa ccatatctgc agct 104

<210> SEQ ID NO 141
<211> LENGTH: 102
<212> TYPE: DNA
<213> ORGANISM: Artificial Sequence
<220> FEATURE:
<223> OTHER INFORMATION: fig 1c +83/-6bp

<400> SEQUENCE: 141
caaccatatc cacagccgca agaccatcgc aacccatcta gcccgcgccc tgcaactcgc 60
cggggccgat gttctgccat cacaacaacc atatctgcag ct 102

<210> SEQ ID NO 142
<211> LENGTH: 110
<212> TYPE: DNA
<213> ORGANISM: Artificial Sequence
<220> FEATURE:
<223> OTHER INFORMATION: fig 1c +158bp

<400> SEQUENCE: 142
caaccatatc cacagccgca acaagcaccg ggacaagccc atcagagagc aagcggagaa 60
catcatccat ctcttccacc atttccatca caacaaccat atctgcagct 110

<210> SEQ ID NO 143
<211> LENGTH: 160

<212> TYPE: DNA
<213> ORGANISM: Artificial Sequence
<220> FEATURE:
<223> OTHER INFORMATION: Fig 4a AJ133612

<400> SEQUENCE: 143
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 144
<211> LENGTH: 160
<212> TYPE: DNA
<213> ORGANISM: Artificial Sequence
<220> FEATURE:
<223> OTHER INFORMATION: Fig 4a 1

<400> SEQUENCE: 144
gttagagttc cagtgccaca attgcagcca caaaatccat ctcagcaaca accacaaaag 60
caagttccat tggtacaaca acaacaattt ccagggcagc aacaaccatt tccaccacaa 120
cagccatatc cgcagctgca accatttcca tcacaacaac 160

<210> SEQ ID NO 145
<211> LENGTH: 160
<212> TYPE: DNA
<213> ORGANISM: Artificial Sequence
<220> FEATURE:
<223> OTHER INFORMATION: fig 4a 2

<400> SEQUENCE: 145
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagctgca accatttcca tcacaacaac 160

<210> SEQ ID NO 146
<211> LENGTH: 160
<212> TYPE: DNA
<213> ORGANISM: Artificial Sequence
<220> FEATURE:
<223> OTHER INFORMATION: fig 4a 8

<400> SEQUENCE: 146
gttagagttc cagtgccaca attgcagcca caaaatccat ctcagcaaca accacaaaag 60
caagttccat tggtacaaca acaacaattt ccagggcagc aacaaccatt tccaccacaa 120
cagccatatc cgcagctgca accatttcca tcacaacaac 160

<210> SEQ ID NO 147
<211> LENGTH: 160
<212> TYPE: DNA
<213> ORGANISM: Artificial Sequence
<220> FEATURE:
<223> OTHER INFORMATION: fig 4a 9

<400> SEQUENCE: 147
gttagagttc cagtgccaca accgcagcca caaaatccat ctcagccaca gccacaaggg 60
caagttccat tggtacaaca acaacaattt ccagggcagc aacaacaatt tccaccacaa 120
cagccatatc cgcagccgca accatttcca tcacaacaac 160

<210> SEQ ID NO 148

<211> LENGTH: 146
<212> TYPE: DNA
<213> ORGANISM: Artificial Sequence
<220> FEATURE:
<223> OTHER INFORMATION: fig 4a 11

<400> SEQUENCE: 148
gttagagttc cagtgccaca attgcagcca caaaatccat atcagcaaca gccacaagag 60
caagttccat tggtacaaca acaacaattt ctagggcagc aacaacaatt tccaccacaa 120
caaccatatc tgcagctgca accatt 146

<210> SEQ ID NO 149
<211> LENGTH: 160
<212> TYPE: DNA
<213> ORGANISM: Artificial Sequence
<220> FEATURE:
<223> OTHER INFORMATION: fig 4a 13

<400> SEQUENCE: 149
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacaggcaca accatttcca tcacaacagc 160

<210> SEQ ID NO 150
<211> LENGTH: 160
<212> TYPE: DNA
<213> ORGANISM: Artificial Sequence
<220> FEATURE:
<223> OTHER INFORMATION: fig 4a 15

<400> SEQUENCE: 150
gttagagttc cagtgccaca attgcagcca caaaatccat ctcagcaaca gccacaagag 60
caagttccat tggtacaaca acaaaaattt ctagggcagc aacaacaatt tccaccacaa 120
caaccatatc catagccgcc accatttcca tcacaacaac 160

<210> SEQ ID NO 151
<211> LENGTH: 160
<212> TYPE: DNA
<213> ORGANISM: Artificial Sequence
<220> FEATURE:
<223> OTHER INFORMATION: fig 4a 18

<400> SEQUENCE: 151
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacaggcgca accatttcca tcacaacaac 160

<210> SEQ ID NO 152
<211> LENGTH: 163
<212> TYPE: DNA
<213> ORGANISM: Artificial Sequence
<220> FEATURE:
<223> OTHER INFORMATION: fig 4a 19

<400> SEQUENCE: 152
gttagagttc cagtgccaca attgcagccg caaaatccat ctcaacaaca accacaagag 60
caagttccat tgatgcaaca acaacaacaa tttccagggc agcaagaaca atttccacca 120
caacagccat atccgcatca gcaaccattt ccatcacaac aac 163

<210> SEQ ID NO 153
<211> LENGTH: 160
<212> TYPE: DNA
<213> ORGANISM: Artificial Sequence
<220> FEATURE:
<223> OTHER INFORMATION: fig 4a 20

<400> SEQUENCE: 153
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagctgca accatttcca tcacaacaac 160

<210> SEQ ID NO 154
<211> LENGTH: 160
<212> TYPE: DNA
<213> ORGANISM: Artificial Sequence
<220> FEATURE:
<223> OTHER INFORMATION: fig 4a 21

<400> SEQUENCE: 154
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 155
<211> LENGTH: 160
<212> TYPE: DNA
<213> ORGANISM: Artificial Sequence
<220> FEATURE:
<223> OTHER INFORMATION: fig 4a 22

<400> SEQUENCE: 155
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 156
<211> LENGTH: 160
<212> TYPE: DNA
<213> ORGANISM: Artificial Sequence
<220> FEATURE:
<223> OTHER INFORMATION: fig 4a 23

<400> SEQUENCE: 156
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 157
<211> LENGTH: 149
<212> TYPE: DNA
<213> ORGANISM: Artificial Sequence
<220> FEATURE:
<223> OTHER INFORMATION: fig 4a 26

<400> SEQUENCE: 157
gttagagttc cagtgccaca attgcagcca caaaatccat ctcagcaaca accacaagag 60
caagttccat tggtgcaaca acaacaattt ctagggcagc aataaccatt tcgaccacaa 120
caaccatatc cacagccgca accatttcc 149

<210> SEQ ID NO 158
<211> LENGTH: 160
<212> TYPE: DNA
<213> ORGANISM: Artificial Sequence
<220> FEATURE:
<223> OTHER INFORMATION: fig 4a 27

<400> SEQUENCE: 158
gttagagttc cagtgccaca attgcagcca caaaatccat ctcagcaaca accacaagag 60
caagttccat tggtacaaca acagcaattt ccagggcagc aacaaccatt tccaccacaa 120
caaccatatc cgcagccgca accatttcca tcacaacaac 160

<210> SEQ ID NO 159
<211> LENGTH: 160
<212> TYPE: DNA
<213> ORGANISM: Artificial Sequence
<220> FEATURE:
<223> OTHER INFORMATION: fig 4a 28

<400> SEQUENCE: 159
gttagagttc cagtgccaca attgcagcca caaaatccat ctcagcaaca cccacaagag 60
caagttccgt tggtacaaca acaacaattt ctagggcagc aacaatcatt tccaccacaa 120
caaccatatc cacagccgca accatttcca tcacaacaac 160

<210> SEQ ID NO 160
<211> LENGTH: 160
<212> TYPE: DNA
<213> ORGANISM: Artificial Sequence
<220> FEATURE:
<223> OTHER INFORMATION: fig 4a 32

<400> SEQUENCE: 160
gttagagttc cagtgccaca attgcagcca caaaatccat ctcagcaaca gccacaagag 60
caagttccat tggtacaaca acaaaaattt ctatggcagc aacaacaatt tccaccacaa 120
caaccagatc cacagccgca accatttcca tcacaacaac 160

<210> SEQ ID NO 161
<211> LENGTH: 160
<212> TYPE: DNA
<213> ORGANISM: Artificial Sequence
<220> FEATURE:
<223> OTHER INFORMATION: fig 4a 35

<400> SEQUENCE: 161
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 162
<211> LENGTH: 160
<212> TYPE: DNA
<213> ORGANISM: Artificial Sequence
<220> FEATURE:
<223> OTHER INFORMATION: fig 4a 37

<400> SEQUENCE: 162
gttagagttc cagtgccaca attgcagcca caaaatccat ctcagcaaca accacaagag 60
caagttccat tggtacaaca acagcaattt ccagggcagc aacaaccatt tccaccacaa 120
cagccatatc cgcagccgca accatttcca tcacaacaac 160

<210> SEQ ID NO 163
<211> LENGTH: 160
<212> TYPE: DNA
<213> ORGANISM: Artificial Sequence
<220> FEATURE:
<223> OTHER INFORMATION: fig 4a 40

<400> SEQUENCE: 163
gttagagttc cagtgccaca attgcagcca caaaatccat ctcagcaaca gccacaagag 60
caagttccat tggtacaaca acaaaaattt ctaggggagc aacaacaatt tccaccacaa 120
caactagatc cacagccgca accatttcca tcacaacaac 160

<210> SEQ ID NO 164
<211> LENGTH: 160
<212> TYPE: DNA
<213> ORGANISM: Artificial Sequence
<220> FEATURE:
<223> OTHER INFORMATION: fig 4a 42

<400> SEQUENCE: 164
gttagagttc cagtgccaca attgcagctg caaaatccat ctatgcaaca accacaagag 60
caagttccat tggtgcaaca acaacaattt ctagggcagc aacaaacatt tccaccacaa 120
caaccatatc cacagccgca accatttcca gcacaacaac 160

<210> SEQ ID NO 165
<211> LENGTH: 160
<212> TYPE: DNA
<213> ORGANISM: Artificial Sequence
<220> FEATURE:
<223> OTHER INFORMATION: fig 4a 44

<400> SEQUENCE: 165
gttagagttc cagtgccaca attgcagcca caaaatccat ctcagcaata gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 166
<211> LENGTH: 160
<212> TYPE: DNA
<213> ORGANISM: Artificial Sequence
<220> FEATURE:
<223> OTHER INFORMATION: fig 4a 45

<400> SEQUENCE: 166
gttagagttc cagtgccaca attgcagcca caaaatccat ctcagcaaca gccacaagag 60
caagttccat tggtacaaca acaacaattt ctagggcagc aacaacaatt tccaccacaa 120
caaccatatc cgcagccgca accatttcca tcacaacaac 160

<210> SEQ ID NO 167
<211> LENGTH: 160
<212> TYPE: DNA
<213> ORGANISM: Artificial Sequence
<220> FEATURE:
<223> OTHER INFORMATION: fig 4a 47

<400> SEQUENCE: 167
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacagccaca accatttcca tcacaacagc 160

<210> SEQ ID NO 168
<211> LENGTH: 160
<212> TYPE: DNA
<213> ORGANISM: Artificial Sequence
<220> FEATURE:
<223> OTHER INFORMATION: fig 4a 48

<400> SEQUENCE: 168
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 169
<211> LENGTH: 160
<212> TYPE: DNA
<213> ORGANISM: Artificial Sequence
<220> FEATURE:
<223> OTHER INFORMATION: fig 4a 53

<400> SEQUENCE: 169
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 170
<211> LENGTH: 160
<212> TYPE: DNA
<213> ORGANISM: Artificial Sequence
<220> FEATURE:
<223> OTHER INFORMATION: fig 4a 55

<400> SEQUENCE: 170
gttagagttc cagtgccaca attgcagcca caaaatccat ctcagcaaca gccacaagag 60
caagttccgt tggtacaaca acaacaattt ctagggcagc aacaaccatt tccaccacaa 120
caaccatatc cacagccgca accatttcca tcacaacaac 160

<210> SEQ ID NO 171
<211> LENGTH: 160
<212> TYPE: DNA
<213> ORGANISM: Artificial Sequence
<220> FEATURE:
<223> OTHER INFORMATION: fig 4a 56

<400> SEQUENCE: 171
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 172
<211> LENGTH: 160
<212> TYPE: DNA
<213> ORGANISM: Artificial Sequence
<220> FEATURE:

<223> OTHER INFORMATION: fig 4a 58

<400> SEQUENCE: 172
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 173
<211> LENGTH: 160
<212> TYPE: DNA
<213> ORGANISM: Artificial Sequence
<220> FEATURE:
<223> OTHER INFORMATION: fig 4a 64

<400> SEQUENCE: 173
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 174
<211> LENGTH: 160
<212> TYPE: DNA
<213> ORGANISM: Artificial Sequence
<220> FEATURE:
<223> OTHER INFORMATION: fig 4a 65

<400> SEQUENCE: 174
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 175
<211> LENGTH: 160
<212> TYPE: DNA
<213> ORGANISM: Artificial Sequence
<220> FEATURE:
<223> OTHER INFORMATION: fig 4a 66

<400> SEQUENCE: 175
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 176
<211> LENGTH: 160
<212> TYPE: DNA
<213> ORGANISM: Artificial Sequence
<220> FEATURE:
<223> OTHER INFORMATION: fig 4a 67

<400> SEQUENCE: 176
gttagagttc cagtgccaca attgcagcca caaaatccat ctcagcaaca gccacaagag 60
caagttccat tggtacaaca acaacaattt ctggggcagc aacaaccatt tccaccacaa 120
caaccatatc cacagccgca accatttcca tcacaacaac 160

<210> SEQ ID NO 177
<211> LENGTH: 160
<212> TYPE: DNA
<213> ORGANISM: Artificial Sequence
<220> FEATURE:
<223> OTHER INFORMATION: fig 4a 68

<400> SEQUENCE: 177
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 178
<211> LENGTH: 160
<212> TYPE: DNA
<213> ORGANISM: Artificial Sequence
<220> FEATURE:
<223> OTHER INFORMATION: fig 4a 69

<400> SEQUENCE: 178
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac 160

<210> SEQ ID NO 179
<211> LENGTH: 160
<212> TYPE: DNA
<213> ORGANISM: Artificial Sequence
<220> FEATURE:
<223> OTHER INFORMATION: fig 4a 70

<400> SEQUENCE: 179
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 180
<211> LENGTH: 160
<212> TYPE: DNA
<213> ORGANISM: Artificial Sequence
<220> FEATURE:
<223> OTHER INFORMATION: fig 4a 71

<400> SEQUENCE: 180
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 181
<211> LENGTH: 160
<212> TYPE: DNA
<213> ORGANISM: Artificial Sequence
<220> FEATURE:
<223> OTHER INFORMATION: fig 4a 74

<400> SEQUENCE: 181
gttagagttc cagtgccaca attgcagcca caaaatccat ctcagcaaca accacaagag 60
caagttccat tggtacaaca acagcaattt ccagggcagc aacaaccatt tccaccacaa 120
caaccatatc cgcagccgca accatttcca tcacaacaac 160

<210> SEQ ID NO 182
<211> LENGTH: 160
<212> TYPE: DNA

<213> ORGANISM: Artificial Sequence
<220> FEATURE:
<223> OTHER INFORMATION: fig 4a 75

<400> SEQUENCE: 182
gttagagttc cagtgccaca attgcagcca caaaatccat ctcagcaaca accacaagag 60
caagttccat tggtacaaca acaacaattt ctagggcagc aacaacaatt tccaacacaa 120
caaccatatc tgcagccgca accatttcca tcacaacaac 160

<210> SEQ ID NO 183
<211> LENGTH: 160
<212> TYPE: DNA
<213> ORGANISM: Artificial Sequence
<220> FEATURE:
<223> OTHER INFORMATION: fig 4a 77

<400> SEQUENCE: 183
gttagagttc cagtgccaca attgcagcca caaaatccat ctcagcaaca cccacaagag 60
caagttccgt tggtacaaca acaacaattt ctagggcagc aacaatcatt tccaccacaa 120
caaccatatc cacagccgca accatttcca tcacaacaac 160

<210> SEQ ID NO 184
<211> LENGTH: 160
<212> TYPE: DNA
<213> ORGANISM: Artificial Sequence
<220> FEATURE:
<223> OTHER INFORMATION: fig4a 78

<400> SEQUENCE: 184
gttagagttc cagtgccaca attgcagcca caaaatccat ctcagcaaca gccacaagag 60
caagttccat tggtacaaca acaaaaattt ctatggcagc aacaacaatt tccaccacaa 120
caaccagatc cacagccgca accatttcca tcacaacaac 160

<210> SEQ ID NO 185
<211> LENGTH: 160
<212> TYPE: DNA
<213> ORGANISM: Artificial Sequence
<220> FEATURE:
<223> OTHER INFORMATION: fig 4a 80

<400> SEQUENCE: 185
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaactac 160

<210> SEQ ID NO 186
<211> LENGTH: 160
<212> TYPE: DNA
<213> ORGANISM: Artificial Sequence
<220> FEATURE:
<223> OTHER INFORMATION: fig 4a 81

<400> SEQUENCE: 186
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 187
<211> LENGTH: 160

<212> TYPE: DNA
<213> ORGANISM: Artificial Sequence
<220> FEATURE:
<223> OTHER INFORMATION: fig 4a 84

<400> SEQUENCE: 187
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 188
<211> LENGTH: 160
<212> TYPE: DNA
<213> ORGANISM: Artificial Sequence
<220> FEATURE:
<223> OTHER INFORMATION: fig 4a 85

<400> SEQUENCE: 188
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac 160

<210> SEQ ID NO 189
<211> LENGTH: 159
<212> TYPE: DNA
<213> ORGANISM: Artificial Sequence
<220> FEATURE:
<223> OTHER INFORMATION: Fig 4a contin AJ133612

<400> SEQUENCE: 189
catatctgca gctgcaacca tttccgcagc cgcaactacc atatccgcag ccgcaactac 60
catatccgca gccgcaacta catatccgca gccgcaacca tttcgaccac aacaaccata 120
tccacaatcg caaccacagt attcgcaacc acaacaacc 159

<210> SEQ ID NO 190
<211> LENGTH: 139
<212> TYPE: DNA
<213> ORGANISM: Artificial Sequence
<220> FEATURE:
<223> OTHER INFORMATION: Fig 4a contin 1

<400> SEQUENCE: 190
catatatgca gctgcaacca tttccgcagc cgcaactacc atatccgcag ccgcaactac 60
catatccgca gccgcaacca tttcgaccac aacaatcata tccacaaccg caaccacagt 120
attcgcaacc acaacaacc 139

<210> SEQ ID NO 191
<211> LENGTH: 139
<212> TYPE: DNA
<213> ORGANISM: Artificial Sequence
<220> FEATURE:
<223> OTHER INFORMATION: fig 4a contin 2

<400> SEQUENCE: 191
catatatgca gctgcaacca tttccgcagc cgcaactacc atatccgcag ccgcaactac 60
catatccgca gccgcaacca tttcgaccac aacaatcata tccacaaccg caaccacagt 120
attcgcaacc acaacaacc 139

<210> SEQ ID NO 192

<211> LENGTH: 139
<212> TYPE: DNA
<213> ORGANISM: Artificial Sequence
<220> FEATURE:
<223> OTHER INFORMATION: fig 4a contin 8

<400> SEQUENCE: 192
catatatgca gctgcaacca tttccgcagc cgcaactacc atatccgcag ccgcaactac 60
catatccgca gccgcaacca tttcgaccac aacaatcata tccacaaccg caaccacagt 120
atccgcaacc acaacaacc 139

<210> SEQ ID NO 193
<211> LENGTH: 133
<212> TYPE: DNA
<213> ORGANISM: Artificial Sequence
<220> FEATURE:
<223> OTHER INFORMATION: fig 4 contin 9

<400> SEQUENCE: 193
catatctgca attgcaacca tttccacaac cgcaaccatt tccgccacaa ctaccatatc 60
cgcagccacc accattttca ccacaacaac aatatccaca accgcaacca cagtatccgc 120
aaccacaaca acc 133

<210> SEQ ID NO 194
<211> LENGTH: 96
<212> TYPE: DNA
<213> ORGANISM: Artificial Sequence
<220> FEATURE:
<223> OTHER INFORMATION: fig 4 contin 11

<400> SEQUENCE: 194
ttcgcagccg caactaccat attcgcagcc gcgaccattt cgaccacaac aaccatatcc 60
acaaccgcaa ccacagtatt cgcaaccaca acaacc 96

<210> SEQ ID NO 195
<211> LENGTH: 118
<212> TYPE: DNA
<213> ORGANISM: Artificial Sequence
<220> FEATURE:
<223> OTHER INFORMATION: fig 4 contin 13

<400> SEQUENCE: 195
catatctgca gctgcaacca tttccgcagc cgcaactacc atattcgcag ccacaaccat 60
ttcgaccaca acaaccatat cctcaaccgc aaccacagta ttcgcaacca caacaacc 118

<210> SEQ ID NO 196
<211> LENGTH: 118
<212> TYPE: DNA
<213> ORGANISM: Artificial Sequence
<220> FEATURE:
<223> OTHER INFORMATION: fig 4a contin 15

<400> SEQUENCE: 196
catatctgca gttgcaacca tttccgcagc cgcaactacc atatttgcag ccgcaaccat 60
ttcgaccaca acaaccatat ccacaaccgt aaccacagta ttcgcaacca caacaacc 118

<210> SEQ ID NO 197
<211> LENGTH: 118
<212> TYPE: DNA
<213> ORGANISM: Artificial Sequence
<220> FEATURE:
<223> OTHER INFORMATION: fig 4a contin 18

<400> SEQUENCE: 197
catatctgca gctgcaacca tttccgcagc cgcaactacc atattcgcag ccacaaccat 60
ttcgaccaca acaaccatat ccacaaccgc aaccacagta ttcgcaacca caacaacc 118

<210> SEQ ID NO 198
<211> LENGTH: 115
<212> TYPE: DNA
<213> ORGANISM: Artificial Sequence
<220> FEATURE:
<223> OTHER INFORMATION: fig 4a contin 19

<400> SEQUENCE: 198
catatccgca gccgcaacca tttccgccac aactaccata tccgcagacg caaccatttc 60
caccacaaca accatatcca caaccgcaac cacagtatcc gcaaccacaa caacc 115

<210> SEQ ID NO 199
<211> LENGTH: 139
<212> TYPE: DNA
<213> ORGANISM: Artificial Sequence
<220> FEATURE:
<223> OTHER INFORMATION: fig 4a contin 20

<400> SEQUENCE: 199
catatatgca gctgcaacca tttccgcagc cgcaactacc atatccgcag ccgcaactac 60
catatccgca gccgcaacca tttcgaccac aacaatcata tccacaaccg caaccacagt 120
atccgcaacc acaacaacc 139

<210> SEQ ID NO 200
<211> LENGTH: 139
<212> TYPE: DNA
<213> ORGANISM: Artificial Sequence
<220> FEATURE:
<223> OTHER INFORMATION: fig 4a contin 21

<400> SEQUENCE: 200
catatctgca gctgcagcca tttccgcagc cgcaactacc atatccgcag ccgcatctac 60
catatccgca gccgcaacca tttcgaccac aacaaccata tccacaaccg caaccacagt 120
attcgcaacc acaacaacc 139

<210> SEQ ID NO 201
<211> LENGTH: 139
<212> TYPE: DNA
<213> ORGANISM: Artificial Sequence
<220> FEATURE:
<223> OTHER INFORMATION: fig 4a contin 22

<400> SEQUENCE: 201
catatctgca gctgcaacca tttccgcagc cgcaactacc atatccgcag ccgcaactac 60
catatccgca gccgcaacca tttcgaccac aacaaccata tccacaatcg caaccacagt 120
attcgcaacc acaacaacc 139

<210> SEQ ID NO 202
<211> LENGTH: 139
<212> TYPE: DNA
<213> ORGANISM: Artificial Sequence
<220> FEATURE:
<223> OTHER INFORMATION: fig 4a contin 23

<400> SEQUENCE: 202
catatctgca gctgcaacca tttccgcagc cgcaactacc atatccgcag ccgcaactac 60
catatccgca gccgcaacca tttcgaccac aacaaccata tccacaaccg caaccacagt 120
attcgcaacc acaacaacc 139

<210> SEQ ID NO 203
<211> LENGTH: 90
<212> TYPE: DNA
<213> ORGANISM: Artificial Sequence
<220> FEATURE:
<223> OTHER INFORMATION: fig 4a contin 26

<400> SEQUENCE: 203
tccacaacta ccatgtccgc agccgcaacc atttccacca caacaatcat atccacaacc 60
acaaccacag tatccgcaac cacaacaacc 90

<210> SEQ ID NO 204
<211> LENGTH: 139
<212> TYPE: DNA
<213> ORGANISM: Artificial Sequence
<220> FEATURE:
<223> OTHER INFORMATION: fig 4a contin 27

<400> SEQUENCE: 204
catatctgca gctgcaacca tttccgcagc cgcaactacc atatccgcag ccgcaactac 60
catatccgca gccgcaacca tttcgaccac aacaaccata tccacaaccg caaccacagt 120
attcgcaacc acaacaacc 139

<210> SEQ ID NO 205
<211> LENGTH: 118
<212> TYPE: DNA
<213> ORGANISM: Artificial Sequence
<220> FEATURE:
<223> OTHER INFORMATION: fig 4a contin 28

<400> SEQUENCE: 205
catatctgca gctgcaacca tttccgcagc cgcaactacc atatttgcag ccacaaccat 60
ttcgaccaca acaaccatat ccacaaccgc aaccacaata ttcgcaacca caacaacc 118

<210> SEQ ID NO 206
<211> LENGTH: 118
<212> TYPE: DNA
<213> ORGANISM: Artificial Sequence
<220> FEATURE:
<223> OTHER INFORMATION: fig 4a contin 32

<400> SEQUENCE: 206
catatctgca gttgcaacca tttccgcagc cgcaactacc atattcgtag tcgcaaccat 60
ttcgaccaca acaaccatat ccacgaccgc aaccacagta ttcgcaacca caacaacc 118

<210> SEQ ID NO 207
<211> LENGTH: 118
<212> TYPE: DNA
<213> ORGANISM: Artificial Sequence
<220> FEATURE:
<223> OTHER INFORMATION: fig 4a contin 35

<400> SEQUENCE: 207
catatctgca gctgcaacca ttttcgcagc cgcaactacc atattcgcag ccacaaccat 60
ttcgaccaca acaaccatat ccacaaccgc aaccacagta ttcgcaacca caacaacc 118

<210> SEQ ID NO 208
<211> LENGTH: 118
<212> TYPE: DNA
<213> ORGANISM: Artificial Sequence
<220> FEATURE:
<223> OTHER INFORMATION: fig 4a 37

<400> SEQUENCE: 208
catatctgca gctgcaacca tttccgcagc cgcaactacc atatccgcag ccgcaaccat 60
ttcgaccaca acaaccatat ccacaaccgc aaccacagta ttcgcaacca caacaacc 118

<210> SEQ ID NO 209
<211> LENGTH: 118
<212> TYPE: DNA
<213> ORGANISM: Artificial Sequence
<220> FEATURE:
<223> OTHER INFORMATION: fig 4a contin 40

<400> SEQUENCE: 209
catatctgca gctgcaacca tttccgcagc cgcaactacc atattcgcag ccgcaaccat 60
ttcgaccaca acaaccatat ccacaaccgc aaccacagta ttcgcaacca caacaacc 118

<210> SEQ ID NO 210
<211> LENGTH: 133
<212> TYPE: DNA
<213> ORGANISM: Artificial Sequence
<220> FEATURE:
<223> OTHER INFORMATION: fig 4a contin 42

<400> SEQUENCE: 210
catatccgca gccgcaacca tttccacagc cgcaaccttt tccgccacaa ctaccctatc 60
cgcagccgca accatttccc ccacaacaac catatccaca accgcaaaca caacatccgc 120
aaccacaaca acc 133

<210> SEQ ID NO 211
<211> LENGTH: 118
<212> TYPE: DNA
<213> ORGANISM: Artificial Sequence
<220> FEATURE:
<223> OTHER INFORMATION: fig 4a contin 44

<400> SEQUENCE: 211
catatctgca gctgcaacca tttccgcagc cgcaactagc atattcgcag ccacaaccat 60
tttgaccaca acaaccatat ccacaaccgc aaccacagta ttcgcaacca caacaacc 118

<210> SEQ ID NO 212
<211> LENGTH: 118
<212> TYPE: DNA
<213> ORGANISM: Artificial Sequence
<220> FEATURE:
<223> OTHER INFORMATION: fig 4a contin 45

<400> SEQUENCE: 212
catatctgca gctgcaacca ttttcgcagc cgcaactacc atattcgcag ccgcaaccat 60
ttcgaccaca acaaccatat ccacaaccgc aaccatagta ttcgcaacca caacaacc 118

<210> SEQ ID NO 213
<211> LENGTH: 118
<212> TYPE: DNA
<213> ORGANISM: Artificial Sequence
<220> FEATURE:
<223> OTHER INFORMATION: fig 4a contin 47

<400> SEQUENCE: 213
catatctgca gctgcaacca tttccgcagc cgcaactacc atattcgcag ccacaaccat 60
ttcgaccaca acaaccatat cctcaaccgc aaccacagta ttcgcaacca caacaacc 118

<210> SEQ ID NO 214
<211> LENGTH: 160
<212> TYPE: DNA
<213> ORGANISM: Artificial Sequence
<220> FEATURE:
<223> OTHER INFORMATION: fig 4a contin 48

<400> SEQUENCE: 214
catatctgca gctgcaacca tttccgcagc cgcaactacc atatccgcag ccgcaactac 60
catatccgca gccgcaacta ccatatccgc agccgcaacc atttcgacca caacaaccat 120
atccacaatc gcaaccacag tattcgcaac cacaacaacc 160

<210> SEQ ID NO 215
<211> LENGTH: 118
<212> TYPE: DNA
<213> ORGANISM: Artificial Sequence
<220> FEATURE:
<223> OTHER INFORMATION: fig 4a contin 53

<400> SEQUENCE: 215
catatctgca actgcaacca tttctgcagc cgcaactacc atattcacag ccacaaccat 60
ttcgaccaca acaaccatat ccacaaccgc aaccacagta ttcgcaacca caacaacc 118

<210> SEQ ID NO 216
<211> LENGTH: 118
<212> TYPE: DNA
<213> ORGANISM: Artificial Sequence
<220> FEATURE:
<223> OTHER INFORMATION: fig 4a contin 55

<400> SEQUENCE: 216
catatctgca actgcaacca tttccgcagc cgcaactatc atattcgcag ccacaaccat 60
ttcgaccaca acaaccatat ccacaaccgc aaccacagta ttcgcaacca caacaacc 118

<210> SEQ ID NO 217
<211> LENGTH: 121
<212> TYPE: DNA
<213> ORGANISM: Artificial Sequence
<220> FEATURE:
<223> OTHER INFORMATION: fig 4a contin 56

<400> SEQUENCE: 217
catatctgca gctgcaacca tttccgcagc cgcaactaga cccatattcg cagccacaac 60
catttcgacc acaacaacca tatccacaac cgcaaccaca gtattcgcaa ccacaacaac 120
c 121

<210> SEQ ID NO 218
<211> LENGTH: 118
<212> TYPE: DNA
<213> ORGANISM: Artificial Sequence
<220> FEATURE:
<223> OTHER INFORMATION: fig 4a contin 58

<400> SEQUENCE: 218
catatctgca gctgcaacca tttccacagc cgcaactacc atattcgcca ccacaaccat 60
ttcgaccaca acaaccatat ccacaaccgc aaccacagta ttcgcaacca caacaacc 118

<210> SEQ ID NO 219
<211> LENGTH: 118
<212> TYPE: DNA
<213> ORGANISM: Artificial Sequence
<220> FEATURE:
<223> OTHER INFORMATION: fig 4a contin 64

<400> SEQUENCE: 219
catatctgca actgcaacca tttccgcagc cgcaactacc atattcacag ccacaaccat 60
ttcgaccaca acaaccatat ccacaaccgc aaccacagta ttcgcaacca caacaacc 118

<210> SEQ ID NO 220
<211> LENGTH: 118
<212> TYPE: DNA
<213> ORGANISM: Artificial Sequence
<220> FEATURE:
<223> OTHER INFORMATION: fig 4a contin 65

<400> SEQUENCE: 220
catatctgca gctgcaacca tttccgcagc cgcaactacc atattcacag ccacaaccat 60
ttcgaccaca acaaccatat ccacaaccgc aaccatagta ttcgcaacca caacaacc 118

<210> SEQ ID NO 221
<211> LENGTH: 139
<212> TYPE: DNA
<213> ORGANISM: Artificial Sequence
<220> FEATURE:
<223> OTHER INFORMATION: fig 4a contin 66

<400> SEQUENCE: 221
catatctgca gctgcagcca tttccgcagc cgcaactacc atatccgcag ccgcatctac 60
catatccgca gccgcaacca tttcgaccac aacaaccata tccacaaccg caaccacagt 120
atccgcaacc acaacaacc 139

<210> SEQ ID NO 222
<211> LENGTH: 118
<212> TYPE: DNA
<213> ORGANISM: Artificial Sequence
<220> FEATURE:
<223> OTHER INFORMATION: fig 4a contin 67

<400> SEQUENCE: 222
catatctaca gctgcaacca tttccgtagc tgcaacaacc atattcgcag ccgcaaccat 60
ttcgaccaca acaaccatat ccacaaccgc aaccacagta ttcgcaacca caacaacc 118

<210> SEQ ID NO 223
<211> LENGTH: 139
<212> TYPE: DNA
<213> ORGANISM: Artificial Sequence
<220> FEATURE:
<223> OTHER INFORMATION: fig 4a contin 68

<400> SEQUENCE: 223
catatctgca gctgcaacca tttccgcagc cgcaactacc atatccgcag ccgcaactac 60
catatccgca gccgcaacca tttcgaccac aacaaccata tccacaatcg caaccacagt 120
atccgcaacc acaacaacc 139

<210> SEQ ID NO 224
<211> LENGTH: 139
<212> TYPE: DNA
<213> ORGANISM: Artificial Sequence
<220> FEATURE:
<223> OTHER INFORMATION: fig 4a contin 69

<400> SEQUENCE: 224
catatctgca gctgcaacca tttccgcagc cgcaactacc atatccgcag ccgcaactac 60
catatccgca gccgcaacca tttcgaccac aacaaccata tccacaaccg caaccacagt 120
atccgcaacc acaacaacc 139

<210> SEQ ID NO 225
<211> LENGTH: 118
<212> TYPE: DNA
<213> ORGANISM: Artificial Sequence
<220> FEATURE:
<223> OTHER INFORMATION: fig 4a contin 70

<400> SEQUENCE: 225
catatctgca actgcaacca tttccgcagc cgcaactacc atattcgcaa ccacaaccat 60
ttcgaccaca acaaccatat ccacaaccgc aaccacagta ttcgcaacca caacaacc 118

<210> SEQ ID NO 226
<211> LENGTH: 118
<212> TYPE: DNA
<213> ORGANISM: Artificial Sequence
<220> FEATURE:
<223> OTHER INFORMATION: fig 4a contin 71

<400> SEQUENCE: 226
catatctgca gctgcaacca tttccacagc cgcaactacc atattcgcaa ccacaaccat 60
ttcgaccaca acaaccatat ccacaaccgc aaccacagta ttcgcaacca caacaacc 118

<210> SEQ ID NO 227
<211> LENGTH: 139
<212> TYPE: DNA
<213> ORGANISM: Artificial Sequence
<220> FEATURE:
<223> OTHER INFORMATION: fig 4a contin 74

<400> SEQUENCE: 227
catatctgca gctgcaacca tttccgcagc cgcaactacc atatccgcag ccgcaactac 60
catatccgca gccgcaacca tttcgaccac aacaaccata tccacaaccg caaccacagt 120
atccgcaacc acaacaacc 139

<210> SEQ ID NO 228
<211> LENGTH: 120
<212> TYPE: DNA
<213> ORGANISM: Artificial Sequence
<220> FEATURE:
<223> OTHER INFORMATION: fig 4a contin 75

<400> SEQUENCE: 228
catatctgca gctgcaacca ttttcgcagc cgcaactacc catattcgca gccgcaacca 60
tttcgaccac aacaaccata tccacaaccg caaccacagt attcgcaacc acaacaacca 120

<210> SEQ ID NO 229
<211> LENGTH: 118
<212> TYPE: DNA
<213> ORGANISM: Artificial Sequence
<220> FEATURE:
<223> OTHER INFORMATION: fig 4a contin 77

<400> SEQUENCE: 229
catatctgca gctgcaacca tttccgcagc cgcaactacc atatttgcag ccacaaccat 60
ttcgaccaca acaaccatat ccacaaccgc aaccacaata tccgcaacca caacaacc 118

<210> SEQ ID NO 230
<211> LENGTH: 118
<212> TYPE: DNA
<213> ORGANISM: Artificial Sequence
<220> FEATURE:
<223> OTHER INFORMATION: fig 4a contin 78

<400> SEQUENCE: 230
catatctgca gttgcaacca tttccgcagc cgcaactacc atattcgtag tcgcaaccat 60
ttcgaccaca acaaccatat ccacgaccgc aaccacagta tccgcaacca caacaacc 118

<210> SEQ ID NO 231
<211> LENGTH: 118
<212> TYPE: DNA
<213> ORGANISM: Artificial Sequence
<220> FEATURE:
<223> OTHER INFORMATION: fig 4a contin 80

<400> SEQUENCE: 231
catatctgca gctgcaacca tttccgcagc cgcaactacc atattcacag ccacaaccat 60
ttcgaccaca acaaccatat ccacaaccgc aaccacagta ttcgcaacca caacaacc 118

<210> SEQ ID NO 232
<211> LENGTH: 61
<212> TYPE: DNA
<213> ORGANISM: Artificial Sequence
<220> FEATURE:
<223> OTHER INFORMATION: fig 4a contin 81

<400> SEQUENCE: 232
catatctgca actgcaacca tttccgcagc cgcaactacc atattcgcaa ccacaacaac 60
c 61

<210> SEQ ID NO 233
<211> LENGTH: 61
<212> TYPE: DNA
<213> ORGANISM: Artificial Sequence
<220> FEATURE:
<223> OTHER INFORMATION: fig 4a contin 84

<400> SEQUENCE: 233
catatctgca gctgcaacca tttccacagc cgcaactacc atattcgcaa ccacaacaac 60
c 61

<210> SEQ ID NO 234

<211> LENGTH: 118
<212> TYPE: DNA
<213> ORGANISM: Artificial Sequence
<220> FEATURE:
<223> OTHER INFORMATION: fig 4a contin 85

<400> SEQUENCE: 234
catatctgca gctgcaacca ttttcgcagc cgcaactacc atattcgcag ccacaaccat 60
ttcgaccaca acaaccatat ccacaaccgc aaccacagta tccgcaacca caacaacc 118

<210> SEQ ID NO 235
<211> LENGTH: 159
<212> TYPE: DNA
<213> ORGANISM: Artificial Sequence
<220> FEATURE:
<223> OTHER INFORMATION: fig 4b AJ133612

<400> SEQUENCE: 235
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaa 159

<210> SEQ ID NO 236
<211> LENGTH: 147
<212> TYPE: DNA
<213> ORGANISM: Artificial Sequence
<220> FEATURE:
<223> OTHER INFORMATION: fig 4b 1

<400> SEQUENCE: 236
gttagagttc cagtgccaca attgcagcca caaaatccat ctcagcaaca accacaagag 60
caagttccat tggtgcaaca acaacaattt ctagggcagc aacaacaaca atttccaggg 120
caacaacaac catttccacc acaacag 147

<210> SEQ ID NO 237
<211> LENGTH: 159
<212> TYPE: DNA
<213> ORGANISM: Artificial Sequence
<220> FEATURE:
<223> OTHER INFORMATION: fig 4b 2

<400> SEQUENCE: 237
gttagagttc cagtgccaca attgcagcca caaaatccat ctcagcaaca cccacaagag 60
caagttccgt tggtacaaca acaacaattt ctagggcagc aacaatcatt tccaccacaa 120
caaccatatc cacagccgca accatttcca tcacaacaa 159

<210> SEQ ID NO 238
<211> LENGTH: 123
<212> TYPE: DNA
<213> ORGANISM: Artificial Sequence
<220> FEATURE:
<223> OTHER INFORMATION: fig 4b 3

<400> SEQUENCE: 238
gttagagttc cagtgccaca attgcagcca caaaatccat ctcagcaaca accacaagag 60
caagttccat tggtgcaaca acaacaattt ctagggcagc aataaccatt tcgaccacaa 120
caa 123

<210> SEQ ID NO 239
<211> LENGTH: 159

<212> TYPE: DNA
<213> ORGANISM: Artificial Sequence
<220> FEATURE:
<223> OTHER INFORMATION: fig 4b 4

<400> SEQUENCE: 239
gttagagttc cagtgccaca attgcagcca caaaatccat ctcagcaaca accacaagag 60
caagttccat tggtacaaca acagcaattt ccagggcagc aacaaccatt tccaccacaa 120
cagccatatc cgcagccgca accatttcca tcacaacaa 159

<210> SEQ ID NO 240
<211> LENGTH: 159
<212> TYPE: DNA
<213> ORGANISM: Artificial Sequence
<220> FEATURE:
<223> OTHER INFORMATION: fig 4b 5

<400> SEQUENCE: 240
gttagagttc cagtgccaca attgtagccg caaaatccat ctcaacaacg accacaatag 60
taatttccgt tggtgcaaca acaacaattt ccagggcagc aacaaccatt cccaccacaa 120
cagccatatc cgcagccgca accgtttctg tcacaacaa 159

<210> SEQ ID NO 241
<211> LENGTH: 147
<212> TYPE: DNA
<213> ORGANISM: Artificial Sequence
<220> FEATURE:
<223> OTHER INFORMATION: fig 4b 6

<400> SEQUENCE: 241
gttagagttc cagtgccaca attgcagcca caaaatccat ctcagcaaca accacaagag 60
caagttctat tggtgcaaca acaaccattt ctagggcagc aacaacaaca atttccaggg 120
cagcaataac catttcgacc acaacag 147

<210> SEQ ID NO 242
<211> LENGTH: 159
<212> TYPE: DNA
<213> ORGANISM: Artificial Sequence
<220> FEATURE:
<223> OTHER INFORMATION: fig 4b 7

<400> SEQUENCE: 242
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 243
<211> LENGTH: 147
<212> TYPE: DNA
<213> ORGANISM: Artificial Sequence
<220> FEATURE:
<223> OTHER INFORMATION: fig 4b 8

<400> SEQUENCE: 243
gttagagttc cagtgccaca attgcaacca gaaaatccat ctcagcaaca accacaagag 60
caagttccat tggtgcaaca acaacaattt ctagggcagc aacaacaaca atttccaggg 120
cagcaataac catttcgacc acaacag 147

<210> SEQ ID NO 244

<211> LENGTH: 147
<212> TYPE: DNA
<213> ORGANISM: Artificial Sequence
<220> FEATURE:
<223> OTHER INFORMATION: fig 4b 9

<400> SEQUENCE: 244
gttagagttc cagtgccaca attgcagcca caaaatccat ctcagcaaca accacaagag 60
caagttccat tggtgcaaca acaacaattt ctagggcagt aacaacaaca atttccaggg 120
caacaacaac catttccacc ataacag 147

<210> SEQ ID NO 245
<211> LENGTH: 162
<212> TYPE: DNA
<213> ORGANISM: Artificial Sequence
<220> FEATURE:
<223> OTHER INFORMATION: fig 4b 10

<400> SEQUENCE: 245
gttagagttc cagtgccaca attgcagccg caaaatccat ctcaacaaca accacaagag 60
caagttccat tgatgcaaca acaacaacaa tttccagggc agcaagaaca atttccacca 120
caacagccat atccgcatca gcaaccattt ccatcacaac aa 162

<210> SEQ ID NO 246
<211> LENGTH: 159
<212> TYPE: DNA
<213> ORGANISM: Artificial Sequence
<220> FEATURE:
<223> OTHER INFORMATION: fig 4b 11

<400> SEQUENCE: 246
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacaggcaca accatttcca tcacaacag 159

<210> SEQ ID NO 247
<211> LENGTH: 159
<212> TYPE: DNA
<213> ORGANISM: Artificial Sequence
<220> FEATURE:
<223> OTHER INFORMATION: fig 4b 12

<400> SEQUENCE: 247
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacagccaca accatttcca tcacaacag 159

<210> SEQ ID NO 248
<211> LENGTH: 159
<212> TYPE: DNA
<213> ORGANISM: Artificial Sequence
<220> FEATURE:
<223> OTHER INFORMATION: fig 4b 13

<400> SEQUENCE: 248
gttagagttc cagtgccaca attgcagcca caaaatccat ctcagcaaca gccacaagag 60
caagttccat tggtacaaca acaaaaattt ctagggcagc aacaacaatt tccaccacaa 120
caaccatatc catagccgcc accatttcca tcacaacaa 159

<210> SEQ ID NO 249
<211> LENGTH: 147
<212> TYPE: DNA
<213> ORGANISM: Artificial Sequence
<220> FEATURE:
<223> OTHER INFORMATION: fig 4b 14

<400> SEQUENCE: 249
gttagagttc cagtgccaca attgcagcca caaaatccat ctcagcaaca accacaagag 60
caagttccat tggtgcaaca acaacaattt ctagggcagc aacaacaaca ttttccaggg 120
caacaacaac catttccacc acaacag 147

<210> SEQ ID NO 250
<211> LENGTH: 159
<212> TYPE: DNA
<213> ORGANISM: Artificial Sequence
<220> FEATURE:
<223> OTHER INFORMATION: fig 4b 15

<400> SEQUENCE: 250
gttagagttc cagtgccaca attgcagcca taaaatccat ctcagcaaca gccacaagag 60
caagttccat tggtacaaca acaacaattt ctagggcagc aacaaccatt tccaccacaa 120
caaccatatc cacaggcgca accatttcca tcacaacaa 159

<210> SEQ ID NO 251
<211> LENGTH: 146
<212> TYPE: DNA
<213> ORGANISM: Artificial Sequence
<220> FEATURE:
<223> OTHER INFORMATION: fig 4b 16

<400> SEQUENCE: 251
gttagagttc cagtgccaca attgcagcca caaaatccat atcagcaaca gccacaagag 60
caagttccat tggtacaaca acaacaattt ctagggcagc aacaacaatt tccaccacaa 120
caaccatatc tgcagctgca accatt 146

<210> SEQ ID NO 252
<211> LENGTH: 159
<212> TYPE: DNA
<213> ORGANISM: Artificial Sequence
<220> FEATURE:
<223> OTHER INFORMATION: fig 4b 17

<400> SEQUENCE: 252
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagctgca accatttcca tcacaacaa 159

<210> SEQ ID NO 253
<211> LENGTH: 159
<212> TYPE: DNA
<213> ORGANISM: Artificial Sequence
<220> FEATURE:
<223> OTHER INFORMATION: fig 4b 18

<400> SEQUENCE: 253
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 254
<211> LENGTH: 159
<212> TYPE: DNA
<213> ORGANISM: Artificial Sequence
<220> FEATURE:
<223> OTHER INFORMATION: fig 4b 19

<400> SEQUENCE: 254
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 255
<211> LENGTH: 159
<212> TYPE: DNA
<213> ORGANISM: Artificial Sequence
<220> FEATURE:
<223> OTHER INFORMATION: fig 4b 20

<400> SEQUENCE: 255
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 256
<211> LENGTH: 159
<212> TYPE: DNA
<213> ORGANISM: Artificial Sequence
<220> FEATURE:
<223> OTHER INFORMATION: fig 4b 21

<400> SEQUENCE: 256
gttagagttc cagtgccaca attgcagcca caaaatccat ctcagcaaca gccacaagag 60
caagttccat tggtacaaca ccaacaattt ctagggcagc aacaaccatt tccaccacaa 120
caaccatatc cacagccgca accatttcca tcacaacaa 159

<210> SEQ ID NO 257
<211> LENGTH: 159
<212> TYPE: DNA
<213> ORGANISM: Artificial Sequence
<220> FEATURE:
<223> OTHER INFORMATION: fig 4b 22

<400> SEQUENCE: 257
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaa 159

<210> SEQ ID NO 258
<211> LENGTH: 159
<212> TYPE: DNA
<213> ORGANISM: Artificial Sequence
<220> FEATURE:
<223> OTHER INFORMATION: fig 4b 23

<400> SEQUENCE: 258
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 259
<211> LENGTH: 159
<212> TYPE: DNA
<213> ORGANISM: Artificial Sequence
<220> FEATURE:
<223> OTHER INFORMATION: fig 4b 24

<400> SEQUENCE: 259
gttagagttc cagtgccaca attgcagcca caaaatccat ctcagcaaca gccacaagag 60
caagttccat tggtacaaca acaaaaattt ctatggcagc aacaacaatt tccaccacaa 120
caaccagatc cacagccgca accatttcca tcacaacaa 159

<210> SEQ ID NO 260
<211> LENGTH: 159
<212> TYPE: DNA
<213> ORGANISM: Artificial Sequence
<220> FEATURE:
<223> OTHER INFORMATION: fig 4b 25

<400> SEQUENCE: 260
gttagagttc cagtgccaca attgcagcca caaaatccat ctcagcaaca accacaagag 60
caagttccat tggtacaaca acagcaattt ccagggcagc aacaaccatt tccaccacaa 120
caaccatatc cgcagccgca accatttcca tcacaacaa 159

<210> SEQ ID NO 261
<211> LENGTH: 159
<212> TYPE: DNA
<213> ORGANISM: Artificial Sequence
<220> FEATURE:
<223> OTHER INFORMATION: fig 4b 26

<400> SEQUENCE: 261
gttagagttc cagtgccaca accgcagcca caaaatccat ctcagccaca gccacaaggg 60
caagttccat tggtacaaca acaacaattt ctagggcagc aacaacaatt tccaccacaa 120
cagccatatc cgcagccgca accatttcca tcacaacaa 159

<210> SEQ ID NO 262
<211> LENGTH: 159
<212> TYPE: DNA
<213> ORGANISM: Artificial Sequence
<220> FEATURE:
<223> OTHER INFORMATION: fig 4b 27

<400> SEQUENCE: 262
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 263
<211> LENGTH: 159
<212> TYPE: DNA
<213> ORGANISM: Artificial Sequence
<220> FEATURE:
<223> OTHER INFORMATION: fig 4b 28

<400> SEQUENCE: 263
gttagagttc cagtgccaca attgcagcca caaaatccat ctcagcaaca accacaaaag 60
caagttccat tggtgcaaca acaacaattt ctagggcagc aacaaccatt tccaccacaa 120
cagccatatc cgcagccgca accatttcca tcacaacaa 159

<210> SEQ ID NO 264
<211> LENGTH: 159
<212> TYPE: DNA
<213> ORGANISM: Artificial Sequence
<220> FEATURE:
<223> OTHER INFORMATION: fig 4b 30

<400> SEQUENCE: 264
gttagagttc cagtgccaca attgcagcca caaaatccat ctcagcaaca gccacaagag 60
caagttccat tggtacaaca acaaaaattt ctaggggagc aacaacaatt tccaccacaa 120
caactagatc cacagccgca accatttcca tcacaacaa 159

<210> SEQ ID NO 265
<211> LENGTH: 159
<212> TYPE: DNA
<213> ORGANISM: Artificial Sequence
<220> FEATURE:
<223> OTHER INFORMATION: fig 4b 31

<400> SEQUENCE: 265
gttagagttc cagtgccaca attgcagccg caaaatccat ctcagcaaca accacaagag 60
caagttccgt tggtgcaaca acaacaatat ccagggcagc aacaaccatt tccaccacaa 120
caaccatatc cgcagccgca accatttcca tcacaacaa 159

<210> SEQ ID NO 266
<211> LENGTH: 159
<212> TYPE: DNA
<213> ORGANISM: Artificial Sequence
<220> FEATURE:
<223> OTHER INFORMATION: fig 4b 32

<400> SEQUENCE: 266
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 267
<211> LENGTH: 159
<212> TYPE: DNA
<213> ORGANISM: Artificial Sequence
<220> FEATURE:
<223> OTHER INFORMATION: fig 4b 33

<400> SEQUENCE: 267
gttagagttc cagtgccaca attgcagcca caaaatccat ctcagcaaca accacaaaag 60
caagttccat tggtacaaca acaacaattt ccagggcagc aacaaccatt tccaccacaa 120
cagccatatc cgcagctgca accatttcca tcacaacaa 159

<210> SEQ ID NO 268
<211> LENGTH: 159
<212> TYPE: DNA
<213> ORGANISM: Artificial Sequence
<220> FEATURE:

<223> OTHER INFORMATION: fig 4b 34

<400> SEQUENCE: 268
gttagagttc cagtgccaca attgcagcca caaaatccat ctcagcaaca gccacaagag 60
caagttccat tggtacaaca acaacaattt ctggggcagc aacaaccatt tccaccacaa 120
caaccatatc cacagccgca accatttcca tcacaacaa 159

<210> SEQ ID NO 269
<211> LENGTH: 159
<212> TYPE: DNA
<213> ORGANISM: Artificial Sequence
<220> FEATURE:
<223> OTHER INFORMATION: fig 4b 35

<400> SEQUENCE: 269
gttagagttc cagtgccaca attgcagcca caaaatccat ctcagcaaca gccacaagag 60
caagttccat tggtacaaca acaacaattt ctagggcagc aacaacaatt tccaccacaa 120
caaccatatc cgcagccgca accatttcca tcacaacaa 159

<210> SEQ ID NO 270
<211> LENGTH: 159
<212> TYPE: DNA
<213> ORGANISM: Artificial Sequence
<220> FEATURE:
<223> OTHER INFORMATION: fig 2b 36

<400> SEQUENCE: 270
gttagagttc cagtgccaca attgcagcca caaaatccat ctcagcaata gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 271
<211> LENGTH: 159
<212> TYPE: DNA
<213> ORGANISM: Artificial Sequence
<220> FEATURE:
<223> OTHER INFORMATION: fig 4b 37

<400> SEQUENCE: 271
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagctgca accatttcca tcacaacaa 159

<210> SEQ ID NO 272
<211> LENGTH: 159
<212> TYPE: DNA
<213> ORGANISM: Artificial Sequence
<220> FEATURE:
<223> OTHER INFORMATION: fig 4b 38

<400> SEQUENCE: 272
gttagagttc cagtgccaca attgcagcca caaaatccat ctcagcaaca gccacaagag 60
caagttccgt tggtacaaca acaacaattt ctagggcagc aacaaccatt tccaccacaa 120
caaccatatc cacagccgca accatttcca tcacaacaa 159

<210> SEQ ID NO 273
<211> LENGTH: 159
<212> TYPE: DNA
<213> ORGANISM: Artificial Sequence
<220> FEATURE:
<223> OTHER INFORMATION: fig 4b 40

<400> SEQUENCE: 273
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacta 159

<210> SEQ ID NO 274
<211> LENGTH: 159
<212> TYPE: DNA
<213> ORGANISM: Artificial Sequence
<220> FEATURE:
<223> OTHER INFORMATION: fig 4b 41

<400> SEQUENCE: 274
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaa 159

<210> SEQ ID NO 275
<211> LENGTH: 159
<212> TYPE: DNA
<213> ORGANISM: Artificial Sequence
<220> FEATURE:
<223> OTHER INFORMATION: fig 4b 42

<400> SEQUENCE: 275
gttagagttc cagtgccaca attgcagccg caaaatccat ctcagcaaca accacaagag 60
caagttccgt tggtgcaaca actacaatat ccagggcaac aacaaccatt tccaccacaa 120
cagccatatc cgcagccgca accatttcca tcacaacaa 159

<210> SEQ ID NO 276
<211> LENGTH: 159
<212> TYPE: DNA
<213> ORGANISM: Artificial Sequence
<220> FEATURE:
<223> OTHER INFORMATION: fig 4b 43

<400> SEQUENCE: 276
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 277
<211> LENGTH: 159
<212> TYPE: DNA
<213> ORGANISM: Artificial Sequence
<220> FEATURE:
<223> OTHER INFORMATION: fig 4b 44

<400> SEQUENCE: 277
gttagagttc cagtgccaca attgcagcta caaaatccat ctcagcaaca gccacaagag 60
caagttccat tggtacaaga acaacaattt ccagggcagc aacaaccatt tccaccacaa 120
cagccatatc cgcagccgca accatttcca tcacaacaa 159

<210> SEQ ID NO 278
<211> LENGTH: 159
<212> TYPE: DNA

<213> ORGANISM: Artificial Sequence
<220> FEATURE:
<223> OTHER INFORMATION: fig 4b 45

<400> SEQUENCE: 278
gttagagttc cagtgccaca attgcagcca caaaatccat ctcagcaaca cccacaagag 60
caagttccgt tggtacaaca acaacaattt ctagggcagc aacaatcatt tccaccacaa 120
caaccatatc cacagccgca accatttcca tcacaacaa 159

<210> SEQ ID NO 279
<211> LENGTH: 159
<212> TYPE: DNA
<213> ORGANISM: Artificial Sequence
<220> FEATURE:
<223> OTHER INFORMATION: fig 4b 46

<400> SEQUENCE: 279
gttagagttc cagtgccaca attgcagcca caaaatccat ctcagcaaca accacaagag 60
caagttccat tggtacaaca acagcaattt ccagggcagc aacaaccatt tccaccacaa 120
cagccatatc cgcagccgca accatttcca tcacaacaa 159

<210> SEQ ID NO 280
<211> LENGTH: 159
<212> TYPE: DNA
<213> ORGANISM: Artificial Sequence
<220> FEATURE:
<223> OTHER INFORMATION: fig 4b 47

<400> SEQUENCE: 280
gttagagttc cagtgccaca attgcagccg caaaatccat ctcagcaaca accacaagag 60
caagtttcat tggtgcaaca acaacaattt ccagggcagc aacaaccatt tccaccacaa 120
cagccatatc cgcagccgca accatttcca tcacaacaa 159

<210> SEQ ID NO 281
<211> LENGTH: 159
<212> TYPE: DNA
<213> ORGANISM: Artificial Sequence
<220> FEATURE:
<223> OTHER INFORMATION: fig 4b 48

<400> SEQUENCE: 281
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaa 159

<210> SEQ ID NO 282
<211> LENGTH: 159
<212> TYPE: DNA
<213> ORGANISM: Artificial Sequence
<220> FEATURE:
<223> OTHER INFORMATION: fig 4b 49

<400> SEQUENCE: 282
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaa 159

<210> SEQ ID NO 283
<211> LENGTH: 159

<212> TYPE: DNA
<213> ORGANISM: Artificial Sequence
<220> FEATURE:
<223> OTHER INFORMATION: fig 4b 52

<400> SEQUENCE: 283
gttagagttc cagtgccaca attgcagcca caaaatccat ctcagcaaca accacaagag 60
caagtttcat tggtacaaca acaacaattt ccagggcagc aacaaccatt tccaccacaa 120
cagccatatc cgcagccgca accatttcca tcacaacaa 159

<210> SEQ ID NO 284
<211> LENGTH: 146
<212> TYPE: DNA
<213> ORGANISM: Artificial Sequence
<220> FEATURE:
<223> OTHER INFORMATION: fig 4b 53

<400> SEQUENCE: 284
gttagagttc cagtgccaca attgcagcca caaaatccat atcagcaaca gccacaagag 60
caagttccat tggtacaaca acaacaattt ctagggcagc aacaacaatt tccaccacaa 120
caaccatatc tgcagctgca accatt 146

<210> SEQ ID NO 285
<211> LENGTH: 159
<212> TYPE: DNA
<213> ORGANISM: Artificial Sequence
<220> FEATURE:
<223> OTHER INFORMATION: fig 4b 59

<400> SEQUENCE: 285
gttagagttc cagtgccaca attgcagcca caaaatccat ctcagcaaca accacaagag 60
caagttccat tggtacaaca acaacaattt ctagggcagc aacaacaatt tccaacacaa 120
caaccatatc tgcagccgca accatttcca tcacaacaa 159

<210> SEQ ID NO 286
<211> LENGTH: 159
<212> TYPE: DNA
<213> ORGANISM: Artificial Sequence
<220> FEATURE:
<223> OTHER INFORMATION: fig 4b 60

<400> SEQUENCE: 286
gttagagttc cagtgccaca attgcagcca caaaatccat ctcagcaaca gccacaagag 60
caagttccat tggtacaaca acaaaaattt ctagggcagc aacaacaatt tccaccacaa 120
caaccatatc catagccgcc accatttcca tcacaacaa 159

<210> SEQ ID NO 287
<211> LENGTH: 159
<212> TYPE: DNA
<213> ORGANISM: Artificial Sequence
<220> FEATURE:
<223> OTHER INFORMATION: fig 4b 68

<400> SEQUENCE: 287
gttagagttc cagtgccaca attgcagcca caaaatccat ctcagcaaca gccacaagag 60
caagttccat tggtacaaca acaaaaattt ctagggtagc aacaacaatt tccaccacaa 120
caacaagatc cacagccgca accatttcca tcacaacaa 159

<210> SEQ ID NO 288

<211> LENGTH: 161
<212> TYPE: DNA
<213> ORGANISM: Artificial Sequence
<220> FEATURE:
<223> OTHER INFORMATION: fig 4b contin AJ133612

<400> SEQUENCE: 288
ccatatctgc agctgcaacc atttccgcag ccgcaactac catatccgca gccgcaacta 60
ccatatccgc agccgcaact accatatccg cagccgcaac catttcgacc acaacaacca 120
tatccacaat cgcaaccaca gtattcgcaa ccacaacaac c 161

<210> SEQ ID NO 289
<211> LENGTH: 116
<212> TYPE: DNA
<213> ORGANISM: Artificial Sequence
<220> FEATURE:
<223> OTHER INFORMATION: fig 4b contin 1

<400> SEQUENCE: 289
ccatatccgc agccgcaacc atttctgcca caactaccat atccgcagcc gcaaccattt 60
ccaccacaac aatcatatcc acaaccacaa ccacaatatc cgcaaccaca acaacc 116

<210> SEQ ID NO 290
<211> LENGTH: 119
<212> TYPE: DNA
<213> ORGANISM: Artificial Sequence
<220> FEATURE:
<223> OTHER INFORMATION: fig 4b contin 2

<400> SEQUENCE: 290
ccatatctgc agctgcaacc atttccgcag ccgcaactac catatttgca gccacaacca 60
tttcgaccac aacaaccata tccacaaccg caaccacaat attcgcaacc acaacaacc 119

<210> SEQ ID NO 291
<211> LENGTH: 116
<212> TYPE: DNA
<213> ORGANISM: Artificial Sequence
<220> FEATURE:
<223> OTHER INFORMATION: fig 4b contin 3

<400> SEQUENCE: 291
ccatatccac agccgcaacc atttcctcca caactaccat gtccgcagcc gcaaccattt 60
ccaccacaac aatcatatcc acaaccacaa ccacagtatc cgcaaccaca acaacc 116

<210> SEQ ID NO 292
<211> LENGTH: 119
<212> TYPE: DNA
<213> ORGANISM: Artificial Sequence
<220> FEATURE:
<223> OTHER INFORMATION: fig 4b contin 4

<400> SEQUENCE: 292
ccatatctgc agctgcaacc atttccgcag ccgcaactac catatccgca gccgcaacca 60
tttcgaccac aacaaccata tccacaaccg caaccacagt attcgcaacc acaacaacc 119

<210> SEQ ID NO 293
<211> LENGTH: 116
<212> TYPE: DNA
<213> ORGANISM: Artificial Sequence
<220> FEATURE:
<223> OTHER INFORMATION: fig 4b contin 5

<400> SEQUENCE: 293
ccatattcgc aaccgtaacc atttccgcca caactaccat atccacaagc gcaaccattt 60
ccaacacaac aaccatatcc acaaccgcaa ccacagtatc cgcaaccaca acaacc 116

<210> SEQ ID NO 294
<211> LENGTH: 116
<212> TYPE: DNA
<213> ORGANISM: Artificial Sequence
<220> FEATURE:
<223> OTHER INFORMATION: fig 4b contin 6

<400> SEQUENCE: 294
ccatatccgc agccgcaact atttcctcca aaactaccat atccgcagcc gcaaccattt 60
acaccacatc aatcatatcc acaaccacaa ccacagtatc cgcaaccaca acaacc 116

<210> SEQ ID NO 295
<211> LENGTH: 119
<212> TYPE: DNA
<213> ORGANISM: Artificial Sequence
<220> FEATURE:
<223> OTHER INFORMATION: fig 4b contin 7

<400> SEQUENCE: 295
ccatatctgc agctgcaacc attttcgcag ccgcaactac catattcgca gccacaacca 60
tttcgaccac aacaaccata tccacaaccg caaccacagt attcgcaacc acaacaacc 119

<210> SEQ ID NO 296
<211> LENGTH: 116
<212> TYPE: DNA
<213> ORGANISM: Artificial Sequence
<220> FEATURE:
<223> OTHER INFORMATION: fig 4b contin 8

<400> SEQUENCE: 296
ccatatccgc agccgcaacc atttcctcca caactaccat gtccgcaacc gcaaccattt 60
ccaccacaac aatcatatcc acaaccacaa ccacagtatc cgcaaccaca acaacc 116

<210> SEQ ID NO 297
<211> LENGTH: 116
<212> TYPE: DNA
<213> ORGANISM: Artificial Sequence
<220> FEATURE:
<223> OTHER INFORMATION: fig 4b contin 9

<400> SEQUENCE: 297
ccatatccgc agccgcaacc atttctgcca caactaccat atccgcagcc gcaaccattt 60
ccaccacaac aatcatatcc acaaccacaa ccacaatatc cgcaaccaca acaacc 116

<210> SEQ ID NO 298
<211> LENGTH: 116
<212> TYPE: DNA
<213> ORGANISM: Artificial Sequence
<220> FEATURE:
<223> OTHER INFORMATION: fig 4b contin 10

<400> SEQUENCE: 298
ccatatccgc agccgcaacc atttccgcca caactaccat atccgcagac gcaaccattt 60
ccaccacaac aaccatatcc acaaccgcaa ccacagtatc cgcaaccaca acaacc 116

<210> SEQ ID NO 299

<211> LENGTH: 119
<212> TYPE: DNA
<213> ORGANISM: Artificial Sequence
<220> FEATURE:
<223> OTHER INFORMATION: fig 4b contin 11

<400> SEQUENCE: 299
ccatatctgc agctgcaacc atttccgcag ccgcaactac catattcgca gccacaacca 60
tttcgaccac aacaaccata tcctcaaccg caaccacagt attcgcaacc acaacaacc 119

<210> SEQ ID NO 300
<211> LENGTH: 119
<212> TYPE: DNA
<213> ORGANISM: Artificial Sequence
<220> FEATURE:
<223> OTHER INFORMATION: fig 4b contin 12

<400> SEQUENCE: 300
ccatatctgc agctgcaacc atttccgcag ccgcaactac catattcgca gccacaacca 60
tttcgaccac aacaaccata tcctcaaccg caaccacagt attcgcaacc acaacaacc 119

<210> SEQ ID NO 301
<211> LENGTH: 119
<212> TYPE: DNA
<213> ORGANISM: Artificial Sequence
<220> FEATURE:
<223> OTHER INFORMATION: fig 4b contin 13

<400> SEQUENCE: 301
ccatatctgc agttgcaacc atttccgcag ccgcaactac catatttgca gccgcaacca 60
tttcgaccac aacaaccata tccacaaccg taaccacagt attcgcaacc acaacaacc 119

<210> SEQ ID NO 302
<211> LENGTH: 116
<212> TYPE: DNA
<213> ORGANISM: Artificial Sequence
<220> FEATURE:
<223> OTHER INFORMATION: fig 4b contin 14

<400> SEQUENCE: 302
ccatatccgc agccgcaacc atttctgcca caactaccat atccgcagcc gcaaccattt 60
ccaccacaac aatcatatcc acaaccacaa ccacaatatc cgcaaccaca acaacc 116

<210> SEQ ID NO 303
<211> LENGTH: 119
<212> TYPE: DNA
<213> ORGANISM: Artificial Sequence
<220> FEATURE:
<223> OTHER INFORMATION: fig 4b contin 15

<400> SEQUENCE: 303
ccatatctgc agctgcaacc atttccgcag ccgcaactac catattcgca gccacaacca 60
tttcgaccac aacaaccata tccacaaccg caaccacagt attcgcaacc acaacaacc 119

<210> SEQ ID NO 304
<211> LENGTH: 96
<212> TYPE: DNA
<213> ORGANISM: Artificial Sequence
<220> FEATURE:
<223> OTHER INFORMATION: fig 4b contin 16

<400> SEQUENCE: 304
ttcgcagccg caactaccat attcgcagcc gcgaccattt cgaccacaac aaccatatcc 60
acaaccgcaa ccacagtatt cgcaaccaca acaacc 96

<210> SEQ ID NO 305
<211> LENGTH: 140
<212> TYPE: DNA
<213> ORGANISM: Artificial Sequence
<220> FEATURE:
<223> OTHER INFORMATION: fig 4b contin 17

<400> SEQUENCE: 305
ccatatatgc agctgcaacc atttccgcag ccgcaactac catatccgca gccgcaacta 60
ccatatccgc agccgcaacc atttcgacca caacaatcat atccacaacc gcaaccacag 120
tattcgcaac cacaacaacc 140

<210> SEQ ID NO 306
<211> LENGTH: 119
<212> TYPE: DNA
<213> ORGANISM: Artificial Sequence
<220> FEATURE:
<223> OTHER INFORMATION: fig 4b contin 18

<400> SEQUENCE: 306
ccatatctgc agctgcaacc atttccacag ccgcaactac catattcgcc accacaacca 60
tttcgaccac aacaaccata tccacaaccg caaccacagt attcgcaacc acaacaacc 119

<210> SEQ ID NO 307
<211> LENGTH: 119
<212> TYPE: DNA
<213> ORGANISM: Artificial Sequence
<220> FEATURE:
<223> OTHER INFORMATION: fig 4b contin 19

<400> SEQUENCE: 307
ccatatctgc aactgcaacc atttctgcag ccgcaactac catattcaca gccacaacca 60
tttcgaccac aacaaccata tccacaaccg caaccacagt attcgcaacc acaacaacc 119

<210> SEQ ID NO 308
<211> LENGTH: 119
<212> TYPE: DNA
<213> ORGANISM: Artificial Sequence
<220> FEATURE:
<223> OTHER INFORMATION: fig 4b contin 20

<400> SEQUENCE: 308
ccatatctgc agctgcaacc atttccgcag ccgcaactac catattcgca gccacaacca 60
tttcgaccac aacaaccata tccacaaccg caaccacagt attcgcaacc acaacaacc 119

<210> SEQ ID NO 309
<211> LENGTH: 119
<212> TYPE: DNA
<213> ORGANISM: Artificial Sequence
<220> FEATURE:
<223> OTHER INFORMATION: fig 4b contin 21

<400> SEQUENCE: 309
ccatatctgc aactgcaacc atttccgcag ccgcaactac catattcaca gccacaacca 60
tttcgaccac aacaaccata tccacaaccg caaccacagt attcgcaacc acaacaacc 119

<210> SEQ ID NO 310
<211> LENGTH: 140
<212> TYPE: DNA
<213> ORGANISM: Artificial Sequence
<220> FEATURE:
<223> OTHER INFORMATION: fig 4b contin 22

<400> SEQUENCE: 310
ccatatctgc agctgcagcc atttccgcag ccgcaactac catatccgca gccgcatcta 60
ccatatccgc agccgcaacc atttcgacca caacaaccat atccacaacc gcaaccacag 120
tattcgcaac cacaacaacc 140

<210> SEQ ID NO 311
<211> LENGTH: 119
<212> TYPE: DNA
<213> ORGANISM: Artificial Sequence
<220> FEATURE:
<223> OTHER INFORMATION: fig 4b contin 23

<400> SEQUENCE: 311
ccatatctgc agctgcaacc atttccacag ccgcaactac catattcgca accacaacca 60
tttcgaccac aacaaccata tccacaaccg caaccacagt attcgcaacc acaacaacc 119

<210> SEQ ID NO 312
<211> LENGTH: 119
<212> TYPE: DNA
<213> ORGANISM: Artificial Sequence
<220> FEATURE:
<223> OTHER INFORMATION: fig 4b contin 24

<400> SEQUENCE: 312
ccatatctgc agttgcaacc atttccgcag ccgcaactac catattcgta gtcgcaacca 60
tttcgaccac aacaaccata tccacgaccg caaccacagt attcgcaacc acaacaacc 119

<210> SEQ ID NO 313
<211> LENGTH: 140
<212> TYPE: DNA
<213> ORGANISM: Artificial Sequence
<220> FEATURE:
<223> OTHER INFORMATION: fig 4b contin 25

<400> SEQUENCE: 313
ccatatctgc agctgcaacc atttccgcag ccgcaactac catatccgca gccgcaacta 60
ccatatccgc agccgcaacc atttcgacca caacaaccat atccacaacc gcaaccacag 120
tattcgcaac cacaacaacc 140

<210> SEQ ID NO 314
<211> LENGTH: 134
<212> TYPE: DNA
<213> ORGANISM: Artificial Sequence
<220> FEATURE:
<223> OTHER INFORMATION: fig 4b contin 26

<400> SEQUENCE: 314
ccatatctgc aattgcaacc atttccacaa ccgcaaccat ttccgccaca actaccatat 60
ccgcagccac caccattttc accacaacaa ccatatccac aaccgcaacc acagtatccg 120
caaccacaac aacc 134

<210> SEQ ID NO 315
<211> LENGTH: 119

<212> TYPE: DNA
<213> ORGANISM: Artificial Sequence
<220> FEATURE:
<223> OTHER INFORMATION: fig 4b contin 27

<400> SEQUENCE: 315
ccatatctgc aactgcaacc atttccgcag ccgcaactac catattcgca accacaacca 60
tttcgaccac aacaaccata tccacaaccg caaccacagt attcgcaacc acaacaacc 119

<210> SEQ ID NO 316
<211> LENGTH: 116
<212> TYPE: DNA
<213> ORGANISM: Artificial Sequence
<220> FEATURE:
<223> OTHER INFORMATION: fig 4b contin 28

<400> SEQUENCE: 316
ccatatccac agccacaacc atttctgcca caactaccat atccgcgtcc gcaaccattt 60
ctaccacaac aaccatatcc acaaccggaa ccacagtatc cgcaaccaca acaacc 116

<210> SEQ ID NO 317
<211> LENGTH: 119
<212> TYPE: DNA
<213> ORGANISM: Artificial Sequence
<220> FEATURE:
<223> OTHER INFORMATION: fig 4b contin 30

<400> SEQUENCE: 317
ccatatctgc agctgcaacc atttccgcag ccgcaactac catattcgca gccgcaacca 60
tttcgaccac aacaaccata tccacaaccg caaccacagt attcgcaacc acaacaacc 119

<210> SEQ ID NO 318
<211> LENGTH: 116
<212> TYPE: DNA
<213> ORGANISM: Artificial Sequence
<220> FEATURE:
<223> OTHER INFORMATION: fig 4b contin 31

<400> SEQUENCE: 318
ccatttctgc agccgcaacc atttctgcta caactaccat atccgcagcc acaaccattt 60
ccaccacaac aaccatatcc acaaccgcaa ccacagtatc cgcaaccaca acaacc 116

<210> SEQ ID NO 319
<211> LENGTH: 119
<212> TYPE: DNA
<213> ORGANISM: Artificial Sequence
<220> FEATURE:
<223> OTHER INFORMATION: fig 4b contin 32

<400> SEQUENCE: 319
ccatatctgc agctgcaacc atttccgcag ccgcaactac catattcaca gccacaacca 60
tttcgaccac aacaaccata tccacaaccg caaccatagt attcgcaacc acaacaacc 119

<210> SEQ ID NO 320
<211> LENGTH: 140
<212> TYPE: DNA
<213> ORGANISM: Artificial Sequence
<220> FEATURE:
<223> OTHER INFORMATION: fig 4b contin 33

<400> SEQUENCE: 320
ccatatatgc agctgcaacc atttccgcag ccgcaactac catatccgca gccgcaacta 60
ccatatccgc agccgcaacc atttcgacca caacaatcat atccacaacc gcaaccacag 120
tattcgcaac cacaacaacc 140

<210> SEQ ID NO 321
<211> LENGTH: 119
<212> TYPE: DNA
<213> ORGANISM: Artificial Sequence
<220> FEATURE:
<223> OTHER INFORMATION: fig 4b contin 34

<400> SEQUENCE: 321
ccatatctac agctgcaacc atttccgtag ctgcaacaac catattcgca gccgcaacca 60
tttcgaccac aacaaccata tccacaaccg caaccacagt attcgcaacc acaacaacc 119

<210> SEQ ID NO 322
<211> LENGTH: 119
<212> TYPE: DNA
<213> ORGANISM: Artificial Sequence
<220> FEATURE:
<223> OTHER INFORMATION: fig 4b contin 35

<400> SEQUENCE: 322
ccatatctgc agctgcaacc attttcgcag ccgcaactac catattcgca gccgcaacca 60
tttcgaccac aacaaccata tccacaaccg caaccatagt attcgcaacc acaacaacc 119

<210> SEQ ID NO 323
<211> LENGTH: 119
<212> TYPE: DNA
<213> ORGANISM: Artificial Sequence
<220> FEATURE:
<223> OTHER INFORMATION: fig 4b contin 36

<400> SEQUENCE: 323
ccatatctgc agctgcaacc atttccgcag ccgcaactag catattcgca gccacaacca 60
ttttgaccac aacaaccata tccacaaccg caaccacagt attcgcaacc acaacaacc 119

<210> SEQ ID NO 324
<211> LENGTH: 119
<212> TYPE: DNA
<213> ORGANISM: Artificial Sequence
<220> FEATURE:
<223> OTHER INFORMATION: fig 4b contin 37

<400> SEQUENCE: 324
ccatatctgc agctgcaacc atttccgcag ccgcaactac catattcaca gccacaacca 60
tttcgaccac aacaaccata tccacaaccg caaccacagt attcgcaacc acaacaacc 119

<210> SEQ ID NO 325
<211> LENGTH: 119
<212> TYPE: DNA
<213> ORGANISM: Artificial Sequence
<220> FEATURE:
<223> OTHER INFORMATION: fig 4b contin 38

<400> SEQUENCE: 325
ccatatctgc aactgcaacc atttccgcag ccgcaactat catattcgca gccacaacca 60
tttcgaccac aacaaccata tccacaaccg caaccacagt attcgcaacc acaacaacc 119

<210> SEQ ID NO 326
<211> LENGTH: 119
<212> TYPE: DNA
<213> ORGANISM: Artificial Sequence
<220> FEATURE:
<223> OTHER INFORMATION: fig 4b contin 40

<400> SEQUENCE: 326
ccatatctgc agctgcaacc atttccgcag ccgcaactac catattcaca gccacaacca 60
tttcgaccac aacaaccata tccacaaccg caaccacagt attcgcaacc acaacaacc 119

<210> SEQ ID NO 327
<211> LENGTH: 140
<212> TYPE: DNA
<213> ORGANISM: Artificial Sequence
<220> FEATURE:
<223> OTHER INFORMATION: fig 4b contin 41

<400> SEQUENCE: 327
ccatatctgc agctgcaacc atttccgcag ccgcaactac catatccgca gccgcaacta 60
ccatatccgc agccgcaacc atttcgacca caacaaccat atccacaacc gcaaccacag 120
tattcgcaac cacaacaacc 140

<210> SEQ ID NO 328
<211> LENGTH: 116
<212> TYPE: DNA
<213> ORGANISM: Artificial Sequence
<220> FEATURE:
<223> OTHER INFORMATION: fig 4b contin 42

<400> SEQUENCE: 328
ccattgccgc aaccgcaacc atttctgcca caactaccat atccgcagcc acaaccattt 60
ccaccacaac aaccatatcc acaaccgcaa ccacagtatc cgcaaccaca acaacc 116

<210> SEQ ID NO 329
<211> LENGTH: 119
<212> TYPE: DNA
<213> ORGANISM: Artificial Sequence
<220> FEATURE:
<223> OTHER INFORMATION: fig 4b contin 43

<400> SEQUENCE: 329
ccatatctgc agctgcaacc atttctgcag ccgcaactac catattcaca gccacaacca 60
tttcgaccac aacaaccata tccacaacca caaccacagt attcgcaacc acaacaacc 119

<210> SEQ ID NO 330
<211> LENGTH: 119
<212> TYPE: DNA
<213> ORGANISM: Artificial Sequence
<220> FEATURE:
<223> OTHER INFORMATION: fig 4b contin 44

<400> SEQUENCE: 330
ccatatctgc agctgcaacc atttccacag ccgcaactac catatccgca gccgcaacca 60
tttcgaccac aacaaccata tccacagccg caaccacagt attcgcaacc acaacaacc 119

<210> SEQ ID NO 331
<211> LENGTH: 119
<212> TYPE: DNA
<213> ORGANISM: Artificial Sequence
<220> FEATURE:
<223> OTHER INFORMATION: fig 4b contin 45

<400> SEQUENCE: 331
ccatatctgc agctgcaacc atttccgcag ccgcaactac catatttgca gccacaacca 60
tttcgaccac aacaaccata tccacaaccg caaccacaat atccgcaacc acaacaacc 119

<210> SEQ ID NO 332
<211> LENGTH: 119
<212> TYPE: DNA
<213> ORGANISM: Artificial Sequence
<220> FEATURE:
<223> OTHER INFORMATION: fig 4b contin 46

<400> SEQUENCE: 332
ccatatctgc agctgcaacc atttccgcag ccgcaactac catatccgca gccgcaacca 60
tttcgaccac aacaaccata tccacaaccg caaccacagt atccgcaacc acaacaacc 119

<210> SEQ ID NO 333
<211> LENGTH: 116
<212> TYPE: DNA
<213> ORGANISM: Artificial Sequence
<220> FEATURE:
<223> OTHER INFORMATION: fig 4b contin 47

<400> SEQUENCE: 333
ccatatccgc agccgcaacc atttccgtca caactaccat atccgcagcc gcaaccattt 60
ccaccacaac aaccctatcc acaaccgcaa ccacaatatc cgcaaccaca acaacc 116

<210> SEQ ID NO 334
<211> LENGTH: 119
<212> TYPE: DNA
<213> ORGANISM: Artificial Sequence
<220> FEATURE:
<223> OTHER INFORMATION: fig 4b contin 48

<400> SEQUENCE: 334
ccatatctgc agctgcaacc attttcgcag ccgcaactac catattcgca gccacaacca 60
tttcgaccac aacaaccata tccacaaccg caaccacagt atccgcaacc acaacaacc 119

<210> SEQ ID NO 335
<211> LENGTH: 161
<212> TYPE: DNA
<213> ORGANISM: Artificial Sequence
<220> FEATURE:
<223> OTHER INFORMATION: fig 4b contin 49

<400> SEQUENCE: 335
ccatatctgc agctgcaacc atttccgcag ccgcaactac catatccgca gccgcaacta 60
ccatatccgc agccgcaact accatatccg cagccgcaac catttcgacc acaacaacca 120
tatccacaat cgcaaccaca gtattcgcaa ccacaacaac c 161

<210> SEQ ID NO 336
<211> LENGTH: 161
<212> TYPE: DNA
<213> ORGANISM: Artificial Sequence
<220> FEATURE:
<223> OTHER INFORMATION: fig 4b contin 52

<400> SEQUENCE: 336
ccatatctgc agctgcaacc atttccgcag ccgcaactac catatccgca gccgcaacta 60
ccatatccgc agccgcaact accatatccg cagccgcaac catttcgacc acaacaacca 120
tatccacaat cgcaaccaca gtattcgcaa ccacaacaac c 161

<210> SEQ ID NO 337
<211> LENGTH: 96
<212> TYPE: DNA
<213> ORGANISM: Artificial Sequence
<220> FEATURE:
<223> OTHER INFORMATION: fig 4b contin 53

<400> SEQUENCE: 337
ttcgcagccg caactaccat attcgcagcc gcgaccattt cgaccacaac aaccatatcc 60
acaaccgcaa ccacagtatc cgcaaccaca acaacc 96

<210> SEQ ID NO 338
<211> LENGTH: 120
<212> TYPE: DNA
<213> ORGANISM: Artificial Sequence
<220> FEATURE:
<223> OTHER INFORMATION: fig 4b contin 59

<400> SEQUENCE: 338
ccatatctgc agctgcaacc attttcgcag ccgcaactac ccatattcgc agccgcaacc 60
atttcgacca caacaaccat atccacaacc gcaaccacag tattcgcaac cacaacaacc 120

<210> SEQ ID NO 339
<211> LENGTH: 119
<212> TYPE: DNA
<213> ORGANISM: Artificial Sequence
<220> FEATURE:
<223> OTHER INFORMATION: fig 4b contin 60

<400> SEQUENCE: 339
ccatatctgc agttgcaacc atttccgcag ccgcaactac catatttgca gccgcaacca 60
tttcgaccac aacaaccata tccacaaccg taaccacagt atccgcaacc acaacaacc 119

<210> SEQ ID NO 340
<211> LENGTH: 119
<212> TYPE: DNA
<213> ORGANISM: Artificial Sequence
<220> FEATURE:
<223> OTHER INFORMATION: fig 4b contin 68

<400> SEQUENCE: 340
ccatatctgc agctgcaacc atttccgcag ccgcaactac catattcgca gccgcaacca 60
tttcgaccac aacaaccata tccacaaccg caaccacagt attcgcaacc acaacaacc 119

<210> SEQ ID NO 341
<211> LENGTH: 161
<212> TYPE: DNA
<213> ORGANISM: Artificial Sequence
<220> FEATURE:
<223> OTHER INFORMATION: fig 4c AJ133612

<400> SEQUENCE: 341
gttagagttc cagtgccaca attgcagcca caaaatccat ctcagcaaca accacaagag 60
caagttccat tggtacaaca acaacaattt ccagggcagc aacaaccatt tccaccacaa 120
cagccatatc cgcagccgca accatttcca tcacaacaac c 161

<210> SEQ ID NO 342
<211> LENGTH: 149
<212> TYPE: DNA
<213> ORGANISM: Artificial Sequence
<220> FEATURE:
<223> OTHER INFORMATION: fig 4c 1

<400> SEQUENCE: 342
gttagagttc cagtgccaca attgcagcca caaaatccat ctcagcaaca accacaagag 60
caagttccat tggtgcaaca acaacaattt ctagggcagc aacaacaaca atttccaggg 120
caacaacaac catttccacc acaacagcc 149

<210> SEQ ID NO 343
<211> LENGTH: 125
<212> TYPE: DNA
<213> ORGANISM: Artificial Sequence
<220> FEATURE:
<223> OTHER INFORMATION: fig 4c 2

<400> SEQUENCE: 343
gttagagttc cagtgccaca attgcagcca caaaatccat atcagcaaca gccacaagag 60
catgttccat tggtacaaca acaacaattt ctagggcagc aacaacaatt tccaccacaa 120
caacc 125

<210> SEQ ID NO 344
<211> LENGTH: 161
<212> TYPE: DNA
<213> ORGANISM: Artificial Sequence
<220> FEATURE:
<223> OTHER INFORMATION: fig 4c 3

<400> SEQUENCE: 344
gttagagttc cagtgccaca atcacagcca caaaatcgat ctcagccaca gccacaaggg 60
caagttccat tggtacaaca acaacaattt ccagggcagc aacaaccatt tccaccacaa 120
cagccatatc cgcagccgca accatttcca tcacaacaac c 161

<210> SEQ ID NO 345
<211> LENGTH: 161
<212> TYPE: DNA
<213> ORGANISM: Artificial Sequence
<220> FEATURE:
<223> OTHER INFORMATION: fig 4c 4

<400> SEQUENCE: 345
gttagagttc cagtgccaca attgtagccg caaaatccat ctcaacaacg accacaatag 60
taatttccgt tggtgcaaca acaacaattt ccagggcagc aacaaccatt cccaccacaa 120
cagccatatc cgcagccgca accgtttctg tcacaacaac c 161

<210> SEQ ID NO 346
<211> LENGTH: 161
<212> TYPE: DNA
<213> ORGANISM: Artificial Sequence
<220> FEATURE:

<223> OTHER INFORMATION: fig 4c 5

<400> SEQUENCE: 346
gttagagttc cagtgccaca attgcagcca caaaatccat ctcagcaaca gccacaagag 60
caagttccat tggtacaaca acaaaaattt ctagggcagc aacaacaatt tccaccacaa 120
caaccagatc cacagccgca accatttgca tcacaacaac c 161

<210> SEQ ID NO 347
<211> LENGTH: 126
<212> TYPE: DNA
<213> ORGANISM: Artificial Sequence
<220> FEATURE:
<223> OTHER INFORMATION: fig 4c 6

<400> SEQUENCE: 347
gttagagttc cagtgccaca attgcagcca caaaatccat ctcagcaaca accacaagag 60
caagttccat tggtgcaaca acaacaattt ctagggcagc aacaacaaca atttccaggg 120
caacaa 126

<210> SEQ ID NO 348
<211> LENGTH: 161
<212> TYPE: DNA
<213> ORGANISM: Artificial Sequence
<220> FEATURE:
<223> OTHER INFORMATION: fig 4c 7

<400> SEQUENCE: 348
gttagagttc cagtgccaca attgcaacca taaaatccat ctcagcaaca gccacaagag 60
caagttccat tggtacaaca acaacaattt ctagggcagc aacaaccatt tccaccacaa 120
caaccatatc cacaggcgca accatttcca tcacaacaac c 161

<210> SEQ ID NO 349
<211> LENGTH: 102
<212> TYPE: DNA
<213> ORGANISM: Artificial Sequence
<220> FEATURE:
<223> OTHER INFORMATION: fig 4c 8

<400> SEQUENCE: 349
gttagagttc cagtgccaca attgcagcca caaaatccat ctcagcaaca accacaagag 60
caagttccat tggtgcaaca acaacaattt ctagggcagc aa 102

<210> SEQ ID NO 350
<211> LENGTH: 126
<212> TYPE: DNA
<213> ORGANISM: Artificial Sequence
<220> FEATURE:
<223> OTHER INFORMATION: fig 4c 9

<400> SEQUENCE: 350
gttagagttc cagtgccaca attgcagcca caaaatccat ctcagcaaca accacaagag 60
caagttctat tggtgcaaca acaaccattt ctagggcagc aacaacaaca atttccaggg 120
cagcaa 126

<210> SEQ ID NO 351
<211> LENGTH: 161
<212> TYPE: DNA
<213> ORGANISM: Artificial Sequence
<220> FEATURE:
<223> OTHER INFORMATION: fig 4c 10

<400> SEQUENCE: 351
gttagagttc cagtgccaca attgcagcca caaaatccat ctcagcaaca gccacaagag 60
caagttccat tggtacaaca acaaaaattt ctagggcagc aacaagaatt tccaccacaa 120
caaccagatc cacagccgca accatttcca tcacaacaac c 161

<210> SEQ ID NO 352
<211> LENGTH: 161
<212> TYPE: DNA
<213> ORGANISM: Artificial Sequence
<220> FEATURE:
<223> OTHER INFORMATION: fig 4c 11

<400> SEQUENCE: 352
gttagagttc cagtgccaca attgcagcca caaaatccat ctcagcaaca gccacaagag 60
caagctccat tggtacaaca acaacaattt ctagggcagc aacaacaatt tccaccacaa 120
caaccatatc cgcagccgca accatttcca tcacaacaac c 161

<210> SEQ ID NO 353
<211> LENGTH: 126
<212> TYPE: DNA
<213> ORGANISM: Artificial Sequence
<220> FEATURE:
<223> OTHER INFORMATION: fig 4c 12

<400> SEQUENCE: 353
gttagagttc cagtgccaca attgcagcca caaaatccat ctcagcaaca accacaagag 60
caagttccat tggtgcaaca acaacaattt ctagggcagt aacaacaaca atttccaggg 120
caacaa 126

<210> SEQ ID NO 354
<211> LENGTH: 126
<212> TYPE: DNA
<213> ORGANISM: Artificial Sequence
<220> FEATURE:
<223> OTHER INFORMATION: fig 4c 14

<400> SEQUENCE: 354
gttagagttc cagtgccaca attgcaacca gaaaatccat ctcagcaaca accacaagag 60
caagttccat tggtgcaaca acaacaattt ctagggcagc aacaacaaca atttccaggg 120
cagcaa 126

<210> SEQ ID NO 355
<211> LENGTH: 126
<212> TYPE: DNA
<213> ORGANISM: Artificial Sequence
<220> FEATURE:
<223> OTHER INFORMATION: fig 4c 15

<400> SEQUENCE: 355
gttagagttc cagtgccaca attgcagcca caaaatccat ctcagcaaca accacaagag 60
caagttccat tggtgcaaca acaacaattt ctagggcagc aacaacaaca atttccaggg 120
caacaa 126

<210> SEQ ID NO 356
<211> LENGTH: 126
<212> TYPE: DNA
<213> ORGANISM: Artificial Sequence
<220> FEATURE:

<223> OTHER INFORMATION: fig 4c 17

<400> SEQUENCE: 356
gttagagttc cagtgccaca attgcagcca caaaatccat ctcagcaaca accacaagag 60
caagttccat tggtgcaaca acaacaattt ctagggcagc aacaacaaca ttttccaggg 120
caacaa 126

<210> SEQ ID NO 357
<211> LENGTH: 161
<212> TYPE: DNA
<213> ORGANISM: Artificial Sequence
<220> FEATURE:
<223> OTHER INFORMATION: fig 4c 18

<400> SEQUENCE: 357
gttagagttc cagtgccaca attgcagcca caaaatccat ctcagcaaca gccacaagag 60
caagttccat tggtacaaca acaacaattt ctggggcagc aacaaccatt tccaccacaa 120
caaccatatc cacagccgca accatttcca tcacaacaac c 161

<210> SEQ ID NO 358
<211> LENGTH: 115
<212> TYPE: DNA
<213> ORGANISM: Artificial Sequence
<220> FEATURE:
<223> OTHER INFORMATION: fig 4c 19

<400> SEQUENCE: 358
gttagagttc cagtgccaca attgcagcca caaaatccat atcagcaaca gccacaagag 60
catgttccat tggtacaaca acaacaattt ctagggcagc aacaacaatt tccac 115

<210> SEQ ID NO 359
<211> LENGTH: 161
<212> TYPE: DNA
<213> ORGANISM: Artificial Sequence
<220> FEATURE:
<223> OTHER INFORMATION: fig 4c 20

<400> SEQUENCE: 359
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 360
<211> LENGTH: 161
<212> TYPE: DNA
<213> ORGANISM: Artificial Sequence
<220> FEATURE:
<223> OTHER INFORMATION: fig 4c 21

<400> SEQUENCE: 360
gttagagttc cagtgccaca attgcagccg caaaatccat ctcagcaaca accacaagag 60
caagttccgt tggtgcaaca acaacaatat ccagggcagc aacaaccatt tccaccacaa 120
caaccatatc cgcagccgca accatttcca tcacaacaac c 161

<210> SEQ ID NO 361
<211> LENGTH: 161
<212> TYPE: DNA
<213> ORGANISM: Artificial Sequence
<220> FEATURE:
<223> OTHER INFORMATION: fig 4c 22

<400> SEQUENCE: 361
gttagagttc cagtgccaca attgcagcca caaaatccat ctcagcaaca gccacaagag 60
caagttccat tggtacaaca acaaaaattt ctagggcagc aacaacaatt tccaccacaa 120
caaccagatc cacagccgca accatttgca tcacaacaac c 161

<210> SEQ ID NO 362
<211> LENGTH: 161
<212> TYPE: DNA
<213> ORGANISM: Artificial Sequence
<220> FEATURE:
<223> OTHER INFORMATION: fig 4c 23

<400> SEQUENCE: 362
gttagagttc cagtgccaca attgcagcca caaaatccat ctcagcaaca accacaagag 60
caagtttcat tggtacaaca acaacaattt ctagggcagc aacaaccatt tccaccacaa 120
caaccatatc cacagccgca accatttcca tcacaacaac c 161

<210> SEQ ID NO 363
<211> LENGTH: 161
<212> TYPE: DNA
<213> ORGANISM: Artificial Sequence
<220> FEATURE:
<223> OTHER INFORMATION: fig 4c 24

<400> SEQUENCE: 363
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca acaatttcca tcacaacaac c 161

<210> SEQ ID NO 364
<211> LENGTH: 161
<212> TYPE: DNA
<213> ORGANISM: Artificial Sequence
<220> FEATURE:
<223> OTHER INFORMATION: fig 4c 25

<400> SEQUENCE: 364
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 365
<211> LENGTH: 161
<212> TYPE: DNA
<213> ORGANISM: Artificial Sequence
<220> FEATURE:
<223> OTHER INFORMATION: fig 4c 26

<400> SEQUENCE: 365
gttagagttc cagtgccaca attgcagcca caaaatccat ctcagcaaca gccacaagag 60
caaattccat tggtacaaca acaataattt ctagggcagc aacaacaatt tccaccacaa 120
caaccatatc cacagccgca accatttcca tcacaacaac c 161

<210> SEQ ID NO 366
<211> LENGTH: 161
<212> TYPE: DNA
<213> ORGANISM: Artificial Sequence
<220> FEATURE:

<223> OTHER INFORMATION: fig 4c 27

<400> SEQUENCE: 366
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 367
<211> LENGTH: 161
<212> TYPE: DNA
<213> ORGANISM: Artificial Sequence
<220> FEATURE:
<223> OTHER INFORMATION: fig 4c 29

<400> SEQUENCE: 367
gttagagttc cagtgccaca attgcaacca taaaatccat ctcagcaaca gccacaagag 60
caagttccat tggtacaaca acaacaattt ctagggcagc aacaaccatt tccaccacaa 120
caaccatatc cacaggcgca accatttcca tcacaacaac c 161

<210> SEQ ID NO 368
<211> LENGTH: 161
<212> TYPE: DNA
<213> ORGANISM: Artificial Sequence
<220> FEATURE:
<223> OTHER INFORMATION: fig 4c 30

<400> SEQUENCE: 368
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc catagccgca accatttcca tcacaacaat c 161

<210> SEQ ID NO 369
<211> LENGTH: 161
<212> TYPE: DNA
<213> ORGANISM: Artificial Sequence
<220> FEATURE:
<223> OTHER INFORMATION: fig 4c 31

<400> SEQUENCE: 369
gttagagttc cagtgccaca attgcagcca caaaatccat ctcagcaaca gccacaagag 60
caagttccat tggtacaaca acaacaattt ctagggaagc aacaaccatt tccaccacaa 120
caaccatatc catagccgca accatttcca tcacaacaat c 161

<210> SEQ ID NO 370
<211> LENGTH: 161
<212> TYPE: DNA
<213> ORGANISM: Artificial Sequence
<220> FEATURE:
<223> OTHER INFORMATION: fig 4c 35

<400> SEQUENCE: 370
gttagagttc cagtgccaca attggagcca caaaatccat ctcagcaaca cccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 371
<211> LENGTH: 161
<212> TYPE: DNA
<213> ORGANISM: Artificial Sequence
<220> FEATURE:
<223> OTHER INFORMATION: fig 4c 36

<400> SEQUENCE: 371
gttagagttc cagtgccaca attgcagcca caaaatccat ctcagcaaca gccacaagag 60
caagttccat tggtacaaca acaaaaattt ctagggcagc aacaagaatt tccaccacaa 120
caaccagatc cacagccgca accatttcca tcacaacaac c 161

<210> SEQ ID NO 372
<211> LENGTH: 161
<212> TYPE: DNA
<213> ORGANISM: Artificial Sequence
<220> FEATURE:
<223> OTHER INFORMATION: fig 4c 39

<400> SEQUENCE: 372
gttagagttc cagtgccaca actgcagcca caaaatccat ctcagcaaca gccacaagag 60
caagttccat tggtataaca acaaaaattt ctagggcagc aacaacaatt tccaccacaa 120
caaccagatc cacagccgca accatttcca tcacaacaac c 161

<210> SEQ ID NO 373
<211> LENGTH: 161
<212> TYPE: DNA
<213> ORGANISM: Artificial Sequence
<220> FEATURE:
<223> OTHER INFORMATION: fig 4c 42

<400> SEQUENCE: 373
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 374
<211> LENGTH: 161
<212> TYPE: DNA
<213> ORGANISM: Artificial Sequence
<220> FEATURE:
<223> OTHER INFORMATION: fig 4c 43

<400> SEQUENCE: 374
gttagagttc cagtgccaca attgcagcca caaaatccat ctcagcaaca gccacaagag 60
caagttccat tggtacaaca acaacaattt atagggcagc aacaaccatt tccaccacaa 120
caaccatatc cacagccgca accatttcca tcacaacaac c 161

<210> SEQ ID NO 375
<211> LENGTH: 161
<212> TYPE: DNA
<213> ORGANISM: Artificial Sequence
<220> FEATURE:
<223> OTHER INFORMATION: fig 4c 45

<400> SEQUENCE: 375
gttagagttc cagtgccaca attgcagcca caaaatccat ctcagcaaca gccacaagag 60
caagttccat tggtacaaca acaacaattt ctagggcagc aacaaccatt tccaccacaa 120
caaccatata cacagccgca accatttcca tcacaacaac c 161

<210> SEQ ID NO 376
<211> LENGTH: 161
<212> TYPE: DNA

<213> ORGANISM: Artificial Sequence
<220> FEATURE:
<223> OTHER INFORMATION: fig 4c 47

<400> SEQUENCE: 376
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 377
<211> LENGTH: 161
<212> TYPE: DNA
<213> ORGANISM: Artificial Sequence
<220> FEATURE:
<223> OTHER INFORMATION: fig 4c 49

<400> SEQUENCE: 377
gttagagttc cagtgccaca attgcagcca caaaatccat ctcagcaaca gccacaagag 60
caagtttcat tggtacaaca acaacaattt ctagggcagc aacaaccatt tccaccacaa 120
caaccatatc cacagccgca accatttcca tcacaactac c 161

<210> SEQ ID NO 378
<211> LENGTH: 161
<212> TYPE: DNA
<213> ORGANISM: Artificial Sequence
<220> FEATURE:
<223> OTHER INFORMATION: fig 4c 50

<400> SEQUENCE: 378
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 379
<211> LENGTH: 161
<212> TYPE: DNA
<213> ORGANISM: Artificial Sequence
<220> FEATURE:
<223> OTHER INFORMATION: fig 4c 57

<400> SEQUENCE: 379
gttagagttc cagtgccaca attgcagcca caaattccat ctcagcaaca accacaagag 60
caagttccat tggtacaaca acaacaattt ctagggcagc aacaacaatt tccaacagaa 120
caaccatatc cgcagccgca accatttcca tcacaacaac c 161

<210> SEQ ID NO 380
<211> LENGTH: 161
<212> TYPE: DNA
<213> ORGANISM: Artificial Sequence
<220> FEATURE:
<223> OTHER INFORMATION: fig 4c 63

<400> SEQUENCE: 380
gttagagttc cagtgccaca attgcagcca caaaatccat ctcagcaata gccacaagag 60
caagttccat tggtacaaca acaacaattt ctagggcagc aacaaccatt tcgaccacaa 120
caaccatatc cacagccgca accatttcca tcacaacaac c 161

<210> SEQ ID NO 381
<211> LENGTH: 161

-continued

<212> TYPE: DNA
<213> ORGANISM: Artificial Sequence
<220> FEATURE:
<223> OTHER INFORMATION: fig 4c 67

<400> SEQUENCE: 381
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 382
<211> LENGTH: 161
<212> TYPE: DNA
<213> ORGANISM: Artificial Sequence
<220> FEATURE:
<223> OTHER INFORMATION: fig 4c 70

<400> SEQUENCE: 382
gttagagttc cagtgccaca attgcagcca caaaatccat ctcagcaaca gccacaagag 60
caagttccat tggtacaaca acaacaattt ctagggcagc aacaaccatt tccaccacaa 120
caaccatatc cacagccgca accatttcca tcacaacaac c 161

<210> SEQ ID NO 383
<211> LENGTH: 161
<212> TYPE: DNA
<213> ORGANISM: Artificial Sequence
<220> FEATURE:
<223> OTHER INFORMATION: fig 4c 74

<400> SEQUENCE: 383
gttagagttc cagtgccaca attgcagcca taaaatccat ctcagcaaca gccacaagag 60
caagttccat tggtacaaca acaacaattt ctagggcagt aacaaccatt tccaccacaa 120
caaccatatc cacagccgca accatttcca tcacaacaac c 161

<210> SEQ ID NO 384
<211> LENGTH: 161
<212> TYPE: DNA
<213> ORGANISM: Artificial Sequence
<220> FEATURE:
<223> OTHER INFORMATION: fig 4c 79

<400> SEQUENCE: 384
gttagagttc cagtgccaca attgcagcca taaaatccat ctcagcaaca gccacaagag 60
caagttccat tggtacaaca acaacaattt ctagggcagt aacaaccatt tccaccacaa 120
caaccatatc cacagccgca accatttcca tcacaacaac c 161

<210> SEQ ID NO 385
<211> LENGTH: 159
<212> TYPE: DNA
<213> ORGANISM: Artificial Sequence
<220> FEATURE:
<223> OTHER INFORMATION: fig 4c contin AJ133612

<400> SEQUENCE: 385
atatctgcag ctgcaaccat ttccgcagcc gcaactacca tatccgcagc cgcaactacc 60
atatccgcag ccgcaactac catatccgca gccgcaacca tttcgaccac aacaaccata 120
tccacaatcg caaccacagt attcgcaacc acaacaacc 159

<210> SEQ ID NO 386

<211> LENGTH: 114
<212> TYPE: DNA
<213> ORGANISM: Artificial Sequence
<220> FEATURE:
<223> OTHER INFORMATION: fig 4c contin 1

<400> SEQUENCE: 386
atatccgcag ccgcaaccat ttctgccaca actaccatat ccgcagccgc aaccatttcc 60
accacaacaa tcatatccac aaccacaacc acaatatccg caaccacaac aacc 114

<210> SEQ ID NO 387
<211> LENGTH: 117
<212> TYPE: DNA
<213> ORGANISM: Artificial Sequence
<220> FEATURE:
<223> OTHER INFORMATION: fig 4c contin 3

<400> SEQUENCE: 387
atatctgcag ctgcaaccat tttcgcagcc gcaactacca tattcacagc cgcgaccatt 60
tcgacaacaa caaccatatc cacaaccgca accacagtat tcgcaaccac aacaacc 117

<210> SEQ ID NO 388
<211> LENGTH: 132
<212> TYPE: DNA
<213> ORGANISM: Artificial Sequence
<220> FEATURE:
<223> OTHER INFORMATION: fig 4c contin 4

<400> SEQUENCE: 388
atatctgcaa ctgcaaccat ttccacaacc gcaaccattt ccgccacaac taccatatcc 60
gcagccacca ccattttcac cacaacaacc atatccacaa ccgcaaccac agtatccgca 120
accacaacaa cc 132

<210> SEQ ID NO 389
<211> LENGTH: 114
<212> TYPE: DNA
<213> ORGANISM: Artificial Sequence
<220> FEATURE:
<223> OTHER INFORMATION: fig 4c contin 5

<400> SEQUENCE: 389
atattcgcaa ccgtaaccat ttccgccaca actaccatat ccacaagcgc aaccatttcc 60
aacacaacaa ccatatccac aaccgcaacc acagtatccg caaccacaac aacc 114

<210> SEQ ID NO 390
<211> LENGTH: 117
<212> TYPE: DNA
<213> ORGANISM: Artificial Sequence
<220> FEATURE:
<223> OTHER INFORMATION: fig 4c contin 6

<400> SEQUENCE: 390
atatctacag ctgcaaccat ttccgcagcc gcaactacca tattcgcagc cgcaaccatt 60
tcgaccacaa caaccatatc tacaaccgca accacagtat tcgcaaccac aacaacc 117

<210> SEQ ID NO 391
<211> LENGTH: 114
<212> TYPE: DNA
<213> ORGANISM: Artificial Sequence
<220> FEATURE:
<223> OTHER INFORMATION: fig 4c contin 7

<400> SEQUENCE: 391
atatccgcag ccgcaaccat ttctgccaca actaccatat ccgcagccgc aaccatttcc 60
accacaacaa tcatatccac aaccacaacc acaatatccg caaccacaac aacc 114

<210> SEQ ID NO 392
<211> LENGTH: 117
<212> TYPE: DNA
<213> ORGANISM: Artificial Sequence
<220> FEATURE:
<223> OTHER INFORMATION: fig 4c contin 8

<400> SEQUENCE: 392
atatctgcag ctgcaaccat ttccgcagcc gcaactacca tattcgcagc cacaaccatt 60
tcgaccacaa caaccatatc cacaaccgca accacagtat tcgcaaccac aacaacc 117

<210> SEQ ID NO 393
<211> LENGTH: 114
<212> TYPE: DNA
<213> ORGANISM: Artificial Sequence
<220> FEATURE:
<223> OTHER INFORMATION: fig 4c contin 8

<400> SEQUENCE: 393
atatccacag ccgcaaccat ttcctccaca actaccatgt ccgcagccgc aaccatttcc 60
accacaacaa tcatatccac aaccacaacc acagtatccg caaccacaac aacc 114

<210> SEQ ID NO 394
<211> LENGTH: 114
<212> TYPE: DNA
<213> ORGANISM: Artificial Sequence
<220> FEATURE:
<223> OTHER INFORMATION: fig 4c contin 9

<400> SEQUENCE: 394
atatccacag ccgcaaccat ttcctccaca actaccatgt ccgcagccgc aaccatttcc 60
accacaacaa tcatatccac aaccacaacc acagtatccg caaccacaac aacc 114

<210> SEQ ID NO 395
<211> LENGTH: 117
<212> TYPE: DNA
<213> ORGANISM: Artificial Sequence
<220> FEATURE:
<223> OTHER INFORMATION: fig 4c contin 10

<400> SEQUENCE: 395
atatctgcag ttgcaaccat ttccgcagcc gcaactacca tattctcagc cgcaaccatt 60
tcgaccacaa caaccatatc cacaactgca accacagtat tcgcaaccac aacaacc 117

<210> SEQ ID NO 396
<211> LENGTH: 117
<212> TYPE: DNA
<213> ORGANISM: Artificial Sequence
<220> FEATURE:
<223> OTHER INFORMATION: fig 4c contin 11

<400> SEQUENCE: 396
atatctgcag ctgcaaccat tttcgcagcc gcaactacca tattcgcagc cgcaaccatt 60
tcgaccacaa caaccatatc cacaaccgca accacagtat tcgcaaccac aacaacc 117

<210> SEQ ID NO 397

<211> LENGTH: 114
<212> TYPE: DNA
<213> ORGANISM: Artificial Sequence
<220> FEATURE:
<223> OTHER INFORMATION: fig 4c contin 12

<400> SEQUENCE: 397
atatccgcag ccgcaaccat ttctgccaca actaccatat ccgcagccgc aaccatttcc 60
accacaacaa tcatatccac aaccacaacc acaatatccg caaccacaac aacc 114

<210> SEQ ID NO 398
<211> LENGTH: 114
<212> TYPE: DNA
<213> ORGANISM: Artificial Sequence
<220> FEATURE:
<223> OTHER INFORMATION: fig 4c contin 14

<400> SEQUENCE: 398
atatccgcag ccgcaaccat ttcctccaca actaccatgt ccgcaaccgc aaccatttcc 60
accacaacaa tcatatccac aaccacaacc acagtatccg caaccacaac aacc 114

<210> SEQ ID NO 399
<211> LENGTH: 114
<212> TYPE: DNA
<213> ORGANISM: Artificial Sequence
<220> FEATURE:
<223> OTHER INFORMATION: fig 4c contin 15

<400> SEQUENCE: 399
atatccgcag ccgcaaccat ttctgccaca actaccatat ccgcagccgc aaccattttc 60
accacaacaa tcatatccac aaccacaacc acaatatccg caaccacaac aacc 114

<210> SEQ ID NO 400
<211> LENGTH: 114
<212> TYPE: DNA
<213> ORGANISM: Artificial Sequence
<220> FEATURE:
<223> OTHER INFORMATION: fig 4c contin 17

<400> SEQUENCE: 400
atatccgcag ccgcaaccat ttctgccaca actaccatat ccgcagccgc aaccatttcc 60
accacaacaa tcatatccac aaccacaacc acaatatccg caaccacaac aacc 114

<210> SEQ ID NO 401
<211> LENGTH: 117
<212> TYPE: DNA
<213> ORGANISM: Artificial Sequence
<220> FEATURE:
<223> OTHER INFORMATION: fig 4c contin 18

<400> SEQUENCE: 401
atatctacag ctgcaaccat ttccacagct gcaacaacca tattcgcagc cgcaaccatt 60
tcgaccacaa caaccatatc cacaaccgca accacagtat tcgcaaccac aacaacc 117

<210> SEQ ID NO 402
<211> LENGTH: 117
<212> TYPE: DNA
<213> ORGANISM: Artificial Sequence
<220> FEATURE:
<223> OTHER INFORMATION: fig 4c contin 19

<400> SEQUENCE: 402
atatctgcag ctgcaaccat tttcgcagcc gcaactacca tattcacagc cgcgaccatt 60
tcgacaacaa caaccatatc cacaaccgca accacagtat ccgcaaccac aacaacc 117

<210> SEQ ID NO 403
<211> LENGTH: 117
<212> TYPE: DNA
<213> ORGANISM: Artificial Sequence
<220> FEATURE:
<223> OTHER INFORMATION: fig 4c contin 20

<400> SEQUENCE: 403
atatctgcag ctgcaaccat ttccgcagcc gcaactacca tattcgcatc cacaaccatt 60
tcgaccacaa caaccatatc cacaaccgca accacagtat tcgcaaccac aacaacc 117

<210> SEQ ID NO 404
<211> LENGTH: 114
<212> TYPE: DNA
<213> ORGANISM: Artificial Sequence
<220> FEATURE:
<223> OTHER INFORMATION: fig 4c contin 21

<400> SEQUENCE: 404
atttctgcag ccgcaaccat ttctgctaca actaccatat ccgcagccac aaccatttcc 60
accacaacaa ccatatccac aaccgcaacc acagtatccg caaccacaac aacc 114

<210> SEQ ID NO 405
<211> LENGTH: 117
<212> TYPE: DNA
<213> ORGANISM: Artificial Sequence
<220> FEATURE:
<223> OTHER INFORMATION: fig 4c contin 22

<400> SEQUENCE: 405
atatctacag ctgcaaccat ttccgcagcc gcaactacca tattcgcagc cgcaaccatt 60
tcgaccacaa caaccatatc tacaaccgca accacagtat ccgcaaccac aacaacc 117

<210> SEQ ID NO 406
<211> LENGTH: 117
<212> TYPE: DNA
<213> ORGANISM: Artificial Sequence
<220> FEATURE:
<223> OTHER INFORMATION: fig 4c contin 23

<400> SEQUENCE: 406
atatctgcag ctgcaaccat ttccgcagcc gcaactacca tattcgcagc cacaaccatt 60
tcgaccacaa caaccatatc cacaaccgca accacagtat tcgcaaccac aacaacc 117

<210> SEQ ID NO 407
<211> LENGTH: 117
<212> TYPE: DNA
<213> ORGANISM: Artificial Sequence
<220> FEATURE:
<223> OTHER INFORMATION: fig 4c contin 24

<400> SEQUENCE: 407
atatctgcag ctgcaaccat ttccacagcc gcaactacca tattcacagc cacaaccatt 60
tcggccacaa caaccatatc cacaaccgca accacagtat tcgcaaccac aacaacc 117

<210> SEQ ID NO 408

<211> LENGTH: 117
<212> TYPE: DNA
<213> ORGANISM: Artificial Sequence
<220> FEATURE:
<223> OTHER INFORMATION: fig 4c contin 25

<400> SEQUENCE: 408
atatctgcaa ctgcaaccat ttccgcagcc gcaactacca tattcgcagc cacaaccatt 60
tcgaccacaa caaccatatc cacaaccgca accacagtat tcgcaaccac aacaacc 117

<210> SEQ ID NO 409
<211> LENGTH: 117
<212> TYPE: DNA
<213> ORGANISM: Artificial Sequence
<220> FEATURE:
<223> OTHER INFORMATION: fig 4c contin 26

<400> SEQUENCE: 409
atatctgcag ttgcaaccat ttccgcagcc gcaactacca tattcgcagc cgcaaccatt 60
tcgaccacaa caaccatatc cacaactgta accacagtat tcgcaaccac aacaacc 117

<210> SEQ ID NO 410
<211> LENGTH: 117
<212> TYPE: DNA
<213> ORGANISM: Artificial Sequence
<220> FEATURE:
<223> OTHER INFORMATION: fig 4c contin 27

<400> SEQUENCE: 410
atatctgcag ctgcaaccat ttccgcagcc gcaactacca tattcgcagc cacaaccatt 60
tcgaccacaa caaccatatc cacaaccgca accacagtat tcgcaaccac aacaacc 117

<210> SEQ ID NO 411
<211> LENGTH: 117
<212> TYPE: DNA
<213> ORGANISM: Artificial Sequence
<220> FEATURE:
<223> OTHER INFORMATION: fig 4c contin 29

<400> SEQUENCE: 411
atatctgcag ctgcaaccat ttccgcagcc gcaactacca tattcgcagc cacaaccatt 60
tcgaccacaa caaccatatc cacaaccgca accacagtat ccgcaaccac aacaacc 117

<210> SEQ ID NO 412
<211> LENGTH: 117
<212> TYPE: DNA
<213> ORGANISM: Artificial Sequence
<220> FEATURE:
<223> OTHER INFORMATION: fig 4c contin 30

<400> SEQUENCE: 412
atatctgcag ctgcaaccat ttccgcagct gcaactacca tatttgcagc cacaaccatt 60
tcgaccacaa caaccatatc cacaaccgca accacagtat tcgcaaccac aacaacc 117

<210> SEQ ID NO 413
<211> LENGTH: 117
<212> TYPE: DNA
<213> ORGANISM: Artificial Sequence
<220> FEATURE:
<223> OTHER INFORMATION: fig 4c contin 31

<400> SEQUENCE: 413
atatctgcag ctgcaaccat ttccgcagct gcaactacca tatttgcagc cacaaccatt 60
tcgaccacaa caaccatatc cacaaccgca accacagtat tcgcaaccac aacaacc 117

<210> SEQ ID NO 414
<211> LENGTH: 117
<212> TYPE: DNA
<213> ORGANISM: Artificial Sequence
<220> FEATURE:
<223> OTHER INFORMATION: fig 4c contin 35

<400> SEQUENCE: 414
atatctgcag ctgcaaccat ttccgcagcc gcaactacca tatttgcagc cacaaccatt 60
tcgaccacaa caaccatatc cacaaccgca accacagtat tcgcaaccac aacaacc 117

<210> SEQ ID NO 415
<211> LENGTH: 117
<212> TYPE: DNA
<213> ORGANISM: Artificial Sequence
<220> FEATURE:
<223> OTHER INFORMATION: fig 4c contin 36

<400> SEQUENCE: 415
atatctgcag ttgcaaccat ttccgcagcc gcaactacca tattctcagc cgcaaccatt 60
tcgaccacaa caaccatatc cacaactgca accacagtat ccgcaaccac aacaacc 117

<210> SEQ ID NO 416
<211> LENGTH: 117
<212> TYPE: DNA
<213> ORGANISM: Artificial Sequence
<220> FEATURE:
<223> OTHER INFORMATION: fig 4c contin 39

<400> SEQUENCE: 416
atatctgcag ctgcaaccat ttccgcagcc gcaactacca tattcgcagc cgcaaccatt 60
tcgaccacaa caaccaaatc cacaaccgca accacagtat tcgcaaccac aacaacc 117

<210> SEQ ID NO 417
<211> LENGTH: 117
<212> TYPE: DNA
<213> ORGANISM: Artificial Sequence
<220> FEATURE:
<223> OTHER INFORMATION: fig 4c contin 42

<400> SEQUENCE: 417
atatctgcag ctgcaaccat ttccgtagcc gcaactacca tatttgcagc cacaaccatt 60
tcgaccacaa caaccatatc cacaaccgca accacaatat tcgcaaccac aacaacc 117

<210> SEQ ID NO 418
<211> LENGTH: 117
<212> TYPE: DNA
<213> ORGANISM: Artificial Sequence
<220> FEATURE:
<223> OTHER INFORMATION: fig 4c contin 43

<400> SEQUENCE: 418
atatctgcaa ctgcaaccat ttccgcagcc gcaactacca tattcgcaac cacaaccatt 60
tcgaccacaa caaccatatc cacaaccgca accacagtat tcgcaaccac aacaacc 117

<210> SEQ ID NO 419

<211> LENGTH: 117
<212> TYPE: DNA
<213> ORGANISM: Artificial Sequence
<220> FEATURE:
<223> OTHER INFORMATION: fig 4c contin 45

<400> SEQUENCE: 419
atatctgcaa ctgcaaccat ttccgcagcc gcaactacca tattcgcagc cacaaccatt 60
tcgaccacaa caaccatatc cacaaccgca accacagtat tcgcaaccac aacaacc 117

<210> SEQ ID NO 420
<211> LENGTH: 117
<212> TYPE: DNA
<213> ORGANISM: Artificial Sequence
<220> FEATURE:
<223> OTHER INFORMATION: fig 4c contin 47

<400> SEQUENCE: 420
atatctgcag ctgcaaccat ttccgcagcc gcaactacca tattcgcatc cacaaccatt 60
tcgaccacaa caaccatatc cacaaccgca accacagtat ccgcaaccac aacaacc 117

<210> SEQ ID NO 421
<211> LENGTH: 117
<212> TYPE: DNA
<213> ORGANISM: Artificial Sequence
<220> FEATURE:
<223> OTHER INFORMATION: fig 4c contin 49

<400> SEQUENCE: 421
atatctgcag ctgcaaccat ttccgcagcc gcaactacca tattcacagc cacaaccatt 60
tcgaccacaa aaaccatatc cacaaccgca accacagtat tcgcaaccac aacaacc 117

<210> SEQ ID NO 422
<211> LENGTH: 117
<212> TYPE: DNA
<213> ORGANISM: Artificial Sequence
<220> FEATURE:
<223> OTHER INFORMATION: fig 4c contin 50

<400> SEQUENCE: 422
atatctgcag ctgcaaccat ttccgcagcc gcaactacca tattcacagc cacaaccatt 60
tcgaccacaa caaccatatc cacaaccaca accacagtat tcgcaaccac aacaacc 117

<210> SEQ ID NO 423
<211> LENGTH: 118
<212> TYPE: DNA
<213> ORGANISM: Artificial Sequence
<220> FEATURE:
<223> OTHER INFORMATION: fig 4c contin 57

<400> SEQUENCE: 423
atatctgtag ctgcaaccat tttcgcagcc gcaactaccc atattcgcag ccccaaccat 60
ttcgaccaca acaaccatat ccacaaccgc aaccacagta ttcgcaacca caacaacc 118

<210> SEQ ID NO 424
<211> LENGTH: 117
<212> TYPE: DNA
<213> ORGANISM: Artificial Sequence
<220> FEATURE:
<223> OTHER INFORMATION: fig 4c contin 63

<400> SEQUENCE: 424
atatctgcag ctgcaaccat ttccgcagcc gcaactacca tattcacagc cacaaccatt 60
tcgaccacaa caaccatatc cacaaccaca accacagtat tcgcaaccac aacaacc 117

<210> SEQ ID NO 425
<211> LENGTH: 117
<212> TYPE: DNA
<213> ORGANISM: Artificial Sequence
<220> FEATURE:
<223> OTHER INFORMATION: fig 4c contin 67

<400> SEQUENCE: 425
atatctgcaa ctgcaaccat ttccgcagcc gcaactacca tattcgcagc cacaaccatt 60
tcgaccacaa caaccatatc cacaaccgca accacagtat ccgcaaccac aacaacc 117

<210> SEQ ID NO 426
<211> LENGTH: 117
<212> TYPE: DNA
<213> ORGANISM: Artificial Sequence
<220> FEATURE:
<223> OTHER INFORMATION: fig 4c contin 70

<400> SEQUENCE: 426
atatctgcag ctgcaaccat ttccgcagcc gcaactacca tattcgcagc cacaaccatt 60
tcgaccacaa caaccatatc cacaaccgca accacagtat ccgcaaccac aacaacc 117

<210> SEQ ID NO 427
<211> LENGTH: 117
<212> TYPE: DNA
<213> ORGANISM: Artificial Sequence
<220> FEATURE:
<223> OTHER INFORMATION: fig 4c contin 74

<400> SEQUENCE: 427
atatctgcag ctgcaaccat ttccgcagcc gcaagtacca tattcgcagc cacaaccatt 60
tcgaccacaa caaccatatc cacaaccgca accacagtat tcgcaaccac aacaacc 117

<210> SEQ ID NO 428
<211> LENGTH: 117
<212> TYPE: DNA
<213> ORGANISM: Artificial Sequence
<220> FEATURE:
<223> OTHER INFORMATION: fig 4c contin 79

<400> SEQUENCE: 428
atatctgcag ctgcaaccat ttccgcagcc gcaagtacca tattcgcagc cacaaccatt 60
tcgaccacaa caaccatatc cacaaccgca accacaatat tcgcaaccac aacaacc 117

<210> SEQ ID NO 429
<211> LENGTH: 106
<212> TYPE: PRT
<213> ORGANISM: Artificial Sequence
<220> FEATURE:
<223> OTHER INFORMATION: bw208 wt 429

<400> SEQUENCE: 429

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Pro Gln Pro
50 55 60

Gln Leu Pro Tyr Pro Gln Pro Gln Leu Pro Tyr Pro Gln Pro Gln Leu
65 70 75 80

Pro Tyr Pro Gln Pro Gln Pro Phe Arg Pro Gln Gln Pro Tyr Pro Gln
85 90 95

Ser Gln Pro Gln Tyr Ser Gln Pro Gln Gln
100 105

<210> SEQ ID NO 430
<211> LENGTH: 99
<212> TYPE: PRT
<213> ORGANISM: Artificial Sequence
<220> FEATURE:
<223> OTHER INFORMATION: bw208 wt 430

<400> SEQUENCE: 430

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Pro Gln Pro
50 55 60

Gln Leu Pro Tyr Pro Gln Pro Gln Leu Pro Tyr Pro Gln Pro Gln Pro
65 70 75 80

Phe Arg Pro Gln Gln Pro Tyr Pro Gln Pro Gln Pro Gln Tyr Ser Gln
85 90 95

Pro Gln Gln

<210> SEQ ID NO 431
<211> LENGTH: 99
<212> TYPE: PRT
<213> ORGANISM: Artificial Sequence
<220> FEATURE:
<223> OTHER INFORMATION: bw208 wt 431

<400> SEQUENCE: 431

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Pro Gln Pro
50 55 60

Gln Leu Pro Tyr Pro Gln Pro Gln Leu Pro Tyr Pro Gln Pro Gln Pro
65 70 75 80

Phe Arg Pro Gln Gln Pro Tyr Pro Gln Ser Gln Pro Gln Tyr Ser Gln
85 90 95

Pro Gln Gln

<210> SEQ ID NO 432
<211> LENGTH: 92
<212> TYPE: PRT

<213> ORGANISM: Artificial Sequence
<220> FEATURE:
<223> OTHER INFORMATION: bw208 wt 432

<400> SEQUENCE: 432

```
Val Arg Val Pro Val Pro Gln Leu Gln Pro Gln Asn Pro Ser Gln Gln
1               5                   10                  15

His Pro Gln Glu Gln Val Pro Leu Val Gln Gln Gln Gln Phe Leu Gly
            20                  25                  30

Gln Gln Gln Ser Phe Pro Pro Gln Gln Pro Tyr Pro Gln Pro Gln Pro
        35                  40                  45

Phe Pro Ser Gln Gln Pro Tyr Leu Gln Leu Gln Pro Phe Pro Gln Pro
    50                  55                  60

Gln Leu Pro Tyr Leu Gln Pro Gln Pro Phe Arg Pro Gln Gln Pro Tyr
65                  70                  75                  80

Pro Gln Pro Gln Pro Gln Tyr Ser Gln Pro Gln Gln
                85                  90
```

<210> SEQ ID NO 433
<211> LENGTH: 92
<212> TYPE: PRT
<213> ORGANISM: Artificial Sequence
<220> FEATURE:
<223> OTHER INFORMATION: bw208 wt 433

<400> SEQUENCE: 433

```
Val Arg Val Pro Val Pro Gln Leu Gln Pro Gln Asn Pro Ser Gln Gln
1               5                   10                  15

His Pro Gln Glu Gln Val Pro Leu Val Gln Gln Gln Gln Phe Leu Gly
            20                  25                  30

Gln Gln Gln Ser Phe Pro Pro Gln Gln Pro Tyr Pro Gln Pro Gln Pro
        35                  40                  45

Phe Pro Ser Gln Gln Pro Tyr Leu Gln Leu Gln Pro Phe Pro Gln Pro
    50                  55                  60

Gln Leu Pro Tyr Leu Gln Pro Gln Pro Phe Arg Pro Gln Gln Pro Tyr
65                  70                  75                  80

Pro Gln Pro Gln Pro Gln Tyr Ser Gln Pro Gln Gln
                85                  90
```

<210> SEQ ID NO 434
<211> LENGTH: 92
<212> TYPE: PRT
<213> ORGANISM: Artificial Sequence
<220> FEATURE:
<223> OTHER INFORMATION: bw208 wt 434

<400> SEQUENCE: 434

```
Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Pro Gln Arg Gln Pro
        35                  40                  45

Phe Pro Ser Gln Gln Pro Tyr Leu Gln Leu Gln Pro Phe Pro Gln Pro
    50                  55                  60

Gln Leu Ser Tyr Ser Gln Pro Gln Pro Phe Arg Pro Gln Gln Pro Tyr
65                  70                  75                  80

Pro Gln Pro Gln Pro Gln Tyr Ser Gln Pro Gln Gln
                85                  90
```

<210> SEQ ID NO 435
<211> LENGTH: 92
<212> TYPE: PRT
<213> ORGANISM: Artificial Sequence
<220> FEATURE:
<223> OTHER INFORMATION: bw208 wt 435

<400> SEQUENCE: 435

```
Val Arg Val Pro Val Pro Gln Leu Gln Pro Ile Ile Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Pro Gln Pro Gln Pro
        35                  40                  45

Phe Pro Ser Gln Gln Pro Tyr Leu Gln Leu Gln Pro Phe Pro Gln Pro
    50                  55                  60

Gln Leu Pro Tyr Ser Gln Pro Gln Pro Phe Arg Pro Gln Gln Pro Tyr
65                  70                  75                  80

Pro Gln Pro Gln Pro Gln Tyr Ser Gln Pro Gln Gln
                85                  90
```

<210> SEQ ID NO 436
<211> LENGTH: 92
<212> TYPE: PRT
<213> ORGANISM: Artificial Sequence
<220> FEATURE:
<223> OTHER INFORMATION: bw208 wt 436

<400> SEQUENCE: 436

```
Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Pro Gln Pro Gln Pro
        35                  40                  45

Phe Pro Ser Gln Gln Pro Tyr Leu Gln Leu Gln Pro Phe Pro Gln Pro
    50                  55                  60

Gln Leu Pro Tyr Ser Gln Pro Gln Pro Phe Arg Pro Gln Gln Pro Tyr
65                  70                  75                  80

Pro Gln Pro Gln Pro Gln Tyr Ser Gln Pro Gln Gln
                85                  90
```

<210> SEQ ID NO 437
<211> LENGTH: 92
<212> TYPE: PRT
<213> ORGANISM: Artificial Sequence
<220> FEATURE:
<223> OTHER INFORMATION: bw208 wt 437

<400> SEQUENCE: 437

```
Val Arg Val Pro Val Pro Gln Leu Gln Pro Gln Asn Pro Ser Gln Gln
1               5                   10                  15

Gln Pro Gln Glu Gln Val Glu Leu Val Gln Gln Gln Gln Phe Leu Gly
            20                  25                  30

Gln Gln Gln Pro Phe Pro Pro Gln Gln Pro Tyr Pro Gln Pro Gln Pro
        35                  40                  45

Phe Pro Ser Gln Gln Pro Tyr Leu Gln Leu Gln Pro Phe Pro Gln Pro
    50                  55                  60
```

Gln Leu Pro Tyr Ser Gln Pro Gln Pro Phe Arg Pro Gln Gln Pro Tyr
65 70 75 80

Pro Gln Pro Gln Pro Gln Tyr Ser Gln Pro Gln Gln
85 90

<210> SEQ ID NO 438
<211> LENGTH: 72
<212> TYPE: PRT
<213> ORGANISM: Artificial Sequence
<220> FEATURE:
<223> OTHER INFORMATION: bw208 wt 438

<400> SEQUENCE: 438

Val Arg Val Pro Val Pro Gln Leu Gln Pro Gln Asn Pro Ser Gln Gln
1 5 10 15

Pro Gln Glu Gln Val Pro Leu Val Gln Gln Gln Gln Phe Leu Gly Gln
20 25 30

Gln Gln Pro Phe Pro Pro Gln Gln Pro Tyr Pro Gln Pro Gln Pro Phe
35 40 45

Pro Ser Gln Gln Pro Tyr Leu Gln Leu Gln Pro Phe Pro Gln Pro Gln
50 55 60

Leu Pro Tyr Ser Gln Pro Gln Gln
65 70

<210> SEQ ID NO 439
<211> LENGTH: 92
<212> TYPE: PRT
<213> ORGANISM: Artificial Sequence
<220> FEATURE:
<223> OTHER INFORMATION: bw208 wt 439

<400> SEQUENCE: 439

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Ser Gln Pro
50 55 60

Gln Leu Pro Tyr Ser Gln Pro Gln Pro Phe Arg Glu Gln Gln Pro Tyr
65 70 75 80

Pro Gln Pro Gln Pro Gln Tyr Pro Gln Pro Gln Gln
85 90

<210> SEQ ID NO 440
<211> LENGTH: 92
<212> TYPE: PRT
<213> ORGANISM: Artificial Sequence
<220> FEATURE:
<223> OTHER INFORMATION: bw208 wt

<400> SEQUENCE: 440

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Ser Gln Pro
50 55 60

Gln Leu Pro Tyr Ser Gln Pro Gln Pro Phe Arg Pro Gln Gln Pro Tyr
65 70 75 80

Pro Gln Pro Gln Pro Gln Tyr Ser Gln Pro Gln Gln
85 90

<210> SEQ ID NO 441
<211> LENGTH: 80
<212> TYPE: PRT
<213> ORGANISM: Artificial Sequence
<220> FEATURE:
<223> OTHER INFORMATION: delections 441

<400> SEQUENCE: 441

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Leu Gln Leu Gln Pro
35 40 45

Phe Pro Gln Pro Gln Leu Pro Tyr Pro Gln Pro Gln Pro Phe Arg Pro
50 55 60

Gln Gln Pro Tyr Pro Gln Pro Gln Pro Gln Tyr Ser Gln Pro Gln Gln
65 70 75 80

<210> SEQ ID NO 442
<211> LENGTH: 80
<212> TYPE: PRT
<213> ORGANISM: Artificial Sequence
<220> FEATURE:
<223> OTHER INFORMATION: delections 442

<400> SEQUENCE: 442

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Ser Gln Gln Pro Tyr Leu Gln Leu Gln Pro
35 40 45

Phe Pro Gln Pro Gln Leu Pro Tyr Ser Gln Pro Gln Pro Phe Arg Pro
50 55 60

Gln Gln Pro Tyr Pro Gln Pro Gln Pro Gln Tyr Ser Gln Pro Gln Gln
65 70 75 80

<210> SEQ ID NO 443
<211> LENGTH: 84
<212> TYPE: PRT
<213> ORGANISM: Artificial Sequence
<220> FEATURE:
<223> OTHER INFORMATION: delections 443

<400> SEQUENCE: 443

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Pro Gln Gln Pro Tyr Pro Gln Pro Tyr Leu
35 40 45

```
Gln Leu Gln Pro Phe Pro Gln Pro Gln Leu Ser Tyr Ser Gln Pro Gln
    50                  55                  60

Pro Phe Arg Glu Gln Gln Pro Tyr Pro Gln Pro Gln Pro Gln Tyr Ser
65                  70                  75                  80

Gln Pro Gln Gln


<210> SEQ ID NO 444
<211> LENGTH: 105
<212> TYPE: PRT
<213> ORGANISM: Artificial Sequence
<220> FEATURE:
<223> OTHER INFORMATION: delections 444

<400> SEQUENCE: 444

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Pro Gly
            20                  25                  30

Gln Gln Gln Pro Phe Pro Pro Gln Gln Pro Tyr Pro Gln Pro Gln Phe
        35                  40                  45

Pro Ser Gln Gln Pro Tyr Leu Gln Leu Gln Pro Phe Pro Gln Pro Gln
    50                  55                  60

Leu Pro Tyr Pro Gln Pro Gln Leu Pro Tyr Pro Gln Pro Gln Leu Pro
65                  70                  75                  80

Tyr Pro Gln Pro Gln Pro Phe Arg Pro Gln Gln Pro Tyr Pro Gln Ser
                85                  90                  95

Gln Pro Gln Tyr Ser Gln Pro Gln Gln
            100                 105


<210> SEQ ID NO 445
<211> LENGTH: 96
<212> TYPE: PRT
<213> ORGANISM: Artificial Sequence
<220> FEATURE:
<223> OTHER INFORMATION: delections 445

<400> SEQUENCE: 445

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Pro Gly
            20                  25                  30

Gln Gln Gln Pro Phe Pro Pro Gln Gln Pro Tyr Pro Gln Pro Gln Ser
        35                  40                  45

Gln Gln Pro Tyr Leu Gln Leu Gln Pro Phe Pro Gln Pro Gln Leu Pro
    50                  55                  60

Tyr Pro Gln Pro Gln Leu Pro Tyr Pro Gln Pro Gln Pro Phe Arg Pro
65                  70                  75                  80

Gln Gln Pro Tyr Pro Gln Ser Gln Pro Gln Tyr Ser Gln Pro Gln Gln
                85                  90                  95


<210> SEQ ID NO 446
<211> LENGTH: 79
<212> TYPE: PRT
<213> ORGANISM: Artificial Sequence
<220> FEATURE:
<223> OTHER INFORMATION: delections 446

<400> SEQUENCE: 446

Val Arg Val Pro Val Pro Gln Leu Gln Pro Gln Asn Pro Ser Gln Gln
1               5                   10                  15
```

Gln Pro Gln Glu Gln Val Pro Leu Val Gln Gln Gln Gln Glu Leu Gly
20 25 30

Gln Gln Gln Pro Phe Pro Pro Gln Gln Pro Tyr Pro Gln Pro Gln Pro
35 40 45

Phe Leu Pro Gln Leu Pro Tyr Pro Arg Pro Gln Pro Phe Leu Pro Gln
50 55 60

Gln Pro Tyr Pro Gln Pro Glu Pro Gln Tyr Pro Gln Pro Gln Gln
65 70 75

<210> SEQ ID NO 447
<211> LENGTH: 67
<212> TYPE: PRT
<213> ORGANISM: Artificial Sequence
<220> FEATURE:
<223> OTHER INFORMATION: delections 447

<400> SEQUENCE: 447

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Tyr Pro Gly
20 25 30

Gln Gln Gln Pro Phe Pro Pro Gln Gln Pro Tyr Pro Gln Pro Gln Pro
35 40 45

Glu Pro Pro Gln Gln Ser Tyr Pro Gln Pro Gln Pro Gln Tyr Pro Gln
50 55 60

Pro Gln Gln
65

<210> SEQ ID NO 448
<211> LENGTH: 66
<212> TYPE: PRT
<213> ORGANISM: Artificial Sequence
<220> FEATURE:
<223> OTHER INFORMATION: delections 448

<400> SEQUENCE: 448

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Pro Pro Gln Pro Phe
35 40 45

Pro Pro Gln Gln Pro Tyr Pro Gln Pro Gln Pro Gln Tyr Pro Gln Pro
50 55 60

Gln Gln
65

<210> SEQ ID NO 449
<211> LENGTH: 55
<212> TYPE: PRT
<213> ORGANISM: Artificial Sequence
<220> FEATURE:
<223> OTHER INFORMATION: delections 449

<400> SEQUENCE: 449

Val Arg Val Pro Val Pro Gln Leu Gln Pro Gln Asn Pro Ser Gln Gln
1 5 10 15

Gln Pro Gln Glu Gln Val Pro Ile Asn Gln Gln Leu Gln Tyr Pro Gly
20 25 30

Gln Gln Gln Pro Phe Pro Pro Gln Gln Pro Tyr Pro Gln Pro Gln Pro
35 40 45

Gln Tyr Pro Gln Pro Gln Gln
50 55

<210> SEQ ID NO 450
<211> LENGTH: 68
<212> TYPE: PRT
<213> ORGANISM: Artificial Sequence
<220> FEATURE:
<223> OTHER INFORMATION: delections 450

<400> SEQUENCE: 450

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Pro Gln Gln Pro Tyr Pro Gln Pro Thr Thr
35 40 45

Ile Ser Thr Thr Thr Thr Ile Ser Thr Thr Ala Thr Thr Val Phe Ala
50 55 60

Thr Thr Thr Thr
65

<210> SEQ ID NO 451
<211> LENGTH: 85
<212> TYPE: PRT
<213> ORGANISM: Artificial Sequence
<220> FEATURE:
<223> OTHER INFORMATION: delections 451

<400> SEQUENCE: 451

Val Arg Val Pro Val Pro Gln Leu Gln Pro Gln Asn Pro Ser Gln Gln
1 5 10 15

Gln Pro Gln Glu Gln Val Pro Ile Asn Gln Gln Gln Gln Phe Leu Gly
20 25 30

Gln Gln Gln Pro Phe Pro Pro Gln Gln Pro Tyr Pro Gln Pro Gln Ser
35 40 45

Ala Ala Ala Thr Ile Ser Ala Ala Ala Thr Thr Ile Glu Thr Ala Thr
50 55 60

Thr Ile Ser Thr Thr Thr Thr Ile Ser Thr Thr Thr Thr Thr Val Phe
65 70 75 80

Ala Thr Thr Ile Thr
85

<210> SEQ ID NO 452
<211> LENGTH: 70
<212> TYPE: PRT
<213> ORGANISM: Artificial Sequence
<220> FEATURE:
<223> OTHER INFORMATION: delections 452

<400> SEQUENCE: 452

Val Arg Val Pro Val Pro Gln Leu Gln Pro Asn Pro Ser Gln Gln Gln
1 5 10 15

Pro Gln Glu Gln Val Pro Leu Val Gln Gln Gln Gln His Asn Asn His
20 25 30

Ile Cys Ser Cys Asn His Phe Arg Ser Arg Asn Tyr His Ile Arg Ser
35 40 45

His Asn His Phe Asp His Asn Asn His Ile His Asn Arg Asn His Ser
50 55 60

Ile Arg Asn His Asn Asn
65 70

<210> SEQ ID NO 453
<211> LENGTH: 73
<212> TYPE: PRT
<213> ORGANISM: Artificial Sequence
<220> FEATURE:
<223> OTHER INFORMATION: delections 453

<400> SEQUENCE: 453

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gly
20 25 30

Gln Gln Gln Pro Phe Pro Pro Gln Gln Pro Tyr Pro Gln Pro His His
35 40 45

Phe His His Asn Asn His Ile Cys Asn Cys Asn His Phe Arg Ser Arg
50 55 60

Asn Tyr His Ile Arg Asn His Asn Asn
65 70

<210> SEQ ID NO 454
<211> LENGTH: 118
<212> TYPE: PRT
<213> ORGANISM: Artificial Sequence
<220> FEATURE:
<223> OTHER INFORMATION: insertions 454

<400> SEQUENCE: 454

Val Arg Val Pro Val Pro Gln Leu Gln Pro Gln Asn Pro Ser Gln Gln
1 5 10 15

Gln Arg Gln Glu Gln Val Arg Ile Asn Gln Gln Gln Gln Phe Leu Gly
20 25 30

Gln Gln Gln Arg Phe Pro Arg Gln Gln Pro Tyr Pro Gln Pro Gln Asp
35 40 45

His Arg Asn Pro Ser Ser Pro Arg Pro Ala Thr Arg Arg Gly Arg Cys
50 55 60

Ser Val Ser Arg Phe Arg Ser Pro Gly Gln Cys His His Asn Asn His
65 70 75 80

Ile Cys Ser Cys Asn His Phe Arg Ser Arg Asn Tyr His Ile Arg Ser
85 90 95

Arg Asn His Phe Asp Glu Asn Asn His Ile His Asn Arg Asn His Ser
100 105 110

Ile Arg Asn His Asn Asn
115

<210> SEQ ID NO 455
<211> LENGTH: 104
<212> TYPE: PRT
<213> ORGANISM: Artificial Sequence
<220> FEATURE:
<223> OTHER INFORMATION: insertions 455

<400> SEQUENCE: 455

Val Arg Ile Ile Arg Val Arg Gln Leu Gln Arg Gln Asn Pro Ser Gln
1 5 10 15

```
Gln His Arg Gln Glu Gln Val Arg Leu Tyr Gln Gln Gln Gln Phe Leu
            20                  25                  30

Gly Gln Gln Gln Ser Phe Pro Arg Gln Gln Pro Tyr Arg Gln Pro Gln
        35                  40                  45

Arg Phe Phe Asn Trp Ile Cys Asn Asn Lys Thr Pro Phe Pro Ser Gln
    50                  55                  60

Gln Pro Tyr Leu Gln Leu Gln Pro Phe Ser Gln Pro Gln Leu Pro Tyr
65                  70                  75                  80

Ser Gln Pro Gln Pro Phe Arg Pro Gln Gln Pro Tyr Pro Gln Pro Gln
                85                  90                  95

Pro Gln Tyr Ser Gln Pro Gln Gln
            100


<210> SEQ ID NO 456
<211> LENGTH: 104
<212> TYPE: PRT
<213> ORGANISM: Artificial Sequence
<220> FEATURE:
<223> OTHER INFORMATION: insertions 456

<400> SEQUENCE: 456

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Leu Arg Tyr Pro Leu
        35                  40                  45

Ile Leu Trp Ile Thr Val Leu Pro Pro Leu Ser Pro Phe Pro Ser Gln
    50                  55                  60

Gln Pro Tyr Leu Gln Leu Gln Pro Phe Ser Gln Pro Gln Leu Pro Tyr
65                  70                  75                  80

Ser Gln Pro Gln Pro Phe Arg Pro Gln Gln Pro Tyr Pro Gln Pro Gln
                85                  90                  95

Pro Gln Tyr Ser Gln Pro Gln Gln
            100


<210> SEQ ID NO 457
<211> LENGTH: 106
<212> TYPE: PRT
<213> ORGANISM: Artificial Sequence
<220> FEATURE:
<223> OTHER INFORMATION: insertions 457

<400> SEQUENCE: 457

Val Arg Val Phe Val Phe Gln Gln Pro Gln Asn Pro Ser Gln Gln Gln
1               5                   10                  15

Pro Gln Glu Gln Val Arg Ile Met Gln Gln Gln Gln Phe Leu Gly Gln
            20                  25                  30

Gln Gln Arg Phe Pro Phe Gln Gln Pro Tyr Pro Gln Pro Gly Asn Arg
        35                  40                  45

Leu Ala Ala Pro Arg Ile Met Gln His Phe Phe Gly Val Pro Phe Pro
    50                  55                  60

Ser Gln Gln Pro Tyr Leu Gln Leu Gln Pro Phe Ser Gln Pro Gln Leu
65                  70                  75                  80

Pro Tyr Ser Gln Pro Gln Pro Phe Arg Pro Gln Gln Pro Tyr Pro Gln
                85                  90                  95

Pro Gln Pro Gln Tyr Ser Gln Pro Gln Gln
            100                 105
```

<210> SEQ ID NO 458
<211> LENGTH: 108
<212> TYPE: PRT
<213> ORGANISM: Artificial Sequence
<220> FEATURE:
<223> OTHER INFORMATION: insertions 458

<400> SEQUENCE: 458

```
Val Arg Val Phe Val Phe Gln Leu Gln Pro Gln Asn Pro Ser Gln Gln
1               5                   10                  15

Gln Pro Gln Glu Gln Val Phe Leu Tyr Gln Gln Gln Gln Phe Leu Gly
            20                  25                  30

Gln Gln Gln Pro Phe Pro Pro Gln Gln Pro Tyr Pro Gln Pro Gln Arg
        35                  40                  45

Gly Phe Arg Arg Ala Gly Arg His Gly Gln Cys Val Gly Leu Arg Pro
    50                  55                  60

Pro Phe Pro Ser Gln Gln Pro Tyr Leu Gln Leu Gln Pro Phe Pro Gln
65                  70                  75                  80

Pro Gln Leu Ser Tyr Gln Pro Gln Pro Phe Arg Pro Gln Gln Leu Tyr
                85                  90                  95

Pro Gln Pro Gln Pro Gln Tyr Ser Gln Pro Gln Gln
            100                 105
```

<210> SEQ ID NO 459
<211> LENGTH: 100
<212> TYPE: PRT
<213> ORGANISM: Artificial Sequence
<220> FEATURE:
<223> OTHER INFORMATION: THA53 wt 459

<400> SEQUENCE: 459

```
Val Arg Val Pro Val Pro Gln Leu Gln Pro Gln Asn Pro Ser Gln Gln
1               5                   10                  15

Gln Pro Gln Glu Cys Ala Ile Pro Leu Val Gln Gln Gln Gln Phe Pro
            20                  25                  30

Gly Gln Gln Gln Pro Phe Pro Pro Gln Gln Pro Tyr Pro Gln Pro Gln
        35                  40                  45

Pro Glu Pro Ser Gln Gln Pro Tyr Leu Gln Leu Gln Pro Phe Pro Gln
    50                  55                  60

Pro Gln Leu Pro Tyr Pro Gln Pro Gln Leu Pro Tyr Pro Gln Pro Gln
65                  70                  75                  80

Pro Phe Arg Pro Gln Gln Pro Tyr Pro Gln Pro Gln Pro Gln Tyr Ser
                85                  90                  95

Gln Pro Gln Gln
            100
```

<210> SEQ ID NO 460
<211> LENGTH: 92
<212> TYPE: PRT
<213> ORGANISM: Artificial Sequence
<220> FEATURE:
<223> OTHER INFORMATION: THA53 wt 460

<400> SEQUENCE: 460

```
Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30
```

Gln Gln Gln Gln Phe Pro Thr Gln Gln Pro Tyr Leu Gln Pro Gln Pro
35 40 45

Glu Pro Ser Gln Gln Pro Tyr Leu Gln Leu Gln Pro Phe Ser Gln Pro
50 55 60

Gln Leu Pro Ile Phe Ala Ala Ala Thr Ile Ser Thr Thr Thr Thr Ile
65 70 75 80

Ser Thr Thr Ala Thr Thr Val Phe Ala Thr Thr Thr
85 90

<210> SEQ ID NO 461
<211> LENGTH: 92
<212> TYPE: PRT
<213> ORGANISM: Artificial Sequence
<220> FEATURE:
<223> OTHER INFORMATION: THA53 wt 461

<400> SEQUENCE: 461

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Pro Gly
20 25 30

Gln Gln Gln Pro Phe Pro Pro Gln Gln Pro Tyr Pro Gln Pro Gln Pro
35 40 45

Phe Pro Ser Gln Gln Pro Tyr Leu Gln Leu Gln Pro Phe Pro Gln Pro
50 55 60

Gln Leu Pro Tyr Pro Gln Pro Gln Pro Phe Arg Pro Gln Gln Pro Tyr
65 70 75 80

Pro Gln Pro Gln Pro Gln Tyr Ser Gln Pro Gln Gln
85 90

<210> SEQ ID NO 462
<211> LENGTH: 85
<212> TYPE: PRT
<213> ORGANISM: Artificial Sequence
<220> FEATURE:
<223> OTHER INFORMATION: THA53 wt 462

<400> SEQUENCE: 462

Val Arg Val Pro Val Pro Gln Leu Gln Pro Gln Asn Pro Ser His Pro
1 5 10 15

Gln Glu Gln Val Pro Leu Val Phe Leu Gly Gln Gln Gln Ser Phe Pro
20 25 30

Pro Gln Gln Pro Tyr Pro Gln Pro Gln Pro Phe Pro Ser Gln Gln Pro
35 40 45

Tyr Leu Gln Leu Gln Pro Phe Pro Gln Pro Gln Leu Pro Tyr Leu Gln
50 55 60

Pro Gln Pro Phe Arg Pro Gln Gln Pro Tyr Pro Gln Pro Gln Pro Gln
65 70 75 80

Tyr Ser Pro Gln Gln
85

<210> SEQ ID NO 463
<211> LENGTH: 84
<212> TYPE: PRT
<213> ORGANISM: Artificial Sequence
<220> FEATURE:
<223> OTHER INFORMATION: delections 463

<400> SEQUENCE: 463

Val Arg Val Pro Val Pro Gln Leu Gln Pro Gln Asn Pro Ser Gln Gln
1 5 10 15

Pro Glu Gln Val Pro Leu Val Gln Gln Gln Gln Phe Leu Gly Gln Gln
20 25 30

Gln Pro Phe Pro Pro Gln Gln Pro Phe Pro Ser Gln Leu Pro Tyr Leu
35 40 45

Gln Leu Gln Pro Phe Pro Gln Pro Gln Leu Pro Tyr Ser Gln Pro Gln
50 55 60

Pro Phe Arg Pro Gln Gln Pro Tyr Pro Gln Pro Gln Pro Gln Tyr Ser
65 70 75 80

Gln Pro Gln Gln

<210> SEQ ID NO 464
<211> LENGTH: 79
<212> TYPE: PRT
<213> ORGANISM: Artificial Sequence
<220> FEATURE:
<223> OTHER INFORMATION: delections 464

<400> SEQUENCE: 464

Val Arg Val Pro Val Pro Gln Leu Gln Pro Gln Asn Pro Ser Gln Gln
1 5 10 15

His Gln Glu Gln Val Pro Leu Val Gln Gln Gln Gln Phe Leu Gly Gln
20 25 30

Gln Gln Pro Phe Pro Ser Gln Gln Pro Tyr Leu Gln Leu Gln Pro Phe
35 40 45

Pro Gln Pro Gln Leu Pro Tyr Leu Gln Pro Gln Pro Phe Arg Pro Gln
50 55 60

Gln Pro Tyr Pro Gln Pro Gln Pro Gln Tyr Ser Gln Pro Gln Gln
65 70 75

<210> SEQ ID NO 465
<211> LENGTH: 80
<212> TYPE: PRT
<213> ORGANISM: Artificial Sequence
<220> FEATURE:
<223> OTHER INFORMATION: delections 465

<400> SEQUENCE: 465

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Glu Leu Gln
20 25 30

Gln Gln Gln Gln Phe Pro Ser Gln Gln Pro Tyr Leu Gln Leu Gln Pro
35 40 45

Phe Ser Gln Pro Gln Leu Pro Ile Phe Ala Ala Ala Thr Ile Ser Thr
50 55 60

Thr Thr Thr Ile Ser Thr Thr Ala Thr Thr Val Ser Ala Thr Thr Thr
65 70 75 80

<210> SEQ ID NO 466
<211> LENGTH: 87
<212> TYPE: PRT
<213> ORGANISM: Artificial Sequence
<220> FEATURE:
<223> OTHER INFORMATION: Delections 466

<400> SEQUENCE: 466

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Pro Gly
            20                  25                  30

Gln Gln Gln Pro Phe Pro Pro Gln Gln Pro Tyr Leu Gln Leu Gln Pro
        35                  40                  45

Phe Pro Gln Pro Gln Leu Pro Tyr Pro Gln Pro Gln Leu Pro Tyr Pro
    50                  55                  60

Gln Pro Gln Pro Phe Arg Pro Gln Gln Pro Tyr Pro Gln Pro Gln Pro
65                  70                  75                  80

Gln Tyr Ser Gln Pro Gln Gln
                85

<210> SEQ ID NO 467
<211> LENGTH: 87
<212> TYPE: PRT
<213> ORGANISM: Artificial Sequence
<220> FEATURE:
<223> OTHER INFORMATION: delections 467

<400> SEQUENCE: 467

Val Arg Val Pro Val Pro Gln Leu Gln Pro Gln Asn Pro Ser Gln Gln
1               5                   10                  15

Gln Pro Gln Glu Gln Val Pro Leu Val Lys Phe Leu Gly Gln Gln Gln
            20                  25                  30

Phe Pro Pro Gln Gln Gln Asp Pro His Asn Asn His Ile Cys Asn Cys
        35                  40                  45

Asn His Glu His Asn Arg Asn His Phe Arg His Asn Tyr His Ile Arg
    50                  55                  60

Ser His His His Phe His His Asn Asn His Ile His Asn Arg Asn His
65                  70                  75                  80

Ser Ile Arg Asn His Asn Asn
                85

<210> SEQ ID NO 468
<211> LENGTH: 84
<212> TYPE: PRT
<213> ORGANISM: Artificial Sequence
<220> FEATURE:
<223> OTHER INFORMATION: delections 468

<400> SEQUENCE: 468

Val Arg Val Glu Val Pro Gln Leu Gln Pro Gln Asn Pro Ser Gln Gln
1               5                   10                  15

Gln Pro Gln Glu Gln Val Pro Leu Ile Gln Gln Gln Gln Phe Leu Gln
            20                  25                  30

Gln Gln Gln Pro Phe Pro Pro Gln Gln Pro Tyr Pro Gln Pro Gln Ser
        35                  40                  45

Ala Ala Ala Thr Ile Ser Ala Ala Ala Thr Thr Ile Phe Ala Ala Thr
    50                  55                  60

Thr Ile Ser Thr Thr Thr Thr Ile Ser Thr Thr Ala Thr Thr Val Ser
65                  70                  75                  80

Ala Thr Thr Thr

<210> SEQ ID NO 469
<211> LENGTH: 89

<212> TYPE: PRT
<213> ORGANISM: Artificial Sequence
<220> FEATURE:
<223> OTHER INFORMATION: delections 469

<400> SEQUENCE: 469

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Pro Gln Pro Gln His
        35                  40                  45

Asn Asn His Ile Cys Asn Cys Asn His Phe Arg Ser Arg Asn Tyr His
    50                  55                  60

Ile Arg Ser His Asn His Phe Asp His Asn Asn His Ile His Asn Arg
65                  70                  75                  80

Asn His Ser Ile Arg Asn His Asn Asn
                85

<210> SEQ ID NO 470
<211> LENGTH: 89
<212> TYPE: PRT
<213> ORGANISM: Artificial Sequence
<220> FEATURE:
<223> OTHER INFORMATION: dp wt 470

<400> SEQUENCE: 470

Arg Val Pro Val Pro Gln Leu Gln Pro Asn Pro Ser Gln Gln Gln Pro
1               5                   10                  15

Gln Glu Gln Gln Pro Leu Val Gln Gln Gln Gln Phe Leu Gly Gln Gln
            20                  25                  30

Pro Phe Pro Pro Gln Gln Pro Tyr Pro Gln Pro Gln Pro Glu Pro Ser
        35                  40                  45

Gln Gln Pro Tyr Leu Gln Leu Gln Pro Phe Pro Gln Pro Gln Val Pro
    50                  55                  60

Tyr Ser Gln Pro Gln Pro Phe Arg Pro Gln Gln Pro Tyr Pro Gln Pro
65                  70                  75                  80

Gln Pro Gln Tyr Ser Gln Pro Gln Gln
                85

<210> SEQ ID NO 471
<211> LENGTH: 91
<212> TYPE: PRT
<213> ORGANISM: Artificial Sequence
<220> FEATURE:
<223> OTHER INFORMATION: Dp wt 471

<400> SEQUENCE: 471

Val Arg Val Pro Val Pro Gln Ile Gln Pro Gln Asn Pro Ser Gln Gln
1               5                   10                  15

Gln Pro Gln Glu Gln Val Pro Leu Val Gln Gln Lys Phe Leu Gly Gln
            20                  25                  30

Gln Gln Gln Phe Pro Pro Gln Gln Pro Asp Pro Gln Pro Gln Pro Glu
        35                  40                  45

Pro Ser Gln Gln Pro Tyr Leu Gln Leu Gln Pro Phe Pro Gln Pro Gln
    50                  55                  60

Leu Pro Tyr Ser Gln Pro Gln Pro Phe Arg Pro Gln Gln Pro Asn Pro
65 70 75 80

Gln Pro Gln Pro Gln Tyr Ser Gln Pro Gln Gln
85 90

<210> SEQ ID NO 472
<211> LENGTH: 90
<212> TYPE: PRT
<213> ORGANISM: Artificial Sequence
<220> FEATURE:
<223> OTHER INFORMATION: dp wt 472

<400> SEQUENCE: 472

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Glu Leu Gly
20 25 30

Gln Gln Gln Phe Pro Gln Gln Pro Tyr Pro Gln Pro Gln Gln Phe Pro
35 40 45

Ser Gln Gln Pro Tyr Leu Gln Leu Gln Pro Phe Pro Gln Pro Gln Leu
50 55 60

Pro Tyr Ser Gln Pro Gln Pro Phe Arg Pro Gln Gln Pro Tyr Pro Gln
65 70 75 80

Pro Gln Pro Gln Tyr Ser Gln Pro Gln Gln
85 90

<210> SEQ ID NO 473
<211> LENGTH: 90
<212> TYPE: PRT
<213> ORGANISM: Artificial Sequence
<220> FEATURE:
<223> OTHER INFORMATION: dp wt 473

<400> SEQUENCE: 473

Arg Val Pro Val Pro Gln Leu Gln Pro Gln Asn Pro Ser Gln Gln Gln
1 5 10 15

Pro Gln Glu Gln Val Pro Leu Val Gln Gln Gln Gln Tyr Pro Gly Gln
20 25 30

Gln Gln Pro Phe Pro Pro Gln Gln Pro Tyr Pro Gln Pro Gln Pro Glu
35 40 45

Pro Ser Gln Gln Pro Phe Leu Gln Pro Gln Pro Phe Leu Leu Gln Leu
50 55 60

Pro Tyr Pro Gln Pro Gln Pro Phe Pro Pro Gln Gln Pro Tyr Pro Gln
65 70 75 80

Pro Gln Pro Gln Tyr Pro Gln Pro Gln Gln
85 90

<210> SEQ ID NO 474
<211> LENGTH: 92
<212> TYPE: PRT
<213> ORGANISM: Artificial Sequence
<220> FEATURE:
<223> OTHER INFORMATION: dp wt 474

<400> SEQUENCE: 474

Val Arg Val Pro Val Pro Gln Leu Gln Pro Gln Asn Pro Ser Gln Gln
1 5 10 15

Gln Pro Gln Phe Gln Val Pro Leu Val Gln Gln Gln Lys Phe Leu Gly
20 25 30

```
Gln Gln Gln Gln Phe Pro Pro Gln Gln Pro Asp Pro Gln Pro Gln Pro
        35                  40                  45

Phe Ala Ser Gln Gln Pro Tyr Leu Gln Leu Gln Pro Phe Pro Gln Pro
    50                  55                  60

Gln Leu Pro Tyr Ser Gln Pro Gln Pro Phe Arg Pro Gln Gln Pro Tyr
65                  70                  75                  80

Leu Gln Pro Gln Pro Gln Tyr Ser Gln Pro Gln Gln
                85                  90


<210> SEQ ID NO 475
<211> LENGTH: 92
<212> TYPE: PRT
<213> ORGANISM: Artificial Sequence
<220> FEATURE:
<223> OTHER INFORMATION: dp wt 475

<400> SEQUENCE: 475

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Lys Phe Leu Gly
            20                  25                  30

Gln Gln Gln Glu Phe Pro Pro Gln Gln Pro Asp Pro Gln Pro Gln Pro
        35                  40                  45

Phe Pro Ser Gln Gln Pro Tyr Leu Gln Leu Gln Pro Phe Pro Gln Pro
    50                  55                  60

Gln Leu Pro Tyr Ser Gln Pro Gln Pro Phe Arg Pro Gln Gln Pro Tyr
65                  70                  75                  80

Pro Gln Leu Gln Pro Gln Tyr Pro Gln Pro Gln Gln
                85                  90


<210> SEQ ID NO 476
<211> LENGTH: 91
<212> TYPE: PRT
<213> ORGANISM: Artificial Sequence
<220> FEATURE:
<223> OTHER INFORMATION: delections 476

<400> SEQUENCE: 476

Val Arg Val Pro Val Pro Gln Leu Gln Pro Gln Asn Pro Ser Gln Gln
1               5                   10                  15

Gln Pro Gln Lys Gln Val Pro Leu Val Gln Gln Gln Gln Glu Leu Gly
            20                  25                  30

Gln Gln Gln Pro Phe Pro Pro Gln Gln Pro Tyr Pro Gln Pro His His
        35                  40                  45

Glu His His Asn Asn His Ile His Ser His Asn His Phe Cys His Asn
    50                  55                  60

Tyr His Ile Arg Val Arg Asn His Glu Tyr His Asn Asn His Ile His
65                  70                  75                  80

Asn Arg Asn His Ser Ile Arg Asn His Asn Asn
                85                  90


<210> SEQ ID NO 477
<211> LENGTH: 89
<212> TYPE: PRT
<213> ORGANISM: Artificial Sequence
<220> FEATURE:
<223> OTHER INFORMATION: delections 477
```

<400> SEQUENCE: 477

Val Arg Val Pro Val Pro Gln Leu Gln Pro Gln Asn Pro Ser Gln Gln
1 5 10 15

Gln Pro Gln Glu Gln Val Pro Leu Val Gln Gln Leu Gln Tyr Pro Gly
20 25 30

Gln Gln Gln Pro Phe Pro Pro Gln Gln Pro Tyr Pro Gln Pro Ile Ser
35 40 45

Ile Thr Thr Ile Ala Ala Thr Ala Thr Ile Ser Ala Thr Thr Thr Ile
50 55 60

Ser Ala Ala Thr Thr Ile Ser Thr Thr Thr Thr Ile Ser Thr Thr Ala
65 70 75 80

Thr Thr Val Ser Ala Thr Thr Thr Thr
85

<210> SEQ ID NO 478
<211> LENGTH: 86
<212> TYPE: PRT
<213> ORGANISM: Artificial Sequence
<220> FEATURE:
<223> OTHER INFORMATION: delections 478

<400> SEQUENCE: 478

Val Arg Val Pro Val Pro Gln Leu Gln Pro Asn Pro Ser Gln Gln Gln
1 5 10 15

Pro Gln Glu Gln Val Pro Leu Val Gln Gln Gln Gln Phe Leu Gly Gln
20 25 30

Gln Pro Phe Pro Pro Gln Gln Pro Tyr Pro Phe Pro Ser Gln Gln Pro
35 40 45

Tyr Leu Gln Leu Gln Pro Phe Pro Gln Pro Gln Val Pro Tyr Ser Gln
50 55 60

Pro Gln Pro Phe Arg Pro Gln Gln Pro Tyr Pro Gln Pro Gln Pro Gln
65 70 75 80

Tyr Ser Gln Pro Gln Gln
85

<210> SEQ ID NO 479
<211> LENGTH: 88
<212> TYPE: PRT
<213> ORGANISM: Artificial Sequence
<220> FEATURE:
<223> OTHER INFORMATION: delections 479

<400> SEQUENCE: 479

Val Arg Val Pro Val Pro Gln Leu Gln Pro Gln Asn Pro Ser Gln Gln
1 5 10 15

Gln Pro Gln Glu Gln Val Pro Leu Val Gln Gln Lys Phe Leu Gly Gln
20 25 30

Gln Gln Gln Phe Pro Pro Gln Gln Thr Asp Pro Gln Pro Gln His Asn
35 40 45

Asn His Ile Cys Ser Cys Asn His Phe Arg Ser Arg Asn Tyr His Ile
50 55 60

Arg Ser Arg Asn His Phe Asp His Asn Asn Gln Ile His Asn Arg Asn
65 70 75 80

His Ser Ile Arg Asn His Asn Asn
85

<210> SEQ ID NO 480

<211> LENGTH: 87
<212> TYPE: PRT
<213> ORGANISM: Artificial Sequence
<220> FEATURE:
<223> OTHER INFORMATION: delections 480

<400> SEQUENCE: 480

```
Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Lys Phe Leu Gly
            20                  25                  30

Gln Gln Gln Glu Phe Pro Pro Gln Gln Pro Asp Pro Gln Pro Gln Gln
        35                  40                  45

Pro Tyr Leu Gln Leu Gln Pro Phe Pro Gln Pro Gln Leu Pro Tyr Ser
    50                  55                  60

Gln Pro Gln Pro Phe Arg Pro Gln Gln Pro Tyr Pro Gln Pro Gln Pro
65                  70                  75                  80

Gln Tyr Pro Gln Pro Gln Gln
                85
```

<210> SEQ ID NO 481
<211> LENGTH: 85
<212> TYPE: PRT
<213> ORGANISM: Artificial Sequence
<220> FEATURE:
<223> OTHER INFORMATION: delections 481

<400> SEQUENCE: 481

```
Val Arg Val Pro Val Pro Gln Leu Gln Pro Gln Asn Pro Ser Gln Gln
1               5                   10                  15

Gln Pro Gln Glu Gln Val Pro Leu Ile Gln Gln Gln Gln Phe Leu Gly
            20                  25                  30

Gln Gln Gln Pro Phe Pro Pro Gln Gln Pro Tyr Pro Gln Pro Gln Ser
        35                  40                  45

Ala Ala Ala Thr Ile Ser Ala Ala Ala Thr Thr Ile Phe Ala Ala Thr
    50                  55                  60

Thr Ile Ser Thr Thr Thr Thr Ile Ser Thr Thr Ala Thr Thr Val Ser
65                  70                  75                  80

Ala Thr Thr Thr Thr
                85
```

<210> SEQ ID NO 482
<211> LENGTH: 79
<212> TYPE: PRT
<213> ORGANISM: Artificial Sequence
<220> FEATURE:
<223> OTHER INFORMATION: delections 482

<400> SEQUENCE: 482

```
Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Ile Gly
            20                  25                  30

Gln Gln Gln Pro Glu Pro Pro Gln Gln Pro Tyr Leu Gln Leu Gln Pro
        35                  40                  45

Phe Pro Gln Pro Gln Leu Pro Tyr Ser Gln Pro Gln Pro Phe Arg Pro
    50                  55                  60

Gln Gln Pro Tyr Pro Gln Pro Gln Pro Tyr Ser Gln Pro Gln Gln
65                  70                  75
```

<210> SEQ ID NO 483
<211> LENGTH: 80
<212> TYPE: PRT
<213> ORGANISM: Artificial Sequence
<220> FEATURE:
<223> OTHER INFORMATION: delections 483

<400> SEQUENCE: 483

Val Arg Val Pro Val Pro Gln Leu Gln Pro Gln Asn Pro Ser Gln Gln
1 5 10 15

Gln Pro Gln Glu Gln Val Pro Leu Val Gln Gln Gln Gln Phe Leu Gln
20 25 30

Gln Gln Gln Pro Phe Pro Ser Gln Gln Pro Tyr Leu Gln Leu Gln Pro
35 40 45

Phe Pro Gln Pro Gln Leu Pro Tyr Ser Gln Pro Gln Pro Phe Arg Pro
50 55 60

Gln Gln Pro Tyr Pro Gln Pro Gln Pro Gln Tyr Ser Gln Pro Gln Gln
65 70 75 80

<210> SEQ ID NO 484
<211> LENGTH: 146
<212> TYPE: PRT
<213> ORGANISM: Artificial Sequence
<220> FEATURE:
<223> OTHER INFORMATION: insertions 484

<400> SEQUENCE: 484

Val Arg Val Pro Val Pro Gln Leu Gln Pro Gln Asn Pro Ser Gln Gln
1 5 10 15

Gln Pro Gln Glu Gln Ala Pro Leu Val Gln Gln Gln Gln Phe Leu Gly
20 25 30

Gln Gln Gln Gln Phe Pro Pro Gln Gln Pro Tyr Pro Gln Pro Gln Leu
35 40 45

Trp Ile Pro Gln Gln Pro Tyr Leu Gln Leu Pro Asp Ile Ile His Trp
50 55 60

Asn Gln Leu Leu Leu Gln Gln Phe Leu Gly Gln Gln Gln Pro Phe Pro
65 70 75 80

Pro Gln Gln Pro Tyr Pro Gln Pro Gln Gln Pro Tyr Leu Gln Thr Asp
85 90 95

Met Val Ala Ala Ile Ser Ile Ser Ile Thr Thr Thr Ile Ser Thr Ala
100 105 110

Ala Thr Ile Ser Thr Ala Ala Thr Thr Ile Phe Ala Ala Ala Thr Ile
115 120 125

Ser Thr Thr Thr Thr Ile Ser Thr Thr Ala Thr Thr Val Phe Ala Thr
130 135 140

Thr Thr
145

<210> SEQ ID NO 485
<211> LENGTH: 146
<212> TYPE: PRT
<213> ORGANISM: Artificial Sequence
<220> FEATURE:
<223> OTHER INFORMATION: insertions 485

<400> SEQUENCE: 485

Val Arg Val Pro Val Pro Gln Leu Gln Pro Gln Asn Pro Ser Gln Gln
1 5 10 15

Gln Pro Gln Glu Gln Ala Pro Leu Val Gln Gln Gln Gln Phe Leu Gly
20 25 30

Gln Gln Gln Gln Phe Pro Pro Gln Gln Pro Tyr Pro Gln Pro Gln Leu
35 40 45

Trp Ile Pro Gln Gln Pro Tyr Leu Gln Leu Pro Asp Ile Ile His Trp
50 55 60

Asn Gln Leu Leu Leu Gln Gln Phe Leu Gly Gln Gln Gln Pro Phe Pro
65 70 75 80

Pro Gln Gln Pro Tyr Pro Gln Pro Gln Gln Pro Tyr Leu Gln Thr Asp
85 90 95

Met Val Ala Ala Ile Ser Ile Ser Ile Thr Thr Thr Ile Ser Thr Ala
100 105 110

Ala Thr Ile Ser Thr Ala Ala Thr Thr Ile Phe Ala Ala Ala Thr Ile
115 120 125

Ser Thr Thr Thr Thr Ile Ser Thr Thr Ala Thr Thr Val Ser Ala Thr
130 135 140

Thr Thr
145

<210> SEQ ID NO 486
<211> LENGTH: 100
<212> TYPE: DNA
<213> ORGANISM: Artificial Sequence
<220> FEATURE:
<223> OTHER INFORMATION: fig 7 DP wild type

<400> SEQUENCE: 486
caatttctag ggcagcaaca accatttcca ccacaacaac catatccaca gccgcaacca 60
tttccatcac aacaaccata tctgcaactg caaccatttc 100

<210> SEQ ID NO 487
<211> LENGTH: 99
<212> TYPE: DNA
<213> ORGANISM: Artificial Sequence
<220> FEATURE:
<223> OTHER INFORMATION: fig 7 -1bp

<400> SEQUENCE: 487
caatttctag ggcagcaaca accatttcca ccacaacagc catatccgca gccgcaccat 60
ttccatcaca acaaccatat ccacagccac aaccatttc 99

<210> SEQ ID NO 488
<211> LENGTH: 96
<212> TYPE: DNA
<213> ORGANISM: Artificial Sequence
<220> FEATURE:
<223> OTHER INFORMATION: fig 7 -4bp

<400> SEQUENCE: 488
caatttctag ggcagcaaca acaatttcca acagaacaac catatccgca gccgcaaatc 60
cttcacaact accatatctg tagctgcaac catttc 96

<210> SEQ ID NO 489
<211> LENGTH: 95
<212> TYPE: DNA
<213> ORGANISM: Artificial Sequence
<220> FEATURE:
<223> OTHER INFORMATION: fig 4 -5bp

<400> SEQUENCE: 489
caatatccag ggcaacaaca accatttcca ccacaacagc catatccgca gcccatttcc 60
atcacaacaa ccattgccgc aaccgcaacc atttc 95

<210> SEQ ID NO 490
<211> LENGTH: 92
<212> TYPE: DNA
<213> ORGANISM: Artificial Sequence
<220> FEATURE:
<223> OTHER INFORMATION: fig 7 -8bp

<400> SEQUENCE: 490
caatttctag ggcagcaaca accatttcca ccacaacagc catatccgca gccttccatc 60
acaacaacca tatccacagc cacaaccatt tc 92

<210> SEQ ID NO 491
<211> LENGTH: 90
<212> TYPE: DNA
<213> ORGANISM: Artificial Sequence
<220> FEATURE:
<223> OTHER INFORMATION: fig 7 -10bp

<400> SEQUENCE: 491
aaatttctag ggcagcaaca acaatttcca ccacaacaaa cagatccaca gccgcaacac 60
aacaaccata tctgcagctg caaccatttc 90

<210> SEQ ID NO 492
<211> LENGTH: 88
<212> TYPE: DNA
<213> ORGANISM: Artificial Sequence
<220> FEATURE:
<223> OTHER INFORMATION: fig 7 -12bp

<400> SEQUENCE: 492
caatttctag ggcagtaaca accatttcca ccacaacaac catatccatt tccatcacaa 60
caaccatatc tgcagctgca accatttc 88

<210> SEQ ID NO 493
<211> LENGTH: 85
<212> TYPE: DNA
<213> ORGANISM: Artificial Sequence
<220> FEATURE:
<223> OTHER INFORMATION: fig 7 -15bp

<400> SEQUENCE: 493
aaatttctag ggcagcaaca agaatttcca ccacaacaac cagatccaca gccgcaacaa 60
ccatatctgc agttgcaacc atttc 85

<210> SEQ ID NO 494
<211> LENGTH: 77
<212> TYPE: DNA
<213> ORGANISM: Artificial Sequence
<220> FEATURE:
<223> OTHER INFORMATION: fig 7 -23bp

<400> SEQUENCE: 494
caatttctag ggcagcaaca accatttcca ccacaacaac catatccaca gccgcaatct 60
gcagctgcaa ccatttc 77

<210> SEQ ID NO 495

<211> LENGTH: 64
<212> TYPE: DNA
<213> ORGANISM: Artificial Sequence
<220> FEATURE:
<223> OTHER INFORMATION: fig 7 -36bp (1)

<400> SEQUENCE: 495
caatttctag ggcagcaaca accatttcca tcacaacaac catatctgca actgcaacca 60
tttc 64

<210> SEQ ID NO 496
<211> LENGTH: 64
<212> TYPE: DNA
<213> ORGANISM: Artificial Sequence
<220> FEATURE:
<223> OTHER INFORMATION: fig 6 -36bp (2)

<400> SEQUENCE: 496
caatatccag ggcagcaaca accatttcca tcacaacaac catttctgca gccgcaacca 60
tttc 64

<210> SEQ ID NO 497
<211> LENGTH: 64
<212> TYPE: DNA
<213> ORGANISM: Artificial Sequence
<220> FEATURE:
<223> OTHER INFORMATION: fig 7 -36bp (3)

<400> SEQUENCE: 497
caatttctag ggcagcaaca accatttcca tcacaacaac catatctgca actgcaacca 60
tttc 64

<210> SEQ ID NO 498
<211> LENGTH: 52
<212> TYPE: DNA
<213> ORGANISM: Artificial Sequence
<220> FEATURE:
<223> OTHER INFORMATION: fig 7b DP wild type

<400> SEQUENCE: 498
caacaaccat atccacagcc gcaaccattt ccatcacaac aaccatatct gc 52

<210> SEQ ID NO 499
<211> LENGTH: 92
<212> TYPE: DNA
<213> ORGANISM: Artificial Sequence
<220> FEATURE:
<223> OTHER INFORMATION: fig 7b +40bp

<400> SEQUENCE: 499
caacaaccat atccacagcc gcaacaacca tatttgcaga cttgagatat ggttgctgcc 60
atatccattt ccatcacaac aaccatatct ac 92

<210> SEQ ID NO 500
<211> LENGTH: 94
<212> TYPE: DNA
<213> ORGANISM: Artificial Sequence
<220> FEATURE:
<223> OTHER INFORMATION: fig 7b +82bp

<400> SEQUENCE: 500
caacagccat atccgcagcc gcaaatcctt cacaactacc atatctgtag ctgcaaccat 60
ttgttgccat ttccatcaca actaccatat ctgc 94

<210> SEQ ID NO 501
<211> LENGTH: 98
<212> TYPE: DNA
<213> ORGANISM: Artificial Sequence
<220> FEATURE:
<223> OTHER INFORMATION: fig 7b +166bp

<400> SEQUENCE: 501
caacaaccat atccgcagcc gcaattgtgg attccacaac aaccatatct ccaactacca 60
gatatcatat ccatttccat cacaacaacc atatctac 98

<210> SEQ ID NO 502
<211> LENGTH: 100
<212> TYPE: DNA
<213> ORGANISM: Artificial Sequence
<220> FEATURE:
<223> OTHER INFORMATION: fig 8 TAH53 wt

<400> SEQUENCE: 502
caatttccag ggcagcaaca accatttcca ccacaacagc catatccgca gccgcaacca 60
tttccatcac aacaaccata tctgcagctg caaccatttc 100

<210> SEQ ID NO 503
<211> LENGTH: 93
<212> TYPE: DNA
<213> ORGANISM: Artificial Sequence
<220> FEATURE:
<223> OTHER INFORMATION: fig 8 -8bp
<220> FEATURE:
<221> NAME/KEY: misc_feature
<222> LOCATION: 93..93
<223> OTHER INFORMATION: /note="n is a, c, g, or t"

<400> SEQUENCE: 503
caatttctag ggcagcaaca accatttcca ccacaacagc catatccgca gccttccatc 60
acaacaacca tatccacagc cacaaccatt tcn 93

<210> SEQ ID NO 504
<211> LENGTH: 91
<212> TYPE: DNA
<213> ORGANISM: Artificial Sequence
<220> FEATURE:
<223> OTHER INFORMATION: fig 8 -9bp

<400> SEQUENCE: 504
caatttctag ggcagcaaca accatttcca ccacaacaac catatccaca gccgcaatca 60
caactaccat atctgcagct gcaaccattt c 91

<210> SEQ ID NO 505
<211> LENGTH: 90
<212> TYPE: DNA
<213> ORGANISM: Artificial Sequence
<220> FEATURE:
<223> OTHER INFORMATION: fig 8 -10bp

<400> SEQUENCE: 505
caatttctag ggcagcaaca accatttcca ccacaacaac catatccaca gccgcaacac 60
aacaaccata tctgcaactg caaccatttc 90

<210> SEQ ID NO 506
<211> LENGTH: 82
<212> TYPE: DNA

-continued

<213> ORGANISM: Artificial Sequence
<220> FEATURE:
<223> OTHER INFORMATION: fig 8 -18bp

<400> SEQUENCE: 506
caatttctag ggcagcaaca accatttcca ccacaacaac catttccatc acaactacca 60
tatctgcagc tgcaaccatt tc 82

<210> SEQ ID NO 507
<211> LENGTH: 81
<212> TYPE: DNA
<213> ORGANISM: Artificial Sequence
<220> FEATURE:
<223> OTHER INFORMATION: fig 8 -19bp

<400> SEQUENCE: 507
aaatttctag ggtagcaaca acaatttcca ccacaacaac aagatccaca caacaaccat 60
atctgcaatt gcaaccattt c 81

<210> SEQ ID NO 508
<211> LENGTH: 77
<212> TYPE: DNA
<213> ORGANISM: Artificial Sequence
<220> FEATURE:
<223> OTHER INFORMATION: fig 8 -23bp

<400> SEQUENCE: 508
caatttctag ggcagcaaca accatttcca ccacaacaac catatccaca gccgcaatct 60
gcagctgcaa ccatttc 77

<210> SEQ ID NO 509
<211> LENGTH: 64
<212> TYPE: DNA
<213> ORGANISM: Artificial Sequence
<220> FEATURE:
<223> OTHER INFORMATION: fig 8 -36bp

<400> SEQUENCE: 509
caatttctag ggcagcaaca atcatttcca tcacaacaac catatctgca gctgcaacca 60
tttc 64

<210> SEQ ID NO 510
<211> LENGTH: 64
<212> TYPE: DNA
<213> ORGANISM: Artificial Sequence
<220> FEATURE:
<223> OTHER INFORMATION: fig 8 -36bp (2)

<400> SEQUENCE: 510
caatttctag ggcagcaaca accatttcca tcacaacaac catatctgca gctgcaacca 60
tttc 64

<210> SEQ ID NO 511
<211> LENGTH: 64
<212> TYPE: DNA
<213> ORGANISM: Artificial Sequence
<220> FEATURE:
<223> OTHER INFORMATION: fig 8 -36bp (3)

<400> SEQUENCE: 511
caatttctag ggcagcaaca acaatttcca acacaacaac catatctgca gctgcaacca 60
tttt 64

<210> SEQ ID NO 512
<211> LENGTH: 64
<212> TYPE: DNA
<213> ORGANISM: Artificial Sequence
<220> FEATURE:
<223> OTHER INFORMATION: fig 8 -36bp (4)

<400> SEQUENCE: 512
caatttctag ggcagcaaca acaatttcca tcacaacaac catatctgca gctgcaacca 60
tttt 64

<210> SEQ ID NO 513
<211> LENGTH: 64
<212> TYPE: DNA
<213> ORGANISM: Artificial Sequence
<220> FEATURE:
<223> OTHER INFORMATION: fig 8 -36bp (5)

<400> SEQUENCE: 513
caatttctag ggcagcaaca accatttcca tcacaacaac catatccaca gccacaacca 60
tttc 64

<210> SEQ ID NO 514
<211> LENGTH: 64
<212> TYPE: DNA
<213> ORGANISM: Artificial Sequence
<220> FEATURE:
<223> OTHER INFORMATION: fig 8 -36bp (6)

<400> SEQUENCE: 514
caatttctag ggcagcaaca accatttcca tcacaacaac catatccaca gccacaacca 60
tttc 64

<210> SEQ ID NO 515
<211> LENGTH: 64
<212> TYPE: DNA
<213> ORGANISM: Artificial Sequence
<220> FEATURE:
<223> OTHER INFORMATION: fig 8 -36bp (7)

<400> SEQUENCE: 515
caatttctag ggcagcaata accatttcga ccacaacaac catatccaca gccgcaacca 60
tttc 64

<210> SEQ ID NO 516
<211> LENGTH: 64
<212> TYPE: DNA
<213> ORGANISM: Artificial Sequence
<220> FEATURE:
<223> OTHER INFORMATION: fig 8 -36bp (8)

<400> SEQUENCE: 516
caatttccag ggcagcaaca accatttcca ccacaacagc catatctgca gctgcaacca 60
tttc 64

<210> SEQ ID NO 517
<211> LENGTH: 64
<212> TYPE: DNA
<213> ORGANISM: Artificial Sequence
<220> FEATURE:
<223> OTHER INFORMATION: fig 8 -36bp (9)

<400> SEQUENCE: 517
caatttctag ggcagcaaca accatttcca tcacaacaac catatctgca gctgcaacca 60
tttc 64

<210> SEQ ID NO 518
<211> LENGTH: 57
<212> TYPE: DNA
<213> ORGANISM: Artificial Sequence
<220> FEATURE:
<223> OTHER INFORMATION: fig 8 -49bp
<220> FEATURE:
<221> NAME/KEY: misc_feature
<222> LOCATION: 57..57
<223> OTHER INFORMATION: /note="n is a, c, g, or t"

<400> SEQUENCE: 518
caatttccag ggcagcaaca accatttcca ccacaacagc catatccgca gccgcan 57

<210> SEQ ID NO 519
<211> LENGTH: 47
<212> TYPE: DNA
<213> ORGANISM: Artificial Sequence
<220> FEATURE:
<223> OTHER INFORMATION: fig 8 -54bp
<220> FEATURE:
<221> NAME/KEY: misc_feature
<222> LOCATION: 47..47
<223> OTHER INFORMATION: /note="n is a, c, g, or t"

<400> SEQUENCE: 519
caatttccag ggcagcaaca accatttcca ccacaacagc catatcn 47

<210> SEQ ID NO 520
<211> LENGTH: 72
<212> TYPE: DNA
<213> ORGANISM: Artificial Sequence
<220> FEATURE:
<223> OTHER INFORMATION: fig 8b THA53 wt

<400> SEQUENCE: 520
caacaaccat ttccaccaca acagccatat ccgcagccgc aaccatttcc atcacaacaa 60
ccatatctgc ag 72

<210> SEQ ID NO 521
<211> LENGTH: 100
<212> TYPE: DNA
<213> ORGANISM: Artificial Sequence
<220> FEATURE:
<223> OTHER INFORMATION: fig 8b +103bp

<400> SEQUENCE: 521
caacaaccat ttccaccaca acagccatat ccgcagccgc aagagatcag tgtaacctct 60
aacctagcct ccatttccat cacaacaacc atatccgcag 100

<210> SEQ ID NO 522
<211> LENGTH: 100
<212> TYPE: DNA
<213> ORGANISM: Artificial Sequence
<220> FEATURE:
<223> OTHER INFORMATION: fig 9 BW208wt

<400> SEQUENCE: 522
tccagtgcca caattgcagc cacaaaatcc atctcagcaa cagccacaag agcaagttcc 60
attggtacaa caacaaaaat ttctagggga gcaacaacaa 100

-continued

<210> SEQ ID NO 523
<211> LENGTH: 93
<212> TYPE: DNA
<213> ORGANISM: Artificial Sequence
<220> FEATURE:
<223> OTHER INFORMATION: fig 9 -7bp

<400> SEQUENCE: 523
tccagtgcca caattgcagc cacaaaatcc atctcagcaa caaccacaag agcattggta 60
caacaacaac aatttccagg gcagcaacaa cca 93

<210> SEQ ID NO 524
<211> LENGTH: 91
<212> TYPE: DNA
<213> ORGANISM: Artificial Sequence
<220> FEATURE:
<223> OTHER INFORMATION: fig 9 -9bp

<400> SEQUENCE: 524
tccagtgcca caattgcagc cataaaatcc atctcagcaa cagccacaag agcaagttca 60
acaacaacaa tttctagggc agcaacaacc a 91

<210> SEQ ID NO 525
<211> LENGTH: 90
<212> TYPE: DNA
<213> ORGANISM: Artificial Sequence
<220> FEATURE:
<223> OTHER INFORMATION: fig 9 -10bp

<400> SEQUENCE: 525
tccagtgcca caattgcagc cacaaaatcc atctcagcaa cagccacaac attggtacaa 60
caacaaaaat ttctagggca gcaacaacaa 90

<210> SEQ ID NO 526
<211> LENGTH: 87
<212> TYPE: DNA
<213> ORGANISM: Artificial Sequence
<220> FEATURE:
<223> OTHER INFORMATION: fig 9 -13bp

<400> SEQUENCE: 526
tccagtgcca caattgcagc cacaaaatcc atctcagcaa caaccacatt ggtgcaacaa 60
caacaatttc tagggcagca ataacca 87

<210> SEQ ID NO 527
<211> LENGTH: 85
<212> TYPE: DNA
<213> ORGANISM: Artificial Sequence
<220> FEATURE:
<223> OTHER INFORMATION: fig 9 -15bp

<400> SEQUENCE: 527
tccagtgcca caattgcagc cacaaaatcc atctcagcaa caaccacaag agcaagttca 60
acaatttcta gggcagcaat aacca 85

<210> SEQ ID NO 528
<211> LENGTH: 84
<212> TYPE: DNA
<213> ORGANISM: Artificial Sequence
<220> FEATURE:
<223> OTHER INFORMATION: fig 9 -16bp

<400> SEQUENCE: 528
tccagtgcca caattgcagc cataaaatcc atctcagcaa cagccacaag acaacaacaa 60
caatttctag ggcagcaaca acca 84

<210> SEQ ID NO 529
<211> LENGTH: 79
<212> TYPE: DNA
<213> ORGANISM: Artificial Sequence
<220> FEATURE:
<223> OTHER INFORMATION: fig 9 -21bp

<400> SEQUENCE: 529
tccagtgcca caattgcagc cacaaaatcc atctcagcaa cagccacaag agcaacaatt 60
tctagggcag caacaacaa 79

<210> SEQ ID NO 530
<211> LENGTH: 77
<212> TYPE: DNA
<213> ORGANISM: Artificial Sequence
<220> FEATURE:
<223> OTHER INFORMATION: fig 9 -23bp

<400> SEQUENCE: 530
tccagtgcca caattgcagc cacaaaatcc atctcagcaa cagccacaag agcaagtttc 60
tagggcagca acaacca 77

<210> SEQ ID NO 531
<211> LENGTH: 76
<212> TYPE: DNA
<213> ORGANISM: Artificial Sequence
<220> FEATURE:
<223> OTHER INFORMATION: fig 9 -24bp

<400> SEQUENCE: 531
tccagtgcca caattgcagc cacaaaatcc atctcagcaa caaccacaag agcaagttct 60
agggcagcaa caacaa 76

<210> SEQ ID NO 532
<211> LENGTH: 72
<212> TYPE: DNA
<213> ORGANISM: Artificial Sequence
<220> FEATURE:
<223> OTHER INFORMATION: fig 9 -28bp

<400> SEQUENCE: 532
tccagtgcca caattgcagc cacaaaatcc atctcggtgc aacaacaaca atttctaggg 60
cagcaacaac aa 72

<210> SEQ ID NO 533
<211> LENGTH: 71
<212> TYPE: DNA
<213> ORGANISM: Artificial Sequence
<220> FEATURE:
<223> OTHER INFORMATION: fig 9 -29bp

<400> SEQUENCE: 533
tccagtgcca caattgcagc cacaaaatcc cattggtgca acaacaacaa tttctagggc 60
agcaacaaca a 71

<210> SEQ ID NO 534
<211> LENGTH: 69

<212> TYPE: DNA
<213> ORGANISM: Artificial Sequence
<220> FEATURE:
<223> OTHER INFORMATION: fig 9 -31bp

<400> SEQUENCE: 534
tccagtgcca caattgcagc cacaaaatcc atggtacaac aacaaaaatt tctagggcag 60
caacaacaa 69

<210> SEQ ID NO 535
<211> LENGTH: 70
<212> TYPE: DNA
<213> ORGANISM: Artificial Sequence
<220> FEATURE:
<223> OTHER INFORMATION: fig 9 -30bp

<400> SEQUENCE: 535
tccagtgcca caattgcagc cacaaaatcc atctcagcaa caaccacaat ttctagggca 60
gcaacaacaa 70

<210> SEQ ID NO 536
<211> LENGTH: 68
<212> TYPE: DNA
<213> ORGANISM: Artificial Sequence
<220> FEATURE:
<223> OTHER INFORMATION: fig 9 -32bp

<400> SEQUENCE: 536
tccagtgcca caattgcagc cacaaaatcc atctcagcaa cagccacaag agcaagttgc 60
aacaacaa 68

<210> SEQ ID NO 537
<211> LENGTH: 67
<212> TYPE: DNA
<213> ORGANISM: Artificial Sequence
<220> FEATURE:
<223> OTHER INFORMATION: fig 9 -33bp

<400> SEQUENCE: 537
tccagtgcca caattgcagc cacaaaatcc atctcaacaa caaaaatttc tatggcagca 60
acaacaa 67

<210> SEQ ID NO 538
<211> LENGTH: 57
<212> TYPE: DNA
<213> ORGANISM: Artificial Sequence
<220> FEATURE:
<223> OTHER INFORMATION: fig 9 -36bp
<220> FEATURE:
<221> NAME/KEY: misc_feature
<222> LOCATION: 57..57
<223> OTHER INFORMATION: /note="n is a, c, g, or t"

<400> SEQUENCE: 538
tccagtgcca caaccgcagc cacaaaatcc atctcagcca cagccacaag ggcaagn 57

<210> SEQ ID NO 539
<211> LENGTH: 61
<212> TYPE: DNA
<213> ORGANISM: Artificial Sequence
<220> FEATURE:
<223> OTHER INFORMATION: fig 9 -39bp

<400> SEQUENCE: 539
tccagtgcca caattgcagc cacaaaatcc atctcagcaa caaccacaag agcaataacc 60
a 61

<210> SEQ ID NO 540
<211> LENGTH: 52
<212> TYPE: DNA
<213> ORGANISM: Artificial Sequence
<220> FEATURE:
<223> OTHER INFORMATION: fig 9 -48bp

<400> SEQUENCE: 540
tccagtgcca caattggtac aacaacaaca atttctaggg cagcaacaac ca 52

<210> SEQ ID NO 541
<211> LENGTH: 53
<212> TYPE: DNA
<213> ORGANISM: Artificial Sequence
<220> FEATURE:
<223> OTHER INFORMATION: fig 9 -55bp
<220> FEATURE:
<221> NAME/KEY: misc_feature
<222> LOCATION: 53..53
<223> OTHER INFORMATION: /note="n is a, c, g, or t"

<400> SEQUENCE: 541
tccagtgcca caattgcagc cacaaaatcc atctcagcaa cagccacaag agn 53

<210> SEQ ID NO 542
<211> LENGTH: 43
<212> TYPE: DNA
<213> ORGANISM: Artificial Sequence
<220> FEATURE:
<223> OTHER INFORMATION: fig 9 -57bp

<400> SEQUENCE: 542
tccagtgcca caattgcagc cacaaaatcc acagcaataa cca 43

<210> SEQ ID NO 543
<211> LENGTH: 60
<212> TYPE: DNA
<213> ORGANISM: Artificial Sequence
<220> FEATURE:
<223> OTHER INFORMATION: fig 9 -82bp
<220> FEATURE:
<221> NAME/KEY: misc_feature
<222> LOCATION: 60..60
<223> OTHER INFORMATION: /note="n is a, c, g, or t"

<400> SEQUENCE: 543
tccagtgcca caattgcagc cacaaaatcc atctcagcaa cagccacaag agcaagttcn 60

<210> SEQ ID NO 544
<211> LENGTH: 44
<212> TYPE: DNA
<213> ORGANISM: Artificial Sequence
<220> FEATURE:
<223> OTHER INFORMATION: fig 9 -111bp
<220> FEATURE:
<221> NAME/KEY: misc_feature
<222> LOCATION: 44..44
<223> OTHER INFORMATION: /note="n is a, c, g, or t"

<400> SEQUENCE: 544
tccagtgcca caattgcagc cacaaaatcc atctcagcaa cagn 44

```
<210> SEQ ID NO 545
<211> LENGTH: 100
<212> TYPE: DNA
<213> ORGANISM: Artificial Sequence
<220> FEATURE:
<223> OTHER INFORMATION: fig 9b BW208 wt

<400> SEQUENCE: 545

tccagtgcca caattgcagc cacaaaatcc atctcagcaa cagccacaag agcaagttcc     60

attggtacaa caacaaaaat ttctagggga gcaacaacaa                          100


<210> SEQ ID NO 546
<211> LENGTH: 101
<212> TYPE: DNA
<213> ORGANISM: Artificial Sequence
<220> FEATURE:
<223> OTHER INFORMATION: fig 9b +1bp

<400> SEQUENCE: 546

tccagtgcca caattgcagt cacaaaatcc atctcagcaa caaccacaag agcaagttca     60

cattggtgca acaacaacaa tttctagggc agcaacaaca a                        101


<210> SEQ ID NO 547
<211> LENGTH: 191
<212> TYPE: DNA
<213> ORGANISM: Artificial Sequence
<220> FEATURE:
<223> OTHER INFORMATION: fig 10a BW208wt

<400> SEQUENCE: 547

caatttccag ggcagcaaca accatttcca ccacaacagc catatccgca gccgcaacca     60

tttccatcac aacaaccata tctgcagctg caaccatttc cgcagccgca actaccatat    120

tcgcagccac aaccatttcg accacaacaa ccatatccac aaccgcaacc acagtattcg    180

caaccacaac a                                                         191


<210> SEQ ID NO 548
<211> LENGTH: 173
<212> TYPE: DNA
<213> ORGANISM: Artificial Sequence
<220> FEATURE:
<223> OTHER INFORMATION: fig 10a -18bp

<400> SEQUENCE: 548

caatttctag ggcagcaaca accatttcca ccacaacaac catatccatc acaacagcca     60

tatctgcagc tgcaaccatt tccgcagccg caactaccat attcgcagcc acaaccattt    120

cgaccacaac aaccatatcc acaaccgcaa ccacagtatt cgcaaccaca aca           173


<210> SEQ ID NO 549
<211> LENGTH: 173
<212> TYPE: DNA
<213> ORGANISM: Artificial Sequence
<220> FEATURE:
<223> OTHER INFORMATION: fig 10a -18bp (2)

<400> SEQUENCE: 549

caatttctag ggcagcaaca atcatttcca ccacaacaac catttccatc acaacaacca     60

tatctgcagc tgcaaccatt ttcgcagccg caactaccat attcgcagcc gcaaccattt    120

cgaccacaac aaccatatcc acaaccgcaa ccatagtatt cgcaaccaca aca           173
```

<210> SEQ ID NO 550
<211> LENGTH: 163
<212> TYPE: DNA
<213> ORGANISM: Artificial Sequence
<220> FEATURE:
<223> OTHER INFORMATION: fig 10a -28bp

<400> SEQUENCE: 550
caatttccag ggcagcaaca accatttcca ccacaacagc catatccgca tatctgcagc 60
tgcagccatt tccgcagccg caactaccat atccgcagcc gcatctacca tatccgcagc 120
cgcaaccatt tcgaccacaa caaccatatc cacaaccgca acc 163

<210> SEQ ID NO 551
<211> LENGTH: 155
<212> TYPE: DNA
<213> ORGANISM: Artificial Sequence
<220> FEATURE:
<223> OTHER INFORMATION: fig 10a -36bp

<400> SEQUENCE: 551
caatttctag ggcagcaaca acaatttcca ccacaacaac catatctgca gctgcaacca 60
ttttcgcagc cgcaactacc atattcgcag ccgcgaccat ttcgaccaca acaaccatat 120
ccacaaccgc aaccacagta ttcgcaacca caaca 155

<210> SEQ ID NO 552
<211> LENGTH: 152
<212> TYPE: DNA
<213> ORGANISM: Artificial Sequence
<220> FEATURE:
<223> OTHER INFORMATION: fig 10a -39bp

<400> SEQUENCE: 552
caatttctag ggcagcaaca accatttcca tcacaacaac catatccaca gccacaacca 60
tttctgccac aactaccata tccgcgtccg caaccatttc taccacaaca accatatcca 120
caaccggaac cacagtatcc gcaaccacaa ca 152

<210> SEQ ID NO 553
<211> LENGTH: 137
<212> TYPE: DNA
<213> ORGANISM: Artificial Sequence
<220> FEATURE:
<223> OTHER INFORMATION: fig 10a -54bp

<400> SEQUENCE: 553
caatttctag ggcagcaaca accatttcca ccacaacaac catatccaca gccgcaacta 60
ccatattcac agccacaacc atttcgacca caacaaccat atccacaacc gcaaccacag 120
tattcgcaac cacaaca 137

<210> SEQ ID NO 554
<211> LENGTH: 116
<212> TYPE: DNA
<213> ORGANISM: Artificial Sequence
<220> FEATURE:
<223> OTHER INFORMATION: fig 10a -75bp

<400> SEQUENCE: 554
caatatccag ggcagcaaca accatttcca ccacaacaac catatccgca gccgcaacca 60
tttccaccac aacaatcata tccacaacca caaccacagt atccgcaacc acaaca 116

<210> SEQ ID NO 555

<211> LENGTH: 80
<212> TYPE: DNA
<213> ORGANISM: Artificial Sequence
<220> FEATURE:
<223> OTHER INFORMATION: fig 10a -111bp

<400> SEQUENCE: 555
caatttccag ggcagcaaca accatttcca tcacaacaac catatctgca gctgcagcca 60
tttccgcaac cacaacaacc 80

<210> SEQ ID NO 556
<211> LENGTH: 80
<212> TYPE: DNA
<213> ORGANISM: Artificial Sequence
<220> FEATURE:
<223> OTHER INFORMATION: fig 10a -111bp (2)

<400> SEQUENCE: 556
caatttctag ggcagcaaca accatttcca ccacaacaac catatccgca gccgcaacca 60
tttccgcaac cacaacaacc 80

<210> SEQ ID NO 557
<211> LENGTH: 80
<212> TYPE: DNA
<213> ORGANISM: Artificial Sequence
<220> FEATURE:
<223> OTHER INFORMATION: fig 10a -111bp (3)

<400> SEQUENCE: 557
caatatccag ggcaacaaca accatttcca ccacaacagc catatccaca accacaacca 60
caatatccgc aaccacaaca 80

<210> SEQ ID NO 558
<211> LENGTH: 112
<212> TYPE: DNA
<213> ORGANISM: Artificial Sequence
<220> FEATURE:
<223> OTHER INFORMATION: fig 10b TAH53 wt

<400> SEQUENCE: 558
caatttccag ggcagcaaca accatttcca ccacaacagc catatccgca gccgcaacca 60
tttccatcac aacaaccata tctgcagctg caaccatttc cgcagccgca ac 112

<210> SEQ ID NO 559
<211> LENGTH: 76
<212> TYPE: DNA
<213> ORGANISM: Artificial Sequence
<220> FEATURE:
<223> OTHER INFORMATION: fig 10b -36bp

<400> SEQUENCE: 559
caatttctag ggcagcaaca atcatttcca tcacaacaac catatctgca gctgcaacca 60
tttccgcagc cgcaac 76

<210> SEQ ID NO 560
<211> LENGTH: 76
<212> TYPE: DNA
<213> ORGANISM: Artificial Sequence
<220> FEATURE:
<223> OTHER INFORMATION: fig 10b -36bp (2)

<400> SEQUENCE: 560
caatttctag ggcagcaaca accatttcca tcacaacaac catatctgca gctgcaacca 60
tttccgcagc cgcaac 76

<210> SEQ ID NO 561
<211> LENGTH: 76
<212> TYPE: DNA
<213> ORGANISM: Artificial Sequence
<220> FEATURE:
<223> OTHER INFORMATION: fig 10b -36bp(3)

<400> SEQUENCE: 561
caatttctag ggcagcaaca acaatttcca acacaacaac catatctgca gctgcaacca 60
ttttcgcagc cgcaac 76

<210> SEQ ID NO 562
<211> LENGTH: 73
<212> TYPE: DNA
<213> ORGANISM: Artificial Sequence
<220> FEATURE:
<223> OTHER INFORMATION: fig 10b -36bp (4)

<400> SEQUENCE: 562
caatttctag ggcagcaaca accatttcca tcacaacaac catatccaca gccacaacca 60
tttctgccac aac 73

<210> SEQ ID NO 563
<211> LENGTH: 73
<212> TYPE: DNA
<213> ORGANISM: Artificial Sequence
<220> FEATURE:
<223> OTHER INFORMATION: fig 10b -36bp(5)

<400> SEQUENCE: 563
caatttctag ggcagcaaca accatttcca tcacaacaac catatccaca gccacaacca 60
tttctgccac aac 73

<210> SEQ ID NO 564
<211> LENGTH: 73
<212> TYPE: DNA
<213> ORGANISM: Artificial Sequence
<220> FEATURE:
<223> OTHER INFORMATION: fig 10b -36bp (6)

<400> SEQUENCE: 564
caatttctag ggcagcaaca accatttcca tcacaacaac catatccaca gccacaacca 60
tttctgccac aac 73

<210> SEQ ID NO 565
<211> LENGTH: 76
<212> TYPE: DNA
<213> ORGANISM: Artificial Sequence
<220> FEATURE:
<223> OTHER INFORMATION: fig 10b -36bp (7)

<400> SEQUENCE: 565
caatttccag ggcagcaaca accatttcca ccacaacagc catatctgca gctgcaacca 60
tttccgcagc cgcaac 76

<210> SEQ ID NO 566

<211> LENGTH: 76
<212> TYPE: DNA
<213> ORGANISM: Artificial Sequence
<220> FEATURE:
<223> OTHER INFORMATION: fig 10b -36bp (8)

<400> SEQUENCE: 566
caatttctag ggcagcaaca accatttcca tcacaacaac catatctgca gctgcaacca 60
tttccgcagc cgcaac 76

<210> SEQ ID NO 567
<211> LENGTH: 58
<212> TYPE: DNA
<213> ORGANISM: Artificial Sequence
<220> FEATURE:
<223> OTHER INFORMATION: fig 10b -54bp

<400> SEQUENCE: 567
caatttccag ggcagcaaca accatttcca ccacaacagc catatccgca gccgcaac 58

<210> SEQ ID NO 568
<211> LENGTH: 100
<212> TYPE: DNA
<213> ORGANISM: Artificial Sequence
<220> FEATURE:
<223> OTHER INFORMATION: fig 10c DP wt

<400> SEQUENCE: 568
caatttctag ggcagcaaca accatttcca ccacaacaac catatccaca gccgcaacca 60
tttccatcac aacaaccata tctgcaactg caaccatttc 100

<210> SEQ ID NO 569
<211> LENGTH: 85
<212> TYPE: DNA
<213> ORGANISM: Artificial Sequence
<220> FEATURE:
<223> OTHER INFORMATION: fig 10c -15bp

<400> SEQUENCE: 569
aaatttctag ggcagcaaca agaatttcca ccacaacaac cagatccaca gccgcaacaa 60
ccatatctgc agttgcaacc atttc 85

<210> SEQ ID NO 570
<211> LENGTH: 64
<212> TYPE: DNA
<213> ORGANISM: Artificial Sequence
<220> FEATURE:
<223> OTHER INFORMATION: fig '10c -36bp

<400> SEQUENCE: 570
caatttctag ggcagcaaca accatttcca tcacaacaac catatctgca actgcaacca 60
tttc 64

<210> SEQ ID NO 571
<211> LENGTH: 64
<212> TYPE: DNA
<213> ORGANISM: Artificial Sequence
<220> FEATURE:
<223> OTHER INFORMATION: fig 10c -36bp (2)

<400> SEQUENCE: 571
caatttctag ggcagcaaca accatttcca tcacaacaac catatctgca actgcaacca 60
tttc 64

<210> SEQ ID NO 572
<211> LENGTH: 64
<212> TYPE: DNA
<213> ORGANISM: Artificial Sequence
<220> FEATURE:
<223> OTHER INFORMATION: fig 10c -36bp (3)

<400> SEQUENCE: 572
caatatccag ggcagcaaca accatttcca tcacaacaac catttctgca gccgcaacca 60
tttc 64

<210> SEQ ID NO 573
<211> LENGTH: 830
<212> TYPE: DNA
<213> ORGANISM: Artificial Sequence
<220> FEATURE:
<223> OTHER INFORMATION: fig 12 BW208 wt group 1

<400> SEQUENCE: 573
atgaagacct tactcatcca aacaatcctc gtgatggcaa taaccatcgc caccgccaat 60
atgcaggtcg accctagcgg ccaagtacca tggccacaac aacaaccatt cccgcagcct 120
caccaaccat tctcccagca accgcaacaa acatttcccc aaccccaaca aacattcccc 180
catcaaccac aacaacaatt ttcccagcct cagcaaccac aacaacaatt tatccagccc 240
caacaaccat tcccccaaca accacaacaa acatatcccc agcgaccaca acaaccattc 300
ccccagactc aacaacccca acaaccattt ccccagtccc agcaaccaca acaacctttt 360
ccccagcccc aacaacaatt cccgcagccc caacaaccac aacaatcatt cccccaacaa 420
caaccatcgt tgattcaaca atctctacaa caacagttga acccatgcaa gaatttcctc 480
ttgcaacaat gcaaacctgt gtccttggtg tcatccctct ggtcaatgat cttgccacga 540
agcgattgcc aggtgatgcg gcaacaatgt tgccaacaac tagcacaaat tcctcagcaa 600
ctccagtgtg cagccatcca tagcatcgtg cattccatca tcatgcagca agaacaacaa 660
gaacaacgac agggtgtgca aatcctggtg ccactgtctc aacagcaaca ggtaggtcaa 720
ggtactctcg tccaaggtca gggcatcatc caacctcaac aaccagctca attggaggtg 780
attaggtcat tggtgttgca aactcttgca accatgtgca acgtgtatgt 830

<210> SEQ ID NO 574
<211> LENGTH: 827
<212> TYPE: DNA
<213> ORGANISM: Artificial Sequence
<220> FEATURE:
<223> OTHER INFORMATION: fig 12 BW208wt group 2

<400> SEQUENCE: 574
atgaagacct tactcatcct aacaatcctt gcgatggcaa caacaatcgc cactgccaat 60
atgcaggtcg accctagcag ccgagtacaa tggccacaag aacaaccacc cccccagtcc 120
caacaaccat tctcccagca accacaacaa atatttcccc aaccccaaca aacattcccc 180
catcaaccac aacaagcatt tctccaacct caacaaacat tcccccgtcg accacaacaa 240
caatttcccc agccccagca accacaacaa ccatttcctc agccccaaca accccaacta 300
ccatttcccc aacaaccaca acaaccattc ccccagcctc aacaacccca acaaccattt 360
ccccagtcac agcaaccaca acaacctttt ccccagcccc aacaacaatt tccgcagccc 420
caacaaccac aacaatcatt cccccaacaa caacaatgga tgattcagtc atttctacaa 480
caacagatga acccctgcaa gaatttcctc ttgcagcaat gcaaccctgt gtcattggtg 540
tcatctctcg tgtcaataat cttgccacga agtgattgcc agctgatgca gcaacaatgt 600
tgccaacaac tagcacaaat tcctcaacaa ctccagtgcg cagccatcca caacgtcgcg 660
cattccatca tcatgcagca agaacaacaa cgaggcgtgc agatcctgcg gccactattt 720
cagctcgccc agggtctggg tatcatccaa cctcaacaac cagctcaatt ggaggggatc 780
aggtcattgg tattgaaaac tcttccaacc atgtgcaacg tgtatgt 827

<210> SEQ ID NO 575
<211> LENGTH: 920
<212> TYPE: DNA
<213> ORGANISM: Artificial Sequence
<220> FEATURE:
<223> OTHER INFORMATION: fig 12 BW208wt group 3

<400> SEQUENCE: 575
atgaagacct tactcatcct gacaatcatt gcggtggcac taactaccac caccgccaat 60
atacaggtcg accctagtgg ccaagtacaa tggccacaac aacaacaacc attcccccag 120
ccccaacaac cacaacaaat ttttccccaa ccccaacaaa cattccccca tcaaccacaa 180
caagcatttc cccaacccca acaaacattc ccccatcaac cacaacaaca atttccccag 240
ccccagcaac cacaacaacc atttccccag caaccacaac aacaatttcc ccagccccaa 300
caaccacaac aaccatttcc ccagcaacca caacaacaat ttccccagcc ccaacaacca 360
caacaaccat ttccccagcc ccaacaaccc caactaccat ttccgcaaca accacaacaa 420
ccattccccc agcctcaaca accccaacaa ccatttcccc agttacagca accacaacaa 480
cctttacccc agccccaaca accgcaacaa ccattccccc agcaacaaca accattgatt 540
cagccatacc tacaacaaca gatgaacccc tgcaagaatt acctcttgca acaatgcaac 600
cctgtgtcat tggtgtcatc cctcgtgtca atgatcttgc cacgaagtga ttgcaaggtg 660
atgcggcaac aatgttgcca acaactagca cagattcctc agcagctcca gtgcgcagcc 720
atccatggcg tcgtgcattc catcatcatg cagcaagaac gacaacaaca acaacaacaa 780
caacaaggca tacagatcat gcggccacta tttcagctcg tccagggtca gggcatcatc 840
caacctcaac aaccagctca attggaggtg atcaggtcat tggtattggg aactcttcca 900
accatgtgca acgtgtatgt 920

<210> SEQ ID NO 576
<211> LENGTH: 809
<212> TYPE: DNA
<213> ORGANISM: Artificial Sequence
<220> FEATURE:
<223> OTHER INFORMATION: fig 12 BW208wt group 4

<400> SEQUENCE: 576
atgaagacct tactcatccw aacaatccty gygatggcaa taaccatcgg caccgccaat 60
atscaggtcg accctagcrg ccaagtacaa tggcyacaac aacaacyagt cccmcagcyy 120
camcarccat tmtcccagca accacaacaa acatttcccc raccycaaca aacattcccc 180
catcaaccac aacaacaakt tycccagcct cagcaaccac aacaacmatt tctccagccc 240
cgacaaccat tcccccaaca accacaacaa ccatatcccc agcaaccaca gcaaccgttc 300
ccccagactc aacaacccca acaaccattt ccccagtcca agcaaccaca acaacctttt 360
ccccagcccc aacaaccgca acaatcattc cccccaacaac aaccatcgtt gattcaacaa 420
tctctacaac aacagttgaa cccatgcaag aatttcctct tgcagcaatg caaacctgtg 480
tccttggtgt catcsctctg gtcaatcatc ttgccaccaa gcgattgcca ggtgatgcgg 540
caacaatgtt gtcaacaact agcacaaatt cctcagcaac tccagtgtgc agccatccat 600
agcgtcgtgc attccatcat catgcagcaa gaacaacaag aacaactaca gggtgtgcaa 660
atcctggtgc cactgtctca acagcaacaa gtgggtcaag gtattctcgt ccagggtcaa 720
ggcatcatcc aacctcaaca accagctcaa ttggaggtga tcaggtcatt ggtgttgcaa 780
actcttccaa ccatgtgcaa cgtgtatgt 809

<210> SEQ ID NO 577
<211> LENGTH: 918
<212> TYPE: DNA
<213> ORGANISM: Artificial Sequence
<220> FEATURE:
<223> OTHER INFORMATION: fig 12 BW208wt group 5

<400> SEQUENCE: 577
atgaagacct tactcatcct gacaatcctt gcgatggcaa taaccatcgg caccgccaat 60
atccaggtcg accctagcgg ccaagtacaa tggctacaac aacaactagt cccccagctc 120
caacagccat tatcccagca accacaacaa acatttcccc aacctcaaca aacattcccc 180
catcaaccac aacaacaagt tccccagcct cagcaaccac aacaaccatt tctccagccc 240
caacaaccat tcccccaaca accacaacaa ccattccccc agactcaaca accacaacaa 300
ccatttcccc agcaaccaca acaaccattt ccccagactc aacaacccca acaaccattt 360
ccccaacaac cacaacaacc attcccccag actcaacaac cccaacaacc atttccccag 420
ctccagcaac cacaacaacc ttttccccag ccccaacaac aattgccgca gccccaacaa 480
ccgcaacaat cattccccca acaacaacgg ccattcattc aaccatctct acaacaacag 540
ttgaacccat gcaagaatat cctcttgcaa caatgcaaac ctgcgtcatt ggtgtcatcc 600
ctctggtcaa taatctggcc acaaagcgat tgccaagtga tgcggcaaca atgctgccaa 660
caactagcac agattcctca acagctccag tgcgcagcca tccatagcgt cgtgcattcc 720
atcatcatgc agcagcagca gcaacaacaa caacaacaag gcatgcatat ctttctgcca 780
ctatctcagc agcaacaggt gggtcaaggt tctctagtcc aaggccaggg catcatccaa 840
ccacaacaac cagctcaatt ggaggcgatc agatcattgg tgttgcaaac tcttccatcc 900
atgtgcaacg tgtatgta 918

<210> SEQ ID NO 578
<211> LENGTH: 100
<212> TYPE: DNA
<213> ORGANISM: Artificial Sequence
<220> FEATURE:
<223> OTHER INFORMATION: fig 12b BW208 wt group 1

<400> SEQUENCE: 578
cccagcgacc acaacaacca ttcccccaga ctcaacaacc ccaacaacca tttccccagt 60
cccagcaacc acaacaacct tttccccagc cccaacaaca 100

<210> SEQ ID NO 579
<211> LENGTH: 100
<212> TYPE: DNA
<213> ORGANISM: Artificial Sequence
<220> FEATURE:
<223> OTHER INFORMATION: fig 12b t544-47

<400> SEQUENCE: 579
cccagcgacc acaacaacca ttcccccaga ctcaacaacc ccaacaacca tttccccagt 60
cccagcaacc acaacaacct tttccccagc cccaacaaca 100

<210> SEQ ID NO 580
<211> LENGTH: 100
<212> TYPE: DNA
<213> ORGANISM: Artificial Sequence
<220> FEATURE:
<223> OTHER INFORMATION: fig 12b T544-48

<400> SEQUENCE: 580
cccagcgacc acaacaacca ttcccccaga ctcaacaacc ccaacaacca tttccccagt 60
cccagcaacc acaacaacct tttccccagc cccaacaaca 100

<210> SEQ ID NO 581
<211> LENGTH: 100
<212> TYPE: DNA
<213> ORGANISM: Artificial Sequence
<220> FEATURE:
<223> OTHER INFORMATION: fig 12b T544-50

<400> SEQUENCE: 581
cccagcgacc acaacaacca ttcccccaga ctcaacaacc ccaacaacca tttccccagt 60
cccagcaacc acaacaacct tttccccagc cccaacaaca 100

<210> SEQ ID NO 582
<211> LENGTH: 99
<212> TYPE: DNA
<213> ORGANISM: Artificial Sequence
<220> FEATURE:
<223> OTHER INFORMATION: fig 12b T544-52

<400> SEQUENCE: 582
cccagcgacc acaacaacca ttcccccaga ctcaacaacc ccaacaacca tttccccagt 60
cccagcaacc acaacaacct ttccccagcc ccaacaaca 99

<210> SEQ ID NO 583
<211> LENGTH: 100
<212> TYPE: DNA
<213> ORGANISM: Artificial Sequence
<220> FEATURE:
<223> OTHER INFORMATION: fig 12b T544-53

<400> SEQUENCE: 583
cccagcgacc acaacaacca ttcccccaga ctcaacaacc ccaacaacca tttccccagt 60
cccagcaacc acaacaacct tttccccagc cccaacaaca 100

<210> SEQ ID NO 584
<211> LENGTH: 100
<212> TYPE: DNA
<213> ORGANISM: Artificial Sequence
<220> FEATURE:
<223> OTHER INFORMATION: fig 12b T544-57

<400> SEQUENCE: 584
cccagccacc acaacaacca ttcccccaga ctcaacaacc ccaacaacca tttccccagt 60
cccagcaacc acaacaacct tttccccagc cccaacaaca 100

<210> SEQ ID NO 585

<211> LENGTH: 100
<212> TYPE: DNA
<213> ORGANISM: Artificial Sequence
<220> FEATURE:
<223> OTHER INFORMATION: fig 12b T544-59

<400> SEQUENCE: 585
cccagcgacc acaacaacca ttcccccaga ctcaacaacc cctacaacca tttccccagt 60
cccagcaacc acaacaacct tttccccagc cccaacaaca 100

<210> SEQ ID NO 586
<211> LENGTH: 100
<212> TYPE: DNA
<213> ORGANISM: Artificial Sequence
<220> FEATURE:
<223> OTHER INFORMATION: fig 12b T544-61

<400> SEQUENCE: 586
cccagcgacc acaacaacca ttcccccaga ctcaacaacc ccaacaacca tttccccagt 60
cccagcaacc acaacaacct tttccccagc cccaacaaca 100

<210> SEQ ID NO 587
<211> LENGTH: 100
<212> TYPE: DNA
<213> ORGANISM: Artificial Sequence
<220> FEATURE:
<223> OTHER INFORMATION: fig 12b T544-67

<400> SEQUENCE: 587
cccagcgacc acaacaacca ttcccccaga ctcaacaacc ccaacaacca tttccccagt 60
cccagcaacc acaacaacct tctccccagc cccaacaaca 100

<210> SEQ ID NO 588
<211> LENGTH: 100
<212> TYPE: DNA
<213> ORGANISM: Artificial Sequence
<220> FEATURE:
<223> OTHER INFORMATION: fig 12b T544-69

<400> SEQUENCE: 588
cccagcgacc acaacaacca ttcccccaga ctcaacaacc ccaacaacca tttccccagt 60
cccagcaacc acaacaacct tttccccagc cccaacaaca 100

<210> SEQ ID NO 589
<211> LENGTH: 100
<212> TYPE: DNA
<213> ORGANISM: Artificial Sequence
<220> FEATURE:
<223> OTHER INFORMATION: fig 12b T544-71

<400> SEQUENCE: 589
cccagcgacc acaacaacca ttcccccaga ctcaacaacc ccaacaacca tttccccagt 60
cccagcaacc acaacaacct tttccccagc cccaacaaca 100

<210> SEQ ID NO 590
<211> LENGTH: 100
<212> TYPE: DNA
<213> ORGANISM: Artificial Sequence
<220> FEATURE:
<223> OTHER INFORMATION: fig 12b T544-72

<400> SEQUENCE: 590
cccagcgacc acaacaacca ttcccccaga ctcaacaacc ccaacaacca tttccccagt 60
cccagcaacc acaacaacct tttccccagc cccaacaaca 100

<210> SEQ ID NO 591
<211> LENGTH: 95
<212> TYPE: DNA
<213> ORGANISM: Artificial Sequence
<220> FEATURE:
<223> OTHER INFORMATION: fig 12b T544-73

<400> SEQUENCE: 591
cccagcgacc acaaccattc ccccagactc aacaacccca acaaccattt ccccagtccc 60
agcaaccaca acaaccttmc ccagccccaa caaca 95

<210> SEQ ID NO 592
<211> LENGTH: 100
<212> TYPE: DNA
<213> ORGANISM: Artificial Sequence
<220> FEATURE:
<223> OTHER INFORMATION: fig 12b T544-75

<400> SEQUENCE: 592
cccagcgacc acaacaacca ttcccccaga ctcaacaacc ccaacaacga tttccccagt 60
cccagcaacc acaacaacct tttccccagc cccaacaaca 100

<210> SEQ ID NO 593
<211> LENGTH: 99
<212> TYPE: DNA
<213> ORGANISM: Artificial Sequence
<220> FEATURE:
<223> OTHER INFORMATION: fig 12b T544-79

<400> SEQUENCE: 593
cccagcgacc acaacaacca ttcccccaca ctcaacaacc ccaacaacca tttccccagc 60
ccagcaacca caacaacctt ttccccagcc ccaacaaca 99

<210> SEQ ID NO 594
<211> LENGTH: 100
<212> TYPE: DNA
<213> ORGANISM: Artificial Sequence
<220> FEATURE:
<223> OTHER INFORMATION: fig 12b T544-80

<400> SEQUENCE: 594
cccagcgacc acaacaacca ttcccccaga ctcaacaacc ccaacaacca tttccccagt 60
cccagcaacc acaacaacct tttccccagc cccaacaaca 100

<210> SEQ ID NO 595
<211> LENGTH: 100
<212> TYPE: DNA
<213> ORGANISM: Artificial Sequence
<220> FEATURE:
<223> OTHER INFORMATION: fig 12b T544-81

<400> SEQUENCE: 595
cccagcgacc acaacaacca ttcccccaga ctcaacaacc ccaacaacca tttccccagt 60
cccagcaacc acaacaacct tttccccagc cccaacaaca 100

<210> SEQ ID NO 596

<211> LENGTH: 100
<212> TYPE: DNA
<213> ORGANISM: Artificial Sequence
<220> FEATURE:
<223> OTHER INFORMATION: fig 12b T544-82

<400> SEQUENCE: 596
cccagcgacc acracaacca ttgccgcaca ctcaacaacc ccaacaacca tttcgccagt 60
cccagcaacc acaacaacct tttgcccagc cccaacaaca 100

<210> SEQ ID NO 597
<211> LENGTH: 100
<212> TYPE: DNA
<213> ORGANISM: Artificial Sequence
<220> FEATURE:
<223> OTHER INFORMATION: fig 12b T544-85

<400> SEQUENCE: 597
cccagcgacc acaacaacca ttcccccaga ctcaacaacc ccaacaacca tttccccagt 60
cccagcaacc acaacaacct tttccccagc cccaacaaca 100

<210> SEQ ID NO 598
<211> LENGTH: 129
<212> TYPE: DNA
<213> ORGANISM: Artificial Sequence
<220> FEATURE:
<223> OTHER INFORMATION: fig 12b BWT208wt group 2

<400> SEQUENCE: 598
gcaaccacaa caaccatttc ctcagcccaa caaccccaac taccatttcc ccaacaacca 60
caacaaccat tcccccagcc tcaacaaccc caacaacgca accacaacaa ccatttcccc 120
agtcacagc 129

<210> SEQ ID NO 599
<211> LENGTH: 116
<212> TYPE: DNA
<213> ORGANISM: Artificial Sequence
<220> FEATURE:
<223> OTHER INFORMATION: fig 12b T544-54

<400> SEQUENCE: 599
gcaaccacaa caaccatttc ctcagcccca acaaccccaa ctaccatttc cccaacaacc 60
acaacaacca ttcccccagc ctcaacaacc ccaacaacca tttccccagt cacagc 116

<210> SEQ ID NO 600
<211> LENGTH: 116
<212> TYPE: DNA
<213> ORGANISM: Artificial Sequence
<220> FEATURE:
<223> OTHER INFORMATION: fig 12b T544-74

<400> SEQUENCE: 600
gcaaccacaa caaccatttc ctcagcccca acaaccccaa ctaccatttc cccaacaacc 60
acaacaacca ttcccccagc ctcaacaacc ccaacaacca tttccccagt cacagc 116

<210> SEQ ID NO 601
<211> LENGTH: 116
<212> TYPE: DNA
<213> ORGANISM: Artificial Sequence
<220> FEATURE:
<223> OTHER INFORMATION: T544-83

<400> SEQUENCE: 601
gcaaccacaa caaccatttc ctcagcccca acaaccccaa ctaccatttc cccaacaacc 60
acaacaacca ttcccccagc ctcaacaacc ccaacaacca tttccccagt cacagc 116

<210> SEQ ID NO 602
<211> LENGTH: 224
<212> TYPE: DNA
<213> ORGANISM: Artificial Sequence
<220> FEATURE:
<223> OTHER INFORMATION: bw208 wt, group 3

<400> SEQUENCE: 602
gcaaccacaa caaccatttc cccagcaacc acaacaacaa tttccccagc cccaacaacc 60
acaacaacca tttccccagc aaccacaaca acaatttccc cagccccaac aaccacaaca 120
accatttccc cagccccaac aaccccaact accatttccg caacaaccac aacaaccatt 180
cccccagcct caacaacccc aacaaccatt tccccagtta cagc 224

<210> SEQ ID NO 603
<211> LENGTH: 224
<212> TYPE: DNA
<213> ORGANISM: Artificial Sequence
<220> FEATURE:
<223> OTHER INFORMATION: T544-58

<400> SEQUENCE: 603
gcaaccacaa caaccatttc cccagcaacc acaacaacaa tttccccagc cccaacaacc 60
acaacaacca tttccccagc aaccacaaca acaacttccc cagccccaac aaccacaaca 120
accatttccc cagccccaac aaccccaact accatttccg caacaaccac aacaaccatt 180
cccccagcct caacaacccc aacaaccatt tccccagtta cagc 224

<210> SEQ ID NO 604
<211> LENGTH: 223
<212> TYPE: DNA
<213> ORGANISM: Artificial Sequence
<220> FEATURE:
<223> OTHER INFORMATION: T544-65

<400> SEQUENCE: 604
gcaaccacaa caaccatttc cccagcaacc acaacaacaa tttccccagc cccaacaacc 60
acaacaacat ttccccagca accacaacaa caatttcccc agcctcaaca accacaacaa 120
ccatttcccc agccccaaca accccaacta ccatttccgc aacaaccaca acaaccattc 180
ccccagcctc aacaacccca acaaccattt ccccagttac agc 223

<210> SEQ ID NO 605
<211> LENGTH: 100
<212> TYPE: DNA
<213> ORGANISM: Artificial Sequence
<220> FEATURE:
<223> OTHER INFORMATION: fig 12b BW208wt group 4

<400> SEQUENCE: 605
cccagcaacc acagcaaccg ttcccccaga ctcaacaacc ccaacaacca tttccccagt 60
ccaagcaacc acaacaacct tttccccagc cccaacaacc 100

<210> SEQ ID NO 606
<211> LENGTH: 100
<212> TYPE: DNA

<213> ORGANISM: Artificial Sequence
<220> FEATURE:
<223> OTHER INFORMATION: fig 12b T544-66

<400> SEQUENCE: 606
cccagcaacc acagcaaccg ttcccccaga ctcaacaacc ccaacaacca tttccccagt 60
ccaagcaacc acaacaacct tttccccagc cccaacaacc 100

<210> SEQ ID NO 607
<211> LENGTH: 100
<212> TYPE: DNA
<213> ORGANISM: Artificial Sequence
<220> FEATURE:
<223> OTHER INFORMATION: fig 12b T544-55

<400> SEQUENCE: 607
cccagcaacc acagcaaccg ttcccccaga ctcaacaacc ccaacaacca tttccccagt 60
ccaagcaacc acaacaacct tttccccagc cccaacaacc 100

<210> SEQ ID NO 608
<211> LENGTH: 100
<212> TYPE: DNA
<213> ORGANISM: Artificial Sequence
<220> FEATURE:
<223> OTHER INFORMATION: fig 12b T544-84

<400> SEQUENCE: 608
cccagcaacc acagcaaccg ttcccccaga ctcaacaacc ccaacaacca tttccccagt 60
ccaagcaacc acaacaacct tttccccagc cccaacaacc 100

<210> SEQ ID NO 609
<211> LENGTH: 100
<212> TYPE: DNA
<213> ORGANISM: Artificial Sequence
<220> FEATURE:
<223> OTHER INFORMATION: fig 12b T544-68

<400> SEQUENCE: 609
cccagcaacc acagcaaccg ttcccccaga ctcaacaacc ccaacaacca tttccccagt 60
ccaagcaacc acaacaacct tttccccagc cccaacaacc 100

<210> SEQ ID NO 610
<211> LENGTH: 100
<212> TYPE: DNA
<213> ORGANISM: Artificial Sequence
<220> FEATURE:
<223> OTHER INFORMATION: fig 12c con T545-2

<400> SEQUENCE: 610
cccagcgacc acaacaacca ttcccccaga ctcaacaacc ccaacaacca tttccccagt 60
cccagcaacc acaacaacct tttccccagc cccaacaaca 100

<210> SEQ ID NO 611
<211> LENGTH: 100
<212> TYPE: DNA
<213> ORGANISM: Artificial Sequence
<220> FEATURE:
<223> OTHER INFORMATION: T545 Group 1 T545-5

<400> SEQUENCE: 611
cccagcgacc acaacaacca ttcccccaga ctcaacaacc ccaacaacca tttccccagt 60
cccagcaacc acaacaacct tttccccagc cccaacaaca 100

<210> SEQ ID NO 612
<211> LENGTH: 100
<212> TYPE: DNA
<213> ORGANISM: Artificial Sequence
<220> FEATURE:
<223> OTHER INFORMATION: T454, Group 1 T545-8

<400> SEQUENCE: 612
cccagcgacc acaacaacca ttcccccaga ctcaacaacc ccaacaacca tttccccagt 60
cccagcaacc acaacaacct tttccccagc cccaacaaca 100

<210> SEQ ID NO 613
<211> LENGTH: 100
<212> TYPE: DNA
<213> ORGANISM: Artificial Sequence
<220> FEATURE:
<223> OTHER INFORMATION: T545, Group 1 T545-12

<400> SEQUENCE: 613
cccagcgacc acaacaacca ttcccccaga ctcaacaacc ccaacaacca tttccccact 60
cccagcaacc acaacaacct tttccccagc cccaacaaca 100

<210> SEQ ID NO 614
<211> LENGTH: 100
<212> TYPE: DNA
<213> ORGANISM: Artificial Sequence
<220> FEATURE:
<223> OTHER INFORMATION: T545, Group 1 T545-13

<400> SEQUENCE: 614
cccagcgacc acaacaacca ttcccccaga ctcaacaacc ccaacaacca tttccccagt 60
cccagcaacc acaacaacct tttccccagc cccaacaaca 100

<210> SEQ ID NO 615
<211> LENGTH: 100
<212> TYPE: DNA
<213> ORGANISM: Artificial Sequence
<220> FEATURE:
<223> OTHER INFORMATION: T545, Group 1 T545-14

<400> SEQUENCE: 615
cccagcgacc acaacaacca ttcccccaga ctcaacaacc ccaacaacca tttccccagt 60
cccagcaacc acaacaacct tttccccagc cccaacaaca 100

<210> SEQ ID NO 616
<211> LENGTH: 100
<212> TYPE: DNA
<213> ORGANISM: Artificial Sequence
<220> FEATURE:
<223> OTHER INFORMATION: T545, Group 1 T545-18

<400> SEQUENCE: 616
cccagcgacc acaacaacca ttcccccaga ctcaacaacc ccaacaacca tttccccagt 60
cccagcaacc acaacaacct tttccccagc cccaacaaca 100

<210> SEQ ID NO 617

<211> LENGTH: 100
<212> TYPE: DNA
<213> ORGANISM: Artificial Sequence
<220> FEATURE:
<223> OTHER INFORMATION: T545, Group 1 T545-19

<400> SEQUENCE: 617
cccagcgacc acaacaacca ttcccccaga ctcaacaacc ccaacaacca tttccccagt 60
cccagcaacc acaacaacct tttccccagc cccaacaaca 100

<210> SEQ ID NO 618
<211> LENGTH: 100
<212> TYPE: DNA
<213> ORGANISM: Artificial Sequence
<220> FEATURE:
<223> OTHER INFORMATION: T545, Group 1 T545-22

<400> SEQUENCE: 618
cccagcgacc acaacaacca ttcccccaga ctcaacaacc ccaacaacca tttccccagt 60
cccagcaacc acaacaacct tttccccagc cccaacaaca 100

<210> SEQ ID NO 619
<211> LENGTH: 100
<212> TYPE: DNA
<213> ORGANISM: Artificial Sequence
<220> FEATURE:
<223> OTHER INFORMATION: T545, Group 1 T545-27

<400> SEQUENCE: 619
cccagcgacc acaacaacca ttcccccaga ctcaacaacc ccaacaacca tttccccagt 60
cccagcaacc acaacaacct tttccccagc cccaacaaca 100

<210> SEQ ID NO 620
<211> LENGTH: 100
<212> TYPE: DNA
<213> ORGANISM: Artificial Sequence
<220> FEATURE:
<223> OTHER INFORMATION: T545, Group 1 T545-35

<400> SEQUENCE: 620
cccagcgacc acaacaacca ttcccccaga ctcaacaacc ccaacaacca tttccccagt 60
cccagcaacc acaacaacct tttccccagc cccaacaaca 100

<210> SEQ ID NO 621
<211> LENGTH: 100
<212> TYPE: DNA
<213> ORGANISM: Artificial Sequence
<220> FEATURE:
<223> OTHER INFORMATION: T545, Group 1 T545-36

<400> SEQUENCE: 621
cccagcaacc acaacaacca ttcccccaga ctcaacaacc ccaacaacca tttccccagt 60
cccagcaacc acaacaacct tttccccagc cccaacaaca 100

<210> SEQ ID NO 622
<211> LENGTH: 100
<212> TYPE: DNA
<213> ORGANISM: Artificial Sequence
<220> FEATURE:
<223> OTHER INFORMATION: T545 Group 1, T545-37

<400> SEQUENCE: 622
cccagcgacc acaacaacca ttcccccaga ctcaacaacc ccaacaacca tttccccagt 60
cccagcaacc acaacaacct tttccccagc cccaacaaca 100

<210> SEQ ID NO 623
<211> LENGTH: 102
<212> TYPE: DNA
<213> ORGANISM: Artificial Sequence
<220> FEATURE:
<223> OTHER INFORMATION: T545, Group 2 T545-16

<400> SEQUENCE: 623
acaaccattc ccccaacaac cccaactacc atttccccaa caaccccaac aaccattccc 60
ccagcctcag caaccccaac aaccatttcc ccagtcacaa ca 102

<210> SEQ ID NO 624
<211> LENGTH: 102
<212> TYPE: DNA
<213> ORGANISM: Artificial Sequence
<220> FEATURE:
<223> OTHER INFORMATION: T545, Group 2 T545-25

<400> SEQUENCE: 624
acaaacattc ccccaacaac cccaactacc atttccccaa caaccccaac aaccattccc 60
ccagcctcag caaccccaac aaccatttcc ccagtcacaa ca 102

<210> SEQ ID NO 625
<211> LENGTH: 132
<212> TYPE: DNA
<213> ORGANISM: Artificial Sequence
<220> FEATURE:
<223> OTHER INFORMATION: T545, Group 2 T545-26

<400> SEQUENCE: 625
acaaccacaa caaccatttc cccagcccca acaaacattc ccccaacaac cccaactacc 60
atttccccaa caaccccaac aaccattccc ccagcctcag caaccccaac aaccatttcc 120
ccagtcacaa ca 132

<210> SEQ ID NO 626
<211> LENGTH: 117
<212> TYPE: DNA
<213> ORGANISM: Artificial Sequence
<220> FEATURE:
<223> OTHER INFORMATION: T545, Group 2 T545-28

<400> SEQUENCE: 626
gcaaccacaa caaccatttc ctcagcccca acaaccccaa ctaccatttc cccaacaacc 60
acaacaacca ttcccccagc ctcaacaacc ccaacaacca tttccccagt cacagca 117

<210> SEQ ID NO 627
<211> LENGTH: 201
<212> TYPE: DNA
<213> ORGANISM: Artificial Sequence
<220> FEATURE:
<223> OTHER INFORMATION: BW208 wt, group 3

<400> SEQUENCE: 627
gcaaccacaa caaccatttc cccagcaacc acaacaacaa tttccccagc cccaacaacc 60
acaacagcaa ccacaacaac aatttcccca gccccaacaa ccaaccattt ccccaacaac 120
cccaactacc atttccgcaa caaccacaac aaccattccc ccagcctcaa caaccccaac 180
aaccatttcc cagttacagc a 201

<210> SEQ ID NO 628
<211> LENGTH: 225
<212> TYPE: DNA
<213> ORGANISM: Artificial Sequence
<220> FEATURE:
<223> OTHER INFORMATION: T545, Group 3 T545-11

<400> SEQUENCE: 628
gcaaccacaa caaccatttc cccagcaacc acaacaacaa tttccccagc cccaacaacc 60
acaacaacca tttccccagc aaccacaaca acaatttccc cagccccaac aaccacaaca 120
accatttccc cagccccaac aaccccaact accatttccg caacaaccac aacaaccatt 180
cccccagcct caacaacccc aacaaccatt tccccagtta cagca 225

<210> SEQ ID NO 629
<211> LENGTH: 216
<212> TYPE: DNA
<213> ORGANISM: Artificial Sequence
<220> FEATURE:
<223> OTHER INFORMATION: T545, Group 3 T545-20

<400> SEQUENCE: 629
acaaccacaa caacaatttc tccagccaca acaaccattc cccccaacaac cacaacaacc 60 atatccccag caaccacaac aaccattccc ccagactcaa caaccccaac aactatttcc 120
ccagtcccag caaccacaac aaccatatcc ccagcaacca caacaaccat tcccccagac 180
tcaacaaccc caacaacaat ttccccaatc ccagca 216

<210> SEQ ID NO 630
<211> LENGTH: 225
<212> TYPE: DNA
<213> ORGANISM: Artificial Sequence
<220> FEATURE:
<223> OTHER INFORMATION: T545, Group 3 T545-29

<400> SEQUENCE: 630
gcaaccacaa caaccatttc cccagcaacc acaacaacaa tttccccagc cccaacaacc 60
acaacaacca tttccccagc aaccacaaca acaatttccc cagccccaac aaccacaaca 120
accatttccc cagccccaac aaccccaact accatttccg caacaaccac aacaaccatt 180
cccccagcct caacaacccc aacaaccatt tccccagtta cagca 225

<210> SEQ ID NO 631
<211> LENGTH: 219
<212> TYPE: DNA
<213> ORGANISM: Artificial Sequence
<220> FEATURE:
<223> OTHER INFORMATION: T545, Group 3 T545-34

<400> SEQUENCE: 631
acaaccacaa caaccatttc cccagcaacc acaacaacca ttcccccaga ctcaacagcc 60
acaacaacca tttccccagc aaccacaaca accatttccc cagcaaccac aacaaccatt 120
tccccagccc caacaagccc aactaccatt tccccaacaa ccacaacaac cattccccca 180
gcctcaacaa ccccaacaac catttcccca gtcacagca 219

<210> SEQ ID NO 632
<211> LENGTH: 100

<212> TYPE: DNA
<213> ORGANISM: Artificial Sequence
<220> FEATURE:
<223> OTHER INFORMATION: T545, Group 4 T545-1

<400> SEQUENCE: 632
ccccagcaac cacagcaacc gttcccccag actcaacaac cccaacaacc atttccccag 60
tccaagcaac cacaacaacc ttttccccag ccccaacaac 100

<210> SEQ ID NO 633
<211> LENGTH: 100
<212> TYPE: DNA
<213> ORGANISM: Artificial Sequence
<220> FEATURE:
<223> OTHER INFORMATION: T545, Group 4 T545-3

<400> SEQUENCE: 633
ccccagcaac cacagcaacc gttcccccag actcaacaac cccaacaacc atttccccag 60
tccaagcaac cacaacaacc ttttccccag ccccaacaac 100

<210> SEQ ID NO 634
<211> LENGTH: 100
<212> TYPE: DNA
<213> ORGANISM: Artificial Sequence
<220> FEATURE:
<223> OTHER INFORMATION: T545, Group 5 T545-4

<400> SEQUENCE: 634
ccccagcaac cacagcaacc gttcccccag actcaacaac cccaacaacc atttccccag 60
tccaagcaac cacaacaacc ttttccccag ccccaacaac 100

<210> SEQ ID NO 635
<211> LENGTH: 100
<212> TYPE: DNA
<213> ORGANISM: Artificial Sequence
<220> FEATURE:
<223> OTHER INFORMATION: T545, Group 5 T545-9

<400> SEQUENCE: 635
ccccaacaac cacaacaacc attcccccag actcaacaac cccaacaacc atttccccag 60
tccaagcaac cacaacaacc ttttccccag ccccaacaac 100

<210> SEQ ID NO 636
<211> LENGTH: 100
<212> TYPE: DNA
<213> ORGANISM: Artificial Sequence
<220> FEATURE:
<223> OTHER INFORMATION: T545, Group 4 T545-10

<400> SEQUENCE: 636
ccccagcaac cacagcaacc gttcccccag actcaacaac cccaacaacc atttccccag 60
tccaagcaac cacaacaacc ttttccccag ccccaacaac 100

<210> SEQ ID NO 637
<211> LENGTH: 100
<212> TYPE: DNA
<213> ORGANISM: Artificial Sequence
<220> FEATURE:
<223> OTHER INFORMATION: T545, Group 4 T545-21

-continued

<400> SEQUENCE: 637
ccccagcaac cacagcaacc gttcccccag actcaacaac cccaacaacc atttccccag 60
tccaagcaac cacaacaacc ttttccccag ccccaacaac 100

<210> SEQ ID NO 638
<211> LENGTH: 100
<212> TYPE: DNA
<213> ORGANISM: Artificial Sequence
<220> FEATURE:
<223> OTHER INFORMATION: T545, Group 4 T545-24

<400> SEQUENCE: 638
ccccagcaac cacagcaacc gttcccccag actcaacaac cccaacaacc atttccccag 60
tccaagcaac cacaacaacc ttttccccag ccccaacaac 100

<210> SEQ ID NO 639
<211> LENGTH: 100
<212> TYPE: DNA
<213> ORGANISM: Artificial Sequence
<220> FEATURE:
<223> OTHER INFORMATION: T545, Group 4 T545-30

<400> SEQUENCE: 639
ccccagcaac cacagcaacc gttcccccag actcaacaac cccaacaacc atttccccag 60
tccaagcaac cacaacaacc ttttccccag ccccaacaac 100

<210> SEQ ID NO 640
<211> LENGTH: 174
<212> TYPE: DNA
<213> ORGANISM: Artificial Sequence
<220> FEATURE:
<223> OTHER INFORMATION: BW208 wt, group 5

<400> SEQUENCE: 640
cacaacaacc attcccccag actcaacaac cacaacaacc atttccccag caaccacaac 60
aaccatttcc ccagactcaa caaccccaac aaccatttcc cacaaccaca acaaccattc 120
ccccagactc aacaacccaa caaccatttc cccagcagca accacaacaa cctt 174

<210> SEQ ID NO 641
<211> LENGTH: 183
<212> TYPE: DNA
<213> ORGANISM: Artificial Sequence
<220> FEATURE:
<223> OTHER INFORMATION: T545, Group 5 T545-6

<400> SEQUENCE: 641
aaccacaaca accattcccc cagactcaac aaccacaaca accatttccc cagcaaccac 60
aacaaccatt cccccagact caacaaccac aacaaccatt tccccaacaa ccacaacaac 120
cattccccca gactcaacaa ccccaacaac catttcccca gctccagcaa ccacaacaac 180
ctt 183

<210> SEQ ID NO 642
<211> LENGTH: 179
<212> TYPE: DNA
<213> ORGANISM: Artificial Sequence
<220> FEATURE:
<223> OTHER INFORMATION: T545, Group 5 T545-7

<400> SEQUENCE: 642
cacaacaacc attcccccag actcaacaac cacaacaacc atttccccag caaccacaac 60
aaccatttcc ccagachaac aaccccaaca accatttccc caacaaccac aacaaccatt 120
cccccagact caacaaccca aacaaccatt tccccagctc cagcaaccac aacaacctt 179

<210> SEQ ID NO 643
<211> LENGTH: 1133
<212> TYPE: DNA
<213> ORGANISM: Artificial Sequence
<220> FEATURE:
<223> OTHER INFORMATION: Group 1 bw208 wt group 1

<400> SEQUENCE: 643
tttgtcctcc ttgccatggc gatgaagatc gccactgccg ctagggagtt aaaccctagc 60
aacaaagagt tacaatcacc tcaacaatca ttttcccatc aacaaccatt tccacacagc 120
agccatatcc acaacaacca tatccatcac agcaaccata tccatcgcaa caaccatttc 180
ccacacccca acaacaattt ccccagcaat cacaacaacc atttacccag ccccaacaac 240
cgaccccctt acaaccacaa caaccattcc cccagcaacc ccaacaacca caacaacctt 300
ttccacaacc ccaacaacca tttccctggc aaccacaaca accatttccc cagacccaac 360
aatcgttccc tctccaacca caacagccat tcccccagca acaaccattt ccccagcccc 420
aactaccatt cccccagtaa tcagaacaaa taattcccca gcaaccccaa caaccattcc 480
ccctgcaacc gcaacaacca ttcccccagc aaccccaaca accatttccc cagccccaac 540
aaccaatccc cgtgcaacca caacaatcat tcccccaaca atcccaacaa tcacaacaac 600
cttttgccca gccccaacaa ttatttcctg aactccaaca accaattccc cagcaaccac 660
aacaaccatt ccccctgcac ccgcaacaac cattccccca gcaaccgcaa caaccattcc 720
cccagcaacc gcaacaatca tttccccagc aaccacaaca accattcccc cagcaaccgc 780
aacaaccatt cccccatcat ccacaacaac cattccctca acaaccacaa caaccattcc 840
ccctacgacc gcaacaacca tttccccagc aaccccaaca atcacaccaa tcatttcccc 900
agccccaacc ccagcaaccc caacaaccat ccatccttca accacaacaa ccattacccc 960
aacaaccaca acaaccattt caacagcccc aacaacaatt atcccagcaa ccagaacaaa 1020
caatttccca gcaaccccaa caaccattcc cccagcaacc acaccaacct caacaaccat 1080
atccacaaca acaaccatat gggagtagtc ttacaagcat cggtggccaa tga 1133

<210> SEQ ID NO 644
<211> LENGTH: 1140
<212> TYPE: DNA
<213> ORGANISM: Artificial Sequence
<220> FEATURE:
<223> OTHER INFORMATION: Group 1 T545-105

<400> SEQUENCE: 644
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc atttccctgg caaccacaac aaccatttcc ccagacccaa 360
caatcgttcc ctctccaacc acaacagcca ttcccccagc aaccccaaca accatttccc 420
cagccccaac taccattccc ccagcaatca gaacaaataa ttccccagca accccaacaa 480
ccattccccc tgcaaccgca acaaccattc ccccagcaac cccaacaacc atttccccag 540
ccccaacaac caatccccgt gcaaccacaa caatcattcc ccctacaatc ccaacaatca 600
caacaacctt ttgcccagcc ccaacaatta tttcctgaac tccaacaacc aattccccag 660
caaccacaac aaccattccc cctgcaaccg caacaaccat tcccccagca accgcaacaa 720
ccattccccc agcaaccgca acaatcattt ccccagcaac cacaacaacc attcccccag 780
caaccgcaac aaccattccc ccaacaacca caacaaccat tccctcaaca accacaacaa 840
ccattccccc tacgaccgca acaaccattt ccccagcaac cccaacaatc acaacaagca 900
tttccccggg ccccaacccc agcaacccca acaaccatcc atccttcaac cacaacaacc 960
attaccccaa caaccacaac aaccatttca acagccccaa caacaattat cccagcaacc 1020
aggacaaaca atttcccagc aaccccaaca accattcccc cagcaaccac accaacctca 1080
acaaccatat ccacaacaac aaccatatgg gagtagtctt acaagcatcg gtggccaatg 1140

<210> SEQ ID NO 645
<211> LENGTH: 1139
<212> TYPE: DNA
<213> ORGANISM: Artificial Sequence
<220> FEATURE:
<223> OTHER INFORMATION: Group 1 T545-153

<400> SEQUENCE: 645
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc atttccctgg caaccacaac aaccatttcc ccagacccaa 360
caatcgttcc ctctccaacc acaacagcca ttcccccagc aaccccaaca accatttccc 420
cagccccaac taccattccc ccagcaatca gaacaaataa ttccccagaa ccccaacaac 480
cattccccct gcaaccgcaa caaccattcc cccagcaacc ccaacaacca tttccccagc 540
cccaacaacc aatccccgtg caaccacaac aatcattccc ccaacaatcc caacaatcac 600
aacaaccttt tgcccagccc caacaattat ttcctgaact ccaacaacca attccccagc 660
aaccacaaca accattcccc ctgcaaccgc aacaaccatt cccccagcaa ccgcaacaac 720
cattccccca gcaaccgcaa caatcatttc cccagcaacc acaacaacca ttcccccagc 780
aaccgcaaca accattcccc caacaaccac aacaaccatt ccctcaacaa ccacaacaac 840
cattccccct acgaccgcaa caaccatttc cccagcaacc ccaacaatca caaccaccat 900
ttccccagcc ccaaccccag caaccccaac aaccatccat ccttcaacca caacaaccat 960
taccccaaca accacaacaa ccatttcaac agccccaaca acaattatcc cagcaaccag 1020
aacaaacaat ttcccagcaa ccccaacaac cattccccca gcaaccacac caacctcaac 1080
aaccatatcc acaacaacaa ccatatggga gtagtcttac aagcatcggt ggccaatga 1139

<210> SEQ ID NO 646
<211> LENGTH: 1057
<212> TYPE: DNA
<213> ORGANISM: Artificial Sequence
<220> FEATURE:
<223> OTHER INFORMATION: Group 1, Bw208 wt gorup 2

<400> SEQUENCE: 646

```
tttgtcctcc ttgccatggc gatgaacatc gccactgccg ctaggcagct aaaccctagc     60
aacaaagagt tacaatcacc tcaacaatca ttttcccatc aacaacaacc atttccccag    120
aagtcatatc cacaacaacc atatccatca catcaaccat atccattgca acaaccattt    180
cctacacccc aacaacaatt tccccagcaa tcacaacaac catttcccca accccaacaa    240
ccgacccccc tacaaccaca acaaccattc cccagcaac cacaacaacc ttttccacag     300
ccccaacaac catttccttg gcaaccacaa caaccatttc cccagaccca acaatcgttc    360
cctctgcaac cacaacagcc atttccccag caaccccaac aaccatttcc ccagccccaa    420
ctaccattcc cacaacaacc agaacaaata attccccagc caaaccaaca accattcccc    480
ctgcaaccgc aacaaccatt cccccaacaa ccattccccc agcaacccca ataaccattt    540
ccccagtccc aacaaccaat ccccgtgcaa ctacaacaac cattacccca acaatcccaa    600
caatcacaac aaccttttcc ccggcctcaa caattatttc ctgaactcca acaaccaatt    660
ccccagcaac cacaacaacc attccccctg cacccgcaac aaccatcccc ccagcaatca    720
caacaaccat tcccccaaca accacaacaa ccttcccccct acaaccacaa caaccatccc    780
ccctacaacc gcaacaacca ttttcccagc aaccccaaca atcacaacaa tcatttcccc    840
agccccaacc ccagcaaccc caacaaccat ccatcctgca accacaacaa ccacaacaac    900
catttctgca gccccaacaa caattatccc agcaactaga acaaacaatt tcccagcaac    960
cccaacaacc aaccccccag caaccacacc aacctcaaca accatatcca caacaacaac   1020
catctgggag tagtcttaca agcatcggtg gccaatg                            1057
```

<210> SEQ ID NO 647
<211> LENGTH: 1058
<212> TYPE: DNA
<213> ORGANISM: Artificial Sequence
<220> FEATURE:
<223> OTHER INFORMATION: T544-119

<400> SEQUENCE: 647

```
tttgtcctcc ttgccatggc gatgaacatc gccactgccg ctaggcagct aaaccctagc     60
aacaaagagt tacaatcacc tcaacaatca ttttcccatc aacaacaacc atttccacag    120
aagtcatatc cacaacaacc atatccatca catcaaccat atccattgca acaaccattt    180
cctacacccc aacaacaatt tccccagcaa tcacaacaac catttcccca accccaacaa    240
ccgatccccc tacaaccaca acaaccattc cccagcaac cacaacaacc ttttccacag     300
ccccaacaac catttccttg gcaaccacaa caaccatttc cccagaccca acaatcgttc    360
cctctgcaac cacaacagcc atttccccag caaccccaac aaccatttcc ccagccccaa    420
ctaccattcc cacaacaacc agaacaaata attccccagc caaaccaaca accattcccc    480
ctgcaaccgc aacaaccatt cccccaacaa ccattccccc agcaacccca ataaccattt    540
ccccagtccc aacaaccaat ccccgtgcaa ctacaacaac cattacccca acaatcccaa    600
caatcacaac aaccttttcc ccggcctcaa caattatttc ctggactcca acaaccaatt    660
ccccagcaac cacaacaacc attccccctg cacccgcaac aaccatcccc ccagcaatca    720
caacaaccat tcccccaaca gccacaacaa cctttccccc tacaaccaca acaaccatcc    780
cccctacaac cgcaacaacc attttcccag caaccccaac aatcacaaca atcatttccc    840
```

cagccccaac cccagcaacc ccaacaacca tccatcctgc aaccacaaca accacaacaa 900
ccatttctgc agccccaaca acaatyatcc cagcaactag atcaaacaat tttccagcaa 960
ccccaacaac caaccccccca gcaaccacac caacctcaac aaccatatcc acaacaacaa 1020
ccatctggga gtagtcttac aagcatcggt ggccaatg 1058

<210> SEQ ID NO 648
<211> LENGTH: 1076
<212> TYPE: DNA
<213> ORGANISM: Artificial Sequence
<220> FEATURE:
<223> OTHER INFORMATION: T544-120

<400> SEQUENCE: 648
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240
ccgaccccct tacaaccaca acaaccattc ccccagcaac cccaacaacc acaacaacct 300
tttccacaac cccaacaacc atttccctgg caaccacaac aaccatttcc ccagacccaa 360
caatcgttcc ctctgcaacc acaacaacca ttcccccagc aaccccaaca accatttccc 420
cagccccaac taccattctc ccagcaacca gaacaaataa ttccccagcc accccaacaa 480
ccattccccc tgcaaccgca acaaccattc ccccagcaac cccaacaacc attgccccaa 540
caaccccaac aaccatttcc ccagccccaa caaccaatcc ccgtgcaacc acaataacca 600
ttcccccaac aatcccaaca atcacaacaa cctttttcccc ggcctcaaca attatttcat 660
caactccaac aaccaattcc ccagcaacca caacaaccat tccccctgca cccgcaacaa 720
ccatcccccc agcaatcaca acaaccattc ccccaacaac cacaacaacc tttcccccta 780
caaccacaac aaccatcccc cctacaaccg caacaaccat tttcgcagca accccaacaa 840
tcacaacaat catttcccca gacccaaccc cagcaacccc aacaaccatc catcctgcaa 900
ccacaacaac cacaacaaca atttctgcag ccccaacaac aattatccca gcaactagaa 960
caaacaattt cccagcaacc ccaacaacca accccccagc aaccacacca acctcaacaa 1020
ccatatccac aacaacaacc atctgggagt agtcttacaa gcatcggtgg ccaatg 1076

<210> SEQ ID NO 649
<211> LENGTH: 1056
<212> TYPE: DNA
<213> ORGANISM: Artificial Sequence
<220> FEATURE:
<223> OTHER INFORMATION: T545-156

<400> SEQUENCE: 649
tttgtcctcc ttgccatggc gatgaacatc gccactgccg ctaggcagct aaaccctagc 60
aacaaagagt tacaatcacc tcaacaatca ttttcccatc aacaacaacc atttccacag 120
aagtcatatc cacaacaacc atatccatca catcaaccat atccattgca acaaccattt 180
cctacacccc aacaacaatt tccccagcaa tcacaacaac catttcccca accccaacaa 240
ccgacccccc tacaaccaca acaaccattc ccccagcaac cacaacaacc tttccacagc 300
cccaacaacc atttccttgg caaccacaac aaccatttcc ccagacccaa caatcgttcc 360
ctctgcaacc acaacagcca tttccccagc aaccccaaca accatttccc cagccccaac 420
taccattccc acaacaacca gaacaaataa ttccccagcc aaaccaacaa ccattccccc 480
tgcaaccgca acaaccattc ccccaacaac cattcccccca gcaaccccaa taaccatttc 540
cccagtccca acaaccaatc cccgtgcaac tacaacaacc attaccccaa caatcccaac 600
aatcacaaca accttttccc cggcctcaac aattatttcc tgaactccaa caaccaattc 660
cccagcaacc acaacaacca ttccccctgc acccgcaaca accatccccc cagcaatcac 720
aacaaccatt ccccaacaac cacaacaacc tttcccccta caaccacaac aaccatcccc 780
cctacaaccg caacaaccat tttcccagca accccaacaa tcacaacaat catttcccca 840
gccccaaccc caacaacccc aacaaccatc catcctgcaa ccacaacaac cacaacaacc 900
gtttctgcag ccccaacaac aattatccca gcaactagaa caaacaattt cccagcaacc 960
ccaacaacca accccccagc aaccacacca acctcaacaa ccatatccac aacaacaacc 1020
atctgggagt agtcttacaa gcaccggtgg ccaatg 1056

<210> SEQ ID NO 650
<211> LENGTH: 948
<212> TYPE: DNA
<213> ORGANISM: Artificial Sequence
<220> FEATURE:
<223> OTHER INFORMATION: T544-159

<400> SEQUENCE: 650
tttgtcctcc ttgccatggc gatgaacgtc gccactgccg ctaggcagct aaaccctagc 60
aacaaagagt tacaatcacc ccaacaatca tcttcccatc aacaacaacc atttccacag 120
aagtcatatc cacaacaacc atatccatca catcaaccat atccattgca acaaccattt 180
cctacacccc aacaacaatt tccccagcaa tcacaacaac cattttcccc aaccccaaca 240
acaatcgttc cctctgcaac cacaacagcc atttccccag caaccccaac aaccatttcc 300
ccagccccaa ctaccattcc cacaacaacc agaacaaata attccccagc caaaccaaca 360
accattcccc ctgcaaccgc gacaaccatt cccccaacaa ccattccccc agcaacccca 420
ataaccattt ccccagtccc aacaaccaat ccccgtgcaa ctacaacaac cattacccca 480
acaatcccaa caatcacaac aaccttttcc ccggcctcaa caattatttc ctgaactcca 540
acaaccaatt ccccagcaac cacaacaacc attccccctg cacccgcaac aaccatcccc 600
ccagcaatca caacaaccat tcccccaaca accacaacaa cctttccccc tacaaccaca 660
acaaccatcc cccctacaac cgcaacaacc attttcccag caaccccaac aatcacaaca 720
atcatttccc cagccccaac cccagcaacc ccaacaacca tccatcctgc aaccacaaca 780
accacaacaa ccatttctgc agccccaaca acaattatcc cagcaactag aacaaacaat 840
ttcccagcaa ccccaacaac caacccccca gcaaccacac caacctcaac aaccatatcc 900
acaacaacaa ccatctggga gtagtcttac aagcatcggt ggccaatg 948

<210> SEQ ID NO 651
<211> LENGTH: 380
<212> TYPE: DNA
<213> ORGANISM: Artificial Sequence
<220> FEATURE:
<223> OTHER INFORMATION: Bw208 wt(1) group 3

<400> SEQUENCE: 651
tttgtcctcc ttgccatggc gatgaacatc gccactgccg ctaggcagct aaaccctagc 60
aacaaagagt tacaatcacc tcaacaatca ttttcccatc aacaaacaga agtcatatcc 120
acaacaacca tatccatcac atcaaccata tccattgcaa caaccatttc ctacaccaac 180
aacaatttcc ccagcaatca caacaaccat ttccccaacc ccaacaaccg accccctac 240 aaccacaaca accattcccc cagcaaccac aacaacctca acaaccatat ccacaacaac 300
aaccatcacc caacaatcca acagccattc ccccagcaac cacaccaatg tgagtagtct 360
tacaagcatc ggtggccaat 380

<210> SEQ ID NO 652
<211> LENGTH: 561
<212> TYPE: DNA
<213> ORGANISM: Artificial Sequence
<220> FEATURE:
<223> OTHER INFORMATION: Bw208 wt (2) group 3

<400> SEQUENCE: 652
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccattgca acaaccattt 180
cccaccccaa caacaatttc cccagcaatc acaacaacca tttacccagc cccaacaacc 240 gacccccctta caaccacaac aaccattccc ccagcaaccc caacaaccac aacaaccatt 300
tccacaaccc caacaaccat ttccctggcg accacaacaa ccatttcccc agacccaaca 360
atcgttccct ctccaaccac aacagccatt cccccagcaa cccaacaacc atttccccag 420
ccccaactac cattccccca gcaatcagaa caaataattc ccagcaaccc caacaaccaa 480
ccccccagca accacaccaa cccaacaacc aaccacaaca acaaccatct gggagtagtc 540
ttacaagcat cggtggccaa t 561

<210> SEQ ID NO 653
<211> LENGTH: 529
<212> TYPE: DNA
<213> ORGANISM: Artificial Sequence
<220> FEATURE:
<223> OTHER INFORMATION: T544113

<400> SEQUENCE: 653
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc atttccctgg caaccacaac aaccatttcc ccagacccaa 360
caatcgttcc ctctccaacc acaacagcca ttcccccagc aaccccaaca accatttccc 420
cagccccaac taccattccc ccagcaatca gaacaaataa ttccccagca accccaacaa 480
ccattccccc tgcaaccgca acaaccattc ccccagcaac cccaacaac 529

<210> SEQ ID NO 654
<211> LENGTH: 810
<212> TYPE: DNA
<213> ORGANISM: Artificial Sequence
<220> FEATURE:
<223> OTHER INFORMATION: T544131

<400> SEQUENCE: 654
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240
ccgacccccc ttacaaccac aacaaccatt cccccagcaa ccccaacaac cacaacaacc 300
ttttccacaa ccccaacaac catttccctg gcaaccacaa caaccatttc cccagaccca 360
acaatcgttc cctctccaac cacaacaacc attcccccag caaccccaac aaccatttcc 420
ccagccccaa ctaccattcc cccagcaatc agaacaaata attccccagc aaccccaaca 480
accattcccc ctgcaaccgc aacaaccatt cccccacaac cccaacaacc atttccccag 540
ccccaacaac caatccccgt gcaaccacaa caatcattcc cccaacaatc ccaacaatca 600
caacaacctt ttgcccagcc ccaacaatta tttcctcaac tccaacaacc aattccccag 660
caaccacaac aaccattccc cctgcaaccg caacaaccat tcccccagca accccaacaa 720
ccattccccc cagcaaccac accaacctca acaaccatat ccacaacaac aaccatatgg 780
gagtagtctt acaagcatcg gtggccaatg 810

<210> SEQ ID NO 655
<211> LENGTH: 779
<212> TYPE: DNA
<213> ORGANISM: Artificial Sequence
<220> FEATURE:
<223> OTHER INFORMATION: T544128

<400> SEQUENCE: 655
tttgtcctcc ttgccatggc gatgaagatc gccactgccg ctagggagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aaccacaatt tccccagcaa tcacaacaac catttaccca gccccaacaa 240
ccgacccccc tacaaccaca acaaccattc cccagcaac cccaacaacc acaacaacct 300
tttccacagc cccaacaacc atttccctgg caaccacaac aaccatttcc ccagacccaa 360
caatcgttcc ctctccaacc acaacaacca ttcccccagc aaccccaaca accatttccc 420
cagccccaac tacaattccc ccagcaacca gaacaaataa ttccccagca accccaacaa 480
ccattccccc tacgaccgca acaaccattt ccccagcaac cccaacaatc acaacaatca 540
tttccccagc cccaacccca gcaaccccaa caaccatcca tccttcaacc acaacaacca 600
ttaccccaac aaccacaaca accatttcaa cagccccaac aacaattacc ccagcaacca 660
gaacaaacaa tttcccagca accccaacaa ccattccccc agcaaccaca ccaacctcaa 720
caaccatatc cacaacaaca accatatggg agtagtctta caagcatcgg tggccaatg 779

<210> SEQ ID NO 656
<211> LENGTH: 671
<212> TYPE: DNA
<213> ORGANISM: Artificial Sequence
<220> FEATURE:
<223> OTHER INFORMATION: T544129

<400> SEQUENCE: 656
tttgtcctcc ttgccatggc gatgaacatc gccactgccg ctagggagtt aaaccctagc 60
aacaaagagt tacaatcacc tcaacaatca ttttcccatc gacaacaacc atttccacag 120
cagtcatatc cacaacaacc atatccatca catcaaccat atccatcgca acaaccattt 180
cctacacccc aacaacaatt tccccagcaa tcacaacaac catttaccca accccaacaa 240

```
ccgacccccc tacaaccaca acaaccattc ccccagcaac cccaacaacc acaacaacct    300

tttccacaac cccaacaacc atttccctgg caaccacaac aaccatttcc ccagacccga    360

caatcgttcc ctctccaacc acaacagcca ttcccccagc aaccccaaca accatttccc    420

cagccccaac taccattccc ccagcaatca gaacaaataa ttccccagca accccaacaa    480

ccatccatcc tgcaaccaca acaaccacaa caaccatttc tgcagcccca acaacaatta    540

tcccagcaac tagaacaaac aatttcccag caaccccaac aaccaatccc ccagcaacca    600

caccaacctc aacaaccata tccacaacaa caaccatctg ggagtagtct tacaagcatc    660

ggtggccaat g                                                          671
```

<210> SEQ ID NO 657
<211> LENGTH: 490
<212> TYPE: DNA
<213> ORGANISM: Artificial Sequence
<220> FEATURE:
<223> OTHER INFORMATION: T54431

<400> SEQUENCE: 657

```
tttgtcctcc ttgccatggc gatgaacatc gccactgccg ctaggcagct aaaccctagc     60

aacaaagagt tacaatcacc tcaacaatca ttttcccatc aacaacaacc atttccacag    120

aagtcatatc cacaacaacc atatccatca catcaaccat atccatcgca acaaccattt    180

cctacacccc aacaacaatt tccccagcaa tcacaacaac catttaccca accccaacaa    240

ccgacccccc tacaaccaca acaaccattc ccccagcaac cacaacaacc ttttccacag    300

ccccaacaac catttccttg gcaaccacaa caaccatttc cccagaccca acaatcgttc    360

cctctccaac cacaacagcc atttccccag caaccccaac aaccattccc cagcaaccac    420

accaacctca acaaccatat ccacaacaac aaccatatgg gagtagtctt acaagcatcg    480

gtggccaatg                                                           490
```

<210> SEQ ID NO 658
<211> LENGTH: 560
<212> TYPE: DNA
<213> ORGANISM: Artificial Sequence
<220> FEATURE:
<223> OTHER INFORMATION: T54471

<400> SEQUENCE: 658

```
ttgtcctcct tgccatggcg atgaacatcg ccactgccgc taggcagcta aaccctagca     60

acaaagagtt acaatcacct caacaatcat ttcccatca acaacaacca tttccacaga    120

agtcacatcc acaacaacca tatccatcac atcaaccata tccatcgcaa caaccatttc    180

ctacacccca acaacaattt ccccagcaat cacaacaacc atttacccaa ccccaacaac    240

cgacccccct acaaccacaa caaccattcc cccagcaacc acaacaacct tttccacagc    300

cccaacaacc atttccttgg caaccacaac aaccatttcc ccagacccaa caatcgttcc    360

ctctccaacc acaacagcca tttccccagc aaccccaaca accatttccc cagccccaac    420

taccattccc acaacaacca gaacaaacaa ttccccagca accccaacaa ccattccccc    480

cagcaaccac accaacctca acaaccatat ccacaacaac aaccatatgg gagtagtctt    540

acaagcatcg gtggccaatg                                                560
```

<210> SEQ ID NO 659
<211> LENGTH: 642
<212> TYPE: DNA
<213> ORGANISM: Artificial Sequence

<220> FEATURE:
<223> OTHER INFORMATION: T54472

<400> SEQUENCE: 659
tttgtcctcc ttgccatggc gatgaacatc gccactgccg ctaggcagct aaaccctagc 60
aacaaagagt tacaatcacc tcaacaatca ttttcccatc aacaacaacc atttccacag 120
aagtcatatc cacaacaacc atatccatca catcaaccat atccatcgca acaaccattt 180
cctacacccc aacaacaatt tccccagcaa tcacaacaac catttaccca accccaacaa 240
ccgacccccc tacaaccaca acaaccattc ccccagcaac cacaacaacc ttttccacag 300
ccccaacaac catttccttg gcaaccacaa caaccatttc cccagaccca acaatcgttc 360
cctctccaac cacaacagcc atttccccag caaccccaac aaccatttcc ccagccccaa 420
ctaccattcc cacaacaacc agaacaaata attccccagc caaaccaaca accattcccc 480
ctgcaaccgc aacaaccatt cccccaacaa ccattccccc agcaacccca ataaccattt 540
ccccagtccc aacaaccaat ccccgtgcaa ctacaacaac cattacccca acaatcccaa 600
caatcacaac aaccttttcc ccggcctcaa caattatttc ct 642

<210> SEQ ID NO 660
<211> LENGTH: 668
<212> TYPE: DNA
<213> ORGANISM: Artificial Sequence
<220> FEATURE:
<223> OTHER INFORMATION: T54419

<400> SEQUENCE: 660
tttgtcctcc ttgccatggc gatgaacatc gccactgccg ctaggcagct aaaccctagc 60
aacaaagagt tacaatcacc tcaacaatca ttttcccatc aacaacaacc atttccacag 120
aagtcatatc cacaacaacc atatccatca catcaaccat atccatcgca acaaccattt 180
cctacacccc aacaacaatt tccccagcaa tcacaacaac catttaccca accacaacaa 240
ccattccccc tacaaccgca acaaccattc ccccagcaac cacaacaacc attccccctg 300
caactgcaac aacccttttcc ccaacaacca caacaaccat ttccctaaca accacaacaa 360
cctttgcccc tacaaccaca acaaccattc cccctacaac cgcaacaacc attttcccag 420
caaccccaac aatcacaact atcatttcca cagcaacaac cccagcaacc ccaacaacca 480
tccatcctgc aaccacaaca accacagcaa ccatttctgc agccccaaca acaattatcc 540
cagcaactag aacaaacaat ttcccagcaa ccccaacaac caatccccca gcaaccacac 600
caacctcaac aaccatatcc acaacaacaa ccatctggga gtagtcttac aagcatcggt 660
ggccaatg 668

<210> SEQ ID NO 661
<211> LENGTH: 650
<212> TYPE: DNA
<213> ORGANISM: Artificial Sequence
<220> FEATURE:
<223> OTHER INFORMATION: T54420

<400> SEQUENCE: 661
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc atttccccaa caaccacaac aacctttccc cctacaacca 360
caacaaccat ccccccctaca accgcaacaa ccattttccc agcaacccca acaatcacaa 420
caatcatttc cacagcaaca accccagcaa ccccaacaac catccatcct gcaaccacaa 480
caaccacaac aaccatttct gcagccccaa caacaattat cccagcaact agaacaaaca 540
atttcccagc aaccccaaca accaaccccc cagcaaccac accaacctca acaaccatat 600
ccacaacaac aaccatctgg gagtagtctt acaagcatcg gtggccaatg 650

<210> SEQ ID NO 662
<211> LENGTH: 491
<212> TYPE: DNA
<213> ORGANISM: Artificial Sequence
<220> FEATURE:
<223> OTHER INFORMATION: T54434

<400> SEQUENCE: 662
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
aagtcatatc cacaacaacc atatccatca catcaaccat atccatcgca acaaccattt 180
cctacacccc aacaacaatt tccccagcaa tcacaacaac catttaccca accccaacaa 240
ccgacccccc tacaaccaca acaaccattc ccccagcaac cacaacaacc ttttccacaa 300
ccccaacaac catttccttg gcaaccacaa caaccatttc cccagaccca acaatcattc 360
cctctgcaac cgcaacagcc atttccccag caaccccaac aaccaacccc ccagcaacca 420
caccaacctc aacaaccata tccacaacaa caaccatctg ggagtagtct tacaagcatc 480
ggtggccaat g 491

<210> SEQ ID NO 663
<211> LENGTH: 407
<212> TYPE: DNA
<213> ORGANISM: Artificial Sequence
<220> FEATURE:
<223> OTHER INFORMATION: T54435

<400> SEQUENCE: 663
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc attcccccag caaccacacc aacctcaaca accatatcca 360
caacaacaac catatgggag tagtcttaca agcatcggtg gccaatg 407

<210> SEQ ID NO 664
<211> LENGTH: 353
<212> TYPE: DNA
<213> ORGANISM: Artificial Sequence
<220> FEATURE:
<223> OTHER INFORMATION: T54438

<400> SEQUENCE: 664
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240
ccgaccccct tacaacccca acaaccaacc ccccagcaac cacaccaacc tcaacaacca 300
tatccacaac aacaaccatc tgggagtagt cttacaagca tcggtggcca atg 353

<210> SEQ ID NO 665
<211> LENGTH: 620
<212> TYPE: DNA
<213> ORGANISM: Artificial Sequence
<220> FEATURE:
<223> OTHER INFORMATION: T54439

<400> SEQUENCE: 665
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240
ccgaccccct tacaaccaca acaaccattc ccccagcaac cccaacaacc acaacaacca 300
tttcctcaac aaccacaaca accattcccc ctacgaccgc aacaaccatt tccccagcaa 360
ccccaacaat cacaacaatt atttccccag ccccaacccc agcaacccca acaaccatcc 420
acccttcaac cacaacaacc attaccccaa caaccacaac aaccatttca acagccccaa 480
caacaattat cccagcaacc agaacaaaca atttcccagc aaccccaaca accattcccc 540
cagcaaccac accaacctca acaaccatat ccacaacaac aaccatatgg gagtagtctt 600
acaagcatcg gtggccaatg 620

<210> SEQ ID NO 666
<211> LENGTH: 482
<212> TYPE: DNA
<213> ORGANISM: Artificial Sequence
<220> FEATURE:
<223> OTHER INFORMATION: T54543

<400> SEQUENCE: 666
tttgtcctcc ttgccatggc gatgaacatc gccactgccg ctagggagtt aaaccctagc 60
aacaaagagt tacaatcacc tcaacaatca tttccccagc aaccacaaca accatttcca 120
cagcaaccgc aacaaccatt cccccaacca tcacaacaac catttcctca acaaccacaa 180
caaccattcc ccctacgacc ccaacaacca tttccccagc aaccccaaca atcacaacaa 240
tcatttaccc agccccaacc ccagcaaccc caacaaccat ccatcctcca accacaacaa 300
ccattacccc aacaaccaca acaaccattt caacagcccc aacaacaatt atcccagcaa 360
ccagaacaaa caatttccca gcaaccccaa caaccattcc cccagcaacc acaccaacct 420
caacaaccat atccacaaca acaaccatat gggagtagtc ttacaagcat cggtggccaa 480
tg 482

<210> SEQ ID NO 667
<211> LENGTH: 561
<212> TYPE: DNA
<213> ORGANISM: Artificial Sequence
<220> FEATURE:
<223> OTHER INFORMATION: T54548

<400> SEQUENCE: 667
tttgtcctcc ttgccatggc gatgaacatc gccactgccg ctaggcagct aaaccctagc 60
aacaaagagt tacaatcacc tcaacaatca ttttcccatc aacaacaacc atttccacag 120
aagtcatatc cacaacaacc atatccatca catcaaccat atccattgca acaaccattt 180
cctacacccc aacaacaatt tccccagcaa tcacaacaac catttaccca accccaacaa 240
ccgacccccc tacaaccaca acaaccattc ccccagcaac cacaacaacc ttttccacag 300
ccccaacaac catttccttc ccaaccacaa caaccatttc cccagaccca acaatcgttc 360
cctctgcaac cacaacagcc atttccccag caaccccaac aaccatttcc ccagccccaa 420
ctaccattcc cacaacaacc agagcaaata attccccagc caaaccaaca accattcccc 480
ctgcaaccgc aacaaccatt cccccaacaa ccattccccc agcaacccca ataaccgtct 540
taccagtccc aacaaccaat c 561

<210> SEQ ID NO 668
<211> LENGTH: 353
<212> TYPE: DNA
<213> ORGANISM: Artificial Sequence
<220> FEATURE:
<223> OTHER INFORMATION: T545-104

<400> SEQUENCE: 668
tttgtcctcc ttgccatggc gatgaacatc gccactgccg ctaggcagct aaaccctagc 60
aacaaagagt tacaatcacc tcaacaatca ttttcccatc aacaacaacc atttccacag 120
aagtcatatc cacaacaacc atatccatca catcaaccat atccattgca acaaccattt 180
cctacacccc aacaacaatt tccccagcaa tcacaacaac catttaccca accccaacaa 240
ccgacccccc agcaacccca acaaccattc ccccagcaac cacaccaacc tcaacaacca 300
tatccacaac aacaaccata tgggagtagt cttacaagca tcggtggcca atg 353

<210> SEQ ID NO 669
<211> LENGTH: 365
<212> TYPE: DNA
<213> ORGANISM: Artificial Sequence
<220> FEATURE:
<223> OTHER INFORMATION: T545-109

<400> SEQUENCE: 669
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccatca cagcaaccat atccatcgca acaaccattt 180
cccacacccc aacaacaatt tccccagcaa tcacaacaac catttaccca gccccaacaa 240 ccgacccccct tacaaccaca acaaccattc ccccagcaac cccaacaacc acaacaacct 300
tttccacaac cccaacaacc atttccctgg caaccacaac aaccatttcc ccagacccaa 360
caatc 365

<210> SEQ ID NO 670
<211> LENGTH: 1004
<212> TYPE: DNA
<213> ORGANISM: Artificial Sequence
<220> FEATURE:
<223> OTHER INFORMATION: BW208 wt (1) group 4

<400> SEQUENCE: 670
tttgcctcct tgccatggcg atgaagatcg ccactgccgc tagggagtta aaccctagca 60
acaaagagtt acaatcacct caacaatcat tttcccatca acaaaaccat ttccacagca 120
gccatatcca caacaaccat atccatcaca gcaaccatat ccatcgcaac aaccatttcc 180
cacaccccaa caacaatttc cccagcaatc acaacaacca tttacccagc cccaacaacc 240
gaccccctta caaccacaac aaccattccc ccagaaaccc caacaaccac aacaaccttt 300
tccacaaccc caacaaccat ttccctggca accacaacga ccatttcccc agcccaacaa 360
tcgttccctc tccaaccaca acagccattc ccccagcaac cccaacaacc atttccccag 420
cccctaccat tcccccagca atcagaacaa ataattcccc agcaacccca acaaccattc 480
cccctgcaac cgcaacaacc attcccccag caaccccaac aaccatttcc ccagacaacc 540
aatccccgtg caaccacaac aatcattccc ccaacaatcc caacaatcac aacaaccttt 600
tgcccagccc caacaattat ttcctgaact ccagcaacca attccccagc aaccacaaca 660
accattccct gcaaccgcaa caaccattcc cccagcaacc gcaacaacca ttcccccagc 720
aaccgcaaca atcatttccc cagcaaccac aacaaccatt cccccagcaa ccgcaacaac 780
cattccccag caacccaaca accatccatc cttcaaccac aacaaccatt accccaacaa 840
ccacaacaac cattcaacag cccccaacaa ttatcccagc aaccagaaca aacatttccc 900
agcaacccca acaaccattc cccccagcaa ccacaccaac ctcaacaacc atatccacaa 960
caacaaccat atgggagtag tctacaagca tcggtggcca atga 1004

<210> SEQ ID NO 671
<211> LENGTH: 926
<212> TYPE: DNA
<213> ORGANISM: Artificial Sequence
<220> FEATURE:
<223> OTHER INFORMATION: BW208 wt (2) group 4

<400> SEQUENCE: 671
tgtcctcctt gccatggcga tgaacatcgc cactgccgct aggcagctaa accctagcaa 60
caaagagtta caatcacctc aacaatcatt ttcccatcaa caaccatttc cacagaagtc 120
atatccacaa caaccatatc catcacatca accatatcca ttgcaacaac catttcctac 180
accccaacaa caatttcccc agcaatcaca acaaccattt ccccaacccc aacaaccgac 240
ccccctacaa ccacaacaac cattccccca gcaaccacaa caacctttttc cacagcccca 300
acaaccattt ccttggcaac cacaacaacc atttccccag acccaacaat cgttccctct 360
gcaaccacaa cagccatttc cccagcaacc ccaacaacca tttccccagc cccaactacc 420
attcccacaa caaccagaac aaataattcc ccagccaaac caacaaccat tccccctgca 480
accgcaacaa ccattccccc aacaaccatt cccccagcaa cccaaaacca tttccccaga 540
acaaccaatc cccgtgacta caacaaccat taccccaaca atcccaacaa tcacaacaac 600
cttttccccg gcctcaacaa ttatttcctg aactccaaca accaattccc cagcaaccac 660
aacaaccatt cctcccagca accccaacaa tcacaacaat catttcccca gccccaaccc 720
cagcaacccc aacaaccatc catcctgcaa ccacaacaac cacaacaacc atttctgcag 780
cccaacaaca attatcccag caactagaac aaacaatttc ccagcaaccc caacaaccaa 840
ccccccagca accacaccaa cctcaacaac catatccaca acaacaacca tctgggagta 900
gtcttacaag catcggtggc caatga 926

<210> SEQ ID NO 672
<211> LENGTH: 538
<212> TYPE: DNA
<213> ORGANISM: Artificial Sequence
<220> FEATURE:
<223> OTHER INFORMATION: BW208 wt (3) group 4

<400> SEQUENCE: 672
tttccctcct tgccatggcg atgaagatcg ccactgccgc tagggagtta aaccctagca 60
acaaagagtt acaatcacct caacaatcat tttcccatca acaaaaccat ttccaccagc 120
catatccaca acaaccatat ccatcacagc aaccatatcc atcgcaacaa ccatttccca 180
caccccaaca acaatttccc cagcaatcac aacaaccatt tacccagccc cacaaccgac 240
ccccttacaa ccacaacaac cattccccca gcaaccccaa caaccacaac aacccttcca 300
caaccccaac aaccatttcc ctggcgacca caacaaccat ttccccagac ccaacaatcg 360
ttccctctcc aaccacaaca gccattcccc cagccccaac aaccatttcc ccccaactac 420
cattccccca gcaatcagaa caaataattc cccagcaacc ccaacaacca accccccagc 480
aaccacacca acctcaacaa ccatatccac aacaacaacc atctgggagt agtcttac 538

<210> SEQ ID NO 673
<211> LENGTH: 806
<212> TYPE: DNA
<213> ORGANISM: Artificial Sequence
<220> FEATURE:
<223> OTHER INFORMATION: T544-63

<400> SEQUENCE: 673
tttccctcct tgccatggcg atgaacatcg ccactgccgc taggcagcta aaccctagca 60
acaaagagtt acaatcacct caacaatcat tttcccatca acaacaacca tttccacaga 120
agccatatcc acaacaacca tatccatcac atcaaccata tccattgcaa caaccatttc 180
ccacacccca acaacaattt ccccagcccc aacaaccgac ccccctacaa ccacaacaac 240
cattccccca gcaaccacaa caaccattcc acagccccaa caatcatttc cttggcaacc 300
acaacaacca tttccccaga cccaacaatc gttccctctg caaccacaac aaccattccc 360
ccagcaaccc caacaaccat ttccccagcc ccaactacca ttctcccagc aaccagaaca 420
aataattccc cagccacccc aacaaccatt ccccctgcaa ccgcaacaac cattccccca 480
gcaaccccaa caaccattgc cccaacaacc ccaacaacca tttccccagc cccaacaacc 540
aatccccgtg caaccacaat aaccattccc ccaacaatcc caacaatcac aacaaccttt 600
cccccggccc caacaattat ttcctgaact gcaacaacca atcccccagc aaccacaaca 660
accattcccc ctacaacccc aacaaccatt cccccagcaa ccacaacaac cattccccct 720
gcaactccaa caaccattcc cccaacaacc acaacaacca ttcccccaac aaccacaaca 780
acctttgcct ctacaaccac aacaac 806

<210> SEQ ID NO 674
<211> LENGTH: 752
<212> TYPE: DNA
<213> ORGANISM: Artificial Sequence
<220> FEATURE:
<223> OTHER INFORMATION: T544-112

<400> SEQUENCE: 674
tttgtcctcc ttgccatggc gatgaacatc gccactgccg ctaggcagct aaaccctagc 60
aacaaagagt tacaatcacc tcaacaatca ttttcccatc aacaacaacc atttccacag 120

```
aagccatatc cacaacaacc atatccatca catcaaccat atccattgca acaaccattt    180

cccacacccc aacaacaatt tccccagccc aacaaccgac ccccctacaa ccacaacaac    240

cattccccca gcaaccacaa caaccttttc cacagcccca acaatcattt ccttggcaac    300

cacaacaacc atttccccag acccaacaat cgttccctct gcaaccacaa caaccattcc    360

cccagcaacc ccaacaacca tttccccagc cccaactacc attctcccag caaccagaac    420

aaataattcc ccagccaccc caacaaccat tccccctgca accgcaacaa ccattccccc    480

agcaacccca acaaccattt ccctggcaac cacaacaacc atttccccag acccaacaat    540

cgttccctct ccaaccacaa cagccattcc cccagcaacc ccaacaacca tttccccagc    600

cccaactacc attcccccag caatcagaac aaataattcc ccccaacaat cccaacaatc    660

acaacaacct tttgcccagc cccaacaatt atccctgaac tccaacaacc aattccccag    720

caaccacaac aaccattccc cctgcaatcg ca                                  752
```

<210> SEQ ID NO 675
<211> LENGTH: 1019
<212> TYPE: DNA
<213> ORGANISM: Artificial Sequence
<220> FEATURE:
<223> OTHER INFORMATION: T545-130
<220> FEATURE:
<221> NAME/KEY: misc_feature
<222> LOCATION: 859..859
<223> OTHER INFORMATION: /note="n is a, c, g, or t"
<220> FEATURE:
<221> NAME/KEY: misc_feature
<222> LOCATION: 883..883
<223> OTHER INFORMATION: /note="n is a, c, g, or t"
<220> FEATURE:
<221> NAME/KEY: misc_feature
<222> LOCATION: 889..889
<223> OTHER INFORMATION: /note="n is a, c, g, or t"
<220> FEATURE:
<221> NAME/KEY: misc_feature
<222> LOCATION: 891..891
<223> OTHER INFORMATION: /note="n is a, c, g, or t"

<400> SEQUENCE: 675

```
tttccctcct tgccatggcg atgaagatcg ccactgccgc tagggagtta aaccctagca     60

acaaagagtt acaatcacct caacaatcat tttcccatca acaacaacca tttccacagc    120

agccatatcc acaacaacca tatccatcac agcaaccata tccatcgcaa caaccatttc    180

ccacacccca acaacaattt ccccagcaat cacaacaacc atttacccag ccccaacaac    240

cgaccccctt acaaccacaa caaccattcc cccagcaacc ccaacaacca caacaacctt    300

ttccacaacc ccaacaacca tttccctggc aaccacaaca accatttccc cagacccaac    360

aatcgttccc tctccaacca caacagccat tcccccagca accccaacaa ccatttcccc    420

agccccaact accattcccc cagcaatcag aacaaataat tccccagcaa ccccaacaac    480

cattcccccct gcaaccgcaa caaccattcc cccagcaacc ccaacaacca tttccccagc    540

cccaacaacc aatccccgtg caaccacaac aatcattccc ccaacaatcc caacaatcac    600

aacaaccatt gcccagcccc aacaattact tcctgaactc caacaaccaa ttccccagca    660

accacaacaa ccattccccc tgcaaccgca acaaccattc ccccagcaac cgcaacaacc    720

attcccccag caaccgcaac aatcatttcc ccagcaacca caacaaccat tcccccagca    780

accgcaacaa ccattccccc aacaaccaca acaaccattc cctcaacaac cacaacaacc    840

attcccccta cgaccgcanc aaccatttcc ccagcaaccc canaatcana naatcatttc    900
```

cccagccact gcccagcaac cccaacaacc attcccccca gcaaccacac caacctcaac 960
aaccatatcc acaacaacaa ccatatggga gtagtcttac aagcatcggt ggccaatca 1019

<210> SEQ ID NO 676
<211> LENGTH: 59
<212> TYPE: DNA
<213> ORGANISM: Artificial Sequence
<220> FEATURE:
<223> OTHER INFORMATION: BW208 wt (1)

<400> SEQUENCE: 676
aaccaccaca acaattcccc caacaacaat ttccaatacc atacccaccc cagcaatca 59

<210> SEQ ID NO 677
<211> LENGTH: 59
<212> TYPE: DNA
<213> ORGANISM: Artificial Sequence
<220> FEATURE:
<223> OTHER INFORMATION: BW208 wt (2)

<400> SEQUENCE: 677
aaccaccaca acaattcccc caacaacaat ttccaatacc atacccaccc caacaatca 59

<210> SEQ ID NO 678
<211> LENGTH: 59
<212> TYPE: DNA
<213> ORGANISM: Artificial Sequence
<220> FEATURE:
<223> OTHER INFORMATION: T544-16

<400> SEQUENCE: 678
aaccaccaca acaattcccc caacaacaat ttccaatacc atacccaccc cagcaatca 59

<210> SEQ ID NO 679
<211> LENGTH: 59
<212> TYPE: DNA
<213> ORGANISM: Artificial Sequence
<220> FEATURE:
<223> OTHER INFORMATION: T544-25

<400> SEQUENCE: 679
aaccaccaca acaattcccc caacaacaat ttccaatacc atacccaccc cagcaatca 59

<210> SEQ ID NO 680
<211> LENGTH: 59
<212> TYPE: DNA
<213> ORGANISM: Artificial Sequence
<220> FEATURE:
<223> OTHER INFORMATION: T544-26

<400> SEQUENCE: 680
aaccaccaca acaattcccc caacaacaat ttccaatacc atacccaccc cagcaatca 59

<210> SEQ ID NO 681
<211> LENGTH: 59
<212> TYPE: DNA
<213> ORGANISM: Artificial Sequence
<220> FEATURE:
<223> OTHER INFORMATION: T544-30

<400> SEQUENCE: 681
aaccaccaca acaattcccc caacaacaat ttccaatacc atacccaccc cagcaatca 59

<210> SEQ ID NO 682
<211> LENGTH: 60

<212> TYPE: DNA
<213> ORGANISM: Artificial Sequence
<220> FEATURE:
<223> OTHER INFORMATION: T545-40

<400> SEQUENCE: 682
aaccaccaca acaattcccc ccaacaacaa tttccaatac catacccacc ccagcaatca 60

<210> SEQ ID NO 683
<211> LENGTH: 60
<212> TYPE: DNA
<213> ORGANISM: Artificial Sequence
<220> FEATURE:
<223> OTHER INFORMATION: T545-41

<400> SEQUENCE: 683
aaccaccaca acaattcccc ccaacaacaa tttccaatac catacccacc ccagcaatca 60

<210> SEQ ID NO 684
<211> LENGTH: 60
<212> TYPE: DNA
<213> ORGANISM: Artificial Sequence
<220> FEATURE:
<223> OTHER INFORMATION: T544-42

<400> SEQUENCE: 684
aaccaccaca acaattcccc ccaacaacaa tttccaatac catacccacc ccagcaatca 60

<210> SEQ ID NO 685
<211> LENGTH: 59
<212> TYPE: DNA
<213> ORGANISM: Artificial Sequence
<220> FEATURE:
<223> OTHER INFORMATION: T544-45

<400> SEQUENCE: 685
aaccaccaca acaattcccc caacaacaat ttccaatacc atacccaccc caacaatca 59

<210> SEQ ID NO 686
<211> LENGTH: 59
<212> TYPE: DNA
<213> ORGANISM: Artificial Sequence
<220> FEATURE:
<223> OTHER INFORMATION: T544-46

<400> SEQUENCE: 686
aaccaccaca acaattcccc caacaacaat ttccaatacc atacccaccc cagcaatca 59

<210> SEQ ID NO 687
<211> LENGTH: 59
<212> TYPE: DNA
<213> ORGANISM: Artificial Sequence
<220> FEATURE:
<223> OTHER INFORMATION: T544-68

<400> SEQUENCE: 687
aaccaccaca acaattcccc caacaacaat ttccaatacc atacccaccc cagcaatca 59

<210> SEQ ID NO 688
<211> LENGTH: 59
<212> TYPE: DNA
<213> ORGANISM: Artificial Sequence
<220> FEATURE:
<223> OTHER INFORMATION: T544-97

<400> SEQUENCE: 688
aaccaccaca acaattcccc caacaacaat ttccaatacc atacccaccc caacaatca 59

<210> SEQ ID NO 689
<211> LENGTH: 59
<212> TYPE: DNA
<213> ORGANISM: Artificial Sequence
<220> FEATURE:
<223> OTHER INFORMATION: T544-115

<400> SEQUENCE: 689
aaccaccaca acaattcccc caacaacaat ttccaatacc atacccaccc cagcaatca 59

<210> SEQ ID NO 690
<211> LENGTH: 60
<212> TYPE: DNA
<213> ORGANISM: Artificial Sequence
<220> FEATURE:
<223> OTHER INFORMATION: T544-116

<400> SEQUENCE: 690
aaccaccaca acaattcccc ccaacaacaa tttccaatac catacccacc cctgcaatca 60

<210> SEQ ID NO 691
<211> LENGTH: 59
<212> TYPE: DNA
<213> ORGANISM: Artificial Sequence
<220> FEATURE:
<223> OTHER INFORMATION: T544-125

<400> SEQUENCE: 691
agcaaccaca acaatttctc caacaacaat ttccaatacc atacccaccc cagcaatca 59

<210> SEQ ID NO 692
<211> LENGTH: 56
<212> TYPE: DNA
<213> ORGANISM: Artificial Sequence
<220> FEATURE:
<223> OTHER INFORMATION: T544-122

<400> SEQUENCE: 692
aaccacaaca attcccccaa caacaatttc caataccata cccaccccag caatca 56

<210> SEQ ID NO 693
<211> LENGTH: 59
<212> TYPE: DNA
<213> ORGANISM: Artificial Sequence
<220> FEATURE:
<223> OTHER INFORMATION: T545-154

<400> SEQUENCE: 693
aaccaccaca acaattcccc caacaacaat ttccaatacc atacccaccc cagcaatca 59

<210> SEQ ID NO 694
<211> LENGTH: 59
<212> TYPE: DNA
<213> ORGANISM: Artificial Sequence
<220> FEATURE:
<223> OTHER INFORMATION: T545-157

<400> SEQUENCE: 694
aaccaccaca acaattcccc caacaacaat ttccaatacc atacccaccc cagcaatca 59

<210> SEQ ID NO 695

<211> LENGTH: 59
<212> TYPE: DNA
<213> ORGANISM: Artificial Sequence
<220> FEATURE:
<223> OTHER INFORMATION: T545-158

<400> SEQUENCE: 695
aaccaccaca acaattcccc caacaacaat ttccaatacc atacccaccc cagcaatca 59

<210> SEQ ID NO 696
<211> LENGTH: 59
<212> TYPE: DNA
<213> ORGANISM: Artificial Sequence
<220> FEATURE:
<223> OTHER INFORMATION: T545-161

<400> SEQUENCE: 696
aaccaccaca acaattcccc caacaacaat ttccaatacc atacccaccc cagcaatca 59

<210> SEQ ID NO 697
<211> LENGTH: 50
<212> TYPE: DNA
<213> ORGANISM: Artificial Sequence
<220> FEATURE:
<223> OTHER INFORMATION: LMWBW208 wt

<400> SEQUENCE: 697
cccatccaac aacaaccaca accatttcca caacagccac catgttcaca 50

<210> SEQ ID NO 698
<211> LENGTH: 50
<212> TYPE: DNA
<213> ORGANISM: Artificial Sequence
<220> FEATURE:
<223> OTHER INFORMATION: LMW T544-1

<400> SEQUENCE: 698
cccatccaac aacaaccaca accatttcca caacagccac catgttcaca 50

<210> SEQ ID NO 699
<211> LENGTH: 50
<212> TYPE: DNA
<213> ORGANISM: Artificial Sequence
<220> FEATURE:
<223> OTHER INFORMATION: LMW-T544-2

<400> SEQUENCE: 699
ccgatccaac aacaaccaca accatttcca caacagccac catgttcaca 50

<210> SEQ ID NO 700
<211> LENGTH: 50
<212> TYPE: DNA
<213> ORGANISM: Artificial Sequence
<220> FEATURE:
<223> OTHER INFORMATION: LMW-T544-3

<400> SEQUENCE: 700
cccatccaac aacaaccaca ccaatttcca caacagcaac catgttcaca 50

<210> SEQ ID NO 701
<211> LENGTH: 50
<212> TYPE: DNA
<213> ORGANISM: Artificial Sequence
<220> FEATURE:
<223> OTHER INFORMATION: LMW-T544-5

<400> SEQUENCE: 701
cccatccaac aacaaccaca accatttcca caacagcrac catgttcaca 50

<210> SEQ ID NO 702
<211> LENGTH: 50
<212> TYPE: DNA
<213> ORGANISM: Artificial Sequence
<220> FEATURE:
<223> OTHER INFORMATION: LMWT544-6

<400> SEQUENCE: 702
cccatccaac aacaaccaca ccaatttcca caacagcaac catgttcaca 50

<210> SEQ ID NO 703
<211> LENGTH: 50
<212> TYPE: DNA
<213> ORGANISM: Artificial Sequence
<220> FEATURE:
<223> OTHER INFORMATION: LMW-T544-7

<400> SEQUENCE: 703
cccatccaac aacaaccaca accatttcca caacagccac catgttcaca 50

<210> SEQ ID NO 704
<211> LENGTH: 50
<212> TYPE: DNA
<213> ORGANISM: Artificial Sequence
<220> FEATURE:
<223> OTHER INFORMATION: LMWT544-9

<400> SEQUENCE: 704
cccatccaac aacaaccaca accatttcca caacagccac catgttcaca 50

<210> SEQ ID NO 705
<211> LENGTH: 50
<212> TYPE: DNA
<213> ORGANISM: Artificial Sequence
<220> FEATURE:
<223> OTHER INFORMATION: LMVVT544-11

<400> SEQUENCE: 705
cccatccaac aacaaccaca ccaatttcca caacagcaac catgttcaca 50

<210> SEQ ID NO 706
<211> LENGTH: 50
<212> TYPE: DNA
<213> ORGANISM: Artificial Sequence
<220> FEATURE:
<223> OTHER INFORMATION: LMW T544-12

<400> SEQUENCE: 706
cccatccaac aacaaccaca accatttcca caacagccac catgttcaca 50

<210> SEQ ID NO 707
<211> LENGTH: 50
<212> TYPE: DNA
<213> ORGANISM: Artificial Sequence
<220> FEATURE:
<223> OTHER INFORMATION: LMWT544-70

<400> SEQUENCE: 707
cccatccaac aacaaccaca accatttcca caacagccac catgttcaca 50

<210> SEQ ID NO 708

<211> LENGTH: 51
<212> TYPE: DNA
<213> ORGANISM: Artificial Sequence
<220> FEATURE:
<223> OTHER INFORMATION: LMWT544-72

<400> SEQUENCE: 708
ccttgtccaa caacaaccac aaccatttcc acaacagcaa ccatgttcac a 51

<210> SEQ ID NO 709
<211> LENGTH: 50
<212> TYPE: DNA
<213> ORGANISM: Artificial Sequence
<220> FEATURE:
<223> OTHER INFORMATION: LMW T544-73

<400> SEQUENCE: 709
cccatccaac aacaaccaca ccaatttcca caacagcaac catgttcaca 50

<210> SEQ ID NO 710
<211> LENGTH: 50
<212> TYPE: DNA
<213> ORGANISM: Artificial Sequence
<220> FEATURE:
<223> OTHER INFORMATION: LMWT544-74

<400> SEQUENCE: 710
cccatccaac aacaaccaca accatttcca caacagccac catgttcaca 50

<210> SEQ ID NO 711
<211> LENGTH: 50
<212> TYPE: DNA
<213> ORGANISM: Artificial Sequence
<220> FEATURE:
<223> OTHER INFORMATION: LMVV-T544-78

<400> SEQUENCE: 711
cctgtccaac aacaaccaca accatttcca caacagcaac catgttcaca 50

<210> SEQ ID NO 712
<211> LENGTH: 50
<212> TYPE: DNA
<213> ORGANISM: Artificial Sequence
<220> FEATURE:
<223> OTHER INFORMATION: LMW-T544-79

<400> SEQUENCE: 712
cccatccaac aacaaccaca accatttcca caacagccac catgttcaca 50

<210> SEQ ID NO 713
<211> LENGTH: 50
<212> TYPE: DNA
<213> ORGANISM: Artificial Sequence
<220> FEATURE:
<223> OTHER INFORMATION: LMW-T544-80

<400> SEQUENCE: 713
cccatccaac aacaaccaca ccaatttcca caacagcaac catgttcaca 50

<210> SEQ ID NO 714
<211> LENGTH: 50
<212> TYPE: DNA
<213> ORGANISM: Artificial Sequence
<220> FEATURE:
<223> OTHER INFORMATION: 2ASF8_BW208 wt

<400> SEQUENCE: 714
cgcagccgcc ggccatccac aaccatttcc atcctcagga cagagtcacg 50

<210> SEQ ID NO 715
<211> LENGTH: 50
<212> TYPE: DNA
<213> ORGANISM: Artificial Sequence
<220> FEATURE:
<223> OTHER INFORMATION: 2ASF8 T544-1

<400> SEQUENCE: 715
cgcagccgcc ggccatccac aaccatttcc atcctcagga cagagtcacg 50

<210> SEQ ID NO 716
<211> LENGTH: 50
<212> TYPE: DNA
<213> ORGANISM: Artificial Sequence
<220> FEATURE:
<223> OTHER INFORMATION: 2ASF8-T544-25

<400> SEQUENCE: 716
cgcagccgcc ggccatccac aaccatttcc atcctcagga cagagtcacg 50

<210> SEQ ID NO 717
<211> LENGTH: 50
<212> TYPE: DNA
<213> ORGANISM: Artificial Sequence
<220> FEATURE:
<223> OTHER INFORMATION: 2ASF8-T544-26

<400> SEQUENCE: 717
cgcagccgcc ggccatccac aaccatttcc atcctcagga cagagtcacg 50

<210> SEQ ID NO 718
<211> LENGTH: 50
<212> TYPE: DNA
<213> ORGANISM: Artificial Sequence
<220> FEATURE:
<223> OTHER INFORMATION: 2ASF8-T544-27

<400> SEQUENCE: 718
cgcagccgcc ggccatccac aaccatttcc atcctcagga cagagtcacg 50

<210> SEQ ID NO 719
<211> LENGTH: 50
<212> TYPE: DNA
<213> ORGANISM: Artificial Sequence
<220> FEATURE:
<223> OTHER INFORMATION: 2ASF8 T544-28

<400> SEQUENCE: 719
cgcagccgcc ggccatccac aaccatttcc atcctcagga cagagtcacg 50

<210> SEQ ID NO 720
<211> LENGTH: 50
<212> TYPE: DNA
<213> ORGANISM: Artificial Sequence
<220> FEATURE:
<223> OTHER INFORMATION: 2ASF8-T544-112

<400> SEQUENCE: 720
cgcagccgcc ggccatccac aaccatttcc atcctcagga cagagtcacg 50

<210> SEQ ID NO 721

<211> LENGTH: 50
<212> TYPE: DNA
<213> ORGANISM: Artificial Sequence
<220> FEATURE:
<223> OTHER INFORMATION: 2ASF8 T544-114

<400> SEQUENCE: 721
cgcagccgcc ggccatccac aaccatttcc atcctcagga cagagtcacg 50

<210> SEQ ID NO 722
<211> LENGTH: 50
<212> TYPE: DNA
<213> ORGANISM: Artificial Sequence
<220> FEATURE:
<223> OTHER INFORMATION: ASD6_BW208 wt

<400> SEQUENCE: 722
cgcaaccgcc ggccttccac aaccatttcc accctcagga caaagccacg 50

<210> SEQ ID NO 723
<211> LENGTH: 50
<212> TYPE: DNA
<213> ORGANISM: Artificial Sequence
<220> FEATURE:
<223> OTHER INFORMATION: 2ASD6 T544-1

<400> SEQUENCE: 723
cgcaaccgcc ggccttccac aaccatttcc accctcagga caaagccacg 50

<210> SEQ ID NO 724
<211> LENGTH: 50
<212> TYPE: DNA
<213> ORGANISM: Artificial Sequence
<220> FEATURE:
<223> OTHER INFORMATION: 2ASD6-1-544-2

<400> SEQUENCE: 724
cgcaaccgcc ggccttccac aaccatttcc accctcagga caaagccacg 50

<210> SEQ ID NO 725
<211> LENGTH: 50
<212> TYPE: DNA
<213> ORGANISM: Artificial Sequence
<220> FEATURE:
<223> OTHER INFORMATION: 2ASD6-1-544-30

<400> SEQUENCE: 725
cgcaaccgcc ggccttccac aaccatttcc accctcagga caaagccacg 50

<210> SEQ ID NO 726
<211> LENGTH: 50
<212> TYPE: DNA
<213> ORGANISM: Artificial Sequence
<220> FEATURE:
<223> OTHER INFORMATION: 2ASD6-1-544-31

<400> SEQUENCE: 726
cgcaaccgcc ggccttccac aaccatttcc accctcagga caaagccacg 50

<210> SEQ ID NO 727
<211> LENGTH: 50
<212> TYPE: DNA
<213> ORGANISM: Artificial Sequence
<220> FEATURE:
<223> OTHER INFORMATION: 2ASD6-1-544-35

<400> SEQUENCE: 727
cgcaaccgcc ggccttccac aaccatttcc accctcagga caaagccacg 50

<210> SEQ ID NO 728
<211> LENGTH: 50
<212> TYPE: DNA
<213> ORGANISM: Artificial Sequence
<220> FEATURE:
<223> OTHER INFORMATION: 2ASD6-1-544-36

<400> SEQUENCE: 728
cgcaaccgcc ggccttccac aaccatttcc accctcagga caaagccacg 50

<210> SEQ ID NO 729
<211> LENGTH: 50
<212> TYPE: DNA
<213> ORGANISM: Artificial Sequence
<220> FEATURE:
<223> OTHER INFORMATION: 2ASD6 T544-37

<400> SEQUENCE: 729
cgcaaccgcc ggccttccac aaccatttcc accctcagga caaagccacg 50

<210> SEQ ID NO 730
<211> LENGTH: 50
<212> TYPE: DNA
<213> ORGANISM: Artificial Sequence
<220> FEATURE:
<223> OTHER INFORMATION: 2ASD6-1-544-44

<400> SEQUENCE: 730
cgcaaccgcc ggccttccac aaccatttcc accctcagga caaagccacg 50

<210> SEQ ID NO 731
<211> LENGTH: 50
<212> TYPE: DNA
<213> ORGANISM: Artificial Sequence
<220> FEATURE:
<223> OTHER INFORMATION: 2ASD6 T544-49

<400> SEQUENCE: 731
cgcaaccgcc ggccttccac aaccatttcc accctcagga caaagccacg 50

<210> SEQ ID NO 732
<211> LENGTH: 50
<212> TYPE: DNA
<213> ORGANISM: Artificial Sequence
<220> FEATURE:
<223> OTHER INFORMATION: 7BL_BW208

<400> SEQUENCE: 732
accggttgaa caaagcccgc aaccatttcc atatggttgc cccagtgttc 50

<210> SEQ ID NO 733
<211> LENGTH: 50
<212> TYPE: DNA
<213> ORGANISM: Artificial Sequence
<220> FEATURE:
<223> OTHER INFORMATION: 78L-T544-138

<400> SEQUENCE: 733
accggttgaa caaagcccgc aaccatttcc atatggttgc cccagtgttc 50

<210> SEQ ID NO 734

<211> LENGTH: 50
<212> TYPE: DNA
<213> ORGANISM: Artificial Sequence
<220> FEATURE:
<223> OTHER INFORMATION: 7BL-T544-139

<400> SEQUENCE: 734
accggttgaa caaagcccgc aaccatttcc atatggttgc cccagtgttc 50

<210> SEQ ID NO 735
<211> LENGTH: 50
<212> TYPE: DNA
<213> ORGANISM: Artificial Sequence
<220> FEATURE:
<223> OTHER INFORMATION: 7BL-T544-140

<400> SEQUENCE: 735
accggttgaa caaagcccgc aaccatttcc atatggttgc cccagtgttc 50

<210> SEQ ID NO 736
<211> LENGTH: 50
<212> TYPE: DNA
<213> ORGANISM: Artificial Sequence
<220> FEATURE:
<223> OTHER INFORMATION: 7BL-T544

<400> SEQUENCE: 736
actggttgaa caaagcccgc aaccatttcc atatggttgc cccagtgttc 50

<210> SEQ ID NO 737
<211> LENGTH: 50
<212> TYPE: DNA
<213> ORGANISM: Artificial Sequence
<220> FEATURE:
<223> OTHER INFORMATION: 7BL-T544-142

<400> SEQUENCE: 737
accggttgaa caaagcccgc aaccatttcc atatggttgc cccagtgttc 50

<210> SEQ ID NO 738
<211> LENGTH: 50
<212> TYPE: DNA
<213> ORGANISM: Artificial Sequence
<220> FEATURE:
<223> OTHER INFORMATION: 7BL-T544-143

<400> SEQUENCE: 738
accggttgaa caaagcccgc aaccatttcc atatggttgc cccagtgttc 50

<210> SEQ ID NO 739
<211> LENGTH: 50
<212> TYPE: DNA
<213> ORGANISM: Artificial Sequence
<220> FEATURE:
<223> OTHER INFORMATION: 7BL-T544-1

<400> SEQUENCE: 739
accggttgaa caaagcccgc aaccatttcc atatggttgc cccagtgttc 50

<210> SEQ ID NO 740
<211> LENGTH: 50
<212> TYPE: DNA
<213> ORGANISM: Artificial Sequence
<220> FEATURE:
<223> OTHER INFORMATION: 7BL-1544-145

<400> SEQUENCE: 740
accggttgaa caaagcccgc aaccatttcc atatggttgc cccagtgttc 50

<210> SEQ ID NO 741
<211> LENGTH: 50
<212> TYPE: DNA
<213> ORGANISM: Artificial Sequence
<220> FEATURE:
<223> OTHER INFORMATION: 7BL-T544-146

<400> SEQUENCE: 741
accggttgaa caaagcccgc aaccatttcc atatggttgc cccagtgttc 50

<210> SEQ ID NO 742
<211> LENGTH: 50
<212> TYPE: DNA
<213> ORGANISM: Artificial Sequence
<220> FEATURE:
<223> OTHER INFORMATION: 7BL-T544-14

<400> SEQUENCE: 742
accggttgaa caacgcccgc aaccatttcc atatggttgc cccagtgttc 50

<210> SEQ ID NO 743
<211> LENGTH: 100
<212> TYPE: DNA
<213> ORGANISM: Artificial Sequence
<220> FEATURE:
<223> OTHER INFORMATION: BW208 wt, group 4

<400> SEQUENCE: 743
ccccagcaac cacagcaacc gttcccccag actcaacaac cccaacaacc atttccccag 60
tccaagcaac cacaacaacc ttttccccag ccccaacaac 100

<210> SEQ ID NO 744
<211> LENGTH: 21
<212> TYPE: DNA
<213> ORGANISM: Artificial Sequence
<220> FEATURE:
<223> OTHER INFORMATION: aGli900 F1

<400> SEQUENCE: 744
gttagagttc cagtgccaca a 21

<210> SEQ ID NO 745
<211> LENGTH: 20
<212> TYPE: DNA
<213> ORGANISM: Artificial Sequence
<220> FEATURE:
<223> OTHER INFORMATION: 33mer1R2_Ok

<400> SEQUENCE: 745
ggttgttgtg gttgcgrata 20

<210> SEQ ID NO 746
<211> LENGTH: 19
<212> TYPE: DNA
<213> ORGANISM: Artificial Sequence
<220> FEATURE:
<223> OTHER INFORMATION: BAR1F

<400> SEQUENCE: 746
gtctgcacca tcgtcaacc 19

<210> SEQ ID NO 747
<211> LENGTH: 20
<212> TYPE: DNA
<213> ORGANISM: Artificial Sequence
<220> FEATURE:
<223> OTHER INFORMATION: BAR2R

<400> SEQUENCE: 747
gaagtccagc tgccagaaac 20

<210> SEQ ID NO 748
<211> LENGTH: 20
<212> TYPE: DNA
<213> ORGANISM: Artificial Sequence
<220> FEATURE:
<223> OTHER INFORMATION: fJG218F

<400> SEQUENCE: 748
taaggtcctc tccgcctaca 20

<210> SEQ ID NO 749
<211> LENGTH: 20
<212> TYPE: DNA
<213> ORGANISM: Artificial Sequence
<220> FEATURE:
<223> OTHER INFORMATION: fJG218R

<400> SEQUENCE: 749
ggcggtaagg atctgagcta 20

<210> SEQ ID NO 750
<211> LENGTH: 22
<212> TYPE: DNA
<213> ORGANISM: Artificial Sequence
<220> FEATURE:
<223> OTHER INFORMATION: M13 Reverse

<400> SEQUENCE: 750
tcacacagga aacagctatg ac 22

<210> SEQ ID NO 751
<211> LENGTH: 24
<212> TYPE: DNA
<213> ORGANISM: Artificial Sequence
<220> FEATURE:
<223> OTHER INFORMATION: M13 Forward

<400> SEQUENCE: 751
cgccagggtt ttcccagtca cgac 24

<210> SEQ ID NO 752
<211> LENGTH: 20
<212> TYPE: DNA
<213> ORGANISM: Artificial Sequence
<220> FEATURE:
<223> OTHER INFORMATION: KanR_Fw

<400> SEQUENCE: 752
ttatgcctct tccgaccatc 20

<210> SEQ ID NO 753
<211> LENGTH: 20
<212> TYPE: DNA
<213> ORGANISM: Artificial Sequence
<220> FEATURE:
<223> OTHER INFORMATION: KanR_Rv

<400> SEQUENCE: 753
attccgactc gtccaacatc 20

<210> SEQ ID NO 754
<211> LENGTH: 20
<212> TYPE: DNA
<213> ORGANISM: Artificial Sequence
<220> FEATURE:
<223> OTHER INFORMATION: PvUbi1_Fw

<400> SEQUENCE: 754
cgtctcgcaa aatagcacaa 20

<210> SEQ ID NO 755
<211> LENGTH: 20
<212> TYPE: DNA
<213> ORGANISM: Artificial Sequence
<220> FEATURE:
<223> OTHER INFORMATION: PvUbi1_Rv

<400> SEQUENCE: 755
cataatcgat cgaggggaga 20

<210> SEQ ID NO 756
<211> LENGTH: 20
<212> TYPE: DNA
<213> ORGANISM: Artificial Sequence
<220> FEATURE:
<223> OTHER INFORMATION: STA_Fw

<400> SEQUENCE: 756
gctgcgtata tgatgcgatg 20

<210> SEQ ID NO 757
<211> LENGTH: 20
<212> TYPE: DNA
<213> ORGANISM: Artificial Sequence
<220> FEATURE:
<223> OTHER INFORMATION: STA_Rv

<400> SEQUENCE: 757
gactcaagaa tgggcagctc 20

<210> SEQ ID NO 758
<211> LENGTH: 20
<212> TYPE: DNA
<213> ORGANISM: Artificial Sequence
<220> FEATURE:
<223> OTHER INFORMATION: OCS_Fw

<400> SEQUENCE: 758
ccggtttcgg ttcattctaa 20

<210> SEQ ID NO 759
<211> LENGTH: 20
<212> TYPE: DNA
<213> ORGANISM: Artificial Sequence
<220> FEATURE:
<223> OTHER INFORMATION: OCS_Rv

<400> SEQUENCE: 759
gttgaatggt gcccgtaact 20

<210> SEQ ID NO 760

<211> LENGTH: 20
<212> TYPE: DNA
<213> ORGANISM: Artificial Sequence
<220> FEATURE:
<223> OTHER INFORMATION: pJG001

<400> SEQUENCE: 760
atcgatcgtg gtgtcgaagt 20

<210> SEQ ID NO 761
<211> LENGTH: 27
<212> TYPE: DNA
<213> ORGANISM: Artificial Sequence
<220> FEATURE:
<223> OTHER INFORMATION: pJG002

<400> SEQUENCE: 761
tgatggaaat ggcgttttat tattaca 27

<210> SEQ ID NO 762
<211> LENGTH: 21
<212> TYPE: DNA
<213> ORGANISM: Artificial Sequence
<220> FEATURE:
<223> OTHER INFORMATION: pJG003

<400> SEQUENCE: 762
actcaaaggc ggtaatacgg t 21

<210> SEQ ID NO 763
<211> LENGTH: 20
<212> TYPE: DNA
<213> ORGANISM: Artificial Sequence
<220> FEATURE:
<223> OTHER INFORMATION: pJG004

<400> SEQUENCE: 763
tcgtaatccc acacactggc 20

<210> SEQ ID NO 764
<211> LENGTH: 20
<212> TYPE: DNA
<213> ORGANISM: Artificial Sequence
<220> FEATURE:
<223> OTHER INFORMATION: pJG005

<400> SEQUENCE: 764
actaacagaa catcggcccc 20

<210> SEQ ID NO 765
<211> LENGTH: 19
<212> TYPE: DNA
<213> ORGANISM: Artificial Sequence
<220> FEATURE:
<223> OTHER INFORMATION: pJG006

<400> SEQUENCE: 765
agaccttcct catctttgc 19

<210> SEQ ID NO 766
<211> LENGTH: 20
<212> TYPE: DNA
<213> ORGANISM: Artificial Sequence
<220> FEATURE:
<223> OTHER INFORMATION: pJG007

<400> SEQUENCE: 766
tgctgcgata atggtggttg 20

<210> SEQ ID NO 767
<211> LENGTH: 27
<212> TYPE: DNA
<213> ORGANISM: Artificial Sequence
<220> FEATURE:
<223> OTHER INFORMATION: pJG008

<400> SEQUENCE: 767
tgttatagtt ccaatatttt tgccaat 27

<210> SEQ ID NO 768
<211> LENGTH: 18
<212> TYPE: DNA
<213> ORGANISM: Artificial Sequence
<220> FEATURE:
<223> OTHER INFORMATION: pJG009

<400> SEQUENCE: 768
ttgagcgatg cacaaagc 18

<210> SEQ ID NO 769
<211> LENGTH: 20
<212> TYPE: DNA
<213> ORGANISM: Artificial Sequence
<220> FEATURE:
<223> OTHER INFORMATION: pJG010

<400> SEQUENCE: 769
cgcctcgtat ttgatgttca 20

<210> SEQ ID NO 770
<211> LENGTH: 20
<212> TYPE: DNA
<213> ORGANISM: Artificial Sequence
<220> FEATURE:
<223> OTHER INFORMATION: pJG011

<400> SEQUENCE: 770
gtaacagctt gccgatggac 20

<210> SEQ ID NO 771
<211> LENGTH: 18
<212> TYPE: DNA
<213> ORGANISM: Artificial Sequence
<220> FEATURE:
<223> OTHER INFORMATION: pJG012

<400> SEQUENCE: 771
gcctccttcc tgatgttc 18

<210> SEQ ID NO 772
<211> LENGTH: 20
<212> TYPE: DNA
<213> ORGANISM: Artificial Sequence
<220> FEATURE:
<223> OTHER INFORMATION: pJG013

<400> SEQUENCE: 772
tgccggtgta cacttctagt 20

<210> SEQ ID NO 773

<211> LENGTH: 19
<212> TYPE: DNA
<213> ORGANISM: Artificial Sequence
<220> FEATURE:
<223> OTHER INFORMATION: pJG014

<400> SEQUENCE: 773
atgaagacct taytcatcc 19

<210> SEQ ID NO 774
<211> LENGTH: 18
<212> TYPE: DNA
<213> ORGANISM: Artificial Sequence
<220> FEATURE:
<223> OTHER INFORMATION: pJG015

<400> SEQUENCE: 774
acatacacgt tgcacatg 18

<210> SEQ ID NO 775
<211> LENGTH: 20
<212> TYPE: DNA
<213> ORGANISM: Artificial Sequence
<220> FEATURE:
<223> OTHER INFORMATION: pJG020

<400> SEQUENCE: 775
tttgtcctcc ttgccatggc 20

<210> SEQ ID NO 776
<211> LENGTH: 24
<212> TYPE: DNA
<213> ORGANISM: Artificial Sequence
<220> FEATURE:
<223> OTHER INFORMATION: pJG021

<400> SEQUENCE: 776
atacttataa cgtcgctccc agat 24

<210> SEQ ID NO 777
<211> LENGTH: 24
<212> TYPE: DNA
<213> ORGANISM: Artificial Sequence
<220> FEATURE:
<223> OTHER INFORMATION: pJG021

<400> SEQUENCE: 777
atacttataa cgtcgctccc agat 24

<210> SEQ ID NO 778
<211> LENGTH: 19
<212> TYPE: DNA
<213> ORGANISM: Artificial Sequence
<220> FEATURE:
<223> OTHER INFORMATION: pJG022

<400> SEQUENCE: 778
tcattggcca ccgatgctt 19

<210> SEQ ID NO 779
<211> LENGTH: 12
<212> TYPE: PRT
<213> ORGANISM: Artificial Sequence
<220> FEATURE:
<223> OTHER INFORMATION: peptide

<400> SEQUENCE: 779

Gln Pro Phe Pro Gln Pro Glu Gln Pro Phe Pro Trp
1 5 10

<210> SEQ ID NO 780
<211> LENGTH: 9
<212> TYPE: PRT
<213> ORGANISM: Artificial Sequence
<220> FEATURE:
<223> OTHER INFORMATION: peptide

<400> SEQUENCE: 780

Pro Phe Pro Gln Pro Glu Leu Pro Tyr
1 5

<210> SEQ ID NO 781
<211> LENGTH: 9
<212> TYPE: PRT
<213> ORGANISM: Artificial Sequence
<220> FEATURE:
<223> OTHER INFORMATION: peptide

<400> SEQUENCE: 781

Pro Gln Pro Glu Leu Pro Tyr Pro Gln
1 5

<210> SEQ ID NO 782
<211> LENGTH: 9
<212> TYPE: PRT
<213> ORGANISM: Artificial Sequence
<220> FEATURE:
<223> OTHER INFORMATION: peptide

<400> SEQUENCE: 782

Pro Tyr Pro Gln Pro Glu Leu Pro Tyr
1 5

<210> SEQ ID NO 783
<211> LENGTH: 252
<212> TYPE: DNA
<213> ORGANISM: Artificial Sequence
<220> FEATURE:
<223> OTHER INFORMATION: gRNA cassette
<220> FEATURE:
<221> NAME/KEY: misc_feature
<222> LOCATION: 21..40
<223> OTHER INFORMATION: /note="n is a, c, g, or t"
<220> FEATURE:
<221> NAME/KEY: misc_feature
<222> LOCATION: 137..156
<223> OTHER INFORMATION: /note="n is a, c, g, or t"

<400> SEQUENCE: 783
gttcactgcc gtataggcag nnnnnnnnnn nnnnnnnnnn gttttagagc tagaaatagc 60
aagttaaaat aaggctagtc cgttatcaac ttgaaaaagt ggcaccgagt cggtgcgttc 120
actgccgtat aggcagnnnn nnnnnnnnnn nnnnnngttt tagagctaga aatagcaagt 180
taaaataagg ctagtccgtt atcaacttga aaaagtggca ccgagtcggt gcgttcactg 240
ccgtataggc ag 252

<210> SEQ ID NO 784
<211> LENGTH: 20
<212> TYPE: DNA
<213> ORGANISM: Artificial Sequence
<220> FEATURE:

<223> OTHER INFORMATION: sgAlpha-1

<400> SEQUENCE: 784
gccacaagag caagttccat 20

<210> SEQ ID NO 785
<211> LENGTH: 20
<212> TYPE: DNA
<213> ORGANISM: Artificial Sequence
<220> FEATURE:
<223> OTHER INFORMATION: sgAlpha-2

<400> SEQUENCE: 785
ggttgtgatg gaaatggttg 20

<210> SEQ ID NO 786
<211> LENGTH: 98
<212> TYPE: DNA
<213> ORGANISM: Artificial Sequence
<220> FEATURE:
<223> OTHER INFORMATION: BW208 wt, group 1

<400> SEQUENCE: 786
cagcgaccac aacaaccatt cccccagact caacaacccc aacaaccatt tccccagtcc 60
cagcaaccac aacaaccttt tccccagccc caacaaca 98

<210> SEQ ID NO 787
<211> LENGTH: 85
<212> TYPE: DNA
<213> ORGANISM: Artificial Sequence
<220> FEATURE:
<223> OTHER INFORMATION: BW208 wt, group 2

<400> SEQUENCE: 787
gcaaccacaa caaccatttc ctcagcccca acaaccccaa ctaccatttc cccaacaacc 60
acaacaacca ttcccccagc ctcaa 85

<210> SEQ ID NO 788
<211> LENGTH: 148
<212> TYPE: DNA
<213> ORGANISM: Artificial Sequence
<220> FEATURE:
<223> OTHER INFORMATION: T54538

<400> SEQUENCE: 788
tttgtcctcc ttgccatggc gatgaacatc gccactgccg ctaggcagtt aaaccctagc 60
aacaaagagt tacaatcacc tcaacaatca ttttcccatc aacaacaacc atttccacag 120
cagccatatc cacaacaacc atatccat 148

<210> SEQ ID NO 789
<211> LENGTH: 23
<212> TYPE: DNA
<213> ORGANISM: Artificial Sequence
<220> FEATURE:
<223> OTHER INFORMATION: DsgGlia20-1
<220> FEATURE:
<221> NAME/KEY: misc_feature
<222> LOCATION: 21
<223> OTHER INFORMATION: /note="n is a, c, g, or t"

<400> SEQUENCE: 789
tatggttgtt gtggtcgaaa ngg 23

<210> SEQ ID NO 790
<211> LENGTH: 23
<212> TYPE: DNA
<213> ORGANISM: Artificial Sequence
<220> FEATURE:
<223> OTHER INFORMATION: DsgDQ2.5-1
<220> FEATURE:
<221> NAME/KEY: misc_feature
<222> LOCATION: 21
<223> OTHER INFORMATION: /note="n is a, c, g or t"

<400> SEQUENCE: 790
ggatatggta gttgcggctg ngg 23

<210> SEQ ID NO 791
<211> LENGTH: 23
<212> TYPE: DNA
<213> ORGANISM: Artificial Sequence
<220> FEATURE:
<223> OTHER INFORMATION: DsgDQ2.5Gli1a
<220> FEATURE:
<221> NAME/KEY: misc_feature
<222> LOCATION: 21
<223> OTHER INFORMATION: /note="n is a, c, g or t"

<400> SEQUENCE: 791
ggtagttgcg gctgcggaaa ngg 23

<210> SEQ ID NO 792
<211> LENGTH: 24
<212> TYPE: DNA
<213> ORGANISM: Artificial Sequence
<220> FEATURE:
<223> OTHER INFORMATION: sgCpf1Alpha-1
<220> FEATURE:
<221> NAME/KEY: misc_feature
<222> LOCATION: 4
<223> OTHER INFORMATION: /note="n is a, c, g or t"

<400> SEQUENCE: 792
tttntggctg caattgtggc actg 24

<210> SEQ ID NO 793
<211> LENGTH: 24
<212> TYPE: DNA
<213> ORGANISM: Artificial Sequence
<220> FEATURE:
<223> OTHER INFORMATION: sgCpf1Alpha-2
<220> FEATURE:
<221> NAME/KEY: misc_feature
<222> LOCATION: 4
<223> OTHER INFORMATION: /note="n is a, c, g or t"

<400> SEQUENCE: 793
tttncatcac aacaaccata tctg 24

<210> SEQ ID NO 794
<211> LENGTH: 24
<212> TYPE: DNA
<213> ORGANISM: Artificial Sequence
<220> FEATURE:
<223> OTHER INFORMATION: sgCpf1Alpha-3
<220> FEATURE:
<221> NAME/KEY: misc_feature
<222> LOCATION: 4
<223> OTHER INFORMATION: /note="n is a, c, g or t"

<400> SEQUENCE: 794
tttntagggc agcaacaacc attt 24

<210> SEQ ID NO 795
<211> LENGTH: 24
<212> TYPE: DNA
<213> ORGANISM: Artificial Sequence
<220> FEATURE:
<223> OTHER INFORMATION: sgCpf133mer1
<220> FEATURE:
<221> NAME/KEY: misc_feature
<222> LOCATION: 4
<223> OTHER INFORMATION: /note="n is a, c, g or t"

<400> SEQUENCE: 795
tttncgcagc cgcaactacc atat 24

<210> SEQ ID NO 796
<211> LENGTH: 24
<212> TYPE: DNA
<213> ORGANISM: Artificial Sequence
<220> FEATURE:
<223> OTHER INFORMATION: sgCpf1Glia20
<220> FEATURE:
<221> NAME/KEY: misc_feature
<222> LOCATION: 4
<223> OTHER INFORMATION: /note="n is a, c, g or t"

<400> SEQUENCE: 796
tttngaccac aacaaccata tcca 24

<210> SEQ ID NO 797
<211> LENGTH: 24
<212> TYPE: DNA
<213> ORGANISM: Artificial Sequence
<220> FEATURE:
<223> OTHER INFORMATION: sgCpf1Omega-1
<220> FEATURE:
<221> NAME/KEY: misc_feature
<222> LOCATION: 4
<223> OTHER INFORMATION: /note="n is a, c, g or t"

<400> SEQUENCE: 797
tttntcctcc ttgccatggc gatg 24

<210> SEQ ID NO 798
<211> LENGTH: 24
<212> TYPE: DNA
<213> ORGANISM: Artificial Sequence
<220> FEATURE:
<223> OTHER INFORMATION: sgCpf1Omega-2
<220> FEATURE:
<221> NAME/KEY: misc_feature
<222> LOCATION: 4
<223> OTHER INFORMATION: /note="n is a, c, g or t"

<400> SEQUENCE: 798
tttnccatca acaacaacca tttc 24

<210> SEQ ID NO 799
<211> LENGTH: 24
<212> TYPE: DNA
<213> ORGANISM: Artificial Sequence
<220> FEATURE:
<223> OTHER INFORMATION: sgCpf1Omega-3
<220> FEATURE:
<221> NAME/KEY: misc_feature
<222> LOCATION: 4
<223> OTHER INFORMATION: /note="n is a, c, g or t"

<400> SEQUENCE: 799
tttnccagca accccaacaa ccat 24

<210> SEQ ID NO 800
<211> LENGTH: 24
<212> TYPE: DNA
<213> ORGANISM: Artificial Sequence
<220> FEATURE:
<223> OTHER INFORMATION: sgCpf1Gamma-1
<220> FEATURE:
<221> NAME/KEY: misc_feature
<222> LOCATION: 4
<223> OTHER INFORMATION: /note="n is a, c, g or t"

<400> SEQUENCE: 800
tttncccaac cccaacaaac attc 24

<210> SEQ ID NO 801
<211> LENGTH: 24
<212> TYPE: DNA
<213> ORGANISM: Artificial Sequence
<220> FEATURE:
<223> OTHER INFORMATION: sgCpf1Gamma-2
<220> FEATURE:
<221> NAME/KEY: misc_feature
<222> LOCATION: 4
<223> OTHER INFORMATION: /note="n is a, c, g or t"

<400> SEQUENCE: 801
tttntgctag ttgttggcaa catt 24

<210> SEQ ID NO 802
<211> LENGTH: 24
<212> TYPE: DNA
<213> ORGANISM: Artificial Sequence
<220> FEATURE:
<223> OTHER INFORMATION: sgCpf1Gamma-3
<220> FEATURE:
<221> NAME/KEY: misc_feature
<222> LOCATION: 4
<223> OTHER INFORMATION: /note="n is a, c, g or t"

<400> SEQUENCE: 802
tttntccagc cccaacaacc attc 24

<210> SEQ ID NO 803
<211> LENGTH: 24
<212> TYPE: DNA
<213> ORGANISM: Artificial Sequence
<220> FEATURE:
<223> OTHER INFORMATION: sgCpf1Gamma-4
<220> FEATURE:
<221> NAME/KEY: misc_feature
<222> LOCATION: 4
<223> OTHER INFORMATION: /note="n is a, c, g or t"

<400> SEQUENCE: 803
tttnttgggg ttggggaaat gttt 24

<210> SEQ ID NO 804
<211> LENGTH: 20
<212> TYPE: DNA
<213> ORGANISM: Artificial Sequence
<220> FEATURE:
<223> OTHER INFORMATION: DsgGlia20-1

<400> SEQUENCE: 804
tatggttgtt gtggtcgaaa 20

<210> SEQ ID NO 805

<211> LENGTH: 20
<212> TYPE: DNA
<213> ORGANISM: Artificial Sequence
<220> FEATURE:
<223> OTHER INFORMATION: DsgDQ2.5-1

<400> SEQUENCE: 805
ggatatggta gttgcggctg 20

<210> SEQ ID NO 806
<211> LENGTH: 20
<212> TYPE: DNA
<213> ORGANISM: Artificial Sequence
<220> FEATURE:
<223> OTHER INFORMATION: DsgDQ2.5Gli1a

<400> SEQUENCE: 806
ggtagttgcg gctgcggaaa 20

<210> SEQ ID NO 807
<211> LENGTH: 20
<212> TYPE: DNA
<213> ORGANISM: Artificial Sequence
<220> FEATURE:
<223> OTHER INFORMATION: sgCpf1Alpha-1

<400> SEQUENCE: 807
tggctgcaat tgtggcactg 20

<210> SEQ ID NO 808
<211> LENGTH: 20
<212> TYPE: DNA
<213> ORGANISM: Artificial Sequence
<220> FEATURE:
<223> OTHER INFORMATION: sgCpf1Alpha-2

<400> SEQUENCE: 808
catcacaaca accatatctg 20

<210> SEQ ID NO 809
<211> LENGTH: 20
<212> TYPE: DNA
<213> ORGANISM: Artificial Sequence
<220> FEATURE:
<223> OTHER INFORMATION: sgCpf1Alpha-3

<400> SEQUENCE: 809
tagggcagca acaaccattt 20

<210> SEQ ID NO 810
<211> LENGTH: 20
<212> TYPE: DNA
<213> ORGANISM: Artificial Sequence
<220> FEATURE:
<223> OTHER INFORMATION: sgCpf133mer1

<400> SEQUENCE: 810
cgcagccgca actaccatat 20

<210> SEQ ID NO 811
<211> LENGTH: 20
<212> TYPE: DNA
<213> ORGANISM: Artificial Sequence
<220> FEATURE:
<223> OTHER INFORMATION: sgCpf1Glia20

<400> SEQUENCE: 811
gaccacaaca accatatcca 20

<210> SEQ ID NO 812
<211> LENGTH: 20
<212> TYPE: DNA
<213> ORGANISM: Artificial Sequence
<220> FEATURE:
<223> OTHER INFORMATION: sgCpf1Omega-1

<400> SEQUENCE: 812
tcctccttgc catggcgatg 20

<210> SEQ ID NO 813
<211> LENGTH: 20
<212> TYPE: DNA
<213> ORGANISM: Artificial Sequence
<220> FEATURE:
<223> OTHER INFORMATION: sgCpf1Omega-2

<400> SEQUENCE: 813
ccatcaacaa caaccatttc 20

<210> SEQ ID NO 814
<211> LENGTH: 20
<212> TYPE: DNA
<213> ORGANISM: Artificial Sequence
<220> FEATURE:
<223> OTHER INFORMATION: sgCpf1Omega-3

<400> SEQUENCE: 814
ccagcaaccc caacaaccat 20

<210> SEQ ID NO 815
<211> LENGTH: 20
<212> TYPE: DNA
<213> ORGANISM: Artificial Sequence
<220> FEATURE:
<223> OTHER INFORMATION: sgCpf1Gamma-1

<400> SEQUENCE: 815
cccaacccca acaaacattc 20

<210> SEQ ID NO 816
<211> LENGTH: 20
<212> TYPE: DNA
<213> ORGANISM: Artificial Sequence
<220> FEATURE:
<223> OTHER INFORMATION: sgCpf1Gamma-2

<400> SEQUENCE: 816
tgctagttgt tggcaacatt 20

<210> SEQ ID NO 817
<211> LENGTH: 20
<212> TYPE: DNA
<213> ORGANISM: Artificial Sequence
<220> FEATURE:
<223> OTHER INFORMATION: sgCpf1Gamma-3

<400> SEQUENCE: 817
tccagcccca acaaccattc 20

<210> SEQ ID NO 818

<211> LENGTH: 20
<212> TYPE: DNA
<213> ORGANISM: Artificial Sequence
<220> FEATURE:
<223> OTHER INFORMATION: sgCpf1Gamma-4

<400> SEQUENCE: 818
ttggggttgg ggaaatgttt 20

<210> SEQ ID NO 819
<211> LENGTH: 3684
<212> TYPE: DNA
<213> ORGANISM: Artificial Sequence
<220> FEATURE:
<223> OTHER INFORMATION: nucleic acid sequence of Ta-LbCpf1

<400> SEQUENCE: 819
atgagcaagc tggagaagtt tacgaattgc tacagtctgt ccaagacgtt gcgcttcaag 60
gccataccag tcgggaagac tcaagagaac atagacaaca agcgactcct tgtggaagac 120
gagaaacgcg cggaggacta taagggggtc aaaaagcttc ttgacagata ctatttgtct 180
tttataaacg atgtcctaca ttctatcaaa ttaaagaatc tcaacaatta catctcgcta 240
tttcgaaaga agacgcggac ggaaaaggaa aacaaagaat tagaaaatct tgagataaat 300
cttcgtaagg aaatagccaa ggcttttaaa ggcaacgaag gctataagtc actattcaaa 360
aaagatatca ttgaaacaat ccttcccgaa ttcctagacg acaaggatga aatcgcactg 420
gttaattcat tcaacgggtt cacgactgca ttcactggat tcttcgataa tcgggaaaat 480
atgttttcag aggaggccaa gtccacgtca atcgctttta ggtgcataaa tgaaaattta 540
acccggtata tatccaatat ggatatcttt gagaaggtag acgccatatt tgacaagcat 600
gaagtgcaag aaattaagga aaagattctc aacagtgact atgacgtgga ggactttttc 660
gagggggaat tcttcaattt cgtactaact caggagggca tagatgtcta taacgcgatc 720
atcggtgggt tcgtgactga gagtggcgaa aagatcaagg gtttgaacga gtatataaat 780
ttatataacc agaagaccaa gcaaaagctt cctaagttta agccactcta taaacaggta 840
ctgagcgacc gggaaagcct ttccttttac ggcgaaggat atacatcgga cgaagaagta 900
ctggaggtat tccgcaacac attgaacaaa aattctgaga ttttcagctc cataaaaaag 960
ttggaaaaac ttttcaaaaa ttttgatgaa tactcttcgg cgggaatctt cgttaagaac 1020
gggcctgcta tttcaaccat tagcaaagac atcttcggcg aatggaatgt tattcgcgat 1080
aaatggaatg ctgagtacga cgatatacac cttaagaaga aggctgttgt cacagaaaaa 1140
tatgaagacg accggaggaa gtcattcaag aagattggtt ctttcagcct cgaacagctg 1200
caggagtatg ctgatgctga cctctcagtg gtggagaaac ttaaggagat tattatccaa 1260
aaggttgacg agatatacaa agtgtatggc agctctgaga aacttttcga tgcagatttt 1320
gtgctagaga aatcactaaa gaaaaacgac gcggtggtgg caattatgaa ggacttgctc 1380
gactctgtta agagctttga gaactacata aaggcgttct tcggcgaggg caaggagacc 1440
aacagagatg agtccttcta cggtgacttt gtcttggcgt acgacattct tttgaaggtg 1500
gatcacattt atgacgctat tagaaattac gtcacgcaga agccgtattc taaagataaa 1560
ttcaaactgt attttcagaa tccacagttc atgggtggct gggataagga taaagagact 1620
gattacaggg caacaatcct ccgctacggc agtaagtatt atctggcgat catggataaa 1680
aaatacgcca agtgcttgca aaagattgat aaagacgacg tgaacggaaa ttatgagaag 1740
attaattata aacttctacc ggggccaaac aagatgttgc caaaggtctt cttctctaaa 1800
aagtggatgg cttattacaa tccgagcgag gatatacaaa agatttacaa aaacggtacg 1860
tttaagaagg gtgacatgtt taatttgaac gactgtcaca agctcattga ctttttttaag 1920 gattctatct caagataccc taaatggagt aacgcatacg attttaactt cagtgagaca 1980
gagaagtaca aagacatcgc aggtttttac agagaggttg aggagcaggg atacaaagtt 2040
agctttgagt cagcgagtaa gaaggaggtc gataaactgg tggaggaggg taagctgtac 2100
atgttccaga tctacaataa ggatttctca gacaagtcgc acggtacgcc aaacctccat 2160
acaatgtact ttaagttgtt gttcgacgag aacaatcacg ggcaaatccg gctgtctggg 2220
ggagcagagt tgtttatgcg gcgagcatcg ctgaagaagg aggagctcgt tgttcatcct 2280
gcaaattctc cgatcgccaa taagaaccca gacaatccga agaagaccac tactctctcc 2340
tacgatgtct acaaggataa gcgtttctcc gaggaccaat acgagctcca tatcccaatc 2400
gccattaaca agtgtcccaa gaacattttc aagatcaata cagaggtgcg cgtcctgctg 2460
aagcacgatg acaaccccta cgttattgga attgatcgtg gggagcgcaa cctgctctac 2520
atcgttgttg tggatggaaa gggaaacatt gtggagcaat actccctgaa cgagattatc 2580
aacaacttta acgggatcag gattaagact gactaccact cactcctcga caagaaggag 2640
aaggagaggt ttgaggcgcg tcagaactgg accagcatcg agaacatcaa ggagctcaag 2700
gctggataca tctcccaagt ggtccacaag atctgcgagc tggtcgagaa gtacgacgcg 2760
gtcatcgccc tggaggacct caactcgggg ttcaagaact cccgtgtgaa ggtcgagaag 2820
caggtctacc aaaagttcga gaagatgctc atcgataagc tgaactacat ggtggataag 2880
aagtcgaacc catgcgctac cggcggcgcg ctcaagggct accaaatcac caacaagttc 2940
gagagcttca agagcatgtc cacccaaaac gggttcatct tctacatccc cgcgtggctg 3000
acctcgaaga tcgatccgag caccggcttc gtgaacctcc tgaagaccaa gtacaccagc 3060
atcgccgact cgaagaagtt catctcgtcc ttcgacagga tcatgtacgt cccggaggag 3120
gacctcttcg agttcgcgct ggactacaag aacttcagcc gcaccgacgc cgactacatc 3180
aagaagtgga agctctactc gtacggcaac aggatccgca tcttcaggaa ccctaagaag 3240
aacaacgtct tcgactggga ggaggtgtgc ctgacctccg cgtacaagga gctcttcaac 3300
aagtacggca tcaactacca acaaggcgac atccgcgccc tgctctgcga gcaaagcgac 3360
aaggcgttct actcctcgtt catggccctg atgagcctca tgctccagat gcgcaactcc 3420
atcaccggca ggaccgacgt ggacttcctg atctccccccg tgaagaactc cgacggcatc 3480
ttctacgact ccaggaacta cgaggcccag gagaacgcca tcctccccaa gaacgccgac 3540
gccaacggcg cctacaacat cgccaggaag gtgctctggg ccatcggcca attcaagaag 3600
gccgaggacg agaagctcga caaggtcaag atcgccatca gcaacaagga gtggctcgag 3660
tacgcccaga ccagcgtcaa gcac 3684

<210> SEQ ID NO 820
<211> LENGTH: 3684
<212> TYPE: DNA
<213> ORGANISM: Artificial Sequence
<220> FEATURE:
<223> OTHER INFORMATION: nucleic acid sequence of Ta-dLbCpf1 D832A E925A
D1148A

<400> SEQUENCE: 820
atgagcaagc tggagaagtt tacgaattgc tacagtctgt ccaagacgtt gcgcttcaag 60
gccataccag tcgggaagac tcaagagaac atagacaaca agcgactcct tgtggaagac 120

-continued

```
gagaaacgcg cggaggacta taagggggtc aaaaagcttc ttgacagata ctatttgtct    180
tttataaacg atgtcctaca ttctatcaaa ttaaagaatc tcaacaatta catctcgcta    240
tttcgaaaga agacgcggac ggaaaaggaa aacaaagaat tagaaaatct tgagataaat    300
cttcgtaagg aaatagccaa ggcttttaaa ggcaacgaag gctataagtc actattcaaa    360
aaagatatca ttgaaacaat ccttcccgaa ttcctagacg acaaggatga aatcgcactg    420
gttaattcat tcaacgggtt cacgactgca ttcactggat tcttcgataa tcgggaaaat    480
atgttttcag aggaggccaa gtccacgtca atcgctttta ggtgcataaa tgaaaattta    540
acccggtata tatccaatat ggatatcttt gagaaggtag acgccatatt tgacaagcat    600
gaagtgcaag aaattaagga aaagattctc aacagtgact atgacgtgga ggactttttc    660
gagggggaat tcttcaattt cgtactaact caggagggca tagatgtcta taacgcgatc    720
atcggtgggt tcgtgactga gagtggcgaa aagatcaagg gtttgaacga gtatataaat    780
ttatataacc agaagaccaa gcaaaagctt cctaagttta agccactcta taaacaggta    840
ctgagcgacc gggaaagcct ttccttttac ggcgaaggat atacatcgga cgaagaagta    900
ctggaggtat tccgcaacac attgaacaaa aattctgaga ttttcagctc cataaaaaag    960
ttggaaaaac ttttcaaaaa ttttgatgaa tactcttcgg cgggaatctt cgttaagaac   1020
gggcctgcta tttcaaccat tagcaaagac atcttcggcg aatggaatgt tattcgcgat   1080
aaatggaatg ctgagtacga cgatatacac cttaagaaga aggctgttgt cacagaaaaa   1140
tatgaagacg accggaggaa gtcattcaag aagattggtt ctttcagcct cgaacagctg   1200
caggagtatg ctgatgctga cctctcagtg gtggagaaac ttaaggagat tattatccaa   1260
aaggttgacg agatatacaa agtgtatggc agctctgaga aacttttcga tgcagatttt   1320
gtgctagaga aatcactaaa gaaaaacgac gcggtggtgg caattatgaa ggacttgctc   1380
gactctgtta agagctttga gaactacata aaggcgttct tcggcgaggg caaggagacc   1440
aacagagatg agtccttcta cggtgacttt gtcttggcgt acgacattct tttgaaggtg   1500
gatcacattt atgacgctat tagaaattac gtcacgcaga agccgtattc taaagataaa   1560
ttcaaactgt attttcagaa tccacagttc atgggtggct gggataagga taaagagact   1620
gattacaggg caacaatcct ccgctacggc agtaagtatt atctggcgat catggataaa   1680
aaatacgcca agtgcttgca aaagattgat aaagacgacg tgaacggaaa ttatgagaag   1740
attaattata aacttctacc ggggccaaac aagatgttgc caaaggtctt cttctctaaa   1800
aagtggatgg cttattacaa tccgagcgag gatatacaaa agatttacaa aaacggtacg   1860
tttaagaagg gtgacatgtt taatttgaac gactgtcaca agctcattga ctttttttaag   1920
gattctatct caagataccc taaatggagt aacgcatacg attttaactt cagtgagaca   1980
gagaagtaca aagacatcgc aggtttttac agagaggttg aggagcaggg atacaaagtt   2040
agctttgagt cagcgagtaa gaaggaggtc gataaactgg tggaggaggg taagctgtac   2100
atgttccaga tctacaataa ggatttctca gacaagtcgc acggtacgcc aaacctccat   2160
acaatgtact ttaagttgtt gttcgacgag aacaatcacg ggcaaatccg gctgtctggg   2220
ggagcagagt tgtttatgcg gcgagcatcg ctgaagaagg aggagctcgt tgttcatcct   2280
gcaaattctc cgatcgccaa taagaaccca gacaatccga agaagaccac tactctctcc   2340
tacgatgtct acaaggataa gcgtttctcc gaggaccaat acgagctcca tatcccaatc   2400
gccattaaca agtgtcccaa gaacattttc aagatcaata cagaggtgcg cgtcctgctg   2460
```

aagcacgatg acaaccccta cgttattgga attgctcgtg gggagcgcaa cctgctctac 2520
atcgttgttg tggatggaaa gggaaacatt gtggagcaat actccctgaa cgagattatc 2580
aacaacttta acgggatcag gattaagact gactaccact cactcctcga caagaaggag 2640
aaggagaggt ttgaggcgcg tcagaactgg accagcatcg agaacatcaa ggagctcaag 2700
gctggataca tctcccaagt ggtccacaag atctgcgagc tggtcgagaa gtacgacgcg 2760
gtcatcgccc tggccgacct caactcgggg ttcaagaact cccgtgtgaa ggtcgagaag 2820
caggtctacc aaaagttcga gaagatgctc atcgataagc tgaactacat ggtggataag 2880
aagtcgaacc catgcgctac cggcggcgcg ctcaagggct accaaatcac caacaagttc 2940
gagagcttca agagcatgtc cacccaaaac gggttcatct tctacatccc cgcgtggctg 3000
acctcgaaga tcgatccgag caccggcttc gtgaacctcc tgaagaccaa gtacaccagc 3060
atcgccgact cgaagaagtt catctcgtcc ttcgacagga tcatgtacgt cccggaggag 3120
gacctcttcg agttcgcgct ggactacaag aacttcagcc gcaccgacgc cgactacatc 3180
aagaagtgga agctctactc gtacggcaac aggatccgca tcttcaggaa ccctaagaag 3240
aacaacgtct tcgactggga ggaggtgtgc ctgacctccg cgtacaagga gctcttcaac 3300
aagtacggca tcaactacca acaaggcgac atccgcgccc tgctctgcga gcaaagcgac 3360
aaggcgttct actcctcgtt catggccctg atgagcctca tgctccagat gcgcaactcc 3420
atcaccggca ggaccgacgt ggccttcctg atctccccgc tgaagaactc cgacggcatc 3480
ttctacgact ccaggaacta cgaggcccag gagaacgcca tcctccccaa gaacgccgac 3540
gccaacggcg cctacaacat cgccaggaag gtgctctggg ccatcggcca attcaagaag 3600
gccgaggacg agaagctcga caaggtcaag atcgccatca gcaacaagga gtggctcgag 3660
tacgcccaga ccagcgtcaa gcac 3684

<210> SEQ ID NO 821
<211> LENGTH: 684
<212> TYPE: DNA
<213> ORGANISM: Artificial Sequence
<220> FEATURE:
<223> OTHER INFORMATION: APOBEC1

<400> SEQUENCE: 821
atgtcatcgg agaccggccc tgttgctgtt gaccccaccc tgcggcggag aatcgagcca 60
cacgagttcg aggtgttctt cgacccaagg gagctccgca aggagacgtg cctcctgtac 120
gagatcaact ggggcggcag gcactccatc tggaggcaca ccagccaaaa caccaacaag 180
cacgtggagg tcaacttcat cgagaagttc accaccgaga ggtacttctg cccaaacacc 240
cgctgctcca tcacctggtt cctgtcctgg agcccatgcg gcgagtgctc cagggccatc 300
accgagttcc tcagccgcta cccacacgtc accctgttca tctacatcgc caggctctac 360
caccacgccg acccaaggaa caggcagggc ctccgcgacc tgatctccag cggcgtgacc 420
atccaaatca tgaccgagca ggagtccggc tactgctgga ggaacttcgt caactactcc 480
ccaagcaacg aggcccactg gccaaggtac ccacacctct gggtgcgcct ctacgtgctg 540
gagctgtact gcatcatcct cggcctgcca ccatgcctca acatcctgag gcgcaagcaa 600
ccacagctga ccttcttcac catcgccctc caaagctgcc actaccagag gctcccacca 660
cacatcctgt gggctaccgg cctc 684

<210> SEQ ID NO 822
<211> LENGTH: 4155

<212> TYPE: DNA
<213> ORGANISM: Artificial Sequence
<220> FEATURE:
<223> OTHER INFORMATION: nucleic acid sequence of nTaCas9 D10A

<400> SEQUENCE: 822
atgaaggaca agaagtactc gatcggcctc gccatcggga cgaactcagt tggctgggcc 60
gtgatcaccg acgagtacaa ggtgccctct aagaagttca aggtcctggg gaacaccgac 120
cgccattcca tcaagaagaa cctcatcggc gctctcctgt tcgacagcgg ggagaccgct 180
gaggctacga ggctcaagag aaccgctagg cgccggtaca cgagaaggaa gaacaggatc 240
tgctacctcc aagagatttt ctccaacgag atggccaagg ttgacgattc attcttccac 300
cgcctggagg agtctttcct cgtggaggag gataagaagc acgagcggca tcccatcttc 360
ggcaacatcg tggacgaggt tgcctaccac gagaagtacc ctacgatcta ccatctgcgg 420
aagaagctcg tggactccac cgataaggcg gacctcagac tgatctacct cgctctggcc 480
cacatgatca agttccgcgg ccatttcctg atcgaggggg atctcaaccc agacaacagc 540
gatgttgaca agctgttcat ccaactcgtg cagacctaca accaactctt cgaggagaac 600
ccgatcaacg cctctggcgt ggacgcgaag gctatcctgt ccgcgaggct ctcgaagtcc 660
aggaggctgg agaacctgat cgctcagctc ccaggcgaga agaagaacgg cctgttcggg 720
aacctcatcg ctctcagcct ggggctcacc ccgaacttca agtcgaactt cgatctcgct 780
gaggacgcca agctgcaact ctccaaggac acctacgacg atgacctcga taacctcctg 840
gcccagatcg gcgatcaata cgcggacctg ttcctcgctg ccaagaacct gtcggacgcc 900
atcctcctgt cagatatcct ccgcgtgaac accgagatca cgaaggctcc actctctgcc 960
tccatgatca agcgctacga cgagcaccat caggatctga ccctcctgaa ggcgctggtc 1020
cgccaacagc tcccggagaa gtacaaggag attttcttcg atcagtcgaa gaacggctac 1080
gctgggtaca tcgacggcgg ggcctcacaa gaggagttct acaagttcat caagccaatc 1140
ctggagaaga tggacggcac ggaggagctc ctggtgaagc tcaacaggga ggacctcctg 1200
cggaagcaga gaaccttcga taacggcagc atcccccacc aaatccatct cggggagctg 1260
cacgccatcc tgagaaggca agaggacttc taccctttcc tcaaggataa ccgggagaag 1320
atcgagaaga tcctgacctt cagaatccca tactacgtcg gccctctcgc gcgggggaac 1380
tcaagattcg cttggatgac ccgcaagtct gaggagacca tcacgccgtg gaacttcgag 1440
gaggtggtgg acaagggcgc tagcgctcag tcgttcatcg agaggatgac caacttcgac 1500
aagaacctgc ccaacgagaa ggtgctccct aagcactcgc tcctgtacga gtacttcacc 1560
gtctacaacg agctcacgaa ggtgaagtac gtcaccgagg gcatgcgcaa gccagcgttc 1620
ctgtccgggg agcagaagaa ggctatcgtg gacctcctgt tcaagaccaa ccggaaggtc 1680
acggttaagc aactcaagga ggactacttc aagaagatcg agtgcttcga ttcggtcgag 1740
atcagcggcg ttgaggaccg cttcaacgcc agcctcggga cctaccacga tctcctgaag 1800
atcatcaagg ataaggactt cctggacaac gaggagaacg aggatatcct ggaggacatc 1860
gtgctgaccc tcacgctgtt cgaggacagg gagatgatcg aggagcgcct gaagacgtac 1920
gcccatctct tcgatgacaa ggtcatgaag caactcaagc gccggagata caccggctgg 1980
gggaggctgt cccgcaagct catcaacggc atccgggaca agcagtccgg gaagaccatc 2040
ctcgacttcc tcaagagcga tggcttcgcc aacaggaact tcatgcaact gatccacgat 2100
gacagcctca ccttcaagga ggatatccaa aaggctcaag tgagcggcca gggggactcg 2160

-continued

```
ctgcacgagc atatcgcgaa cctcgctggc tccccccgcga tcaagaaggg catcctccag   2220

accgtgaagg ttgtggacga gctcgtgaag gtcatgggcc ggcacaagcc tgagaacatc   2280

gtcatcgaga tggccagaga gaaccaaacc acgcagaagg ggcaaaagaa ctctagggag   2340

cgcatgaagc gcatcgagga gggcatcaag gagctggggt cccaaatcct caaggagcac   2400

ccagtggaga acacccaact gcagaacgag aagctctacc tgtactacct ccagaacggc   2460

agggatatgt acgtggacca agagctggat atcaaccgcc tcagcgatta cgacgtcgat   2520

catatcgttc cccagtcttt cctgaaggat gactccatcg acaacaaggt cctcaccagg   2580

tcggacaaga accgcggcaa gtcagataac gttccatctg aggaggtcgt taagaagatg   2640

aagaactact ggaggcagct cctgaacgcc aagctgatca cgcaaaggaa gttcgacaac   2700

ctcaccaagg ctgagagagg cgggctctca gagctggaca aggccggctt catcaagcgg   2760

cagctggtcg agaccagaca aatcacgaag cacgttgcgc aaatcctcga ctctcggatg   2820

aacacgaagt acgatgagaa cgacaagctg atcagggagg ttaaggtgat caccctgaag   2880

tctaagctcg tctccgactt caggaaggat ttccagttct acaaggttcg cgagatcaac   2940

aactaccacc atgcccatga cgcttacctc aacgctgtgg tcggcaccgc tctgatcaag   3000

aagtacccaa agctggagtc cgagttcgtg tacggggact acaaggttta cgatgtgcgc   3060

aagatgatcg ccaagtcgga gcaagagatc ggcaaggcta ccgccaagta cttcttctac   3120

tcaaacatca tgaacttctt caagaccgag atcacgctgg ccaacggcga gatccggaag   3180

agaccgctca tcgagaccaa cggcgagacg ggggagatcg tgtgggacaa gggcagggat   3240

ttcgcgaccg tccgcaaggt tctctccatg ccccaggtga acatcgtcaa gaagaccgag   3300

gtccaaacgg gcgggttctc aaaggagtct atcctgccta agcggaacag cgacaagctc   3360

atcgccagaa agaaggactg ggacccaaag aagtacggcg ggttcgacag ccctaccgtg   3420

gcctactcgg tcctggttgt ggcgaaggtt gagaagggca agtccaagaa gctcaagagc   3480

gtgaaggagc tcctggggat caccatcatg gagaggtcca gcttcgagaa gaacccaatc   3540

gacttcctgg aggccaaggg ctacaaggag gtgaagaagg acctgatcat caagctcccg   3600

aagtactctc tcttcgagct ggagaacggc aggaagagaa tgctggcttc cgctggcgag   3660

ctccagaagg ggaacgagct cgcgctgcca agcaagtacg tgaacttcct ctacctggct   3720

tcccactacg agaagctcaa gggcagcccg gaggacaacg agcaaaagca gctgttcgtc   3780

gagcagcaca agcattacct cgacgagatc atcgagcaaa tctccgagtt cagcaagcgc   3840

gtgatcctcg ccgacgcgaa cctggataag gtcctctccg cctacaacaa gcaccgggac   3900

aagcccatca gagagcaagc ggagaacatc atccatctct tcaccctgac gaacctcggc   3960

gctcctgctg ctttcaagta cttcgacacc acgatcgatc ggaagagata cacctccacg   4020

aaggaggtcc tggacgcgac cctcatccac cagtcgatca ccggcctgta cgagacgagg   4080

atcgacctct cacaactcgg cggggataag agacccgcag caaccaagaa ggcagggcaa   4140

gcaaagaaga agaag                                                    4155
```

<210> SEQ ID NO 823
<211> LENGTH: 21
<212> TYPE: RNA
<213> ORGANISM: Artificial Sequence
<220> FEATURE:
<223> OTHER INFORMATION: crRNA for Lachnospiraceae bacterium (Lb)

-continued

<400> SEQUENCE: 823
uaauuucuac uaaguguaga u 21